United States Patent
Zhang et al.

(10) Patent No.: US 9,096,593 B2
(45) Date of Patent: Aug. 4, 2015

(54) COMPOUNDS AND METHODS FOR KINASE MODULATION, AND INDICATIONS THEREFOR

(71) Applicant: Plexxikon Inc., Berkeley, CA (US)

(72) Inventors: Jiazhong Zhang, Foster City, CA (US); Prabha N. Ibrahim, Mountain View, CA (US); Ryan Bremer, Oakland, CA (US); Wayne Spevak, Berkeley, CA (US); Hanna Cho, Oakland, CA (US)

(73) Assignee: Plexxikon Inc., Berkeley, CA (US)

(*) Notice: Subject to any disclaimer, the term of this patent is extended or adjusted under 35 U.S.C. 154(b) by 0 days.

(21) Appl. No.: 14/033,291

(22) Filed: Sep. 20, 2013

(65) Prior Publication Data

US 2014/0045840 A1 Feb. 13, 2014

Related U.S. Application Data

(63) Continuation of application No. 12/939,998, filed on Nov. 4, 2010, now abandoned.

(60) Provisional application No. 61/259,093, filed on Nov. 6, 2009.

(51) Int. Cl.
| | |
|---|---|
| *C07D 401/14* | (2006.01) |
| *A61K 31/4427* | (2006.01) |
| *C07D 471/04* | (2006.01) |
| *A61K 31/437* | (2006.01) |
| *A61K 31/506* | (2006.01) |
| *C07D 401/04* | (2006.01) |

(52) U.S. Cl.
CPC ............ *C07D 471/04* (2013.01); *A61K 31/437* (2013.01); *A61K 31/4427* (2013.01); *A61K 31/506* (2013.01); *C07D 401/04* (2013.01); *C07D 401/14* (2013.01)

(58) Field of Classification Search
CPC .......................... C07D 401/14; A61K 31/4427
USPC .................... 544/331; 546/113; 514/275, 300
See application file for complete search history.

(56) References Cited

U.S. PATENT DOCUMENTS

| | | | |
|---|---|---|---|
| 2,234,705 | A | 3/1941 | Duennebier et al. |
| 2,413,258 | A | 12/1946 | Soday |
| 4,150,949 | A | 4/1979 | Smith |
| 4,301,159 | A | 11/1981 | Ogata et al. |
| 4,439,444 | A | 3/1984 | Nisato et al. |
| 4,568,649 | A | 2/1986 | Bertoglio-Matte |
| 4,595,780 | A | 6/1986 | Ogata et al. |
| 4,626,513 | A | 12/1986 | Burton et al. |
| 4,634,701 | A | 1/1987 | De Vincentiis |
| 4,714,693 | A | 12/1987 | Targos |
| 4,727,395 | A | 2/1988 | Oda et al. |
| 4,863,945 | A | 9/1989 | Friebe et al. |
| 5,120,782 | A | 6/1992 | Hubsch et al. |
| 5,143,854 | A | 9/1992 | Pirrung et al. |
| 5,338,849 | A | 8/1994 | Festal et al. |
| 5,360,882 | A | 11/1994 | Dougherty et al. |
| 5,426,039 | A | 6/1995 | Wallace et al. |
| 5,432,177 | A | 7/1995 | Baker et al. |
| 5,434,049 | A | 7/1995 | Okano et al. |
| 5,449,614 | A | 9/1995 | Danos et al. |
| 5,474,935 | A | 12/1995 | Chatterjee et al. |
| 5,486,525 | A | 1/1996 | Summers, Jr. et al. |
| 5,556,752 | A | 9/1996 | Lockhart et al. |
| 5,576,319 | A | 11/1996 | Baker et al. |
| 5,580,859 | A | 12/1996 | Felgner et al. |
| 5,631,236 | A | 5/1997 | Woo et al. |
| 5,632,957 | A | 5/1997 | Heller et al. |
| 5,658,775 | A | 8/1997 | Gilboa |
| 5,681,959 | A | 10/1997 | Bishop et al. |
| 5,700,637 | A | 12/1997 | Southern |
| 5,700,809 | A | 12/1997 | Leeson et al. |
| 5,712,285 | A | 1/1998 | Curtis et al. |
| 5,721,118 | A | 2/1998 | Scheffler |
| 5,744,305 | A | 4/1998 | Fodor et al. |
| 5,747,276 | A | 5/1998 | Hoch et al. |
| 5,763,198 | A | 6/1998 | Hirth et al. |

(Continued)

FOREIGN PATENT DOCUMENTS

| | | |
|---|---|---|
| CA | 2550361 | 4/2014 |
| EP | 0 154 734 | 9/1985 |

(Continued)

OTHER PUBLICATIONS

Beaucage and Iyer, Advances in the Synthesis of Oligonucleotides by the Phosphoramidite Approach, Tetrahedron (1992) 48:2223-2311.

(Continued)

*Primary Examiner* — Deepak Rao
(74) *Attorney, Agent, or Firm* — Sheppard Mullin Richter & Hampton LLP

(57) ABSTRACT

Compounds and salts thereof, formulations thereof, conjugates thereof, derivatives thereof, forms thereof and uses thereof are described. In certain aspects and embodiments, the described compounds or salts thereof, formulations thereof, conjugates thereof, derivatives thereof, or forms thereof are active on Fms protein kinase, or on Fms and Kit protein kinase, or on Fms and Flt-3 protein kinase. Also described are methods of use thereof to treat diseases and conditions, including diseases and conditions associated with activity of Fms protein kinase, Kit protein kinase, or Flt-3 protein kinase including rheumatoid arthritis, osteoarthritis, multiple sclerosis, Alzheimer's disease, Parkinson's disease, glomerulonephritis, interstitial nephritis, Lupus nephritis, tubular necrosis, diabetic nephropathy, renal hypertrophy, acute myeloid leukemia, melanoma, multiple myeloma, metastatic breast cancer, prostate cancer, pancreatic cancer, neurofibromatosis, brain metastases, and gastrointestinal stromal tumors.

22 Claims, No Drawings

(56) References Cited

U.S. PATENT DOCUMENTS

| | | |
|---|---|---|
| 5,770,456 A | 6/1998 | Holmes |
| 5,800,992 A | 9/1998 | Fodor et al. |
| 5,807,522 A | 9/1998 | Brown et al. |
| 5,830,645 A | 11/1998 | Pinkel et al. |
| 5,840,485 A | 11/1998 | Lebl et al. |
| 5,856,174 A | 1/1999 | Lipshutz et al. |
| 5,858,995 A | 1/1999 | Kawai et al. |
| 5,877,007 A | 3/1999 | Housey |
| 5,908,401 A | 6/1999 | Henley |
| 5,952,362 A | 9/1999 | Cournoyer et al. |
| 5,958,930 A | 9/1999 | Gangjee |
| 5,959,098 A | 9/1999 | Goldberg et al. |
| 5,965,452 A | 10/1999 | Kovacs et al. |
| 6,013,440 A | 1/2000 | Lipshutz et al. |
| 6,022,963 A | 2/2000 | McGall et al. |
| 6,025,155 A | 2/2000 | Hadlaczky et al. |
| 6,045,996 A | 4/2000 | Cronin et al. |
| 6,048,695 A | 4/2000 | Bradley et al. |
| 6,054,270 A | 4/2000 | Southern |
| 6,090,912 A | 7/2000 | Lebl et al. |
| 6,096,718 A | 8/2000 | Weitzman et al. |
| 6,107,478 A | 8/2000 | Pedersen et al. |
| 6,110,456 A | 8/2000 | During et al. |
| 6,110,458 A | 8/2000 | Freeman et al. |
| 6,113,913 A | 9/2000 | Brough et al. |
| 6,117,681 A | 9/2000 | Salmons et al. |
| 6,161,776 A | 12/2000 | Byles |
| 6,178,384 B1 | 1/2001 | Kolossváry |
| 6,235,769 B1 | 5/2001 | Clary |
| 6,243,980 B1 | 6/2001 | Bronstein et al. |
| 6,258,606 B1 | 7/2001 | Kovacs |
| 6,261,776 B1 | 7/2001 | Pirrung et al. |
| 6,277,489 B1 | 8/2001 | Abbott et al. |
| 6,277,628 B1 | 8/2001 | Johann et al. |
| 6,288,234 B1 | 9/2001 | Griffin |
| 6,294,330 B1 | 9/2001 | Michnick et al. |
| 6,310,074 B1 | 10/2001 | Depreux et al. |
| 6,350,786 B1 | 2/2002 | Albano et al. |
| 6,545,014 B2 | 4/2003 | Verner |
| 6,653,309 B1 | 11/2003 | Saunders et al. |
| 6,858,860 B2 | 2/2005 | Hosono et al. |
| 6,897,207 B2 | 5/2005 | Cox et al. |
| 7,259,165 B2 | 8/2007 | Bernotas et al. |
| 7,271,262 B2 | 9/2007 | La Greca et al. |
| 7,361,763 B2 | 4/2008 | Arnold et al. |
| 7,361,764 B2 | 4/2008 | Arnold et al. |
| 7,452,993 B2 | 11/2008 | Arnold et al. |
| 7,498,342 B2 | 3/2009 | Ibrahim et al. |
| 7,504,509 B2 | 3/2009 | Ibrahim et al. |
| 7,582,637 B2 | 9/2009 | Arnold et al. |
| 7,601,839 B2 | 10/2009 | Arnold et al. |
| 7,626,021 B2 | 12/2009 | Arnold et al. |
| 7,846,941 B2 | 12/2010 | Zhang et al. |
| 7,863,288 B2 | 1/2011 | Ibrahim et al. |
| 7,863,289 B2 | 1/2011 | Spevak et al. |
| 7,893,075 B2 | 2/2011 | Zhang et al. |
| 7,947,708 B2 | 5/2011 | Ibrahim et al. |
| 7,994,185 B2 | 8/2011 | Rheault |
| 8,067,638 B2 | 11/2011 | Kai et al. |
| 8,129,404 B2 | 3/2012 | Ibrahim et al. |
| 8,143,271 B2 | 3/2012 | Ibrahim et al. |
| 8,404,700 B2 | 3/2013 | Ibrahim et al. |
| 8,415,469 B2 | 4/2013 | Ibrahim et al. |
| 8,722,702 B2 | 5/2014 | Zhang et al. |
| 2001/0001449 A1 | 5/2001 | Kiliany et al. |
| 2001/0008765 A1 | 7/2001 | Shinoki et al. |
| 2001/0012537 A1 | 8/2001 | Anderson et al. |
| 2001/0014448 A1 | 8/2001 | Chappa et al. |
| 2001/0014449 A1 | 8/2001 | Nerenberg et al. |
| 2001/0016322 A1 | 8/2001 | Caren et al. |
| 2001/0018642 A1 | 8/2001 | Balaban et al. |
| 2001/0019827 A1 | 9/2001 | Dawson et al. |
| 2003/0003004 A1 | 1/2003 | Stones et al. |
| 2003/0219489 A1 | 11/2003 | Curatolo et al. |
| 2004/0002534 A1 | 1/2004 | Lipson et al. |
| 2004/0022534 A1 | 2/2004 | Amano et al. |
| 2004/0073274 A1 | 4/2004 | Cook et al. |
| 2004/0077595 A1 | 4/2004 | Cheng et al. |
| 2004/0142864 A1 | 7/2004 | Bremer et al. |
| 2004/0167030 A1 | 8/2004 | Bernotas et al. |
| 2005/0026792 A1 | 2/2005 | Cartwright |
| 2005/0031692 A1 | 2/2005 | Beyerinck et al. |
| 2005/0085463 A1 | 4/2005 | Weiner et al. |
| 2005/0154014 A1 | 7/2005 | Bloxham et al. |
| 2005/0164300 A1 | 7/2005 | Artis et al. |
| 2005/0170431 A1 | 8/2005 | Ibrahim et al. |
| 2005/0256151 A1 | 11/2005 | Salom et al. |
| 2006/0018726 A1 | 1/2006 | Hall |
| 2006/0024361 A1 | 2/2006 | Odidi et al. |
| 2006/0035898 A1 | 2/2006 | Arnold et al. |
| 2006/0058324 A1 | 3/2006 | Caparro et al. |
| 2006/0058339 A1 | 3/2006 | Ibrahim et al. |
| 2006/0058340 A1 | 3/2006 | Ibrahim et al. |
| 2006/0167403 A1 | 7/2006 | Henley et al. |
| 2007/0032519 A1 | 2/2007 | Zhang et al. |
| 2007/0049615 A1 | 3/2007 | Ibrahim et al. |
| 2007/0054963 A1 | 3/2007 | Lifshitz-Liron et al. |
| 2007/0072862 A1 | 3/2007 | Dimauro et al. |
| 2007/0161666 A1 | 7/2007 | Blumenkopf et al. |
| 2007/0218138 A1 | 9/2007 | Bittorf et al. |
| 2007/0225306 A1 | 9/2007 | Choi et al. |
| 2007/0287711 A1 | 12/2007 | Arnold et al. |
| 2008/0004661 A1 | 1/2008 | Silverstone |
| 2008/0079906 A1 | 4/2008 | Finn |
| 2008/0167338 A1 | 7/2008 | Spevak et al. |
| 2008/0188514 A1 | 8/2008 | Wu et al. |
| 2009/0005356 A1 | 1/2009 | Blaney et al. |
| 2009/0076046 A1 | 3/2009 | Zhang et al. |
| 2009/0143352 A1 | 6/2009 | Arnold et al. |
| 2009/0286783 A1 | 11/2009 | Ibrahim et al. |
| 2009/0306056 A1 | 12/2009 | Arnold et al. |
| 2009/0306086 A1 | 12/2009 | Ibrahim et al. |
| 2009/0306087 A1 | 12/2009 | Ibrahim et al. |
| 2010/0249118 A1 | 9/2010 | Ibrahim et al. |
| 2010/0286142 A1 | 11/2010 | Ibrahim et al. |
| 2010/0286178 A1 | 11/2010 | Ibrahim et al. |
| 2010/0310659 A1 | 12/2010 | Desai et al. |
| 2011/0028511 A1 | 2/2011 | Hildbrand et al. |
| 2011/0092538 A1 | 4/2011 | Speval et al. |
| 2011/0112127 A1 | 5/2011 | Zhang et al. |
| 2011/0112136 A1 | 5/2011 | Diodone et al. |
| 2011/0152258 A1 | 6/2011 | Ibrahim et al. |
| 2011/0183988 A1 | 7/2011 | Ibrahim et al. |
| 2011/0230482 A1 | 9/2011 | Zhang et al. |
| 2011/0263595 A1 | 10/2011 | Zhang et al. |
| 2012/0053177 A1 | 3/2012 | Ibrahim et al. |
| 2012/0165366 A1 | 6/2012 | Ibrahim et al. |
| 2012/0245174 A1 | 9/2012 | Ibrahim et al. |
| 2012/0309756 A1 | 12/2012 | Ibrahim et al. |
| 2013/0172375 A1 | 7/2013 | Albano et al. |
| 2013/0178473 A1 | 7/2013 | Zhang et al. |
| 2013/0261117 A1 | 10/2013 | Ibrahim et al. |
| 2013/0274259 A1 | 10/2013 | Zhang et al. |
| 2013/0303534 A1 | 11/2013 | Ibrahim et al. |
| 2014/0028373 A1 | 1/2014 | Voelker et al. |
| 2014/0037617 A1 | 2/2014 | Bollag et al. |
| 2014/0094611 A1 | 4/2014 | Ibrahim et al. |
| 2014/0128373 A1 | 5/2014 | Ibrahim et al. |
| 2014/0243365 A1 | 8/2014 | Zhang et al. |
| 2014/0288070 A1 | 9/2014 | Bollag et al. |

FOREIGN PATENT DOCUMENTS

| | | |
|---|---|---|
| EP | 0 148 725 | 5/1987 |
| EP | 0 344 603 | 10/1991 |
| EP | 0 465 970 | 1/1992 |
| EP | 0 870 768 | 10/1998 |
| EP | 0 596 406 | 12/1998 |
| EP | 1 267 111 | 12/2002 |
| EP | 1 388 541 | 2/2004 |
| EP | 0 988 863 | 4/2004 |
| EP | 0 580 860 | 12/2004 |
| EP | 1 368 001 | 10/2005 |
| EP | 1 749 829 | 2/2007 |

(56) References Cited

FOREIGN PATENT DOCUMENTS

| | | |
|---|---|---|
| EP | 0 901 786 | 7/2007 |
| EP | 2 036 990 | 4/2014 |
| GB | 1 198 301 | 7/1970 |
| GB | 1 451 299 | 3/1975 |
| GB | 2 292 143 | 2/1996 |
| GB | 2 292 145 | 2/1996 |
| GB | 2 298 198 | 8/1996 |
| GB | 2 299 581 | 10/1996 |
| JP | 06-135946 | 5/1994 |
| JP | 10-087629 | 4/1998 |
| JP | 10-130269 | 5/1998 |
| JP | 2000-95708 | 4/2000 |
| JP | 2001-278886 | 10/2001 |
| JP | 15-073357 | 3/2003 |
| WO | WO-93/13099 | 7/1993 |
| WO | WO-94/14808 | 7/1994 |
| WO | WO-94/20459 | 9/1994 |
| WO | WO-94/20497 | 9/1994 |
| WO | WO-95/04742 | 2/1995 |
| WO | WO-95/07910 | 3/1995 |
| WO | WO-95/28387 | 10/1995 |
| WO | WO-96/00226 | 1/1996 |
| WO | WO-96/17958 | 1/1996 |
| WO | WO-96/05200 | 2/1996 |
| WO | WO-96/11929 | 4/1996 |
| WO | WO-96/18738 | 8/1996 |
| WO | WO-96/38131 | 12/1996 |
| WO | WO-97/03967 | 2/1997 |
| WO | WO-97/46313 | 12/1997 |
| WO | WO-97/46558 | 12/1997 |
| WO | WO-97/49703 | 12/1997 |
| WO | WO-98/06433 | 2/1998 |
| WO | WO-98/22457 | 5/1998 |
| WO | WO-98/47899 | 10/1998 |
| WO | WO-99/00386 | 1/1999 |
| WO | WO-99/09217 | 2/1999 |
| WO | WO-99/32106 | 7/1999 |
| WO | WO-99/32433 | 7/1999 |
| WO | WO-99/51231 | 10/1999 |
| WO | WO-99/51232 | 10/1999 |
| WO | WO-99/51233 | 10/1999 |
| WO | WO-99/51234 | 10/1999 |
| WO | WO-99/51595 | 10/1999 |
| WO | WO-99/51596 | 10/1999 |
| WO | WO-99/51773 | 10/1999 |
| WO | WO-00/09162 | 2/2000 |
| WO | WO-00/12514 | 3/2000 |
| WO | WO-00/17202 | 3/2000 |
| WO | WO-00/29411 | 5/2000 |
| WO | WO-00/12074 | 8/2000 |
| WO | WO-00/53582 | 9/2000 |
| WO | WO-00/55153 | 9/2000 |
| WO | WO-00/64898 | 11/2000 |
| WO | WO-00/71506 | 11/2000 |
| WO | WO-00/71537 | 11/2000 |
| WO | WO-00/75139 | 12/2000 |
| WO | WO-01/09121 | 2/2001 |
| WO | WO-01/24236 | 4/2001 |
| WO | WO-01/29036 | 4/2001 |
| WO | WO-01/46196 | 6/2001 |
| WO | WO-01/62255 | 8/2001 |
| WO | WO-01/60822 | 9/2001 |
| WO | WO-01/74786 | 10/2001 |
| WO | WO-01/98299 | 12/2001 |
| WO | WO-02/18346 | 3/2002 |
| WO | WO-02/00657 | 6/2002 |
| WO | WO-02/078780 | 10/2002 |
| WO | WO-02/083175 | 10/2002 |
| WO | WO-02/085896 | 10/2002 |
| WO | WO-02/102783 | 12/2002 |
| WO | WO-03/000258 | 1/2003 |
| WO | WO-03/000267 | 1/2003 |
| WO | WO-03/003004 | 1/2003 |
| WO | WO-03/004472 | 1/2003 |
| WO | WO-03/006459 | 1/2003 |
| WO | WO-03/008422 | 1/2003 |
| WO | WO-03/011868 | 2/2003 |
| WO | WO-03/020698 | 3/2003 |
| WO | WO-03/028724 | 4/2003 |
| WO | WO-03/037862 | 5/2003 |
| WO | WO-03/064413 | 8/2003 |
| WO | WO-03/068221 | 8/2003 |
| WO | WO-03/051838 | 9/2003 |
| WO | WO-03/082289 | 10/2003 |
| WO | WO-03/082868 | 10/2003 |
| WO | WO-03/082869 | 10/2003 |
| WO | WO-03/062236 | 12/2003 |
| WO | WO-03/087087 | 12/2003 |
| WO | WO-03/101990 | 12/2003 |
| WO | WO-2004/005283 | 1/2004 |
| WO | WO-2004/009600 | 1/2004 |
| WO | WO-2004/009601 | 1/2004 |
| WO | WO-2004/014369 | 2/2004 |
| WO | WO-2004/016609 | 2/2004 |
| WO | WO-2004/016610 | 2/2004 |
| WO | WO-2004/024895 | 3/2004 |
| WO | WO-2004/052880 | 6/2004 |
| WO | WO-2004/054581 | 7/2004 |
| WO | WO-2004/056830 | 7/2004 |
| WO | WO-2004/065393 | 8/2004 |
| WO | WO-2004/065394 | 8/2004 |
| WO | WO-2004/069138 | 8/2004 |
| WO | WO-2004/054974 | 9/2004 |
| WO | WO-2004/074278 | 9/2004 |
| WO | WO-2004/074286 | 9/2004 |
| WO | WO-2004/078756 | 9/2004 |
| WO | WO-2004/078923 | 9/2004 |
| WO | WO-2004/101565 | 11/2004 |
| WO | WO-2005/005426 | 1/2005 |
| WO | WO-2005/028475 | 3/2005 |
| WO | WO-2005/028624 | 3/2005 |
| WO | WO-2005/030128 | 4/2005 |
| WO | WO-2005/030709 | 4/2005 |
| WO | WO-2005/034869 | 4/2005 |
| WO | WO-2005/044181 | 5/2005 |
| WO | WO-2005/058891 | 6/2005 |
| WO | WO-2005/062795 | 7/2005 |
| WO | WO-2005/063746 | 7/2005 |
| WO | WO-2005/063747 | 7/2005 |
| WO | WO-2005/066347 | 7/2005 |
| WO | WO-2005/082367 | 9/2005 |
| WO | WO-2005/085244 | 9/2005 |
| WO | WO-2005/086904 | 9/2005 |
| WO | WO-2005/092896 | 10/2005 |
| WO | WO-2005/095400 | 10/2005 |
| WO | WO-2005/103050 | 10/2005 |
| WO | WO-2005/115363 | 12/2005 |
| WO | WO-2005/115374 | 12/2005 |
| WO | WO-2005/116035 | 12/2005 |
| WO | WO-2006/004984 | 1/2006 |
| WO | WO-2006/009755 | 1/2006 |
| WO | WO-2006/009797 | 1/2006 |
| WO | WO-2006/010637 | 2/2006 |
| WO | WO-2006/015123 | 2/2006 |
| WO | WO-2006/015124 | 2/2006 |
| WO | WO-2006/063167 | 6/2006 |
| WO | WO-2006/114180 | 11/2006 |
| WO | WO-2006/114520 | 11/2006 |
| WO | WO-2006/127587 | 11/2006 |
| WO | WO-2006/137376 | 12/2006 |
| WO | WO-2007/002325 | 1/2007 |
| WO | WO-2007/002433 | 1/2007 |
| WO | WO-2007/009799 | 1/2007 |
| WO | WO-2007/013896 | 2/2007 |
| WO | WO-2007/022380 | 2/2007 |
| WO | WO-2007/106236 | 9/2007 |
| WO | WO-2008/058341 | 5/2008 |
| WO | WO-2008-063888 | 5/2008 |
| WO | WO-2008/064255 | 5/2008 |
| WO | WO-2008/064265 | 5/2008 |
| WO | WO-2008/065417 | 6/2008 |
| WO | WO-2008/079903 | 7/2008 |
| WO | WO-2008/079906 | 7/2008 |
| WO | WO-2008/079909 | 7/2008 |

(56) References Cited

FOREIGN PATENT DOCUMENTS

| WO | WO-2008/076779 | 8/2008 |
|---|---|---|
| WO | WO-2008/064265 | 11/2008 |
| WO | WO-2008/138755 | 11/2008 |
| WO | WO-2009/012283 | 1/2009 |
| WO | WO-2009/012791 | 1/2009 |
| WO | WO-2009/111277 | 9/2009 |
| WO | WO-2009/111278 | 9/2009 |
| WO | WO-2009/111279 | 9/2009 |
| WO | WO-2009/111280 | 9/2009 |
| WO | WO-2009/115084 | 9/2009 |
| WO | WO-2009/143024 | 11/2009 |
| WO | WO-2010/020905 | 2/2010 |
| WO | WO-2010/059658 | 5/2010 |
| WO | WO-2010/104945 | 9/2010 |
| WO | WO-2010/104973 | 9/2010 |
| WO | WO-2010/114928 | 10/2010 |
| WO | WO-2010/129567 | 11/2010 |
| WO | WO-2010/129570 | 11/2010 |
| WO | WO-2011/015522 | 2/2011 |
| WO | WO 2011/060216 | 5/2011 |
| WO | WO-2011/063159 | 5/2011 |
| WO | WO-2011/079133 | 6/2011 |
| WO | WO-2011/133637 | 10/2011 |
| WO | WO-2012/032236 | 3/2012 |
| WO | WO-2012/037060 | 3/2012 |
| WO | WO-2012/138809 | 10/2012 |
| WO | WO-2012/158957 | 11/2012 |
| WO | WO-2012/161776 | 11/2012 |

OTHER PUBLICATIONS

Bundgaard, Design of Prodrugs, p. 1 (1985).
Burns et al., c-FMS Inhibitors: A Patent Review, Expert Opinion Ther. Patents (2011), 21(2), pp. 147-165.
Clohisy et al., Review of Cellular Mechanisms of Tumor Osteolysis, Clinical Orthopaedics and Related Research 373:104-114 (2000).
Damasio, Alzheimer's Disease and Related Dementias, Cecil Textbook of Medicine, 20$^{th}$ Ed. vol. 2, pp. 1992-1996 (1996).
Ertl et al., Fast calculation of molecular polar surface area as a sum of fragment-based contributions and its application to the prediction of drug transport properties, J Med Chem. (2000), 43:3714-3717.
Feng et al. Tyrosines 559 and 807 in the Cytoplasmic Tail of the Macrophage Colony Stimulating Factor Receptor Play Distinct Roles in Osteoclast Differentiation and Function, Endocrinology 143:4868-4874 (2002).
Flanagan & Lader, Update on the biologic effects of macrophage colony-stimulating factor; Curr Opin Hematol. (1998), 5:181-5.
Gura, Systems for Identifying New Drugs are often Faulty, Cancer Models, Science, vol. 278, No. 5340, pp. 1041-1042 (1997).
International Search Report and Written Opinion dated Jan. 14, 2011 in application PCT/US2010/055519.
Johnson et al., Relationships between drug activity of NCI preclinical in vitro and in vivo models and early clinical trials, British Journal of Cancer, 64(10): 1424-1431 (2001).
Kodama et al, Congenital Osteoclast Deficiency in Osteopetrotic (op/op) Mice is Cured by Injections of Macrophage colony-stimulating Factor; J. Exp. Med. (1991), 173: 269-72.
Lawicki et al., The pretreatment plasma level and disgnostic utility of M-CSF in benign breast tumor and breast cancer patients, Clinica Chimica Acta. 371: 112-116, (2006).
Layzer, Degenerative Diseases of the Nervous System, Cecil Textbook of Medicine, 20$^{th}$ Ed., vol. 2, pp. 2050-2057 (1996).
Le Meur et al., Macrophage accumulation at a site of renal inflammation is dependent on the M-CSF/c-fms pathway; J Leukocyte Biology, (2002), 72: 530-537.
Lee et al., FMS-like tyrosine kinase 3 inhibitors: a patent review, Expert Opinion Ther. Patents (2100) 21(4) pp. 483-503.
Libby, Inflammation in atherosclerosis, Nature, (2002), 420:868-874.
Motoyoshi, Biological activities and clinical application of M-CSF, Int J Hematol. (1998), 67:109-22.

Pearce et al. Failure modes in anticancer drug discovery and development, Cancer Drug Design and Discovery Edited by Stephen Neidle. Chapter 18, pp. 424-435 (2008).
Qiao, et al., Role of Macrophage Colony-Stimulating Factor in Atherosclerosis, Am. J. Path. (199)7;150:1687-1699.
Ridge et al, FMS mutations in myelodysplastic, leukemic, and normal subjects, Proc. Nat. Acad. Sci., (1990), 87:1377-1380.
Robinson et al., Stimulation of Bone Marrow Colony Growth in Vitro by Human Urine; Blood, (1969), 33:396-9.
Rodan, et al, Therapeutic Approaches to Bone Diseases, Science, (2000), 289:1508.
Shibata et al, Alveolar macrophage deficiency in osteopetrotic mice deficient in macrophage colony-stimulating factor is spontaneously corrected with age and associated with matrix metalloproteinase expression and emphysema, Blood 98:2845-2852 (2001).
Silverman, Prodrugs and Drug Delivery Systems, The Organic Chemistry of Drug Design and Drug Action, pp. 352-399 (1992).
Simone, Oncology: Introduction, Cecil Textbook of Medicine, 20$^{th}$ Ed. vol. 1, pp. 1004-1010 (1996).
Specchia et al. Constitutive expression of IL-1 β, M-CSF and c-fms during the myeloid blastic phase of chronic myelogenous leukaemia, Br J Haematol, (1992), 80(3):310-316.
Teitelbaum, Bone Resorption by Osteoclasts, Science, (2000), 289:1504.
Wyckoff et al., Direct visualization of macrophage-assisted tumor cell intravasation in mammary tumors. Cancer Research, 67(6): 2649-2656, (2007).
U.S. Appl. No. 61/054,445, filed May 19, 2008, Ibrahim et al.
U.S. Appl. No. 61/060,418, filed Jun. 10, 2008, Ibrahim et al.
Abou-Khalil, et al., "Delayed bone regeneration is linked to chronic inflammation in murine muscular dystrophy," J. Bone Miner. Res., (2013), DOI 10.1002/jbmr.2038.
Ahmad, K., "BRAF mutation common to 70% of thyroid carcinomas," *The Lancet, Oncology*, (2003), 4:330.
Alfthan, K., "Surface Plasmon Resonance Biosensors as a Tool in Antibody Engineering," *Biosensors & Bioelectronics*, (1998), 13:653-663.
Allegretti, et al., "Palladium-Catalysed Functionalisation at 4- and 6-Position of the 7-Azaindole System," *Synlett*, (2001), 5:609-612.
Al-Obeidi, et al., "Peptide and Peptidomimetic Libraries," *Mol Biotechnol.*, (1998), 9:205-223.
Arbiser, "Why targeted therapy hasn't worked in advanced cancer," *The Journal of Clinical Investigation*, (2007), 117(10):2762-2765.
Alvarez, et al., "Synthesis of 3-Aryl- and 3-Heteroaryl-7-Azaindoles," *Synthesis*, (1999), 4:615-620.
Amersdorfer, et al., "Phage Libraries for Generation of Anti-Botulinum scFv Antibodies," *Methods in Molecular Biology*, (2000), 145:219-240.
Amiel, et al., "Hirschsprung disease, associated syndromes and genetics: a review," *J Med Genet.*, (2008), 45:1-14.
Anderson, et al., "Cooperative Catalyst Effects in Palladium-Mediated Cyanation Reactions of Aryl Halides and Triflates," *J. Org. Chem.*, (1998), 63:8224-8228.
Antonini, et al., "Synthesis of 4-Amino-1-β-D-Ribofuranosyl-1H-pyrrolo[2,3-b]pyridine (1-Deazatubercidin) as a Potential Antitumor Agent," *J. Med. Chem.*, (1982), 25:1258-1261.
Arthan et al., "Leukemia inhibitory factor can mediate Ras/Raf/MEK/ERK-induced growth inhibitory signaling in medullary thyroid cancer cells," *Cancer Letters* (2010), 297:31-41.
Ashman, et al., "The biology of stem cell factor and its receptor C-kit," The International Journal of Biochemistry & Cell Biology, (1999), 31:1037-1051.
Baghestanian, et al., "A Case of Malignant Mastocytosis with Circulating Mast Cell Precursors: Biologic and Phenotypic Characterization of the Malignant Clone," *Leuk.*, (1996), 10:159-166.
Bagshaw et al., "Measurement of Ligand Binding to Proteins," Spectrophotometry and Spectrofluorimetry: A Practical Approach, (1987), 4:91-113.
Bagshawe, K., "Antibody-Directed Enzyme Prodrug Therapy: A Review," *Drug Dev. Res.*, (1995), 34:220-230.
Balak, et. al., "Novel D761Y and Common Secondary T790M Mutations in Epidermal Growth Factor Receptor 13 Mutant Lung

(56) References Cited

OTHER PUBLICATIONS

Adenocarcinomas with Acquired Resistance to Kinase Inhibitors," Clin Cancer Res., (2006), 12:6494-501.
Bancalari, et al., "Blood Markers of Early and Late Airway Responses to Allergen in Asthmatic Subjects. Relationship with Functional Findings," Allergy, (1997), 52:32-40.
Banker, G.S. et al, "Modern Pharmaceutics, 3ed.", *Marcel Dekker*, New York, (1996), p. 596.
Bartlett, et al., "CAVEAT: A Program to Facilitate the Structure-Derived Design of Biologically Active Molecules," *Royal Society of Chemistry*, (1989), 78:I80-I96.
Barton, et al., "The chemistry of pentavalent organobismuth reagents. Part X. Studies on the phenylation and oxidation of phenols," *Tetrahedron*, (1987), 43(2):323-332.
Bashford, et al., "Measurement of Ligand Binding to Proteins," Spectrophotometry and Spectrofluorimetry: A Practical Approach, (1987), 4:91-113.
Basta, et al., "High-dose Intravenous Immunoglobulin Exerts Its Beneficial Effect in Patients with Dermatomyositis by Blocking Endomysial Deposition of Activated Complement Fragments," *J Clin Invest.*, (1994), 94:1729-1735.
Basto, et al., "Mutation analysis of B-RAF gene in human gliomas," *Acta Neuropathol.*, (2005), 109:207-210.
Bayindir et al., "Cellular mesoblastic nephroma (infantile renal fibrosarcoma): institutional review of clinical, diagnostic imaging, and pathologic features of a distinctive neoplasm of infancy," *Pediatr. Radiol.*, (2009), 39(10):1066-74.
Bedi, et al., "BCR-ABL-Mediated Inhibition of Apoptosis With Delay of G2/M Transition After DNA Damage: A Mechanism of Resistance to Multiple Anticancer Agents," *Blood*, (1995), 86:1148-1158.
Bell, J.E., "Fluorescence: Solution Studies" *Spectroscopy in Biochemistry*, vol. I, (1981),(4):155-194.
Bellone, et al., "Growth Stimulation of Colorectal Carcinoma Cells Via the c-Kit Receptor is Inhibited by TGF-β1," *J. Cell Physiol.*, (1997), 172:1-11.
Berdel, et al., "Recombinant Human Stem Cell Factor Stimulates Growth of a Human Glioblastoma Cell Line Expressing c-kit Protooncogene," *Canc. Res.*, (1992), 52:3498-3502.
Bertolini, et al., "A New Rational Hypothesis for the Pharmacophore of the Active Metabolite of Leflunomide, a Potent Immunosuppressive Drug," *J. Med. Chem.*, (1997), 40:2011-2016.
Bjorntrop, "Neuroendocrine Pertuirbations as a Cause of Insulin Resistance," *Diabetes Metab. Res. Rev.*, (1999), 15:427-441.
Bloom, et al., "The Preparation of 2-Alkylaminobenzimidazoles," *J. Org. Chem.*, (1939), 14-19.
Blundell, et al., "Knowledge-Based Protein Modelling and Design," *Eur. J. Biochem.*, (1988), 172:513-520.
Bode, et al., "Mutations in the tyrosine kinase domain of the EGFR gene are rare in synovial sarcoma," *Modern Pathology*, (2006), 19:541-547.
Bohm, H-J., "On the Use of LUDI to Search the Fine Chemicals Directory for Ligands of Proteins of Known Three-Dimensional Structure," *J. Comp. Aided Molec. Design*, (1994), 8:623-632.
Bokenmeyer, et al., "Expression of Stem-Cell Factor and Its Receptor c-kit Protein in Normal Testicular Tissue and Malignant Germ-Cell Tumours," *J. Cancer Res. Clin. Oncol.*, (1996), 122:301-306.
Bolger, et al., "Computer Modeling of Combining Site Structure of Anti-Hapten Monoclonal Antibodies," *Methods Enz.*, (1991), 203:21-45.
Bongarzone, et al., "High Frequency of Activation of Tyrosine Kinase Oncogenes in Human Papillary Thyroid Carcinoma," *Oncogene*, (1989), 4(12):1457-1462.
Bothwell, M., "Keeping Track of Neurotrophin Receptors," *Cell*, (1991), 65:915-918.
Bouzakri, et al., "MAP4K4 Gene silencing in Human Skeletal Muscle Prevents Tumor Necrosis Factor-a-induced Insulin Resistance," *J. Biol. Chem.*, (2007), 282:7783-7789.
Bouzas-Rodriguez et al., Neurotrophin-3 production promotes human neuroblastoma cell survival by inhibiting TrkC-induced apoptosis, *J. Clin. Invest.*, 120(3):850-8 (2010).
Bowtell, D., "Options Available From Start to Finish for Obtaining Expression Data by Microarray," *Nature Genetics Supp.*, (1999), 21:25-32.
Breindl, "No Melanocyte is an Island: In Melanoma, Interfeon, Roles Need Rethinking," *BioWorld Today*, (2011), 22(17): 1;5.
Brenner, et al., "Encoded Combinatorial Chemistry," *Proc. Natl. Acad. Sci. USA*, (1992), 89:5381-5383.
Broudy, V., "Stem Cell Factor and Hematopoiesis," *Blood*, (1997), 90:1345-1364.
Brunger, A. T., "Free R Value: a Novel Statistical Quantity for Assessing the Accuracy of Crystal Structures," *Nature*, (1992), 355:472-475.
Buchschacher, et al., "Human Immunodeficiency Virus Vectors for Inducible Expression of Foreign Genes," *J. Virol.*, (1992), 66:2731-2739.
Calabresi, et al., "Section IX: Chemotherapy of neoplastic diseases," *Goodman & Gilman's the Pharmacological Basis of Therapeutics, Tenth Edition, McGraw-Hill Medical Publishing Division*, (2001), pp. 1381, 1383-1385 and 1388.
Capon, et al., "Designing CD4 Immunoadhesins for AIDS Therapy," *Nature*, (1989), 337:525-531.
Carell, et al., "New Promise in Combinatorial Chemistry: Synthesis, Characterization, and Screening of Small-Molecule Libraries in Solution," *Chem. Biol.*, (1995), 2:171-183.
Carpino, et al., "p62dok: A Constitutively Tyrosine-Phosphorylated, GAP-Associated Protein in Chronic Myelogenous Leukemia Progenitor Cells," *Cell*, (1997), 88:197-204.
Castells, et al., "The Presence of Membrane-Bound Stem Cell Factor on Highly Immature Nonmetachromatic Mast Cells in the Peripheral Blood of a Patient with Aggressive Systemic Mastocytosis," *J. Aller. Clin. Immunol.*, (1996), 98:831-840.
Castellone, et al., "A novel de novo germ-line V292M mutation in the extracellular region of RET in a patient with phaeochromocytoma and medullary thyroid carcinoma: functional characterization," *Clinical Endocrinology*, (2010), 73:529-534.
Chabala, J., "Solid-Phase Combinatorial Chemistry and Novel Tagging Methods for Identifying Leads," *Curr Opin Biotechnol.*, (1995), 6:632-639.
Chappell et al., "Ras/Raf/MEK/ERK and PI3K/PTEN/Akt/mTOR Inhibitors: Rationale and Importance to Inhibiting These Pathways in Human Health," *Oncotarget*, (2011), 2(3):135-164.
Chayer, et al., "Synthesis of Carboranylpyrroles," *Tetrahedron Lett.*, (2001), 42(44):7759-7761.
Checovich, et al., "Fluorescence Polarization—a New Tool for Cell and Molecular Biology," *Nature*, (1995), 375:254-256.
Chou, et al., "Chemotherapeutic Synergism, Potentiation and Antagonism," *Encyclopedia of Human Biology, Academic Press*, (1991), 2:371-379.
Chou, et al., "Computerized Quantitation of Synergism and Antagonism of Taxol, Topotecan, and Cisplatin Against Human Teratocarcinoma Cell Growth: a Rational Approach to Clinical Protocol Design," *J. Natl. Cancer Inst.*, (1994), 86:1517-1524.
Chou, et al., "Quantitative analysis of Dose-Effect Relationships: The Combined Effects of Multiple Drugs or Enzyme Inhibitors," Adv. Enzyme Regul., (1984), 22:27-55.
Chou, et al., "Synergism and Antagonism in Chemotherapy," *Academic Press*, (1991), Chapter 2:61-102.
Clark, et al., "PROLIGAND: An Approach to De Novo Molecular Design. 1. Application to the Design of Organic Molecules," J. Comp. Aided Molec. Design, (1995), 9:13-32.
Coe, et al., "Solution-Phase Combinatorial Chemistry," *Mol Divers.*, (1999), 4:31-38.
Coelho, et al., "Studies of RET gene expression and acetylcholinesterase activity in a series of sporadic Hirschsprung's disease," *Pediatr Surg Int*, (2008), 24:1017-1021.
Cohen, et al., "Expression of Stem Cell Factor and C-Kit in Human Neuroblastoma," *Blood*, (1994), 84:3465-3472.
Collins, et al., "A small interfereing RNA screen for modulators of tumor cell motility identifies MAP4K4 as a prommigratory kinase," *Proc. Natl. Acad. Sci. USA*, (2006), 103:3775-3780.

(56) References Cited

OTHER PUBLICATIONS

Collioud, et al., "Oriented and Covalent Immobilization of Target Molecules to Solid Supports: Synthesis and Application of a Light-Activatable and Thiol-Reactive Cross-Linking Reagent," *Bioconjugate Chem.*, (1993), 4:528-536.
Colman, P.M., "Structure-Based Drug Design," *Current Opinion in Struc. Biol.*, (1994), 4:868-874.
Columbo, et al., "The Human Recombinant c-kit Receptor Ligand, rhSCF, Induces Mediator Release From Human Cutaneous Mast Cells and Enhances IgE-Dependent Mediator Release From Both Skin Mast Cells and Peripheral Blood Basophils," *J. Immunol.*, (1992), 149:599-608.
Coniglio, et al., "Microglial stimulation of glioblastoma invasion involves epidermal growth factor receptor (EGFR) and colony stimulating factor 1 receptor (CSF-1R) signaling," *Mol. Med.*, (2012), 18:519-527.
Costa, et al., "The Cells of the Allergic Response," *JAMA*, (1997), 278:1815-1822.
Coste, et al., "Coupling N-Methylated Amino Acids Using PyBroP1 and PyCloP Halogenophosphonium Salts: Mechanism and Fields of Application," *Journal of Organic Chemistry*, (1994), 59:2437-2446.
Coulie, et al., "Recombinant Human Neurotropic Factors Accelerate Colonic Transit and Relieve Constipation in Humans," Gastroenterology, (2000), 119:41-50.
Creighton, T., "An Empirical Approach to Protein Conformation Stability and Flexibility," *Biopolymers*, (1983), 22(1):49-58.
Crouch, et al., "The use of ATP bioluminescence as a measure of cell proliferation and cytotoxicity," Journal of Immunological Methods, (1993), 160:81-88.
Crump, M., "Inhibition of Raf Kinase in the Treatment of Acute Myeloid Leukemia," *Curr. Pharm. Design*, (2002), 8(25):2243-2248.
Curtin, et al., "Discovery and Evaluation of a Series of 3-Acylindole Imidazopyridine Platelet-Activating Factor Antagonists," J. Med. Chem., (1998), 41:74-95.
Curtin, et al., "Somatic activation of KIT in distinct subtypes of melanoma," *J. of Clinical Oncology*, (2006), 24(26): 4340-4345.
Cwirla, et al., "Peptides on Phage: A Vast Library of Peptides for Identifying Ligands," *Biochemistry*, (1990), 87:6378-6382.
Dai, et al., "Targeted disruption of the mouse colony-stimulating factor 1 receptor gene results in osteopetrosis, mononuclear phagocyte deficiency, increased primitive progenitor cell frequencies, and reproductive defects," *Blood*, (2002), 99:111-120.
Dandliker, et al., "Equilibrium and Kinetic Inhibition Assays Based Upon Fluorescence Polarization," *Methods in Enzymology*, (1981), 74:3-28.
Das-Gupta et al., "Acridine Derivatives, Part VI," *J. Indian Chem. Society*, (1941), 18:25-28.
Dastych, et al., "Stem Cell Factor Induces Mast Cell Adhesion to Fibronectin," *J. Immunol.*, (1994), 152:213-219.
Davies, et al., "Mutations of the BRAF gene in human cancer," *Nature*, (2002), 417:949-954.
Demetri, G.D., "Targeting c-kit mutations in solid tumors: Scientific rationale and novel therapeutic options," *Seminars in Oncology*, (2001), 28(5), Supp. 17:19-26.
Denardo, et al., "Leukocyte complexity predicts breast cancer survival and functionally regulates response to chemotherapy," *Cancer Discovery*, (2011), 54-67.
Dewar, et al., "Inhibition of c-fms by Imatinib Expanding the Spectrum of Treatment," *Cell Cycle*, (2005), 4(7):851-853.
Dobeli, et al., "Recombinant Fusion Proteins for the Industrial Production of Disulfide Bridge containing Peptides: Purification, Oxidation without Cancatamer Formation, and Selective Cleavage," *Protein Expr. Purif.*, (1998), 12:404-414.
Dolle, et al., "Comprehensive Survey of Combinatorial Library Synthesis: 1998," *J. Comb. Chem.*, (1999), 1:235-282.
Dong, et al., "BRAF Oncogenic Mutations Correlate with Progression rather than Initiation of Human Melanoma," *Cancer Research*, (2003), 63:3883-3885.

Donis-Keller, et al., "Mutations in the RET Proto-Oncogene are Associated with MEN 2A and FMTC," *Hum Mol Genet.*, (1993), 2(7):851-856.
Dorwald, "Side Reactions in Organic Synthesis: A Guide to Successful Synthesis Design," *Wiley-VCH*, (2005), Preface p. IX.
Douma, et al., "Suppression of anoikis and induction of metastasis by the neurotropic receptor TrkB," *Nature*, (2004), 430:1034-1039.
Doyle, eta al., "Alkyl Nitrite-metal halide Deamination Reactions. 6. Direct Synthesis of Arenediazonium Tetrafluoroborate Salts from Aromatic Amines, tert-Butyl Nitrite, and Boron Trifluoride Etherate in Anhydrous Media," *J. Org. Chem.*, (1979), 44:1572.
Dube, et al., "Reductive N-Alkylation of Amides, Carbamates and Ureas," *Tetrahedron Lett.*, (1999), 40:2295-2298.
Dumas, "Protein kinase inhibitors: emerging pharmacophores 1997-2000," *Exp. Opin. Ther. Patents*, (2001), 11 (3): 405-429.
Durbec, et al., "GDNF Signalling Through the Ret Receptor Tyrosine Kinase," *Nature*, (1996), 381:789-793.
Dutcher et al., "Studies of the C11H8N2OS Degradation Product of Gliotoxin," *J. Am. Chem. Soc.*, (1951), 73:4139-4141.
Dyson, et al., "The Human Papilloma Virus 13 16 E7 Oncoprotein is Able to Bind to the Retinoblastoma Gene Product," Science, (1989), 243:934-937.
Eklund, et al., "Treatment of rheumatoid arthritis with imatinib mesylate: clinical improvements in three refractory cases," *Annals of Medicine*, (2003), 35:362-367.
Eliseev, et al., "Dynamic Combinatorial Chemistry: Evolutionary Formation and Screening of Molecular Libraries," *Current Topics in Microbiology & Immunology*, (1999), 243:159-172.
Engelman et al., "Effective use of PI3K and MEK inhibitors to treat mutant Kras G12D and PIK3CA H1047R murine lung cancers," *Nature Medicine*, (2008), 14(12):1351-1356.
Enjalbal, et al., "Mass Spectrometry in Combinatorial Chemistry," *Mass Spectrometry Reviews*, (2000), 19:139-161.
Escribano, et al., "Expression of the c-kit (CD117) Molecule in Normal and Malignant Hematopoiesis," *Leuk. Lymph.*, (1998), 30:459-466.
Felder, E.R., "The Challenge of Preparing and Testing Combinatorial Compound Libraries in the Fast Lane, at the Front End of Drug Development," Chimia., (1994), 48:531-541.
Feng, et al., "Stable in Vivo Gene Transduction Via a Novel Adenoviral/Retroviral Chimeric Vector," *Nature Biotechnology*, (1997), 15:866-870.
Finotto, et al., "Glucocorticoids Disease Tissue Mast Cell Number by Reducing the Production of the c-kit Ligand, Stem Cell Factor, by Resident Cells," J. Clin. Invest., (1997), 99:1721-1728.
Fischer et al., "Targeting receptor tyrosine kinase signalling in small cell lung cancer (SCLC): What have we learned so far?," *Cancer Treatment Reviews*, (2007), 33:391-406.
Fivash, et al., "BIAcore for macromolecular interaction," *Current Opinion in Biotechnology*, (1998), 9:97-101.
Franz, et al., "Sulfuranes. X. A Reagent for the Facile Cleavage of Secondary Amides," *JACS*, (1973), 95(6):2017-2019.
Friesen et al., "Hydroxypropyl Methylcellulose Acetate Succinate-Based Spray-Dried Dispersions: An Overview," *Molecular Pharmaceutics*, (2008), 5(6):1003-1019.
Furitsu, et al., "Identification of Mutations in the Coding Sequence of the Proto-oncogene c-kit in a Human Mast Cell Leukemia Cell Line Causing Ligand-independent Activation of the c-kit Product," J. Clin. Invest., (1993), 92:1736-1744.
Furuta, et al., "Stem Cell Factor Influences Mast Cell Mediator Release in Response to Eosinophil-Derived Granule Major Basic Protein," *Blood*, (1998), 92:1055-1061.
Gallego et al., "Increased opioid dependence in a mouse model of panic disorder," *Front Behav. Neurosci.*, (2010), 3:60.
Gallop, et al., "Applications of Combinatorial Technologies to Drug Discovery. 1. Background and Peptide Combinatorial Libraries," J. Med. Chem., (1994), 37:1233-1251.
Galofre, et al., "Evaluation and Treatment of Thyroid Nodules: A Clinical Guide," *Mt Sinai J Med.*, (2008), 75:299-311.
Garzya et al., "Indium(III)-catalysed aryl sulfonylation reactions," *Tetrahedron Letters*, (2004), 45:1499-1501.
Gassman, et al., "Specific Ortho Substitution of Aromatic Heterocyclic Amines," *J Am Chem Society*, (1973), 95(13):4453-4455.

(56) References Cited

OTHER PUBLICATIONS

Ghebre-Sellassie, Isaac; Martin, Charles., "Pharmaceuticast Extrusion Technology," *Marcer, Dekker, Inc., New York. Basel. CRC Press*, (2003), p. 238.
Gimbel, et al., "Braf mutations are associated with increased mortality in colorectal cancer," *Journal of the American College of Surgeons*, (2004), 199:S91-S92.
Girgis, et.al., "The Synthesis of 5-Azaindoles by Substitution-Rearrangement of 7-Azaindoles upon Treatment with Certain Primary Amines," *J. Heterocyclic. Chem.*, (1989), 26:317-325.
Golkar, et al., "Mastocytosis," *Lancet*, (1997), 349:1379-1385.
Golub, et al., "Molecular Classifcation of Cancer: Class Discovery and Class Prediction by Gene Expression Monitoring," *Science*, (1999), 286:531-537.
Goodford, P.J., "A Computational Procedure for Determining Energetically Favorable Binding Sites on Biologically Important Macromolecules," *J. Med. Chem.*, (1985), 28:849-857.
Goodsell, et al., "Automated Docking of Substrates to Proteins by Simulated Annealing," *Proteins: Structure, Function, and Genetics*, (1990), 8:195-202.
Gordon et al., "Detection of Peroxides and Their Removal," *The Chemist's Companion: A Handbook of Practical Data, Techniques, and References*, (1972), p. 437.
Gordon, et al., "Applications of Combinatorial Technologies to Drug Discovery. 2. Combinatorial Organic Synthesis, Library Screening Strategies, and Future Directions," J. Med. Chem., (1994), 37:1385-1401.
Gram, H., "Phage Display in Proteolysis and Signal Transduction," *Combinatorial Chemistry & High Throughput Screening*, (1999), 2:19-28.
Gravert, et al., "Synthesis on Soluble Polymers: New Reactions and the Construction of Small Molecules," *Curr Opin Chem Biol.*, (1997), 1:107-113.
Greer, J., "Model Structure for the Inflammatory Protein C5a," *Science*, (1985), 228:1055-1060.
Grieco, et al., "PTC is a Novel Rearranged Form of the ret Proto-Oncogene and is Frequently Detected in Vivo in Human Thyroid Papillary Carcinomas," *Cell*, (1990), 60(4):557-563.
Guida, W., "Software for Structure-Based Drug Design," *Current Opinion in Struc. Biol.*, (1994), 4:777-781.
Hafner, et al., "Isothermal Amplification and Multimerization of DNA by Bst DNA Polymerase," *Biotechniques*, (2001), 30(4):852-867.
Hallek, et al., "Interaction of the Receptor Tyrosine Kinase p145c-kit with the p210bcr/abl Kinase in Myeloid Cells," *Brit. J Haem.*, (1996), 94:5-16.
Halvorson, et al., "A Blocking Antibody to Nerve Growth Factor Attenuates Skeletal Pain Induced by Prostate Tumor Cells Growing in Bone," *Cancer Res.*, (2005), 65:9426-9435.
Hamel, et al., "The Road Less Traveled: c-kit and Stem Cell Factor," *J. Neuro-Onc.*, (1997), 35:327-333.
Hancock et al., "Characteristics and Significance of the Amorphous State in Pharmaceutical Systems," *Journal of Pharmaceutical Sciences*, (1997), 86(1):1-12.
Hands, et al., "A convenient Method for the Preparation of 5-, 6- and 7-Azaindoles and Their Derivatives," *Synthesis*, (1996), 877-882.
Hanselman, et al., "A cDNA-Dependant Scintillation Proximity Assay for Quantifying Apolipoprotein A1," *J. Lipid Res.*, (1997), 38:2365-2373.
Hasegawa et al., "Visualizing Mechanosensory Endings of TrkC-Expressing Neurons in HS3ST-2-hPLAP Mice," *J Comp. Neurol.*, (2008), 511(4):543-556.
Hassan, et al., "Expression of Protooncogene c-kit and Its Ligand Stem Cell Factor (SCF) in Gastric Carcinoma Cell Lines," *Digest. Dis. Science*, (1998), 43:8-14.
Hassan, et al., "Stem Cell Factor as a Survival and Growth Factor in Human Normal and Malignant Hematopoiesis," *Acta. Hem.*, (1996), 95:257-262.
Hayashi, et al., "Dichloro[1,1 19-bis(diphenylophosphino)ferrocene]palladium-(II), an Effective Catalyst for Cross-Coupling of Secondary and Primary Alkyl Grignard and Alkylzinc Reagents with Organic Halides," *J. Am. Chem. Soc.*, (1984), 106:158-163.
Haydock et al., "Analogues of clofibrate and clobuzarit containing fluorine in the side chains," *Eur. J. Med. Chem.*, (1984), 19(3):205-214.
He et al. "c-Fms Signaling Mediates Neurofibromatosis Type-1 Osteoclast Gain-in-Functions," *PLoS One*, (2012), 7(11): 1-9.
He, et al., "Gamma-secretase activating protein, a therapeutic target for Alzheimer's disease," *Nature*, (2010), 467(7311):95-98.
Heacock, et al., "Orientation and Relative Reaction rate Factors in aromatic Substitution by the Benzensulfonimido Radical," *J. Am. Chem. Soc.*, (1960), 82:3460-3463.
Heim, et al., "Engineering Green Fluorescent Protein for Improved Brightness, Longer Wavelengths and Fluorescence Resonance Energy Transfer," *Curr. Biol.*, (1996), 6:178-182.
Heinrich, et al., "PDGFRA Activating Mutations in Gastrointestinal Stromal Tumors," *Science*, (2003), 299:708-710.
Heinrich, M. C. et al., "Inhibition of KIT Tyrosine Kinase Activity: A Novel Molecular Approach to the Treatment of KIT-Positive Malignancies," J. Clin. Oncol., (2002), 20(6):1692-1703.
Hentschel et al., "BCR-ABL-and Ras-independent activiation of Raf as a novel mechanism of Imatinib resistance in CML," (2012), http://www.ncbi.nlm.nih.gov/pubmed/2163917.
Herbst, et al., "Differential Effects of W Mutations on p145c-kit Tyrosine Kinase Activity and Substrate Interaction," *J. Biol. Chem.*, (1992), 267:13210-13216.
Hibi, et al., "Coexpression of the stem cell factor and the c-kit genes in small-cell lung cancer," *Oncogene*, (1991), 6:2291-2296.
Hirota, et al., "Gain-of-function Mutations of c-kit in Human Gastrointestinal Stromal Tumors," *Science*, (1998), 279:577-580.
Hoffmann, "m-Trifluoromethylbenzenesulfonyl Chloride," *Organic Syntheses*, (1981), 60:121-126.
Hogaboam, et al., "Novel Role of Transmembrane SCF for Mast Cell Activation and Eotaxin Production in Mast Cell-Fibroblast Interactions," *J. Immunol.*, (1998), 160:6166-6171.
Holmes, et al., "Long-term effects of Aβ42 immunisation in Alzheimer's disease: follow-up of a randomised, placebo-controlled phase I trail," *Lancet* (2008) 372:216-233.
Hood, et al., "Tumor Regression by Targeted Gene Delivery to the Neovasculature," *Science*, (2002), 296: 2404-2407.
Houghten, et al., "Generation and Use of Synthetic Peptide Combinatorial Libraries for Basic Research and Drug Discovery," *Nature*, (1991), 354:84-86.
Houghten, R., "Parallel Array and Mixture-Based Synthetic Combinatorial Chemistry: Tools for the Next Millennium," *Annu Rev Pharmacol Toxicol.*, (2000), 40:273-282.
Houghten, R., "Peptide Libraries: Criteria and Trends," *Trends Genet.*, (1993), 9:235-239.
Hudson, et al., "A Simple Method for the Determination of Serum Acid Phosphatase," *J. Urology*, (1947), 58:89-92.
Hughes-Jones, et al., "Synthesis of Rh Fv Phage-Antibodies Using VH and VL Germline Genes," *British Journal of Haematology*, (1999), 105:811-816.
Ibrahim et al., "Pyrrolo[2,3-b]pyridine derivatives as protein kinase inhibitors and their preparation, pharmaceutical compositions and use in the treatment of diseases," *Caplus*, (2007), 11300.
Iemura, et al., "The c-kit Ligand, Stem Cell Factor, Promotes Mast Cell Survival by Suppressing Apoptosis," *Amer. J. Pathol.*, (1994), 144:321-328.
Inoue, et al., "Coexpression of the c-kit Receptor and the Stem Cell Factor in Gynecological Tumors," *Cancer Res.*, (1994), 54:3049-3053.
Isbel, et al., "Local macrophage proliferation correlates with increased renal M-CSF expression in human glomerulonephritis," *Nephrol Dial Transplant*, (2001), 16:1638-1647.
Ishizaka, et al., "Human ret Proto-Oncogene Mapped to Chromsome 10q11.2," *Oncogene*, (1989), 4(12):1519-1521.
Isozaki, et al., "Deficiency of c-kit cells in patients with a myopathic form of chronic idiopathic intestinal pseudo-obstruction," *Amer. J. of Gast.*, (1997), 9:332-334.
Ivanisevic et al., "Uses of X-Ray Powder Diffraction in the Pharmaceutical Industry," *Pharm Sci Encyc:DDDM*, (2010), pp. 1-42.

(56) References Cited

OTHER PUBLICATIONS

Iwane, et al., "Myosin Subfragment-1 is Fully Equipped with Factors Essential for Motor Function," *Biochem. and Biophys. Res. Comm.*, (1997), 230:76-80.
Izquierdo, et al., "Differential Expression of the c-kit Proto-Oncogene in Germ Cel Tumours," *J. Pathol.*, (1995), 177:253-258.
Jaiswal et al., Combined Targeting of BRAF and CRAF or BRAF and PI3K Effector Pathways is Requred for Efficacy in NRAS Mutant Tumors, *PLoS One*, (2009), 4(5):e5717.
Jarugula, et al., "Nonlinear Pharmacokinetics of 5-Fluorouracil in Rats," *J Pharm Sci.*, (1997), 86(6):756-757.
Jensen, et al., "Pharmacological targeting of the KIT growth factor receptor: a therapeutic consideration for mast cell disorders," *Brit J Pharmacology*, (2008), 154:1572-1582.
Jing, et al., "GDNF-Induced Activation of the Ret Protein Tyrosine Kinase is Mediated by GDNFR-a, a Novel Receptor for GDNF," *Cell*, (1996), 85:1113-1124.
Johann, et al., "GLVR1, a Receptor for gibbon Ape Leukemia Virus, Is Homologous to a Phosphate Permease of *Neurospora crassa* and is Expressed at High Levels in the Brain and Thymus," J. Virol., (1992), 66:1635-1640.
Johnston, M., "Gene Chips: Array of hope for understanding gene regulation," *Curr. Biol.*, (1998), 8:R171-R174.
Jones, et al., "Antiestrogens. 2. Structure-Activity Studies in a Series of 3-Aroyl-2-arylbenzo[b]thiophene Derivatives Leading to [6-Hydroxy-2-(4-hydroxyphenyl)benzo(b)thien-3-yl](4-[2-(1-piperidinyl)ethoxy]-phenyl]methanone Hydrochloride (LY156758), a Remarkably Effective Estrogen Antagonist with Only Minimal Intrinsic Estrogenicity," *J. Med. Chem.*, (1984), 27(8):1057-1066.
Jones, R., "Biology and Treatment of Chronic Myeloid Leukemia," *Curr. Opin. Onc.*, (1997), 9:3-7.
Jones, T., "Interactive Computer Graphics: FRODO," *Methods in Enzymology*, (1985), 115:157-171.
Jongh et al. "The Role of Interleukin-6 in Nociception and Pain," *Anesth Analg*, (2003), (96):1096-103.
Jose, et al., "Blockade or Macrophage colony-Stimulating Factor Reduces Macrophage Proliferation and Accumulation in Renal Allograft Rejection," Am J Transplant, (2003), 3(3):294-300.
Joseph-McCarthy, D., "Computational Approaches to Structure-Based Ligand Design," *Pharmacology & Therapeutics*, (1999), 84:179-191.
Joule et al., "Indole and its Derivatives," *Science of Synthesis*, (2001), 10:618-652.
Kahl, et al., "A Multiple-Approach Scintillation Proximity Assay to Measure the Association Between Ras and Raf," *Anal. Biochem.*, (1996), 243:282-283.
Kassel, et al., "Local increase in the number of mast cells and expression of nerve growth factor in the bronchus of asthmatic patients after repeated inhalation of allergen at low-dose," *Clin. Exp. Allergy*, (2001), 31:1432-1440.
Katritzky, et al., "Regiospecific C-Acylation of Pyrroles and Indoles Using N-Acylbenzotriazoles," *J. Org. Chem.*, (2003), 68:5720-5723.
Kay, et al., "Eosinophils and Eosinophil-Associated Cytokines in Allergic Inflammation," *Int. Arch. Aller. Immunol.*, (1997), 113:196-199.
Kern, et al., "Direct Hybridization of Large-Insert Genomic Clones on High-Density Gridded cDNA Filter Arrays," *Biotechniques*, (1997), 23:120-124.
Khazak et al., "Selective Raf Inhibition in Cancer Therapy," (2012), http://www.ncbu.nlm.nih.gov/pms/articles/PMC2720036.
Kim, et al., "A Merger of Rational Drug Design and Combinatorial Chemistry: Development and Application of Peptide Secondary Structure Mimetics," *Combinatorial Chemistry & High Throughput Screening*, (2000), 3:167-183.
Kim, et al., Database CAS on STN Preparation of 2-anilino-4-indolyl pyrimidines as tyrosine kinase inhibitors, abstract, 2002) (Columbus, OH, USA) No. 138:55974.
Kinashi, et al., "Steel Factor and c-kit Cell-Matrix Adhesion," *Blood*, (1994), 83:1033-1038.

Kirkpatrick, et al., "Structure-Based Drug Design: Combinatorial Chemistry and Molecular Modeling," *Combinatorial Chemistry & High Throughput Screening*, (1999), 2:211-221.
Kitamura, et al., "Synthesis of Quinolines and 2H-Dihydropyrroles by Nucleophilic Substitution at the Nitrogen Atom of Oxime Derivatives," *Synthesis*, (2003), 15:2415-2426.
Kline, et al., "Studies by 1H Nuclear Magnetic Resonance and Distance Geometry of the Solution Conformation of the x-Amylase Inhibitor Tendamistat," J. Mol. Biol., (1986), 189:377-382.
Knighton, et al., "Structural Basis of the Intrasteric Regulation of Myosin Light Chain Kinases," *Science*, (1992), 258:130-135.
Kolaskar, et al., "A Semi-Empirical Method for Prediction of Antigenic Determinants on Protein Antigens," *FEBS Lett.*, (1990), 276:172-174.
Komoyira, et al., "Design, synthesis and biological activity of amidinobicyclic compounds (derivatives of DX-9065a) as a factor Xa inhibitors: SAR study of S1 and aryl binding sites," *Bioorg. Med. Chem.*, (2004), 12: 2099-2114.
Kondoh, et al., "An in vivo model for receptor tyrosine kinase autocrine/paracrine activation: auto-stimulated Kit receptor acts as a tumor promoting factor in papillomavirus-induced tumorigenesis," *Oncogene*, (1995), 10:341-347.
Kondoh, et al., "Establishment and Further Characterization of a Line of Transgenic Mice Showing Testicular Tumorigenesis at 100% Incidence," *J. Urol.*, (1994), 152:2151-2154.
Kondoh, et al., "Very High Incidence of Germ Cell tumorigenesis (Seminomagenesis) in Human Papillomavirus Type 16 Transgenic Mice," *J. Virol.*, (1991), 65:3335-3339.
Konishi, et al., "Overexpression of leucocyte common antigen (LAR) P-subunit in thyroid carcinomas," *Brit J Cancer*, (2003), 88:1223-1228.
Konno et al., "Influence of Different Polymers on the Crystallization Tendency of Molecularly Dispersed Amorphous Felodipine," *Journal of Pharmaceutical Sciences*, (2006), 95(12):2692-2705.
Kroll, et al., "A Malfunctional Prokaryotic Protein Expression System: Overproduction, Affinity Purification, and Selective Detection," *DNA Cell. Biol.*, (1993), 12:441-453.
Kubo et al., "Resequencing Analysis of the Human Tyrosine Kinase Gene Family in Pancreatic Cancer," *Pancreas*, (2009), 38(7):e200-e206.
Kubo et al., "Resequencing and copy number analysis of the human tyrosine kinase gene family in poorly differentiated gastric cancer," *Carcinogenesis*, (2009), 30(11 ): 1857-1864.
Kundu, et al., "Combinatorial Chemistry: Polymer Supported Synthesis of Peptide and Non-Peptide Libraries," *Progress in Drug Research*, (1999), 53:89-156.
Kunisada, et al., "Murine Cutaneous Mastocytosis and Epidermal Melanocytosis Induced by Keratinocyte Expression of Transgenic Stem Cell Factor," *J. Exp. Med.*, (1998), 187:1565-1573.
Kunkel, T., "Rapid and Efficient Site-Specific Mutagenesis Without Phenotypic Selection," *Methods in Enzymology*, (1987), 154:367-382.
Kunkel, T., "Rapid and Efficient Site-Specific Mutagenesis Without Phenotypic Selection" *Proc. Natl. Acad. Sci. USA*, (1985), 82: 488-492.
Kunnimalaiyaan, et al., "The Raf-1 pathway: a molecular target for treatment of select neuroendocrine tumors?" *Anticancer Drugs*, (2006), 17(2):139-42.
Kuntz, et al., "A Geometric Approach to Macromolecule-Ligand Interactions," *J. Mol. Biol.*, (1982), 161:269-288.
Kuntz, et al., "Structure-Based Molecular Design," *Acc. Chem. Res.*, (1994), 27:117-123.
Lahm, et al., "Interleukin 4 Down-Regulates Expression of c-kit and Autocrine Stem Cell Factor in Human Colorectal Carcinoma Cells," *Cell Growth & Differ.*, (1995), 6:1111-1118.
Lala, et al., "Role of nitric oxide in tumor progression: Lessons from experimental tumors," *Cancer and Metastasis Reviews*, (1998), 17:91-106.
Lam, et al., "A new type of synthetic peptide library for identifying ligand-binding activity," *Nature*, (1991), 354: 82-84.
Lambros et al., "Genomic profile of a secretory breast cancer with an ETV6-NTRK3 duplication," *J. Clin. Pathol.*, (2009), 62(7):604-12.

(56) References Cited

OTHER PUBLICATIONS

Langham et al., "Metalation and Halogen-Metal Interconversion Reactions of Some Halogenated Phenyl Ethers," *J. of the Am. Chem. Society*, (1941), 63:545-549.
Lebl, et al., "One-Bead-One-Structure Combinatorial Libraries," *Biopolymers*, (1995), 37:177-198.
Lee, et al., "HLA-DR-Triggered Inhibition of Hemopoiesis Involves Fas/Fas Ligand Interactions and is Prevented by c-kit Ligand," *J. Immunol.*, (1997), 159:3211-3219.
Lee, et al., "Mast Cells: A Cellular Link Between Autoantibodies and Inflammatory Arthritis," *Science*, (2002), 297:1689-1692.
Leuner, et al., "Improving drug solubility for oral delivery using solid dispersions," *European Journal of Pharma. and Biopharma.*, (2000), 50(1):47-60.
Levin, et al., "Neoplasms of the Central Nervous System," *Cancer Principles & Practice of Oncology*, (1997), 2:2022-2082.
Levis et al., "A FLT3 tyrosine kinase inhibitor is selectively cytotoxic to acute myeloid leukemia blasts harboring FL T3 internal tandem duplication mutations," *Blood*, (2001), 98:885-887.
Li, et al., "Abrogation of c-kit/Steel Factor-Dependent Tumorigenesis by Kinase Defective Mutants of the c-kit Receptor: c-kit Kinase Defective Mutants as Candidate Tools for Cancer Gene Therapy," *Canc. Res.*, (1996), 56:4343-4346.
Liparoto, et al., "Biosensor Analysis of the Interleukin-2 Receptor Complex," *Journal of Molecular Recognition*, (1999), 12:316-321.
Lipinski, et al., "Experimental and Computational Approaches to Estimate Solubility and Permeability in Drug Discovery and Development Settings," *Advanced Drug Delivery Reviews*, (1997), 23:3-25.
Lipschultz, et al., "Experimental design for analysis of complex kinetics using surface plasmon resonance," *Methods*, (2000), 20(3):310-318.
Liu, et al., "Sorafenib Blocks the RAF/MEK/ERK Pathway, Inhibits Tumor Angiogenesis, and Induces Tumor Cell Apoptosis in Hepatocellular Carcinoma Model PLC/PRF/5," *Cancer Res.*, (2006), 66:11852-11858.
Liu, et al., "CD68 Expression is Markedly Different in Crohn's Disease and the Colitis Associated with Chronic Granulomatous Disease," *Inflamm. Bowel Dis.*, (2009), 15(8): 1213-1217.
London, et al., "Expression of Stem Cell Factor Receptor (c-kit) by the Malignant Mast Cells from Spontaneous Canine Mast Cell Tumors," *J. Compar. Pathol.*, (1996), 115:399-414.
Longley, et al., "Altered Metabolism of Mast-cell Growth Factor (c-kit Ligand) in Cutaneous Mastocytosis," *New Engl. J. Med.*, (1993), 328:1302-1307.
Longley, et al., "Chymase Cleavage of Stem Cell Factor Yields a Bioactive Soluble Product," *Proc. Natl. Acad. Sci.*, (1997), 94:9017-9021.
Longley, et al., "Somatic c-KIT Activating Mutation in Urticaria Pigmentosa and Aggressive Mastocytosis: Establishment of Clonality in a Human Mast Cell Neoplasm," *Nat. Gen.*, (1996), 12:312-314.
Louvet et al., "Tyrosine kinase inhibitors reverse type 1 diabetes in nonobese diabetic mice," *Proc. Nat. Acad. Sci.*, (2008), 105(48): 18895-18900.
Loveland, et al., "Stem Cell Factor and c-kit in the Mammalian Testis: Lessons Originating from Mother Nature 19s Gene Knockouts," *J. Endocrinol.*, (1997), 153:337-344.
Lu, et al., "Oriented Immobilization of Fab 19 Fragments on Silica Surfaces," *Anal. Chem.*, (1995), 67:83-87.
Lukacs, et al., "Stem Cell Factor (c-kit Ligand) Influences Eosinophil Recruitment and Histamine Levels in Allergic Airway Inflammation," *J. Immunol.*, (1996), 156:3945-3951.
Luo, et al., "Close Linkage with the RET Proto-Oncogene and Boundaries of Deletion Mutations in Autosomal Dominant Hirschsprung Disease," *Hum Mol Genet.*, (1993), 2(11):1803-1808.
Lyman, et al., "c-kit Ligand and Flt3 Ligand: Stem/Progenitor Cell Factors With Overlapping Yet Distinct Activities," *Blood*, (1998), 91:1101-1134.

Ma, et al., "Indolinone Derivatives Inhibit Constitutively Activated KIT Mutants and Kill Neoplastic Mast Cells," *J Invest Dermatol.*, (2000), 114:392-394.
Ma, et al., "The c-KIT Mutation Causing Human Mastocytosis is Resistant to ST1571 and Other KIT Kinase Inhibitors; Kinases with Enzymatic Site Mutations Show Different Inhibitor Sensitivity Profiles Than Wild-type Kinases and Those With Regulatory-Type Mutations," *Blood*, (2002), 99:1741-1744.
Machens, et al., "Modification of multiple endocrine neoplasia 2A phenotype by cell membrane proximity of RET mutations in exon 10," *Endocrine-Related Cancer*, (2009), 16:171-177.
Machida, et al., "Mitogen-activated Protein Kinase Kinase Kinase Kinase 4 as a Putative Effector of Rap2 to Activate the c-Jun N-terminal Kinase," *J. Biol. Chem.*, (2004), 279:15711-15714.
Mack, et al., "Functional identification of kinases essential for T-cell activation through a genetic suppression screen," *Immunol. Lett.*, (2005), 96:129-145.
Madden, et al., "Synthetic Combinatorial Libraries: Views on Techniques and Their Application," *Perspectives in Drug Discovery and Design*, (1994), 2:269-285.
Madhusdan et al., "Tyrosine kinase inhibitors in cancer therapy," *Clinical Biochemistry*, (2004), 37:618-635.
Malmborg, et al., "BIAcore as a Tool in Antibody Engineering," *Journal of Immunological Methods*, (1995), 183:7-13.
Malmqvist, et al., "Biomolecular Interaction Analysis: Affinity Biosensor Technologies for Functional Analysis of Proteins," *Current Opinion in Chemical Biology*, (1997), 1:378-383.
Malmqvist, M., "BIACORE: An Affinity Biosensor System for Characterization of Biomolecular Interactions," *Biochemical Society Transactions*, (1999), 27:335-340.
Markiewicz, et al., "Synthetic Oligonucleotide Combinatorial Libraries and Their Applications," *Il Farmaco*, (2000), 55:174-177.
Marchetti et al., "Frequent Mutations in the Neurotrophic Tyrosine Receptor Kinase Gene Family in Large Cell Neuroendocrine Carcinoma of the Lung," *Hum. Mutat.*, (2008), 29(5):609-16.
Marshall, et al., "Blockade of colony stimulating Factor-1 (CSF-1) Leads to inhibition of DSS-induced colitis," *Inflamm. Bowel Dis.*, (2007), 13(2): 219-224.
Martin, Y., "Computer-Assisted Rational Drug Design," *Methods Enz.*, (1991), 203:587-613.
Matayoshi, et al., "Actions of brain-derived neurotrophic factor on spinal nociceptive transmission during inflammation in the rat," *J Physiol.*, (2005), 569:685-695.
Matsumoto, et al., "Physical properties of solid molecular dispersions of indomethacin with poly(vinylpyrrolindone) and poly(vinylpyrrolidone-co-vinyl-acetate) in relation to indomethacin crystallization," Pharmaceutical Research, (1999), 16(11):1722-1728.
Mazeas, et. al., "Synthesis of new melatoninergic ligands including azaindole moiety," *Heterocycles*, (1999), 50:1065-1080.
McArthur et al., "Safety and efficacy of vemurafenib in BRAFV600E and BRAFV600K mutation-positive melanoma (BRUM-3): extended follow-up of phase 3, randomized, open-label study," *Lancet. Oncol.*, (2014), 15(3), 323-332.
McCall, et al., "Characterization of Anti-Mouse FcγRII Single-Chain Fv Fragments Derived from Human Phage Display Libraries," *Immunotechnology*, (1998), 4:71-87.
McDermott et al., "Identification of genotype-correlated sensitivity to selective kinase inhibitors by using high throughput tumor cell line profiling," *PNAS*,(2007), 104(50): 19936-19941.
McPherson, A., "Current Approaches to Macromolecule Crystallization," *Eur. J. Biochem.*, (1990), 189:1-23.
Mettey et al., "Aloisines, a New family of CDK.GSK-3 Inhibitors. SAR Study, Crystal Structure in Complex with CDK2, Enzyme Selectivity, and Cellular Effects," *J. Med. Chem.*, (2003), 46:222-236.
Mekori, et al., "The Role of c-Kit and Its Ligand, Stem Cell Factor, in Mast Cell Apoptosis," *Int. Arch. Allergy Immunol.*, (1995), 107:136-138.
Mekori, et al., "Transforming Growth Factor-β Prevents Stem Cell Factor-Mediated Rescue of Mast Cells from Apoptosis After IL-3 Deprivation," *J. Immunol.*, (1994), 153:2194-2203.

(56) References Cited

OTHER PUBLICATIONS

Meltzer, E. O., "The pharmacological basis for the treatment of perennial allergic rhinitis and non-allergic rhinitis with topical corticosteroids," *Aller.*, (1997), 52:33-40.
Meng, et al., "Automated Docking with Grid-Based Energy Evaluation," *J. Compt. Chem.*, (1992), 13:505-524.
Menke et al., "Sunlight triggers cutaneous lupus through a CSF-1-dependent mechanism in MRL-$Fas^{lpr}$ mice," *Journal of Immunology*, (2008), 181: 7367-7379.
Merour, et al., "Synthesis and Reactivity of 7-Azaindoles (1H-Pyrrolo[2,3-b]pyridine)," *Curr. Org. Chem.*, (2001), 5:471-506.
Merritt, A., "Solution Phase Combinatorial Chemistry," *Comb Chem High Throughput Screen*, (1998), 1:57-72.
Metcalf, D., "Lineage Commitment in the Progeny of Murine Hematopoietic Preprogenitor Cells: Influence of Thrombopoietin and Interleukin 5," *Proc. Natl. Acad. Sci.*, (1998), 95:6408-6412.
Metcalfe, D. "Classification and Diagnosis of Mastocytosis: Current Status," *J. Invest. Derm.*, (1991), 93:2S-4S.
Metcalfe, et al., "Mast Cells," *Physiol. Rev.*, (1997), 77:1033-1079.
Muela Pomeda, et al., "Efecto De Codisolventes Y Dispersiones Solida De Polivinilpirrolidona K-30 En La Solubilidad Tel Tiabendazol," *Departamento de Farmacia y Tecnologia Farmaceutica. Facultad de Farmacia. Universidad de Alcala*, (2002), pp. 85-87.
Miller et al., "FLOG: A System to Select Quasi-Flexible Ligands Complementary to a Receptor of Known Three-Dimensional Structure," *J. Comp. Aided Molec. Design*, (1994), 8:153-174.
Minakata, et al., "Functionalization of 1H-Pyrrolo[2,3-b]pyridine," *Bulletin of the Chemical Society of Japan*, (1992), 65(11):2992-2997.
Minakata, et al., "Regioselective Funtionalization of 1H-Pyrrolo[2,3-b]pyridine Via its N-Oxide," *Synthesis*, (1992), 661-663.
Miranker, at al., "Functionality Maps of Binding Sites: A Multiple Copy Simultaneous Search Method," *Proteins: Structure, Function, and Genetics*, (1991), 11:29-34.
Mitra, et al., "Fluorescence Resonance Energy Transfer Between Blue-Emitting and Red-Shifted Excitation Derivatives of the Green Fluorescent Protein," *Gene*, (1996), 173:13-17.
Miyaura, et al., "Palladium-Catalyzed Cross-Coupling Reactions of Organoboron Compounds," *Chem. Rev.*, (1995), 95:2457-2483.
Mokhtari, et al., "Potential utility of small tyrosine kinase inhibitors in the treatment of diabetes," *Clinical Science*, (2010), 118(4):241-247.
Mol, et al., "Structural Basis for the Autoinhibition and STI-571 Inhibition of c-Kit Tyrosine Kinase," *J. Biol. Chem.*, (2004), 279:31655-31663.
Mol, et al., "Structure of a c-Kit Product Complex Reveals the Basis for Kinase Transactivation," *J. Biol. Chem.*, (2003), 278:31461-31464.
Morgan, et al., "Isolation and Characterization of a Cloned Growth Factor Dependent Macrophage Cell Line, BAC1.2F5," *J. of Cell. Physiology*, (1987), 130:420-427.
Murphy, et al., "Expression of macrophage colony-stimulating factor receptor is increased in the $A\beta PP^{V717F}$ transgenic mouse model of Alzheimer's disease," *Am. J. of Pathology*, (2000), 157:(3) 895-904.
Murty, et al., "A Genetic Perspective of Male Germ Cell Tumors," *Sem. Oncol.*, (1998), 25:133-144.
Naclerio, et al., "Rhinitis and Inhalant Allergens," *JAMA*, (1997), 278:1842-1848.
Nagafuji, et al., "A General Synthesis of Pyrroles and Fused Pyrrole Systems from Ketones and Amino Acids," *J. Org. Chem.*, (1996), 61:4999-5003.
Nagata, et al., "Elevated Expression of the Proto-Oncogene c-kit in Patients with Mastocytosis," *Leukemia*, (1998), 12:175-181.
Nahm et al., "N-Methoxy-N-Methylamides as Effective Acylating Agents," *Tetrahedron Lett.*, (1981), 22(39):3815-3818.
Nakagawara, et al., "Expression and Function of TRK-B an BDNF in Human Neuroblastomas," *Mol. Cell Biol.*, (1994), 14:759-767.
Nakai et al., "New Potent Antagonists of Leukotrienes C4 and D4. 01. Synthesis and Structure-Activity Relationships," *J. Med. Chem.*, (1988), 31:(1):84-91.

Nassentein, et al., "The Neurotrophins Nerve Growth Factor, Brain-derived Neurotrophic Factor, Neurotrophin-3, and Neurotrophin-4 Are Survival and Activation Factors for Eosinophils in Patients with Allergic Bronchial Asthma," *J. Exp. Med.*, (2003), 198:455-467.
Natali, et al., "Breast cancer is associated with loss of the c-kit oncogene product," Int. J. Cancer, (1992) 52:713-717.
Navaza, J., "AMoRe: an Automated Package for Molecular Replacement," *Acta Cryst.*, (1994), A50:157-163.
Neidle, et al., "Molecular Modeling to Study DNA Intercalation by Anti-Tumor Drugs," *Methods Enz.*, (1991), 203:433-458.
Ng, et al., "Engineering Protein-Lipid Interactions: Targeting of Histidine-Tagged Proteins to Metal-Chelating Lipid Monolayers," *Langmuir*, (1995), 11:4048-4055.
Nicholls, et al., "Protein Folding and Association: Insights From the Interfacial and Thermodynamic Properties of Hydrocarbons," *Proteins*, (1991), 11:281-296.
Nichols, et al., "Development of a Scintillation Proximity Assay for Peroxisome Proliferator-Activated Receptor γ Ligand Binding Domain," *Anal. Biochem.*, (1998), 257:112-119.
Niihori, et al., "Germline KRAS and BRAF mutations in cardio-facio-cutaneous syndrome," *Nature Genet.*, (2006), 38(3):294-296.
Ochs, et al., "A phase I/II trial of recombinant methionyl human brain derived neurotrophic factor administered by intrathecal infusion to patients with amyotrophic lateral sclerosis," *Amyotroph Lateral Scler Other Motor Neuron Disord.*, (2000), 1:201-206.
Odegaard et al. "Macrophage-specific PPARg controls alternative activation and improves insulin resistance," *Nature*, (2007), 447: 1116-1121.
Ohno, et al. "A c-fms tyrosine kinase inhibitor, KI202227, suppresses osteoclast differentiation and osteolytic bone destruction in a bone metastasis model," *Mol. Cancer Ther.*, (2006), 5(11):2634-2643. 2634-43.
Ohno, et al., "The orally-active and selective cFMS tyrosine kinase inhibitor Ki20227 inhibits disease progression in a collagen-induced arthritis mouse model," *Eur. J Immunol.*, (2008), 38: 1-9.
Okada, et al., "Gene Therapy Against an Experimental Glioma Using Adeno-Associated Virus Vectors," *Gene Ther.*, (1996), 3:957-964.
Okayama, et al., "Activation of Eosinophils with Cytokines Produced by Lung Mast Cells," *Int. Arch. Aller. Immunol.*, (1997), 114(suppl. 1):75-77.
Okayama, et al., "Human Lung Mast Cells are Enriched in the Capacity to Produce Granulocyte-Macrophage Colony-Stimulating Factor in Response to IgE-Dependent Stimulation," *Eur. J. Immunol.*, (1998), 28:708-715.
Olah, et al., "Synthetic Methods and Reactions: Part 209. Improved Preparation of Aldehydes and Ketones from N,N-Dimethylamides and Grignard Reagents," *Synthesis*, (1984), 228-230.
O'Shannessy, D., "Determination of Kinetic Rate and Equilibrium Binding Constants for Macromolecular Interactions: a Critique of the Surface Plasmon Resonance Literature," *Current Opinions in Biotechnology*, (1994), 5:65-71.
O'Shannessy, et al., "Interpretation of Deviations From Pseudo-First-Order Kinetic Behavior in the Characterization of Ligand Binding by Biosensor Technology," *Analytical Biochemistry*, (1996), 236:275-283.
Ottoni, et al., "Efficient and Simple Methods for the Introduction of the Sulfonyl, Acyl and Alkyl Protecting Groups on the Nitrogen of Indole and its Derivatives," *Tetrahedron*, (1998), 54:13915-13928.
Otwinowski, Z., "Maximum Likelihood Refinement of Heavy Atom Parameters," *Dept. of Molecular Biophysics and Biochemistry*, (1991), 80-86.
Owicki, et al., "Application of Fluorescence Polarization Assays in High-Throughput Screening," Genetic Engineering News, (1997), 17:27.
Panitumumab, (2011),"In Combination with Cisplatin/Gemacitabine", http://clinicaltrials.gov/ct2/show/NCT0132054.
Parker, et al., "Development of High Throughput Screening Assays Using Fluorescence Polarization: Nuclear Receptor-Ligand-Binding and Kinase/Phosphatase Assays," *J Biomol Screen*, (2000), 5:77-88.
Patani et al, "Bioisosterism: a rational approach in drug design," *Chem Rev*, (1996), 96:3147-3176.

(56) References Cited

OTHER PUBLICATIONS

Perrin, D., "Nucleic Acids for Recognition and Catalysis: Landmarks, Limitations, and Looking to the Future," *Combinatorial Chemistry & High Throughput Screening*, (2000), 3:243-269.

Petty, et al., "The effect of systemically administered recombinant human nerve growth factor in healthy human subjects," Ann Neurol., (1994), 36:244-246.

Pflugrath, et al., "Crystal Structure Determination, Refinement and the Molecular Model of the x-Amylase Inhibitor Hoe-467A," *J. Mol. Biol.*, (1986), 189:383-386.

Pierce, et al., "Local anesthetics. I. beta-Monoaklylaminoethyl Esters of Alkoxybenzoic Acids," *J. Am. Chem. Soc.*, (1942), 64:1691-1694.

Pignon, J.M., "C-kit mutations and mast cell disorders a model of activating mutations of growth factor receptors," *Hermatol Cell Ther.*, (1997), 39:114-116.

Plunkett, et al., "A Silicon-Based Linker for Traceless Solid-Phase Synthesis," J. Org. Chem., (1995), 60:6006-6007.

Poul, et al., "Selection of Tumor-Specific Internalizing Human Antibodies from Phage Libraries," *J. Mol. Biol.*, (2000), 301:1149-1161.

Prada et al., "Neurofibroma-associated Macrophages Play Roles in Tumor Growth and Response to Pharmacological Inhibition," *Acta Neuropathol*, (2013), 125: 159-168.

Pratilas et al., "Marker gene showing changes in levels of expression in response to antineoplastic drug therapy and their use of chemotherapy", *Hcalplus*, (2008) 670875.

Price, et al., "Summary report on the ISOBM TD-4 Workshop: analysis of 56 monoclonal antibodies against the MUC1 mucin," *Tumour Biology*, (1998), 19:1-20.

Prien, "Target-family-oriented focused libraries for kinases—Conceptual design aspects and commercial availability," *ChemBioChem*, (2005), 6:500-505.

Rajavashisth, et. al., "Heterozygous Osteopetrotic (op) Mutation Reduces Atherosclerosis in LDL Receptor-deficient Mice," J. Clin. Invest., (1998), 101:2702-2710.

Rajpert-De Meyts, et al., "Expression of the c-kit Protein Product in Carcinoma-in-situ and Invasive Testicular Germ Cell Tumours," *Int. J. Androl.*, (1994), 17:85-92.

Rapp, et al., "Raf kinases in lung tumor development," *Advan. Enzyme Regul.*, (2003) 43:183-195.

Remington: The Science and Practice of Pharmacy, vol. II, (1995), pp. 1454-1460.

Ricotti, et al., "c-kit Is Expressed in Soft Tissue Sarcoma of Neuroectodermic Origin and Its Ligand Prevents Apoptosis of Neoplastic Cells," *Blood*, (1998), 91:2397-2405.

Ritz, et al., "Elevated blood levels of inflammatory monocytes ($CD14^+CD16^+$) in patients with complex regional pain syndrome," *Clin. Exper. Immunology*, (2011), 1-10.

Roberts et al., "Targeting the Raf-MEK-ERK mitogen-activated protein kinase cascade for the treatment of cancer," *Oncogene* (2007) 26:3291-3310.

Roberts, et al., "Generation of an antibody with enhanced affinity and specificity for its antigen by protein engineering," *Nature*, (1987), 328:731-734.

Robinson, et al., "7-Azaindole. I. Synthesis and Conversion to 7-Azatryptophan and Other Derivatives," J. Am. Chem. Soc., (1955), 77:457-460.

Rodriguez-Viciana, et al., "Germline Mutations in Genes Within the MAPK Pathway Cause Cardio-facio-cutaneous Syndrome," *Science*, (2006), 311:1287-1290.

Rosenfeld, M.A., "Human artificial chromosomes get real," *Nat. Genet.*, (1997), 15:333-335.

Rosnet et al., "Isolation and Chromosomal Localization of a Novel FMS-like Tyrosine Kinase Gene," *Genomics*, (1991), 9: 380-385.

Ryan, et al., "Role for the Stem Cell Factor/KIT Complex in Schwann Cell Neoplasia and Mast Cell Proliferation Associated with Neurofibromatosis," J. Neuro. Res., (1994), 37:415-432.

Saify, et al., "Synthesis of some 7-azaindole derivatives: Their cytotoxicity and antibacterial activity," *Pakistan Journal of Scientific and Industrial Research*, (1994), 37(10):439-441.

Saiki, R.K., "Amplification of Genomic DNA," *PCR Protocols, a Guide to Methods and Applications*, (1990), pp. 13-20.

Sambrook, et al., "Introduction of Recombinant Vectors into Mammalian Cells," *Molecular Cloning: A Laboratory Manual*, (1989), 2:16.30-16.37.

Sandlow, et al., "Expression of c-KIT and its Ligand, Stem Cell Factor, in Normal and Subfertile Human Testicular Tissue," *J. Androl.*, (1996), 17:403-408.

Santoro, et al., "The ret Proto-Oncogene is Consistently Expressed in Human Pheochromocytomas and Thyroid Medullary Carcinomas," *Oncogene*, (1990), 5(10):1595-1598.

Sathornsumetee, et al., "AAL881, a Novel Small Molecule Inhibitor of RAF and Vascular Endothelial Growth Factor Receptor Activities, Blocks the Growth of Malignant Glioma," *Cancer Res.*, (2006), 66:8722-8730.

Sawada, et al., "4-(Benzoylindolizinyl)butyric acids; Novel nonsteroidal inhibitors of steroid 5;1-reductase. III," *Chemical and Pharmaceutical Bulletin*, (2001), 49(7):799-813.

Sawada, et al., "Role of Cytokines in Leukemic type Growth of Myelodysplastic CD34+ Cells," *Blood*, (1996), 88:319-327.

Sawai, et al., "Aberrant growth of granulocyte-macrophage progenitors in juvenile chronic myelogenous leukemia in serum-free culture," *Exp. Hem.*, (1996), 2:116-122.

Scheffner, et al., "The E6 Oncoprotein Encoded by Human Papillomavirus Types 16 and 18 Promotes the Degredation of p53," *Cell*, (1990), 63:1129-1136.

Schiemann, et al., "p-Fluorobenzoic Acid," *Org. Syn. Coll.*, (1943), 2:299-301.

Sclabas et al., "Overexpression of Tropomysin-Related Kinase Bin Metastatic Human Pancreatic Cancer Cells," *Clin. Cancer. Res.*,(2005), VII: 440-449.

Schneider, et al., "Functional Purification of a Bacterial ATP-Binding Cassette Transporter Protein (MalK) from the Cytoplasmic Fraction of an Overproducing Strain," *Protein Expr. Purif.*, (1995), 6:10-14.

Schneller, et. al., "Synthesis of 4-Amino-1 H-pyrrolo[2,3-b]pyridine {1,7-Dideazaadenine) and 1H-Pyrrolo[2,3-b]pyridine-4-ol (1,7-Dideazahypoxanthine)," J. Org. Chem., (1980), 45:4045-4048.

Schuhmann, et al., "Immobilization of Enzymes on Langmuir-Blodgett Films via a Membrane-Bound Receptor. Possible Applications for Amperometric Biosensors," Adv. Mater., (1991), 3:388-391.

Schummer, et al., "Inexpensive Handheld Device for the Construction of High-Density Nucleic Acid Arrays," *Biotechniques*, (1997), 23:1087-1092.

Schweizer, et al., "Combinatorial Synthesis of Carbohydrates," *Curr Opin Chem Biol*, (1999), 3(3):291-298.

Serajuddin, A. T. M., "Solid Dispersion of Poorly Water-Soluble Drugs: Early Promises, Subsequent Problems, and Recent Breakthroughs," *J. Pharm. Sci.*, (1999), 8(10), 1058-1066.

Secor, et al., "Mast cells are essential for early onset and severe disease in a murine model of multiple sclerosis," J. Exp. Med., (2000), 5:813-821.

Selvin, P., "Fluorescence Resonance Energy Transfer," *Meth. Enzymol.*, (1995), 246:300-345.

Shah et al., "Development of Novel Microprecipitated Bulk Power(MBP) Technology for Manufacturing Stable Amorphous Formulations of Poorly Soluble Drugs", *International Journal of Pharmaceutics*, (2012), 438: pp. 53-60.

Shah et al., "Improved Human Bioavailability of Vemurafenib, a Practically Insoluble Drug, Using an Amorphous Polymer-Stabilized Solid Dispersion Prepared by a Solvent-Controlled Coprecipitation Process," *Journal of Pharmceutical Sciences*, (2012), pp. 1-15.

Shan, et al., "Prodrug strategies based on intramolecular cyclization reactions," Journal of Pharmaceutical Sciences, (1997), 86(7):765-767.

Sheets, et al., "Efficient Construction of a Large Nonimmune Phage Antibody Library: The Production of High-Affinity Human Single-Chain Antibodies to Protein Antigens," *Proc Natl Acad Sci USA.*, (1998), 95:6157-6162.

Siegel, et al., "Mass Spectral Analysis of a Protein Complex Using Single-Chain Antibodies Selected on a Peptide Target: Applications to Functional Genomics," *Journal of Molecular Biology*, (2000), 302:285-293.

(56) References Cited

OTHER PUBLICATIONS

Sigal, et al., "A Self-Assembled Monolayer for the Binding and Study of histidine-Tagged Proteins by Surface Plasmon Resonance," *Anal. Chem.*, (1996), 68:490-497.

Small et al., "STK-I, the human homolog ofFlk-2/Flt-3, is selectively expressed in CD34+ human bone marrow cells and is involved in the proliferation of early progenitor/stem cells," *Proc. Nat. Acad. Sci.*, (1994), 91: 459-463.

Smalley, et al., "c-KIT signaling as the driving oncogenic event in sub-groups of melanomas," *Histol Histopathol*, (2009), 24:643-650.

Smith, et al., "The Role of kinase inhibitors in the treatment of patients with acute myeloid leukemia," (2013), *Am Soc Clin Oncol Educ Book*, (2013), pp. 313-318.

Solinas-Toldo, et al., "Matrix-Based Comparative Genomic Hybridization Biochips to Screen for Genomic Imbalances," *Genes, Chromosomes & Cancer*, (1997), 20:399-407.

Song, et al., "Isomerism of Bis(7-azaindolyl)methane," *Organic Letters*, (2002), 4(23):4049-4052, Table of content pp. 1-16 and Supporting information pp. 1-15.

Soreafenib, (2012), http://www.cancer.gov/cancertopics/druginfo/sorafenibtosylate.

Sperling, et al., "Expression of the Stem Cell Factor Receptor C-Kit (CD117) in Acute Leukemias," *Haemat.*, (1997), 82:617-621.

Stanulla, et al., "Coexpression of Stem Cell Factor and Its Receptor c-Kit in Human Malignant Glioma Cell Lines," *Act Neuropath.*, (1995), 89:158-165.

Steinman, L., "Multiple sclerosis: A coordinated immunological attack against myelin in the central nervous system," *Cell*, (1996), 85:299-302.

Strohmeyer, et al., "Expression of the C-kit Proto-Oncogene and its Ligand Stem Cell Factor (SCF) in Normal and Malignant Human Testicular Tissue," *J. Urol.*, (2005), 153:511-515.

Strohmeyer, et al., "Expression of the hst-1 and c-kit Protooncogenes in Human Testicular Germ Cell Tumors," *Canc. Res.*, (1991), 51:1811-1816.

Su et al., "Synthesis of bromo-substituted Idoxyl Esters for Cytochemical Demonstration of Enzyme Activity," *J. Am. Chem. Soc.*, (1960), 82:1187-1189.

Sun, C., "Recent Advances in Liquid-Phase Combinatorial Chemistry," *Comb. Chem. & High Throughput Screening*, (1999), 2:299-318.

Sun, et al., "Design, Synthesis, and Evaluations of Substituted 3-[(3- or 4-Carboxyethylpyrrol-2-yl) Methylidenyl]indolin-2-Ones as Inhibitors of VEGF, PGF, and PDGF Receptor Tyrosine Kinases," *J. Med. Chem.*, (1999), 42:5120-5130.

Tada, et al., "Analysis of Cytokine Receptor Messenger RNA Expression in Human Glioblastoma Cells and Normal Astrocytes by Reverse-Transcription Polymerase Chain Reaction," *J. Neuro.*, (1994), 80:1063-1073.

Takahashi, et al., "Activation of a Novel Human Transforming Gene, ret, by DNA Rearrangement," *Cell*, (1985), 42(2):581-588.

Takahashi, et al., "Cloning and Expression of the ret Proto-Oncogene Encoding a Tyrosine Kinase with Two Potential Transmembrane Domains," *Oncogene*, (1988), 3(5):571-578.

Takahashi, et al., "ret Transforming Gene Encodes a Fusion Protein Homologous to Tyrosine Kinases," *Mol Cell Biol.*, (1987), 7:1378-1385.

Tang, et al., "An RNA interference-based screen identifies MAP4K4/ NIK as a negative regulator of PPARγ, adipogenesis, and insulin-responsive hexose transport," *Proc. Natl. Acad. Sci.*, (2006), 103:2087-2092.

Tanno et al., "Evaluation of Hypromellose Acetate Succinate (HPMCAS) as a Carrier in Solid Dispersions," *Drug Development and Industrial Pharmacy*, (2004), 30(1):9-17.

Taylor, et al., "The Rapid Generation of Oligonucleotide-directed Mutations at High Frequency Using Phosphorothloate-Modified DNA," *Nucl. Acids Res.*, (1985), 13:8764-8785.

Thibault, et. al., "Concise and Efficient Synthesis of 4-fluoro-1H-pyrrolo[2,3-b] pyridine," *Org. Lett.*, (2003), 5:5023-5025.

Thomas, et al., "The Eosinophil and its Role in Asthma," *Gen. Pharmac.*, (1996), 27:593-597.

Thomas, et. al., "Light-Emitting Carbazole Derivatives: Potential Electroluminescent Materials," *J. Am. Chem. Soc.*, (2001), 123:9404-9411.

Toste, et al., "A Versatile Procedure for the Preparation of Aryl Thiocyanates Using N-Thiocyanatosuccinimide (NTS)," *Synth. Comm.*, (1995), 25(8):1277-1286.

Toy et al., "Enhanced ovarian cancer tumorigenesis and metastasis by the macrophage colony-stimulating factor," *Neoplasia*, (2009), 11:(2) 136-144.

Toyota, et al., "Expression of c-kit and kit Ligand in Human Colon Carcinoma Cells," Turn Biol., (1993), 14:295-302.

Trupp, et al., "Functional Receptor for GDNF Encoded by the c-ret Proto-Oncogene," Nature., (1996), 381:785-789.

Tsuda, et al., "Microglia and Intractable Chronic Pain," *GLIA*, (2012), pp. 1-7.

Tsujimura, et al., "Ligand-Independent Activation of c-kit Receptor Tyrosine Kinase in a Murine Mastocytoma Cell Line P-815 Generated by a Point Mutation," *Blood*, (1994), 9:2619-2626.

Tsujimura, et al., "Substitution of an Aspartic Acid Results in Constitutive Activation of c-kit Receptor Tyrosine Kinase in a Rat Tumor Mast Cell Line RBL-2H3," *Int. Arch. Aller. Immunol.*, (1995), 106:377-385.

Tsujimura, T., "Role of c-kit Receptor Tyrosine Kinase in the Development, Survival and Neoplastic Transformation of Mast Cells," *Pathol Int.*, (1996), 46:933-938.

Turner, et al., "Nonhematopoeietic Tumor Cell Lines Express Stem Cell Factor and Display c-kit Receptors," Blood, (1992), 80:374-381.

Udenfriend, et al., "Scintillation Proximity Assay: A Sensitive and Continuous Isotopic Method for Monitoring Ligand/Receptor and Antigen/Antibody Interactions," *Anal. Biochem*, (1987), 161:494-500.

Uemura et al., "The Selective M-CSF Receptor Tyrosine Kinase Inhibitor Ki20227 Suppresses Experimental Autoimmune Encephalomyelitis," *J. Neuroimmunology*, (2008), 195: 73-80.

Uritskaya, et al., STN Accession No. 1974-27133; Document No. 08:27133; Abstract of Khimiya Geterotsiklicheskikh Soedinenii (1973), 10:1370-1373.

Vachon, et al., "The influence of microencapsulation using Eudragit RS100 on the hydrolysis kinetics of acetylsalicylic acid," *J. Microencapsulation*, (1997), 14(3):281-301.

Valent, P., "Biology, Classification and Treatment of Human Mastocytosis," *Wein/Klin Wochenschr.*, (1996), 108:385-397.

Van Heyningen, V., "One Gene—Four Syndromes," *Nature*, (1994), 367:319-320.

Van Regenmortel, M.H.V., "Use of biosensors to characterize recombinant proteins," *Developments in Biological Standardization*, (1994), 83:143-151.

Vandelli, et al., "Analysis of release data in the evaluation of the physical state of progesterone in matrix systems," J. Microencapsulation, (1993), 10(1):55-65.

Vely, et al., "BIAcore Analysis to Test Phosphopeptide-SH2 Domain Interactions," *Methods in Molecular Biology*, (2000), 121:313-321.

Verfaillie, C.M., "Chronic myelogenous leukemia: too much or too little growth, or both?" *Leukemia*, (1998), 12:136-138.

Viskochil, D., "It Takes Two to Tango: Mast Cell and Schwann Cell Interactions in Neurofibromas," *J Clin Invest.*, (2003), 112:1791-1793.

Vliagoftis, et al., "The protooncogene c-kit and c-kit ligand in human disease," *Journ. Clin. Immunol*, (1997), 100:435-440.

Wakefield, Basil "Fluorinated Pharmaceuticals" Innovations in Pharmaceutical Technology, (2003), 74:76-78.

Waldo et al., "Heterogeneity of human macrophages in culture and in atherosclerotic plaques," *Am. J. of Pathology*, 172(4): 1112-1126 (2008).

Weber, P., "Physical Principles of Protein Crystallization," *Adv. Protein Chem.*, (1991), 41:1-36.

Wells, et al., "Targeting the RET Pathway in Thyroid Cancer," *Clin Cancer Res.*, (2009), 15(23):7119-7123.

Wendt, et al., "Identification of novel binding interactions in the development of potent, selective 2-naphthamidine inhibitors of urokinase, synthesis, structural analysis, and SAR of γ-Phenyl amide 6-substitution," *J. Med. Chem.*, (2004), 47(2):303-324.

(56) References Cited

OTHER PUBLICATIONS

Wentworth et al., "Pro-Inflammatory CD11C+CD206+ Adipose Tissue Macrophages Are Associated With Insulin Resistance in Human Obesity," *Diabetes*, (2010), 59:1648-1656.
Werness, et al., "Association of Human Papillomavirus Types 16 and 18 E6 Proteins with p53," *Science*, (1990), 248:76-79.
Wessjohann, L., "Synthesis of Natural-Product-Based Compound Libraries," *Curr Opin Chem Biol.*, (2000), 4:303-309.
Wharam, et al., "Specific Detection of DNA and RNA Targets Using a Novel Isothermal Nucleic Acid Amplification Assay Based on the Formation of a Three-Way Junction Structure," *Nucleic Acids Res.*, (2001), 29:1-8.
Wild, et al., "Antibodies to Nerve Growth Factor Reverse Established Tactile Allodynia in Rodent Models of Neuropathic Pain without Tolerance," *J. Pharmacol. Exp. Ther.*, (2007), 322:282-287.
Williams, et al., "Dissection of the Extracellular Human Interferon y Receptor a-Chain into two Immunoglobulin-like domains. Production in an *Escherichia coli* Thioredoxin Gene Fusion Expression system and Recognition by Neutralizing Antibodies," Biochemistry, (1995), 34:1787-1797.
Willmore-Payne, C., et al. "Human malignant melanoma. detection of BRAF- and c-kit-activating mutations by high-resolution amplicon melting analysis," *Humon Pathology*, (2005), 36: pp. 486-493.
Wolff, Manfred E. "Burger's Medicinal Chemistry, 5ed, Part 1", *John Wiley & Sons*, (1995), pp. 975-977.
Woon, et al., "Construction and Characterization of a 10-Fold Genome Equivalent Rat P1-Derived Artificial Chromosome Library," *Genomics*, (1998), 50:306-316.
Wright, et al., "The STE20 Kinase KGK Is Broadly Expressed in Human tumor Cells and Can Modulate Cellular Transformation, Invasion, and Adhesion," *Mol. Cell. Biol.*, (2003), 23:2068-2082.
Wuthrich, K., "Chapter 10: Three-Dimensional Protein Structures by NMR," *NMR of Proteins and Nucleic Acids*, (1986), 10:176-199.
Xing, et al., "BRAF Mutation Predicts a Poorer Clinical Prognosis for Papillary Thyroid Cancer," *J. Clin. Endocrinol. Metab.*, (2005), 90(12):6373-6379.
Xing, M., "BRAF mutation in thyroid cancer," *Endocrine-Related Cancer*, (2005), 12:245-262.
Xu et al., "CSF1R signaling blockade stanches tumor-infiltrating myeloid cells and improves the efficacy of radiotherapy in prostate cancer," *Cancer Res.*, (2013), 73(9): 2782-94.
Xu, et al., "Modulation of Endothelial Cell function by Normal Polyspecific Human Intraveneous immunoglobulins," *Am. J. Path.*, (1998), 153:1257-1266.
Yakhontov, et al., "Derivatives of 7-azaindole. XV. Electrophilic substitution of 4-methyl-7-azaindole and its derivatives," Zhurnal Obshchei Khimii, *HCAPLUS* (1966), 51974.
Yamaguchi, et al., "Calcium Restriction Allows cAMP Activation of the B-Raf/ERK Pathway, Switching Cells to a cAMP-dependent Growth-stimulated Phenotype," *The Journal of Biological Chemistry*, (2004), 279:40419-40430.
Yamaguchi, et al., "Cyclic AMP activates B-Raf and ERK in cyst epithelial cells from autosomal-dominant polycystic kidneys," *Kidney International*, (2003), 63:1983-1994.
Yang, et al., "Identification of Brain-Derived Neurotrophic Factor as a Novel Functional Protein in Hepatocellular Carcinoma," *Cancer Res.*, (2005), 65:219-225.
Yang, et al., "Neurofibromin-Deficient Schwann Cells Secrete a Potent Migratory Stimulus for NF1+/− Mast Cells," *J Clin Invest.*, (2003), 112:1851-1861.
Yang, et al., "Nf1-Dependent tumors require a microenvironment containing Nf1+/−-and c-kit-Dependent bone marrow," *Cell*, (2008), 135:437-448.
Yang, et al., "Synthesis of some 5-substituted indoles," *Heterocycles*, (1992), 34:1169-1175.
Yao, et al., "A Novel Human STE20-related Protein Kinase, HGK, That Specifically Activates the c-Jun N-terminal Kinase Signaling Pathway," *J. Biol. Chem.*, (1999), 274:2118-2125.
Yee, et al., "Role of kit-Ligand in Proliferation and Suppression of Apoptosis in Mast Cells: Basis for Radiosensitivity of White Spotting and Steel Mutant Mice," *J. Exp. Med.*, (1994), 179:1777-1787.
Yeung, et al., "Friedel-Crafts acylation of indoles in acidic imidazolium chloroaluminate ionic liquid at room temperature," *Tetrahedron Letters*, (2002), 43(33), 5793-5795.
Yoshida et al., "Studies on anti-helicobacter pylori agents, Part 1: Benzyloxyisoquinoline derivatives," *Bioorganic & Medicinal Chemistry, Elsevier Science Ltd*,(1999), 7(11):2647-2666.
Yuan, et al., "Human Peripheral Blood Eosinophils Express a Functional c-kit Receptor for Stem Cell Factor that Stimulates Very Late Antigen 4 (VLA-4)-Mediated Cell Adhesion to Fibronectin and Vascular Cell Adhesion Molecule 1 (VCAM-1)," *J. Exp. Med.*, (1997), 186:313-323.
Zaidi et al., "Interferon-γ links ultraviolet radiation to melanomagenesis in mice." *Nature*, (2011), 469: 548-553.
Zanon, et. al., "Copper-Catalyzed Domino Halide Exchange-Cyanation of Aryl Bromides," *J. Am. Chem. Soc.*, (2003), 125:2890-2891.
Zhang, et al., "An effective procedure for the acylation of azaindoles at C-3," Journal of Organic Chemistry, (2002), 67(17):6226-6227.
Zhang, et al., "Design and pharmacology of a highly specific dual FMS and KIT kinase inhibitor," Proc. Natl. Acad. Sci., (2013), 110:(14) 5689-5694.
Notice of Allowance for U.S. Appl. No. 11/016,350 dated Dec. 26, 2007.
Office Action in U.S. Appl. No. 11/016,350 dated Jun. 6, 2007.
Office Action in U.S. Appl. No. 11/016,350 dated Aug. 2, 2007.
Office Action in U.S. Appl. No. 11/016,350 dated Oct. 26, 2007.
International Search Report and Written Opinion dated Nov. 25, 2005 for PCT Patent Application No. PCT/US2004/042470.
Search Report for European Application No. 04814626.0 dated Aug. 4, 2009.
Communication Pursuant to Article 94(3) EPC for European Application No. 04814626.0 dated Jun. 6, 2011.
Office Action in U.S. Appl. No. 11/487,134 dated May 15, 2008.
Office Action in U.S. Appl. No. 11/487,134 dated Aug. 22, 2007.
Notice of Allowance for U.S. Appl. No. 12/082,665 dated Jul. 26, 2011.
Office Action in U.S. Appl. No. 12/082,665 dated Nov. 8, 2010.
Notice of Allowance for U.S. Appl. No. 11/154,988 dated Jun. 6, 2008.
Notice of Allowance for U.S. Appl. No. 11/154,988 dated Jul. 23, 2008.
Notice of Allowance for U.S. Appl. No. 11/154,988 dated Sep. 8, 2008.
Office Action in U.S. Appl. No. 11/154,988 dated Jan. 4, 2008.
Office Action in U.S. Appl. No. 11/154,988 dated Oct. 19, 2007.
International Search Report and Written Opinion dated Apr. 20, 2006 for PCT Patent Application No. PCT/US2005/021231.
Communication Pursuant to Article 94(3) EPC for European Application No. 05789913.0 dated Feb. 15, 2010.
Notice of Allowance for U.S. Appl. No. 12/244,730 dated Jan. 6, 2011.
Notice of Allowance for U.S. Appl. No. 12/244,730 dated Jul. 27, 2010.
Office Action in U.S. Appl. No. 12/244,730 dated Jul. 22, 2010.
Examination Report dated Jun. 27, 2008 for GCC Patent Application No. GCC/P/2005/4795.
Examination Report for Guatemala Patent Application No. PI-2005-00164 dated Jul. 2, 2008.
Search Report for Taiwan Patent Application No. 094120055 dated Aug. 25, 2011.
Notice of Allowance for U.S. Appl. No. 11/435,381 dated May 27, 2010.
Notice of Allowance for U.S. Appl. No. 11/435,381 dated Jul. 27, 2010.
Office Action in U.S. Appl. No. 11/435,381 dated Feb. 19, 2010.
Office Action in U.S. Appl. No. 11/435,381 dated Mar. 4, 2009.
Office Action in U.S. Appl. No. 11/435,381 dated Jun. 1, 2009.
International Search Report and Written Opinion dated Apr. 4, 2007 for PCT Patent Application No. PCT/US2006/018726.
Office Action in U.S. Appl. No. 12/958,376 dated Apr. 18, 2012.

(56) References Cited

OTHER PUBLICATIONS

Notice of Allowance for U.S. Appl. No. 11/473,347 dated Jun. 18, 2010.
Notice of Allowance for U.S. Appl. No. 11/473,347 dated Sep. 8, 2010.
Office Action in U.S. Appl. No. 11/473,347 dated Dec. 18, 2009.
International Search Report and Written Opinion dated Oct. 24, 2006 for PCT Patent Application No. PCT/US2006/024524.
Notice of Allowance for U.S. Appl. No. 12/616,079 dated Oct. 25, 2012.
Office Action in U.S. Appl. No. 12/616,079 dated Feb. 9, 2012.
Office Action in U.S. Appl. No. 12/616,079 dated Jun. 29, 2012.
Office Action in U.S. Appl. No. 12/906,980 dated Feb. 29, 2012.
Office Action in U.S. Appl. No. 12/906,980 dated Oct. 17, 2012.
Notice of Allowance for U.S. Appl. No. 13/216,200 dated Dec. 8, 2011.
Office Action in U.S. Appl. No. 13/243,748 dated Jun. 27, 2013.
Office Action in U.S. Appl. No. 13/243,748 dated Dec. 20, 2013.
Office Action in U.S. Appl. No. 13/786,219 dated Jul. 21, 2014.
Office Action in U.S. Appl. No. 13/786,219 dated Nov. 8, 2013.
Office Action in U.S. Appl. No. 13/866,469 dated Oct. 31, 2013.
Office Action in Taiwan Application No. 102123382 dated Nov. 16, 2013.
International Search Report and Written Opinion dated Oct. 24, 2006 for PCT Patent Application No. PCT/US2006/024361.
Novelty Search Report dated Sep. 24, 2009 for Gulf Cooperation Council Application No. GCC/P/2006/6469.
Examination Report for Pakistan Patent Application No. 0679/2006.
Office Action in Taiwan Application No. 095122373 dated Dec. 9, 2011.
Office Action in Australian Application No. 2006261993 dated Aug. 15, 2011.
Office Action in Colombian Application No. 08-005.567 dated Sep. 9, 2011.
Exam Report in Egyptian Application No. 1439/2007 dated Nov. 3, 2014.
Communication Pursuant to Article 94(3) EPC for European Application No. 06773861.7 dated Apr. 22, 2010.
Communication Pursuant to Article 94(3) EPC for European Application No. 06773861.7 dated Jul. 9, 2009.
Communication Pursuant to Article 94(3) EPC for European Application No. 06773861.7 dated Dec. 21, 2009.
Office Action in Japanese Application No. 2008-518402 dated Nov. 29, 2011.
Office Action in Norwegian Application No. 20076659 dated Aug. 15, 2012.
Office Action for Ukraine Application No. A200800780 dated Jul. 12, 2010.
Notification on the Result of Substantive Examination dated Oct. 17, 2014 for Vietnamese Application No. 1-2010-02238.
Office action in Russian Application No. 2011101140 dated Dec. 24, 2014.
Office Action for Chinese Application No. 20110084299 dated Feb. 7, 2014.
Search Report for European Application No. 11173701.1 dated Mar. 6, 2012.
Search Report for European Application No. 11173701.1 dated Oct. 26, 2011.
Office Action for European Application No. 11173701.1 dated Jan. 13, 2014.
Communication Pursuant to Article 94(3) EPC for European Appln. No. 11173701.1 dated Jan. 4, 2013.
Office Action in Malaysian Applictaion No. PI2011004969 dated Apr. 30, 2014.
Office Action for Chinese Application No. 201210012143 dated Mar. 25, 2014.
Notice of Allowance for U.S. Appl. No. 11/962,044 dated Aug. 13, 2010.
Office Action in U.S. Appl. No. 11/962,044 dated Feb. 17, 2010.
Office Action in U.S. Appl. No. 11/962,044 dated Sep. 23, 2009.
International Search Report and Written Opinion dated Jul. 25, 2008 for PCT Patent Application No. PCT/US2007/088443.
International Search Report and Written Opinion dated Nov. 17, 2008 for PCT Patent Application No. PCT/US2007/088412.
Notice of Allowance for U.S. Appl. No. 11/961,901 dated May 17, 2012.
Office Action in U.S. Appl. No. 11/961,901 dated Jan. 23, 2012.
Office Action in U.S. Appl. No. 11/961,901 dated Aug. 4, 2011.
International Search Report and Written Opinion dated Jul. 3, 2008 for PCT Patent Application No. PCT/US2007/088243.
Notice of Allowance for U.S. Appl. No. 11/960,590 dated Aug. 11, 2010.
International Search Report and Written Opinion dated Jun. 4, 2008 for PCT Patent Application No. PCT/US2007/088231.
Office Action in U.S. Appl. No. 12/981,427 dated Mar. 5, 2013.
International Search Report and Written Opinion dated Jun. 4, 2008 for PCT Patent Application No. PCT/US2007/088237.
Office Action in Peruvian Application No. 1796-2007 dated Sep. 15, 2011.
Notification Prior to Examination for Israeli Application No. 199194 dated May 4, 2010.
Malaysian Examination Report in Malaysian Application Serial No. PI20092547 dated Aug. 15, 2012.
Office Action in New Zealand Application No. 577612 dated Mar. 21, 2012.
Office Action in Philippine Application No. 1-2009-501241 dated Jul. 27, 2012.
Office Action in Russian Application No. 2009122436 dated Dec. 2, 2011.
Communication Pursuant to Article 94(3) EPC for European Application No. 06813186.1 dated Sep. 15, 2009.
International Search Report and Written Opinion dated Jun. 5, 2008 for PCT Patent Application No. PCT/US2007/083910.
International Search Report and Written Opinion dated Jun. 5, 2008 for PCT Patent Application No. PCT/US2007/085289.
Office Action in Peruvian Application No. 1602-2007 dated Sep. 2, 2011.
Office Action in Chinese Application No. 200780050245.3 dated Jul. 20, 2011.
Office Action in Chinese Application No. 201310470059.2 dated Nov. 4, 2014.
Office Action in Colombian Application No. 09-052-610 dated Dec. 23, 2013.
Office Action in Indian Application No. 1879/KOLNP/2009 dated Jul. 11, 2014.
Office Action in Israeli Application No. 198624 dated Apr. 18, 2012.
Malaysian Substantive Examination Report dated Aug. 15, 2012 in Malaysian Application Serial No. PI20092040.
Examination Report dated Mar. 14, 2012 in New Zealand Patent Application Serial No. 577011.
Office Action in Philippine Application No. 12009501009 dated Jul. 27, 2012.
Office Action in Philippine Application No. 12009501009 dated Nov. 24, 2011.
Office Action in Russian Application No. 2009117475 dated Jul. 26, 2011.
Office Action in Korean Application No. 10-2009-7012836 dated May 29, 2014.
Examination Report dated Mar. 13, 2012 2012 in Australian Patent Application Serial No. 2007323644.
Office Action in Canadian Application No. 2670362 dated Dec. 5, 2013.
Office Action in Canadian Application No. 2670362 dated Jul. 14, 2014.
Office Action in Japanese Application No. 2009-538496 dated Jan. 29, 2013.
Office Action in Japanese Application No. 2009-538496 dated Aug. 20, 2013.
Communication Pursuant to Article 94(3) EPC for European Appln. No. 07864681.7 dated Oct. 8, 2012.
Communication Pursuant to Article 94(3) EPC for European Application No. 07864681.7 dated Dec. 2, 2009.

(56) References Cited

OTHER PUBLICATIONS

International Search Report and Written Opinion dated Jul. 28, 2008 for PCT Patent Application No. PCT/US2007/085299.
Notice of Allowance for U.S. Appl. No. 11/986,667 dated Aug. 6, 2010.
Office Action in U.S. Appl. No. 11/986,667 dated Feb. 26, 2010.
Office Action in U.S. Appl. No. 11/986,667 dated Sep. 22, 2009.
Office Action in U.S. Appl. No. 12/958,379 dated Jul. 17, 2012.
Office Action in U.S. Appl. No. 12/958,379 dated Nov. 14, 2012.
Notice of Allowance for U.S. Appl. No. 13/546,923 dated Nov. 19, 2012.
Office Action in U.S. Appl. No. 13/546,923 dated Sep. 18, 2012.
Office Action in U.S. Appl. No. 12/467,194 dated Feb. 3, 2011.
Notice of Allowance for U.S. Appl. No. 12/467,194 dated Dec. 5, 2011.
Office Action in U.S. Appl. No. 12/467,194 dated Jun. 24, 2011.
International Search Report and Written Opinion dated Feb. 18, 2010 for PCT Patent Application No. PCT/US2009/044151.
International Search Report and Written Opinion dated Sep. 22, 2009 for PCT Patent Application No. PCT/US2009/046598.
Notice of Allowance for U.S. Appl. No. 12/773,798 dated Feb. 9, 2012.
Office Action in U.S. Appl. No. 12/733,798 dated Jan. 20, 2011.
Office Action in U.S. Appl. No. 12/773,798 dated Jul. 25, 2011.
International Search Report dated Sep. 13, 2010 in PCT Application No. PCT/US2010/033571.
Office Action in Peruvian ApplicationNo. 1867-2011 dated Nov. 7, 2014.
International Preliminary Report on Patentability dated Nov. 9, 2011 in PCT Application PCT/US2010/033576.
International Search Report and Written Opinion dated Jun. 30, 2010 for PCT Application No. PCT/US2010/033576.
International Search Report and Written Opinion dated Sep. 23, 2011 for PCT Patent Application No. PCT/US2010/061601.
Extended European Search Report for EP Application 100840075.5 dated May 13, 2013.
Office Action in Japanese Application No. 2012-546158 dated Dec. 2, 2014.
Office Action in Russian Application No. 2012131373 dated Jan. 14, 2015.
Office Action in U.S. Appl. No. 12/939,998 dated Mar. 21, 2013.
Office Action in U.S. Appl. No. 12/939,998 dated Oct. 18, 2012.
Office Action in Taiwan Application No. 099138273 dated Aug. 12, 2014.
Office Action in Chinese Application No. 201080060838.X dated Oct. 29, 2014.
Office Action in Colombian Application No. Nov. 5, 2014.
Substantive Report in Chilean Application No. 1180-2012 dated Nov. 26, 2014.
Extended Search Report in European Application No. 10829123.8 dated May 31, 2013.
Office Action Eurasian Application No. 201290210 dated May 2014.
Office Action in Israeli Application No. 219418 dated Oct. 6, 2014.
Office Action in Japanese Application No. 2012-538002 dated Sep. 16, 2014.
Examiners Report in New Zealand Application No. 599866 dated Feb. 14, 2013.
Examination Report in New Zealand Application No. 599866 dated Aug. 22, 2014.
Examiners Report for New Zealand Application No. 629615 dated Sep. 1, 2014.
Office action in Georgia Application No. AP2010012739 dated Oct. 9, 2014.
Office Action and Search Report for Taiwanese Application No. 100113512 dated Dec. 15, 2014.
International Search Report dated Dec. 19, 2011 in PCT Application PCT/US2011/033192.
Supplementary European Search Report for EP Application No. 11772612, dated Oct. 21, 2013.
International Search Report and Written Opinion dated Jan. 25, 2011 for PCT Patent Application No. PCT/US2010/057293.
Office Action in Chilean Application No. 2012-1303 dated Nov. 4, 2014.
Office Action in Colombian Application No. 12-081.901 dated Jun. 28, 2014.
Extended European Search Report for EP Application 10832209.0 dated Apr. 17, 2013.
Office Action in Israeli Application No. 219567 dated Jul. 31, 2014.
Office Action in Russian Application No. 2012125070 dated Dec. 5, 2014.
International Search Report and Written Opinion dated Jun. 11, 2010 for PCT Patent Application No. PCT/US2010/026816.
Substantive Report in Chilean Application No. 2238-2011 dated Oct. 14, 2014.
Office Acton in Philippine Application No. 1-2011-501775 dated Aug. 27, 2014.
Office Action in U.S. Appl. No. 12/721,500 dated May 13, 2011.
Notice of Allowance for U.S. Appl. No. 12/721,500 dated Nov. 2, 2011.
International Search Report and Written Opinion dated Jun. 11, 2010 for PCT Patent Application No. U52010/026856.
Office Action in U.S. Appl. No. 12/752,035 dated Jun. 18, 2013.
Office Action in U.S. Appl. No. 12/752,035 dated Oct. 3, 2012.
International Search Report and Written Opinion dated Oct. 5, 2010 for PCT Patent Application No. PCT/US2010/029489.
Office Action in Taiwan Application No. 099110011 dated Jun. 26, 2012.
Office Action in Canadian Application No. 2,738,573 dated Jan. 10, 2012.
Examiners Report in Australian Application No. 2010232670 dated Jun. 6, 2014.
Office Action in Chinese Application No. 201080012888.0 dated Mar. 10, 2014.
Office Action in Chinese Application No. 20108001288.0 dated Oct. 21, 2014.
Office Action in Chilean Application No. 2011-001903 dated Nov. 28, 2013.
Office Action in Colombia Application No. 11-111.102 dated Jan. 4, 2014.
Office Action in Dominican Republic Application No. P2011-0291 dated Apr. 23, 2012.
Office Action in Eurasion Application No. 20119098 dated Jun. 16, 2014.
Office Action in Eurasian Application No. 201190098 dated Apr. 13, 2014.
Office Action in Indonesian Application No. W-00 2011-02778 dated Nov. 7, 2014.
Office Action in Israeli Application No. 214328 dated Jul. 31, 2013.
Office Action in Japese Patent Application No. 2012-503676 dated May 21, 2013.
Office Action in Mexican Application No. MX/a/2011/008303 dated Sep. 11, 2014.
Office Action in New Zealand Application No. 594398 dated Aug. 16, 2012.
Office Action in Peru Applicantion No. 1471-2011 dated Mar. 23, 2014.
Office Action in Ukraine Application No. a 2011 09548 dated Jun. 4, 2014.
Office Action in Vietnam Application No. 1-2011-02366 dated Feb. 6, 2014.
Office Action in European Application 10722860.3 dated Aug. 21, 2014.
Communication Pursuant to Article 94(3) EPC for European Application No. 10722860.3 dated Mar. 27, 2013.
Supplementary European Search Report for European Patent Application No. EP1278 9648 dated Jul. 7, 2014.
International Search Report and Written Opinion dated May 31, 2012 for PCT Patent Application No. PCT/US2012/023543.
Office Action in Australian Application No. 2012214762 dated May 23, 2014.
Office Action in Canadian Application No. 2826123 dated Jun. 30, 2014.

(56) References Cited

OTHER PUBLICATIONS

Office Action in Chilean Application No. 2228-2013 dated Dec. 18, 2014.
Office Action for Chinese Application No. 2012800170177 dated Jul. 8, 2014.
Office Action in Colombian Application No. 13-187.418 dated Oct. 20, 2014.
Office Action in Costa Rican Application No. 2013-374 dated Feb. 25, 2014.
Office Action in Erasian Application No. 201391019 dated Oct. 6, 2014.
Search Report for European Application No. 12745360.3 dated Jul. 23, 2014.
Office Action in Japanese Application No. 2013-552610 dated Nov. 4, 2014.
Examination Report in New Zealand Application No. 613786 dated May 5, 2014.
Office Action for Thai Application No. 1301004352 dated Sep. 29, 2014.
International Search Report for PCT/US2012/038417 dated Aug. 10, 2012.
Office Action in New Zealand Application No. 617526 dated Aug. 14, 2014.
International Search Report and Written Opinion dated Mar. 31, 2012 for PCT Patent Application No. PCT/US2012/025965.
Exam Report in Australian Application No. 2012200933 dated Jul. 3, 2013.
Office Action in U.S. Appl. No. 12/669,450 dated Dec. 27, 2012.
International Search Report and Written Opinion dated May 7, 2013 for PCT Patent Application No. PCT/US2013/032835.
International Preliminary Report on Patentability dated Sep. 23, 2014 for PCT Application No. PCT/US2013/032835.
Office Action in U.S. Appl. No. 13/793,917 dated Jul. 21, 2014.
International Search Report and Written Opinion dated Jul. 22, 2013 for PCT Patent Application No. PCT/US2013/043400.
Substantive Examination Report for Philippines Application No. 1/2013/501633 dated Dec. 22, 2014.

COMPOUNDS AND METHODS FOR KINASE MODULATION, AND INDICATIONS THEREFOR

CROSS-REFERENCE TO RELATED APPLICATIONS

This Application is a continuation of U.S. application Ser. No. 12/939,998, filed Nov. 4, 2010, which claims priority to U.S. Application No. 61/259,093, filed Nov. 6, 2009, both of which are hereby incorporated by reference in their entirety.

FIELD OF THE INVENTION

Disclosed are novel compounds and uses thereof. In certain embodiments disclosed compounds are Fms kinase inhibitors. In certain embodiments disclosed compounds are both Fms and Kit kinase inhibitors. In certain embodiments disclosed compounds are both Fms and Flt-3 kinase inhibitors.

SUMMARY OF THE INVENTION

In certain aspects and embodiments disclosed herein, compounds are provided, as well as various salts thereof, formulations thereof, conjugates thereof, derivatives thereof, forms thereof and uses thereof. In some embodiments, compounds are of Formula I', Formula I, Formula II', Formula II, Formula IIa, Formula III' or Formula III as described below. In certain embodiments, the compounds inhibit Fms protein kinase selectively relative to other protein kinases, including Kit and Flt-3 protein kinases. In certain embodiments, the compounds inhibit both Fms protein kinase and Kit protein kinase. In certain embodiments, the compounds inhibit both Fms protein kinase and Flt-3 protein kinase. In certain embodiments, the compounds inhibit each of Fms protein kinase, Kit protein kinase and Flt-3 protein kinase.

Also contemplated in accordance with the present invention are methods for the use of the compounds in treating diseases and conditions associated with regulation of the activity of any of Fms protein kinase, Kit protein kinase, and Flt-3 protein kinase, including any mutations of these kinases. Thus, the use of compounds for therapeutic methods involving modulation of protein kinases are provided. In certain embodiments, the compounds are used for therapeutic methods involving modulation of Fms kinase, Fms and Kit kinases, Fms and Flt-3 kinases, or Fms, Kit and Flt-3 kinases including treatment of a variety of indications, including, but not limited to, rheumatoid arthritis, osteoarthritis, osteoporosis, peri-prosthetic osteolysis, systemic sclerosis, demyelinating disorders, multiple sclerosis, Charcot Marie Tooth syndrome, amyotrophic lateral sclerosis, Alzheimer's disease, Parkinson's disease, ulcerative colitis, Crohn's disease, immune thrombocytopenic purpura, atherosclerosis, systemic lupus erythematosis, myelopreparation for autologous transplantation, transplant rejection, glomerulonephritis, interstitial nephritis, Lupus nephritis, tubular necrosis, diabetic nephropathy, renal hypertrophy, type I diabetes, acute pain, inflammatory pain, neuropathic pain, acute myeloid leukemia, melanoma, multiple myeloma, metastatic breast cancer, prostate cancer, pancreatic cancer, lung cancer, ovarian cancer, gliomas, glioblastomas, neurofibromatosis, osteolytic bone metastases, brain metastases, gastrointestinal stromal tumors, and giant cell tumors.

In a first aspect, compounds having the structure according to the following Formula I' are provided:

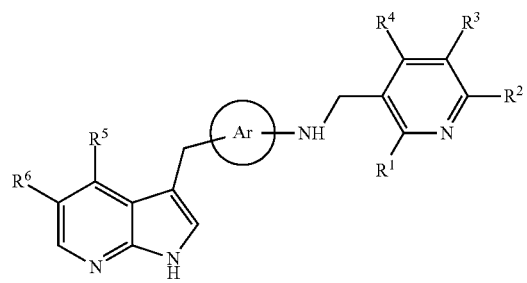

Formula I' or a salt, a prodrug, a tautomer or a stereoisomer thereof, wherein:

Ar is selected from the group consisting of:

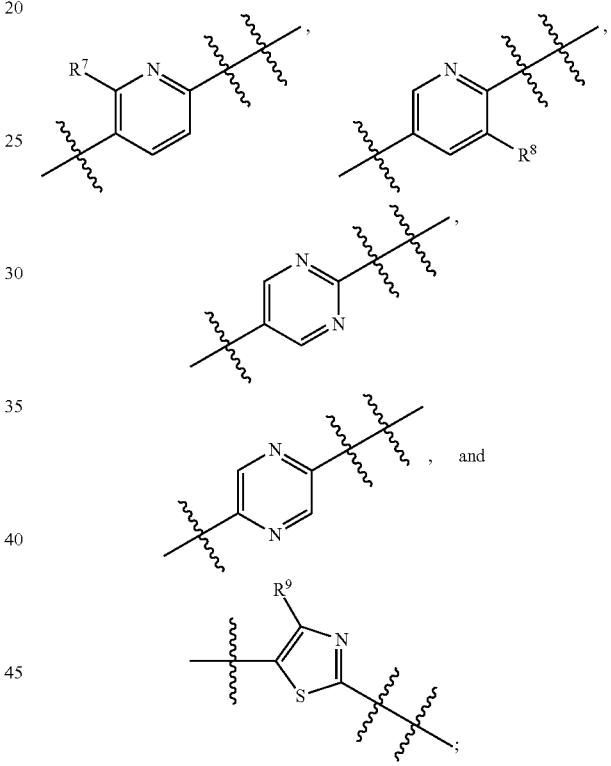

wherein

indicates the point of attachment of Ar to —CH$_2$— of Formula I' and wherein

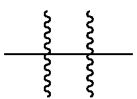

indicates the point of attachment of Ar to —NH— of Formula I';

$R^1$, $R^2$, $R^3$ and $R^4$ are each independently selected from the group consisting of —H, halogen, lower alkyl, halogen substituted lower alkyl, halogen substituted lower alkoxy, alkoxy substituted lower alkyl, cycloalkylamino, —CN, —O—$R^{40}$, —S(O)$_2$—$R^{41}$, —S(O)$_2$—N(H)—$R^{42}$, —N(H)—$R^{42}$, —N($R^{42}$)$_2$, and —N(H)—S(O)$_2$—$R^{43}$, provided that at least two of $R^1$, $R^2$, $R^3$ and $R^4$ are —H and one of $R^1$, $R^2$, $R^3$ and $R^4$ is other than hydrogen, wherein:

$R^{40}$ is lower alkyl, fluoro substituted lower alkyl, methoxy substituted lower alkyl, or cycloalkyl;

$R^{41}$, $R^{42}$ and $R^{43}$ are lower alkyl;

$R^5$ is selected from the group consisting of —H, —F, —Cl, —Br, lower alkyl, halogen substituted alkyl, lower alkenyl, lower alkynyl, cycloalkyl, phenyl, pyrazolyl, —CN, —O—$R^{10}$, —C(O)—N(H)—$R^{11}$, —C(O)—O—$R^{11}$, —S(O)$_2$—$R^{12}$, —S(O)$_2$—N(H)—$R^{11}$, —N(H)—C(O)—$R^{12}$, and —N(H)—S(O)$_2$—$R^{12}$, wherein pyrazolyl is optionally substituted with lower alkyl or heterocycloalkyl;

$R^6$ is selected from the group consisting of H, halogen, lower alkyl, halogen substituted alkyl, lower alkenyl, lower alkynyl, cycloalkyl, phenyl, pyrazolyl, —CN, —O—$R^{13}$, —C(O)—N(H)—$R^{14}$, —C(O)—O—$R^{14}$, —S(O)$_2$—$R^{15}$, —S(O)$_2$—N(H)—$R^{14}$, —N(H)—C(O)—$R^{15}$, and —N(H)—S(O)$_2$—$R^{15}$, wherein pyrazolyl is optionally substituted with lower alkyl or heterocycloalkyl;

$R^7$ is H, halogen, or lower alkyl;

$R^8$ is H, halogen, or lower alkoxy;

$R^9$ is H or halogen;

$R^{10}$ and $R^{13}$ are independently —H, lower alkyl, lower alkyl substituted with —O—CH$_3$, lower alkyl substituted with di-alklylamine, or lower alkyl substituted with heterocycloalkyl;

$R^{11}$ and $R^{14}$ are independently hydrogen or lower alkyl; and $R^{12}$ and $R^{15}$ are each independently lower alkyl, with the proviso that the compound is other than those set forth in Table 1.

In some embodiments, $R^1$, $R^3$ and $R^4$ are each independently selected from the group consisting of —H, lower alkoxy, halogen, halogen substituted lower alkyl, alkoxy substituted lower alkyl, cycloalkylamino, —CN, —O—$R^{40}$, —S(O)$_2$—$R^{41}$, —S(O)$_2$—N(H)—$R^{42}$, N(H)—$R^{42}$, —N($R^{42}$)$_2$, and —N(H)—S(O)$_2$—$R^{43}$, provided that at least two of $R^1$, $R^2$, $R^3$ and $R^4$ are —H and $R^2$ is —F, —Cl or —Br; or $R^1$, $R^2$ and $R^3$ are —H and $R^4$ is —CF$_3$; or $R^1$ and $R^4$ are —H, $R^2$ is —O—CH$_3$, and $R^3$ is —F; or $R^2$ and $R^4$ are —H, $R^1$ is —O—CH$_3$, and $R^3$ is —F;

$R^5$ is selected from the group consisting of —H, —F, —Cl, —Br, lower alkyl, fluoro substituted lower alkyl, lower alkenyl, lower alkynyl, cycloalkyl, phenyl, pyrazolyl, —CN, —O—$R^{10}$, —C(O)—N(H)—$R^{11}$, —C(O)—O—$R^{11}$, —S(O)$_2$—$R^{12}$, —S(O)$_2$—N(H)—$R^{11}$, —N(H)—C(O)—$R^{12}$, and —N(H)—S(O)$_2$—$R^{12}$, wherein pyrazolyl is optionally substituted with lower alkyl or heterocycloalkyl;

$R^6$ is selected from the group consisting of —H, —F, —Cl, —Br, lower alkyl, fluoro substituted lower alkyl, lower alkenyl, lower alkynyl, cycloalkyl, phenyl, pyrazolyl, —CN, —C(O)—N(H)—$R^{14}$, —C(O)—O—$R^{14}$, —S(O)$_2$—$R^{15}$, —S(O)$_2$—N(H)—$R^{14}$, —N(H)—C(O)—$R^{15}$, and —N(H)—S(O)$_2$—$R^{15}$, wherein pyrazolyl is optionally substituted with lower alkyl or heterocycloalkyl;

$R^7$ is —H, —F, —Cl, or —CH$_3$;

$R^8$ is —H, —F, —CH$_3$, or —O—CH$_3$;

$R^9$ is —H or —Cl;

$R^{10}$ and $R^{13}$ are independently —H, lower alkyl, lower alkyl substituted with —O—CH$_3$, lower alkyl substituted with di-alklylamine, or lower alkyl substituted with heterocycloalkyl;

$R^{11}$ and $R^{14}$ are independently hydrogen or lower alkyl; and $R^{12}$ and $R^{15}$ are independently lower alkyl.

In some embodiments, Ar is:

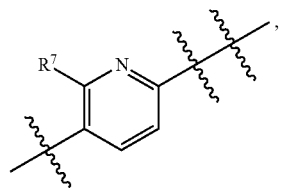

wherein $R^7$ is as defined herein.

In some embodiments, Ar is

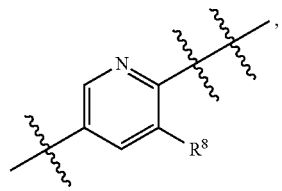

wherein $R^8$ is as defined herein.

In some embodiments, Ar is

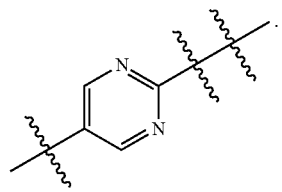

In some embodiments, Ar is

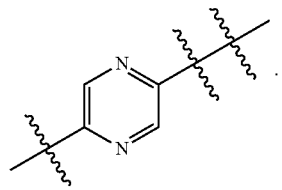

In some embodiments,

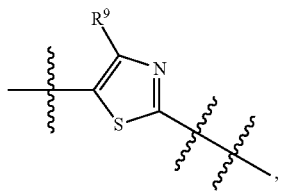

wherein $R^9$ is as defined herein.

In some embodiments, $R^1$, $R^3$ and $R^4$ are H and $R^2$ is halogen. In other embodiments, $R^1$, $R^2$ and $R^3$ are —H and $R^4$ is halo substituted lower alkyl. In other embodiments, $R^1$ and $R^4$ are —H and $R^2$ is lower alkoxy. In some embodiments, $R^3$ is halogen. In yet other embodiments, $R^2$ and $R^4$ are —H, $R^1$ is lower alkoxy and $R^3$ is halogen. In certain instances, i) $R^1$, $R^2$ and $R^3$ are —H and $R^4$ is $CF_3$; or ii) $R^1$ and $R^4$ are —H and $R^2$ is —$OCH_3$; or iii) $R^3$ is F; or iv) $R^2$ and $R^4$ are —H, $R^1$ is $OCH_3$ and $R^3$ is F. The variables $R^5$, $R^6$ and Ar are as defined herein.

In some embodiments of compounds of Formula I', $R^5$ is —F, —Cl, —Br, lower alkyl, fluoro substituted lower alkyl, lower alkenyl, lower alkynyl, cycloalkyl, phenyl, pyrazolyl, —CN, —O—$R^{10}$, —C(O)—N(H)—$R^1$—C(O)—O—$R^1$—S(O)$_2$—$R^{12}$, —S(O)$_2$—N(H)—$R^{11}$, —N(H)—C(O)—$R^{12}$, and —N(H)—S(O)$_2$—$R^{12}$, wherein pyrazolyl is optionally substituted with lower alkyl or heterocycloalkyl. In certain instances, $R^5$ is H. All the other variables are as defined herein.

In some embodiments of compounds of Formula I', $R^5$ is —H. In some embodiments, $R^5$ is —H and $R^6$ is —H, —F, —Cl, —$CH_3$, —$CF_3$, —CN, —O—$CH_3$, —S(O)$_2$—$CH_3$, —C(O)—NH—$CH_3$, —C(O)—O—$CH_3$, —NHC(O)$CH_3$, —NHS(O)$_2CH_3$, or cyclopropyl. All the other variables are as defined herein.

In some embodiments of compounds of Formula I', $R^6$ is selected from the group consisting of H, halo, lower alkyl, lower alkoxy, fluoro substituted lower alkyl, lower alkenyl, lower alkynyl, cycloalkyl, phenyl, pyrazolyl, —CN, —O—$R^{13}$, —C(O)—N(H)—$R^{14}$, —C(O)—O—$R^{14}$, —S(O)$_2$—$R^{15}$, —S(O)$_2$—N(H)—$R^{14}$, —N(H)—C(O)—$R^{15}$, and —N(H)—S(O)$_2$—$R^{15}$, wherein pyrazolyl is optionally substituted with lower alkyl or heterocycloalkyl. In certain instances, $R^6$ is halo, lower alkyl or fluoro substituted lower alkyl. All the other variables are as defined herein.

In some embodiments of compounds of Formula I', $R^6$ is —H. In some embodiments, $R^6$ is —H and $R^5$ is —H, —Cl, —CN, —C≡CH, —O—$CH_3$, or phenyl. In other embodiments, $R^6$ is halo, lower alkyl lower alkoxy, or fluoro substituted lower alkyl. In yet other embodiments, $R^6$ is halogen, methyl, methoxy, trifluoromethyl, or CN. All the other variables are as defined herein.

In some embodiments of compounds of Formula I', $R^7$ is H, halogen or lower alkyl. In other embodiments, $R^7$ is H, —F, —Cl, Br or —$CH_3$. All the other variables are as defined herein.

In some embodiments of compounds of Formula I', $R^8$ is H, halogen or lower alkoxy. In other embodiments, $R^8$ is H, —F, —Cl, Br or —$OCH_3$. All the other variables are as defined herein.

In some embodiments of compounds of Formula I', $R^9$ is H or halogen. In other embodiments, $R^9$ is —H or —Cl. All the other variables are as defined herein.

In some embodiments of compounds of Formula I', $R^1$, $R^3$ and $R^4$ are —H; $R^2$ is —F, —Cl or —Br; and $R^5$ is —H. In some embodiments, $R^1$, $R^3$ and $R^4$ are —H; $R^2$ is —F, —Cl or —Br; $R^5$ is —H; and $R^6$ is —H, —F, —Cl, —$CH_3$, —$CF_3$, —CN, —O—$CH_3$, —S(O)$_2$—$CH_3$, —C(O)—NH—$CH_3$, —C(O)—O—$CH_3$, —NHC(O)$CH_3$, —NHS(O)$_2CH_3$, or cyclopropyl. All the other variables are as defined herein.

In some embodiments of compounds of Formula I', $R^1$, $R^3$ and $R^4$ are —H; $R^2$ is —F, —Cl or —Br; and $R^6$ is —H. In some embodiments, $R^1$, $R^3$ and $R^4$ are —H; $R^2$ is —F, —Cl or —Br; $R^6$ is —H; and $R^5$ is —H, —Cl, —CN, —C≡CH, —O—$CH_3$, or phenyl. All the other variables are as defined herein.

In some embodiments of compounds of Formula I', $R^1$, $R^2$ and $R^3$ are —H; and $R^4$ is —$CF_3$; and $R^5$ is —H. In some embodiments, $R^1$, $R^2$ and $R^3$ are —H; and $R^4$ is —$CF_3$; $R^5$ is —H; and $R^6$ is —H, —F, —Cl, —$CH_3$, —$CF_3$, —CN, —S(O)$_2$—$CH_3$, —C(O)—NH—$CH_3$, —C(O)—O—$CH_3$, —NHC(O)$CH_3$, —NHS(O)$_2CH_3$, or cyclopropyl. All the other variables are as defined herein.

In some embodiments of compounds of Formula I', $R^1$, $R^2$ and $R^3$ are —H; and $R^4$ is —$CF_3$; and $R^6$ is —H. In some embodiments, $R^1$, $R^2$ and $R^3$ are —H; and $R^4$ is —$CF_3$; $R^6$ is —H; and $R^5$ is —H, —Cl, —CN, —C≡CH, —O—$CH_3$, or phenyl. All the other variables are as defined herein.

In some embodiments of compounds of Formula I', $R^1$ and $R^4$ are —H; $R^2$ is —O—$CH_3$; $R^3$ is —F; and $R^5$ is —H. In some embodiments, $R^1$ and $R^4$ are —H; $R^2$ is —O—$CH_3$; $R^3$ is —F; $R^5$ is —H; and $R^6$ is —H, —F, —Cl, —$CH_3$, —$CF_3$, —CN, —O—$CH_3$, —S(O)$_2$—$CH_3$, —C(O)—NH—$CH_3$, —C(O)—O—$CH_3$, —NHC(O)$CH_3$, —NHS(O)$_2CH_3$, or cyclopropyl. All the other variables are as defined herein.

In some embodiments of compounds of Formula I', $R^1$ and $R^4$ are —H; $R^2$ is —O—$CH_3$; $R^3$ is —F; and $R^6$ is —H. In some embodiments, $R^1$ and $R^4$ are —H; $R^2$ is —O—$CH_3$; $R^3$ is —F; $R^6$ is —H; and $R^5$ is —H, —Cl, —CN, —C≡CH, —O—$CH_3$, or phenyl. All the other variables are as defined herein.

In some embodiments of compounds of Formula I', $R^2$ and $R^4$ are —H; $R^1$ is —O—$CH_3$; $R^3$ is —F; and $R^5$ is —H. In some embodiments, $R^2$ and $R^4$ are —H; $R^1$ is —O—$CH_3$; $R^3$ is —F; $R^5$ is —H; and $R^6$ is —H, —F, —Cl, —$CH_3$, —$CF_3$, —CN, —O—$CH_3$, —S(O)$_2$—$CH_3$, —C(O)—NH—$CH_3$, —C(O)—O—$CH_3$, —NHC(O)$CH_3$, —NHS(O)$_2CH_3$, or cyclopropyl. All the other variables are as defined herein.

In some embodiments of compounds of Formula I', $R^2$ and $R^4$ are —H; $R^1$ is —O—$CH_3$; $R^3$ is —F; and $R^6$ is —H. In some embodiments, $R^2$ and $R^4$ are —H; $R^1$ is —O—$CH_3$; $R^3$ is —F; $R^6$ is —H; and $R^5$ is —H, —Cl, —CN, —C≡CH, —O—$CH_3$, or phenyl. All the other variables are as defined herein.

In another aspect, compounds having the structure according to the following Formula I are provided:

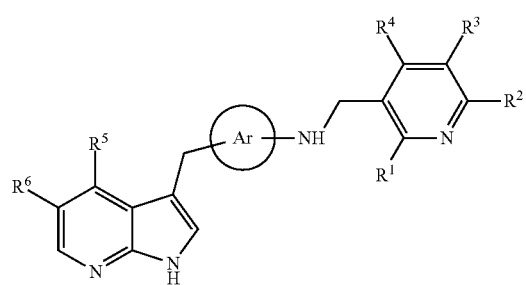

Formula I or a salt, a prodrug, a tautomer or a stereoisomer thereof, wherein:

Ar is selected from the group consisting of

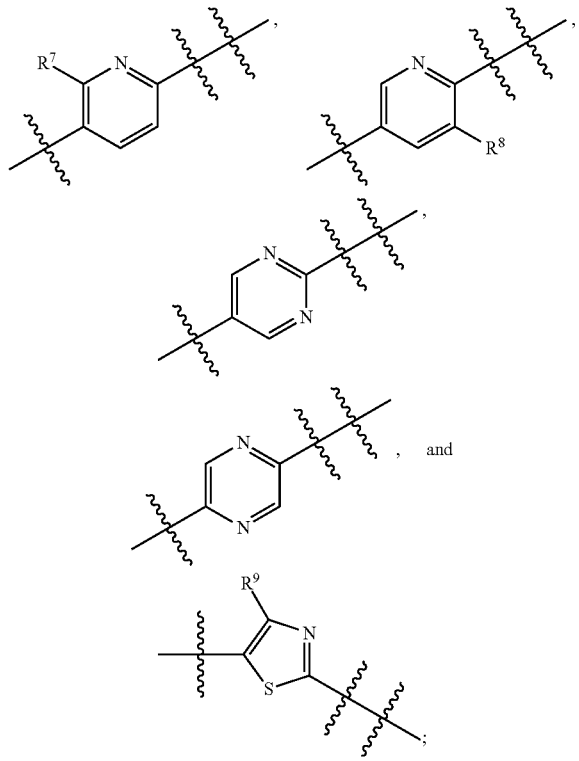

wherein

indicates the point of attachment of Ar to —CH$_2$— of Formula I and wherein

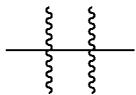 [SMILES: **]

indicates the point of attachment of Ar to —NH— of Formula I;

R$^1$, R$^3$ and R$^4$ are —H and R$^2$ is —F, —Cl or —Br; or R', R$^2$ and R$^3$ are —H and R$^4$ is —CF$_3$; or R$^1$ and R$^4$ are —H, R$^2$ is —O—CH$_3$, and R$^3$ is —F; or R$^2$ and R$^4$ are —H, R$^1$ is —O—CH$_3$, and R$^3$ is —F;

R$^5$ is selected from the group consisting of —H, —F, —Cl, —Br, lower alkyl, fluoro substituted lower alkyl, lower alkenyl, lower alkynyl, cycloalkyl, phenyl, pyrazolyl, —CN, —O—R$^{10}$, —C(O)—N(H)—R$^{11}$, —C(O)—O—R$^{11}$, —S(O)$_2$—R$^{12}$, —S(O)$_2$—N(H)—R$^{11}$, —N(H)—C(O)—R$^{12}$, and —N(H)—S(O)$_2$—R$^{12}$, wherein pyrazolyl is optionally substituted with lower alkyl or heterocycloalkyl;

R$^6$ is selected from the group consisting of —H, —F, —Cl, —Br, lower alkyl, fluoro substituted lower alkyl, lower alkenyl, lower alkynyl, cycloalkyl, phenyl, pyrazolyl, —CN, —C(O)—N(H)—R$^{14}$, —C(O)—O—R$^{14}$, —S(O)$_2$—R$^{15}$, —S(O)$_2$—N(H)—R$^{14}$, —N(H)—C(O)—R$^{15}$, and —N(H)—S(O)$_2$—R$^{15}$, wherein pyrazolyl is optionally substituted with lower alkyl or heterocycloalkyl;

R$^7$ is —H, —F, —Cl, or —CH$_3$;

R$^8$ is —H, —F, —CH$_3$, or —O—CH$_3$;

R$^9$ is —H or —Cl;

R$^{10}$ and R$^{13}$ are independently —H, lower alkyl, lower alkyl substituted with —O—CH$_3$, lower alkyl substituted with di-alklylamine, or lower alkyl substituted with heterocycloalkyl;

R$^{11}$ and R$^{14}$ are independently hydrogen or lower alkyl; and

R$^{12}$ and R$^{15}$ are independently lower alkyl.

In some embodiments of compounds of Formula I, R$^5$ is —H. In some embodiments, R$^5$ is —H and R$^6$ is —H, —F, —Cl, —CH$_3$, —CF$_3$, —CN, —O—CH$_3$, —S(O)$_2$—CH$_3$, —C(O)—NH—CH$_3$, —C(O)—O—CH$_3$, —NHC(O)CH$_3$, —NHS(O)$_2$CH$_3$, or cyclopropyl.

In some embodiments of compounds of Formula I, R$^6$ is —H. In some embodiments, R$^6$ is —H and R$^5$ is —H, —Cl, —CN, —C≡CH, —O—CH$_3$, or phenyl.

In some embodiments of compounds of Formula I, R$^1$, R$^3$ and R$^4$ are —H; R$^2$ is —F, —Cl or —Br; and R$^5$ is —H. In some embodiments, R', R$^3$ and R$^4$ are —H; R$^2$ is —F, —Cl or —Br; R$^5$ is —H; and R$^6$ is —H, —F, —Cl, —CH$_3$, —CF$_3$, —CN, —O—CH$_3$, —S(O)$_2$—CH$_3$, —C(O)—NH—CH$_3$, —C(O)—O—CH$_3$, —NHC(O)CH$_3$, —NHS(O)$_2$CH$_3$, or cyclopropyl.

In some embodiments of compounds of Formula I, R$^1$, R$^3$ and R$^4$ are —H; R$^2$ is —F, —Cl or —Br; and R$^6$ is —H. In some embodiments, R$^1$, R$^3$ and R$^4$ are —H; R$^2$ is —F, —Cl or —Br; R$^6$ is —H; and R$^5$ is —H, —Cl, —CN, —C≡CH, —O—CH$_3$, or phenyl.

In some embodiments of compounds of Formula I, R$^1$, R$^2$ and R$^3$ are —H; and R$^4$ is —CF$_3$; and R$^5$ is —H. In some embodiments, R$^1$, R$^2$ and R$^3$ are —H; and R$^4$ is —CF$_3$; R$^s$ is —H; and R$^6$ is —H, —F, —Cl, —CH$_3$, —CF$_3$, —CN, —O—CH$_3$, —S(O)$_2$—CH$_3$, —C(O)—NH—CH$_3$, —C(O)—O—CH$_3$, —NHC(O)CH$_3$, —NHS(O)$_2$CH$_3$, or cyclopropyl.

In some embodiments of compounds of Formula I, R$^1$, R$^2$ and R$^3$ are —H; and R$^4$ is —CF$_3$; and R$^6$ is —H. In some embodiments, R$^1$, R$^2$ and R$^3$ are —H; and R$^4$ is —CF$_3$; R$^6$ is —H; and R$^5$ is —H, —Cl, —CN, —C≡CH, —O—CH$_3$, or phenyl.

In some embodiments of compounds of Formula I, R$^1$ and R$^4$ are —H; R$^2$ is —O—CH$_3$; R$^3$ is —F; and R$^5$ is —H. In some embodiments, R$^1$ and R$^4$ are —H; R$^2$ is —O—CH$_3$; R$^3$ is —F; R$^S$ is —H; and R$^6$ is —H, —F, —Cl, —CH$_3$, —CF$_3$, —CN, —O—CH$_3$, —S(O)$_2$—CH$_3$, —C(O)—NH—CH$_3$, —C(O)—O—CH$_3$, —NHC(O)CH$_3$, —NHS(O)$_2$CH$_3$, or cyclopropyl.

In some embodiments of compounds of Formula I, R$^1$ and R$^4$ are —H; R$^2$ is —O—CH$_3$; R$^3$ is —F; and R$^6$ is —H. In some embodiments, R$^1$ and R$^4$ are —H; R$^2$ is —O—CH$_3$; R$^3$ is —F; R$^6$ is —H; and R$^5$ is —H, —Cl, —CN, —CCH, —O—CH$_3$, or phenyl.

In some embodiments of compounds of Formula I, R$^2$ and R$^4$ are —H; R$^1$ is —O—CH$_3$; R$^3$ is —F; and R$^5$ is —H. In some embodiments, R$^2$ and R$^4$ are —H; R$^1$ is —O—CH$_3$; R$^3$ is —F; R$^5$ is —H; and R$^6$ is —H, —F, —Cl, —CH$_3$, —CF$_3$, —CN, —O—CH$_3$, —S(O)$_2$—CH$_3$, —C(O)—NH—CH$_3$, —C(O)—O—CH$_3$, —NHC(O)CH$_3$, —NHS(O)$_2$CH$_3$, or cyclopropyl.

In some embodiments of compounds of Formula I, $R^2$ and $R^4$ are —H; $R^1$ is —O—$CH_3$; $R^3$ is —F; and $R^6$ is —H. In some embodiments, $R^2$ and $R^4$ are —H; $R^1$ is —O—$CH_3$; $R^3$ is —F; $R^6$ is —H; and $R^5$ is —H, —Cl, —CN, —CCH, —O—$CH_3$, or phenyl.

In one embodiment of compounds of Formulae I and I', the compound is selected from the group consisting of:

[5-(5-Bromo-1H-pyrrolo[2,3-b]pyridin-3-ylmethyl)-6-fluoro-pyridin-2-yl]-(5-fluoro-2-methoxy-pyridin-3-ylmethyl)-amine (P-1497), (6-Chloro-pyridin-3-ylmethyl)-[5-(1H-pyrrolo[2,3-b]pyridin-3-ylmethyl)-pyridin-2-yl]-amine (P-1498), (6-Chloro-pyridin-3-ylmethyl)-[6-fluoro-5-(1H-pyrrolo[2,3-b]pyridin-3-ylmethyl)-pyridin-2-yl]-amine (P-1499), (5-Fluoro-2-methoxy-pyridin-3-ylmethyl)-[6-fluoro-5-(1H-pyrrolo[2,3-b]pyridin-3-ylmethyl)-pyridin-2-yl]-amine (P-1500),

[6-Fluoro-5-(1H-pyrrolo[2,3-b]pyridin-3-ylmethyl)-pyridin-2-yl]-(4-trifluoromethyl-pyridin-3-ylmethyl)-amine (P-1501), (5-Fluoro-6-methoxy-pyridin-3-ylmethyl)-[5-(1H-pyrrolo[2,3-b]pyridin-3-ylmethyl)-pyridin-2-yl]-amine (P-1502), (5-Fluoro-2-methoxy-pyridin-3-ylmethyl)-[5-(1H-pyrrolo[2,3-b]pyridin-3-ylmethyl)-pyridin-2-yl]-amine (P-1403),

[5-(1H-Pyrrolo[2,3-b]pyridin-3-ylmethyl)-pyridin-2-yl]-(4-trifluoromethyl-pyridin-3-ylmethyl)-amine (P-1504),

[5-(5-Chloro-1H-pyrrolo[2,3-b]pyridin-3-ylmethyl)-pyridin-2-yl]-(5-fluoro-2-methoxy-pyridin-3-ylmethyl)-amine (P-1505),

[6-Chloro-5-(1H-pyrrolo[2,3-b]pyridin-3-ylmethyl)-pyridin-2-yl]-(5-fluoro-6-methoxy-pyridin-3-ylmethyl)-amine (P-1506), (6-Chloro-pyridin-3-ylmethyl)-[6-chloro-5-(1H-pyrrolo[2,3-b]pyridin-3-ylmethyl)-pyridin-2-yl]-amine (P-1508),

[6-Chloro-5-(1H-pyrrolo[2,3-b]pyridin-3-ylmethyl)-pyridin-2-yl]-(5-fluoro-2-methoxy-pyridin-3-ylmethyl)-amine (P-1509),

[6-Chloro-5-(1H-pyrrolo[2,3-b]pyridin-3-ylmethyl)-pyridin-2-yl]-(4-trifluoromethyl-pyridin-3-ylmethyl)-amine (P-1510), (5-Fluoro-6-methoxy-pyridin-3-ylmethyl)-[5-(1H-pyrrolo[2,3-b]pyridin-3-ylmethyl)-pyrimidin-2-yl]-amine (P-1513), (6-Chloro-pyridin-3-ylmethyl)-[5-(1H-pyrrolo[2,3-b]pyridin-3-ylmethyl)-pyrimidin-2-yl]-amine (P-1515),

[5-(1H-Pyrrolo[2,3-b]pyridin-3-ylmethyl)-pyrimidin-2-yl]-(4-trifluoromethyl-pyridin-3-ylmethyl)-amine (P-1516), (5-Fluoro-2-methoxy-pyridin-3-ylmethyl)-[5-(1H-pyrrolo[2,3-b]pyridin-3-ylmethyl)-pyrimidin-2-yl]-amine (P-1520),

[4-Chloro-5-(1H-pyrrolo[2,3-b]pyridin-3-ylmethyl)-thiazol-2-yl]-(5-fluoro-6-methoxy-pyridin-3-ylmethyl)-amine (P-1521), (6-Chloro-pyridin-3-ylmethyl)-[4-chloro-5-(1H-pyrrolo[2,3-b]pyridin-3-ylmethyl)-thiazol-2-yl]-amine (P-1523),

[4-Chloro-5-(1H-pyrrolo[2,3-b]pyridin-3-ylmethyl)-thiazol-2-yl]-(5-fluoro-2-methoxy-pyridin-3-ylmethyl)-amine (P-1524),

[4-Chloro-5-(1H-pyrrolo[2,3-b]pyridin-3-ylmethyl)-thiazol-2-yl]-(4-trifluoromethyl-pyridin-3-ylmethyl)-amine (P-1525), (5-Fluoro-2-methoxy-pyridin-3-ylmethyl)-[5-(5-methyl-1H-pyrrolo[2,3-b]pyridin-3-ylmethyl)-pyridin-2-yl]-amine (P-1528), (5-Fluoro-6-methoxy-pyridin-3-ylmethyl)-[5-(5-methyl-1H-pyrrolo[2,3-b]pyridin-3-ylmethyl)-pyridin-2-yl]-amine (P-1529), (6-Chloro-pyridin-3-ylmethyl)-[5-(5-methyl-1H-pyrrolo[2,3-b]pyridin-3-ylmethyl)-pyridin-2-yl]-amine (P-1531), (5-Fluoro-6-methoxy-pyridin-3-ylmethyl)-[6-methyl-5-(5-methyl-1H-pyrrolo[2,3-b]pyridin-3-ylmethyl)-pyridin-2-yl]-amine (P-1533), (6-Chloro-pyridin-3-ylmethyl)-[6-methyl-5-(5-methyl-1H-pyrrolo[2,3-b]pyridin-3-ylmethyl)-pyridin-2-yl]-amine (P-1535), (5-Fluoro-2-methoxy-pyridin-3-ylmethyl)-[6-methyl-5-(5-methyl-1H-pyrrolo[2,3-b]pyridin-3-ylmethyl)-pyridin-2-yl]-amine (P-1536),

[6-Methyl-5-(5-methyl-1H-pyrrolo[2,3-b]pyridin-3-ylmethyl)-pyridin-2-yl]-(4-trifluoromethyl-pyridin-3-ylmethyl)-amine (P-1537),

[6-Chloro-5-(5-methyl-1H-pyrrolo[2,3-b]pyridin-3-ylmethyl)-pyridin-2-yl]-(5-fluoro-6-methoxy-pyridin-3-ylmethyl)-amine (P-1540),

[6-Chloro-5-(5-methyl-1H-pyrrolo[2,3-b]pyridin-3-ylmethyl)-pyridin-2-yl]-(6-chloro-pyridin-3-ylmethyl)-amine (P-1542),

[6-Chloro-5-(5-methyl-1H-pyrrolo[2,3-b]pyridin-3-ylmethyl)-pyridin-2-yl]-(5-fluoro-2-methoxy-pyridin-3-ylmethyl)-amine (P-1543),

[6-Chloro-5-(5-methyl-1H-pyrrolo[2,3-b]pyridin-3-ylmethyl)-pyridin-2-yl]-(4-trifluoromethyl-pyridin-3-ylmethyl)-amine (P-1544), (5-Fluoro-2-methoxy-pyridin-3-ylmethyl)-[3-methoxy-5-(5-methyl-1H-pyrrolo[2,3-b]pyridin-3-ylmethyl)-pyridin-2-yl]-amine (P-1547), (5-Fluoro-6-methoxy-pyridin-3-ylmethyl)-[3-methoxy-5-(5-methyl-1H-pyrrolo[2,3-b]pyridin-3-ylmethyl)-pyridin-2-yl]-amine (P-1548), (6-Chloro-pyridin-3-ylmethyl)-[3-methoxy-5-(5-methyl-1H-pyrrolo[2,3-b]pyridin-3-ylmethyl)-pyridin-2-yl]-amine (P-1550),

[3-Methoxy-5-(5-methyl-1H-pyrrolo[2,3-b]pyridin-3-ylmethyl)-pyridin-2-yl]-(4-trifluoromethyl-pyridin-3-ylmethyl)-amine (P-1551), (5-Fluoro-6-methoxy-pyridin-3-ylmethyl)-[3-methyl-5-(5-methyl-1H-pyrrolo[2,3-b]pyridin-3-ylmethyl)-pyridin-2-yl]-amine (P-1555), (6-Chloro-pyridin-3-ylmethyl)-[3-methyl-5-(5-methyl-1H-pyrrolo[2,3-b]pyridin-3-ylmethyl)-pyridin-2-yl]-amine (P-1557), (5-Fluoro-2-methoxy-pyridin-3-ylmethyl)-[3-methyl-5-(5-methyl-1H-pyrrolo[2,3-b]pyridin-3-ylmethyl)-pyridin-2-yl]-amine (P-1558),

[3-Methyl-5-(5-methyl-1H-pyrrolo[2,3-b]pyridin-3-ylmethyl)-pyridin-2-yl]-(4-trifluoromethyl-pyridin-3-ylmethyl)-amine (P-1559), (5-Fluoro-6-methoxy-pyridin-3-ylmethyl)-[3-fluoro-5-(5-methyl-1H-pyrrolo[2,3-b]pyridin-3-ylmethyl)-pyridin-2-yl]-amine (P-1563), (6-Chloro-pyridin-3-ylmethyl)-[3-fluoro-5-(5-methyl-1H-pyrrolo[2,3-b]pyridin-3-ylmethyl)-pyridin-2-yl]-amine (P-1565), (5-Fluoro-2-methoxy-pyridin-3-ylmethyl)-[3-fluoro-5-(5-methyl-1H-pyrrolo[2,3-b]pyridin-3-ylmethyl)-pyridin-2-yl]-amine (P-1566),

[3-Fluoro-5-(5-methyl-1H-pyrrolo[2,3-b]pyridin-3-ylmethyl)-pyridin-2-yl]-(4-trifluoromethyl-pyridin-3-ylmethyl)-amine (P-1567),

[5-(5-Methyl-1H-pyrrolo[2,3-b]pyridin-3-ylmethyl)-pyrimidin-2-yl]-(4-trifluoromethyl-pyridin-3-ylmethyl)-amine (P-1570), (5-Fluoro-6-methoxy-pyridin-3-ylmethyl)-[5-(5-methyl-1H-pyrrolo[2,3-b]pyridin-3-ylmethyl)-thiazol-2-yl]-amine (P-1579), (6-Chloro-pyridin-3-ylmethyl)-[5-(5-methyl-1H-pyrrolo[2,3-b]pyridin-3-ylmethyl)-thiazol-2-yl]-amine (P-1581),

[5-(5-Methyl-1H-pyrrolo[2,3-b]pyridin-3-ylmethyl)-thiazol-2-yl]-(4-trifluoromethyl-pyridin-3-ylmethyl)-amine (P-1582), (5-Fluoro-6-methoxy-pyridin-3-ylmethyl)-[5-(5-methoxy-1H-pyrrolo[2,3-b]pyridin-3-ylmethyl)-pyridin-2-yl]-amine (P-1584), (6-Chloro-pyridin-3-ylmethyl)-[5-(5-methoxy-1H-pyrrolo[2,3-b]pyridin-3-ylmethyl)-pyridin-2-yl]-amine (P-1586), (5-Fluoro-2-methoxy-pyridin-3-ylmethyl)-[5-(5-methoxy-1H-pyrrolo[2,3-b]pyridin-3-ylmethyl)-pyridin-2-yl]-amine (P-1587),

[5-(5-Methoxy-1H-pyrrolo[2,3-b]pyridin-3-ylmethyl)-pyridin-2-yl]-(4-trifluoromethyl-pyridin-3-ylmethyl)-amine (P-1588),

[6-Chloro-5-(5-methoxy-1H-pyrrolo[2,3-b]pyridin-3-ylmethyl)-pyridin-2-yl]-(5-fluoro-6-methoxy-pyridin-3-ylmethyl)-amine (P-1590),

[6-Chloro-5-(5-methoxy-1H-pyrrolo[2,3-b]pyridin-3-ylmethyl)-pyridin-2-yl]-(6-chloro-pyridin-3-ylmethyl)-amine (P-1592),

[6-Chloro-5-(5-methoxy-1H-pyrrolo[2,3-b]pyridin-3-ylmethyl)-pyridin-2-yl]-(5-fluoro-2-methoxy-pyridin-3-ylmethyl)-amine (P-1593),

[6-Chloro-5-(5-methoxy-1H-pyrrolo[2,3-b]pyridin-3-ylmethyl)-pyridin-2-yl]-(4-trifluoromethyl-pyridin-3-ylmethyl)-amine (P-1594), (6-Chloro-pyridin-3-ylmethyl)-[6-fluoro-5-(5-methoxy-1H-pyrrolo[2,3-b]pyridin-3-ylmethyl)-pyridin-2-yl]-amine (P-1597),

[6-Fluoro-5-(5-methoxy-1H-pyrrolo[2,3-b]pyridin-3-ylmethyl)-pyridin-2-yl]-(4-trifluoromethyl-pyridin-3-ylmethyl)-amine (P-1598), (5-Fluoro-2-methoxy-pyridin-3-ylmethyl)-[5-(5-methoxy-1H-pyrrolo[2,3-b]pyridin-3-ylmethyl)-pyrimidin-2-yl]-amine (P-1599), (5-Fluoro-6-methoxy-pyridin-3-ylmethyl)-[5-(5-methoxy-1H-pyrrolo[2,3-b]pyridin-3-ylmethyl)-pyrimidin-2-yl]-amine (P-1600), (6-Chloro-pyridin-3-ylmethyl)-[5-(5-methoxy-1H-pyrrolo[2,3-b]pyridin-3-ylmethyl)-pyrimidin-2-yl]-amine (P-1602),

[5-(5-Methoxy-1H-pyrrolo[2,3-b]pyridin-3-ylmethyl)-pyrimidin-2-yl]-(4-trifluoromethyl-pyridin-3-ylmethyl)-amine (P-1603), (6-Chloro-pyridin-3-ylmethyl)-[5-(5-chloro-1H-pyrrolo[2,3-b]pyridin-3-ylmethyl)-6-fluoro-pyridin-2-yl]-amine (P-1607),

[5-(5-Chloro-1H-pyrrolo[2,3-b]pyridin-3-ylmethyl)-6-fluoro-pyridin-2-yl]-(4-trifluoromethyl-pyridin-3-ylmethyl)-amine (P-1608),

[5-(5-Chloro-1H-pyrrolo[2,3-b]pyridin-3-ylmethyl)-pyrimidin-2-yl]-(5-fluoro-6-methoxy-pyridin-3-ylmethyl)-amine (P-1611), (6-Chloro-pyridin-3-ylmethyl)-[5-(5-chloro-1H-pyrrolo[2,3-b]pyridin-3-ylmethyl)-pyrimidin-2-yl]-amine (P-1612),

[5-(5-Chloro-1H-pyrrolo[2,3-b]pyridin-3-ylmethyl)-pyrimidin-2-yl]-(4-trifluoromethyl-pyridin-3-ylmethyl)-amine (P-1613),

[6-Fluoro-5-(5-fluoro-1H-pyrrolo[2,3-b]pyridin-3-ylmethyl)-pyridin-2-yl]-(5-fluoro-6-methoxy-pyridin-3-ylmethyl)-amine (P-1623), (6-Chloro-pyridin-3-ylmethyl)-[6-fluoro-5-(5-fluoro-1H-pyrrolo[2,3-b]pyridin-3-ylmethyl)-pyridin-2-yl]-amine (P-1625),

[6-Fluoro-5-(5-fluoro-1H-pyrrolo[2,3-b]pyridin-3-ylmethyl)-pyridin-2-yl]-(5-fluoro-2-methoxy-pyridin-3-ylmethyl)-amine (P-1626),

[6-Fluoro-5-(5-fluoro-1H-pyrrolo[2,3-b]pyridin-3-ylmethyl)-pyridin-2-yl]-(4-trifluoromethyl-pyridin-3-ylmethyl)-amine (P-1627), (5-Fluoro-6-methoxy-pyridin-3-ylmethyl)-[5-(5-fluoro-1H-pyrrolo[2,3-b]pyridin-3-ylmethyl)-pyrimidin-2-yl]-amine (P-1630), (6-Chloro-pyridin-3-ylmethyl)-[5-(5-fluoro-1H-pyrrolo[2,3-b]pyridin-3-ylmethyl)-pyrimidin-2-yl]-amine (P-1632), (5-Fluoro-2-methoxy-pyridin-3-ylmethyl)-[5-(5-fluoro-1H-pyrrolo[2,3-b]pyridin-3-ylmethyl)-pyrimidin-2-yl]-amine (P-1633),

[5-(5-Fluoro-1H-pyrrolo[2,3-b]pyridin-3-ylmethyl)-pyrimidin-2-yl]-(4-trifluoromethyl-pyridin-3-ylmethyl)-amine (P-1634), (5-Fluoro-6-methoxy-pyridin-3-ylmethyl)-[5-(5-trifluoromethyl-1H-pyrrolo[2,3-b]pyridin-3-ylmethyl)-pyridin-2-yl]-amine (P-1638), (6-Chloro-pyridin-3-ylmethyl)-[5-(5-trifluoromethyl-1H-pyrrolo[2,3-b]pyridin-3-ylmethyl)-pyridin-2-yl]-amine (P-1640), (5-Fluoro-2-methoxy-pyridin-3-ylmethyl)-[5-(5-trifluoromethyl-1H-pyrrolo[2,3-b]pyridin-3-ylmethyl)-pyridin-2-yl]-amine (P-1641), (4-Trifluoromethyl-pyridin-3-ylmethyl)-[5-(5-trifluoromethyl-1H-pyrrolo[2,3-b]pyridin-3-ylmethyl)-pyridin-2-yl]-amine (P-1642), (5-Fluoro-6-methoxy-pyridin-3-ylmethyl)-[6-fluoro-5-(5-trifluoromethyl-1H-pyrrolo[2,3-b]pyridin-3-ylmethyl)-pyridin-2-yl]-amine (P-1646), (6-Chloro-pyridin-3-ylmethyl)-[6-fluoro-5-(5-tri fluoromethyl-1H-pyrrolo[2,3-b]pyridin-3-ylmethyl)-pyridin-2-yl]-amine (P-1648), (5-Fluoro-2-methoxy-pyridin-3-ylmethyl)-[6-fluoro-5-(5-trifluoromethyl-1H-pyrrolo[2,3-b]pyridin-3-ylmethyl)-pyridin-2-yl]-amine (P-1649),

[6-Fluoro-5-(5-trifluoromethyl-1H-pyrrolo[2,3-b]pyridin-3-ylmethyl)-pyridin-2-yl]-(4-trifluoromethyl-pyridin-3-ylmethyl)-amine (P-1650), 3-{2-Fluoro-6-[(5-fluoro-6-methoxy-pyridin-3-ylmethyl)-amino]-pyridin-3-ylmethyl}-1H-pyrrolo[2,3-b]pyridine-5-carbonitrile (P-1654), 3-{6-[(6-Chloro-pyridin-3-ylmethyl)-amino]-2-fluoro-pyridin-3-ylmethyl}-1H-pyrrolo[2,3-b]-pyridine-5-carbonitrile (P-1655), 3-{2-Fluoro-6-[(5-fluoro-2-methoxy-pyridin-3-ylmethyl)-amino]-pyridin-3-ylmethyl}-1H-pyrrolo[2,3-b]pyridine-5-carbonitrile (P-1656), 3-{2-Fluoro-6-[(4-trifluoromethyl-pyridin-3-ylmethyl)-amino]-pyridin-3-ylmethyl}-1H-pyrrolo[2,3-b]pyridine-5-carbonitrile (P-1657),

[5-(5-Cyclopropyl-1H-pyrrolo[2,3-b]pyridin-3-ylmethyl)-pyridin-2-yl]-(5-fluoro-6-methoxy-pyridin-3-ylmethyl)-amine (P-1661), (6-Chloro-pyridin-3-ylmethyl)-[5-(5-cyclopropyl-1H-pyrrolo[2,3-b]pyridin-3-ylmethyl)-pyridin-2-yl]-amine (P-1663),

[5-(5-Cyclopropyl-1H-pyrrolo[2,3-b]pyridin-3-ylmethyl)-pyridin-2-yl]-(5-fluoro-2-methoxy-pyridin-3-ylmethyl)-amine (P-1664),

[5-(5-Cyclopropyl-1H-pyrrolo[2,3-b]pyridin-3-ylmethyl)-pyridin-2-yl]-(4-trifluoromethyl-pyridin-3-ylmethyl)-amine (P-1665), N-(3-{2-Fluoro-6-[(5-fluoro-6-methoxy-pyridin-3-ylmethyl)-amino]-pyridin-3-ylmethyl}-1H-pyrrolo[2,3-b]pyridin-5-yl)-acetamide (P-1670), N-(3-{6-[(6-Chloro-pyridin-3-ylmethyl)-amino]-2-fluoro-pyridin-3-ylmethyl}-1H-pyrrolo[2,3-b]pyridin-5-yl)-acetamide (P-1672), N-(3-{2-Fluoro-6-[(4-tri fluoromethyl-pyridin-3-ylmethyl)-amino]-pyridin-3-ylmethyl}-1H-pyrrolo[2,3-b]pyridin-5-yl)-acetamide (P-1673), N-(3-{2-Fluoro-6-[(5-fluoro-6-methoxy-pyridin-3-ylmethyl)-amino]-pyridin-3-ylmethyl}-1H-pyrrolo[2,3-b]pyridin-5-yl)-methanesulfonamide (P-1677), N-(3-{2-Fluoro-6-[(5-fluoro-2-methoxy-pyridin-3-ylmethyl)-amino]-pyridin-3-ylmethyl}-1H-pyrrolo[2,3-b]pyridin-5-yl)-methanesulfonamide (P-1680), N-(3-{2-Fluoro-6-[(4-tri fluoromethyl-pyridin-3-ylmethyl)-amino]-pyridin-3-ylmethyl}-1H-pyrrolo[2,3-b]pyridin-5-yl)-methanesulfonamide (P-1681),

[6-Fluoro-5-(5-methane sulfonyl-1H-pyrrolo[2,3-b]pyridin-3-ylmethyl)-pyridin-2-yl]-(5-fluoro-6-methoxy-pyridin-3-ylmethyl)-amine (P-1685), (6-Chloro-pyridin-3-ylmethyl)-[6-fluoro-5-(5-methanesulfonyl-1H-pyrrolo[2,3-b]pyridin-3-ylmethyl)-pyridin-2-yl]-amine (P-1687),

[6-Fluoro-5-(5-methane sulfonyl-1H-pyrrolo[2,3-b]pyridin-3-ylmethyl)-pyridin-2-yl]-(5-fluoro-2-methoxy-pyridin-3-ylmethyl)-amine (P-1688),

[6-Fluoro-5-(5-methane sulfonyl-1H-pyrrolo[2,3-b]pyridin-3-ylmethyl)-pyridin-2-yl]-(4-trifluoromethyl-pyridin-3-ylmethyl)-amine (P-1689), 3-{2-Fluoro-6-[(5-fluoro-2-methoxy-pyridin-3-ylmethyl)-amino]-pyridin-3-ylmethyl}-1H-pyrrolo[2,3-b]pyridine-5-carboxylic acid methyl ester (P-1693), 3-{2-Fluoro-6-[(5-fluoro-6-methoxy-pyridin-3-ylmethyl)-amino]-pyridin-3-ylmethyl}-1H-pyrrolo[2,3-b]pyridine-5-carboxylic acid methylamide (P-1694), 3-{2-Fluoro-6-[(5-fluoro-2-methoxy-pyridin-3-ylmethyl)-amino]-pyridin-3-ylmethyl}-1H-pyrrolo[2,3-b]pyridine-5-carboxylic acid methylamide (P-1696), 3-{6-[(6-Chloro-pyridin-3-ylmethyl)-amino]-2-fluoro-pyridin-3-ylmethyl}-1H-pyrrolo[2,3-b]pyridine-5-carboxylic acid methylamide (P-1697), 3-{2-Fluoro-6-[(4-trifluoromethyl-pyridin-3-ylmethyl)-amino]-pyridin-3-ylmethyl}-1H-pyrrolo[2,3-b]pyridine-5-carboxylic acid methylamide (P-1698), (5-Fluoro-2-methoxy-pyridin-3-ylmethyl)-{6-fluoro-5-[5-(1-piperidin-4-yl-1H-pyrazol-4-yl)-1H-pyrrolo[2,3-b]pyridin-3-ylmethyl]-pyridin-2-yl}-amine (P-1703), (5-Fluoro-6-methoxy-pyridin-3-ylmethyl)-{6-fluoro-5-[5-(1-piperidin-4-yl-1H-pyrazol-4-yl)-1H-pyrrolo[2,3-b]pyridin-3-ylmethyl]-pyridin-2-yl}-amine (P-1704), (6-Chloro-pyridin-3-ylmethyl)-{6-fluoro-5-[5-(1-piperidin-4-yl-1H-pyrazol-4-yl)-1H-pyrrolo[2,3-b]pyridin-3-ylmethyl]-pyridin-2-yl}-amine (P-1706), {6-Fluoro-5-[5-(1-piperidin-4-yl-1H-pyrazol-4-yl)-1H-pyrrolo[2,3-b]pyridin-3-ylmethyl]-pyridin-2-yl}-(4-trifluoromethyl-pyridin-3-ylmethyl)-amine (P-1707),

[5-(4-Ethynyl-1H-pyrrolo[2,3-b]pyridin-3-ylmethyl)-pyridin-2-yl]-(5-fluoro-6-methoxy-pyridin-3-ylmethyl)-amine (P-1711), (6-Chloro-pyridin-3-ylmethyl)-[5-(4-ethynyl-1H-pyrrolo[2,3-b]pyridin-3-ylmethyl)-pyridin-2-yl]-amine (P-1713),

[5-(4-Ethynyl-1H-pyrrolo[2,3-b]pyridin-3-ylmethyl)-pyridin-2-yl]-(5-fluoro-2-methoxy-pyridin-3-ylmethyl)-amine (P-1714),

[5-(4-Ethynyl-1H-pyrrolo[2,3-b]pyridin-3-ylmethyl)-pyridin-2-yl]-(4-trifluoromethyl-pyridin-3-ylmethyl)-amine (P-1715), 3-{6-[(6-Chloro-pyridin-3-ylmethyl)-amino]-pyridin-3-ylmethyl}-1H-pyrrolo[2,3-b]pyridine-4-carbonitrile (P-1720), 3-{6-[(5-Fluoro-2-methoxy-pyridin-3-ylmethyl)-amino]-pyridin-3-ylmethyl}-1H-pyrrolo[2,3-b]pyridine-4-carbonitrile (P-1721), 3-{6-[(4-Trifluoromethyl-pyridin-3-ylmethyl)-amino]-pyridin-3-ylmethyl}-1H-pyrrolo[2,3-b]pyridine-4-carbonitrile (P-1722), 3-{6-[(5-Fluoro-6-methoxy-pyridin-3-ylmethyl)-amino]-pyridin-3-ylmethyl}-1H-pyrrolo[2,3-b]pyridine-4-carbonitrile (P-1726), (6-Bromo-pyridin-3-ylmethyl)-[5-(5-chloro-1H-pyrrolo[2,3-b]pyridin-3-ylmethyl)-pyridin-2-yl]-amine (P-2002), (6-Chloro-pyridin-3-ylmethyl)-[5-(5-chloro-1H-pyrrolo[2,3-b]pyridin-3-ylmethyl)-pyridin-2-yl]-amine (P-2003),

[5-(5-Chloro-1H-pyrrolo[2,3-b]pyridin-3-ylmethyl)-pyridin-2-yl]-(6-fluoro-pyridin-3-ylmethyl)-amine (P-2004), (5-Fluoro-6-methoxy-pyridin-3-ylmethyl)-[6-fluoro-5-(5-methoxy-1H-pyrrolo[2,3-b]pyridin-3-ylmethyl)-pyridin-2-yl]-amine (P-2040), (5-Fluoro-6-methoxy-pyridin-3-ylmethyl)-[6-fluoro-5-(1H-pyrrolo[2,3-b]pyridin-3-ylmethyl)-pyridin-2-yl]-amine (P-2041), (5-Fluoro-2-methoxy-pyridin-3-ylmethyl)-[6-fluoro-5-(5-methoxy-1H-pyrrolo[2,3-b]pyridin-3-ylmethyl)-pyridin-2-yl]-amine (P-2042), (5-Fluoro-6-methoxy-pyridin-3-ylmethyl)-[6-fluoro-5-(5-methyl-1H-pyrrolo[2,3-b]pyridin-3-ylmethyl)-pyridin-2-yl]-amine (P-2048), (5-Fluoro-2-methoxy-pyridin-3-ylmethyl)-[6-fluoro-5-(5-methyl-1H-pyrrolo[2,3-b]pyridin-3-ylmethyl)-pyridin-2-yl]-amine (P-2049), (5-Fluoro-2-methoxy-pyridin-3-ylmethyl)-[5-(5-methyl-1H-pyrrolo[2,3-b]pyridin-3-ylmethyl)-pyrimidin-2-yl]-amine (P-2061),

[6-Fluoro-5-(5-methyl-1H-pyrrolo[2,3-b]pyridin-3-ylmethyl)-pyridin-2-yl]-(4-trifluoromethyl-pyridin-3-ylmethyl)-amine (P-2062),

[5-(5-Chloro-1H-pyrrolo[2,3-b]pyridin-3-ylmethyl)-pyridin-2-yl]-(4-trifluoromethyl-pyridin-3-ylmethyl)-amine (P-2063),

[5-(5-Chloro-1H-pyrrolo[2,3-b]pyridin-3-ylmethyl)-pyrimidin-2-yl]-(5-fluoro-2-methoxy-pyridin-3-ylmethyl)-amine (P-2064),

[5-(5-Methyl-1H-pyrrolo[2,3-b]pyridin-3-ylmethyl)-pyridin-2-yl]-(4-trifluoromethyl-pyridin-3-ylmethyl)-amine (P-2070), (5-Fluoro-6-methoxy-pyridin-3-ylmethyl)-[5-(5-methyl-1H-pyrrolo[2,3-b]pyridin-3-ylmethyl)-pyrimidin-2-yl]-amine (P-2073), (6-Chloro-pyridin-3-ylmethyl)-[5-(5-methyl-1H-pyrrolo[2,3-b]pyridin-3-ylmethyl)-pyrimidin-2-yl]-amine (P-2078), (6-Chloro-pyridin-3-ylmethyl)-[6-fluoro-5-(5-methyl-1H-pyrrolo[2,3-b]pyridin-3-ylmethyl)-pyridin-2-yl]-amine (P-2088),

[5-(5-Chloro-1H-pyrrolo[2,3-b]pyridin-3-ylmethyl)-thiazol-2-yl]-(5-fluoro-2-methoxy-pyridin-3-ylmethyl)-amine (P-2152), (5-Fluoro-2-methoxy-pyridin-3-ylmethyl)-[5-(5-methyl-1H-pyrrolo[2,3-b]pyridin-3-ylmethyl)-thiazol-2-yl]-amine (P-2153),

[5-(5-Chloro-1H-pyrrolo[2,3-b]pyridin-3-ylmethyl)-6-fluoro-pyridin-2-yl]-(5-fluoro-6-methoxy-pyridin-3-ylmethyl)-amine (P-2165),

[5-(4-Chloro-1H-pyrrolo[2,3-b]pyridin-3-ylmethyl)-pyridin-2-yl]-(5-fluoro-2-methoxy-pyridin-3-ylmethyl)-amine (P-2170), (5-Fluoro-2-methoxy-pyridin-3-ylmethyl)-[5-(4-phenyl-1H-pyrrolo[2,3-b]pyridin-3-ylmethyl)-pyridin-2-yl]-amine (P-2171), 5-[(5-bromo-1H-pyrrolo[2,3-b]pyridin-3-yl)methyl]-6-fluoro-N-[(5-fluoro-6-methoxy-3-pyridyl)methyl]pyridin-2-amine (P-2203), 3-[[2-fluoro-6-[(5-fluoro-6-methoxy-3-pyridyl)methylamino]-3-pyridyl]methyl]-1H-pyrrolo[2,3-b]pyridine-5-carbonitrile (P-2204), 6-chloro-N-[(5-fluoro-2-methoxy-3-pyridyl)methyl]-5-[(5-methyl-1H-pyrrolo[2,3-b]pyridin-3-yl)methyl]pyridin-2-amine (P-2205), 6-fluoro-N-[(5-fluoro-6-methoxy-3-pyridyl)methyl]-5-[[5-(trifluoromethyl)-1H-pyrrolo[2,3-b]pyridin-3-yl]methyl]pyridin-2-amine (P-2206), and any salt, prodrug, tautomer, or stereoisomer thereof.

In some embodiments of compounds of Formulae I and I', $R^7$ is other than hydrogen. All the other variables are as defined herein.

In one group of embodiments of compounds of Formulae I and I', $R^6$ and $R^7$ are not simulataneously H. All the other variables are as defined herein.

In another group of embodiments of compounds of Formulae I and I', when $R^7$ is halogen, $R^6$ is other than H, halogen, heteroaryl, CN or lower alkyl. In certain instances, when $R^7$ is Cl, $R^6$ is other than H, Cl, pyrrazolyl, CN or $CH_3$. All the other variables are as defined herein.

In another group of embodiments of compounds of Formulae I and I', when $R^7$ is halogen, $R^6$ is other than halo substituted lower alkyl. In certain instances, when $R^7$ is Cl, $R^6$ is other than $CF_3$. All the other variables are as defined herein.

In one group of embodiments of compounds of Formulae I and I', when $R^7$ is halogen, $R^2$ is other than halogen substituted lower alkyl or lower alkoxy. In certain instances, when $R^7$ is F, $R^2$ is other than $CF_3$ or $—OCH_3$. All the other variables are as defined herein.

In another group of embodiments of compounds of Formulae I' and I', when $R^7$ is halogen, $R^6$ is other than halogen, lower alkoxy, hydrogen or CN. In certain instances, when $R^7$ is —F, $R^6$ is other than Cl, $OCH_3$, hydrogen or CN. In other instances, when $R^7$ is —F, $R^3$ is other than F. All the other variables are as defined herein.

In one group of embodiments of compounds of Formulae I and I', when $R^7$ is hydrogen, $R^6$ is other than halogen, hydrogen, lower alkyl, CN, or lower alkoxy. In certain instances, when $R^7$ is hydrogen, $R^6$ is other than H, Cl, F, $CH_3$, CN, $—OCH_3$. All the other variables are as defined herein.

In another group of embodiments of compounds of Formulae I and I', when $R^9$ is halogen, $R^6$ is other than H or halogen. In certain instances, when $R^9$ is Cl, $R^6$ is other than H or Cl. All the other variables are as defined herein.

In another group of embodiments of compounds of Formulae I and I', when Ar is

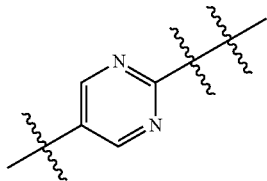, $R^6$ is other than hydrogen. All the other variables are as defined herein.

In another group of embodiments of compounds of Formulae I and I', when Ar is

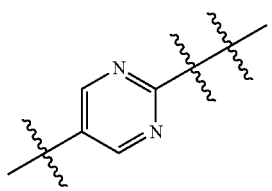, $R^1$, $R^2$, $R^3$ and $R^4$ are not simultaneously hydrogen. All the other variables are as defined herein.

In another group of embodiments of compounds of Formulae I and I', when Ar is

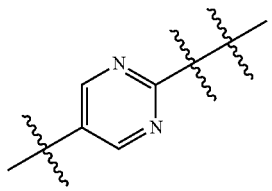, $R^2$ is other than halo substituted lower alkyl, for example, in one embodiment, $R^2$ is other than $CF_3$. All the other variables are as defined herein.

The compounds excluded from Formula I' and Formula I are listed in Table 1 below.

TABLE 1

[6-Chloro-5-(1H-pyrrolo[2,3-b]pyridin-3-ylmethyl)-pyridin-2-yl]-(6-trifluoromethyl-pyridin-3-ylmethyl)-amine (P-0174),
[6-Chloro-5-(5-chloro-1H-pyrrolo[2,3-b]pyridin-3-ylmethyl)-pyridin-2-yl]-(6-trifluoromethyl-pyridin-3-ylmethyl)-amine (P-0176),
{6-Chloro-5-[5-(1-methyl-1H-pyrazol-4-yl)-1H-pyrrolo[2,3-b]pyridin-3-ylmethyl]-pyridin-2-yl}-(6-trifluoromethyl-pyridin-3-ylmethyl)-amine (P-0179),
[5-(5-Chloro-1H-pyrrolo[2,3-b]pyridin-3-ylmethyl)-6-fluoro-pyridin-2-yl]-(6-trifluoromethyl-pyridin-3-ylmethyl)-amine (P-0186),
[6-Fluoro-5-(5-methoxy-1H-pyrrolo[2,3-b]pyridin-3-ylmethyl)-pyridin-2-yl]-(6-trifluoromethyl-pyridin-3-ylmethyl)-amine (P-0187),
[6-Fluoro-5-(1H-pyrrolo[2,3-b]pyridin-3-ylmethyl)-pyridin-2-yl]-(6-trifluoromethyl-pyridin-3-ylmethyl)-amine (P-0188), TABLE 1-continued 3-{2-Chloro-6-[(6-trifluoromethyl-pyridin-3-ylmethyl)-amino]-pyridin-3-ylmethyl}-1H-pyrrolo[2,3-b]pyridine-5-carbonitrile (P-0232),
[6-Chloro-5-(5-methyl-1H-pyrrolo[2,3-b]pyridin-3-ylmethyl)-pyridin-2-yl]-(6-trifluoromethyl-pyridin-3-ylmethyl)-amine (P-0233),
[6-Chloro-5-(5-methyl-1H-pyrrolo[2,3-b]pyridin-3-ylmethyl)-pyridin-2-yl]-(6-trifluoromethyl-pyridin-3-ylmethyl)-amine (P-0234),
[6-Fluoro-5-(1H-pyrrolo[2,3-b]pyridin-3-ylmethyl)-pyridin-2-yl]-(6-methoxy-pyridin-3-ylmethyl)-amine (P-0378),
[5-(5-Chloro-1H-pyrrolo[2,3-b]pyridin-3-ylmethyl)-6-fluoro-pyridin-2-yl]-(6-methoxy-pyridin-3-ylmethyl)-amine (P-0379),
(5-Fluoro-pyridin-3-ylmethyl)-[6-fluoro-5-(1H-pyrrolo[2,3-b]pyridin-3-ylmethyl)-pyridin-2-yl]-amine (P-0414),
3-{2-Fluoro-6-[(5-fluoro-pyridin-3-ylmethyl)-amino]-pyridin-3-ylmethyl}-1H-pyrrolo[2,3-b]pyridine-5-carbonitrite (P-0415),
3-[6-(4-Chloro-benzylamino)-2-fluoro-pyridin-3-ylmethyl]-1H-pyrrolo[2,3-b]pyridine-5-carbonitrile (P-0432),
Pyridin-3-ylmethyl-[5-(1H-pyrrolo[2,3-b]pyridin-3-ylmethyl)-pyridin-2-yl]-amine (P-0094),
(2-Methoxy-pyridin-3-ylmethyl)-[5-(1H-pyrrolo[2,3-b]pyridin-3-ylmethyl)-pyridin-2-yl]-amine (P-0215),
(6-Methoxy-pyridin-3-ylmethyl)-[5-(1H-pyrrolo[2,3-b]pyridin-3-ylmethyl)-pyridin-2-yl]-amine (P-0219),
(5-Methoxy-pyridin-3-ylmethyl)-[5-(1H-pyrrolo[2,3-b]pyridin-3-ylmethyl)-pyridin-2-yl]-amine (P-0222),
(5-Fluoro-pyridin-3-ylmethyl)-[5-(1H-pyrrolo[2,3-b]pyridin-3-ylmethyl)-pyridin-2-yl]-amine (P-0230),
3-{6-[(6-Trifluoromethyl-pyridin-3-ylmethyl)-amino]-pyridin-3-ylmethyl}-1H-pyrrolo[2,3-b]pyridine-5-carbonitrile (P-0273),
(6-Methoxy-pyridin-3-ylmethyl)-[5-(5-methyl-1H-pyrrolo[2,3-b]pyridin-3-ylmethyl)-pyridin-2-yl]-amine (P-0282),
3-{6-[(6-Methoxy-pyridin-3-ylmethyl)-amino]-pyridin-3-ylmethyl}-1H-pyrrolo[2,3-b]pyridine-5-carbonitrile (P-0284),
(2-Methoxy-pyridin-3-ylmethyl)-[5-(5-methyl-1H-pyrrolo[2,3-b]pyridin-3-ylmethyl)-pyridin-2-yl]-amine (P-0285),
[5-(5-Chloro-1H-pyrrolo[2,3-b]pyridin-3-ylmethyl)-pyridin-2-yl]-(2-methoxy-pyridin-3-ylmethyl)-amine (P-0286),
3-{6-[(2-Methoxy-pyridin-3-ylmethyl)-amino]-pyridin-3-ylmethyl}-1H-pyrrolo[2,3-b]pyridine-5-carbonitrile (P-0287),
[5-(5-Chloro-1H-pyrrolo[2,3-b]pyridin-3-ylmethyl)-pyridin-2-yl]-(5-fluoro-pyridin-3-ylmethyl)-amine (P-0324),
[5-(5-Fluoro-1H-pyrrolo[2,3-b]pyridin-3-ylmethyl)-pyridin-2-yl]-(6-methoxy-pyridin-3-ylmethyl)-amine (P-0331),
(6-Methoxy-pyridin-3-ylmethyl)-[5-(5-methoxy-1H-pyrrolo[2,3-b]pyridin-3-ylmethyl)-pyridin-2-yl]-amine (P-0332),
(2-Morpholin-4-yl-pyridin-3-ylmethyl)-[5-(1H-pyrrolo[2,3-b]pyridin-3-ylmethyl)-pyridin-2-yl]-amine (P-0347),
(2,6-Dimethoxy-pyridin-3-ylmethyl)-[5-(1H-pyrrolo[2,3-b]pyridin-3-ylmethyl)-pyridin-2-yl]-amine (P-0370),
(6-Cyclopentyloxy-pyridin-3-ylmethyl)-[5-(1H-pyrrolo[2,3-b]pyridin-3-ylmethyl)-pyridin-2-yl]-amine (P-0374),
[5-(1H-pyrrolo[2,3-b]pyridin-3-ylmethyl)-pyridin-2-yl]-[2-(2,2,2-trifluoro-ethoxy)-pyridin-3-ylmethyl]-amine (P-0376),
(5-Chloro-pyridin-3-ylmethyl)-[5-(1H-pyrrolo[2,3-b]pyridin-3-ylmethyl)-pyridin-2-yl]-amine (P-0400),
[5-(5-Chloro-1H-pyrrolo[2,3-b]pyridin-3-ylmethyl)-pyridin-2-yl]-[6-(2,2,2-trifluoro-ethoxy)-pyridin-3-ylmethyl]-amine (P-0409),
[5-(5-Chloro-1H-pyrrolo[2,3-b]pyridin-3-ylmethyl)-pyridin-2-yl]-(6-trifluoromethyl-pyridin-3-ylmethyl)-amine (P-0181),
[5-(1H-Pyrrolo[2,3-b]pyridin-3-ylmethyl)-pyridin-2-yl]-(6-trifluoromethyl-pyridin-3-ylmethyl)-amine (P-0182),
[4-Chloro-5-(1H-pyrrolo[2,3-b]pyridin-3-ylmethyl)-thiazol-2-yl]-pyridin-3-ylmethyl-amine (P-0164),
[4-Chloro-5-(1H-pyrrolo[2,3-b]pyridin-3-ylmethyl)-thiazol-2-yl]-(6-trifluoromethyl-pyridin-3-ylmethyl)-amine (P-0173),
[5-(5-Chloro-1H-pyrrolo[2,3-b]pyridin-3-ylmethyl)-pyrimidin-2-yl]-pyridin-3-ylmethyl-amine (P-0422),
[5-(5-Chloro-1H-pyrrolo[2,3-b]pyridin-3-ylmethyl)-pyrimidin-2-yl]-(6-trifluoromethyl-pyridin-3-ylmethyl)-amine (P-0429),
2,2-Dimethyl-N-(3-{[5-(1H-pyrrolo[2,3-b]pyridin-3-ylmethyl)-pyridin-2-ylamino]-methyl}-pyridin-2-yl)-propionamide (P-0384),
Methyl-(3-{[5-(1H-pyrrolo[2,3-b]pyridin-3-ylmethyl)-pyridin-2-ylamino]-methyl}-pyridin-2-yl)-amine (P-0385),
Dimethyl-(3-{[5-(1H-pyrrolo[2,3-b]pyridin-3-ylmethyl)-pyridin-2-ylamino]-methyl}-pyridin-2-yl)-amine (P-0399),
[4-Chloro-5-(5-chloro-1H-pyrrolo[2,3-b]pyridin-3-ylmethyl)-thiazol-2-yl]-(3-fluoro-pyridin-4-ylmethyl)-amine (P-0200),
[4-Chloro-5-(5-chloro-1H-pyrrolo[2,3-b]pyridin-3-ylmethyl)-thiazol-2-yl]-pyridin-3-ylmethyl-amine (P-0236),
[4-Chloro-5-(5-chloro-1H-pyrrolo[2,3-b]pyridin-3-ylmethyl)-thiazol-2-yl]-(5-methoxy-pyridin-3-ylmethyl)-amine (P-0241),
[4-Chloro-5-(5-chloro-1H-pyrrolo[2,3-b]pyridin-3-ylmethyl)-thiazol-2-yl]-(6-trifluoromethyl-pyridin-3-ylmethyl)-amine (P-0242), TABLE 1-continued

[4-Chloro-5-(5-chloro-1H-pyrrolo[2,3-b]pyridin-3-ylmethyl)-thiazol-2-yl]-(2-methoxy-pyridin-3-ylmethyl)-amine (P-0247), and
[4-Chloro-5-(1H-pyrrolo[2,3-b]pyridin-3-ylmethyl)-thiazol-2-yl]-(5-methoxy-pyridin-3-ylmethyl)-amine (P-0207).

In a second aspect, the present invention provides compounds having Formula II':

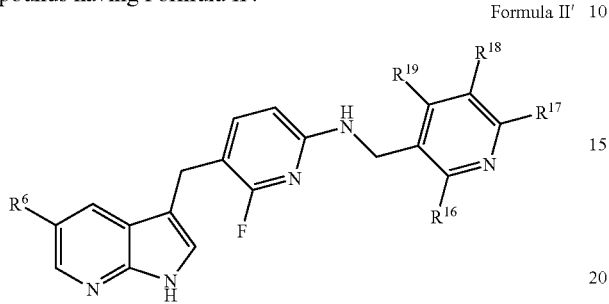

Formula II' or a salt, a prodrug, a tautomer or a stereoisomer thereof,
wherein:
$R^{16}$, $R^{17}$, $R^{18}$ and $R^{19}$ are each independently selected from the group consisting of H, halogen, lower alkyl, lower alkoxy, halo substituted lower alkyl, alkoxy substituted lower alkyl, cycloalkylamino, —CN, —O—$R^{20}$, —S(O)$_2$—$R^{21}$, —S(O)$_2$—N(H)—$R^{22}$, —N(H)—$R^{22}$, —N($R^{22}$)$_2$, and —N(H)—S(O)$_2$—$R^{23}$, provided that at least two of $R^{16}$, $R^{17}$, $R^{18}$ and $R^{19}$ are —H;
$R^{20}$ is lower alkyl, fluoro substituted lower alkyl, methoxy substituted lower alkyl, or cycloalkyl; $R^{21}$ is lower alkyl; $R^{22}$ is lower alkyl; and $R^{23}$ is lower alkyl.

In some embodiments of compounds of Formula II', $R^6$ is selected from the group consisting of halogen, lower alkyl, fluoro substituted lower alkyl, lower alkenyl, lower alkynyl, cycloalkyl, phenyl, pyrazolyl, —CN, —O—$R^{13}$, —C(O)—N(H)—$R^{14}$, —C(O)—O—$R^{14}$, —S(O)$_2$—$R^{15}$, —S(O)$_2$—N(H)—$R^{14}$, —N(H)—C(O)—$R^{15}$, and —N(H)—S(O)$_2$—$R^{15}$, wherein pyrazolyl is optionally substituted with lower alkyl or heterocycloalkyl. In certain instances, $R^6$ is F, Cl, Br, lower alkyl, fluoro substituted lower alkyl, lower alkenyl, —CN, —C(O)—N(H)—$R^{14}$, —N(H)—C(O)—$R^{15}$, —C(O)—O—$R^{14}$, —S(O)$_2$—$R^{15}$, —S(O)$_2$—N(H)—$R^{14}$ or —N(H)—S(O)$_2$—$R^{15}$. In other instances, $R^6$ is methyl, ethyl, propyl, butyl, pentyl or hexyl. All other variables are as defined herein.

In some embodiments, compounds having the structure according to the following Formula II are provided:

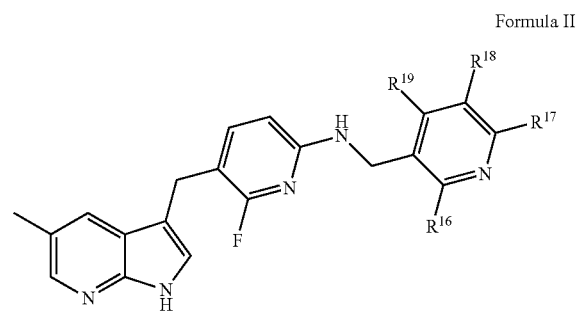

Formula II or a salt, a prodrug, a tautomer or a stereoisomer thereof, wherein:
$R^{16}$, $R^{17}$, $R^{18}$ and $R^{19}$ are independently selected from the group consisting of —H, —F, —Cl, —Br, lower alkyl, fluoro substituted lower alkyl, methoxy substituted lower alkyl, cycloalkylamino, —CN, —O—$R^{20}$, —S(O)$_2$—$R^{21}$, —S(O)$_2$—N(H)—$R^{22}$, —N(H)—$R^{22}$, —N($R^{22}$)$_2$, and —N(H)—S(O)$_2$—$R^{23}$, provided that at least two of $R^{16}$, $R^{17}$, $R^{18}$ and $R^{19}$ are —H;
$R^{20}$ is lower alkyl, fluoro substituted lower alkyl, methoxy substituted lower alkyl, or cycloalkyl;
$R^{21}$ is lower alkyl;
$R^{22}$ is lower alkyl; and
$R^{23}$ is lower alkyl.

In some embodiments of compounds of Formulae II and II', $R^{16}$, $R^{17}$, $R^{18}$ and $R^{19}$ are each independently selected from the group consisting of —H, —F, —Cl, —Br, lower alkyl, fluoro substituted lower alkyl, methoxy substituted lower alkyl, cycloalkylamino, —CN, —O—$R^{20}$, —S(O)$_2$—$R^{21}$, —S(O)$_2$—N(H)—$R^{22}$, —N(H)—$R^{22}$, —N($R^{22}$) and —N(H)—S(O)$_2$—$R^{23}$, provided that at least two of $R^{16}$, $R^{17}$, $R^{18}$ and $R^{19}$ are —H. In some embodiments, $R^{17}$ and $R^{19}$ are H, halogen or lower alkyl. All other variables are as defined herein.

In other embodiments of compounds of Formulae II and II', $R^{16}$, $R^{17}$, $R^{18}$ and $R^{19}$ are each independently selected from H, halogen, lower alkyl, lower alkoxy, halo substituted lower alkyl, —O$R^{20}$, or alkoxy substituted lower alkyl, provided that at least two of $R^{16}$, $R^{17}$, $R^{18}$ and $R^{19}$ are —H. All other variables are as defined herein.

In some embodiments of compounds of Formulae II and II', $R^{16}$, $R^{17}$, and $R^{18}$ are H and $R^{19}$ is —F, —Cl, —Br, lower alkyl, fluoro substituted lower alkyl, methoxy substituted lower alkyl, cycloalkylamino, —CN, —O—$R^{20}$, —S(O)$_2$—$R^{21}$, —N(H)—$R^{22}$, —N($R^{22}$)$_2$ or —N(H)—S(O)$_2$—$R^{23}$. In some embodiments $R^{16}$, $R^{17}$, and $R^{18}$ are H and $R^{19}$ is —F, —Cl, lower alkyl, fluoro substituted lower alkyl, cycloalkylamino, —O—$R^{20}$, —N(H)—$R^{22}$, or —N($R^{22}$)$_2$. In some embodiments $R^{16}$, $R^{17}$, and $R^{18}$ are H and $R^{19}$ is fluoro substituted lower alkyl or —O—$R^{20}$. In some embodiments $R^{16}$, $R^{17}$, and $R^{18}$ are H and $R^{19}$ is —CF$_3$ or —O—CH$_3$. All other variables are as defined herein.

In some embodiments of compounds of Formulae II and II', $R^{16}$, $R^{17}$, and $R^{19}$ are H and $R^{18}$ is —F, —Cl, —Br, lower alkyl, fluoro substituted lower alkyl, methoxy substituted lower alkyl, cycloalkylamino, —CN, —O—$R^{20}$, —S(O)$_2$—$R^{21}$, —N(H)—$R^{22}$, —N($R^{22}$)$_2$, or —N(H)—S(O)$_2$—$R^{23}$. In some embodiments $R^{16}$, $R^{17}$, and $R^{19}$ are H and $R^{18}$ is —F, —Cl, lower alkyl, fluoro substituted lower alkyl, cycloalkylamino, —O—$R^{20}$, —N(H)—$R^{22}$, or —N($R^{22}$)$_2$. In some embodiments $R^{16}$, $R^{17}$, and $R^{19}$ are H and $R^{18}$ is —F, —Cl, or —O—$R^{20}$. In some embodiments $R^{16}$, $R^{17}$, and $R^{19}$ are H and $R^{18}$ is —F, —Cl, or —O—CH$_3$. All other variables are as defined herein.

In some embodiments of compounds of Formulae II and II', $R^{16}$, $R^8$, and $R^{19}$ are H and $R^{17}$ is —F, —Cl, —Br, lower alkyl, fluoro substituted lower alkyl, methoxy substituted lower alkyl, cycloalkylamino, —CN, —O—$R^{20}$, —S(O)$_2$—$R^{21}$, —N(H)—$R^{22}$, —N($R^{22}$)$_2$, or —N(H)—S(O)—$R^{23}$. In some embodiments $R^{16}$, $R^{18}$, and $R^{19}$ are H and $R^{17}$ is —F, —Cl, lower alkyl, fluoro substituted lower alkyl, cycloalkylamino, —O—$R^{20}$, —N(H)—$R^{22}$, or —N($R^{22}$)$_2$. In some embodiments $R^{16}$, $R^{18}$, and $R^{19}$ are H and $R^{17}$ is —Cl, fluoro substituted lower alkyl, cycloalkylamino, or —O—R$^{20}$. In some embodiments R$^{16}$, R$^{18}$, and R$^{19}$ are H and R$^{17}$ is —Cl, —CF$_3$, —O—CH$_3$, or morpholin-4-yl. All other variables are as defined herein.

In some embodiments of compounds of Formulae II and II', R$^{17}$, R$^{18}$, and R$^{19}$ are H and R$^{16}$ is —F, —Cl, —Br, lower alkyl, fluoro substituted lower alkyl, methoxy substituted lower alkyl, cycloalkylamino, —CN, —O—R$^2$, —S(O)$_2$—R$^{21}$, —N(H)—R$^{22}$, —N(R$^{22}$)$_2$, or —N(H)—S(O)$_2$—R$^{23}$. In some embodiments R$^{17}$, R$^{18}$, and R$^{19}$ are H and R$^{16}$ is —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{17}$, R$^{18}$, and R$^{19}$ are H and R$^{16}$ is —F, —CF$_3$, morpholin-4-yl, —O—CH$_3$, —O—CH$_2$CH$_3$, —O—CH(CH$_3$)$_2$, —O—CH$_2$CF$_3$, —O-cyclopentyl, —O-cyclohexyl, or —N(H)—CH$_3$. In some embodiments R$^{17}$, R$^{18}$, and R$^{19}$ are H and R$^{16}$ is —F, —CF$_3$, or —O—CH$_3$. All other variables are as defined herein.

In some embodiments of compounds of Formulae II and II', R$^{16}$ and R$^{17}$ are H; and R$^{18}$ and R$^{19}$ are independently —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)—R$^{23}$. In some embodiments R$^{16}$ and R$^{17}$ are H; and R$^{18}$ and R$^{19}$ are independently —F, —Cl, lower alkyl, fluoro substituted lower alkyl, cycloalkylamino, —O—R$^{20}$, or —N(H)—R$^{22}$, or —N(R$^{22}$)$_2$. In some embodiments R$^{16}$ and R$^{17}$ are H; and R$^{18}$ and R$^{19}$ are independently —F, —Cl, CF$_3$, —O—CH$_3$, or —N(CH$_3$)$_2$. All other variables are as defined herein.

In some embodiments of compounds of Formulae II and II', R$^{16}$ and R$^{18}$ are H; and R$^{17}$ and R$^{19}$ are independently —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{16}$ and R$^{18}$ are H; and R$^{17}$ and R$^{19}$ are independently —F, —Cl, lower alkyl, fluoro substituted lower alkyl, cycloalkylamino, —O—R$^2$, —N(H)—R$^{22}$, or —N(R$^{22}$)$_2$. In some embodiments R$^{16}$ and R$^{18}$ are H; and R$^{17}$ and R$^{19}$ are independently —F, —Cl, CF$_3$, —O—CH$_3$, or —N(CH$_3$)$_2$. In some embodiments R$^{16}$ and R$^{18}$ are H; and R$^{17}$ and R$^{19}$ are independently —CF$_3$ or —O—CH$_3$. All other variables are as defined herein.

In some embodiments of compounds of Formulae II and II', R$^{16}$ and R$^{19}$ are H; and R$^{17}$ and R$^{18}$ are independently —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)—R$^{23}$. In some embodiments R$^{16}$ and R$^{19}$ are H; and R$^{17}$ and R$^{18}$ are independently —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{16}$ and R$^{19}$ are H; and R$^{17}$ and R$^{18}$ are independently —F, —Cl, CF$_3$, —O—CH$_3$, or —N(CH$_3$)$_2$. In some embodiments R$^{16}$ and R$^{19}$ are H; and R$^{17}$ and R$^{18}$ are independently —F or —O—CH$_3$. All other variables are as defined herein.

In some embodiments of compounds of Formulae II and II', R$^{17}$ and R$^{18}$ are H; and R$^{16}$ and R$^{19}$ are independently —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{17}$ and R$^{18}$ are H; and R$^{16}$ and R$^{19}$ are independently —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{17}$ and R$^{18}$ are H; and R$^{16}$ and R$^{19}$ are independently —F, —Cl, CF$_3$, —O—CH$_3$, or —N(CH$_3$)$_2$. All other variables are as defined herein.

In some embodiments of compounds of Formula II, R$^{17}$ and R$^{19}$ are H; and R$^{16}$ and R$^{18}$ are independently —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{17}$ and R$^{19}$ are H; and R$^{16}$ and R$^{18}$ are independently —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{17}$ and R$^{19}$ are H; and R$^{16}$ and R$^{18}$ are independently —F, —Cl, CF$_3$, —O—CH$_3$, or —N(CH$_3$)$_2$. In some embodiments R$^{17}$ and R$^{19}$ are H; and R$^{16}$ and R$^{18}$ are independently —F, —Cl, or —O—CH$_3$. All other variables are as defined herein.

In some embodiments of compounds of Formulae II and II', R$^{18}$ and R$^{19}$ are H; and R$^{16}$ and R$^{17}$ are independently —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{18}$ and R$^{19}$ are H; and R$^{16}$ and R$^{17}$ are independently —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{18}$ and R$^{19}$ are H; and R$^{16}$ and R$^{17}$ are independently —F, —Cl, CF$_3$, —O—CH$_3$, or —N(CH$_3$)$_2$. In some embodiments R$^{18}$ and R$^{19}$ are H; and R$^{16}$ and R$^{17}$ are independently —CF$_3$, —O—CH$_3$, or —N(CH$_3$)$_2$. All other variables are as defined herein.

In some embodiments, compounds having the structure according to the following Formula IIa are provided:

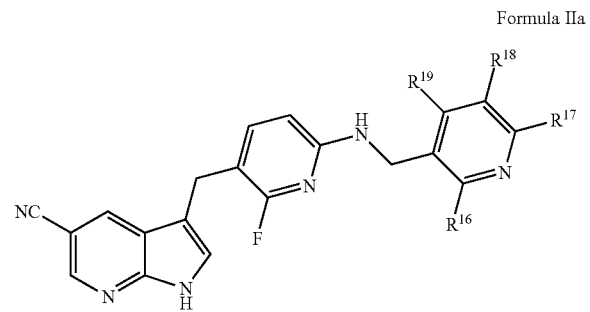

Formula IIa or a salt, a prodrug, a tautomer or a stereoisomer thereof,
wherein:
R$^{16}$, R$^{17}$, R$^{18}$ and R$^{19}$ are independently selected from the group consisting of —H, —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —S(O)$_2$—N(H)—R$^{22}$, —N(H)—R$^{22}$, —N(R$^{22}$)$_2$, and —N(H)—S(O)$_2$—R$^{23}$, provided that at least two of R$^{16}$, R$^{17}$, R$^{18}$ and R$^{19}$ are —H;
R$^{20}$ is lower alkyl, fluoro substituted lower alkyl, methoxy substituted lower alkyl, or cycloalkyl;
R$^{21}$ is lower alkyl;
R$^{22}$ is lower alkyl; and
R$^{23}$ is lower alkyl.

In some embodiments of compounds of Formula IIa, R$^{16}$, R$^{17}$, R$^{18}$ and R$^{19}$ are each independently from the group consisting of —H, —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —S(O)$_2$—N(H)—R$^{22}$, —N(H)—R$^{22}$, —N(R$^{22}$)$_2$, and —N(H)—S(O)$_2$—R$^{23}$, provided that at least two of R$^{16}$, R$^{17}$, R$^{18}$ and R$^{19}$ are —H. In some embodiments, R$^{17}$ and R$^{19}$ are H, halogen or lower alkyl. All other variables are as defined herein.

In other embodiments of compounds of Formula IIa, R$^{16}$, R$^{17}$, R$^{18}$ and R$^{19}$ are each independently selected from H, halogen, lower alkyl, lower alkoxy, halo substituted lower alkyl, —OR$^{20}$, or alkoxy substituted lower alkyl, provided that at least two of R$^{16}$, R$^{17}$, R$^{8}$ and R$^{19}$ are —H. All other variables are as defined herein.

In some embodiments of compounds of Formula IIa, R$^{16}$, R$^{17}$, and R$^{18}$ are H and R$^{19}$ is —F, —Cl, —Br, lower alkyl, fluoro substituted lower alkyl, methoxy substituted lower alkyl, cycloalkylamino, —CN, —O—R$^2$, —S(O)$_2$—R$^{21}$, —N(H)—R$^{22}$, —N(R$^{22}$)$_2$, or —N(H)—S(O)$_2$—R$^{23}$. In some embodiments R$^{16}$, R$^{17}$, and R$^{18}$ are H and R$^{19}$ is —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{16}$, R$^{17}$, and R$^{18}$ are H and R$^{19}$ is fluoro substituted lower alkyl or —O—R$^{20}$. In some embodiments R$^{16}$, R$^{17}$, and R$^{18}$ are H and R$^{19}$ is —CF$_3$ or —O—CH$_3$. All other variables are as defined herein.

In some embodiments of compounds of Formula IIa, R$^{16}$, R$^{17}$, and R$^{19}$ are H and R$^{18}$ is —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{16}$, R$^{17}$, and R$^{19}$ are H and R$^{18}$ is —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{16}$, R$^{17}$, and R$^{19}$ are H and R$^{18}$ is —F, —Cl, or —O—R$^{20}$. In some embodiments R$^{16}$, R$^{17}$, and R$^{19}$ are H and R$^{18}$ is —F, —Cl, or —O—CH$_3$. All other variables are as defined herein.

In some embodiments of compounds of Formula IIa, R$^{16}$, R$^{18}$, and R$^{19}$ are H and R$^{17}$ is —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^2$. In some embodiments R$^{16}$, R$^{18}$, and R$^{19}$ are H and R$^{17}$ is —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{16}$, R$^{18}$, and R$^{19}$ are H and R$^{17}$ is —Cl, fluoro substituted lower alkyl, cycloalkylamino, or —O—R$^{20}$. In some embodiments R$^{16}$, R$^{18}$ and R$^{19}$ are H and R$^{17}$ is —Cl, —CF$_3$, —O—CH$_3$, or morpholin-4-yl. All other variables are as defined herein.

In some embodiments of compounds of Formula IIa, R$^{17}$, R$^{18}$, and R$^{19}$ are H and R$^{16}$ is —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{17}$, R$^{18}$, and R$^{19}$ are H and R$^{16}$ is —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{17}$, R$^{18}$, and R$^{19}$ are H and R$^{16}$ is —F, —CF$_3$, morpholin-4-yl, —O—CH$_3$, —O—CH$_2$CH$_3$, —O—CH(CH$_3$)$_2$, —O—CH$_2$CF$_3$, —O-cyclopentyl, —O-cyclohexyl, or —N(H)—CH$_3$. In some embodiments R$^{17}$, R$^{18}$, and R$^{19}$ are H and R$^{16}$ is —F, —CF$_3$, or —O—CH$_3$. All other variables are as defined herein.

In some embodiments of compounds of Formula IIa, R$^{16}$ and R$^{17}$ are H; and R$^{18}$ and R$^{19}$ are independently —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{16}$ and R$^{17}$ are H; and R$^{18}$ and R$^{19}$ are independently —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{16}$ and R$^{17}$ are H; and R$^{18}$ and R$^{19}$ are independently —F, —Cl, CF$_3$, —O—CH$_3$, or —N(CH$_3$)$_2$. All other variables are as defined herein.

In some embodiments of compounds of Formula IIa, R$^{16}$ and R$^{18}$ are H; and R$^{17}$ and R$^{19}$ are independently —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{16}$ and R$^{18}$ are H; and R$^{17}$ and R$^{19}$ are independently —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{16}$ and R$^{18}$ are H; and R$^{17}$ and R$^{19}$ are independently —F, —Cl, CF$_3$, —O—CH$_3$, or —N(CH$_3$)$_2$. In some embodiments R$^{16}$ and R$^{18}$ are H; and R$^{17}$ and R$^{19}$ are independently —CF$_3$ or —O—CH$_3$. All other variables are as defined herein.

In some embodiments of compounds of Formula IIa, R$^{16}$ and R$^{19}$ are H; and R$^{17}$ and R$^{18}$ are independently —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^2$. In some embodiments R$^{16}$ and R$^{19}$ are H; and R$^{17}$ and R$^{11}$ are independently —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{16}$ and R$^{19}$ are H; and R$^{17}$ and R$^{18}$ are independently —F, —Cl, CF$_3$, —O—CH$_3$, or —N(CH$_3$)$_2$. In some embodiments R$^{16}$ and R$^{19}$ are H; and R$^{17}$ and R$^{18}$ are independently —F or —O—CH$_3$. All other variables are as defined herein.

In some embodiments of compounds of Formula IIa, R$^{17}$ and R$^{18}$ are H; and R$^{16}$ and R$^{19}$ are independently —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{17}$ and R$^{18}$ are H; and R$^{16}$ and R$^{19}$ are independently —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{17}$ and R$^{18}$ are H; and R$^{16}$ and R$^{19}$ are independently —F, —Cl, CF$_3$, —O—CH$_3$, or —N(CH$_3$)$_2$. All the other variables are as defined herein.

In some embodiments of compounds of Formula IIa, R$^{17}$ and R$^{19}$ are H; and R$^{16}$ and R$^{18}$ are independently —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{17}$ and R$^{19}$ are H; and R$^{16}$ and R$^{18}$ are independently —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{17}$ and R$^{19}$ are H; and R$^{16}$ and R$^{18}$ are independently —F, —Cl, CF$_3$, —O—CH$_3$, or —N(CH$_3$)$_2$. In some embodiments R$^{17}$ and R$^{19}$ are H; and R$^{16}$ and R$^{18}$ are independently —F, —Cl, or —O—CH$_3$. All the other variables are as defined herein.

In some embodiments of compounds of Formula IIa, R$^{18}$ and R$^{19}$ are H; and R$^{16}$ and R$^{17}$ are independently —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{18}$ and R$^{19}$ are H; and R$^{16}$ and R$^{17}$ are independently —F, —Cl, lower alkyl, fluoro substituted lower alkyl, cycloalkylamino, —N(H)—R$^{22}$, or —N(R$^{22}$)$_2$. In some embodiments R$^{18}$ and R$^{19}$ are H; and R$^{16}$ and R$^{17}$ are independently —F, —Cl, CF$_3$, —O—CH$_3$, or —N(CH$_3$)$_2$. In some embodiments R$^{18}$ and R$^{19}$ are H; and R$^{16}$ and R$^{17}$ are independently —CF$_3$, —O—CH$_3$, or —N(CH$_3$)$_2$. All the other variables are as defined herein.

In one embodiment of compounds of Formulae II and II' and IIa, the compound is selected from the group consisting of:

[6-Fluoro-5-(5-methyl-1H-pyrrolo[2,3-b]pyridin-3-ylmethyl)-pyridin-2-yl]-(5-fluoro-pyridin-3-ylmethyl)-amine (P-2027),

[6-Fluoro-5-(5-methyl-1H-pyrrolo[2,3-b]pyridin-3-ylmethyl)-pyridin-2-yl]-(6-methoxy-pyridin-3-ylmethyl)-amine (P-2029),

[6-Fluoro-5-(5-methyl-1H-pyrrolo[2,3-b]pyridin-3-ylmethyl)-pyridin-2-yl]-(6-trifluoromethyl-pyridin-3-ylmethyl)-amine (P-2031), (5-Chloro-pyridin-2-ylmethyl)-[6-fluoro-5-(5-methyl-1H-pyrrolo[2,3-b]pyridin-3-ylmethyl)-pyridin-2-yl]-amine (P-2047), (5-Fluoro-6-methoxy-pyridin-3-ylmethyl)-[6-fluoro-5-(5-methyl-1H-pyrrolo[2,3-b]pyridin-3-ylmethyl)-pyridin-2-yl]-amine (P-2048), (5-Fluoro-2-methoxy-pyridin-3-ylmethyl)-[6-fluoro-5-(5-methyl-1H-pyrrolo[2,3-b]pyridin-3-ylmethyl)-pyridin-2-yl]-amine (P-2049), (4-Chloro-benzyl)-[6-fluoro-5-(5-methyl-1H-pyrrolo[2,3-b]pyridin-3-ylmethyl)-pyridin-2-yl]-amine (P-2050), (2-Chloro-benzyl)-[6-fluoro-5-(5-methyl-1H-pyrrolo[2,3-b]pyridin-3-ylmethyl)-pyridin-2-yl]-amine (P-2051),

[6-Fluoro-5-(5-methyl-1H-pyrrolo[2,3-b]pyridin-3-ylmethyl)-pyridin-2-yl]-(2-methoxy-pyridin-3-ylmethyl)-amine (P-2052),

[6-Fluoro-5-(5-methyl-1H-pyrrolo[2,3-b]pyridin-3-ylmethyl)-pyridin-2-yl]-[(S)-1-(4-fluoro-phenyl)-ethyl]-amine (P-2058),

[6-Fluoro-5-(5-methyl-1H-pyrrolo[2,3-b]pyridin-3-ylmethyl)-pyridin-2-yl]-(4-trifluoromethyl-pyridin-3-ylmethyl)-amine (P-2062),

[6-Fluoro-5-(5-methyl-1H-pyrrolo[2,3-b]pyridin-3-ylmethyl)-pyridin-2-yl]-(2-methoxy-pyridin-4-ylmethyl)-amine (P-2065),

[6-Fluoro-5-(5-methyl-1H-pyrrolo[2,3-b]pyridin-3-ylmethyl)-pyridin-2-yl]-(2-methyl-pyridin-4-ylmethyl)-amine (P-2067), (5-Fluoro-2-methoxy-pyridin-4-ylmethyl)-[6-fluoro-5-(5-methyl-1H-pyrrolo[2,3-b]pyridin-3-ylmethyl)-pyridin-2-yl]-amine (P-2071), (2,5-Dimethoxy-benzyl)-[6-fluoro-5-(5-methyl-1H-pyrrolo[2,3-b]pyridin-3-ylmethyl)-pyridin-2-yl]-amine (P-2086), (3,5-Dimethoxy-benzyl)-[6-fluoro-5-(5-methyl-1H-pyrrolo[2,3-b]pyridin-3-ylmethyl)-pyridin-2-yl]-amine (P-2087), (6-Chloro-pyridin-3-ylmethyl)-[6-fluoro-5-(5-methyl-1H-pyrrolo[2,3-b]pyridin-3-ylmethyl)-pyridin-2-yl]-amine (P-2088), (3-Bromo-pyridin-4-ylmethyl)-[6-fluoro-5-(5-methyl-1H-pyrrolo[2,3-b]pyridin-3-ylmethyl)-pyridin-2-yl]-amine (P-2089),

[6-Fluoro-5-(5-methyl-1H-pyrrolo[2,3-b]pyridin-3-ylmethyl)-pyridin-2-yl]-(2-morpholin-4-yl-pyridin-3-ylmethyl)-amine (P-2090),

[6-Fluoro-5-(5-methyl-1H-pyrrolo[2,3-b]pyridin-3-ylmethyl)-pyridin-2-yl]-(6-morpholin-4-yl-pyridin-3-ylmethyl)-amine (P-2091), (3-Chloro-pyridin-4-ylmethyl)-[6-fluoro-5-(5-methyl-1H-pyrrolo[2,3-b]pyridin-3-ylmethyl)-pyridin-2-yl]-amine (P-2092),

[6-Fluoro-5-(5-methyl-1H-pyrrolo[2,3-b]pyridin-3-ylmethyl)-pyridin-2-yl]-(5-fluoro-pyridin-2-ylmethyl)-amine (P-2093),

[6-Fluoro-5-(5-methyl-1H-pyrrolo[2,3-b]pyridin-3-ylmethyl)-pyridin-2-yl]-(3-fluoro-pyridin-4-ylmethyl)-amine (P-2094), (5-{[6-Fluoro-5-(5-methyl-1H-pyrrolo[2,3-b]pyridin-3-ylmethyl)-pyridin-2-ylamino]-methyl}-pyrimidin-2-yl)-methyl-amine (P-2095),

[6-Fluoro-5-(5-methyl-1H-pyrrolo[2,3-b]pyridin-3-ylmethyl)-pyridin-2-yl]-[2-(2,2,2-trifluoro-ethoxy)-pyridin-3-ylmethyl]-amine (P-2096), (2,6-Dimethoxy-pyridin-3-ylmethyl)-[6-fluoro-5-(5-methyl-1H-pyrrolo[2,3-b]pyridin-3-ylmethyl)-pyridin-2-yl]-amine (P-2097), (5-Fluoro-2-methanesulfonyl-benzyl)-[6-fluoro-5-(5-methyl-1H-pyrrolo[2,3-b]pyridin-3-ylmethyl)-pyridin-2-yl]-amine (P-2098), (5-Chloro-pyridin-3-ylmethyl)-[6-fluoro-5-(5-methyl-1H-pyrrolo[2,3-b]pyridin-3-ylmethyl)-pyridin-2-yl]-amine (P-2099), (5-Bromo-pyridin-2-ylmethyl)-[6-fluoro-5-(5-methyl-1H-pyrrolo[2,3-b]pyridin-3-ylmethyl)-pyridin-2-yl]-amine (P-2100),

[6-Fluoro-5-(5-methyl-1H-pyrrolo[2,3-b]pyridin-3-ylmethyl)-pyridin-2-yl]-(3-methyl-pyridin-4-ylmethyl)-amine (P-2101), (3-Chloro-5-fluoro-benzyl)-[6-fluoro-5-(5-methyl-1H-pyrrolo[2,3-b]pyridin-3-ylmethyl)-pyridin-2-yl]-amine (P-2102),

[6-Fluoro-5-(5-methyl-1H-pyrrolo[2,3-b]pyridin-3-ylmethyl)-pyridin-2-yl]-(2-fluoro-pyridin-3-ylmethyl)-amine (P-2103), (3,5-Dimethyl-benzyl)-[6-fluoro-5-(5-methyl-1H-pyrrolo[2,3-b]pyridin-3-ylmethyl)-pyridin-2-yl]-amine (P-2104),

[6-Fluoro-5-(5-methyl-1H-pyrrolo[2,3-b]pyridin-ylmethyl)-pyridin-2-yl]-(5-methoxy-pyridin-3-ylmethyl)-amine (P-2105),

[6-Fluoro-5-(5-methyl-1H-pyrrolo[2,3-b]pyridin-3-ylmethyl)-pyridin-2-yl]-(2-methyl-pyrimidin-5-ylmethyl)-amine (P-2106),

[6-Fluoro-5-(5-methyl-1H-pyrrolo[2,3-b]pyridin-3-ylmethyl)-pyridin-2-yl]-(2-methylamino-pyridin-3-ylmethyl)-amine (P-2107), (3,5-Bis-trifluoromethyl-benzyl)-[6-fluoro-5-(5-methyl-1H-pyrrolo[2,3-b]pyridin-3-ylmethyl)-pyridin-2-yl]-amine (P-2108),

[6-Fluoro-5-(5-methyl-1H-pyrrolo[2,3-b]pyridin-3-ylmethyl)-pyridin-2-yl]-(4-methoxy-pyridin-3-ylmethyl)-amine (P-2109), (2-Ethoxy-pyridin-3-ylmethyl)-[6-fluoro-5-(5-methyl-1H-pyrrolo[2,3-b]pyridin-3-ylmethyl)-pyridin-2-yl]-amine (P-2110),

[6-Fluoro-5-(5-methyl-1H-pyrrolo[2,3-b]pyridin-3-ylmethyl)-pyridin-2-yl]-(2-isopropoxy-pyridin-3-ylmethyl)-amine (P-2111),

[6-Fluoro-5-(5-methyl-1H-pyrrolo[2,3-b]pyridin-3-ylmethyl)-pyridin-2-yl]-(4-methyl-pyridin-2-ylmethyl)-amine (P-2112), (2-Cyclopentyloxy-pyridin-3-ylmethyl)-[6-fluoro-5-(5-methyl-1H-pyrrolo[2,3-b]pyridin-ylmethyl)-pyridin-2-yl]-amine (P-2113), (2-Cyclohexyloxy-pyridin-3-ylmethyl)-[6-fluoro-5-(5-methyl-1H-pyrrolo[2,3-b]pyridin-3-ylmethyl)-pyridin-2-yl]-amine (P-2114),

[6-Fluoro-5-(5-methyl-1H-pyrrolo[2,3-b]pyridin-3-ylmethyl)-pyridin-2-yl]-(2-trifluoromethyl-pyridin-3-ylmethyl)-amine (P-2115),
(2-Chloro-5-fluoro-pyridin-4-ylmethyl)-[6-fluoro-5-(5-methyl-1H-pyrrolo[2,3-b]pyridin-3-ylmethyl)-pyridin-2-yl]-amine (P-2116),
4-{[6-Fluoro-5-(5-methyl-1H-pyrrolo[2,3-b]pyridin-3-ylmethyl)-pyridin-2-ylamino]-methyl}-pyridine-2-carbonitrile (P-2117),
[6-Fluoro-5-(5-methyl-1H-pyrrolo[2,3-b]pyridin-3-ylmethyl)-pyridin-2-yl]-(2-fluoro-pyridin-4-ylmethyl)-amine (P-2118),
[6-Fluoro-5-(5-methyl-1H-pyrrolo[2,3-b]pyridin-3-ylmethyl)-pyridin-2-yl]-(2-trifluoromethyl-pyridin-4-ylmethyl)-amine (P-2119),
(2-Chloro-pyridin-4-ylmethyl)-[6-fluoro-5-(5-methyl-1H-pyrrolo[2,3-b]pyridin-3-ylmethyl)-pyridin-2-yl]-amine (P-2120),
[6-Fluoro-5-(5-methyl-1H-pyrrolo[2,3-b]pyridin-ylmethyl)-pyridin-2-yl]-(2-morpholin-4-yl-pyridin-4-ylmethyl)-amine (P-2121),
[6-Fluoro-5-(5-methyl-1H-pyrrolo[2,3-b]pyridin-3-ylmethyl)-pyridin-2-yl]-(2-pyrrolidin-1-yl-pyridin-4-ylmethyl)-amine (P-2122),
(5-Chloro-2-fluoro-pyridin-3-ylmethyl)-[6-fluoro-5-(5-methyl-1H-pyrrolo[2,3-b]pyridin-3-ylmethyl)-pyridin-2-yl]-amine (P-2123),
(4-Chloro-2-methane sulfonyl-benzyl)-[6-fluoro-5-(5-methyl-1H-pyrrolo[2,3-b]pyridin-3-ylmethyl)-pyridin-2-yl]-amine (P-2124),
(2-Dimethylamino-benzyl)-[6-fluoro-5-(5-methyl-1H-pyrrolo[2,3-b]pyridin-3-ylmethyl)-pyridin-2-yl]-amine (P-2125),
(2-Ethyl-pyrimidin-5-ylmethyl)-[6-fluoro-5-(5-methyl-1H-pyrrolo[2,3-b]pyridin-3-ylmethyl)-pyridin-2-yl]-amine (P-2126),
[6-Fluoro-5-(5-methyl-1H-pyrrolo[2,3-b]pyridin-3-ylmethyl)-pyridin-2-yl]-(2-propyl-pyrimidin-5-ylmethyl)-amine (P-2127),
[6-Fluoro-5-(5-methyl-1H-pyrrolo[2,3-b]pyridin-3-ylmethyl)-pyridin-2-yl]-(2-isopropyl-pyrimidin-5-ylmethyl)-amine (P-2128),
[6-Fluoro-5-(5-methyl-1H-pyrrolo[2,3-b]pyridin-3-ylmethyl)-pyridin-2-yl]-[2-(2-methoxy-ethyl)-pyrimidin-5-ylmethyl]-amine (P-2129),
(2-Butyl-pyrimidin-5-ylmethyl)-[6-fluoro-5-(5-methyl-1H-pyrrolo[2,3-b]pyridin-3-ylmethyl)-pyridin-2-yl]-amine (P-2130),
[6-Fluoro-5-(5-methyl-1H-pyrrolo[2,3-b]pyridin-3-ylmethyl)-pyridin-2-yl]-(5-methyl-pyridin-2-ylmethyl)-amine (P-2131),
(3-Fluoro-5-methyl-benzyl)-[6-fluoro-5-(5-methyl-1H-pyrrolo[2,3-b]pyridin-3-ylmethyl)-pyridin-2-yl]-amine (P-2132),
[6-Fluoro-5-(5-methyl-1H-pyrrolo[2,3-b]pyridin-3-ylmethyl)-pyridin-2-yl]-(3-methoxy-5-trifluoromethyl-benzyl)-amine (P-2133),
(3-Fluoro-5-methoxy-benzyl)-[6-fluoro-5-(5-methyl-1H-pyrrolo[2,3-b]pyridin-3-ylmethyl)-pyridin-2-yl]-amine (P-2134),
[6-Fluoro-5-(5-methyl-1H-pyrrolo[2,3-b]pyridin-3-ylmethyl)-pyridin-2-yl]-(3,4,5-trimethoxy-benzyl)-amine (P-2150),
[6-Fluoro-5-(5-methyl-1H-pyrrolo[2,3-b]pyridin-3-ylmethyl)-pyridin-2-yl]-(5-pyrrolidin-1-yl-pyridin-2-ylmethyl)-amine (P-2151), 5-Fluoro-3-{[6-fluoro-5-(5-methyl-1H-pyrrolo[2,3-b]pyridin-3-ylmethyl)-pyridin-2-ylamino]-methyl}-1-methyl-1H-pyridin-2-one (P-2156),
[5-(5-Chloro-1H-pyrrolo[2,3-b]pyridin-3-ylmethyl)-6-fluoro-pyridin-2-yl]-(5-fluoro-6-methoxy-pyridin-3-ylmethyl)-amine (P-2165),
[6-Fluoro-5-(5-methyl-1H-pyrrolo[2,3-b]pyridin-3-ylmethyl)-pyridin-2-yl]-(2-methoxy-6-trifluoromethyl-pyridin-3-ylmethyl)-amine (P-2166),
[6-Fluoro-5-(5-methyl-1H-pyrrolo[2,3-b]pyridin-3-ylmethyl)-pyridin-2-yl]-(2-dimethylamino-6-trifluoromethyl-pyridin-3-ylmethyl)-amine (P-2167),
[6-Fluoro-5-(5-methyl-1H-pyrrolo[2,3-b]pyridin-3-ylmethyl)-pyridin-2-yl]-(6-methoxy-4-trifluoromethyl-pyridin-3-ylmethyl)-amine (P-2186),
Ethanesulfonic acid (2-{[6-fluoro-5-(5-methyl-1H-pyrrolo[2,3-b]pyridin-3-ylmethyl)-pyridin-2-ylamino]-methyl}-phenyl)-amide (P-2198),
Ethanesulfonic acid (4-fluoro-3-{[6-fluoro-5-(5-methyl-1H-pyrrolo[2,3-b]pyridin-3-ylmethyl)-pyridin-2-ylamino]-methyl}-phenyl)-amide (P-2199),
Ethanesulfonic acid (3-fluoro-5-{[6-fluoro-5-(5-methyl-1H-pyrrolo[2,3-b]pyridin-3-ylmethyl)-pyridin-2-ylamino]-methyl}-phenyl)-amide (P-2202),
5-[(5-bromo-1H-pyrrolo[2,3-b]pyridin-3-yl)methyl]-6-fluoro-N-[(5-fluoro-6-methoxy-3-pyridyl)methyl]pyridin-2-amine (P-2203),
3-[[2-fluoro-6-[(5-fluoro-6-methoxy-3-pyridyl)methylamino]-3-pyridyl]methyl]-1H-pyrrolo[2,3-b]pyridine-5-carbonitrile (P-2204),
6-chloro-N-[(5-fluoro-2-methoxy-3-pyridyl)methyl]-5-[(5-methyl-1H-pyrrolo[2,3-b]pyridin-3-yl)methyl]pyridin-2-amine (P-2205),
6-fluoro-N-[(5-fluoro-6-methoxy-3-pyridyl)methyl]-5-[[5-(trifluoromethyl)-1H-pyrrolo[2,3-b]pyridin-3-yl]methyl]pyridin-2-amine (P-2206), and
any salt, prodrug, tautomer, or stereoisomer thereof.

In a third aspect, the invention provides compounds having Formula III':

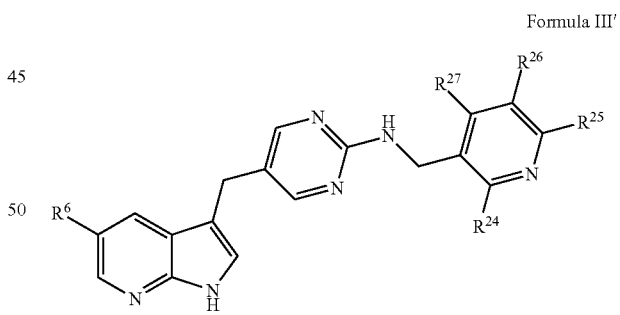

Formula III' or a salt, a prodrug, a tautomer or a stereoisomer thereof, wherein:

$R^{24}$, $R^{25}$, $R^{26}$ and $R^{27}$ are each independently selected from the group consisting of —H, halogen, lower alkyl, lower alkoxy, halo substituted lower alkyl, lower alkoxy, alkoxy substituted lower alkyl, cycloalkylamino, —CN, —O—$R^{28}$, —S(O)$_2$—$R^{29}$, —S(O)$_2$—N(H)—$R^{30}$, —N(H)—$R^{30}$, —N($R^{30}$)$_2$, and —N(H)—S(O)$_2$—$R^{31}$, provided that at least two of $R^{24}$, $R^{25}$, $R^{26}$ and $R^{27}$ are —H; $R^{28}$ is lower alkyl, fluoro substituted lower alkyl, methoxy substituted lower alkyl, or cycloalkyl; $R^{29}$ is lower alkyl; $R^{30}$ is lower alkyl; and $R^{31}$ is lower alkyl.

In some embodiments of compounds of Formula III', $R^6$ is selected from the group consisting of halogen, lower alkyl, lower alkoxy, fluoro substituted lower alkyl, lower alkenyl, lower alkynyl, cycloalkyl, phenyl, pyrazolyl, —CN, —O—$R^{13}$, —C(O)—N(H)—$R^4$, —C(O)—O—$R^{14}$, —S(O)$_2$—$R^{15}$, —S(O)$_2$—N(H)—$R^{14}$, —N(H)—C(O)—$R^{15}$, and —N(H)—S(O)$_2$—$R^{15}$, wherein pyrazolyl is optionally substituted with lower alkyl or heterocycloalkyl. In other embodiments of compounds of Formula III', $R^6$ is F, Cl, Br, lower alkyl, fluoro substituted lower alkyl, lower alkenyl, —CN, —C(O)—N(H)—$R^{14}$, —N(H)—C(O)—$R^{15}$, —C(O)—O—$R^{14}$, —S(O)$_2$—$R^{15}$, —S(O)$_2$—N(H)—$R^{14}$ or —N(H)—S(O)$_2$—$R^{15}$. In some embodiments, $R^6$ is methyl, ethyl, propyl, butyl, pentyl or hexyl. All other variables are as defined herein.

In some embodiments, compounds having the structure according to the following Formula III are provided:

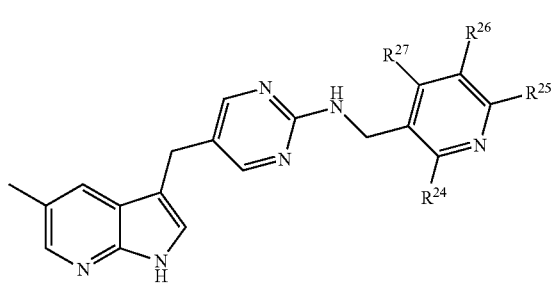

Formula III or a salt, a prodrug, a tautomer or a stereoisomer thereof, wherein:

$R^{24}$, $R^{25}$, $R^{26}$ and $R^{27}$ are independently selected from the group consisting of —H, —F, —Cl, —Br, lower alkyl, fluoro substituted lower alkyl, methoxy substituted lower alkyl, cycloalkylamino, —CN, —O—$R^{28}$, —S(O)$_2$—$R^{29}$, —S(O)$_2$—N(H)—$R^{30}$, —N(H)—$R^{30}$, —N($R^{30}$)$_2$, and —N(H)—S(O)$_2$—$R^{31}$, provided that at least two of $R^{24}$, $R^{25}$, $R^{26}$ and $R^{27}$ are —H;

$R^{28}$ is lower alkyl, fluoro substituted lower alkyl, methoxy substituted lower alkyl, or cycloalkyl;

$R^{29}$ is lower alkyl;

$R^{30}$ is lower alkyl; and $R^{31}$ is lower alkyl.

In some embodiments of compounds of Formulae III and III', $R^{24}$, $R^{25}$, $R^{26}$ and $R^{27}$ are each independently selected from the group consisting of —H, —F, —Cl, —Br, lower alkyl, fluoro substituted lower alkyl, lower alkoxy, methoxy substituted lower alkyl, cycloalkylamino, —CN, —O—$R^{20}$, —S(O)$_2$—$R^{21}$, —S(O)$_2$—N(H)—$R^{22}$, —N(H)—$R^{22}$, —N($R^{22}$)$_2$, and —N(H)—S(O)$_2$—$R^{23}$, provided that at least two of $R^{24}$, $R^{25}$, $R^{26}$ and $R^{27}$ are —H. In some embodiments, $R^{24}$, $R^{25}$, $R^{26}$ and $R^{27}$ are each independently selected from H, halogen, lower alkyl, lower alkoxy, halo substituted lower alkyl, —O$R^{20}$, or alkoxy substituted lower alkyl. All other variables are as defined herein.

In some embodiments of compounds of Formulae III and III', $R^{24}$, $R^{25}$, and $R^{26}$ are H and $R^{27}$ is —F, —Cl, —Br, lower alkyl, fluoro substituted lower alkyl, methoxy substituted lower alkyl, cycloalkylamino, —CN, —O—$R^{28}$, —S(O)$_2$—$R^{29}$, —N(H)—$R^{30}$, —N($R^{30}$)$_2$, or —N(H)—S(O)$_2$—$R^{31}$. In some embodiments $R^{24}$, $R^{25}$, and $R^{26}$ are H and $R^{27}$ is —F, —Cl, lower alkyl, fluoro substituted lower alkyl, cycloalkylamino, —O—$R^{28}$, —N(H)—$R^{30}$, or —N($R^{30}$)$_2$. In some embodiments $R^{24}$, $R^{25}$, and $R^{26}$ are H and $R^{27}$ is fluoro substituted lower alkyl or —O—$R^{28}$. In some embodiments $R^{24}$, $R^{25}$, and $R^{26}$ are H and $R^{27}$ is —CF$_3$ or —O—CH$_3$. All other variables are as defined herein.

In some embodiments of compounds of Formulae III and III', $R^{24}$, $R^{25}$, and $R^{27}$ are H and $R^{26}$ is —F, —Cl, —Br, lower alkyl, fluoro substituted lower alkyl, methoxy substituted lower alkyl, cycloalkylamino, —CN, —O—$R^{28}$, —S(O)$_2$—$R^{29}$, —N(H)—$R^{30}$, —N($R^{30}$)$_2$, or —N(H)—S(O)$_2$—$R^{31}$. In some embodiments $R^{24}$, $R^{25}$, and $R^{27}$ are H and $R^{26}$ is —F, —Cl, lower alkyl, fluoro substituted lower alkyl, cycloalkylamino, —O—$R^2$, —N(H)—$R^{30}$, or —N($R^{30}$)$_2$. In some embodiments $R^{24}$, $R^{25}$, and $R^{27}$ are H and $R^{26}$ is —F, —Cl, or —O—$R^{28}$. In some embodiments $R^{24}$, $R^{25}$, and $R^{27}$ are H and $R^{26}$ is —F, —Cl, or —O—CH$_3$. All other variables are as defined herein.

In some embodiments of compounds of Formulae III and III', $R^{24}$, $R^{26}$, and $R^{27}$ are H and $R^{25}$ is —F, —Cl, —Br, lower alkyl, fluoro substituted lower alkyl, methoxy substituted lower alkyl, cycloalkylamino, —CN, —O—$R^{28}$, —S(O)$_2$—$R^{29}$, —N(H)—$R^{30}$, —N($R^{30}$)$_2$, or —N(H)—S(O)$_2$—$R^{31}$. In some embodiments $R^{24}$, $R^{26}$, and $R^{27}$ are H and $R^{25}$ is —F, —Cl, lower allyl, fluoro substituted lower alkyl, cycloalkylamino, —O—$R^{28}$, —N(H)—$R^{30}$, or —N($R^{30}$)$_2$. In some embodiments $R^{24}$, $R^{26}$, and $R^{27}$ are H and $R^{25}$ is —Cl, fluoro substituted lower alkyl, cycloalkylamino, or —O—$R^{28}$. In some embodiments $R^{24}$, $R^{26}$ and $R^{27}$ are H and $R^{25}$ is —Cl, —CF$_3$, —O—CH$_3$, or 4-methyl-piperazin-1-yl. All other variables are as defined herein.

In some embodiments of compounds of Formulae III and III', $R^{25}$, $R^{26}$, and $R^{27}$ are H and $R^{24}$ is —F, —Cl, —Br, lower alkyl, fluoro substituted lower alkyl, methoxy substituted lower alkyl, cycloalkylamino, —CN, —O—$R^{28}$, —S(O)$_2$—$R^{29}$, —N(H)—$R^{30}$, —N($R^{30}$)$_2$, or —N(H)—S(O)$_2$—$R^{31}$. In some embodiments $R^{25}$, $R^{26}$, and $R^{27}$ are H and $R^{24}$ is —F, —Cl, lower alkyl, fluoro substituted lower alkyl, cycloalkylamino, —O—$R^{28}$, —N(H)—$R^{30}$, or —N($R^{30}$)$_2$. In some embodiments $R^{25}$, $R^{26}$, and $R^{27}$ are H and $R^{24}$ is —F, —CF$_3$, morpholin-4-yl, —O—CH$_3$, —O—CH$_2$CH$_3$, —O—CH(CH$_3$)$_2$, —O—CH$_2$CF$_3$, —O-cyclopentyl, —O-cyclohexyl, or —N(H)—CH$_3$. In some embodiments $R^{25}$, $R^{26}$, and $R^{27}$ are H and $R^{24}$ is —F, —CF$_3$, —O—CH$_3$, —O—CH$_2$CH$_3$, or —O-cyclopentyl. All other variables are as defined herein.

In some embodiments of compounds of Formulae III and III', $R^{24}$ and $R^{25}$ are H; and $R^{26}$ and $R^{27}$ are independently —F, —Cl, —Br, lower alkyl, fluoro substituted lower alkyl, methoxy substituted lower alkyl, cycloalkylamino, —CN, —O—$R^{28}$, —S(O)$_2$—$R^{29}$, —N(H)—$R^{30}$, —N($R^{30}$)$_2$, or —N(H)—S(O)$_2$—$R^{31}$. In some embodiments $R^{24}$ and $R^{25}$ are H; and $R^{26}$ and $R^{27}$ are independently —F, —Cl, lower alkyl, fluoro substituted lower alkyl, cycloalkylamino, —O—$R^{28}$, —N(H)—$R^{30}$, or —N($R^{30}$)$_2$. In some embodiments $R^{24}$ and $R^{25}$ are H; and $R^{26}$ and $R^{27}$ are independently —F, —Cl, CF$_3$, —O—CH$_3$, or —N(CH$_3$)$_2$. All other variables are as defined herein.

In some embodiments of compounds of Formulae III and III', $R^{24}$ and $R^{26}$ are H; and $R^{25}$ and $R^{27}$ are independently —F, —Cl, —Br, lower alkyl, fluoro substituted lower alkyl, methoxy substituted lower alkyl, cycloalkylamino, —CN, —O—$R^{28}$, —S(O)$_2$—$R^{29}$, —N(H)—$R^{30}$, —N($R^{30}$)$_2$, or —N(H)—S(O)$_2$—$R^{31}$. In some embodiments $R^{24}$ and $R^{26}$ are H; and $R^{25}$ and $R^{27}$ are independently —F, —Cl, lower alkyl, fluoro substituted lower alkyl, cycloalkylamino, —O—$R^2$, —N(H)—$R^{30}$, or —N($R^3$)$_2$. In some embodiments $R^{24}$ and $R^{26}$ are H; and $R^{25}$ and $R^{27}$ are independently —F, —Cl, CF$_3$, —O—CH$_3$, or —N(CH$_3$)$_2$. In some embodiments $R^{24}$ and $R^{26}$ are H; and $R^{25}$ and $R^{27}$ are independently —CF$_3$ or —O—CH$_3$. All other variables are as defined herein.

In some embodiments of compounds of Formulae III and III', $R^{24}$ and $R^{27}$ are H; and $R^{25}$ and $R^{26}$ are independently —F, —Cl, —Br, lower alkyl, fluoro substituted lower alkyl, methoxy substituted lower alkyl, cycloalkylamino, —CN, —O—$R^{28}$, —S(O)$_2$—$R^{29}$, —N(H)—$R^3$, —N($R^{30}$)$_2$, or —N(H)—S(O)$_2$—$R^{31}$. In some embodiments $R^{24}$ and $R^{27}$ are H; and $R^{25}$ and $R^{26}$ are independently —F, —Cl, lower alkyl, fluoro substituted lower alkyl, cycloalkylamino, —O—$R^{28}$, —N(H)—$R^{30}$, or —N($R^{30}$)$_2$. In some embodiments $R^{24}$ and $R^{27}$ are H; and $R^{25}$ and $R^{26}$ are independently —F, —Cl, CF$_3$, —O—CH$_3$, or —N(CH$_3$)$_2$. In some embodiments $R^{24}$ and $R^{27}$ are H; and $R^{25}$ and $R^{26}$ are independently —F or —O—CH$_3$. All other variables are as defined herein.

In some embodiments of compounds of Formulae III and III', $R^{25}$ and $R^{26}$ are H; and $R^{24}$ and $R^{27}$ are independently —F, —Cl, —Br, lower alkyl, fluoro substituted lower alkyl, methoxy substituted lower alkyl, cycloalkylamino, —CN, —O—$R^{28}$, —S(O)$_2$—$R^{29}$, —N(H)—$R^{30}$, —N($R^{30}$)$_2$, or —N(H)—S(O)$_2$—$R^{31}$. In some embodiments $R^{25}$ and $R^{26}$ are H; and $R^{24}$ and $R^{27}$ are independently —F, —Cl, lower alkyl, fluoro substituted lower alkyl, cycloalkylamino, —O—$R^{28}$, —N(H)—$R^{30}$, or —N($R^{30}$)$_2$. In some embodiments $R^{25}$ and $R^{26}$ are H; and $R^{24}$ and $R^{27}$ are independently —F, —Cl, CF$_3$, —O—CH$_3$, or —N(CH$_3$)$_2$. All other variables are as defined herein.

In some embodiments of compounds of Formulae III and III', $R^{25}$ and $R^{27}$ are H; and $R^{24}$ and $R^{26}$ are independently —F, —Cl, —Br, lower alkyl, fluoro substituted lower alkyl, methoxy substituted lower alkyl, cycloalkylamino, —CN, —O—$R^{28}$, —S(O)$_2$—$R^{29}$, —N(H)—$R^{30}$, —N($R^{30}$)$_2$, or —N(H)—S(O)$_2$—$R^{31}$. In some embodiments $R^{25}$ and $R^{27}$ are H; and $R^{24}$ and $R^{26}$ are independently —F, —Cl, lower alkyl, fluoro substituted lower alkyl, cycloalkylamino, —O—$R^{28}$, —N(H)—$R^{30}$, or —N($R^{30}$)$_2$. In some embodiments $R^{25}$ and $R^{27}$ are H; and $R^{24}$ and $R^{26}$ are independently —F, —Cl, CF$_3$, —O—CH$_3$, or —N(CH$_3$)$_2$. In some embodiments $R^{25}$ and $R^{27}$ are H; and $R^{24}$ and $R^{26}$ are independently —F or —O—CH$_3$. All other variables are as defined herein.

In some embodiments of compounds of Formulae III and III', $R^{26}$ and $R^{27}$ are H; and $R^{24}$ and $R^{25}$ are independently —F, —Cl, —Br, lower alkyl, fluoro substituted lower alkyl, methoxy substituted lower alkyl, cycloalkylamino, —CN, —O—$R^{28}$, —S(O)$_2$—$R^{29}$, —N(H)—$R^{30}$, —N($R^{30}$)$_2$, or —N(H)—S(O)$_2$—$R^{31}$. In some embodiments $R^{26}$ and $R^{27}$ are H; and $R^{24}$ and $R^{25}$ are independently —F, —Cl, lower alkyl, fluoro substituted lower alkyl, cycloalkylamino, —O—$R^{28}$, —N(H)—$R^{30}$, or —N($R^{30}$)$_2$. In some embodiments $R^{26}$ and $R^{27}$ are H; and $R^{24}$ and $R^{25}$ are independently —F, —Cl, CF$_3$, —O—CH$_3$, or —N(CH$_3$)$_2$. In some embodiments $R^{26}$ and $R^{27}$ are H; and $R^{24}$ and $R^{25}$ are independently —CF$_3$, —O—CH$_3$, or —N(CH$_3$)$_2$. All other variables are as defined herein.

In one embodiment of compounds of Formulae III and III', the compound is selected from the group consisting of:
(5-Fluoro-pyridin-3-ylmethyl)-[5-(5-methyl-1H-pyrrolo[2,3-b]pyridin-3-ylmethyl)-pyrimidin-2-yl]-amine (P-1569),
[5-(5-Methyl-1H-pyrrolo[2,3-b]pyridin-3-ylmethyl)-pyrimidin-2-yl]-(4-trifluoromethyl-pyridin-3-ylmethyl)-amine (P-1570),
(6-Methoxy-pyridin-3-ylmethyl)-[5-(5-methyl-1H-pyrrolo[2,3-b]pyridin-3-ylmethyl)-pyrimidin-2-yl]-amine (P-2057),
(5-Fluoro-2-methoxy-pyridin-3-ylmethyl)-[5-(5-methyl-1H-pyrrolo[2,3-b]pyridin-3-ylmethyl)-pyrimidin-2-yl]-amine (P-2061),
(2-Methoxy-pyridin-4-ylmethyl)-[5-(5-methyl-1H-pyrrolo[2,3-b]pyridin-3-ylmethyl)-pyrimidin-2-yl]-amine (P-2069),
(5-Fluoro-2-methoxy-pyridin-4-ylmethyl)-[5-(5-methyl-1H-pyrrolo[2,3-b]pyridin-3-ylmethyl)-pyrimidin-2-yl]-amine (P-2072),
(5-Fluoro-6-methoxy-pyridin-3-ylmethyl)-[5-(5-methyl-1H-pyrrolo[2,3-b]pyridin-3-ylmethyl)-pyrimidin-2-yl]-amine (P-2073),
[5-(5-Methyl-1H-pyrrolo[2,3-b]pyridin-3-ylmethyl)-pyrimidin-2-yl]-pyridin-2-ylmethyl-amine (P-2076),
[5-(5-Methyl-1H-pyrrolo[2,3-b]pyridin-3-ylmethyl)-pyrimidin-2-yl]-pyridin-3-ylmethyl-amine (P-2077),
(6-Chloro-pyridin-3-ylmethyl)-[5-(5-methyl-1H-pyrrolo[2,3-b]pyridin-3-ylmethyl)-pyrimidin-2-yl]-amine (P-2078),
(6-Methyl-pyridin-2-ylmethyl)-[5-(5-methyl-1H-pyrrolo[2,3-b]pyridin-3-ylmethyl)-pyrimidin-2-yl]-amine (P-2079),
[5-(5-Methyl-1H-pyrrolo[2,3-b]pyridin-3-ylmethyl)-pyrimidin-2-yl]-(6-trifluoromethyl-pyridin-3-ylmethyl)-amine (P-2080),
[5-(5-Methyl-1H-pyrrolo[2,3-b]pyridin-3-ylmethyl)-pyrimidin-2-yl]-(6-morpholin-4-yl-pyridin-2-ylmethyl)-amine (P-2081),
[5-(5-Methyl-1H-pyrrolo[2,3-b]pyridin-3-ylmethyl)-pyrimidin-2-yl]-(6-pyrrolidin-1-yl-pyridin-2-ylmethyl)-amine (P-2082),
(5-Ethyl-pyridin-2-ylmethyl)-[5-(5-methyl-1H-pyrrolo[2,3-b]pyridin-3-ylmethyl)-pyrimidin-2-yl]-amine (P-2083),
(3-Methyl-pyridin-4-ylmethyl)-[5 (5-methyl-1H-pyrrolo[2,3-b]pyridin-3-ylmethyl)-pyrimidin-2-yl]-amine (P-2084),
[5 (5-Methyl-1H-pyrrolo[2,3-b]pyridin-3-ylmethyl)-pyrimidin-2-yl]-(2-morpholin-4-yl-pyridin-4-ylmethyl)-amine (P-2085),
[5 (5-Methyl-1H-pyrrolo[2,3-b]pyridin-3-ylmethyl)-pyrimidin-2-yl]-pyridin-4-ylmethyl-amine (P-2138),
(2-Methoxy-pyridin-3-ylmethyl)-[5-(5-methyl-1H-pyrrolo[2,3-b]pyridin-3-ylmethyl)-pyrimidin-2-yl]-amine (P-2139),
[6-(4-Methyl-piperazin-1-yl)-pyridin-3-ylmethyl]-[5-(5-methyl-1H-pyrrolo[2,3-b]pyridin-3-ylmethyl)-pyrimidin-2-yl]-amine (P-2140),
(2-Methyl-pyridin-4-ylmethyl)-[5-(5-methyl-1H-pyrrolo[2,3-b]pyridin-3-ylmethyl)-pyrimidin-2-yl]-amine (P-2141),
(2-Ethoxy-pyridin-3-ylmethyl)-[5-(5-methyl-1H-pyrrolo[2,3-b]pyridin-3-ylmethyl)-pyrimidin-2-yl]-amine (P-2142),
(2-Cyclopentyloxy-pyridin-3-ylmethyl)-[5-(5-methyl-1H-pyrrolo[2,3-b]pyridin-3-ylmethyl)-pyrimidin-2-yl]-amine (P-2148),
(2-Cyclopentyloxy-pyridin-4-ylmethyl)-[5-(5-methyl-1H-pyrrolo[2,3-b]pyridin-3-ylmethyl)-pyrimidin-2-yl]-amine (P-2149), and
any salt, prodrug, tautomer, or stereoisomer thereof.

In a fourth aspect, compounds are provided, wherein the compound is selected from the group consisting of:
[5-(5-Chloro-1H-pyrrolo[2,3-b]-pyridin-3-ylmethyl)-pyridin-2-yl]-(2,6-dimethoxy-pyridin-3-ylmethyl)-amine (P-1496),
[6-Chloro-5-(1H-pyrrolo[2,3-b]pyridin-3-ylmethyl)-pyridin-2-yl]-(5-fluoro-pyridin-3-ylmethyl)-amine (P-1507),
[6-Chloro-5-(1H-pyrrolo[2,3-b]pyridin-3-ylmethyl)-pyridin-2-yl]-(6-methoxy-pyridin-3-ylmethyl)-amine (P-1511),
[6-Chloro-5-(1H-pyrrolo[2,3-b]pyridin-3-ylmethyl)-pyridin-2-yl]-(2-methoxy-pyridin-3-ylmethyl)-amine (P-1512),
(5-Fluoro-pyridin-3-ylmethyl)-[5-(1H-pyrrolo[2,3-b]pyridin-3-ylmethyl)-pyrimidin-2-yl]-amine (P-1514), (6-Methoxy-pyridin-3-ylmethyl)-[5-(1H-pyrrolo[2,3-b]pyridin-3-ylmethyl)-pyrimidin-2-yl]-amine (P-1517),
[5-(1H-Pyrrolo[2,3-b]pyridin-3-ylmethyl)-pyrimidin-2-yl]-(6-trifluoromethyl-pyridin-3-ylmethyl)-amine (P-1518),
(2-Methoxy-pyridin-3-ylmethyl)-[5-(1H-pyrrolo[2,3-b]pyridin-3-ylmethyl)-pyrimidin-2-yl]-amine (P-1519),
[4-Chloro-5-(1H-pyrrolo[2,3-b]pyridin-3-ylmethyl)-thiazol-2-yl]-(5-fluoro-pyridin-3-ylmethyl)-amine (P-1522),
[4-Chloro-5-(1H-pyrrolo[2,3-b]pyridin-3-ylmethyl)-thiazol-2-yl]-(6-methoxy-pyridin-3-ylmethyl)-amine (P-1526),
[4-Chloro-5-(1H-pyrrolo[2,3-b]pyridin-3-ylmethyl)-thiazol-2-yl]-(2-methoxy-pyridin-3-ylmethyl)-amine (P-1527),
(5-Fluoro-pyridin-3-ylmethyl)-[5-(5-methyl-1H-pyrrolo[2,3-b]pyridin-3-ylmethyl)-pyridin-2-yl]-amine (P-1530),
(6-Methoxy-pyridin-3-ylmethyl)-[6-methyl-5-(5-methyl-1H-pyrrolo[2,3-b]pyridin-3-ylmethyl)-pyridin-2-yl]-amine (P-1532),
(5-Fluoro-pyridin-3-ylmethyl)-[6-methyl-5-(5-methyl-1H-pyrrolo[2,3-b]pyridin-3-ylmethyl)-pyridin-2-yl]-amine (P-1534),
[6-Methyl-5-(5-methyl-1H-pyrrolo[2,3-b]pyridin-3-ylmethyl)-pyridin-2-yl]-(6-trifluoromethyl-pyridin-3-ylmethyl)-amine (P-1538),
(2-Methoxy-pyridin-3-ylmethyl)-[6-methyl-5-(5-methyl-1H-pyrrolo[2,3-b]pyridin-3-ylmethyl)-pyridin-2-yl]-amine (P-1539),
[6-Chloro-5-(5-methyl-1H-pyrrolo[2,3-b]pyridin-3-ylmethyl)-pyridin-2-yl]-(5-fluoro-pyridin-3-ylmethyl)-amine (P-1541),
[6-Chloro-5-(5-methyl-1H-pyrrolo[2,3-b]pyridin-3-ylmethyl)-pyridin-2-yl]-(6-methoxy-pyridin-3-ylmethyl)-amine (P-1545),
[6-Chloro-5-(5-methyl-1H-pyrrolo[2,3-b]pyridin-3-ylmethyl)-pyridin-2-yl]-(2-methoxy-pyridin-3-ylmethyl)-amine (P-1546),
(5-Fluoro-pyridin-3-ylmethyl)-[3-methoxy-5-(5-methyl-1H-pyrrolo[2,3-b]pyridin-3-ylmethyl)-pyridin-2-yl]-amine (P-1549),
[3-Methoxy-5-(5-methyl-1H-pyrrolo[2,3-b]pyridin-3-ylmethyl)-pyridin-2-yl]-(6-methoxy-pyridin-3-ylmethyl)-amine (P-1552),
[3-Methoxy-5-(5-methyl-1H-pyrrolo[2,3-b]pyridin-3-ylmethyl)-pyridin-2-yl]-(2-methoxy-pyridin-3-ylmethyl)-amine (P-1553),
(6-Methoxy-pyridin-3-ylmethyl)-[3-methyl-5-(5-methyl-1H-pyrrolo[2,3-b]pyridin-3-ylmethyl)-pyridin-2-yl]-amine (P-1554),
(5-Fluoro-pyridin-3-ylmethyl)-[3-methyl-5-(5-methyl-1H-pyrrolo[2,3-b]pyridin-3-ylmethyl)-pyridin-2-yl]-amine (P-1556),
[3-Methyl-5-(5-methyl-1H-pyrrolo[2,3-b]pyridin-3-ylmethyl)-pyridin-2-yl]-(6-trifluoromethyl-pyridin-3-ylmethyl)-amine (P-1560),
(2-Methoxy-pyridin-3-ylmethyl)-[3-methyl-5-(5-methyl-1H-pyrrolo[2,3-b]pyridin-3-ylmethyl)-pyridin-2-yl]-amine (P-1561),
[3-Fluoro-5-(5-methyl-1H-pyrrolo[2,3-b]pyridin-3-ylmethyl)-pyridin-2-yl]-(6-methoxy-pyridin-3-ylmethyl)-amine (P-1562),
[3-Fluoro-5-(5-methyl-1H-pyrrolo[2,3-b]pyridin-3-ylmethyl)-pyridin-2-yl]-(5-fluoro-pyridin-3-ylmethyl)-amine (P-1564),
[3-Fluoro-5-(5-methyl-1H-pyrrolo[2,3-b]pyridin-3-ylmethyl)-pyridin-2-yl]-(2-methoxy-pyridin-3-ylmethyl)-amine (P-1568),
(5-Fluoro-pyridin-3-ylmethyl)-[5-(5-methyl-1H-pyrrolo[2,3-b]pyridin-3-ylmethyl)-thiazol-2-yl]-amine (P-1580),
[5-(5-Methoxy-1H-pyrrolo[2,3-b]pyridin-3-ylmethyl)-pyridin-2-yl]-(6-trifluoromethyl-pyridin-3-ylmethyl)-amine (P-1583),
(5-Fluoro-pyridin-3-ylmethyl)-[5-(5-methoxy-1H-pyrrolo[2,3-b]pyridin-3-ylmethyl)-pyridin-2-yl]-amine (P-1585),
(2-Methoxy-pyridin-3-ylmethyl)-[5-(5-methoxy-1H-pyrrolo[2,3-b]pyridin-3-ylmethyl)-pyridin-2-yl]-amine (P-1589),
[6-Chloro-5-(5-methoxy-1H-pyrrolo[2,3-b]pyridin-3-ylmethyl)-pyridin-2-yl]-(5-fluoro-pyridin-3-ylmethyl)-amine (P-1591),
[6-Chloro-5-(5-methoxy-1H-pyrrolo[2,3-b]pyridin-3-ylmethyl)-pyridin-2-yl]-(6-methoxy-pyridin-3-ylmethyl)-amine (P-1595),
[6-Chloro-5-(5-methoxy-1H-pyrrolo[2,3-b]pyridin-3-ylmethyl)-pyridin-2-yl]-(2-methoxy-pyridin-3-ylmethyl)-amine (P-1596),
(5-Fluoro-pyridin-3-ylmethyl)-[5-(5-methoxy-1H-pyrrolo[2,3-b]pyridin-3-ylmethyl)-pyrimidin-2-yl]-amine (P-1601),
(6-Methoxy-pyridin-3-ylmethyl)-[5-(5-methoxy-1H-pyrrolo[2,3-b]pyridin-3-ylmethyl)-pyrimidin-2-yl]-amine (P-1604),
[5-(5-Methoxy-1H-pyrrolo[2,3-b]pyridin-3-ylmethyl)-pyrimidin-2-yl]-(6-trifluoromethyl-pyridin-3-ylmethyl)-amine (P-1605),
(2-Methoxy-pyridin-3-ylmethyl)-[5-(5-methoxy-1H-pyrrolo[2,3-b]pyridin-3-ylmethyl)-pyrimidin-2-yl]-amine (P-1606),
[5-(5-Chloro-1H-pyrrolo[2,3-b]pyridin-3-ylmethyl)-6-fluoro-pyridin-2-yl]-(2-methoxy-pyridin-3-ylmethyl)-amine (P-1609),
[5-(5-Chloro-1H-pyrrolo[2,3-b]pyridin-3-ylmethyl)-pyrimidin-2-yl]-(2-methoxy-pyridin-3-ylmethyl)-amine (P-1614),
[6-Fluoro-5-(5-fluoro-1H-pyrrolo[2,3-b]pyridin-3-ylmethyl)-pyridin-2-yl]-(6-methoxy-pyridin-3-ylmethyl)-amine (P-1622),
[6-Fluoro-5-(5-fluoro-1H-pyrrolo[2,3-b]pyridin-3-ylmethyl)-pyridin-2-yl]-(5-fluoro-pyridin-3-ylmethyl)-amine (P-1624),
[6-Fluoro-5-(5-fluoro-1H-pyrrolo[2,3-b]pyridin-3-ylmethyl)-pyridin-2-yl]-(6-trifluoromethyl-pyridin-3-ylmethyl)-amine (P-1628),
[6-Fluoro-5-(5-fluoro-1H-pyrrolo[2,3-b]pyridin-3-ylmethyl)-pyridin-2-yl]-(2-methoxy-pyridin-3-ylmethyl)-amine (P-1629),
(5-Fluoro-pyridin-3-ylmethyl)-[5-(5-fluoro-1H-pyrrolo[2,3-b]pyridin-3-ylmethyl)-pyrimidin-2-yl]-amine (P-1631),
[5-(5-Fluoro-1H-pyrrolo[2,3-b]pyridin-3-ylmethyl)-pyrimidin-2-yl]-(6-methoxy-pyridin-3-ylmethyl)-amine (P-1635),
[5-(5-Fluoro-1H-pyrrolo[2,3-b]pyridin-3-ylmethyl)-pyrimidin-2-yl]-(6-trifluoromethyl-pyridin-3-ylmethyl)-amine (P-1636),
[5-(5-Fluoro-1H-pyrrolo[2,3-b]pyridin-3-ylmethyl)-pyrimidin-2-yl]-(2-methoxy-pyridin-3-ylmethyl)-amine (P-1637),
(5-Fluoro-pyridin-3-ylmethyl)-[5-(5-trifluoromethyl-1H-pyrrolo[2,3-b]pyridin-3-ylmethyl)-pyridin-2-yl]-amine (P-1639),
(6-Methoxy-pyridin-3-ylmethyl)-[5-(5-trifluoromethyl-1H-pyrrolo[2,3-b]pyridin-3-ylmethyl)-pyridin-2-yl]-amine (P-1643),
(6-Trifluoromethyl-pyridin-3-ylmethyl)-[5-(5-trifluoromethyl-1H-pyrrolo[2,3-b]pyridin-3-ylmethyl)-pyridin-2-yl]-amine (P-1644), (2-Methoxy-pyridin-3-ylmethyl)-[5-(5-trifluoromethyl-1H-pyrrolo[2,3-b]pyridin-3-ylmethyl)-pyridin-2-yl]-amine (P-1645), (5-Fluoro-pyridin-3-ylmethyl)-[6-fluoro-5-(5-tri fluoromethyl-1H-pyrrolo[2,3-b]pyridin-3-ylmethyl)-pyridin-2-yl]-amine (P-1647),

[6-Fluoro-5-(5-trifluoromethyl-1H-pyrrolo[2,3-b]pyridin-3-ylmethyl)-pyridin-2-yl]-(6-methoxy-pyridin-3-ylmethyl)-amine (P-1651),

[6-Fluoro-5-(5-trifluoromethyl-1H-pyrrolo[2,3-b]pyridin-3-ylmethyl)-pyridin-2-yl]-(6-trifluoromethyl-pyridin-3-ylmethyl)-amine (P-1652),

[6-Fluoro-5-(5-trifluoro methyl-1H-pyrrolo[2,3-b]pyridin-3-ylmethyl)-pyridin-2-yl]-(2-methoxy-pyridin-3-ylmethyl)-amine (P-1653), 3-{2-Fluoro-6-[(6-methoxy-pyridin-3-ylmethyl)-amino]-pyridin-3-ylmethyl}-1H-pyrrolo[2,3-b]pyridine-5-carbonitrile (P-1658), 3-{2-Fluoro-6-[(6-trifluoromethyl-pyridin-3-ylmethyl)-amino]-pyridin-3-ylmethyl}-1H-pyrrolo[2,3-b]pyridine-5-carbonitrile (P-1659), 3-{2-Fluoro-6-[(2-methoxy-pyridin-3-ylmethyl)-amino]-pyridin-3-ylmethyl}-1H-pyrrolo[2,3-b]pyridine-5-carbonitrile (P-1660),

[5-(5-Cyclopropyl-1H-pyrrolo[2,3-b]pyridin-3-ylmethyl)-pyridin-2-yl]-(5-fluoro-pyridin-3-ylmethyl)-amine (P-1662),

[5-(5-Cyclopropyl-1H-pyrrolo[2,3-b]pyridin-3-ylmethyl)-pyridin-2-yl]-(6-methoxy-pyridin-3-ylmethyl)-amine (P-1666),

[5-(5-Cyclopropyl-1H-pyrrolo[2,3-b]pyridin-3-ylmethyl)-pyridin-2-yl]-(6-trifluoromethyl-pyridin-3-ylmethyl)-amine (P-1667),

[5-(5-Cyclopropyl-1H-pyrrolo[2,3-b]pyridin-3-ylmethyl)-pyridin-2-yl]-(2-methoxy-pyridin-3-ylmethyl)-amine (P-1668), N-(3-{2-Fluoro-6-[(5-fluoro-pyridin-3-ylmethyl)-amino]-pyridin-3-ylmethyl}-1H-pyrrolo[2,3-b]pyridin-5-yl)-acetamide (P-1671), N-(3-{2-Fluoro-6-[(6-methoxy-pyridin-3-ylmethyl)-amino]-pyridin-3-ylmethyl}-1H-pyrrolo[2,3-b]pyridin-5-yl)-acetamide (P-1674), N-(3-{2-Fluoro-6-[(6-tri fluoromethyl-pyridin-3-ylmethyl)-amino]-pyridin-3-ylmethyl}-1H-pyrrolo[2,3-b]pyridin-5-yl)-acetamide (P-1675), N-(3-{2-Fluoro-6-[(2-methoxy-pyridin-3-ylmethyl)-amino]-pyridin-3-ylmethyl}-1H-pyrrolo[2,3-b]pyridin-5-yl)-acetamide (P-1676), N-(3-{2-Fluoro-6-[(5-fluoro-pyridin-3-ylmethyl)-amino]-pyridin-3-ylmethyl}-1H-pyrrolo[2,3-b]pyridin-5-yl)-methanesulfonamide (P-1678), N-(3-{2-Fluoro-6-[(6-methoxy-pyridin-3-ylmethyl)-amino]-pyridin-3-ylmethyl}-1H-pyrrolo[2,3-b]pyridin-5-yl)-methanesulfonamide (P-1682), N-(3-{2-Fluoro-6-[(6-trifluoromethyl-pyridin-3-ylmethyl)-amino]-pyridin-3-ylmethyl}-1H-pyrrolo[2,3-b]pyridin-5-yl)-methanesulfonamide (P-1683), N-(3-{2-Fluoro-6-[(2-methoxy-pyridin-3-ylmethyl)-amino]-pyridin-3-ylmethyl}-1H-pyrrolo[2,3-b]pyridin-5-yl)-methanesulfonamide (P-1684),

[6-Fluoro-5-(5-methane sulfonyl-1H-pyrrolo[2,3-b]pyridin-3-ylmethyl)-pyridin-2-yl]-(5-fluoro-pyridin-3-ylmethyl)-amine (P-1686),

[6-Fluoro-5-(5-methanesulfonyl-1H-pyrrolo[2,3-b]pyridin-3-ylmethyl)-pyridin-2-yl]-(6-methoxy-pyridin-3-ylmethyl)-amine (P-1690),

[6-Fluoro-5-(5-methane sulfonyl-1H-pyrrolo[2,3-b]pyridin-3-ylmethyl)-pyridin-2-yl]-(6-trifluoromethyl-pyridin-3-ylmethyl)-amine (P-1691),

[6-Fluoro-5-(5-methane sulfonyl-1H-pyrrolo[2,3-b]pyridin-3-ylmethyl)-pyridin-2-yl]-(2-methoxy-pyridin-3-ylmethyl)-amine (P-1692), 3-{2-Fluoro-6-[(5-fluoro-pyridin-3-ylmethyl)-amino]-pyridin-3-ylmethyl}-1H-pyrrolo[2,3-b]pyridine-5-carboxylic acid methylamide (P-1695), 3-{2-Fluoro-6-[(6-methoxy-pyridin-3-ylmethyl)-amino]-pyridin-3-ylmethyl}-1H-pyrrolo[2,3-b]pyridine-5-carboxylic acid methylamide (P-1699), 3-{2-Fluoro-6-[(6-trifluoromethyl-pyridin-3-ylmethyl)-amino]-pyridin-3-ylmethyl}-1H-pyrrolo[2,3-b]pyridine-5-carboxylic acid methylamide (P-1700), 3-{2-Fluoro-6-[(2-methoxy-pyridin-3-ylmethyl)-amino]-pyridin-3-ylmethyl}-1H-pyrrolo[2,3-b]pyridine-5-carboxylic acid methylamide (P-1701), 4-[4-(3-{2-Fluoro-6-[(5-fluoro-2-methoxy-pyridin-3-ylmethyl)-amino]-pyridin-3-ylmethyl}-1H-pyrrolo[2,3-b]pyridin-5-yl)-pyrazol-1-yl]-piperidine-1-carboxylic acid tert-butyl ester (P-1702), {6-Fluoro-5-[5-(1-piperidin-4-yl-1H-pyrazol-4-yl)-1H-pyrrolo[2,3-b]pyridin-3-ylmethyl]-pyridin-2-yl}-(5-fluoro-pyridin-3-ylmethyl)-amine (P-1705), {6-Fluoro-5-[5-(1-piperidin-4-yl-1H-pyrazol-4-yl)-1H-pyrrolo[2,3-b]pyridin-3-ylmethyl]-pyridin-2-yl}-(6-methoxy-pyridin-3-ylmethyl)-amine (P-1708), {6-Fluoro-5-[5-(1-piperidin-4-yl-1H-pyrazol-4-yl)-1H-pyrrolo[2,3-b]pyridin-3-ylmethyl]-pyridin-2-yl}-(6-trifluoromethyl-pyridin-3-ylmethyl)-amine (P-1709), {6-Fluoro-5-[5-(1-piperidin-4-yl-1H-pyrazol-4-yl)-1H-pyrrolo[2,3-b]pyridin-3-ylmethyl]-pyridin-2-yl}-(2-methoxy-pyridin-3-ylmethyl)-amine (P-1710),

[5-(4-Ethynyl-1H-pyrrolo[2,3-b]pyridin-3-ylmethyl)-pyridin-2-yl]-(5-fluoro-pyridin-3-ylmethyl)-amine (P-1712),

[5-(4-Ethynyl-1H-pyrrolo[2,3-b]pyridin-3-ylmethyl)-pyridin-2-yl]-(6-methoxy-pyridin-3-ylmethyl)-amine (P-1716),

[5-(4-Ethynyl-1H-pyrrolo[2,3-b]pyridin-3-ylmethyl)-pyridin-2-yl]-(6-trifluoromethyl-pyridin-3-ylmethyl)-amine (P-1717),

[5-(4-Ethynyl-1H-pyrrolo[2,3-b]pyridin-3-ylmethyl)-pyridin-2-yl]-(2-methoxy-pyridin-3-ylmethyl)-amine (P-1718), 3-{[(5-Fluoro-pyridin-3-ylmethyl)-amino]-pyridin-3-ylmethyl}-1H-pyrrolo[2,3-b]pyridine-4-carbonitrile (P-1719), 3-{6-[(6-Methoxy-pyridin-3-ylmethyl)-amino]-pyridin-3-ylmethyl}-1H-pyrrolo[2,3-b]pyridine-4-carbonitrile (P-1723), 3-{6-[(6-Trifluoromethyl-pyridin-3-ylmethyl)-amino]-pyridin-3-ylmethyl}-1H-pyrrolo[2,3-b]pyridine-4-carbonitrile (P-1724), 3-{6-[(2-Methoxy-pyridin-3-ylmethyl)-amino]-pyridin-3-ylmethyl}-1H-pyrrolo[2,3-b]pyridine-4-carbonitrile (P-1725),

[6-Fluoro-5-(4-methyl-7H-pyrrolo[2,3-d]pyrimidin-5-ylmethyl)-pyridin-2-yl]-(5-fluoro-pyridin-3-ylmethyl)-amine (P-1727), (6-Chloro-pyridin-3-ylmethyl)-[6-fluoro-5-(4-methyl-7H-pyrrolo[2,3-d]pyrimidin-5-ylmethyl)-pyridin-2-yl]-amine (P-1728), (5-Fluoro-2-methoxy-pyridin-3-ylmethyl)-[6-fluoro-5-(4-methyl-7H-pyrrolo[2,3-d]pyrimidin-5-ylmethyl)-pyridin-2-yl]-amine (P-1729),

[6-Fluoro-5-(4-methyl-7H-pyrrolo[2,3-d]pyrimidin-5-ylmethyl)-pyridin-2-yl]-(4-trifluoromethyl-pyridin-3-ylmethyl)-amine (P-1730),
[6-Fluoro-5-(4-methyl-7H-pyrrolo[2,3-d]pyrimidin-5-ylmethyl)-pyridin-2-yl]-(6-methoxy-pyridin-3-ylmethyl)-amine (P-1731),
[6-Fluoro-5-(4-methyl-7H-pyrrolo[2,3-d]pyrimidin-5-ylmethyl)-pyridin-2-yl]-(6-trifluoromethyl-pyridin-3-ylmethyl)-amine (P-1732),
(5-Fluoro-6-methoxy-pyridin-3-ylmethyl)-[6-fluoro-5-(4-methyl-7H-pyrrolo[2,3-d]pyrimidin-5-ylmethyl)-pyridin-2-yl]-amine (P-1733),
[6-Fluoro-5-(4-methyl-7H-pyrrolo[2,3-d]pyrimidin-5-ylmethyl)-pyridin-2-yl]-(2-methoxy-pyridin-3-ylmethyl)-amine (P-1734),
[5-(5-Chloro-1H-pyrrolo[2,3-b]pyridin-3-ylmethyl)-6-fluoro-pyridin-2-yl]-(5-fluoro-pyridin-3-ylmethyl)-amine (P-2001),
[5-(5-Chloro-1H-pyrrolo[2,3-b]-pyridin-3-ylmethyl)-pyrimidin-2-yl]-[(S)-1-(4-fluoro-phenyl)-ethyl]-amine (P-2005),
(3-Chloro-benzyl)-[5-(5-fluoro-1H-pyrrolo[2,3-b]pyridin-3-ylmethyl)-1-methyl-1H-pyrazol-3-yl]-amine (P-2006),
(3-Chloro-4-methyl-benzyl)-[5-(5-chloro-1H-pyrrolo[2,3-b]pyridin-3-ylmethyl)-pyrimidin-2-yl]-amine (P-2007),
[5-(5-Chloro-1H-pyrrolo[2,3-b]pyridin-3-ylmethyl)-pyrimidin-2-yl]-(3,4-difluoro-benzyl)-amine (P-2008),
[5-(5-Chloro-1H-pyrrolo[2,3-b]pyridin-3-ylmethyl)-pyrimidin-2-yl]-(3-fluoro-5-trifluoromethyl-benzyl)-amine (P-2009),
[5-(5-Chloro-1H-pyrrolo[2,3-b]pyridin-3-ylmethyl)-pyrimidin-2-yl]-(3-trifluoromethoxy-benzyl)-amine (P-2010),
[5-(5-Chloro-1H-pyrrolo[2,3-b]pyridin-3-ylmethyl)-pyrimidin-2-yl]-(3-fluoro-4-trifluoromethyl-benzyl)-amine (P-2011),
(4-Chloro-benzyl)-[5-(5-chloro-1H-pyrrolo[2,3-b]pyridin-3-ylmethyl)-pyrimidin-2-yl]-methyl-amine (P-2012),
[5-(5-Chloro-1H-pyrrolo[2,3-b]pyridin-3-ylmethyl)-pyrimidin-2-yl]-(3-methyl-benzyl)-amine (P-2013),
[5-(5-Chloro-1H-pyrrolo[2,3-b]pyridin-3-ylmethyl)-pyrimidin-2-yl]-(3-fluoro-4-methyl-benzyl)-amine (P-2014),
[2-(3-Chloro-phenyl)-ethyl]-[5-(5-chloro-1H-pyrrolo[2,3-b]pyridin-3-ylmethyl)-pyrimidin-2-yl]-amine (P-2015),
[5-(5-Chloro-1H-pyrrolo[2,3-b]pyridin-3-ylmethyl)-1H-pyrazol-3-yl]-(4-fluoro-benzyl)-amine (P-2016),
[5-(5-Bromo-1H-pyrrolo[2,3-b]pyridin-3-ylmethyl)-pyridin-2-yl]-(6-methoxy-pyridin-3-ylmethyl)-amine (P-2017),
[5-(4-Methoxy-1H-pyrrolo[2,3-b]pyridin-3-ylmethyl)-pyridin-2-yl]-(6-trifluoromethyl-pyridin-3-ylmethyl)-amine (P-2018),
[5-(5-Methyl-1H-pyrrolo[2,3-b]pyridin-3-ylmethyl)-pyridin-2-yl]-(6-trifluoromethyl-pyridin-3-ylmethyl)-amine (P-2019),
[2-(2-Chloro-phenyl)-ethyl]-[5-(5-chloro-1H-pyrrolo[2,3-b]pyridin-3-ylmethyl)-pyrimidin-2-yl]-amine (P-2020),
[5-(5-Chloro-1H-pyrrolo[2,3-b]pyridin-3-ylmethyl)-pyrimidin-2-yl]-[2-(4-fluoro-phenyl)-ethyl]-amine (P-2021),
[5-(5-Chloro-1H-pyrrolo[2,3-b]-pyridin-3-ylmethyl)-pyrimidin-2-yl]-[2-(6-methyl-pyridin-2-yl)-ethyl]-amine (P-2022),
[5-(5-Fluoro-1H-pyrrolo[2,3-b]pyridin-3-ylmethyl)-pyridin-2-yl]-(6-trifluoromethyl-pyridin-3-ylmethyl)-amine (P-2023),
[5-(5-Methoxy-1H-pyrrolo[2,3-b]pyridin-3-ylmethyl)-pyridin-2-yl]-(6-trifluoromethyl-pyridin-3-ylmethyl)-amine (P-2024),
Butyl-[5-(5-chloro-1H-pyrrolo[2,3-b]pyridin-3-ylmethyl)-pyrimidin-2-yl]-amine (P-2026),
[6-Fluoro-5-(5-methoxy-1H-pyrrolo[2,3-b]pyridin-3-ylmethyl)-pyridin-2-yl]-(5-fluoro-pyridin-3-ylmethyl)-amine (P-2028),
[6-Fluoro-5-(5-methoxy-1H-pyrrolo[2,3-b]pyridin-3-ylmethyl)-pyridin-2-yl]-(6-methoxy-pyridin-3-ylmethyl)-amine (P-2030),
(4-Chloro-benzyl)-[6-fluoro-5-(5-methoxy-1H-pyrrolo[2,3-b]pyridin-3-ylmethyl)-pyridin-2-yl]-amine (P-2032),
(2-Fluoro-benzyl)-[5-(4-methoxy-1H-pyrrolo[2,3-b]pyridin-3-ylmethyl)-pyridin-2-yl]-amine (P-2033),
(2-Chloro-benzyl)-[6-fluoro-5-(5-methoxy-1H-pyrrolo[2,3-b]pyridin-3-ylmethyl)-pyridin-2-yl]-amine (P-2034),
(2-Chloro-benzyl)-[6-fluoro-5-(4-methoxy-1H-pyrrolo[2,3-b]pyridin-3-ylmethyl)-pyridin-2-yl]-amine (P-2035),
(2-Chloro-benzyl)-[5-(4-methoxy-1H-pyrrolo[2,3-b]pyridin-3-ylmethyl)-pyridin-2-yl]-amine (P-2036),
(4-Chloro-benzyl)-[6-fluoro-5-(4-methoxy-1H-pyrrolo[2,3-b]pyridin-3-ylmethyl)-pyridin-2-yl]-amine (P-2037),
[5-(5-Chloro-1H-pyrrolo[2,3-b]pyridin-3-ylmethyl)-pyrimidin-2-yl]-(6-methoxy-pyridin-3-ylmethyl)-amine (P-2038),
[5-(5-Fluoro-1H-pyrrolo[2,3-b]pyridin-3-ylmethyl)-pyrimidin-2-yl]-(1-thiazol-2-yl-ethyl)-amine (P-2039),
[6-Fluoro-5-(5-methoxy-1H-pyrrolo[2,3-b]pyridin-3-ylmethyl)-pyridin-2-yl]-(2-methoxy-pyridin-3-ylmethyl)-amine (P-2043),
(5-Chloro-pyridin-2-ylmethyl)-[6-fluoro-5-(1H-pyrrolo[2,3-b]pyridin-3-ylmethyl)-pyridin-2-yl]-amine (P-2044),
[6-Fluoro-5-(1H-pyrrolo[2,3-b]pyridin-3-ylmethyl)-pyridin-2-yl]-(2-methoxy-pyridin-3-ylmethyl)-amine (P-2045),
[1-(4-Fluoro-phenyl)-propyl]-[5-(5-fluoro-1H-pyrrolo[2,3-b]pyridin-3-ylmethyl)-pyrimidin-2-yl]-amine (P-2053),
[1-(4-Fluoro-phenyl)-cyclopropyl]-[5-(5-fluoro-1H-pyrrolo[2,3-b]pyridin-3-ylmethyl)-pyrimidin-2-yl]-amine (P-2055),
[(S)-1-(4-Fluoro-phenyl)-ethyl]-[5-(5-fluoro-1H-pyrrolo[2,3-b]pyridin-3-ylmethyl)-pyrimidin-2-yl]-amine (P-2056),
[5-(5-Chloro-1H-pyrrolo[2,3-b]pyridin-3-ylmethyl)-pyrimidin-2-yl]-(2-methoxy-pyridin-4-ylmethyl)-amine (P-2074),
[5-(5-Chloro-1H-pyrrolo[2,3-b]-pyridin-3-ylmethyl)-6-fluoro-pyridin-2-yl]-(2-methyl-pyridin-4-ylmethyl)-amine (P-2075),
(5-Fluoro-2-methoxy-pyridin-4-ylmethyl)-[5-(1H-pyrrolo[2,3-b]pyridin-3-ylmethyl)-pyrimidin-2-yl]-amine (P-2135),
(5-Fluoro-2-methoxy-pyridin-4-ylmethyl)-[5-(5-methoxy-1H-pyrrolo[2,3-b]pyridin-3-ylmethyl)-pyrimidin-2-yl]-amine (P-2136),
[3-Methoxy-5-(5-methyl-1H-pyrrolo[2,3-b]pyridin-3-ylmethyl)-pyridin-2-yl]-(6-trifluoromethyl-pyridin-3-ylmethyl)-amine (P-2143),
[5-(5-Chloro-1H-pyrrolo[2,3-b]pyridin-3-ylmethyl)-thiazol-2-yl]-(6-trifluoromethyl-pyridin-3-ylmethyl)-amine (P-2144),
[5-(5-Methyl-1H-pyrrolo[2,3-b]pyridin-3-ylmethyl)-thiazol-2-yl]-(6-trifluoromethyl-pyridin-3-ylmethyl)-amine (P-2145),
[3-Fluoro-5-(5-methyl-1H-pyrrolo[2,3-b]pyridin-3-ylmethyl)-pyridin-2-yl]-(6-trifluoromethyl-pyridin-3-ylmethyl)-amine (P-2146),
[3-Fluoro-5-(5-methoxy-1H-pyrrolo[2,3-b]pyridin-3-ylmethyl)-pyridin-2-yl]-(6-trifluoromethyl-pyridin-3-ylmethyl)-amine (P-2147),

[5-(5-Chloro-1H-pyrrolo[2,3-b]pyridin-3-ylmethyl)-thiazol-2-yl]-(6-methoxy-pyridin-3-ylmethyl)-amine (P-2154),
(6-Methoxy-pyridin-3-ylmethyl)-[5-(5-methyl-1H-pyrrolo[2,3-b]pyridin-3-ylmethyl)-thiazol-2-yl]-amine (P-2155),
3-{[5-(5-Chloro-1H-pyrrolo[2,3-b]pyridin-3-ylmethyl)-pyrimidin-2-ylamino]-methyl}-5-fluoro-1-methyl-1H-pyridin-2-one (P-2157),
[5-(5-Chloro-1H-pyrrolo[2,3-b]pyridin-3-ylmethyl)-thiazol-2-yl]-(2-methoxy-pyridin-3-ylmethyl)-amine (P-2158),
(2-Methoxy-pyridin-3-ylmethyl)-[5-(5-methyl-1H-pyrrolo[2,3-b]pyridin-3-ylmethyl)-thiazol-2-yl]-amine (P-2159),
(6-Methoxy-pyridin-2-ylmethyl)-[5-(5-methyl-1H-pyrrolo[2,3-b]pyridin-3-ylmethyl)-thiazol-2-yl]-amine (P-2162),
[5-(5-Chloro-1H-pyrrolo[2,3-b]pyridin-3-ylmethyl)-thiazol-2-yl]-(6-methoxy-pyridin-2-ylmethyl)-amine (P-2163),
[5-(5-Chloro-1H-pyrrolo[2,3-b]-pyridin-3-ylmethyl)-thiazol-2-yl]-(2,6-dimethoxy-pyridin-3-ylmethyl)-amine (P-2164),
5-Fluoro-N-[6-fluoro-5-(5-methyl-1H-pyrrolo[2,3-b]pyridin-3-ylmethyl)-pyridin-2-yl]-2-methoxy-nicotinamide (P-2168),
[5-(5-Chloro-1H-pyrrolo[2,3-b]pyridin-3-ylmethyl)-3-fluoro-pyridin-2-yl]-(6-trifluoromethyl-pyridin-3-ylmethyl)-amine (P-2172),
[5-(5-Chloro-1H-pyrrolo[2,3-b]pyridin-3-ylmethyl)-pyrimidin-2-yl]-(5-fluoro-pyridin-3-ylmethyl)-amine (P-2176),
N-[6-Fluoro-5-(5-methyl-1H-pyrrolo[2,3-b]pyridin-3-ylmethyl)-pyridin-2-yl]-C-phenyl-methanesulfonamide (P-2181), and
any salt, prodrug, tautomer, or stereoisomer thereof.

In reference to compounds herein, unless clearly indicated to the contrary, specification of a compound or group of compounds includes salts of such compound(s) (including pharmaceutically acceptable salts), formulations of such compound(s) (including pharmaceutically acceptable formulations), conjugates thereof, derivatives thereof, forms thereof, prodrugs thereof, and all stereoisomers thereof. In reference to compositions, kits, methods of use, etc. of compounds as described herein (i.e. compounds of the invention), it is understood (unless indicated otherwise) that a compound as described herein includes compounds of Formulae I and I' including all sub-embodiments thereof, compounds of Formulae II, II' and IIa, including all sub-embodiments thereof, compounds of Formulae III and III' including all sub-embodiments thereof, and compounds as listed in the fourth aspect above.

In a fifth aspect, methods are provided for treating any of a Fms and/or Kit and/or Flt-3 protein kinase mediated disease or condition in an animal subject in need thereof, wherein the method involves administering to the subject an effective amount of any one or more compound(s) as described herein. In certain embodiments, the method involves administering to the subject an effective amount of a compound as described herein in combination with one or more other therapies for the disease or condition.

In a sixth aspect, the invention provides methods for treating a Fms protein kinase mediated disease or condition in an animal subject in need thereof, wherein the method involves administering to the subject an effective amount of any one or more compound(s) as described herein. In one embodiment, the method involves administering to the subject an effective amount of a compound as described herein in combination with one or more other therapies for the disease or condition.

In a seventh aspect, the invention provides methods for treating a Kit protein kinase mediated disease or condition in an animal subject in need thereof, wherein the method involves administering to the subject an effective amount of any one or more compound(s) as described herein. In one embodiment, the method involves administering to the subject an effective amount of a compound described herein in combination with one or more other therapies for the disease or condition.

In an eighth aspect, a compound as described herein will have an $IC_{50}$ of less than 500 nm, less than 100 nM, less than 50 nM, less than 20 nM, less than 10 nM, less than 5 nM, or less than 1 nM as determined in a generally accepted Fms kinase activity assay. In some embodiments, the compound is selective relative to other protein kinases, such that the ratio of $IC_{50}$ for another kinase assessed comparably, divided by the $IC_{50}$ for Fms kinase is >20, also >30, also >40, also >50, also >60, also >70, also >80, also >90, also >100, wherein the other protein kinase includes, but is not limited to CSK, Insulin receptor kinase, AMPK, PDGFR or VEGFR.

In a ninth aspect, a compound as described herein will have an $IC_{50}$ of less than 500 nm, less than 100 nM, less than 50 nM, less than 20 nM, less than 10 nM, less than 5 nM, or less than 1 nM as determined in a generally accepted Kit kinase activity assay. In some embodiments, the compound is selective relative to other protein kinases, such that the ratio of $IC_{50}$ for another kinase assessed comparably divided by the $IC_{50}$ for Kit kinase is >20, also >30, also >40, also >50, also >60, also >70, also >80, also >90, also >100, wherein the other protein kinase includes, but is not limited to CSK, Insulin receptor kinase, AMPK, PDGFR or VEGFR.

In a tenth aspect, a compound as described herein is a dual Fms/Kit inhibitor, i.e. will be approximately equipotent with respect to inhibition of Fms kinase and Kit kinase. In some embodiments the compound will have an $IC_{50}$ of less than 500 nm, less than 100 nM, less than 50 nM, less than 20 nM, less than 10 nM, less than 5 nM, or less than 1 nM as determined in a generally accepted Fms kinase activity assay and will have an $IC_{50}$ of less than 500 nm, less than 100 nM, less than 50 nM, less than 20 nM, less than 10 nM, less than 5 nM, or less than 1 nM as determined in a comparable generally accepted Kit kinase activity assay, wherein the ratio of $IC_{50}$ for Kit kinase divided by the $IC_{50}$ for Fms kinase is in the range of 20 to 0.05, also 10 to 0.1, also 5 to 0.2. In some embodiments, the compound is selective relative to protein kinases other than Kit, such that the ratio of $IC_{50}$ for another kinase assessed comparably, divided by the $IC_{50}$ for Fms kinase is >20, also >30, also >40, also >50, also >60, also >70, also >80, also >90, also >100, wherein the other protein kinase includes, but is not limited to CSK, Insulin receptor kinase, AMPK, PDGFR or VEGFR. In one embodiment, the dual Fms/Kit inhibitor is a compound selected from the group consisting of:

(6-Methoxy-pyridin-3-ylmethyl)-[3-methyl-5-(5-methyl-1H-pyrrolo[2,3-b]pyridin-3-ylmethyl)-pyridin-2-yl]-amine (P-1554),
[3-Fluoro-5-(5-methyl-1H-pyrrolo[2,3-b]pyridin-3-ylmethyl)-pyridin-2-yl]-(6-methoxy-pyridin-3-ylmethyl)-amine (P-1562),
(6-Chloro-pyridin-3-ylmethyl)-[5-(5-chloro-1H-pyrrolo[2,3-b]pyridin-3-ylmethyl)-pyridin-2-yl]-amine (P-2003),
[5-(5-Chloro-1H-pyrrolo[2,3-b]pyridin-3-ylmethyl)-pyridin-2-yl]-(6-fluoro-pyridin-3-ylmethyl)-amine (P-2004),
[5-(5-Chloro-1H-pyrrolo[2,3-b]pyridin-3-ylmethyl)-pyrimidin-2-yl]-(3,4-difluoro-benzyl)-amine (P-2008),
[5-(5-Chloro-1H-pyrrolo[2,3-b]pyridin-3-ylmethyl)-pyrimidin-2-yl]-(3-methyl-benzyl)-amine (P-2013),
[5-(5-Methyl-1H-pyrrolo[2,3-b]pyridin-3-ylmethyl)-pyridin-2-yl]-(6-trifluoromethyl-pyridin-3-ylmethyl)-amine (P-2019),

[6-Fluoro-5-(5-methyl-1H-pyrrolo[2,3-b]pyridin-3-ylmethyl)-pyridin-2-yl]-(6-trifluoromethyl-pyridin-3-ylmethyl)-amine (P-2031),
(4-Chloro-benzyl)-[6-fluoro-5-(5-methoxy-1H-pyrrolo[2,3-b]pyridin-3-ylmethyl)-pyridin-2-yl]-amine (P-2032),
(4-Chloro-benzyl)-[6-fluoro-5-(4-methoxy-1H-pyrrolo[2,3-b]pyridin-3-ylmethyl)-pyridin-2-yl]-amine (P-2037),
(6-Methyl-pyridin-2-ylmethyl)-[5-(5-methyl-1H-pyrrolo[2,3-b]pyridin-3-ylmethyl)-pyrimidin-2-yl]-amine (P-2079),
[5-(5-Methyl-1H-pyrrolo[2,3-b]pyridin-3-ylmethyl)-pyrimidin-2-yl]-(6-morpholin-4-yl-pyridin-2-ylmethyl)-amine (P-2081),
[5-(5-Methyl-1H-pyrrolo[2,3-b]pyridin-3-ylmethyl)-pyrimidin-2-yl]-(6-pyrrolidin-1-yl-pyridin-2-ylmethyl)-amine (P-2082),
[6-Fluoro-5-(5-methyl-1H-pyrrolo[2,3-b]pyridin-3-ylmethyl)-pyridin-2-yl]-(5-methyl-pyridin-2-ylmethyl)-amine (P-2131),
[3-Fluoro-5-(5-methyl-1H-pyrrolo[2,3-b]pyridin-3-ylmethyl)-pyridin-2-yl]-(6-trifluoromethyl-pyridin-3-ylmethyl)-amine (P-2146),
[3-Fluoro-5-(5-methoxy-1H-pyrrolo[2,3-b]pyridin-3-ylmethyl)-pyridin-2-yl]-(6-trifluoromethyl-pyridin-3-ylmethyl)-amine (P-2147),
(2-Cyclopentyloxy-pyridin-3-ylmethyl)-[5-(5-methyl-1H-pyrrolo[2,3-b]pyridin-3-ylmethyl)-pyrimidin-2-yl]-amine (P-2148),
[5-(5-Chloro-1H-pyrrolo[2,3-b]pyridin-3-ylmethyl)-thiazol-2-yl]-(6-methoxy-pyridin-3-ylmethyl)-amine (P-2154),
[5-(5-Chloro-1H-pyrrolo[2,3-b]pyridin-3-ylmethyl)-thiazol-2-yl]-(6-methoxy-pyridin-2-ylmethyl)-amine (P-2163),
[5-(5-Chloro-1H-pyrrolo[2,3-b]pyridin-3-ylmethyl)-3-fluoro-pyridin-2-yl]-(6-trifluoromethyl-pyridin-3-ylmethyl)-amine (P-2172),
Ethanesulfonic acid (2-{[6-fluoro-5-(5-methyl-1H-pyrrolo[2,3-b]pyridin-3-ylmethyl)-pyridin-2-ylamino]-methyl}-phenyl)-amide (P-2198),
Ethanesulfonic acid (3-fluoro-5-{[6-fluoro-5-(5-methyl-1H-pyrrolo[2,3-b]pyridin-3-ylmethyl)-pyridin-2-ylamino]-methyl}-phenyl)-amide (P-2202),
5-[(5-bromo-1H-pyrrolo[2,3-b]pyridin-3-yl)methyl]-6-fluoro-N-[(5-fluoro-6-methoxy-3-pyridyl)methyl]pyridin-2-amine (P-2203),
3-[[2-fluoro-6-[(5-fluoro-6-methoxy-3-pyridyl)methylamino]-3-pyridyl]methyl]-1H-pyrrolo[2,3-b]pyridine-5-carbonitrile (P-2204),
6-chloro-N-[(5-fluoro-2-methoxy-3-pyridyl)methyl]-5-[(5-methyl-1H-pyrrolo[2,3-b]pyridin-3-yl)methyl]pyridin-2-amine (P-2205),
6-fluoro-N-[(5-fluoro-6-methoxy-3-pyridyl)methyl]-5-[[5-(trifluoromethyl)-1H-pyrrolo[2,3-b]pyridin-3-yl]methyl]pyridin-2-amine (P-2206), and
any salt, prodrug, tautomer, or stereoisomer thereof.

In an eleventh aspect, a compound as described herein is a Fms selective inhibitor, i.e. will selectively inhibit Fms kinase relative to Kit kinase. In some embodiments the compound will have an $IC_{50}$ of less than 500 nm, less than 100 nM, less than 50 nM, less than 20 nM, less than 10 nM, less than 5 nM, or less than 1 nM as determined in a generally accepted Fms kinase activity assay and when determined in a comparable generally accepted Kit kinase activity assay will have a ratio of $IC_{50}$ for Kit kinase divided by the $IC_{50}$ for Fms kinase of >20, also >30, also >40, also >50, also >60, also >70, also >80, also >90, also >100. In some embodiments, the compound is also selective relative to protein kinases other than Kit, such that the ratio of $IC_{50}$ for another kinase assessed comparably, divided by the $IC_{50}$ for Fms kinase is >20, also >30, also >40, also >50, also >60, also >70, also >80, also >90, also >100, wherein the other protein kinase includes, but is not limited to Flt-3, CSK, Insulin receptor kinase, AMPK, PDGFR or VEGFR. In one embodiment, the Fms selective inhibitor is a compound selected from the group consisting of:
[5-(5-Chloro-1H-pyrrolo[2,3-b]pyridin-3-ylmethyl)-pyridin-2-yl]-(2,6-dimethoxy-pyridin-3-ylmethyl)-amine (P-1496),
[6-Fluoro-5-(5-fluoro-1H-pyrrolo[2,3-b]pyridin-3-ylmethyl)-pyridin-2-yl]-(6-methoxy-pyridin-3-ylmethyl)-amine (P-1622),
N-(3-{2-Fluoro-6-[(5-fluoro-2-methoxy-pyridin-3-ylmethyl)-amino]-pyridin-3-ylmethyl}-1H-pyrrolo[2,3-b]pyridin-5-yl)-acetamide (P-1669),
N-(3-{6-[(6-Chloro-pyridin-3-ylmethyl)-amino]-2-fluoro-pyridin-3-ylmethyl}-1H-pyrrolo[2,3-b]pyridin-5-yl)-methanesulfonamide (P-1679),
[5-(5-Chloro-1H-pyrrolo[2,3-b]pyridin-3-ylmethyl)-6-fluoro-pyridin-2-yl]-(5-fluoro-pyridin-3-ylmethyl)-amine (P-2001),
[6-Fluoro-5-(5-methoxy-1H-pyrrolo[2,3-b]pyridin-3-ylmethyl)-pyridin-2-yl]-(5-fluoro-pyridin-3-ylmethyl)-amine (P-2028),
[6-Fluoro-5-(5-methyl-1H-pyrrolo[2,3-b]pyridin-3-ylmethyl)-pyridin-2-yl]-(6-methoxy-pyridin-3-ylmethyl)-amine (P-2029),
[6-Fluoro-5-(5-methoxy-1H-pyrrolo[2,3-b]pyridin-3-ylmethyl)-pyridin-2-yl]-(6-methoxy-pyridin-3-ylmethyl)-amine (P-2030),
[5-(5-Chloro-1H-pyrrolo[2,3-b]pyridin-3-ylmethyl)-pyrimidin-2-yl]-(6-methoxy-pyridin-3-ylmethyl)-amine (P-2038),
[6-Fluoro-5-(5-methoxy-1H-pyrrolo[2,3-b]pyridin-3-ylmethyl)-pyridin-2-yl]-(2-methoxy-pyridin-3-ylmethyl)-amine (P-2043),
[6-Fluoro-5-(1H-pyrrolo[2,3-b]pyridin-3-ylmethyl)-pyridin-2-yl]-(2-methoxy-pyridin-3-ylmethyl)-amine (P-2045),
(5-Fluoro-6-methoxy-pyridin-3-ylmethyl)-[6-fluoro-5-(5-methyl-1H-pyrrolo[2,3-b]pyridin-3-ylmethyl)-pyridin-2-yl]-amine (P-2048),
(5-Fluoro-2-methoxy-pyridin-3-ylmethyl)-[6-fluoro-5-(5-methyl-1H-pyrrolo[2,3-b]pyridin-3-ylmethyl)-pyridin-2-yl]-amine (P-2049),
[6-Fluoro-5-(5-methyl-1H-pyrrolo[2,3-b]pyridin-3-ylmethyl)-pyridin-2-yl]-(2-methoxy-pyridin-3-ylmethyl)-amine (P-2052),
(6-Methoxy-pyridin-3-ylmethyl)-[5-(5-methyl-1H-pyrrolo[2,3-b]pyridin-3-ylmethyl)-pyrimidin-2-yl]-amine (P-2057),
(5-Fluoro-2-methoxy-pyridin-3-ylmethyl)-[5-(5-methyl-1H-pyrrolo[2,3-b]pyridin-3-ylmethyl)-pyrimidin-2-yl]-amine (P-2061),
[6-Fluoro-5-(5-methyl-1H-pyrrolo[2,3-b]pyridin-3-ylmethyl)-pyridin-2-yl]-(4-trifluoromethyl-pyridin-3-ylmethyl)-amine (P-2062),
[5-(5-Chloro-1H-pyrrolo[2,3-b]pyridin-3-ylmethyl)-pyridin-2-yl]-(4-trifluoromethyl-pyridin-3-ylmethyl)-amine (P-2063),
[5-(5-Chloro-1H-pyrrolo[2,3-b]pyridin-3-ylmethyl)-pyrimidin-2-yl]-(5-fluoro-2-methoxy-pyridin-3-ylmethyl)-amine (P-2064),
[6-Fluoro-5-(5-methyl-1H-pyrrolo[2,3-b]pyridin-3-ylmethyl)-pyridin-2-yl]-(2-methyl-pyridin-4-ylmethyl)-amine (P-2067),

[5-(5-Methyl-1H-pyrrolo[2,3-b]pyridin-3-ylmethyl)-pyridin-2-yl]-(4-trifluoromethyl-pyridin-3-ylmethyl)-amine (P-2070),
(5-Fluoro-2-methoxy-pyridin-4-ylmethyl)-[6-fluoro-5-(5-methyl-1H-pyrrolo[2,3-b]pyridin-3-ylmethyl)-pyridin-2-yl]-amine (P-2071),
(5-Fluoro-6-methoxy-pyridin-3-ylmethyl)-[5-(5-methyl-1H-pyrrolo[2,3-b]pyridin-3-ylmethyl)-pyrimidin-2-yl]-amine (P-2073),
[5-(5-Chloro-1H-pyrrolo[2,3-b]pyridin-3-ylmethyl)-6-fluoro-pyridin-2-yl]-(2-methyl-pyridin-4-ylmethyl)-amine (P-2075),
(6-Chloro-pyridin-3-ylmethyl)-[5-(5-methyl-1H-pyrrolo[2,3-b]pyridin-3-ylmethyl)-pyrimidin-2-yl]-amine (P-2078),
(6-Chloro-pyridin-3-ylmethyl)-[6-fluoro-5-(5-methyl-1H-pyrrolo[2,3-b]pyridin-3-ylmethyl)-pyridin-2-yl]-amine (P-2088),
(2,6-Dimethoxy-pyridin-3-ylmethyl)-[6-fluoro-5-(5-methyl-1H-pyrrolo[2,3-b]pyridin-3-ylmethyl)-pyridin-2-yl]-amine (P-2097),
[6-Fluoro-5-(5-methyl-1H-pyrrolo[2,3-b]pyridin-3-ylmethyl)-pyridin-2-yl]-(2-fluoro-pyridin-3-ylmethyl)-amine (P-2103),
[6-Fluoro-5-(5-methyl-1H-pyrrolo[2,3-b]pyridin-3-ylmethyl)-pyridin-2-yl]-(2-fluoro-pyridin-4-ylmethyl)-amine (P-2118),
(2-Methoxy-pyridin-3-ylmethyl)-[5-(5-methyl-1H-pyrrolo[2,3-b]pyridin-3-ylmethyl)-pyrimidin-2-yl]-amine (P-2139),
3-{[5-(5-Chloro-1H-pyrrolo[2,3-b]pyridin-3-ylmethyl)-pyrimidin-2-ylamino]-methyl}-5-fluoro-1-methyl-1H-pyridin-2-one (P-2157),
[5-(5-Chloro-1H-pyrrolo[2,3-b]pyridin-3-ylmethyl)-6-fluoro-pyridin-2-yl]-(5-fluoro-6-methoxy-pyridin-3-ylmethyl)-amine (P-2165),
[5-(5-Chloro-1H-pyrrolo[2,3-b]pyridin-3-ylmethyl)-pyrimidin-2-yl]-(5-fluoro-pyridin-3-ylmethyl)-amine (P-2176),
3-{2-Fluoro-6-[(5-fluoro-2-methoxy-pyridin-3-ylmethyl)-amino]-pyridin-3-ylmethyl}-1H-pyrrolo[2,3-b]pyridine-5-carbonitrile (P-2193),
5-[(5-bromo-1H-pyrrolo[2,3-b]pyridin-3-yl)methyl]-6-fluoro-N-[(5-fluoro-6-methoxy-3-pyridyl)methyl]pyridin-2-amine (P-2203),
3-[[2-fluoro-6-[(5-fluoro-6-methoxy-3-pyridyl)methylamino]-3-pyridyl]methyl]-1H-pyrrolo[2,3-b]pyridine-5-carbonitrile (P-2204),
6-chloro-N-[(5-fluoro-2-methoxy-3-pyridyl)methyl]-5-[(5-methyl-1H-pyrrolo[2,3-b]pyridin-3-yl)methyl]pyridin-2-amine (P-2205),
6-fluoro-N-[(5-fluoro-6-methoxy-3-pyridyl)methyl]-5-[[5-(trifluoromethyl)-1H-pyrrolo[2,3-b]pyridin-3-yl]methyl]pyridin-2-amine (P-2206), and
any salt, prodrug, tautomer, or stereoisomer thereof.

In a twelfth aspect, a compound as described herein is a dual Fms/Flt-3 inhibitor, i.e. will be approximately equipotent with respect to inhibition of Fms kinase and Flt-3 kinase. In some embodiments the compound will have an $IC_{50}$ of less than 500 nm, less than 100 nM, less than 50 nM, less than 20 nM, less than 10 nM, less than 5 nM, or less than 1 nM as determined in a generally accepted Fms kinase activity assay and will have an $IC_{50}$ of less than 500 nm, less than 100 nM, less than 50 nM, less than 20 nM, less than 10 nM, less than 5 nM, or less than 1 nM as determined in a comparable generally accepted Flt-3 kinase activity assay, wherein the ratio of $IC_{50}$ for Flt-3 kinase divided by the $IC_{50}$ for Fms kinase is in the range of 20 to 0.05, also 10 to 0.1, also 5 to 0.2. In some embodiments, the compound is selective relative to protein kinases other than Flt-3, such that the ratio of $IC_{50}$ for another kinase assessed comparably, divided by the $IC_{50}$ for Fms kinase is >20, also >30, also >40, also >50, also >60, also >70, also >80, also >90, also >100, wherein the other protein kinase includes, but is not limited to CSK, Insulin receptor kinase, AMPK, PDGFR or VEGFR. In some embodiments, the dual Fms/Flt-3 inhibitor also inhibits Kit. In one embodiment, the dual Fms/Flt-3 inhibitor is a compound selected from the group consisting of:
(6-Trifluoromethyl-pyridin-3-ylmethyl)-[5-(5-trifluoromethyl-1H-pyrrolo[2,3-b]pyridin-3-ylmethyl)-pyridin-2-yl]-amine (P-1644),
(5-Fluoro-6-methoxy-pyridin-3-ylmethyl)-[6-fluoro-5-(5-trifluoromethyl-1H-pyrrolo[2,3-b]pyridin-3-ylmethyl)-pyridin-2-yl]-amine (P-1646),
[5-(5-Cyclopropyl-1H-pyrrolo[2,3-b]pyridin-3-ylmethyl)-pyridin-2-yl]-(6-trifluoromethyl-pyridin-3-ylmethyl)-amine (P-1667),
(6-Chloro-pyridin-3-ylmethyl)-[5-(5-chloro-1H-pyrrolo[2,3-b]pyridin-3-ylmethyl)-pyridin-2-yl]-amine (P-2003),
[5-(5-Chloro-1H-pyrrolo[2,3-b]pyridin-3-ylmethyl)-pyridin-2-yl]-(6-fluoro-pyridin-3-ylmethyl)-amine (P-2004),
[5-(5-Chloro-1H-pyrrolo[2,3-b]pyridin-3-ylmethyl)-pyrimidin-2-yl]-(3-fluoro-5-trifluoromethyl-benzyl)-amine (P-2009),
[5-(5-Methyl-1H-pyrrolo[2,3-b]pyridin-3-ylmethyl)-pyridin-2-yl]-(6-trifluoromethyl-pyridin-3-ylmethyl)-amine (P-2019),
[6-Fluoro-5-(5-methyl-1H-pyrrolo[2,3-b]pyridin-3-ylmethyl)-pyridin-2-yl]-(6-methoxy-pyridin-3-ylmethyl)-amine (P-2029),
[6-Fluoro-5-(5-methoxy-1H-pyrrolo[2,3-b]pyridin-3-ylmethyl)-pyridin-2-yl]-(6-methoxy-pyridin-3-ylmethyl)-amine (P-2030),
[6-Fluoro-5-(5-methyl-1H-pyrrolo[2,3-b]pyridin-3-ylmethyl)-pyridin-2-yl]-(6-trifluoromethyl-pyridin-3-ylmethyl)-amine (P-2031),
(4-Chloro-benzyl)-[6-fluoro-5-(5-methoxy-1H-pyrrolo[2,3-b]pyridin-3-ylmethyl)-pyridin-2-yl]-amine (P-2032),
(2-Chloro-benzyl)-[6-fluoro-5-(5-methoxy-1H-pyrrolo[2,3-b]pyridin-3-ylmethyl)-pyridin-2-yl]-amine (P-2034),
(4-Chloro-benzyl)-[6-fluoro-5-(4-methoxy-1H-pyrrolo[2,3-b]pyridin-3-ylmethyl)-pyridin-2-yl]-amine (P-2037),
[5-(5-Chloro-1H-pyrrolo[2,3-b]pyridin-3-ylmethyl)-pyrimidin-2-yl]-(6-methoxy-pyridin-3-ylmethyl)-amine (P-2038),
(5-Fluoro-6-methoxy-pyridin-3-ylmethyl)-[6-fluoro-5-(5-methoxy-1H-pyrrolo[2,3-b]pyridin-3-ylmethyl)-pyridin-2-yl]-amine (P-2040),
(5-Fluoro-6-methoxy-pyridin-3-ylmethyl)-[6-fluoro-5-(H-pyrrolo[2,3-b]pyridin-3-ylmethyl)-pyridin-2-yl]-amine (P-2041),
(5-Chloro-pyridin-2-ylmethyl)-[6-fluoro-5-(1H-pyrrolo[2,3-b]pyridin-3-ylmethyl)-pyridin-2-yl]-amine (P-2044),
(5-Chloro-pyridin-2-ylmethyl)-[6-fluoro-5-(5-methyl-1H-pyrrolo[2,3-b]pyridin-3-ylmethyl)-pyridin-2-yl]-amine (P-2047),
(5-Fluoro-6-methoxy-pyridin-3-ylmethyl)-[6-fluoro-5-(5-methyl-1H-pyrrolo[2,3-b]pyridin-3-ylmethyl)-pyridin-2-yl]-amine (P-2048),
(4-Chloro-benzyl)-[6-fluoro-5-(5-methyl-1H-pyrrolo[2,3-b]pyridin-3-ylmethyl)-pyridin-2-yl]-amine (P-2050),
(6-Methoxy-pyridin-3-ylmethyl)-[5-(5-methyl-1H-pyrrolo[2,3-b]pyridin-3-ylmethyl)-pyrimidin-2-yl]-amine (P-2057),

[5-(5-Chloro-1H-pyrrolo[2,3-b]pyridin-3-ylmethyl)-6-fluoro-pyridin-2-yl]-(5-fluoro-6-methoxy-pyridin-3-ylmethyl)-amine (P-2165),
5-[(5-bromo-1H-pyrrolo[2,3-b]pyridin-3-yl)methyl]-6-fluoro-N-[(5-fluoro-6-methoxy-3-pyridyl)methyl]pyridin-2-amine (P-2203),
3-[[2-fluoro-6-[(5-fluoro-6-methoxy-3-pyridyl)methylamino]-3-pyridyl]methyl]-1H-pyrrolo[2,3-b]pyridine-5-carbonitrile (P-2204),
6-chloro-N-[(5-fluoro-2-methoxy-3-pyridyl)methyl]-5-[(5-methyl-1H-pyrrolo[2,3-b]pyridin-3-yl)methyl]pyridin-2-amine (P-2205),
6-fluoro-N-[(5-fluoro-6-methoxy-3-pyridyl)methyl]-5-[[5-(trifluoromethyl)-1H-pyrrolo[2,3-b]pyridin-3-yl]methyl]pyridin-2-amine (P-2206), and
any salt, prodrug, tautomer, or stereoisomer thereof.

In one embodiment, the dual Fms/Flt-3 inhibitor is a compound selected from the group consisting of:
(6-Trifluoromethyl-pyridin-3-ylmethyl)-[5-(5-trifluoromethyl-1H-pyrrolo[2,3-b]pyridin-3-ylmethyl)-pyridin-2-yl]-amine (P-1644),
(5-Fluoro-6-methoxy-pyridin-3-ylmethyl)-[6-fluoro-5-(5-trifluoromethyl-1H-pyrrolo[2,3-b]pyridin-3-ylmethyl)-pyridin-2-yl]-amine (P-1646),
[5-(5-Cyclopropyl-1H-pyrrolo[2,3-b]pyridin-3-ylmethyl)-pyridin-2-yl]-(6-trifluoromethyl-pyridin-3-ylmethyl)-amine (P-1667),
[5-(5-Chloro-1H-pyrrolo[2,3-b]pyridin-3-ylmethyl)-pyrimidin-2-yl]-(3-fluoro-5-trifluoromethyl-benzyl)-amine (P-2009),
(2-Chloro-benzyl)-[6-fluoro-5-(5-methoxy-1H-pyrrolo[2,3-b]pyridin-3-ylmethyl)-pyridin-2-yl]-amine (P-2034),
(4-Chloro-benzyl)-[6-fluoro-5-(4-methoxy-1H-pyrrolo[2,3-b]pyridin-3-ylmethyl)-pyridin-2-yl]-amine (P-2037),
(5-Fluoro-6-methoxy-pyridin-3-ylmethyl)-[6-fluoro-5-(5-methoxy-1H-pyrrolo[2,3-b]pyridin-3-ylmethyl)-pyridin-2-yl]-amine (P-2040),
(5-Fluoro-6-methoxy-pyridin-3-ylmethyl)-[6-fluoro-5-(1H-pyrrolo[2,3-b]pyridin-3-ylmethyl)-pyridin-2-yl]-amine (P-2041),
(5-Chloro-pyridin-2-ylmethyl)-[6-fluoro-5-(1H-pyrrolo[2,3-b]pyridin-3-ylmethyl)-pyridin-2-yl]-amine (P-2044),
(5-Chloro-pyridin-2-ylmethyl)-[6-fluoro-5-(5-methyl-1H-pyrrolo[2,3-b]pyridin-3-ylmethyl)-pyridin-2-yl]-amine (P-2047),
(4-Chloro-benzyl)-[6-fluoro-5-(5-methyl-1H-pyrrolo[2,3-b]pyridin-3-ylmethyl)-pyridin-2-yl]-amine (P-2050),
5-[(5-bromo-1H-pyrrolo[2,3-b]pyridin-3-yl)methyl]-6-fluoro-N-[(5-fluoro-6-methoxy-3-pyridyl)methyl]pyridin-2-amine (P-2203),
3-[[2-fluoro-6-[(5-fluoro-6-methoxy-3-pyridyl)methylamino]-3-pyridyl]methyl]-1H-pyrrolo[2,3-b]pyridine-5-carbonitrile (P-2204),
6-chloro-N-[(5-fluoro-2-methoxy-3-pyridyl)methyl]-5-[(5-methyl-1H-pyrrolo[2,3-b]pyridin-3-yl)methyl]pyridin-2-amine (P-2205),
6-fluoro-N-[(5-fluoro-6-methoxy-3-pyridyl)methyl]-5-[[5-(trifluoromethyl)-1H-pyrrolo[2,3-b]pyridin-3-yl]methyl]pyridin-2-amine (P-2206), and
any salt, prodrug, tautomer, or stereoisomer thereof.

Further to any of the aspects and embodiments referred to herein, a compound as described herein also inhibits the effects of a mutation of the kinase (e.g. Fms mutant, Kit mutant, Flt-3 mutant), including, but not limited to, a mutation that is related to a disease state, such as a cancer.

In a thirteenth aspect, compositions are provided that include a therapeutically effective amount of any one or more compound(s) as described herein and at least one pharmaceutically acceptable carrier, excipient, and/or diluent, including combinations of any two or more compounds as described herein. The composition can further include a plurality of different pharmacologically active compounds, which can include a plurality of compounds as described herein. In certain embodiments, the composition can include any one or more compound(s) as described herein along with one or more compounds that are therapeutically effective for the same disease indication. In one aspect, the composition includes any one or more compound(s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer.

In a fourteenth aspect, methods are provided for modulating the activity of a Fms and/or Kit and/or Flt-3 protein kinase, including any mutations thereof, by contacting the protein kinase with an effective amount of any one or more compound(s) as described herein.

In a fifteenth aspect, the invention provides methods for treating a disease or condition mediated by Fms and/or Kit and/or Flt-3, including any mutations thereof, in a subject in need thereof by administering to the subject an effective amount of a composition including any one or more compound(s) as described herein. In one embodiment, the invention provides methods for treating a disease or condition mediated by Fms and/or Kit, including any mutations thereof, in a subject in need thereof by administering to the subject an effective amount of a composition including any one or more compound(s) as described herein in combination with one or more other suitable therapies for treating the disease.

In a sixteenth aspect, the invention provides methods for treating a disease or condition mediated by Fms, including any mutations thereof, in a subject in need thereof by administering to the subject an effective amount of a composition including any one or more compound(s) as described herein. In one embodiment, the invention provides methods for treating a disease or condition mediated by Fms, including any mutations thereof, in a subject in need thereof by administering to the subject an effective amount of a composition including any one or more compound(s) as described herein in combination with one or more other suitable therapies for treating the disease.

In a seventeenth aspect, the invention provides methods for treating a disease or condition mediated by Kit, including any mutations thereof, in a subject in need thereof by administering to the subject an effective amount of a composition including any one or more compound(s) as described herein. In one embodiment, the invention provides methods for treating a disease or condition mediated by Kit, including any mutations thereof, in a subject in need thereof by administering to the subject an effective amount of a composition including any one or more compound(s) as described herein in combination with one or more other suitable therapies for treating the disease.

In an eighteenth aspect, the invention provides methods for treating a disease or condition mediated by Flt-3, including any mutations thereof, in a subject in need thereof by administering to the subject an effective amount of a composition including any one or more compound(s) as described herein. In one embodiment, the invention provides methods for treating a disease or condition mediated by Flt-3, including any mutations thereof, in a subject in need thereof by administering to the subject an effective amount of a composition including any one or more compound(s) as described herein in combination with one or more other suitable therapies for treating the disease.

In a nineteenth aspect, the invention provides methods for treating a disease or condition mediated by Fms and Flt-3, including any mutations thereof, in a subject in need thereof by administering to the subject an effective amount of a composition including any one or more compound(s) as described herein. In one embodiment, the invention provides methods for treating a disease or condition mediated by Fms and Flt-3, including any mutations thereof, in a subject in need thereof by administering to the subject an effective amount of a composition including any one or more compound(s) as described herein in combination with one or more other suitable therapies for treating the disease.

In a twentieth aspect, the invention provides methods for treating a disease or condition mediated by Fms and Kit, including any mutations thereof, in a subject in need thereof by administering to the subject an effective amount of a composition including any one or more compound(s) as described herein. In one embodiment, the invention provides methods for treating a disease or condition mediated by Fms and Kit, including any mutations thereof, in a subject in need thereof by administering to the subject an effective amount of a composition including any one or more compound(s) as described herein in combination with one or more other suitable therapies for treating the disease.

In a twenty-first aspect, the invention provides a method of treating a cancer in a subject in need thereof by administering to the subject an effective amount of a composition including any one or more compound(s) as described herein, in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, γ-ray, or electron, proton, neutron, or ac particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), surgery, or bone marrow and stem cell transplantation.

In a twenty-second aspect, the invention provides a method of treating a cancer in a subject in need thereof by administering to the subject an effective amount of a composition including any one or more compound(s) as described herein, in combination with one or more suitable chemotherapeutic agents. In one embodiment, the one or more suitable chemotherapeutic agents is selected from an alkylating agent, including, but not limited to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, and uramustine; an antibiotic, including, but not limited to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limited to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, raltitrexed, tegafur-uracil, thioguanine, trimethoprim, trimetrexate, and vidarabine; an immunotherapy, including, but not limited to, alemtuzumab, bevacizumab, cetuximab, galiximab, gemtuzumab, panitumumab, pertuzumab, rituximab, tositumomab, trastuzumab, 90Y ibritumomab tiuxetan, ipilimumab, and tremelimumab; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, larotaxel, ortataxel, paclitaxel, DHA-paclitaxel, and tesetaxel; a retinoid, including, but not limited to, alitretinoin, bexarotene, fenretinide, isotretinoin, and tretinoin; an alkaloid, including, but not limited to, demecolcine, homoharringtonine, vinblastine, vincristine, vindesine, vinflunine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not limited to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-α, and interleukin-2; and other chemotherapeutics, including, but not limited to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. temsirolimus, everolimus, deforolimus), PI3K inhibitors (e.g. BEZ235, GDC-0941, XL147, XL765), Cdk4 inhibitors (e.g. PD-332991), Akt inhibitors, Hsp90 inhibitors (e.g. tanespimycin) and farnesyltransferase inhibitors (e.g. tipifarnib). Preferably, the method of treating a cancer involves administering to the subject an effective amount of a composition including any one or more compound(s) of Formulae I or I' in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-α, interleukin-2, or erlotinib.

In a twenty-third aspect, the invention provides a method of treating a disease or condition in a subject in need thereof, by administering to the subject a therapeutically effective amount of any one or more compound(s) as described herein, a prodrug of such compound, a pharmaceutically acceptable salt of such compound or prodrug, or a pharmaceutically acceptable formulation of such compound or prodrug. The compound can be alone or can be part of a composition. In one embodiment, the invention provides a method of treating a disease or condition in a subject in need thereof, by administering to the subject a therapeutically effective amount of any one or more compound(s) as described herein, a prodrug of such compound, a pharmaceutically acceptable salt of such compound or prodrug, or a pharmaceutically acceptable formulation of such compound or prodrug in combination with one or more other suitable therapies for the disease or condition.

In a twenty-fourth aspect, the invention provides kits that include a compound or composition thereof as described herein. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a Fms and/or Kit protein kinase mediated disease or condition; the invention kit includes written instructions for use and/or other indication that the compound or composition is suitable or approved for administration to a mammal, e.g., a human, for a Fms and/or Kit protein kinase-mediated disease or condition; and the compound or composition is packaged in unit dose or single dose form, e.g., single dose pills, capsules, or the like.

In aspects and embodiments involving treatment of a disease or condition with one or more of the compounds described herein, the invention provides methods for treating a Kit-mediated disease or condition in a subject in need thereof (e.g. a mammal such as a human, other primates, sports animals, animals of commercial interest such as cattle, farm animals such as horses, or pets such as dogs and cats), e.g., a disease or condition characterized by abnormal Kit activity (e.g. kinase activity). In some embodiments invention methods may involve administering to the subject suffering from or at risk of a c-kit-mediated disease or condition an effective amount of one or more compound(s) as described herein. In one embodiment, the Kit mediated disease is selected from the group consisting of malignancies, including, but not limited to, mast cell tumors, small cell lung cancer, non-small cell lung cancer (NSCLC), testicular cancer, pancreatic cancer, breast cancer, merkel cell carcinoma, carcinomas of the female genital tract, sarcomas of neuroectodermal origin, colorectal carcinoma, carcinoma in situ, gastrointestinal stromal tumors (GISTs), tumor angiogenesis, glioblastoma, astrocytoma, neuroblastoma, neurofibromatosis (including Schwann cell neoplasia associated with neurofibromatosis), acute myeloid leukemia, acute lymphocytic leukemia, chronic myeloid leukemia, mastocytosis, melanoma, and canine mast cell tumors; cardiovascular disease, including but not limited to atherosclerosis, cardiomyopathy, heart failure, pulmonary arterial hypertension and pulmonary fibrosis; inflammatory and autoimmune indications, including, but not limited to, allergy, anaphylaxis, asthma, rheumatoid arthritis, allergic rhinitis, multiple sclerosis, inflammatory bowel disease, transplant rejection, hypereosinophilia, urticaria and dermatitis; gastrointestinal indications, including but not limited to gastroesophageal reflux disease (GERD), esophagitis, and gastrointestinal tract ulcers; ophthalmic indications, including but not limited to uveitis and retinitis; and neurologic indications, including but not limited to migraine.

In aspects and embodiments involving treatment of a disease or condition with one or more of the compounds described herein, the invention provides methods for treating a Fms-mediated disease or condition in a subject in need thereof (e.g. a mammal such as a human, other primates, sports animals, animals of commercial interest such as cattle, farm animals such as horses, or pets such as dogs and cats), e.g., a disease or condition characterized by abnormal Fms activity (e.g. kinase activity). In some embodiments, invention methods may involve administering to the subject suffering from or at risk of a Fms-mediated disease or condition an effective amount of one or more compound(s) as described herein. In one embodiment, the Fms mediated disease is selected from the group consisting of inflammatory and autoimmune indications, including, but not limited to, rheumatoid arthritis, osteoarthritis, psoriatic arthritis, psoriasis, dermatitis, ankylosing spondylitis, polymyositis, derlatomyositis, systemic sclerosis, juvenile idiopathic arthritis, polymyalgia rheumatica, Sjogren's disease, Langerhan's cell histiocytosis (LCH), Still's disease, inflammatory bowel disease, ulcerative colitis, Crohn's disease, systemic lupus erythematosis (SLE), immune thrombocytopenic purpura (ITP), myelopreparation for autologous transplantation, transplant rejection, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, osteodystrophy, increased risk of fracture, Paget's disease, hypercalcemia, infection-mediated osteolysis (e.g. osteomyelitis), and peri-prosthetic or wear-debris-mediated osteolysis; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the nervous system, including, but not limited to, demyelinating disorders (e.g. multiple sclerosis, Charcot Marie Tooth syndrome), amyotrophic lateral sclerosis (ALS), myasthenia gravis, chronic demyelinating polyneuropathy, other demyelinating disorders, stroke, Alzheimer's disease and Parkinson's disease; pain, including, but not limited to, chronic pain, acute pain, inflammatory pain, neuropathic pain, bone pain; malignancies, including, but not limited to, multiple myeloma, acute myeloid leukemia (AML), chronic myeloid leukemia (CML), lung cancer, pancreatic cancer, prostate cancer, breast cancer, ovarian cancer, neuroblastoma, sarcoma, ostcosarcoma, giant cell tumors, (e.g. giant cell tumor of bone, giant cell tumor of tendon sheath (TGCT)), pigmented villonodular synovitis (PVNS), tumor angiogenesis, melanoma, glioblastoma multiforme, glioma, other tumors of the central nervous system, metastasis of tumors to other tissues, osteolytic bone metastases, and other chronic myeloproliferative diseases such as myelofibrosis; vasculitis, including but not limited to collagen vascular disease, polyarteritis nodosa, Behcet's disease, sarcoidosis, familiar Mediterranean fever, Churg-Strauss vasculitis, temporal arteritis, giant cell arteritis, Takayasu's arteritis; ophthalmic indications, including but not limited to uveitis, scleritis, retinitis, age related macular degeneration, choroidal neovascularization, diabetic retinopathy; inherited disorders, including but not limited to cherubism, neurofibromatosis; infectious disease indications, including but not limited to infections associated with human immunodeficiency virus, hepatitis B virus, hepatitis C virus, human granulocytic anaplasmosis; lysosomal storage disorders, including but not limited to Gaucher's disease, Fabry's disease, Niemann-Pick disease; gastrointestinal indications, including but not limited to liver cirrhosis; pulmonary indications, including but not limited to pulmonary fibrosis, acute lung injury (e.g. ventilator-induced, smoke- or toxin-induced); and surgical indications, including but not limited to (cardiopulmonary) bypass surgery, vascular surgery, and vascular grafts.

In aspects and embodiments involving treatment of a disease or condition with one or more of the compounds described herein, the invention provides methods for treating a disease or condition mediated by Fms and Kit in a subject in need thereof (e.g. a mammal such as a human, other primates, sports animals, animals of commercial interest such as cattle, farm animals such as horses, or pets such as dogs and cats), e.g., a disease or condition characterized by abnormal Fms activity and Kit activity (e.g. kinase activity). In some embodiments, invention methods may involve administering to the subject suffering from or at risk of a disease or condition mediated by Fms and Kit an effective amount of one or more compound(s) as described herein. In one embodiment, the condition mediated by Fms and Kit is selected from the group consisting of rheumatoid arthritis, osteoarthritis, psoriatic arthritis, psoriasis, dermatitis, allergy, anaphylaxis, asthma, allergic rhinitis, ankylosing spondylitis, polymyositis, dermatomyositis, systemic sclerosis, juvenile idiopathic arthritis, polymyalgia rheumatica, Sjogren's disease, Langerhan's cell histiocytosis, Still's disease, inflammatory bowel disease, ulcerative colitis, Crohn's disease, systemic lupus erythematosis, immune thrombocytopenic purpura, myelopreparation for autologous transplantation, transplant rejection, chronic obstructive pulmonary disease, emphysema, Kawasaki's Disease, hemophagocytic syndrome, multicentric reticulohistiocytosis, hypereosinophilia, and urticaria type I diabetes, type IT diabetes, insulin resistance, hyperglycemia, obesity, and lipolysis, osteoporosis, osteodystrophy, increased risk of fracture, Paget's disease, hypercalcemia, infection-mediated osteolysis, and peri-prosthetic or wear-debris-mediated osteolysis, endometriosis, nephritis, tubular necrosis, diabetes-associated renal complications, and renal hypertrophy, multiple sclerosis, Charcot Marie Tooth syndrome, amyotrophic lateral sclerosis, myasthenia gravis, chronic demyelinating polyneuropathy, other demyelinating disorders, stroke, Alzheimer's disease and Parkinson's disease, acute pain, neuropathic pain, inflammatory pain, chronic pain, migraine, multiple myeloma, acute lymphocytic leukemia, acute myeloid leukemia, chronic myeloid leukemia, mast cell tumors, canine mast cell tumors, lung cancer, testicular cancer, pancreatic cancer, prostate cancer, breast cancer, ovarian cancer, merkel cell carcinoma, carcinomas of the female genital tract, colorectal carcinoma, carcinoma in situ, gastrointestinal stromal tumors, tumor angiogenesis, astrocytoma, neuroblastoma, sarcoma, osteosarcoma, sarcomas of neuroectodermal origin, giant cell tumor of bone, giant cell tumor of tendon sheath, pigmented villonodular synovitis, melanoma, glioblastoma, glioblastoma multiforme, glioma, other tumors of the central nervous system, neurofibromatosis (including Schwann cell neoplasia associated with neurofibromatosis), mastocytosis, metastasis of tumors to other tissues, osteolytic bone metastases, and other chronic myeloproliferative diseases such as myelofibrosis, collagen vascular disease, polyarteritis nodosa, Behcet's disease, sarcoidosis, familiar Mediterranean fever, Churg-Strauss vasculitis, temporal arteritis, giant cell arteritis, Takayasu's arteritis, uveitis, scleritis, retinitis, age related macular degeneration, choroidal neovascularization, diabetic retinopathy, cherubism, neurofibromatosis, infections associated with human immunodeficiency virus, hepatitis B virus, hepatitis C virus, human granulocytic anaplasmosis, Gaucher's disease, Fabry's disease, Niemann-Pick disease, liver cirrhosis, gastroesophageal reflux disease, esophagitis, and gastrointestinal tract ulcers, pulmonary fibrosis, acute lung injury, bypass surgery, vascular surgery, and vascular grafts, atherosclerosis, cardiomyopathy, heart failure, and pulmonary arterial hypertension.

In aspects and embodiments involving treatment of a disease or condition with one or more of the compounds described herein, the invention provides methods for treating a disease or condition mediated by Fms and Flt-3 in a subject in need thereof (e.g. a mammal such as a human, other primates, sports animals, animals of commercial interest such as cattle, farm animals such as horses, or pets such as dogs and cats), e.g., a disease or condition characterized by abnormal Fms activity and flt-3 activity (e.g. kinase activity). In some embodiments, invention methods may involve administering to the subject suffering from or at risk of a disease or condition mediated by Fms and Flt-3 an effective amount of one or more compound(s) as described herein. In one embodiment, the condition mediated by Fins and Flt-3 is acute myeloid leukemia.

In aspects and embodiments involving treatment of a disease or condition with one or more of the compounds described herein, invention methods may involve administering an effective amount of one or more compound(s) as described herein to a subject in need thereof suffering from or at risk of a disease or condition selected from the group consisting of rheumatoid arthritis, osteoarthritis, osteoporosis, peri-prosthetic osteolysis, systemic sclerosis, demyelinating disorders, multiple sclerosis, Charcot Marie Tooth syndrome, amyotrophic lateral sclerosis, Alzheimer's disease, Parkinson's disease, ulcerative colitis, Crohn's disease, immune thrombocytopenic purpura, atherosclerosis, systemic lupus erythematosis, myelopreparation for autologous transplantation, transplant rejection, glomerulonephritis, interstitial nephritis, Lupus nephritis, tubular necrosis, diabetic nephropathy, renal hypertrophy, type I diabetes, acute pain, inflammatory pain, neuropathic pain, acute myeloid leukemia, melanoma, multiple myeloma, metastatic breast cancer, prostate cancer, pancreatic cancer, lung cancer, ovarian cancer, gliomas, glioblastomas, neurofibromatosis, osteolytic bone metastases, brain metastases, gastrointestinal stromal tumors, and giant cell tumors.

In aspects and embodiments involving treatment of a disease or condition with one or more of the compounds described herein, invention methods may involve administering an effective amount of one or more compound(s) as described herein to a subject in need thereof suffering from or at risk of a disease or condition selected from the group consisting of rheumatoid arthritis, gastrointestinal stromal tumors, melanoma, and neurofibromatosis, wherein the compound is an inhibitor of Kit, i.e. has an $IC_{50}$ of less than 500 nm, less than 100 nM, less than 50 nM, less than 20 nM, less than 10 nM, less than 5 nM, or less than 1 nM as determined in a generally accepted Kit kinase activity assay.

In aspects and embodiments involving treatment of a disease or condition with one or more of the compounds described herein, invention methods may involve administering an effective amount of one or more compound(s) as described herein to a subject in need thereof suffering from or at risk of a disease or condition selected from the group consisting of multiple sclerosis, glioblastoma, Alzheimer's disease, Parkinson's disease, rheumatoid arthritis, osteoarthritis, atherosclerosis, systemic lupus erythematosus, glomerulonephritis, interstitial nephritis, Lupus nephritis, tubular necrosis, diabetic nephropathy, and renal hypertrophy, wherein the compound is a Fms selective inhibitor, i.e. has an $IC_{50}$ of less than 500 nm, less than 100 nM, less than 50 nM, less than 20 nM, less than 10 nM, less than 5 nM, or less than 1 nM as determined in a generally accepted Fms kinase activity assay and when determined in a comparable generally accepted Kit kinase activity assay will have a ratio of $IC_{50}$ for Kit kinase divided by the $IC_{50}$ for Fms kinase of >20, also >30, also >40, also >50, also >60, also >70, also >80, also >90, also >100; in some embodiments, the compound is also selective relative to protein kinases other than Kit, such that the ratio of $IC_{50}$ for another kinase assessed comparably, divided by the $IC_{50}$ for Fms kinase is >20, also >30, also >40, also >50, also >60, also >70, also >80, also >90, also >100, wherein the other protein kinase includes, but is not limited to Flt-3, CSK, Insulin receptor kinase, AMPK, PDGFR or VEGFR.

In aspects and embodiments involving treatment of a disease or condition with one or more of the compounds described herein, invention methods may involve administering an effective amount of one or more compound(s) as described herein to a subject in need thereof suffering from or at risk of a disease or condition selected from the group consisting of multiple sclerosis, glioblastoma, Alzheimer's disease, and Parkinson's disease, wherein the compound is a Fms selective inhibitor, i.e. has an $IC_{50}$ of less than 500 nm, less than 100 nM, less than 50 nM, less than 20 nM, less than 10 nM, less than 5 nM, or less than 1 nM as determined in a generally accepted Fms kinase activity assay and when determined in a comparable generally accepted Kit kinase activity assay will have a ratio of $IC_{50}$ for Kit kinase divided by the $IC_{50}$ for Fms kinase of >20, also >30, also >40, also >50, also >60, also >70, also >80, also >90, also >100, and wherein the compound effectively crosses the blood brain barrier; in some embodiments, the compound is also selective relative to protein kinase other than Kit, such that the ratio of $IC_{50}$ for another kinase assessed comparably divided by the $IC_{50}$ for Fms kinase is >20, also >30, also >40, also >50, also >60, also >70, also >80, also >90, also >100, wherein the other protein kinase includes, but is not limited to Flt-3, CSK, Insulin receptor kinase, AMPK, PDGFR or VEGFR.

In aspects and embodiments involving treatment of a disease or condition with one or more of the compounds described herein, invention methods may involve administering an effective amount of one or more compound(s) as described herein to a subject in need thereof suffering from or at risk of a disease or condition selected from the group consisting of rheumatoid arthritis, osteoarthritis, atherosclerosis, systemic lupus erythematosus, glomerulonephritis, interstitial nephritis, Lupus nephritis, tubular necrosis, diabetic nephropathy, and renal hypertrophy, wherein the compound is a Fms selective inhibitor, i.e. has an $IC_{50}$ of less than 500 nm, less than 100 nM, less than 50 nM, less than 20 nM, less than 10 nM, less than 5 nM, or less than 1 nM as determined in a generally accepted Fms kinase activity assay and when determined in a comparable generally accepted Kit kinase activity assay will have a ratio of $IC_{50}$ for Kit kinase divided by the $IC_{50}$ for Fms kinase of >20, also >30, also >40, also >50, also >60, also >70, also >80, also >90, also >100, and wherein the compound does not effectively cross the blood brain barrier; in some embodiments, the compound is also selective relative to protein kinase other than Kit, such that the ratio of $IC_{50}$ for another kinase assessed comparably divided by the $IC_{50}$ for Fms kinase is >20, also >30, also >40, also >50, also >60, also >70, also >80, also >90, also >100, wherein the other protein kinase includes, but is not limited to Flt-3, CSK, Insulin receptor kinase, AMPK, PDGFR or VEGFR.

In aspects and embodiments involving treatment of a disease or condition with one or more of the compounds described herein, invention methods may involve administering an effective amount of one or more compound(s) as described herein to a subject in need thereof suffering from or at risk of a disease or condition selected from the group consisting of metastatic breast cancer, prostate cancer, multiple myeloma, melanoma, brain metastases, neurofibromatosis, gastrointestinal stromal tumors, rheumatoid arthritis, and multiple sclerosis, wherein the compound is a dual Fms/Kit inhibitor, i.e. has an $IC_{50}$ of less than 500 nm, less than 100 nM, less than 50 nM, less than 20 nM, less than 10 nM, less than 5 nM, or less than 1 nM as determined in a generally accepted Fms kinase activity assay and will have an $IC_{50}$ of less than 500 nm, less than 100 nM, less than 50 nM, less than 20 nM, less than 10 nM, less than 5 nM, or less than 1 nM as determined in a comparable generally accepted Kit kinase activity assay, wherein the ratio of $IC_{50}$ for Kit kinase divided by the $IC_{50}$ for Fms kinase is in the range of 20 to 0.05, also 10 to 0.1, also 5 to 0.2; in some embodiments, the compound is also selective relative to protein kinase other than Kit, such that the ratio of $IC_{50}$ for another kinase assessed comparably divided by the $IC_{50}$ for Fms kinase is >20, also >30, also >40, also >50, also >60, also >70, also >80, also >90, also >100, wherein the other protein kinase includes, but is not limited to CSK, Insulin receptor kinase, AMPK, PDGFR or VEGFR.

In aspects and embodiments involving treatment of a disease or condition with one or more of the compounds described herein, invention methods may involve administering an effective amount of one or more compound(s) as described herein to a subject in need thereof suffering from or at risk of acute myeloid leukemia, wherein the compound is a dual Fms/Flt-3 inhibitor, i.e. has an $IC_{50}$ of less than 500 nm, less than 100 nM, less than 50 nM, less than 20 nM, less than 10 nM, less than 5 nM, or less than 1 nM as determined in a generally accepted Fms kinase activity assay and will have an $IC_{50}$ of less than 500 nm, less than 100 nM, less than 50 nM, less than 20 nM, less than 10 nM, less than 5 nM, or less than 1 nM as determined in a comparable generally accepted Flt-3 kinase activity assay, wherein the ratio of $IC_{50}$ for Flt-3 kinase divided by the $IC_{50}$ for Fms kinase is in the range of 20 to 0.05, also 10 to 0.1, also 5 to 0.2; in some embodiments, the compound is also selective relative to protein kinase other than Flt-3, such that the ratio of $IC_{50}$ for another kinase assessed comparably divided by the $IC_{50}$ for Fms kinase is >20, also >30, also >40, also >50, also >60, also >70, also >80, also >90, also >100, wherein the other protein kinase includes, but is not limited to CSK, Insulin receptor kinase, AMPK, PDGFR or VEGFR.

In a twenty-fifth aspect, one or more compounds or compositions as described herein can be used in the preparation of a medicament for the treatment of a Kit-mediated disease or condition selected from the group consisting of malignancies, including, but not limited to, mast cell tumors, small cell lung cancer, non-small cell lung cancer, testicular cancer, pancreatic cancer, breast cancer, merkel cell carcinoma, carcinomas of the female genital tract, sarcomas of neuroectodermal origin, colorectal carcinoma, carcinoma in situ, gastrointestinal stromal tumors, tumor angiogenesis, glioblastoma, astrocytoma, neuroblastoma, neurofibromatosis (including Schwann cell neoplasia associated with neurofibromatosis), acute myeloid leukemia, acute lymphocytic leukemia, chronic myeloid leukemia, mastocytosis, melanoma, and canine mast cell tumors; cardiovascular disease, including but not limited to atherosclerosis, cardiomyopathy, heart failure, pulmonary arterial hypertension, and pulmonary fibrosis; inflammatory and autoimmune indications, including, but not limited to, allergy, anaphylaxis, asthma, rheumatoid arthritis, allergic rhinitis, multiple sclerosis, inflammatory bowel disease, transplant rejection, hypereosinophilia, urticaria and dermatitis; gastrointestinal indications, including but not limited to gastroesophageal reflux disease, esophagitis, and gastrointestinal tract ulcers; ophthalmic indications, including but not limited to uveitis and retinitis; and neurologic indications, including but not limited to migraine. The invention further provides one or more compounds or compositions as described herein for use in treating a Kit-mediated disease or condition as described herein.

In a twenty-sixth aspect, one or more compounds as described herein can be used in the preparation of a medicament for the treatment of a Fms-mediated disease or condition selected from the group consisting of inflammatory and autoimmune indications, including, but not limited to, rheumatoid arthritis, osteoarthritis, psoriatic arthritis, psoriasis, dermatitis, ankylosing spondylitis, polymyositis, dermatomyositis, systemic sclerosis, juvenile idiopathic arthritis, polymyalgia rheumatica, Sjogren's disease, Langerhan's cell histiocytosis (LCH), Still's disease, inflammatory bowel disease, ulcerative colitis, Crohn's disease, systemic lupus erythematosis (SLE), immune thrombocytopenic purpura (ITP), myelopreparation for autologous transplantation, transplant rejection, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, osteodystrophy, increased risk of fracture, Paget's disease, hypercalcemia, infection-mediated osteolysis (e.g. osteomyelitis), and peri-prosthetic or wear-debris-mediated osteolysis; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the nervous system, including, but not limited to, demyelinating disorders (e.g. multiple sclerosis, Charcot Marie Tooth syndrome), amyotrophic lateral sclerosis (ALS), myasthenia gravis, chronic demyelinating polyneuropathy, other demyelinating disorders, stroke, Alzheimer's disease and Parkinson's disease; pain, including, but not limited to, chronic pain, acute pain, inflammatory pain, neuropathic pain, bone pain; malignancies, including, but not limited to, multiple myeloma, acute myeloid leukemia (AML), chronic myeloid leukemia (CML), lung cancer, pancreatic cancer, prostate cancer, breast cancer, ovarian cancer, neuroblastoma, sarcoma, osteosarcoma, giant cell tumors, (e.g. giant cell tumor of bone, giant cell tumor of tendon sheath (TGCT)), pigmented villonodular synovitis (PVNS), tumor angiogenesis, melanoma, glioblastoma multiforme, glioma, other tumors of the central nervous system, metastasis of tumors to other tissues, osteolytic bone metastases, and other chronic myeloproliferative diseases such as myelofibrosis; vasculitis, including but not limited to collagen vascular disease, polyarteritis nodosa, Behcet's disease, sarcoidosis, familiar Mediterranean fever, Churg-Strauss vasculitis, temporal arteritis, giant cell arteritis, Takayasu's arteritis; ophthalmic indications, including but not limited to uveitis, scleritis, retinitis, age related macular degeneration, choroidal neovascularization, diabetic retinopathy; inherited disorders, including but not limited to cherubism, neurofibromatosis; infectious disease indications, including but not limited to infections associated with human immunodeficiency virus, hepatitis B virus, hepatitis C virus, human granulocytic anaplasmosis; lysosomal storage disorders, including but not limited to Gaucher's disease, Fabry's disease, Niemann-Pick disease; gastrointestinal indications, including but not limited to liver cirrhosis; pulmonary indications, including but not limited to pulmonary fibrosis, acute lung injury (e.g. ventilator-induced, smoke- or toxin-induced); and surgical indications, including but not limited to (cardiopulmonary) bypass surgery, vascular surgery, and vascular grafts. The invention further provides one or more compounds or compositions as described herein for use in treating a Fms-mediated disease or condition as described herein.

In a twenty-seventh aspect, one or more compounds as described herein can be used in the preparation of a medicament for the treatment of a Fms-mediated and Kit-mediated disease or condition selected from the group consisting of rheumatoid arthritis, osteoarthritis, psoriatic arthritis, psoriasis, dermatitis, allergy, anaphylaxis, asthma, allergic rhinitis, ankylosing spondylitis, polymyositis, dermatomyositis, systemic sclerosis, juvenile idiopathic arthritis, polymyalgia rheumatica, Sjogren's disease, Langerhan's cell histiocytosis, Still's disease, inflammatory bowel disease, ulcerative colitis, Crohn's disease, systemic lupus erythematosis, immune thrombocytopenic purpura, myclopreparation for autologous transplantation, transplant rejection, chronic obstructive pulmonary disease, emphysema, Kawasaki's Disease, hemophagocytic syndrome, multicentric reticulohistiocytosis, hypereosinophilia, and urticaria type I diabetes, type II diabetes, insulin resistance, hyperglycemia, obesity, and lipolysis, osteoporosis, osteodystrophy, increased risk of fracture, Paget's disease, hypercalcemia, infection-mediated osteolysis, and peri-prosthetic or wear-debris-mediated osteolysis, endometriosis, nephritis, tubular necrosis, diabetes-associated renal complications, and renal hypertrophy, multiple sclerosis, Charcot Marie Tooth syndrome, amyotrophic lateral sclerosis, myasthenia gravis, chronic demyelinating polyneuropathy, other demyelinating disorders, stroke, Alzheimer's disease and Parkinson's disease, acute pain, neuropathic pain, inflammatory pain, chronic pain, migraine, multiple myeloma, acute lymphocytic leukemia, acute myeloid leukemia, chronic myeloid leukemia, mast cell tumors, canine mast cell tumors, lung cancer, testicular cancer, pancreatic cancer, prostate cancer, breast cancer, ovarian cancer, merkel cell carcinoma, carcinomas of the female genital tract, colorectal carcinoma, carcinoma in situ, gastrointestinal stromal tumors, tumor angiogenesis, astrocytoma, neuroblastoma, sarcoma, osteosarcoma, sarcomas of neuroectodermal origin, giant cell tumor of bone, giant cell tumor of tendon sheath, pigmented villonodular synovitis, melanoma, glioblastoma, glioblastoma multiforme, glioma, other tumors of the central nervous system, neurofibromatosis (including Schwann cell neoplasia associated with neurofibromatosis), mastocytosis, metastasis of tumors to other tissues, osteolytic bone metastases, and other chronic myeloproliferative diseases such as myelofibrosis, collagen vascular disease, polyarteritis nodosa, Behcet's disease, sarcoidosis, familiar Mediterranean fever, Churg-Strauss vasculitis, temporal arteritis, giant cell arteritis, Takayasu's arteritis, uveitis, scleritis, retinitis, age related macular degeneration, choroidal neovascularization, diabetic retinopathy, cherubism, neurofibromatosis, infections associated with human immunodeficiency virus, hepatitis B virus, hepatitis C virus, human granulocytic anaplasmosis, Gaucher's disease, Fabry's disease, Niemann-Pick disease, liver cirrhosis, gastroesophageal reflux disease, esophagitis, and gastrointestinal tract ulcers, pulmonary fibrosis, acute lung injury, bypass surgery, vascular surgery, and vascular grafts, atherosclerosis, cardiomyopathy, heart failure, and pulmonary arterial hypertension. The invention further provides one or more compounds or compositions as described herein for use in treating a Fms-mediated and Kit-mediated disease or condition as described herein.

In a twenty-eighth aspect, one or more compounds as described herein can be used in the preparation of a medicament for the treatment of a disease or condition selected from the group consisting of rheumatoid arthritis, osteoarthritis, osteoporosis, peri-prosthetic osteolysis, systemic sclerosis, demyelinating disorders, multiple sclerosis, Charcot Marie Tooth syndrome, amyotrophic lateral sclerosis, Alzheimer's disease, Parkinson's disease, ulcerative colitis, Crohn's disease, immune thrombocytopenic purpura, myelopreparation for autologous transplantation, transplant rejection, glomerulonephritis, interstitial nephritis, Lupus nephritis, tubular necrosis, diabetic nephropathy, renal hypertrophy, type I diabetes, acute pain, inflammatory pain, neuropathic pain, acute myeloid leukemia, melanoma, multiple myeloma, metastatic breast cancer, prostate cancer, pancreatic cancer, lung cancer, ovarian cancer, gliomas, glioblastomas, neurofibromatosis, osteolytic bone metastases, brain metastases, gastrointestinal stromal tumors, and giant cell tumors.

In a twenty-ninth aspect, one or more compounds as described herein that are Kit inhibitors can be used in the preparation of a medicament for the treatment of rheumatoid arthritis, gastrointestinal stromal tumors, melanoma or neurofibromatosis.

In a thirtieth aspect, one or more compounds as described herein that are Fms selective inhibitors can be used in the preparation of a medicament for the treatment of multiple sclerosis, glioblastoma, Alzheimer's disease, Parkinson's disease, rheumatoid arthritis, osteoarthritis, atherosclerosis, systemic lupus erythematosus, glomerulonephritis, interstitial nephritis, Lupus nephritis, tubular necrosis, diabetic nephropathy, or renal hypertrophy.

In a thirty-first aspect, one or more compounds as described herein that are Fms selective inhibitors that effectively cross the blood brain barrier can be used in the preparation of a medicament for the treatment of multiple sclerosis, glioblastoma, Alzheimer's disease, or Parkinson's disease.

In a thirty-second aspect, one or more compounds as described herein that are Fms selective inhibitors that do not effectively cross the blood brain barrier can be used in the preparation of a medicament for the treatment of rheumatoid arthritis, osteoarthritis, atherosclerosis, systemic lupus erythematosus, glomerulonephritis, interstitial nephritis, Lupus nephritis, tubular necrosis, diabetic nephropathy, or renal hypertrophy.

In a thirty-third aspect, one or more compounds as described herein that are dual Fms/Kit inhibitors can be used in the preparation of a medicament for the treatment of metastatic breast cancer, prostate cancer, multiple myeloma, melanoma, acute myeloid leukemia, brain metastases, neurofibromatosis, gastrointestinal stromal tumors, rheumatoid arthritis, or multiple sclerosis.

In a thirty-fourth aspect, one or more compounds as described herein that are dual Fms/Flt-3 inhibitors can be used in the preparation of a medicament for the treatment of acute myeloid leukemia.

In a thirty-fifth aspect, the invention provides an intermediate compound of Formula V:

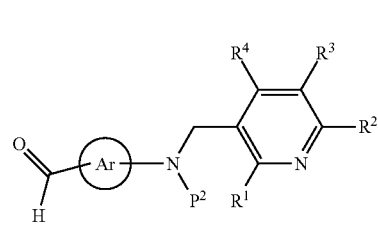

Formula V or a stereoisomer thereof, wherein:

$P^2$ is an amino protecting group;

Ar is selected from the group consisting of:

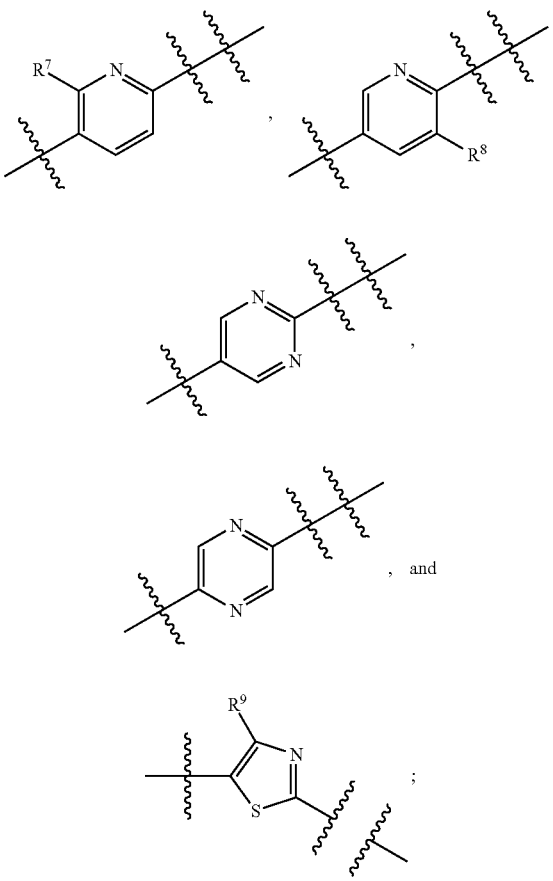

wherein

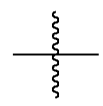

indicates the point of attachment of Ar to —CH$_2$— of Formula I and wherein

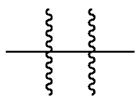 [SMILES: **]

indicates the point of attachment of Ar to —NH— of Formula I;

R$^1$, R$^2$, R$^3$ and R$^4$ are each independently selected from the group consisting of H, halogen, lower alkyl, halogen substituted lower alkyl, alkoxy substituted lower alkyl, cycloalkylamino, —CN, —O—R$^{40}$, —S(O)$_2$—R$^{41}$, —S(O)$_2$—N(H)—R$^{42}$, —N(H)—R$^{42}$, —N(R$^{42}$)$_2$, and —N(H)—S(O)$_2$—R$^{43}$, provided that at least two of R$^1$, R$^2$, R$^3$ and R$^4$ are —H and one of R$^1$, R$^2$, R$^3$ and R$^4$ is other than hydrogen, wherein:

R$^{40}$ is lower alkyl, fluoro substituted lower alkyl, methoxy substituted lower alkyl, or cycloalkyl;

R$^{41}$, R$^{42}$ and R$^{43}$ are lower alkyl. In some embodiments, the variables Ar, R$^7$, R$^8$, R$^9$, R$^1$, R$^2$, R$^3$ and R$^4$ are as defined herein.

In a thirty-sixth aspect, the invention provides a method for preparing a compound of Formula I':

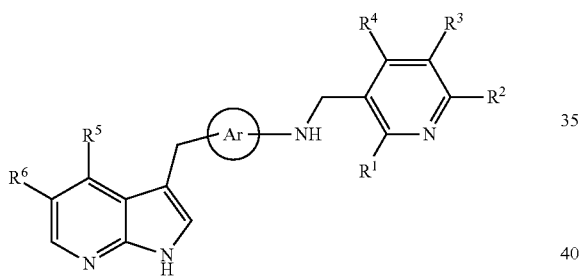

Formula I'

The method includes contacting a compound of Formula IV:

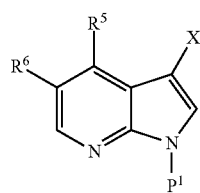

Formula IV with a compound of Formula V:

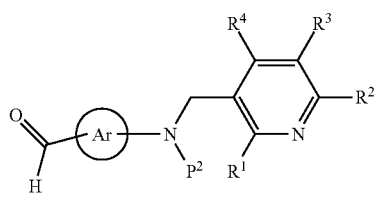

Formula V under conditions sufficient to form the compound of Formula I, wherein:

P$^1$ and P$^2$ are each independently an amino protecting group;

X is H or a halogen;

Ar is selected from the group consisting of:

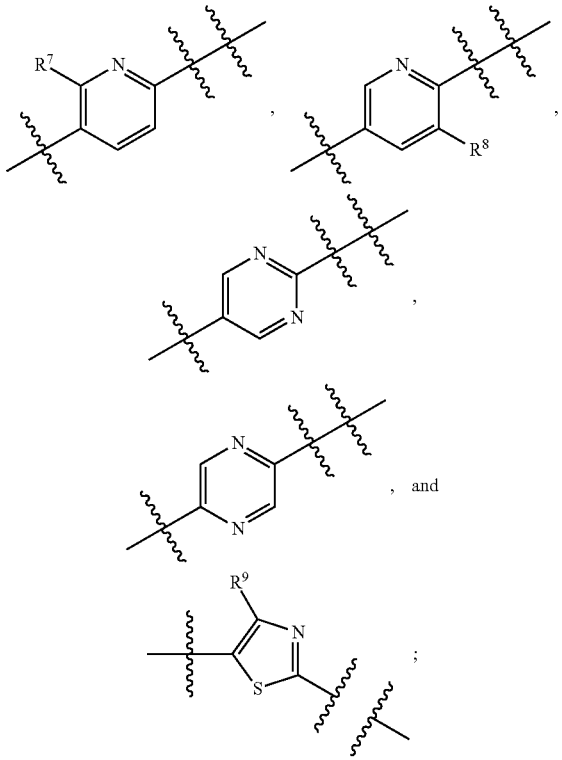

wherein

indicates the point of attachment of Ar to —CH$_2$— of Formula I and wherein

indicates the point of attachment of Ar to —NH— of Formula I;

R$^1$, R$^2$, R$^3$ and R$^4$ are each independently selected from the group consisting of —H, lower alkyl, halogen substituted lower alkyl, alkoxy substituted lower alkyl, cycloalkylamino, —CN, —O—R$^{40}$, —S(O)$_2$—R$^{41}$, —S(O)$_2$—N(H)—R$^4$, —N(H)—R$^{42}$, —N(R$^{42}$)$_2$, and —N(H)—S(O)$_2$—R$^{43}$, provided that at least two of R$^1$, R$^2$, R$^3$ and R$^4$ are —H and one of R$^1$, R$^2$, R$^3$ and R$^4$ is other than hydrogen, wherein:

R$^{40}$ is lower alkyl, fluoro substituted lower alkyl, methoxy substituted lower alkyl, or cycloalkyl;

R$^{41}$, R$^{42}$ and R$^{43}$ are lower alkyl;

R$^5$ is selected from the group consisting of —H, —F, —Cl, —Br, lower alkyl, halogen substituted alkyl, lower alkenyl, lower alkynyl, cycloalkyl, phenyl, pyrazolyl, —CN, —O—R$^{10}$, —C(O)—N(H)—R$^{11}$, C(O)—O—R$^{11}$, —S(O)$_2$—R$^{12}$, —S(O)$_2$—N(H)—R$^{11}$, —N(H)—C(O)—R$^{12}$, and —N(H)—S(O)$_2$—R$^{12}$, wherein pyrazolyl is optionally substituted with lower alkyl or heterocycloalkyl;

R$^6$ is selected from the group consisting of H, halogen, lower alkyl, halogen substituted alkyl, lower alkenyl, lower alkynyl, cycloalkyl, phenyl, pyrazolyl, —CN, —O—R$^{13}$, —C(O)—N(H)—R$^{14}$, —C(O)—O—R$^{14}$, —S(O)$_2$—R$^{15}$, —S(O)$_2$—N(H)—R$^{14}$, —N(H)—C(O)—R$^{15}$, and —N(H)—S(O)$_2$—R$^{15}$, wherein pyrazolyl is optionally substituted with lower alkyl or heterocycloalkyl;

R$^7$ is H, halogen or lower alkyl;

R$^8$ is H, halogen, lower alkyl or lower alkoxy;

R$^9$ is H or halogen;

R$^{10}$ and R$^{13}$ are independently —H, lower alkyl, lower alkyl substituted with —O—CH$_3$, lower alkyl substituted with di-alklylamine, or lower alkyl substituted with heterocycloalkyl;

R$^{11}$ and R$^{14}$ are independently hydrogen or lower alkyl; and

R$^{12}$ and R$^{15}$ are each independently lower alkyl, with the proviso that the compound is other than those set forth in Table 1. P$^1$ and P$^2$ are amino protecting groups as described herein. In one embodiment, P$^2$ is t-butoxycabonyl. In another embodiment, P$^1$ is phenylsulfonyl. In one embodiment, the contacting is performed by reacting the compounds of Formula IV with the compounds of Formula V in the presence of a strong base, such as alkali metal hydroxide. Exemplary alkali metal hydroxides include NaOH, KOH and LiOH. In another embodiment, the contacting includes forming a Grignard reagent of compounds of Formula IV and further reacting the Grignard reagent of compounds of Formula IV with the compounds of Formula V. In yet another embodiment, the contacting includes reacting the compounds of Formula IV with the compounds of Formula V in the presence of a palladium complex. In some embodiments, the variables R$^5$ and R$^6$ are as defined in any of the embodiments above for compounds of Formula I. In some embodiments, the variables R$^1$, R$^2$, R$^3$ and R$^4$ are as defined in any of the embodiments above for compounds of Formula I.

In some embodiments, the invention provides a method of preparing a compound of Formula II':

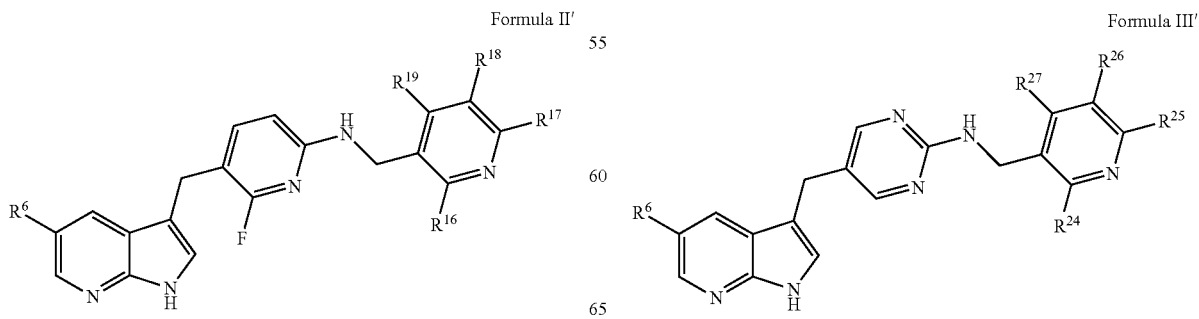

Formula II'

The method includes contacting a compound of Formula VI:

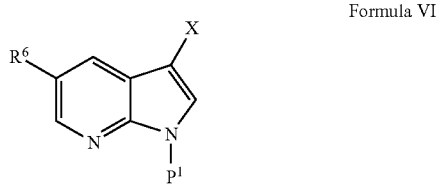

Formula VI with a compound of Formula VII:

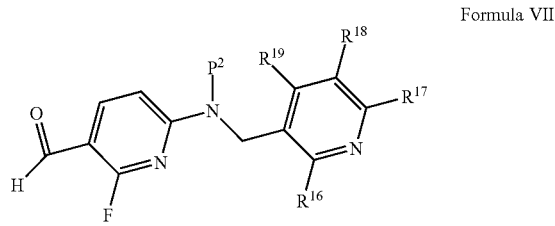

Formula VII under conditions sufficient to form the compound of Formula II', wherein P$^1$ and P$^2$ are each independently an amino protecting group; X is H or a halogen; R$^6$ is selected from the group consisting of H, halogen, lower alkyl, halogen substituted alkyl, lower alkenyl, lower alkynyl, cycloalkyl, phenyl, pyrazolyl, —CN, —O—R$^{13}$, —C(O)—N(H)—R$^{14}$, —C(O)—O—R$^{14}$, —S(O)$_2$—R$^{15}$, —S(O)$_2$—N(H)—R$^{14}$, —N(H)—C(O)—R$^{15}$, and —N(H)—S(O)$_2$—R$^{15}$, wherein pyrazolyl is optionally substituted with lower alkyl or heterocycloalkyl. R$^{16}$, R$^{17}$, R$^{18}$ and R$^{19}$ are each independently selected from H, halogen, lower alkyl, lower alkoxy, halo substituted lower alkyl, —OR$^{20}$, or alkoxy substituted lower alkyl. In one embodiment, R$^6$ is lower alkyl. In another embodiment, R$^6$ is CH$_3$ or CN. In another embodiment, R$^6$ is methyl, ethyl or propyl. P$^1$ and P$^2$ are amino protecting groups as described herein. In one embodiment, P$^2$ is t-butoxycabonyl. In another embodiment, P$^1$ is phenylsulfonyl. In one embodiment, the contacting is performed by reacting the compounds of Formula VI with the compounds of Formula VII in the presence of a strong base, such as alkali metal hydroxide. Exemplary alkali metal hydroxide include NaOH, KOH and LiOH. In another embodiment, the contacting includes forming a Grignard reagent of compounds of Formula VI and further reacting the Grignard reagent of compounds of Formula VI with the compounds of Formula VII.

In some embodiments, the invention provides a method of preparing a compound of Formula III':

Formula III'

The method includes contacting a compound of Formula VI:

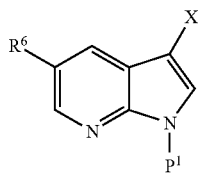

Formula VI with a compound of Formula VII:

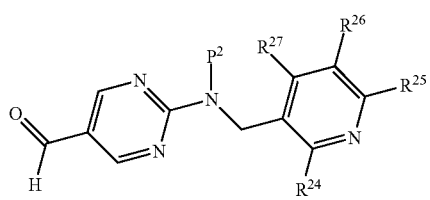

Formula VIII under conditions sufficient to form the compound of Formula II', wherein $P^1$ and $P^2$ are each independently an amino protecting group; X is H or a halogen; $R^6$ is selected from the group consisting of H, halogen, lower alkyl, halogen substituted alkyl, lower alkenyl, lower alkynyl, cycloalkyl, phenyl, pyrazolyl, —CN, —O—$R^{13}$, —C(O)—N(H)—$R^{14}$, —C(O)—O—$R^{14}$, —S(O)$_2$—$R^{15}$, —S(O)$_2$—N(H)—$R^{14}$, —N(H)—C(O)—$R^{15}$, and —N(H)—S(O)$_2$—$R^{15}$, wherein pyrazolyl is optionally substituted with lower alkyl or heterocycloalkyl. $R^{16}$, $R^{17}$, $R^{18}$ and $R^{19}$ are each independently selected from H, halogen, lower alkyl, lower alkoxy, halo substituted lower alkyl, —O$R^{20}$, or alkoxy substituted lower alkyl. In one embodiment, $R^6$ is lower alkyl. In another embodiment, $R^6$ is $CH_3$ or CN. In another embodiment, $R^6$ is methyl, ethyl or propyl. $P^1$ and $P^2$ are amino protecting groups as described herein. In one embodiment, $P^2$ is t-butoxycabonyl. In another embodiment, $P^1$ is phenylsulfonyl. In one embodiment, the contacting is performed by reacting the compounds of Formula VI with the compounds of Formula VIII in the presence of a strong base, such as alkali metal hydroxide. Exemplary alkali metal hydroxide include NaOH, KOH and LiOH. In another embodiment, the contacting includes forming a Grignard reagent of compounds of Formula VI and further reacting the Grignard reagent of compounds of Formula VI with the compounds of Formula VII.

Additional aspects and embodiments will be apparent from the following Detailed Description of the Invention and from the claims.

DETAILED DESCRIPTION OF THE INVENTION

As used herein the following definitions apply unless clearly indicated otherwise:

All atoms designated within a Formula described herein, either within a structure provided, or within the definitions of variables related to the structure, is intended to include any isotope thereof, unless clearly indicated to the contrary. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^1H$, $^2H$, $^3H$; carbon includes for example $^{11}C$, $^{12}C$, $^{13}C$, $^{14}C$; oxygen includes for example $^{16}O$, $^{17}O$, $^{18}O$; nitrogen includes for example $^{13}N$, $^{14}N$, $^{15}N$; sulfur includes for example $^{32}S$, $^{33}S$, $^{34}S$, $^{35}S$, $^{36}S$, $^{37}S$, $^{38}S$; fluoro includes for example $^{17}F$, $^{18}F$, $^{19}F$; chloro includes for example $^{35}Cl$, $^{36}Cl$, $^{37}Cl$, $^{38}Cl$, $^{39}Cl$; and the like.

"Halogen" or "Halo" refers to all halogens, that is, chloro (Cl), fluoro (F), bromo (Br), or iodo (I).

"Lower alkyl" alone or in combination means an alkane-derived radical containing from 1 to 6 carbon atoms (unless specifically defined) that includes a straight chain alkyl or branched alkyl. In many embodiments, a lower alkyl is a straight or branched alkyl group containing from 1-6, 1-4, or 1-2, carbon atoms, such as methyl, ethyl, propyl, isopropyl, butyl, t-butyl, and the like. A lower alkyl may be independently substituted as described herein, unless indicated otherwise, with one or more, preferably 1, 2, 3, 4 or 5, also 1, 2, or 3 substituents, wherein the substituents are as indicated. Furthermore, possible substitutions are attached at any available atom to produce a stable compound. For example "halo substituted lower alkyl" denotes a lower alkyl group substituted with one or more halogen atoms, where preferably the lower alkyl is substituted with 1, 2, 3, 4 or 5 halogen atoms, also 1, 2, or 3 halogen atoms. Furthermore, possible substitutions are attached at any available atom to produce a stable compound. For example "fluoro substituted lower alkyl" denotes a lower alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. Exemplary fluoro substituted lower alkyl includes, but is not limited to, $CF_3$, $CF_2CF_3$, $CH_2CF_3$, and the like. It is understood that substitutions are chemically feasible and attached at any available atom to provide a stable compound.

"Lower alkoxy" refers to those lower alkyl groups as defined herein attached to the remainder of the molecule via an oxygen atom. Representative alkoxy groups include methoxy, ethoxy, n-propoxy, i-propoxy, n-butoxy, n-pentoxy, n-heptoxy, and the like, as well as isomers thereof.

"Lower alkenyl" alone or in combination means a straight or branched hydrocarbon containing 2-6 carbon atoms (unless specifically defined) and at least one, preferably 1-3, more preferably 1-2, most preferably one, carbon to carbon double bond. Carbon to carbon double bonds may be either contained within a straight chain or branched portion. The straight chain or branched lower alkenyl group is chemically feasible and attached at any available point to provide a stable compound. Examples of lower alkenyl groups include ethenyl, propenyl, isopropenyl, butenyl, and the like.

"Lower alkynyl" alone or in combination means a straight or branched hydrocarbon containing 2-6 carbon atoms (unless specifically defined) containing at least one, preferably one, carbon to carbon triple bond. The straight chain or branched lower alkynyl group is chemically feasible and attached at any available point to provide a stable compound. Examples of alkynyl groups include ethynyl, propynyl, butynyl, and the like.

"Cycloalkyl" refers to saturated or unsaturated, non-aromatic monocyclic, bicyclic or tricyclic carbon ring systems of 3-10, also 3-8, more preferably 3-6, ring members per ring, such as cyclopropyl, cyclopentyl, cyclohexyl, adamantyl, and the like.

"Heterocycloalkyl" refers to a saturated or unsaturated non-aromatic cycloalkyl group having from 5 to 10 atoms in which from 1 to 3 carbon atoms in the ring are replaced by heteroatoms of O, S or N, and are optionally fused with benzo or heteroaryl of 5-6 ring members. Heterocycloalkyl is also intended to include oxidized S or N, such as sulfinyl, sulfonyl and N-oxide of a tertiary ring nitrogen. Heterocycloalkyl is also intended to include compounds in which a ring carbon may be oxo substituted, i.e. the ring carbon is a carbonyl group, such as lactones and lactams. The point of attachment of the heterocycloalkyl ring is at a carbon or nitrogen atom such that a stable ring is retained. Examples of heterocycloalkyl groups include, but are not limited to, morpholino, tetrahydrofuranyl, dihydropyridinyl, piperidinyl, pyrrolidinyl, pyrrolidonyl, piperazinyl, dihydrobenzofuryl, and dihydroindolyl.

"Cycloalkylamino" denotes the group —$NR^aR^b$, where $R^a$ and $R^b$ combine with the nitrogen to form a 5-7 membered heterocycloalkyl, where the heterocycloalkyl may contain an additional heteroatom within the ring, such as O, N, or S, and may also be further substituted with lower alkyl. Examples of 5-7 membered heterocycloalkyl include, but are not limited to, piperidine, piperazine, 4-methylpiperazine, morpholine, and thiomorpholine. It is understood that when cycloalkylamino is a substituent on other moieties, these are chemically feasible and attached at any available atom to provide a stable compound.

As used herein "Protecting group" refers to a grouping of atoms that when attached to a reactive group in a molecule masks, reduces or prevents that reactivity. Examples of protecting groups can be found in T. W. Greene and P. G. Wuts, PROTECTIVE GROUPS IN ORGANIC CHEMISTRY, (Wiley, 4th ed. 2006), Beaucage and Iyer, *Tetrahedron* 48:2223-2311 (1992), and Harrison and Harrison et al., COMPENDIUM OF SYNTHETIC ORGANIC METHODS, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), tri-isopropylsilyl (TIPS), phenylsulphonyl and the like (see also, Boyle, A. L. (Editor), CURRENT PROTOCOLS IN NUCLEIC ACID CHEMISTRY, John Wiley and Sons, New York, Volume 1, 2000).

As used herein, "Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

As used herein, the terms "treat", "treating", "therapy", "therapies", and like terms refer to the administration of material, e.g., any one or more compound(s) as described herein in an amount effective to prevent, alleviate, or ameliorate one or more symptoms of a disease or condition, i.e., indication, and/or to prolong the survival of the subject being treated.

As used herein, the term "Fms and/or Kit protein kinase mediated disease or condition" refers to a disease or condition in which the biological function of a Fms protein kinase, including any mutation thereof, a Kit protein kinase, including any mutation thereof, or both a Fms and Kit protein kinase, including any mutations thereof, affects the development, course, and/or symptoms of the disease or condition, and/or in which modulation of the Fms and/or Kit protein kinase alters the development, course, and/or symptoms of the disease or condition. A Fms and/or Kit protein kinase mediated disease or condition includes a disease or condition for which modulation provides a therapeutic benefit, e.g. wherein treatment with Fms and/or Kit protein kinase inhibitor(s), including one or more compound(s) described herein, provides a therapeutic benefit to the subject suffering from or at risk of the disease or condition.

As used herein, the terms "Fms protein kinase mediated disease or condition," "c-fms mediated disease or condition," and the like refer to a disease or condition in which the biological function of a Fms protein kinase, including any mutations thereof, affects the development, course, and/or symptoms of the disease or condition, and/or in which modulation of the Fms protein kinase alters the development, course, and/or symptoms of the disease or condition. The Fms protein kinase mediated disease or condition includes a disease or condition for which Fms inhibition provides a therapeutic benefit, e.g. wherein treatment with Fms inhibitor(s), including one or more compound(s) described herein, provides a therapeutic benefit to the subject suffering from or at risk of the disease or condition.

As used herein, the terms "Kit protein kinase mediated disease or condition," "c-kit mediated disease or condition," and the like refer to a disease or condition in which the biological function of a Kit protein kinase, including any mutations thereof, affects the development, course, and/or symptoms of the disease or condition, and/or in which modulation of the Kit protein kinase alters the development, course, and/or symptoms of the disease or condition. The Kit protein kinase mediated disease or condition includes a disease or condition for which Kit inhibition provides a therapeutic benefit, e.g. wherein treatment with Kit inhibitor(s), including one or more compound(s) described herein, provides a therapeutic benefit to the subject suffering from or at risk of the disease or condition.

As used herein, the term "dual Fms/Kit inhibitor" refers to a compound that inhibits both Fms and Kit protein kinases, i.e. a compound having an $IC_{50}$ of less than 500 nm, less than 100 nM, less than 50 nM, less than 20 nM, less than 10 nM, less than 5 nM, or less than 1 nM as determined in a generally accepted Fms kinase activity assay and having an $IC_{50}$ of less than 500 nm, less than 100 nM, less than 50 nM, less than 20 nM, less than 10 nM, less than 5 nM, or less than 1 nM as determined in a comparable generally accepted Kit kinase activity assay, wherein the activity is approximately equipotent on each. Compounds are considered approximately equipotent if the ratio of $IC_{50}$ for Kit kinase activity divided by the $IC_{50}$ for Fms kinase activity is in the range of 20 to 0.05, also 10 to 0.1, also 5 to 0.2. Such compounds are effective in treating a disease or condition that is either or both of a Fms protein kinase mediated and Kit protein kinase mediated disease or condition. Such compounds are preferably, but not necessarily, selective with respect to other protein kinases, i.e. when compared to another protein kinase, the $IC_{50}$ for the other kinase divided by the $IC_{50}$ for Fms kinase is >20, also >30, also >40, also >50, also >60, also >70, also >80, also >90, also >100. Preferably, the compounds are selective relative to other protein kinases including, but not limited to, CSK, Insulin receptor kinase, AMPK, PDGFR or VEGFR. While it is understood that a dual Fms/Kit inhibitor may be used to treat any Fms protein kinase mediated disease or condition, the dual inhibition of Fms and Kit provides beneficial effects in treating certain diseases or conditions, including, but not limited to, metastatic breast cancer, prostate cancer, multiple myeloma, melanoma, acute myeloid leukemia, brain metastases, neurofibromatosis, gastrointestinal stromal tumors, rheumatoid arthritis, or multiple sclerosis.

As used herein, the term "dual Fms/Flt-3 inhibitor" refers to a compound that inhibits both Fms and Flt-3 protein kinases, i.e. a compound having an $IC_{50}$ of less than 500 nm, less than 100 nM, less than 50 nM, less than 20 nM, less than 10 nM, less than 5 nM, or less than 1 nM as determined in a generally accepted Fms kinase activity assay and having an $IC_{50}$ of less than 500 nm, less than 100 nM, less than 50 nM, less than 20 nM, less than 10 nM, less than 5 nM, or less than 1 nM as determined in a comparable generally accepted Flt-3 kinase activity assay, wherein the activity is approximately equipotent on each. Compounds are considered approximately equipotent if the ratio of $IC_{50}$ for Flt-3 kinase activity divided by the $IC_{50}$ for Fms kinase activity is in the range of 20 to 0.05, also 10 to 0.1, also 5 to 0.2. Such compounds are effective in treating a disease or condition that is either or both of a Fms protein kinase mediated and Flt-3 protein kinase mediated disease or condition. Such compounds are preferably, but not necessarily, selective with respect to other protein kinases, i.e. when compared to another protein kinase, the $IC_{50}$ for the other kinase divided by the $IC_{50}$ for Fms kinase is >20, also >30, also >40, also >50, also >60, also >70, also >80, also >90, also >100. Preferably, the compounds are selective relative to other protein kinases including, but not limited to, CSK, Insulin receptor kinase, AMPK, PDGFR or VEGFR. While it is understood that a dual Fms/Flt-3 inhibitor may be used to treat any Fms protein kinase mediated disease or condition, the dual inhibition of Fms and Flt-3 provides beneficial effects in treating certain diseases or conditions, including, but not limited to, acute myeloid leukemia.

As used herein, the term "Fms selective inhibitor" refers to a compound that selectively inhibits Fms kinase relative to Kit kinase, i.e. a compound having an $IC_{50}$ of less than 500 nm, less than 100 nM, less than 50 nM, less than 20 nM, less than 10 nM, less than 5 nM, or less than 1 nM as determined in a generally accepted Fms kinase activity assay and when determined in a comparable generally accepted Kit kinase activity assay will have a ratio of $IC_{50}$ for Kit kinase divided by the $IC_{50}$ for Fms kinase of >20, also >30, also >40, also >50, also >60, also >70, also >80, also >90, also >100. Such compounds are effective in treating a disease or condition that is Fms protein kinase mediated, without effecting Kit protein kinase. Such compounds are preferably, but not necessarily, selective with respect to other protein kinases, i.e. when compared to another protein kinase, the $IC_{50}$ for the other kinase divided by the $IC_{50}$ for Fms kinase is >20, also >30, also >40, also >50, also >60, also >70, also >80, also >90, also >100. Preferably, the compounds are selective relative to other protein kinases including, but not limited to, CSK, Insulin receptor kinase, AMPK, PDGFR or VEGFR. While it is understood that a Fms selective inhibitor may be used to treat any Fms protein kinase mediated disease or condition, the Fms selectivity provides beneficial effects in treating certain diseases or conditions, including, but not limited to, rheumatoid arthritis, Alzheimer's disease, Parkinson's disease, osteoarthritis, nephritis, diabetic nephropathy, or renal hypertrophy.

As used herein, the term "blood brain barrier" refers to the physical barrier in the circulation system that prevents many substances, including certain small molecule drugs, from entering into the central nervous system (CNS). Drugs which are intended to interact with molecular targets in the CNS must cross the blood brain barrier to reach their intended targets. Conversely, peripherally acting agents should not cross the blood brain barrier so as to avoid any CNS related side effects. The ability of a compound to penetrate the blood brain barrier is expressed as the blood brain barrier permeability or the ratio of the steady-state concentrations of the compound in the brain and in the blood. The experimental blood brain barrier permeability can be measured by in vivo methods. Various methods can be employed for measuring the fraction of compound transported from the blood to brain tissue, including brain blood partitioning, brain perfusion, brain uptake index, and intracerebral microdialysis. However, these in vivo methods are laborious and low-throughput in nature. In practice, in silico computational methods are often used to predict the blood brain barrier permeability prior to in vivo confirmation. Most of the blood brain barrier models that have been built so far are based on the assumption that the majority of the compounds are transported across the blood brain barrier by passive diffusion. Of all the physicochemical properties, polar surface area (PSA) shows the best correlation with the blood brain barrier permeability for passively diffused compounds. Empirical evidence suggests that compounds having a polar surface area of 100 or greater typically have a low probability of crossing the blood brain barrier. Polar surface area is readily calculated from the compound structure using a published algorithm (Ertl et al., J. Med. Chem. 2000, 43:3714-3717). While it is understood that a Fms selective inhibitor may be used to treat any Fms protein kinase mediated disease or condition, compounds that effectively cross the blood brain barrier provide beneficial effects in treating certain diseases or conditions, including, but not limited to, multiple sclerosis, glioblastoma, Alzheimer's disease, and Parkinson's disease, while compounds that do not effectively cross the blood brain barrier provide beneficial effects in treating certain diseases or conditions, including, but not limited to, rheumatoid arthritis, osteoarthritis, atherosclerosis, systemic lupus erythematosus, glomerulonephritis, interstitial nephritis, Lupus nephritis, tubular necrosis, diabetic nephropathy, or renal hypertrophy.

As used herein, the term "solid form" refers to a solid preparation (i.e. a preparation that is neither gas nor liquid) of a pharmaceutically active compound that is suitable for administration to an intended animal subject for therapeutic purposes. The solid form includes any complex, such as a salt, co-crystal or an amorphous complex, as well as any polymorph of the compound. The solid form may be substantially crystalline, semi-crystalline or substantially amorphous. The solid form may be administered directly or used in the preparation of a suitable composition having improved pharmaceutical properties. For example, the solid form may be used in a formulation comprising at least one pharmaceutically acceptable carrier or excipient.

As used herein, the term "substantially crystalline" material embraces material which has greater than about 90% crystallinity; and "crystalline" material embraces material which has greater than about 98% crystallinity.

As used herein, the term "substantially amorphous" material embraces material which has no more than about 10% crystallinity; and "amorphous" material embraces material which has no more than about 2% crystallinity.

As used herein, the term "semi-crystalline" material embraces material which is greater than 10% crystallinity, but no greater than 90% crystallinity; preferably "semi-crystalline" material embraces material which is greater than 20% crystallinity, but no greater than 80% crystallinity. In one aspect of the present invention, a mixture of solid forms of a compound may be prepared, for example, a mixture of amorphous and crystalline solid forms, e.g. to provide a "semi-crystalline" solid form. Such a "semi-crystalline" solid form may be prepared by methods known in the art, for example by mixing an amorphous solid form with a crystalline solid form in the desired ratio. In some instances, a compound mixed with acid or base forms an amorphous complex; a semi-crystalline solid can be prepared employing an amount of compound component in excess of the stoichiometry of the compound and acid or base in the amorphous complex, thereby resulting in an amount of the amorphous complex that is based on the stoichiometry thereof, with excess compound in a crystalline form. The amount of excess compound used in the preparation of the complex can be adjusted to provide the desired ratio of amorphous complex to crystalline compound in the resulting mixture of solid forms. For example, where the amorphous complex of acid or base and compound has a 1:1 stoichiometry, preparing said complex with a 2:1 mole ratio of compound to acid or base will result in a solid form of 50% amorphous complex and 50% crystalline compound. Such a mixture of solid forms may be beneficial as a drug product, for example, by providing an amorphous component having improved biopharmaceutical properties along with the crystalline component. The amorphous component would be more readily bioavailable while the crystalline component would have a delayed bioavailablity. Such a mixture may provide both rapid and extended exposure to the active compound.

As used herein, the term "complex" refers to a combination of a pharmaceutically active compound and an additional molecular species that forms or produces a new chemical species in a solid form. In some instances, the complex may be a salt, i.e. where the additional molecular species provides an acid/base counter ion to an acid/base group of the compound resulting in an acid:base interaction that forms a typical salt. While such salt forms are typically substantially crystalline, they can also be partially crystalline, substantially amorphous, or amorphous forms. In some instances, the additional molecular species, in combination with the pharmaceutically active compound, forms a non-salt co-crystal, i.e. the compound and molecular species do not interact by way of a typical acid:base interaction, but still form a substantially crystalline structure. Co-crystals may also be formed from a salt of the compound and an additional molecular species. In some instances, the complex is a substantially amorphous complex, which may contain salt-like acid:base interactions that do not form typical salt crystals, but instead form a substantially amorphous solid, i.e. a solid whose X-ray powder diffraction pattern exhibits no sharp peaks (e.g. exhibits an amorphous halo).

As used herein, the term "stoichiometry" refers to the molar ratio of two or more reactants that combine to form a complex, for example, the molar ratio of acid or base to compound that form an amorphous complex. For example, a 1:1 mixture of acid or base with compound (i.e. 1 mole acid or base per mole of compound) resulting in an amorphous solid form has a 1:1 stoichiometry.

As used herein, the term "composition" refers to a pharmaceutical preparation suitable for administration to an intended subject for therapeutic purposes that contains at least one pharmaceutically active compound, including any solid form thereof. The composition may include at least one pharmaceutically acceptable component to provide an improved formulation of the compound, such as a suitable carrier or excipient.

As used herein, the term "subject" refers to a living organism that is treated with compounds as described herein, including, but not limited to, any mammal, such as a human, other primates, sports animals, animals of commercial interest such as cattle, farm animals such as horses, or pets such as dogs and cats.

As used herein, the term "biopharmaceutical properties" refers to the pharmacokinetic action of a compound or complex of the present invention, including the dissolution, absorption and distribution of the compound on administration to a subject. As such, certain solid forms of compounds of the invention, such as amorphous complexes of compounds of the invention, are intended to provide improved dissolution and absorption of the active compound, which is typically reflected in improved $C_{max}$ (i.e. the maximum achieved concentration in the plasma after administration of the drug) and improved AUC (i.e. area under the curve of drug plasma concentration vs. time after administration of the drug).

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

Certain compounds of the present invention can exist in unsolvated forms as well as solvated forms, including hydrated forms. "Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

By "assaying" is meant the creation of experimental conditions and the gathering of data regarding a particular result of the experimental conditions. For example, enzymes can be assayed based on their ability to act upon a detectable substrate. A compound can be assayed based on its ability to bind to a particular target molecule or molecules.

As used herein, the term "modulating" or "modulate" refers to an effect of altering a biological activity, especially a biological activity associated with a particular biomolecule such as a protein kinase. For example, an inhibitor of a particular biomolecule modulates the activity of that biomolecule, e.g., an enzyme, by decreasing the activity of the biomolecule, such as an enzyme. Such activity is typically indicated in terms of an inhibitory concentration ($IC_{50}$) of the compound for an inhibitor with respect to, for example, an enzyme.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

"Pain" or a "pain condition" can be acute and/or chronic pain, including, without limitation, arachnoiditis; arthritis (e.g. osteoarthritis, rheumatoid arthritis, ankylosing spondylitis, gout); back pain (e.g. sciatica, ruptured disc, spondylolisthesis, radiculopathy); burn pain; cancer pain;

dysmenorrhea; headaches (e.g. migraine, cluster headaches, tension headaches); head and facial pain (e.g. cranial neuralgia, trigeminal neuralgia); hyperalgesia; hyperpathia; inflammatory pain (e.g. pain associated with irritable bowel syndrome, inflammatory bowel disease, ulcerative colitis, Crohn's disease, cystitis, pain from bacterial, fungal or viral infection); keloid or scar tissue formation; labor or delivery pain; muscle pain (e.g. as a result of polymyositis, dermatomyositis, inclusion body myositis, repetitive stress injury (e.g. writer's cramp, carpal tunnel syndrome, tendonitis, tenosynovitis)); myofascial pain syndromes (e.g. fibromyalgia); neuropathic pain (e.g. diabetic neuropathy, causalgia, entrapment neuropathy, brachial plexus avulsion, occipital neuralgia, gout, reflex sympathetic dystrophy syndrome, phantom limb or post-amputation pain, postherpetic neuralgia, central pain syndrome, or nerve pain resulting from trauma (e.g. nerve injury), disease (e.g. diabetes, multiple sclerosis, Guillan-Barre Syndrome, myasthenia gravis, neurodegenerative diseases such as Parkinson's disease, Alzheimer's disease, amyotrophic lateral sclerosis, or cancer treatment); pain associated with skin disorders (e.g. shingles, herpes simplex, skin tumors, cysts, neurofibromatosis); sports injuries (e.g. cuts, sprains, strains, bruises, dislocations, fractures, spinal chord, head); spinal stenosis; surgical pain; tactile allodynia; temporomandibular disorders; vascular disease or injury (e.g. vasculitis, coronary artery disease, reperfusion injury (e.g. following ischemia, stroke, or myocardial infarcts)); other specific organ or tissue pain (e.g. ocular pain, corneal pain, bone pain, heart pain, visceral pain (e.g. kidney, gall bladder, gastrointestinal), joint pain, dental pain, pelvic hypersensitivity, pelvic pain, renal colic, urinary incontinence); other disease associated pain (e.g. sickle cell anemia, AIDS, herpes zoster, psoriasis, endometriosis, asthma, chronic obstructive pulmonary disease (COPD), silicosis, pulmonary sarcoidosis, esophagitis, heart burn, gastroesophageal reflux disorder, stomach and duodenal ulcers, functional dyspepsia, bone resorption disease, osteoporosis, cerebral malaria, bacterial meningitis); or pain due to graft v. host rejection or allograft rejections.

Kinase Targets and Indications

Protein kinases play key roles in propagating biochemical signals in diverse biological pathways. More than 500 kinases have been described, and specific kinases have been implicated in a wide range of diseases or conditions (i.e., indications), including for example without limitation, cancer, cardiovascular disease, inflammatory disease, neurological disease, and other diseases. As such, kinases represent important control points for small molecule therapeutic intervention. Specific target protein kinases, i.e. Fms kinase and Kit kinase, contemplated by the present invention are described in the art, including, without limitation, as described in U.S. patent application Ser. No. 11/473,347 (see also, PCT publication WO2007002433), the disclosure of which is hereby incorporated by reference with respect to such kinase targets, as well as the following:

Fms: Target kinase Fms (i.e., feline McDonough sarcoma) is a member of the family of genes originally isolated from the Susan McDonough strain of feline sarcoma viruses. Fms is a transmembrane tyrosine kinase of 108.0 kDa coded by chromosome 5q33.2-q33.3 (symbol: CSF1R). The structure of the transmembrane receptor Fms comprises two Ig-like domains, a IgC2-like domain, two additional Ig-like domains, a TM domain, and the TK domain.

Fms is the receptor for the macrophage colony-stimulating factor (M-CSF), and is crucial for the growth and differentiation of the monocyte-macrophage lineage. Upon binding of M-CSF to the extracellular domain of Fms, the receptor dimerizes and trans-autophosphorylates cytoplasmic tyrosine residues.

M-CSF, first described by Robinson and co-workers (Blood. 1969, 33:396-9), is a cytokine that controls the production, differentiation, and function of macrophages. M-CSF stimulates differentiation of progenitor cells to mature monocytes, and prolongs the survival of monocytes. Furthermore, M-CSF enhances cytotoxicity, superoxide production, phagocytosis, chemotaxis, and secondary cytokine production of additional factors in monocytes and macrophages. Examples of such additional factors include granulocyte colony stimulating factor (G-CSF), interleukin-6 (IL-6), and interleukin-8 (IL-8). M-CSF stimulates hematopoiesis, promotes differentiation and proliferation of osteoclast progenitor cells, and has profound effects on lipid metabolism. Furthermore, M-CSF is important in pregnancy. Physiologically, large amounts of M-CSF are produced in the placenta, and M-CSF is believed to play an essential role in trophoblast differentiation (Motoyoshi, Int J Hematol. 1998, 67:109-22). The elevated serum M-CSF levels of early pregnancy may participate in the immunologic mechanisms responsible for the maintenance of the pregnancy (Flanagan & Lader, Curr Opin Hematol. 1998, 5:181-5).

Aberrant expression and/or activation of Fms has been implicated in acute myeloid leukemia, AML (Ridge et al, Proc. Nat. Acad. Sci., 1990, 87:1377-1380). Mutations at codon 301 are believed to lead to neoplastic transformation by ligand independence and constitutive tyrosine kinase activity of the receptor. The tyrosine residue at codon 969 has been shown to be involved in a negative regulatory activity, which is disrupted by amino acid substitutions. Accordingly, Fms mutations are most prevalent (20%) in chronic myelomonocytic leukemia and AML type M4 (23%), both of which are characterized by monocytic differentiation.

A condition related to AML is chronic myeloid leukemia (CML). During the myeloid blast crisis (BC) of CML, non-random additional chromosome abnormalities occur in over 80% of patients. However, these cytogenetic changes have been reported to precede the clinical signs of CML-BC by several months to years suggesting that other biological events may participate in the multistep process of acute transformation of CML. The autocrine production of growth factors has been shown to occur in several hematological malignancies and particularly in AML. Specchia et al [Br J Haematol. 1992 March; 80(3):310-6] have demonstrated that IL-1 beta gene is expressed in almost all cases of CML in myeloid blast crisis, and that a high proportion of cases showed constitutive expression of the M-CSF gene. Many of the same patients in the Specchia et al study demonstrated simultaneous co-expression of Fms. After exposure of leukemic cells to phorbol myristate acetate (PMA), release of M-CSF protein was documented in three of five patients studied; however, no significant interleukin-3 (IL-3), granulocyte-macrophage colony-stimulating factor (GM-CSF) or granulocyte colony-stimulating factor (G-CSF), was detected in these patients. This demonstrates that different patterns of growth factors secretion exist in AML and CML, and that distinct molecular events are likely involved in the control of leukemic proliferation.

The observation that production of M-CSF, the major macrophage growth factor, is increased in tissues during inflammation (Le Meur et al, J. Leukocyte Biology. 2002; 72:530-537) provides a role for Fms in certain diseases. For example, COPD is characterized by airflow limitation that is not fully reversible. The airflow limitation is usually progressive and associated with an abnormal inflammatory response of the lungs to noxious particles or gases. The chronic inflammation of COPD is observed through the airways, parenchyma, and pulmonary vasculature. The inflammatory cell population consists of neutrophils, macrophages, and T lymphocytes, along with eosinophils in some patients. Macrophages are postulated to play an orchestrating role in COPD inflammation by releasing mediators such as TNF-a, IL-8 and LTB4, which are capable of damaging lung structures and/or sustaining neutrophilic inflammation.

Further, M-CSF/fms signaling is critical to osteoclast formation and survival of osteoclast precursors. For example, estrogen loss in menopause results in increased M-CSF and thus increased osteoclast number and bone resorption which leads to increased risk of fracture and osteoporosis. Accordingly, blockage of this signal is a target for the inhibition of bone resorption (Teitelbaum, Science. 2000; 289:1504; Rohan, Science. 2000; 289:1508).

Atherosclerosis, an inflammatory disease of the vessel walls, is associated with significant morbidity and mortality. A effect for Fms inhibition in the treatment and prevention of atherosclerosis depends on several observations (Libby, Nature. 2002; 420:868-874). First, monocytes resident in the arterial intima increase expression of scavenger receptors and internalize modified lipoproteins. The resulting lipid-laden macrophages develop into foam cells characteristic of the atherosclerotic lesion. Macrophages in atheroma secrete cytokines and growth factors involved in lesion progression. Additionally, macrophages replicate within the intima. Through Fms, M-CSF activates the transition from monocyte to lipid-laden macrophage and augments expression of scavenger receptor A. Indeed, atherosclerotic plaques over-express M-CSF which is critical for atherosclerotic progression. Mice deficient in M-CSF have been found to experience less severe atherosclerosis than mice with normal M-CSF (Rajavashisth, et. al., J. Clin. Invest. 1998; 101:2702-2710; Qiao, et. al., Am. J. Path. 1997; 150:1687-1699). Accordingly, inhibitors of Fms disrupt M-CSF signaling, compromising monocyte to macrophage foam cell progression, macrophage survival and replication, and cytokine signaling that participates in lesion progression.

The role of M-CSF and Fms in emphysema appears to involve the regulation of elastin metabolism through control of matrix metalloproteins. M-CSF has a role in the modulation of the accumulation and function of alveolar macrophages (AMs) in vivo (Shibata et al, Blood 2001, 98: pp. 2845-2852). Osteopetrotic (Op/Op) mice have no detectable M-CSF and show variable tissue-specific reductions in macrophage numbers. Accordingly, it was hypothesized that AMs would be decreased in number and have altered function in Op/Op mice because of the absence of M-CSF. Shibata et al found that lung macrophages identified in lung sections were decreased in number in 20-day-old Op/Op mice but not Op/Op mice older than 4 months compared with findings in age-matched littermate controls. The numbers of AMs recovered by bronchoalvcolar lavage (BAL) were also reduced in young but not adult Op/Op mice compared with controls. Importantly, AMs of Op/Op mice spontaneously release higher levels of matrix metalloproteinases (MMPs) than AMs of controls. Consistent with an increased release of MMP, Op/Op mice have abnormal elastin deposition and spontaneously develop emphysema in the absence of molecular or cellular evidence of lung inflammation. Accordingly, the modulation of metalloelastase activity in macrophages by M-CSF may control the degradation of elastin fibers in lungs or blood vessels.

Metastatic cancer cells cause bone destruction, with associated fracture, pain, deformation, and hypercalcaemia, due to production of osteoclasticogenic factors including M-CSF by tumor cells (Clohisy et al, Clin. Orthop. 2000, 373: 104-14). Binding of M-CSF to the Fms product stimulates formation of osteoclasts and osteolytic activity (Kodama et al, J. Exp. Med. 1991, 173: 269-72; Feng et al, Endocrinology 2002, 143: 4868-74). Accordingly, inhibition of osteoclast activity at the level of Fms offers a compelling target for amelioration of bone metastasis. Fms is also a target for amelioration of metastatic breast cancer (Lawicki et al., Clin Chim Acta. 2006, September, 371(1-2):112-6; Wyckoff et al., Cancer Res. 2007, Mar. 15, 67(6):2649-56).

Nephritis is inflammation of the kidneys. It may be caused for example by a bacterial infection of the kidneys or exposure to a toxin. However, nephritis more commonly develops from an abnormal immune reaction, which can occur, for example, when an antibody attacks either the kidney itself or an antigen attached to kidney cells, or when an antigen-antibody complex formed elsewhere in the body attaches to cells in the kidney. Some types of nephritis involve infiltration of kidney tissues by white blood cells and deposits of antibodies. In other types of nephritis, inflammation may consist of tissue swelling or scarring without white blood cells or antibodies. Furthermore, nephritis can occur anywhere in the kidneys. With respect to the glomeruli, progressive damage to glomeruli causes urine production to fall and metabolic waste products to build up in the blood. When damage to glomeruli is severe, inflammatory cells and injured glomerular cells accumulate, compressing the capillaries within the glomerulus and interfering with filtration. Scarring may develop, impairing kidney function and reducing urine production. In some cases, microthrombi may form in the small blood vessels, further decreasing kidney function. Less commonly, nephritis involves the tubulointerstitial tissues; such inflammation is called tubulointerstitial nephritis. When inflammation damages the tubules and the tubulointerstitial tissues, the kidneys may become unable to concentrate urine, eliminate (excrete) metabolic waste products from the body, or balance the excretion of sodium and other electrolytes, such as potassium. When the tubules and tubulointerstitial tissues are damaged, kidney failure often develops. Accordingly, inhibition of Fms offers a target for therapeutic intervention in nephritis due to the modulation of the inflammatory response comprising the etiology of the disease.

Lupus nephritis, i.e., renal involvement in systemic lupus erythematosus (SLE), is a common disease manifestation with a poor prognosis. At least three potentially overlapping, immuno-pathogenic mechanisms for lupus nephritis are supported by experimental data. First, circulating immune complexes consisting chiefly of DNA and anti-DNA are deposited in the kidney. Resulting complement activation and chemotaxis of neutrophils leads to a local inflammatory process. Second, in situ formation of antigen and antibody complexes may similarly lead to complement activation and leucocyte mediated injury. Third, antibodies against specific cellular targets may produce renal injury. An additional mechanism is observed in SLE patients with the antiphospholipid antibody syndrome. Glomerular thrombosis can result from the hypercoagulability that accompanies antibodies directed against negatively charged phospholipid-protein complexes (e.g. biologic false positive VDRL, anticardiolipin antibodies, and lupus anticoagulant). Mesangial lupus nephritis is accompanied by normal diagnostic findings or with a mild degree of proteinuria but typically absence of hypertension or abnormal urinary sediment. Focal and diffuse proliferative lupus glomerulonephritis are often associated with the worst prognosis for renal survival and can be accompanied by nephrotic syndrome, significant hypertension and abnormal urine sediment. Membranous lupus nephritis often presents with proteinuria, moderate to high grade, but usually normal urinary sediment in the absence of hypertension. Mesangial lupus nephropathy is generally associated with an excellent prognosis, whereas proliferative lupus nephropathy, especially diffuse variant, is often characterized by hypertension, red cell casts and significant deterioration of renal function. Nephrotic syndrome in the absence of hypertension, active urinary sediment or significant hypocomplementemia suggest the membranous variant of lupus nephropathy. Membranous nephropathy generally is associated with a good prognosis and relative preservation of renal function. However, in the presence of persistent nephrotic range proteinuria, membranous lupus nephropathy can, in fact, lead to loss of renal function and end stage renal disease (ESRD). Accordingly, inhibition of Fms offers a target for therapeutic intervention in lupus due to the modulation of the inflammatory response comprising the etiology of the disease.

Macrophage accumulation is a prominent feature in many forms of glomerulonephritis. Local proliferation of macrophages within the kidney has been described in human and experimental glomerulonephritis and may have an important role in augmenting the inflammatory response. Isbel et al (Nephrol Dial Transplant 2001, 16: 1638-1647) examined the relationship between local macrophage proliferation and renal expression of M-CSF. Glomerular and tubulointerstitial M-CSF expression was found to be up-regulated in human glomerulonephritis, being most prominent in proliferative forms of disease. Because this correlates with local macrophage proliferation, it suggests that increased renal M-CSF production plays an important role in regulating local macrophage proliferation in human glomerulonephritis. In a model of renal inflammation (UUO—unilateral ureteric obstruction) anti-Fms antibody treatment reduced macrophage accumulation (Le Meur et. al., J Leukocyte Biology, 2002, 72: 530-537). Accordingly, inhibition of Fms offers a target for therapeutic intervention in glomerulonephritis.

Insulin resistance and obesity are hallmark of type II diabetes and there is a strong correlation between insulin resistance and abdominal visceral fact accumulation (Bjorntrop, Diabetes Metab. Res. Rev., 1999, 15: 427-441). Current evidence indicates that macrophages accumulating in adipose tissue release TNF-a and other factors that cause adipocyte changes (hypertrophy, lipolysis, reduced insulin sensitivity) and also promote insulin resistance in surrounding tissues. Therefore, macrophage accumulation in type 2 diabetes is important for disease progression. Accordingly, inhibition of Fms has potential in preventing the development of insulin resistance and hyperglycemia.

Similarly, the observation that production of M-CSF, the major macrophage growth factor, is increased in tissues during inflammation points out a role for Fms in diseases, such as for example inflammatory diseases. More particularly, because elevated levels of M-CSF are found in the disease state, modulation of the activity of Fms can ameliorate disease associated with increased levels of M-CSF.

A Fms inhibitor may be useful in treating inflammatory and autoimmune indications, including, but not limited to, rheumatoid arthritis, osteoarthritis, psoriatic arthritis, psoriasis, dermatitis, ankylosing spondylitis, polymyositis, dermatomyositis, systemic sclerosis, juvenile idiopathic arthritis, polymyalgia rheumatica, Sjogren's disease, Langerhan's cell histiocytosis (LCH), Still's disease, inflammatory bowel syndrome, ulcerative colitis, Crohn's disease, systemic lupus erythematosis (SLE), transplant rejection, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, osteodystrophy, increased risk of fracture, Paget's disease, hypercalcemia, infection-mediated osteolysis (e.g. osteomyelitis), and peri-prosthetic or wear-debris-mediated osteolysis; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the central nervous system, including, but not limited to, multiple sclerosis, amyotrophic lateral sclerosis (ALS), myasthenia gravis, chronic demyelinating polyneuropathy, other demyelinating disorders, stroke, Alzheimer's disease and Parkinson's disease; inflammatory and chronic pain, including, but not limited to, bone pain; malignancies, including, but not limited to, multiple myeloma, acute myeloid leukemia (AML), chronic myeloid leukemia (CML), lung cancer, pancreatic cancer, prostate cancer, breast cancer, ovarian cancer, neuroblastoma, sarcoma, osteosarcoma, giant cell tumor of bone, giant cell tumor of tendon sheath (TGCT), pigmented villonodular synovitis (PVNS), tumor angiogenesis, melanoma, glioblastoma multiforme, glioma, other tumors of the central nervous system, metastasis of tumors to other tissues, and other chronic myeloproliferative diseases such as myelofibrosis; vasculitis, including but not limited to collagen vascular disease, polyarteritis nodosa, Behcet's disease, sarcoidosis, familiar Mediterranean fever, Churg-Strauss vasculitis, temporal arteritis, giant cell arteritis, Takayasu's arteritis; ophthalmic indications, including but not limited to uveitis, scleritis, retinitis, age related macular degeneration, choroidal neovascularization, diabetic retinopathy; inherited disorders, including but not limited to cherubism, neurofibromatosis; infectious disease indications, including but not limited to infections associated with human immunodeficiency virus, hepatitis B virus, hepatitis C virus, human granulocytic anaplasmosis; lysosomal storage disorders, including but not limited to Gaucher's disease, Fabry's disease, Niemann-Pick disease; gastrointestinal indications, including but not limited to liver cirrhosis; pulmonary indications, including but not limited to pulmonary fibrosis, acute lung injury (e.g. ventilator-induced, smoke- or toxin-induced); and surgical indications, including but not limited to (cardiopulmonary) bypass surgery, vascular surgery, and vascular grafts.

Kit: Target kinase Kit (i.e., feline Hardy-Zuckerman 4 sarcoma viral oncogene) is a 109.9 kDa transmembrane tyrosine kinase encoded by chromosome 4q12 (symbol: KIT). Receptor protein tyrosine kinases (RPTKs) regulate key signal transduction cascades that control cellular growth and proliferation. The Stem Cell Factor (SCF) receptor Kit is a type III transmembrane RPTK that includes five extracellular immunoglobulin (IG) domains, a single transmembrane domain, and a split cytoplasmic kinase domain separated by a kinase insert segment. Kit plays an important role in the development of melanocytes, mast, germ, and hematopoietic cells.

Stem Cell Factor (SCF) is a protein encoded by the S1 locus, and has also been called kit ligand (KL) and mast cell growth factor (MGF), based on the biological properties used to identify it (reviewed in Tsujimura, Pathol Int 1996, 46:933-938; Loveland, et al., J. Endocrinol 1997, 153:337-344; Vliagoftis, et al., Clin Immunol 1997, 100:435-440; Broudy, Blood 1997, 90:1345-1364; Pignon, Hermatol Cell Ther 1997, 39:114-116; and Lyman, et al., Blood 1998, 91:1101-1134.). Herein the abbreviation SCF refers to the ligand for Kit.

SCF is synthesized as a transmembrane protein with a molecular weight of 220 or 248 Dalton, depending on alternative splicing of the mRNA to encode exon 6. The larger protein can be proteolytically cleaved to form a soluble, glycosylated protein which noncovalently dimerizes. Both the soluble and membrane-bound forms of SCF can bind to and activate Kit. For example, in the skin, SCF is predominantly expressed by fibroblasts, keratinocytes, and endothelial cells, which modulate the activity of melanocytes and mast cells expressing Kit. In bone, marrow stromal cells express SCF and regulate hematopoiesis of Kit expressing stem cells. In the gastrointestinal tract, intestinal epithelial cells express SCF and affect the interstitial cells of Cajal and intraepithelial lymphocytes. In the testis, sertoli cells and granulosa cells express SCF which regulates spermatogenesis by interaction with Kit on germ cells.

According to OMIM, signaling from Kit is essential for primordial germ cell growth both in vivo and in vitro. Many downstream effectors of the KIT signaling pathway have been identified in other cell types, but how these molecules control primordial germ cell survival and proliferation are unknown. Determination of the KIT effectors acting in primordial germ cells has been hampered by the lack of effective methods to manipulate easily gene expression in these cells. De Miguel et al. (2002) overcame this problem by testing the efficacy of retroviral-mediated gene transfer for manipulating gene expression in mammalian germ cells. They found that primordial germ cells can successfully be infected with a variety of types of retroviruses. They used this method to demonstrate an important role of the AKT1 in regulating primordial germ cell growth (OMIM MIM Number: 164920: Apr. 17, 2006).

Aberrant expression and/or activation of Kit has been implicated in a variety of pathologic states. For example, evidence for a contribution of Kit to neoplastic pathology includes its association with leukemias and mast cell tumors, small cell lung cancer, testicular cancer, and some cancers of the gastrointestinal tract and central nervous system. In addition, Kit has been implicated in playing a role in carcinogenesis of the female genital tract sarcomas of neuroectodermal origin, and Schwann cell neoplasia associated with neurofibromatosis. It was found that mast cells are involved in modifying the tumor microenvironment and enhancing tumor growth (Yang et al., J Clin Invest. 2003, 112:1851-1861; Viskochil, J Clin Invest. 2003, 112:1791-1793). Kit inhibitors can also be used to target melanoma (Smalley et al., Histol Histopathol. 2009, May, 24(5):643-50), gastrointestinal stromal tumors (Demetri, G D, Semin Oncol. 2001, Oct., 28(5 Suppl 17):19-26), neurofibromatosis (Yang et al., Cell, 2008, Oct. 31, 135(3):437-48), and multiple sclerosis (Secor et al., J Exp Med. 2000, Mar. 6, 191(5):813-22).

A Kit inhibitor may be useful in treating malignancies, including, but not limited to, mast cell tumors, small cell lung cancer, non-small cell lung cancer (NSCLC), testicular cancer, pancreatic cancer, breast cancer, merkel cell carcinoma, carcinomas of the female genital tract, sarcomas of neuroectodermal origin, colorectal carcinoma, carcinoma in situ, gastrointestinal stromal tumors (GISTs), tumor angiogenesis, glioblastoma, astrocytoma, neuroblastoma, neurofibromatosis (including Schwann cell neoplasia associated with neurofibromatosis), acute myelocytic leukemia, acute lymphocytic leukemia, chronic myelogenous leukemia, mastocytosis, melanoma, and canine mast cell tumors; cardiovascular disease, including but not limited to atherosclerosis, cardiomyopathy, heart failure, pulmonary arterial hypertension, and pulmonary fibrosis; inflammatory and autoimmune indications, including, but not limited to, allergy, anaphylaxis, asthma, rheumatoid arthritis, allergic rhinitis, multiple sclerosis, inflammatory bowel syndrome, transplant rejection, hypereosinophilia, urticaria and dermatitis; gastrointestinal indications, including but not limited to gastroesophageal reflux disease (GERD), esophagitis, and gastrointestinal tract ulcers; ophthalmic indications, including but not limited to uveitis and retinitis; and neurologic indications, including but not limited to migraine.

Flt3: Target kinase Flt3 (i.e., Fms-like tyrosine kinase 3) is a transmembrane tyrosine kinase of 112.8 kDa encoded by chromosome 13q12 (symbol: FLT3). According to OMIM, Rosnet et al. (Genomics 1991, 9: 380-385) isolated a novel member of the class 3 receptors discussed above. They demonstrated that this gene of the tyrosine kinase family, called FLT3, has strong sequence similarities with other members of the group. Lymphohematopoietic stem cells serve as a reservoir for virtually all blood cells but make up only approximately 0.01% of human or murine marrow cells. The ability to isolate and expand this population has clinical applications in bone marrow transplantations for cancer and genetic diseases. Small et al. (Proc. Nat. Acad. Sci. 1994, 91: 459-463) cloned the cDNA for stem cell tyrosine kinase 1, the human homolog of murine Flk2/Flt3, from a CD34+ hematopoietic stem cell-enriched library. The cDNA encoded a protein of 993 amino acids with 85% identity and 92% similarity to the murine homolog. STK1, which is identical to FLT3, is a member of the type III receptor tyrosine kinase family that includes KIT, FMS, and platelet-derived growth factor receptor. STK1 expression in human blood and marrow is restricted to CD34+ cells, a population greatly enriched by stem/progenitor cells. Antisense oligonucleotides directed against STK1 sequences inhibited hematopoietic colony formation, most strongly in long-term bone marrow cultures. The data suggested that STK1 may function as a growth factor receptor on hematopoietic stem and/or progenitor cells (OMIM MIM Number: 136351: Mar. 3, 2005).

Levis et al., state that Internal tandem duplication (ITD) mutations of the receptor tyrosine kinase FLT3 have been found in 20% to 30% of patients with acute myeloid leukemia (AML). These mutations constitutively activate the receptor and appear to be associated with a poor prognosis. In their study, dose-response cytotoxic assays were performed with AG1295, a tyrosine kinase inhibitor active against FLT3, on primary blasts from patients with AML, and they found that AG1295 was specifically cytotoxic to AML blasts harboring FLT3/ITD mutations. They suggest that these mutations contribute to the leukemic process and that the FLT3 receptor represents a therapeutic target in AML (Levis et al., Blood 2001, 98:885-887). An Flt3 inhibitor may be useful in treating acute myeloid leukemia, myelodysplastic syndrome, acute lymphoblastic leukemia.

Kinase Activity Assays

A number of different assays for kinase activity can be utilized for assaying for active modulators and/or determining specificity of a modulator for a particular kinase or group of kinases. In addition to the assays mentioned in the Examples below, one of ordinary skill in the art can readily identify other assays that can be utilized and can modify an assay for a particular application. For example, numerous papers concerning kinases describe assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

Organic Synthetic Techniques

A wide array of organic synthetic techniques exist in the art to facilitate the construction of potential modulators. Many of these organic synthetic methods are described in detail in standard reference sources utilized by those skilled in the art. One example of such a reference is March, 1994, *Advanced Organic Chemistry; Reactions, Mechanisms and Structure*, New York, McGraw Hill. Thus, the techniques useful to synthesize a potential modulator of kinase function are readily available to those skilled in the art of organic chemical synthesis.

Alternative Compound Forms or Derivatives

Compounds contemplated herein are described with reference to both generic formulae and specific compounds. In addition, invention compounds may exist in a number of different forms or derivatives, all within the scope of the present invention. Alternative forms or derivatives, include, for example, (a) prodrugs, and active metabolites (b) tautomers, isomers (including stereoisomers and regioisomers), and racemic mixtures (c) pharmaceutically acceptable salts and (d) solid forms, including different crystal forms, polymorphic or amorphous solids, including hydrates and solvates thereof, and other forms.

(a) Prodrugs and Metabolites

In addition to the present formulae and compounds described herein, the invention also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. For example, some prodrugs are esters of the active compound; during metabolysis, the ester group is cleaved to yield the active drug. Esters include, for example, esters of a carboxylic acid group, or S-acyl or O-acyl derivatives of thiol, alcohol, or phenol groups. In this context, a common example is an alkyl ester of a carboxylic acid. Prodrugs may also include variants wherein an —NH group of the compound has undergone acylation, such as the 7-position of the pyrrolo[2,3-d]pyrimidine ring or the 1-position of the 1H-pyrrolo[2,3-b]pyridine ring of compounds as described herein, where cleavage of the acyl group provides the free —NH group of the active drug. Some prodrugs are activated enzymatically to yield the active compound, or a compound may undergo further chemical reaction to yield the active compound. Prodrugs may proceed from prodrug form to active form in a single step or may have one or more intermediate forms which may themselves have activity or may be inactive.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the following types:

Oxidative Reactions: Oxidative reactions are exemplified without limitation by reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive reactions: Reductive reactions are exemplified without limitation by reactions such as reduction of carbonyl functionalitites, reduction of alcohol functionalities and carbon-carbon double bonds, reduction of nitrogen-containing functional groups, and other reduction reactions.

Reactions without change in the oxidation state: Reactions without change in the state of oxidation are exemplified without limitation to reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 20040077595, application Ser. No. 10/656,838, incorporated herein by reference.) Such carrier prodrugs are often advantageous for orally administered drugs. In some instances, the transport moiety provides targeted delivery of the drug, for example the drug may be conjugated to an antibody or antibody fragment. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic processes in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity, and can be further metabolized to provide an active metabolite.

Metabolites of a compound may be identified using routine techniques known in the art, and their activities determined using tests such as those described herein. See, e.g., Bertolini et al., 1997, *J. Med. Chem.*, 40:2011-2016; Shan et al., 1997, J Pharm Sci 86(7):756-757; Bagshawe, 1995, *Drug Dev. Res.*, 34:220-230; Wermuth, supra.

(b) Tautomers, Stereoisomers, and Regioisomers

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present invention may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the present invention. Unless specified to the contrary, all such stereoisomeric forms are included within the formulae provided herein.

In some embodiments, a chiral compound of the present invention is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form, such optically pure form being prepared and/or isolated by methods known in the art (e.g. by recrystallization techniques, chiral synthetic techniques (including synthesis from optically pure starting materials), and chromatographic separation using a chiral column.

(c) Pharmaceutically Acceptable Salts

Unless specified to the contrary, specification of a compound herein includes pharmaceutically acceptable salts of such compound. Thus, compounds described herein can be in the form of pharmaceutically acceptable salts, or can be formulated as pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. A compound of the invention may possess a sufficiently acidic, a sufficiently basic, or both functional groups, and accordingly can react with any of a number of inorganic or organic bases, and inorganic and organic acids, to form a pharmaceutically acceptable salt.

Pharmaceutically acceptable salts include acid addition salts such as those containing chloride, bromide, iodide, hydrochloride, acetate, phenylacetate, acrylate, ascorbate, aspartate, benzoate, 2-phenoxybenzoate, 2-acetoxybenzoate, dinitrobenzoate, hydroxybenzoate, methoxybenzoate, methylbenzoate, bicarbonate, butyne-1,4 dioate, hexyne-1,6-dioate, caproate, caprylate, chlorobenzoate, cinnamate, citrate, decanoate, formate, fumarate, glycolate, gluconate, glucarate, glucuronate, glucose-6-phosphate, glutamate, heptanoate, hexanoate, isethionate, isobutyrate, gamma-hydroxybutyrate, phenylbutyrate, lactate, malate, maleate, hydroxymaleate, methylmaleate, malonate, mandelate, nicotinate, nitrate, isonicotinate, octanoate, oleate, oxalate, pamoate, phosphate, monohydrogenphosphate, dihydrogenphosphate, orthophosphate, metaphosphate, pyrophosphate, 2-phosphoglycerate, 3-phosphoglycerate, phthalate, propionate, phenylpropionate, propiolate, pyruvate, quinate, salicylate, 4-aminosalicylate, sebacate, stearate, suberate, succinate, sulfate, pyrosulfate, bisulfate, sulfite, bisulfite, sulfamate, sulfonate, benzenesulfonate (i.e. besylate), ethanesulfonate (i.e. esylate), ethane-1,2-disulfonate, 2-hydroxyethanesulfonate (i.e. isethionate), methanesulfonate (i.e. mesylate), naphthalene-1-sulfonate, naphthalene-2-sulfonate (i.e. napsylate), propanesulfonate, p-toluenesulfonate (i.e. tosylate), xylenesulfonates, cyclohexylsulfamate, tartrate, and trifluoroacetate. These pharmaceutically acceptable acid addition salts can be prepared using the appropriate corresponding acid.

When acidic functional groups, such as carboxylic acid or phenol are present, pharmaceutically acceptable salts also include basic addition salts such as those containing benzathine, chloroprocaine, choline, ethanolamine, diethanolamine, triethanolamine, t-butylamine, dicyclohexylamine, ethylenediamine, N,N'-dibenzylethylenediamine, meglumine, hydroxyethylpyrrolidine, piperidine, morpholine, piperazine, procaine, aluminum, calcium, copper, iron, lithium, magnesium, manganese, potassium, sodium, zinc, ammonium, and mono-, di-, or tri-alkylamines (e.g. diethylamine), or salts derived from amino acids such as L-histidine, L-glycine, L-lysine, and L-arginine. For example, see *Remington's Pharmaceutical Sciences*, 19$^{th}$ ed., Mack Publishing Co., Easton, Pa., Vol. 2, p. 1457, 1995. These pharmaceutically acceptable base addition salts can be prepared using the appropriate corresponding base.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent. If the particular compound is an acid, the desired pharmaceutically acceptable salt may be prepared by any suitable method, for example, treatment of the free acid with an appropriate inorganic or organic base.

(d) Other Compound Forms

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present invention and specified formulae. Whereas salts are formed by acid/base addition, i.e. a free base or free acid of the compound of interest forms an acid/base reaction with a corresponding addition base or addition acid, respectively, resulting in an ionic charge interaction, co-crystals are a new chemical species that is formed between neutral compounds, resulting in the compound and an additional molecular species in the same crystal structure.

In some instances, compounds of the invention are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In combining the compound of the invention with the acid or base, an amorphous complex is preferably formed rather than a crystalline material such as a typical salt or co-crystal. In some instances, the amorphous form of the complex is facilitated by additional processing, such as by spray-drying, mechanochemical methods such as roller compaction, or microwave irradiation of the parent compound mixed with the acid or base. Such methods may also include addition of ionic and/or non-ionic polymer systems, including, but not limited to, hydroxypropyl methyl cellulose acetate succinate (HPMCAS) and methacrylic acid copolymer (e.g. Eudragit® L100-55), that further stabilize the amorphous nature of the complex. Such amorphous complexes provide several advantages. For example, lowering of the melting temperature relative to the free base facilitates additional processing, such as hot melt extrusion, to further improve the biopharmaceutical properties of the compound. Also, the amorphous complex is readily friable, which provides improved compression for loading of the solid into capsule or tablet form.

Additionally, the formulae are intended to cover hydrated or solvated as well as unhydrated or unsolvated forms of the identified structures. For example, the indicated compounds include both hydrated and non-hydrated forms. Other examples of solvates include the structures in combination with a suitable solvent, such as isopropanol, ethanol, methanol, DMSO, ethyl acetate, acetic acid, or ethanolamine.

Formulations and Administration

The methods and compounds will typically be used in therapy for human subjects. However, they may also be used to treat similar or identical indications in other animal subjects. Compounds described herein can be administered by different routes, including injection (i.e. parenteral, including intravenous, intraperitoneal, subcutaneous, and intramuscular), oral, transdermal, transmucosal, rectal, or inhalant. Such dosage forms should allow the compound to reach target cells. Other factors are well known in the art, and include considerations such as toxicity and dosage forms that retard the compound or composition from exerting its effects. Techniques and formulations generally may be found in *Remington: The Science and Practice of Pharmacy*, 21$^{st}$ edition, Lippincott, Williams and Wilkins, Philadelphia, Pa., 2005 (hereby incorporated by reference herein).

In some embodiments, compositions will comprise pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFT), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesium trisilicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-.delta.-cyclodextrin), polysorbates (e.g. polysorbate 80), cetrimide, TPGS (d-alpha-tocopheryl polyethylene glycol 1000 succinate), magnesium lauryl sulfate, sodium lauryl sulfate, polyethylene glycol ethers, di-fatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses), HPC (hydroxypropyl cellulose), hydroxyethyl cellulose, and the like.

In some embodiments, oral administration may be used. Pharmaceutical preparations for oral use can be formulated into conventional oral dosage forms such as capsules, tablets, and liquid preparations such as syrups, elixirs, and concentrated drops. Compounds described herein may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone); oily excipients, including vegetable and animal oils, such as sunflower oil, olive oil, or codliver oil. The oral dosage formulations may also contain disintegrating agents, such as the cross-linked polyvinylpyrrolidone, agar, or alginic acid, or a salt thereof such as sodium alginate; a lubricant, such as talc or magnesium stearate; a plasticizer, such as glycerol or sorbitol; a sweetening such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations. Also provided are dragee cores with suitable coatings. For this purpose, concentrated sugar solutions may be used, which may optionally contain, for example, gum arabic, talc, polyvinylpyrrolidone, carbopol gel, polyethylene glycol, and/or titanium dioxide, lacquer solutions, and suitable organic solvents or solvent mixtures.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols.

In some embodiments, injection (parenteral administration) may be used, e.g., intramuscular, intravenous, intraperitoneal, and/or subcutaneous. Compounds described herein for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, the compounds may be formulated in solid form, including, for example, lyophilized forms, and redissolved or suspended prior to use.

In some embodiments, transmucosal, topical or transdermal administration may be used. In such formulations of compounds described herein, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of compounds described herein for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, compounds are administered as inhalants. Compounds described herein may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds described herein may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of various compounds to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose will be in the range of about 0.01 to 50 mg/kg, also about 0.1 to 20 mg/kg of the subject being treated. Multiple doses may be used.

The compounds described herein may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the invention or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound described herein, or at the same time as a compound described herein. Use in combination also includes use with a therapy or medical procedure that is administered once or infrequently, such as surgery, along with a compound described herein administered within a short time or longer time before or after the other therapy or procedure. In some embodiments, the present invention provides for delivery of a compound described herein and one or more other drug therapeutics delivered by a different route of administration or by the same route of administration. The use in combination for any route of administration includes delivery of a compound described herein and one or more other drug therapeutics delivered by the same route of administration together in any formulation, including formulations where the two compounds are chemically linked in such a way that they maintain their therapeutic activity when administered. In one aspect, the other drug therapy may be co-administered with a compound described

87 herein. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of a compound described herein and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

EXAMPLES

Examples related to the present invention are described below. In most cases, alternative techniques can be used. The examples are intended to be illustrative and are not limiting or restrictive to the scope of the invention. In some examples, the mass spectrometry result indicated for a compound may have more than one value due to the isotope distribution of an atom in the molecule, such as a compound having a bromo or chloro substituent. Compounds in the following examples are characterized by $^1$H and $^{13}$C NMR spectroscopy as well as mass spectrometry.

Unless specifically indicated otherwise, the Formula enumeration and R group enumeration used in the following examples is not related to such enumeration in other sections of this application. The reagents and solvents used in these examples can be readily substituted with appropriate alternatives as are known in the art and isolation of products is readily achieved by methods known in the art, including, but not limited to, extraction, crystallization, and chromatographic methods.

Ring numbering for the 1H-pyrrolo[2,3-b]pyridine in the following Examples is as follows:

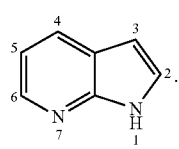

Ring numbering for the 7H-pyrrolo[2,3-d]pyrimidine in the following Examples is as follows:

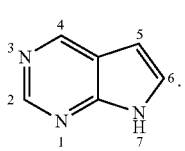

88

Example 1

Synthesis of 5-chloro-3-iodo-1H-pyrrolo[2,3-b]pyridine 2

5-Chloro-3-iodo-1H-pyrrolo[2,3-b]pyridine 2 was prepared in one step from 5-chloro-1H-pyrrolo[2,3-b]pyridine 1 as shown in Scheme 1.

Scheme 1

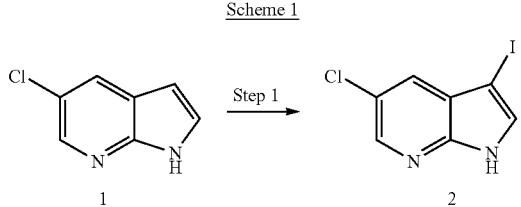 [SMILES: Clc1cnc2[nH]ccc2c1 ; Clc1cnc2[nH]cc(I)c2c1]

Step 1—Preparation of 5-chloro-3-iodo-1H-pyrrolo[2,3-b]pyridine (2)

To a solution of 5-chloro-1H-pyrrolo[2,3-b]pyridine (1, 15.00 g, 98.31 mmol) in 300 mL of dichloromethane under nitrogen, pyridine (7.951 mL, 98.31 mmol) and iodine monochloride (110 mL, 1.0 M in dichloromethane, 110 mmol) were added slowly over 20 minutes. The reaction was stirred at room temperature for 2 hours, then quenched with 100 mL of 1 M aqueous sodium thiosulfate pentahydrate. The layers were separated, solids collected from the aqueous layer by filtration and combined with the organic layer. The aqueous layer was extracted with ethyl acetate, organic layers were combined and washed with brine, then concentrated under vacuum. The resulting solid was washed with 20% ethyl acetate in hexane to provide the desired compound. 5-fluoro-3-iodo-1H-pyrrolo[2,3-b]pyridine is prepared similarly from 5-fluoro-1H-pyrrolo[2,3-b]pyridine.

Example 2

Synthesis of 5-chloro-3-iodo-1-triisopropylsilanyl-1H-pyrrolo[2,3-b]pyridine 4

5-Chloro-3-iodo-1-triisopropylsilanyl-1H-pyrrolo[2,3-b] pyridine 4 was prepared in one step from 5-chloro-3-iodo-1H-pyrrolo[2,3-b]pyridine 2 as shown in Scheme 2.

Scheme 2

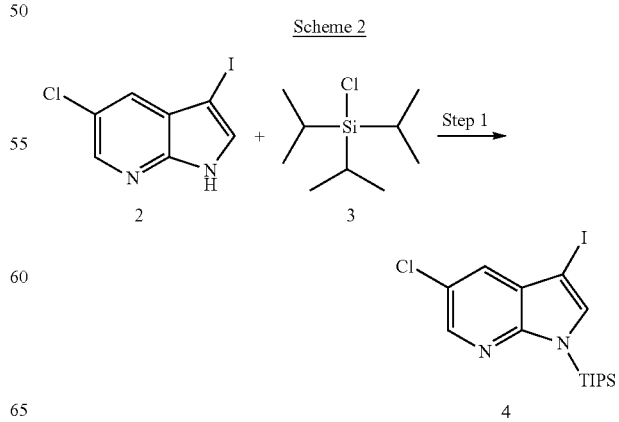

Step 1—Preparation of 5-chloro-3-iodo-1-triisopropylsilanyl-1H-pyrrolo[2,3-b]pyridine (4)

To 5-chloro-3-iodo-1H-pyrrolo[2,3-b]pyridine (2, 16.50 g, 59.25 mmol) in 250.0 mL of N,N-dimethylformamide, sodium hydride (3.10 g, 60% in mineral oil, 77.5 mmol) was added. The reaction was stirred at room temperature for 90 minutes, then triisopropysilyl chloride (3, 13.00 mL, 61.36 mmol) was added slowly. The reaction was stirred at room temperature overnight, then poured into water and extracted with ethyl acetate. The organic layer was dried over sodium sulfate, filtered and the filtrate concentrated under vacuum. The resulting material was purified by silica gel column chromatography, eluting with 20-100% ethyl acetate in hexane. Appropriate fractions were combined and concentrated under vacuum to provide the desired compound (4, 10.0 g). 5-fluoro-3-iodo-1-triisopropylsilanyl-1H-pyrrolo[2,3-b]pyridine is prepared similarly from 5-fluoro-3-iodo-1H-pyrrolo[2,3-b]pyridine.

3-Iodo-5-methoxy-1-triisopropylsilanyl-1H-pyrrolo[2,3-b]pyridine 5, 3-iodo-5-trifluoromethyl-1-triisopropylsilanyl-1H-pyrrolo[2,3-b]pyridine 6, and 3-iodo-4-methoxy-1-triisopropylsilanyl-1H-pyrrolo[2,3-b]pyridine 7

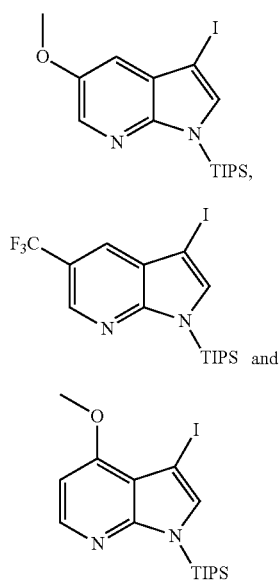

are prepared similarly to the protocol of Scheme 2, replacing 5-chloro-3-iodo-1H-pyrrolo[2,3-b]pyridine 2 with 3-iodo-5-methoxy-1H-pyrrolo[2,3-b]pyridine, 3-iodo-5-trifluoromethyl-1H-pyrrolo[2,3-b]pyridine, and 3-iodo-4-methoxy-1H-pyrrolo[2,3-b]pyridine, respectively. MS (ESI) [M+H]=431.2 (compound 5) and 469.4 (compound 6).

Example 3

Synthesis of 3-iodo-5-methyl-1-triisopropylsilanyl-1H-pyrrolo[2,3-b]pyridine 9

3-Iodo-5-methyl-1-triisopropylsilanyl-1H-pyrrolo[2,3-b]pyridine 9 was prepared in one step from 5-methyl-1-triisopropylsilanyl-1H-pyrrolo[2,3-b]pyridine 8 as shown in Scheme 3.

Scheme 3

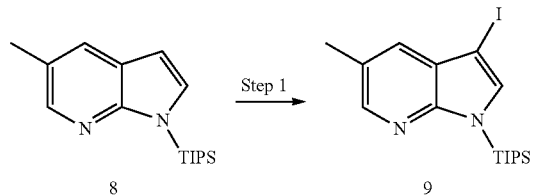

Step 1—Preparation of 3-iodo-5-methyl-1-triisopropylsilanyl-1H-pyrrolo[2,3-b]pyridine (9)

5-Methyl-1-triisopropylsilanyl-1H-pyrrolo[2,3-b]pyridine (8, 1.1 g, 3.8 mmol) and 10 mL of dichloromethane were combined in a round bottom flask and stirred for 10 minutes. A slurry of N-iodosuccinimide (1.0 g, 4.6 mmol) in 5 mL of dichloromethane was added and stirred at room temperature overnight. The reaction was quenched with sodium thiosulfate (20 mL, 1M in water) and the aqueous layer was extracted with ethyl acetate. The combined organic layer was washed with water and brine, dried with sodium sulfate, filtered and the filtrate concentrated under vacuum. The resulting material was purified by silica gel column chromatography, eluting with ethyl acetate and hexanes. Appropriate fractions were combined and concentrated under vacuum to provide the desired compound as a light yellow oil (9, 1.2 g, 75%). MS (ESI) [M+H$^+$]$^+$=415.08.

Example 4

Synthesis of 3-iodo-5-methyl-1H-pyrrolo[2,3-b]pyridine 10

3-Iodo-5-methyl-1H-pyrrolo[2,3-b]pyridine 10 was prepared in one step from 5-methyl-1-triisopropylsilanyl-1H-pyrrolo[2,3-b]pyridine 8 as shown in Scheme 4.

Scheme 4

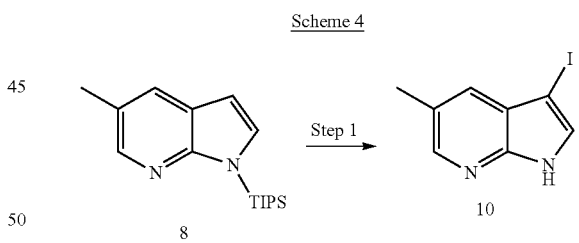

Step 1—Preparation of 3-iodo-5-methyl-1H-pyrrolo[2,3-b]pyridine (10)

To a solution of 5-methyl-1-triisopropylsilanyl-1H-pyrrolo[2,3-b]pyridine (8, 1 g, 2.0 mmol) in 10 mL of tetrahydrofuran, iodine (0.43 g, 1.7 mmol) in 5 mL of tetrahydrofuran was added. The reaction was stirred at room temperature overnight, then quenched with 20 mL of 1M aqueous sodium thiosulfate and extracted with ethyl acetate. The organic layers were combined and washed with water, brine, dried over sodium sulfate, filtered and the filtrate concentrated under vacuum. The resulting material was purified by silica gel column chromatography, eluting with ethyl acetate and hexanes. Appropriate fractions were combined and concentrated under vacuum to provide the desired compound as a white solid (10, 20 mg). MS (ESI) [M+H⁺]⁺=258.70.

Example 5

Synthesis of 1-benzenesulfonyl-5-chloro-3-iodo-1H-pyrrolo[2,3-b]pyridine 12

1-Benzenesulfonyl-5-chloro-3-iodo-1H-pyrrolo[2,3-b]pyridine 12 was prepared in 1 step from 5-chloro-3-iodo-1H-pyrrolo[2,3-b]pyridine 2 and benzenesulfonyl chloride 11 as shown in Scheme 5.

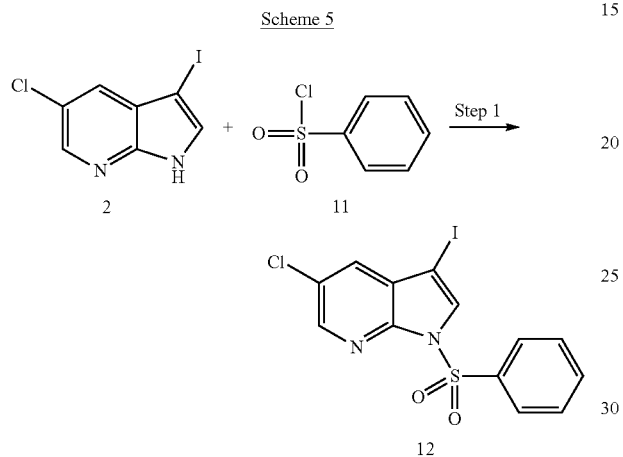

Step 1—Preparation of 1-benzenesulfonyl-5-chloro-3-iodo-1H-pyrrolo[2,3-b]pyridine (12)

To a solution of 5-chloro-3-iodo-1H-pyrrolo[2,3-b]pyridine (2, 5.00 g, 18.0 mmol) in 80.0 mL of N,N-dimethylformamide, sodium hydride (1.1 g, 60% in mineral oil, 27.0 mmol) was added slowly. A solution of benzenesulfonyl chloride (11, 2.40 mL, 18.8 mmol) in 10.0 mL of N,N-dimethylformamide was added dropwise at 0° C. The reaction mixture was stirred at room temperature for 15 hours, then poured into ice water and extracted with ethyl acetate. The organic layer was washed with brine, dried over magnesium sulfate, filtered and the filtrate concentrated under vacuum. The resulting solid was washed with 5% ethyl acetate in hexane, isolated by filtration, and dried to provide the desired compound (12, 5.9 g). ¹H NMR was consistent with the compound structure. 1-Benzenesulfonyl-3-iodo-5-methyl-1H-pyrrolo[2,3-b]pyridine 13

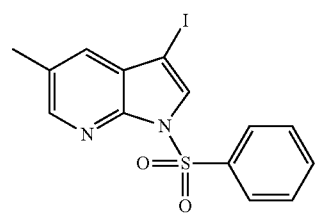

was prepared similarly to this protocol, replacing 5-chloro-3-iodo-1H-pyrrolo[2,3-b]pyridine 2 with 3-iodo-5-methyl-1H-pyrrolo[2,3-b]pyridine 10. 1-Benzenesulfonyl-5-fluoro-3-iodo-1H-pyrrolo[2,3-b]pyridine is prepared similarly from 5-fluoro-3-iodo-1H-pyrrolo[2,3-b]pyridine.

Example 6

Synthesis of 1-benzenesulfonyl-3-iodo-5-methoxy-1H-pyrrolo[2,3-b]pyridine 16

1-Benzenesulfonyl-3-iodo-5-methoxy-1H-pyrrolo[2,3-b]pyridine 16 was prepared in two steps from 5-methoxy-1H-pyrrolo[2,3-b]pyridine 14 as shown in Scheme 6.

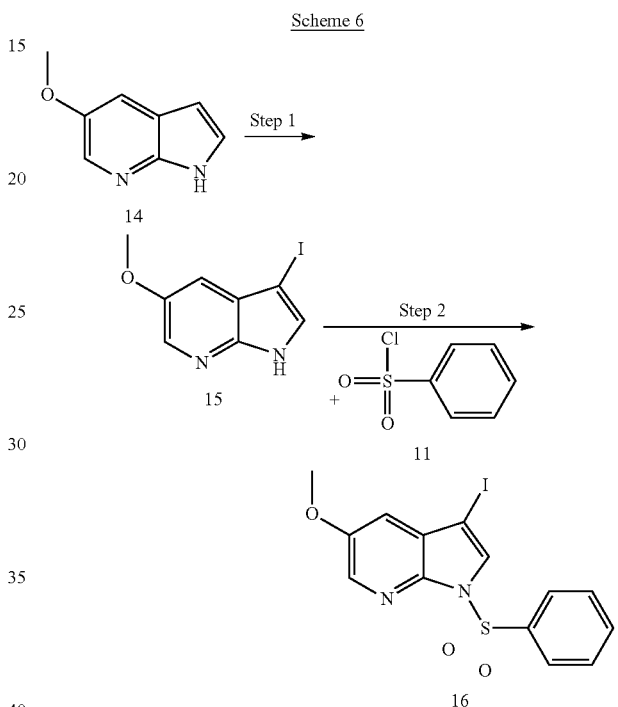

Step 1—Preparation of 3-iodo-5-methoxy-1H-pyrrolo[2,3-b]pyridine (15)

To a solution of 5-methoxy-1H-pyrrolo[2,3-b]pyridine (14, 300 mg, 2.0 mmol) in 30 mL of dichloromethane under nitrogen, iodine monochloride (3 mL, 1.0 M in dichloromethane, 3.0 mmol) was added at −40° C. The reaction was stirred to room temperature, then quenched with 10 mL of 1 M aqueous sodium thiosulfate pentahydrate. The layers were separated and the aqueous layer was extracted with ethyl acetate. The organic layers were combined and washed with water, brine, then dried over sodium sulfate, decolored with activated carbon, filtered and the filtrate concentrated under vacuum. The resulting solid was washed with 20% ethyl acetate in hexane to provide the desired compound (15, 371 mg). MS (ESI) [M+H⁺]⁺=275.03.

Step 2—Preparation of 1-benzenesulfonyl-3-iodo-5-methoxy-1H-pyrrolo[2,3-b]pyridine (16)

To a solution of 3-iodo-5-methoxy-1H-pyrrolo[2,3-b]pyridine (15, 4.30 g, 15.7 mmol) in 53.6 mL of N,N-dimethylformamide under nitrogen, sodium hydride (0.690 g, 60% in mineral oil, 17.2 mmol) was added. After 10 minutes, benzenesulfonyl chloride (11, 2.20 mL, 17.2 mmol) was added and the reaction was cooled in a water bath. The reaction was poured into water and extracted with ethyl acetate. The organic layer was dried over sodium sulfate, filtered and the filtrate purified by silica gel column chromatography, eluting with 30-100% ethyl acetate in hexane. Appropriate fractions were combined and concentrated under vacuum to provide the desired compound (16, 4.60 g).

Example 7

Synthesis of 5-iodo-4-methyl-7-triisopropylsilanyl-7H-pyrrolo[2,3-d]pyrimidine 20

5-Iodo-4-methyl-7-triisopropylsilanyl-7H-pyrrolo[2,3-d]pyrimidine 20 was prepared in two steps from 4-chloro-7H-pyrrolo[2,3-d]pyrimidine 17 as shown in Scheme 7.

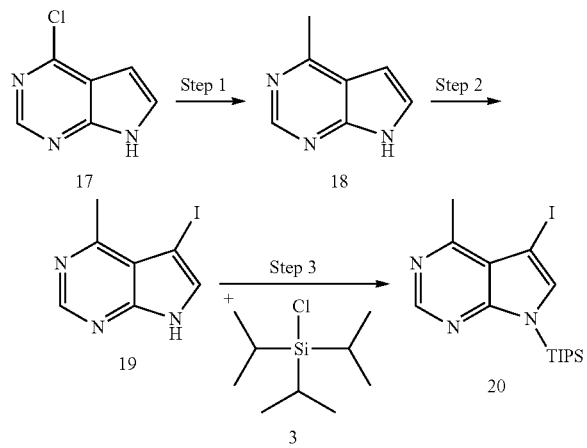

Step 1—Preparation of 4-methyl-7H-pyrrolo[2,3-d]pyrimidine (18)

To 4-chloro-7H-pyrrolo[2,3-d]pyrimidine (17, 5.03 g, 32.8 mmol) in 100 mL of toluene, [1,1'-bis(diphenylphosphino)ferrocene]dichloropalladium(II) 1:1 complex with dichloromethane (0.627 g, 0.328 mmol) was added under nitrogen. After stirring for 10 minutes, methylmagnesium bromide (62.9 mL, 3.00 M in ether, 189 mmol) was added slowly. The reaction was heated at 55° C. overnight, then cooled to −70 to −80° C. and quenched by adding ammonium chloride dropwise. Then 1N hydrochloric acid was added and the pH was adjusted to 7-8 with addition of saturated sodium bicarbonate. This was extracted 3× with ethyl acetate. The combined organic layer was washed with saturated ammonium chloride and brine, then dried with magnesium sulfate, filtered and the filtrate concentrated under vacuum. The resulting material was purified by silica gel column chromatography, eluting with ethyl acetate and dichloromethane, then methanol and dichloromethane. Appropriate fractions were combined and concentrated under vacuum to provide the desired compound as a tan solid (18). MS (ESI) [M+H']⁺=134.

Step 2—Preparation of 5-iodo-4-methyl-7H-pyrrolo[2,3-d]pyrimidine (19)

To 4-methyl-7H-pyrrolo[2,3-d]pyrimidine (18, 0.634 g, 4.76 mmol) in 50 mL of dichloromethane, N-iodosuccinimide (1.3 g, 5.7 mmol) was added and the reaction stirred at room temperature for 45 minutes. The reaction was concentrated under vacuum, then ethyl acetate was added and washed with 1 N aqueous sodium thiosulfate. The organic layer was dried over sodium sulfate, filtered and the filtrate concentrated under vacuum. The resulting material was purified by silica gel column chromatography, eluting with 20-100% ethyl acetate in hexane. Appropriate fractions were combined and concentrated under vacuum to provide the desired compound (19, 0.94 g). MS (ESI) [M+H⁺]⁺=260.26.

Step 3—Preparation of 5-iodo-4-methyl-7-triisopropylsilanyl-7H-pyrrolo[2,3-d]pyrimidine (20)

To 5-iodo-4-methyl-7H-pyrrolo[2,3-d]pyrimidine (19, 323.6 mg, 1.25 mmol) in 8 mL of tetrahydrofuran under nitrogen, sodium hydride (57.41 mg, 60% in mineral oil, 1.44 mmol) was added. The reaction was stirred at room temperature for 10 minutes, then triisopropysilyl chloride (3, 0.304 mL, 1.44 mmol) was added. The reaction was stirred at room temperature for 2 hours, then poured into water and extracted with ethyl acetate. The organic layer was dried over sodium sulfate, filtered and the filtrate concentrated under vacuum to provide the desired compound.

Example 8

Synthesis of 5-cyclopropyl-1H-pyrrolo[2,3-b]pyridine 23

5-Cyclopropyl-1H-pyrrolo[2,3-b]pyridine 23 was prepared in one step from 5-iodo-1H-pyrrolo[2,3-b]pyridine 21 as shown in Scheme 8.

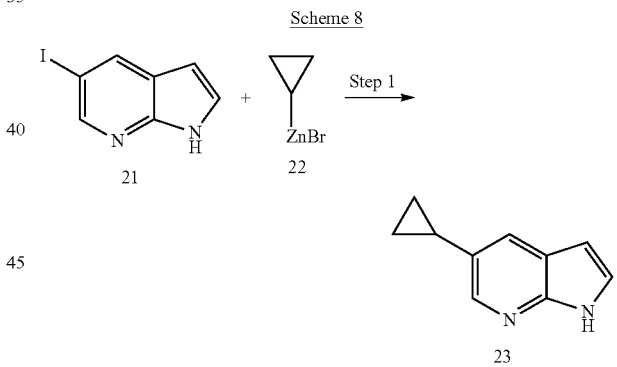

Step 1—Preparation of 5-cyclopropyl-1H-pyrrolo[2,3-b]pyridine (23)

5-Iodo-1H-pyrrolo[2,3-b]pyridine (21, 0.343 g, 1.40 mmol), cyclopropylzinc bromide (22, 12.6 mL, 0.500 M in tetrahydrofuran, 6.32 mmol) and [1,3-bis(diphenylphosphino)propane]-nickel(II) chloride (76.2 mg, 0.14 mmol) and 5.37 mL of 1,4-dioxane were combined in a reaction vessel. The reaction was heated at 100° C. overnight, then methanol was added and the reaction was concentrated under vacuum. Ethyl acetate and water were added to the residue, then filtered through a bed of celite and the celite bed washed with ethyl acetate. The filtrate was separated and the aqueous layer extracted with ethyl acetate. The organic layers were combined and washed with brine, dried over sodium sulfate, filtered and the filtrate concentrated under vacuum. The resulting material was purified by silica gel column chromatography, eluting with ethyl acetate and hexane. Appropriate fraction were combined and concentrated under vacuum to provide the desired compound. MS (ESI) [M+H$^+$]$^+$=159.0.

Example 9

Synthesis of intermediate 5-(1-benzenesulfonyl-5-chloro-1H-pyrrolo[2,3-b]pyridin-3-ylmethyl)-4-chloro-thiazol-2-ylamine 29

5-(1-Benzenesulfonyl-5-chloro-1H-pyrrolo[2,3-b]pyridin-3-ylmethyl)-4-chloro-thiazol-2-ylamine 29 was synthesized in 4 steps from 2-amino-4-chloro-thiazole-5-carbaldehyde 24 as shown in Scheme 9.

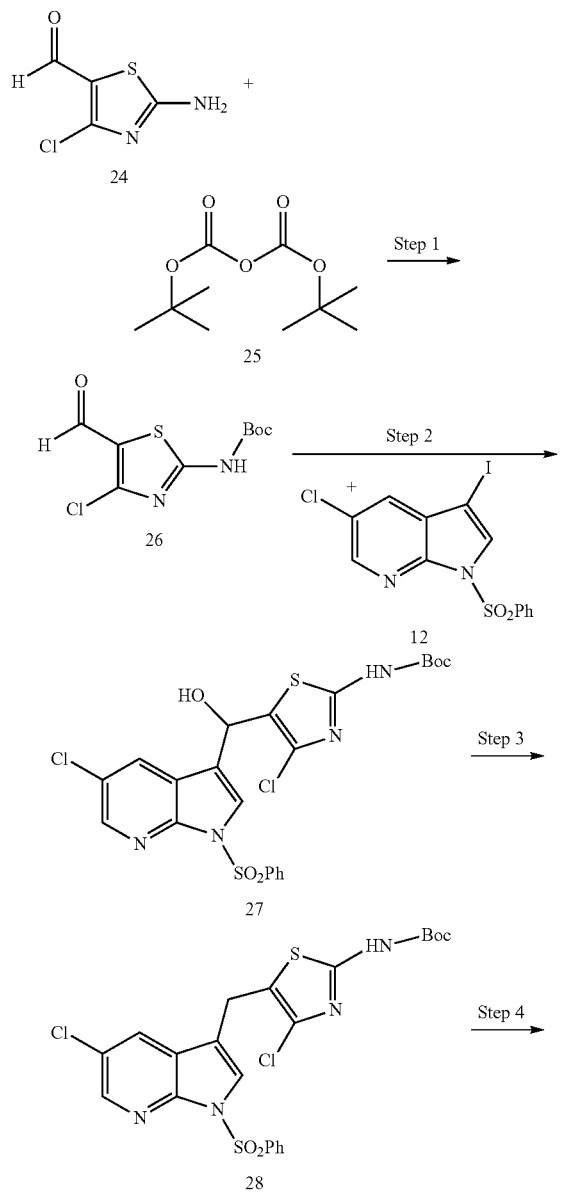

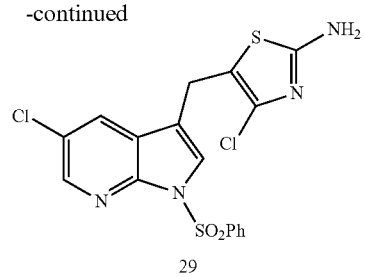

Step 1—Synthesis of (4-chloro-5-formyl-thiazol-2-yl)-carbamic acid tert-butyl ester (26)

To 2-amino-4-chloro-thiazole-5-carbaldehyde (24, 5.00 g, 0.0308 mol) in 122 mL of tetrahydrofuran, di-tert-butyldicarbonate (25, 7.38 g, 0.0338 mol) and 4-dimethylaminopyridine (0.35 g, 0.0029 mol) were added. The reaction was stirred at 58° C. for 2 hours, then concentrated under vacuum and purified with silica gel column chromatography eluting with 20-80% ethyl acetate in hexane. Appropriate fractions were combined and concentrated under vacuum to provide the desired compound as a yellow solid (26, 7.0 g, 87%).

Step 2—Synthesis of 5-[(1-benzenesulfonyl-5-chloro-1H-pyrrolo[2,3-b]pyridin-3-yl)-hydroxy-methyl]-4-chloro-thiazol-2-yl-carbamic acid tert-butyl ester (27)

To a solution of 1-benzenesulfonyl-5-chloro-3-iodo-1H-pyrrolo[2,3-b]pyridine (12, 4.40 g, 10.5 mmol) in 30.0 mL of tetrahydrofuran at −45° C. under nitrogen, a solution of isopropylmagnesium chloride (5.4 mL, 2.0 M in tetrahydrofuran) was added slowly over 10 minutes. The reaction was allowed to warm to −25° C. over 30 minutes, then cooled to −65° C., followed by adding the cold deprotonated (4-chloro-5-formyl-thiazol-2-yl)-carbamic acid tert-butyl ester, which was prepared in situ by adding isopropylmagnesium chloride (5.0 mL, 2.0 M in tetrahydrofuran) to (4-chloro-5-formyl-thiazol-2-yl)-carbamic acid tert-butyl ester (26, 2.51 g, 9.55 mmol) in 23.0 mL of tetrahydrofuran at −78° C. under nitrogen. The reaction was allowed to warm to room temperature over 2 hours, then poured into aqueous ammonium chloride, and extracted with ethyl acetate. The organic layer was dried over anhydrous sodium sulfate, filtered, and the filtrate concentrated under vacuum. The resulting material was purified by silica gel column chromatography eluting with 25-100% ethyl acetate in hexane. Appropriate fractions were combined and concentrated under vacuum to provide the desired compound (27, 3.70 g, 60.3%). MS (ESI) [M+H$^+$]$^+$=554.2.

Step 3—Synthesis of [5-(1-benzenesulfonyl-5-chloro-1H-pyrrolo[2,3-b]pyridin-3-ylmethyl)-4-chloro-thiazol-2-yl]-carbamic acid tert-butyl ester (28)

To 5-[(1-benzenesulfonyl-5-chloro-1H-pyrrolo[2,3-b]pyridin-3-yl)-hydroxy-methyl]-4-chloro-thiazol-2-yl-carbamic acid tert-butyl ester (27, 0.200 g, 0.32 mmol) in 15.0 mL of dichloromethane, triethylsilane (0.600 mL, 376 mmol) and trifluoroacetic acid (0.300 mL, 3.89 mmol) were added. The reaction was stirred at room temperature for 3 hours, then concentrated, poured into aqueous potassium carbonate, and extracted with ethyl acetate. The organic layer was dried over anhydrous sodium sulfate, filtered, and the filtrate concentrated under vacuum. The resulting material was purified by silica gel column chromatography eluting with 25-100% ethyl acetate in hexane to give the desired compound (28, 0.155 g, 88.7%). MS (ESI) [M+H$^+$]$^+$=538.9.

Step 4—Synthesis of 5-(1-Benzenesulfonyl-5-chloro-1H-pyrrolo[2,3-b]pyridin-3-ylmethyl)-4-chloro-thiazol-2-ylamine (29)

To [5-(1-benzenesulfonyl-5-chloro-1H-pyrrolo[2,3-b]pyridin-3-ylmethyl)-4-chloro-thiazol-2-yl]-carbamic acid tert-butyl ester (28, 4.30 g, 7.97 mmol) in 70.0 mL of dichloromethane, a solution of hydrogen chloride (42.0 mL, 4.00 M in 1,4-dioxane) was added. The reaction was stirred at room temperature for 2 days, then concentrated, and triturated with ethyl ether and ethyl acetate to provide the desired compound (29, 2.60 g, 74.2%). MS (ESI) [M+H$^+$]$^+$=439.0.

5-(1-Benzenesulfonyl-1H-pyrrolo[2,3-b]pyridin-3-ylmethyl)-4-chloro-thiazol-2-ylamine 30

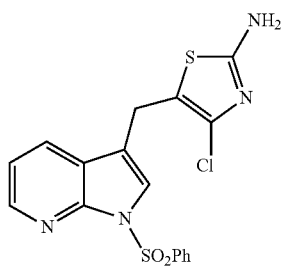

was prepared following the protocol of Scheme 9, substituting 1-benzenesulfonyl-5-chloro-3-iodo-1H-pyrrolo[2,3-b]pyridine 12 with 1-benzenesulfonyl-3-iodo-1H-pyrrolo[2,3-b]pyridine in Step 2. MS (ESI) [M+H$^+$]$^+$=404.4.

Example 10

Synthesis of Aldehyde Reagents

Aldehyde reagents that are used in making compounds are prepared according to the following protocols.

5-Fluoro-1-methyl-2-oxo-1,2-dihydro-pyridine-3-carbaldehyde 33 was prepared in two steps from 5-fluoro-3-iodo-pyridin-2-ol 31 as shown in Scheme 10a.

Scheme 10a

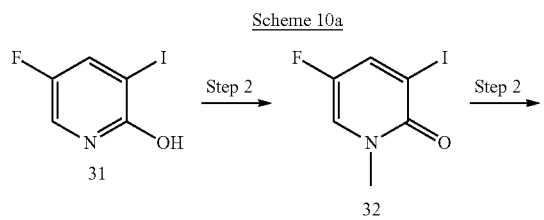

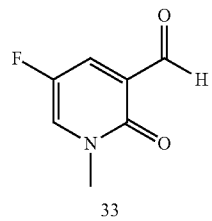

Step 1—Preparation of 5-fluoro-3-iodo-1-methyl-1H-pyridin-2-one (32)

To 5-fluoro-3-iodo-pyridin-2-ol (31, 200 g, 838 mmol) in 3000 mL of acetone was cooled in an ice water bath. Cesium carbonate (354 g, 1088 mmol) was added, then iodomethane (58.1 mL, 929 mmol) was added dropwise over 30 minutes. The reaction was stirred overnight at room temperature. The reaction was concentrated under vacuum and the resulting material partitioned between ethyl acetate and water. The aqueous layer was isolated and adjusted to pH 3-4 with 3 N hydrochloric acid, then extracted with ethyl acetate. The combined organic layers were concentrated under vacuum to provide the desired compound as an off white solid. (32, 150 g, 593 mmol, 70.8%).

Step 2—Preparation of 5-fluoro-1-methyl-2-oxo-1,2-dihydro-pyridine-3-carbaldehyde (33)

5-Fluoro-3-iodo-1-methyl-1H-pyridin-2-one (32, 120.5 g, 476 mmol) was dissolved in 2381 mL of tetrahydrofuran and cooled to −40° C. in a dry ice acetone bath. Isopropylmagnesium chloride (310 mL, 619 mmol) was added dropwise and the mixture was stirred for 30 minutes. Then 92 mL of N,N-dimethylformamide was added and the mixture was allowed to warm to room temperature and stirred overnight. The reaction was quenched by adding 200 mL of 10% aqueous hydrochloric acid, then concentrated under vacuum. The resulting material was purified by silica gel column chromatography, eluting with 100% ethyl acetate. Appropriate fractions were combined and concentrated under vacuum to provide the desired compound as a yellow solid (33, 35 g, 226 mmol, 47.4%).

5-Fluoro-2-methoxy-pyridine-3-carbaldehyde 37 was prepared in three steps from 3-bromo-5-fluoro-2-methoxy-pyridine 34 as shown in Scheme 10b.

Scheme 10b

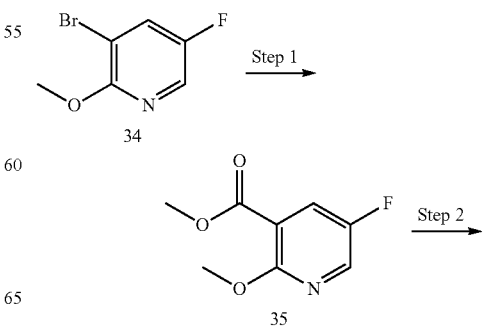

-continued

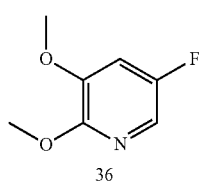 Step 3 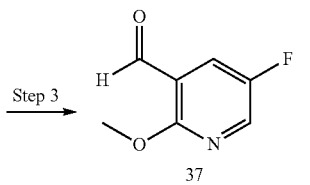

Step 1—Preparation of 5-fluoro-2-methoxy-nicotinic acid methyl ester (35)

In a 2 L Parr bomb, 3-bromo-5-fluoro-2-methoxy-pyridine (34, 14 g, 68.0 mmol), triethylamine (19.10 mL, 136 mmol) and [1,1'-bis(diphenylposphino)ferrocene]-dichloropalladium(II) (1.443 g, 1.767 mmol) were combined with 300 mL of methanol and heated at 100° C. under 100 psi of carbon monoxide overnight. The reaction was concentrated under vacuum, the residue dissolved in dichloromethane, and passed through a plug of silica, eluting with ethyl acetate to provide the desired compound as a white solid (35, 10 g, 54.0 mmol, 79%).

Step 2—Preparation of (5-fluoro-2-methoxy-pyridin-3-yl)-methanol (36)

To 5-fluoro-2-methoxy-nicotinic acid methyl ester (35, 10 g, 54.0 mmol) in 200 mL of tetrahydrofuran, lithium aluminum hydride (81 mL, 1 M in tetrahydrofuran, 81 mmol) was added dropwise at −78° C. and stirred for several hours. The reaction was quenched with dropwise addition of 3 mL water, 3 mL of 15% aqueous sodium hydroxide, and 10 mL of water sequentially, then 200 mL of methyl t-butyl ether was added. Solids were filtered out and the filtrate concentrated under vacuum to provide the desired compound as a white solid (36, 8 g, 50.9 mmol, 94%).

Step 3—Preparation of 5-fluoro-2-methoxy-pyridine-3-carbaldehyde (37)

To (5-fluoro-2-methoxy-pyridin-3-yl)-methanol (36, 8 g, 50.9 mmol) in 300 mL of ethyl acetate, manganese(IV) oxide (39.8 g, 458 mmol) was added and the mixture stirred at room temperature overnight. The reaction mixture was filtered through celite, and the celite bed rinsed with ethyl acetate. The filtrate was concentrated under vacuum, then passed through a plug of silica, eluting with 50% ethyl acetate in heptane to provide the desired compound as a light yellow solid (37, 4.5 g, 29.0 mmol, 57.0% yield).

(2-Fluoro-benzyl)-(5-formyl-pyridin-2-yl)-carbamic acid tert-butyl ester 42 was prepared in three steps from 5-bromo-pyridin-2-ylamine 38 and 2-fluoro-benzaldehyde 39 as shown in Scheme 10c.

Scheme 10c

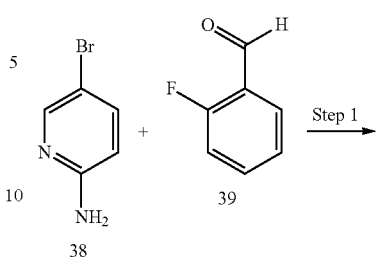

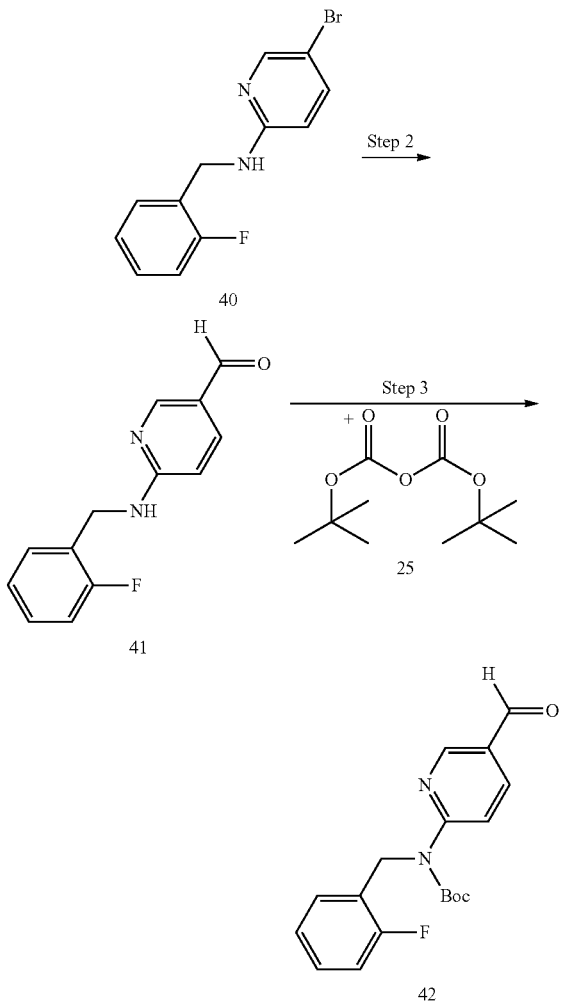

Step 1—Preparation of (5-bromo-pyridin-2-yl)-(2-fluoro-benzyl)-amine (40)

In a round bottom flask, 5-bromo-pyridin-2-ylamine (38, 4.05 g g, 23.4 mmol) was combined with 70.0 mL of acetonitrile, 2-fluoro-benzaldehyde (39, 2.45 mL, 23.4 mmol), triethylsilane (20.0 mL, 125 mmol) and trifluoroacetic acid (10.0 mL, 130 mmol). The reaction was stirred at 80° C. for 3 hours. The reaction was poured into aqueous potassium carbonate and extracted with ethyl acetate. The organic layer was dried over sodium sulfate, filtered and the filtrate concentrated under vacuum. The resulting material was purified by silica gel column chromatography eluting with 20-60% ethyl acetate in hexane. Appropriate fractions were combined and the solvents removed under vacuum to provide the desired compound (40, 5.0 g).

Step 2—Preparation of 6-(2-fluoro-benzylamino)-pyridine-3-carbaldehyde (41)

In a round bottom flask, (5-bromo-pyridin-2-yl)-(2-fluoro-benzyl)-amine (40, 3.90 g, 13.9 mmol) was combined with 60.0 mL of tetrahydrofuran at −78° C. under nitrogen and tert-butyllithium (5.57 mL, 2.50 M in hexane) was added over 5 minutes. After 30 minutes additional tert-butyllithium (17.1 mL, 1.7 M in hexane) was added over 5 minutes. After 25 minutes, N,N-dimethylformamide (2.6 mL, 34 mmol) was added and the mixture was stirred for 70 minutes at −78° C., then allowed to warm up to room temperature for 1 hour. The reaction was poured into aqueous ammonium chloride and extracted with ethyl acetate. The organic portion was dried with sodium sulfate, filtered and filtrate concentrated under vacuum to provide the desired compound (41, 3.0 g), which was used in the next step without further purification.

Step 3—Preparation of (2-fluoro-benzyl)-(5-formyl-pyridin-2-yl)-carbamic acid tert-butyl ester (42)

To 6-(2-fluoro-benzylamino)-pyridine-3-carbaldehyde (41, 3.00 g, 13.0 mmol) in 57.2 mL of tetrahydrofuran, di-tert-butyldicarbonate (25, 4.26 g, 19.5 mmol) and 4-dimethylaminopyridine (0.16 g, 1.3 mmol) and triethylamine (3.6 mL, 26 mmol) were added. The reaction was stirred at room temperature overnight, then poured into water and extracted with ethyl acetate. The organic portion was dried with sodium sulfate, filtered and filtrate concentrated under vacuum. The resulting material was purified by silica gel column chromatography eluting with 20-100% ethyl acetate in hexane. Appropriate fractions were combined and the solvents removed under vacuum to give the desired compound (41, 3.50 g).

Additional aldehydes are prepared similarly to the protocol of Scheme 10c, as shown in the following table, where Step 1, Step 2 and Step 3 reactants are provided in columns 1, 2, and 3, respectively, with the resulting Boc protected aldehyde provided in column 4. Reaction conditions are similar to those described for Scheme 10c, and may vary slightly for each step, for example, any of the solvents, reagents, reaction times, temperatures, work up conditions, or other reaction parameters may be varied employing alternate solvents, reagents, reaction times, temperatures, work up conditions, and the like, as are readily available to one skilled in the art. For example, without limitation, for step 2, the first addition of t-butyllitium is replaced with n-butyllithium in pentane or by isopropylmagnesium chloride in tetrahydrofuran; for step 3, triethylamine is replaced with N,N-diisopropylethylamine, or dichloromethane is used as solvent. Compounds in the following table were characterized by $^1H$ and $^{13}C$ NMR spectroscopy as well as mass spectrometry.

Step 1 Step 2 Step 3 Final aldehyde

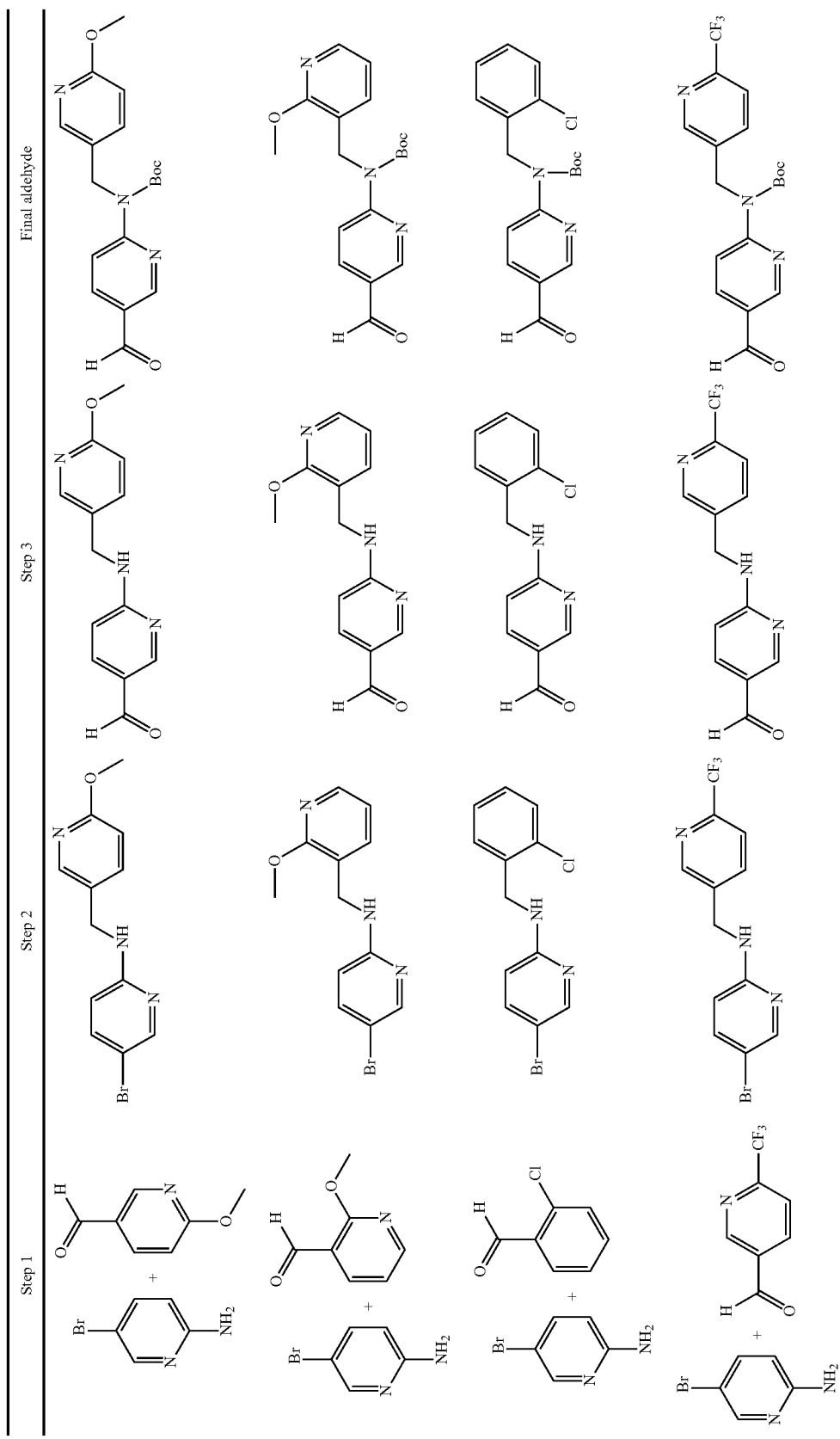

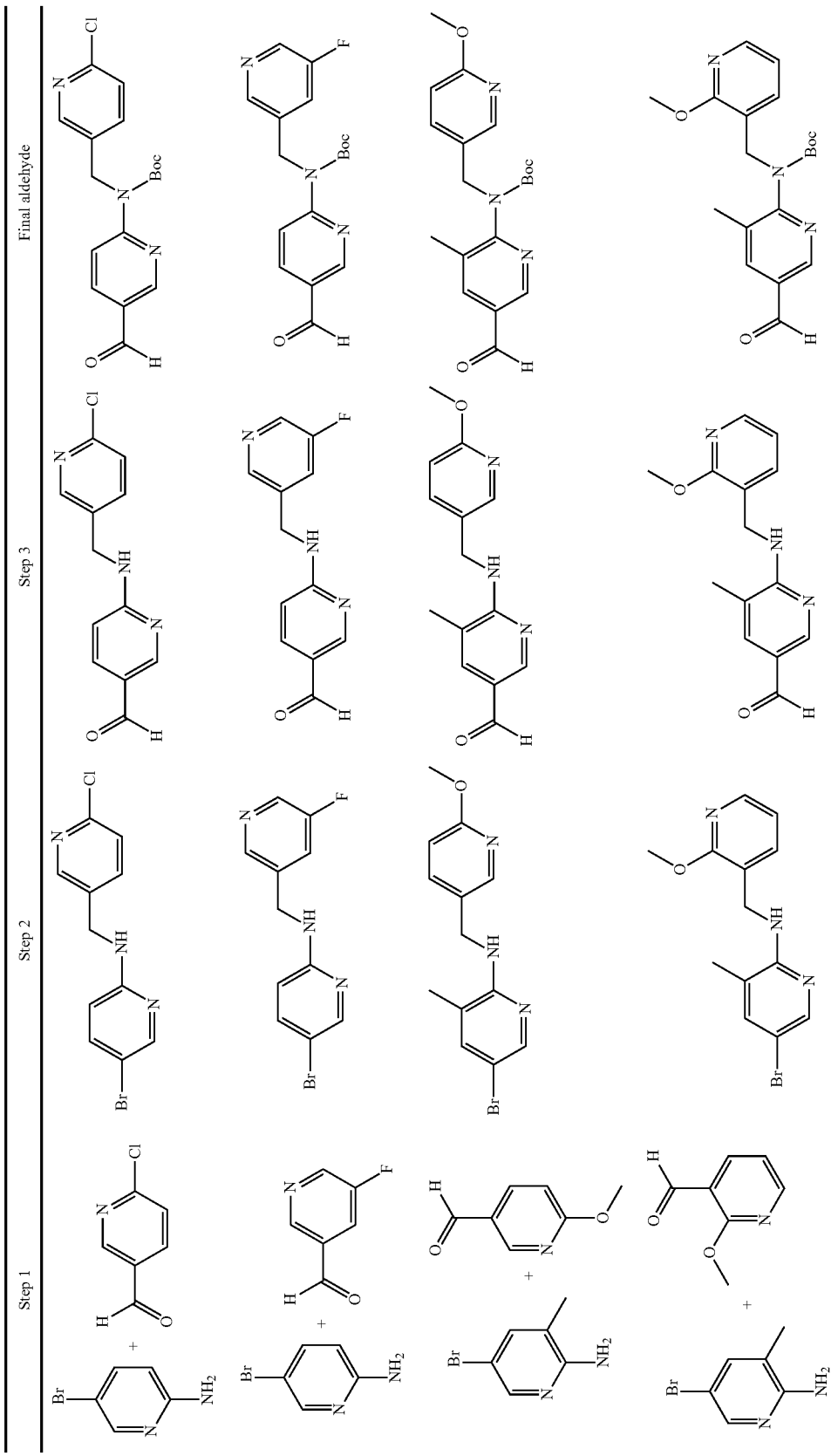

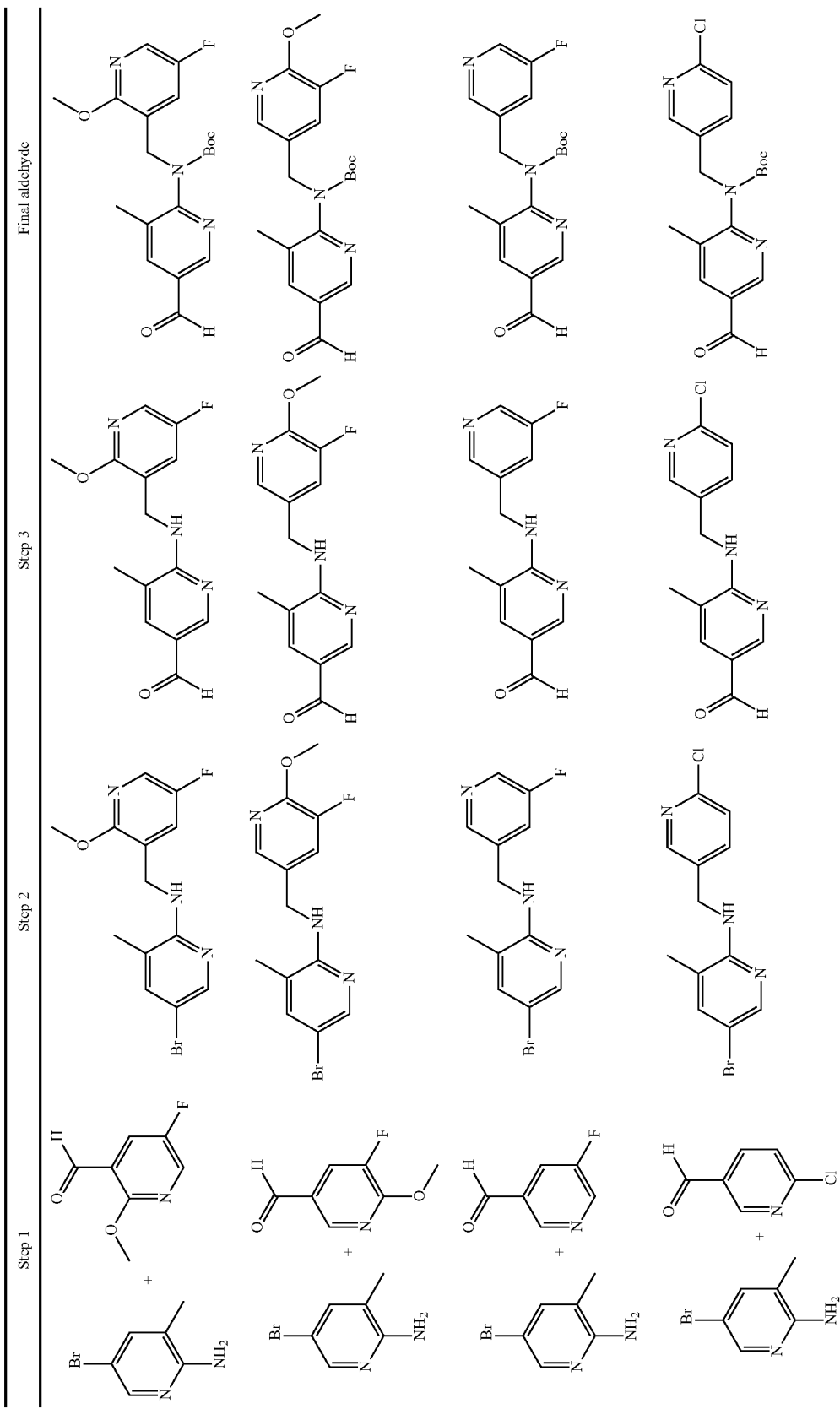

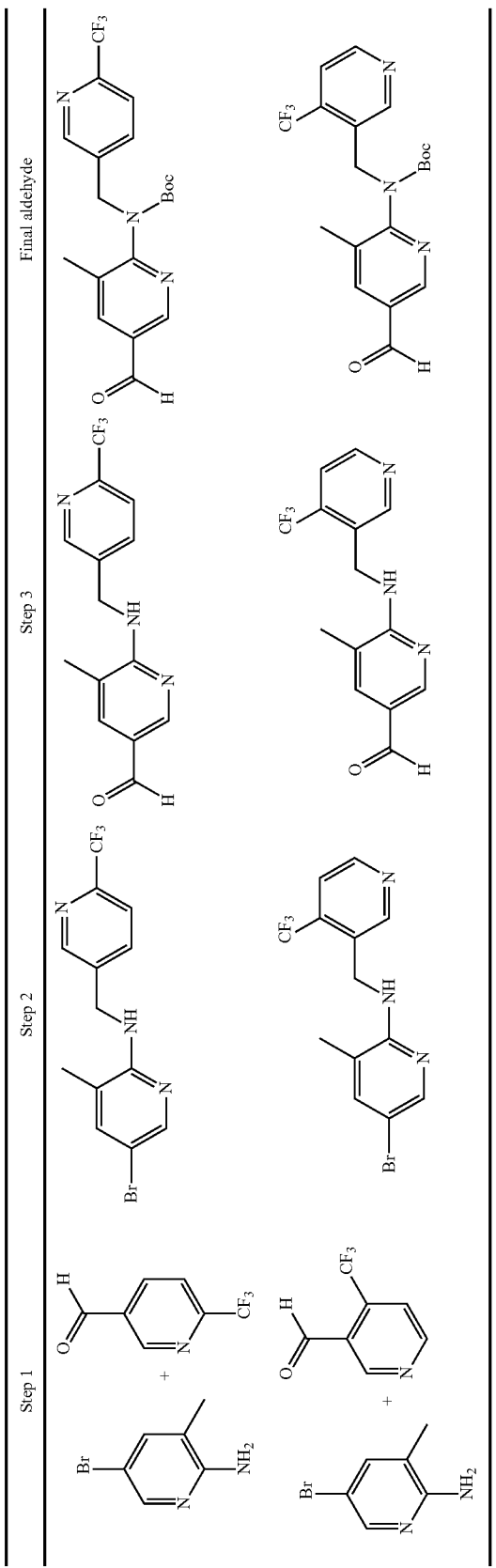

(2-Chloro-benzyl)-(6-fluoro-5-formyl-pyridin-2-yl)-carbamic acid tert-butyl ester 48 was prepared in four steps from 6-fluoro-pyridin-2-ylamine 43 and 2-chloro-benzaldehyde 44 as shown in Scheme 10d.

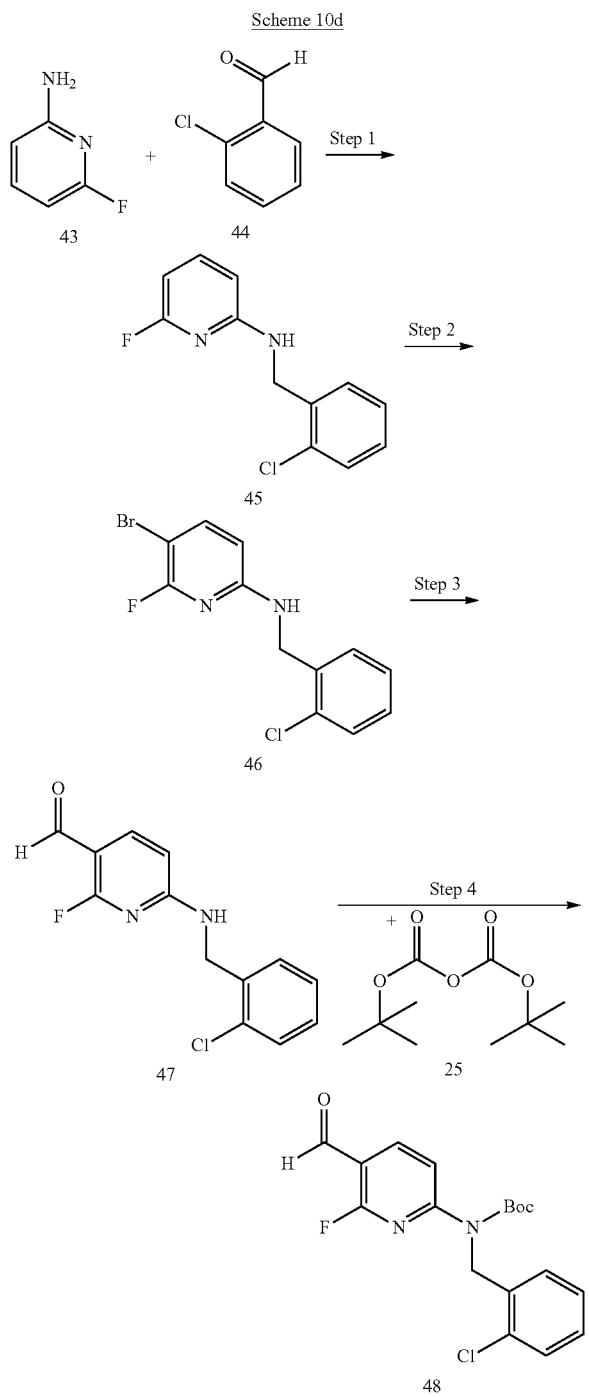

Step 1—Preparation of (2-chloro-benzyl)-(6-fluoro-pyridin-2-yl)-amine (45)

To 6-fluoro-pyridin-2-ylamine (43, 2.47 g, 22.0 mmol) in 60.0 mL of acetonitrile, 2-chloro-benzaldehyde (44, 3.09 g, 22.0 mmol), triethylsilane (14.0 mL, 87.6 mmol) and trifluoroacetic acid (7.00 mL, 90.9 mmol) were added. The reaction was stirred at 80° C. for 4 hours, then solvents removed under vacuum, and the residue was combined with aqueous potassium carbonate and extracted with ethyl acetate. The organic layer was washed with brine, dried over sodium sulfate, filtered and the filtrate concentrated under vacuum to provide the desired compound, which was used in the next step without further purification. MS (ESI) $[M+H^+]^+=272.1$.

Step 2—Preparation of (5-bromo-6-fluoro-pyridin-2-yl)-(2-chloro-benzyl)-amine (46)

To (2-chloro-benzyl)-(6-fluoro-pyridin-2-yl)-amine (45, 4.70 g, 19.8 mmol) in 100.0 mL of acetonitrile, N-bromosuccinimide (3.53 g, 19.8 mmol) in 20.0 mL of acetonitrile was added slowly at room temperature. The reaction was stirred at room temperature for 4 hours, then poured into aqueous potassium carbonate and extracted with ethyl acetate. The organic layer was dried over sodium sulfate, filtered and the filtrate concentrated under vacuum. The resulting material was washed with ethyl acetate in hexane to provide the desired compound (46, 5.0 g).

Step 3—Preparation of 6-(2-chloro-benzylamino)-2-fluoro-pyridine-3-carbaldehyde (47)

To (5-bromo-6-fluoro-pyridin-2-yl)-(2-chloro-benzyl)-amine (46, 1.85 g, 5.86 mmol) in 25.0 mL of tetrahydrofuran under nitrogen at −78° C., isopropylmagnesium chloride (3.00 mL, 2.00 M in tetrahydrofuran, 6.00 mmol) was added over 10 minutes. After 50 minutes, tert-butyllithium (7.80 mL, 1.70 M in hexane, 13.3 mmol) was added over 5 minutes. After 20 minutes, N,N-dimethylformamide (1.09 mL, 14.0 mmol) was added and the reaction mixture stirred at −78° C. for 20 minutes, then brought to room temperature over 30 minutes. The reaction mixture was poured into water and extracted with ethyl acetate. The organic layer was washed with brine, dried over sodium sulfate, filtered and the filtrate concentrated under vacuum. The resulting material was purified by silica gel column chromatography, eluting with 35% ethyl acetate in hexane. The appropriate fractions were combined and the solvents removed under vacuum to provide the desired compound (47, 1.45 g). MS (ESI) $[M+H^+]^+=265.4$.

Step 4—Preparation of (2-chloro-benzyl)-(6-fluoro-5-formyl-pyridin-2-yl)-carbamic acid tert-butyl ester (48)

To 6-(2-chloro-benzylamino)-2-fluoro-pyridine-3-carbaldehyde (47, 1.45 g, 5.48 mmol) in 31.4 mL of tetrahydrofuran, di-tert-butyldicarbonate (25, 1.79 g, 8.22 mmol) and 4-dimethylaminopyridine (78.6 mg, 0.643 mmol) were added. The reaction was stirred at room temperature for 3 hours, then concentrated under vacuum. The resulting material was purified by silica gel column chromatography, eluting with 15-35% ethyl acetate in hexane. Appropriate fractions were combined and the solvents removed under vacuum to provide the desired compound as a colorless oil (48, 1.60 g).

(4-Chloro-benzyl)-(6-fluoro-5-formyl-pyridin-2-yl)-carbamic acid tert-butyl ester 52

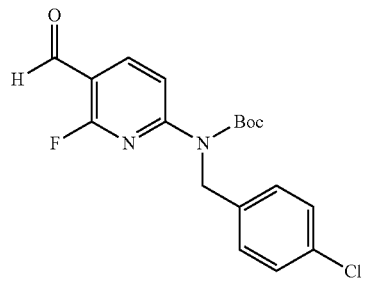

was prepared similarly to the protocol of Scheme 10d, with the first step modified by reacting 2,6-difluoro-pyridine 49 and 4-chloro-benzylamine 50 according the following step 1a.

Scheme 10d Step 1a

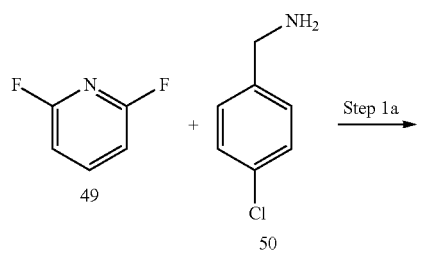

Step 1—Preparation of (4-chloro-benzyl)-(6-fluoro-pyridin-2-yl)-amine (51)

To 2,6-difluoro-pyridine (49, 3.80 g, 33.0 mmol) in 20.0 mL of N-methylpyrrolidone, 4-chloro-benzylamine (50, 5.6 mL, 46.0 mmol) and N,N-diisopropylethylamine (10.0 mL, 57.4 mmol) were added. The reaction was stirred at 90° C. overnight, then poured into water and extracted with ethyl acetate. The organic layer was dried over sodium sulfate, filtered and the filtrate concentrated under vacuum. The resulting material was purified by silica gel column chromatography, eluting with 25% ethyl acetate in hexane. Appropriate fractions were combined and the solvents removed under vacuum, and the resulting material was washed with ethyl acetate/hexane to provide the desired compound as a white solid (51, 5.30 g).

3-methoxy-pyridin-2-ylamine 54, for use in step 1 of Scheme 10d in the preparation of (5-formyl-3-methoxy-pyridin-2-yl)-(4-methoxy-benzyl)-carbamic acid tert-butyl ester 55

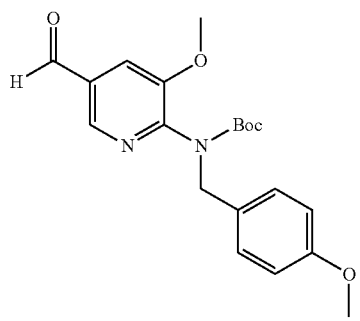

was prepared in one step from 3-methoxy-2-nitro-pyridine 53 by the following step 1b.

Scheme 10d Step 1b

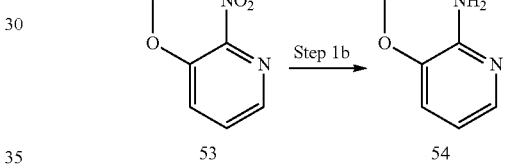

Step 1—Preparation of 3-methoxy-pyridin-2-ylamine (54)

3-Methoxy-2-nitro-pyridine (53, 7.00 g, 45.4 mmol) in 100 mL of methanol, was degassed and palladium (0.7 g, 20%) was added. The reaction was stirred at room temperature for one day under a hydrogen balloon. The reaction was filtered through celite and the filtrate concentrated under vacuum to provide the desired compound (54, 5.555 g). MS (ESI) $[M+H^+]^+=125.3$.

Additional aldehydes are prepared similarly to the protocol of Scheme 10d, as shown in the following table, where Step 1 (or 1a), Step 2, Step 3 and Step 4 reactants are provided in columns 1, 2, 3, and 4, respectively, with the resulting Boc protected aldehyde provided in column 5. Step 1a use is indicated in column 1. Reaction conditions are similar to those described for Scheme 10d, and may vary slightly for each step, for example, any of the solvents, reagents, reaction times, temperatures, work up conditions, or other reaction parameters may be varied employing alternate solvents, reagents, reaction times, temperatures, work up conditions, and the like, as are readily available to one skilled in the art. For example, without limitation, for step 1a, no N,N-diisopropylethylamine is used; for step 3, the addition of isopropylmagnesium chloride is replaced with n-butyllithium in hexane; for step 4, triethylamine is included in the reaction and dichloromethane is used as solvent. Compounds in the following table were characterized by $^1$H and $^{13}$C NMR spectroscopy as well as mass spectrometry.

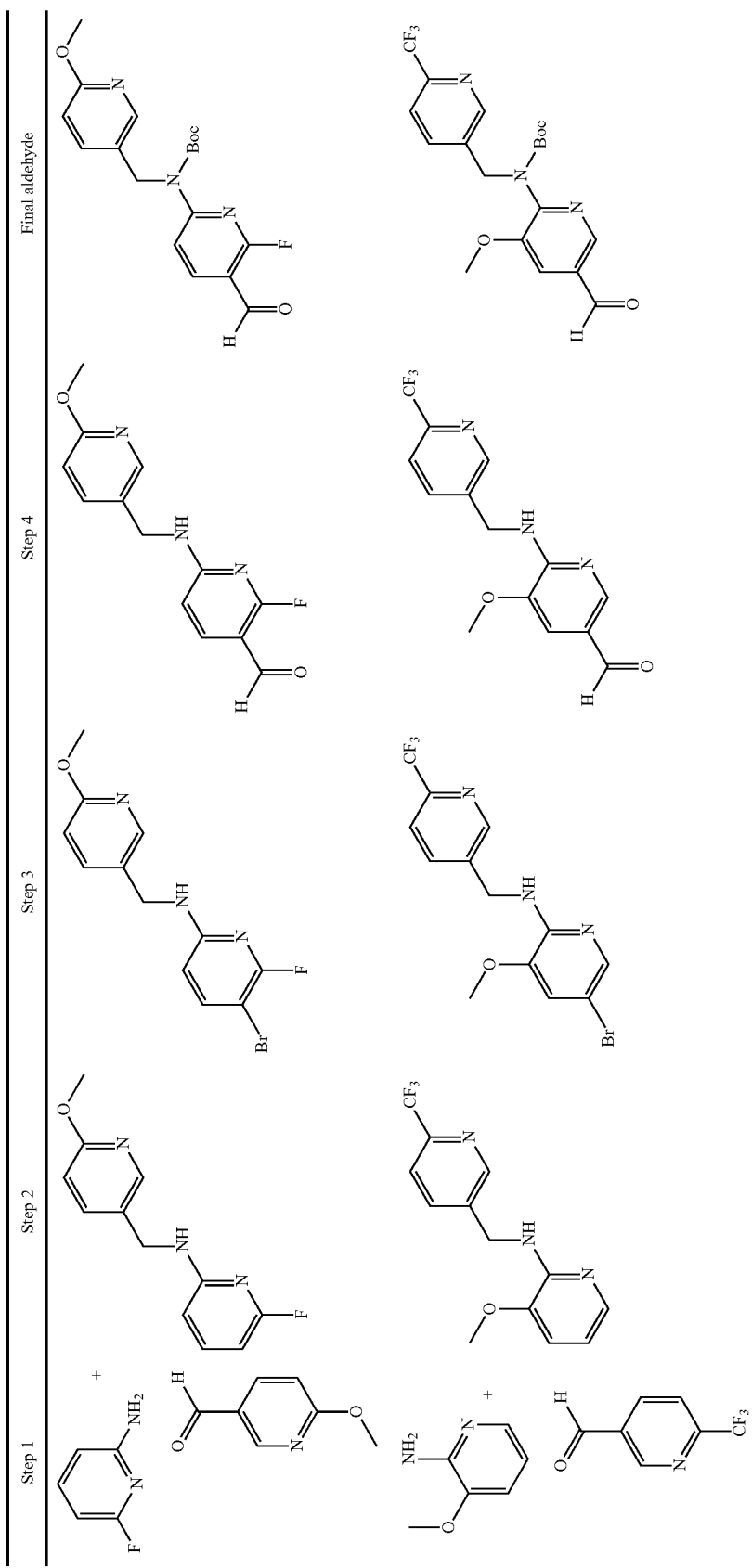

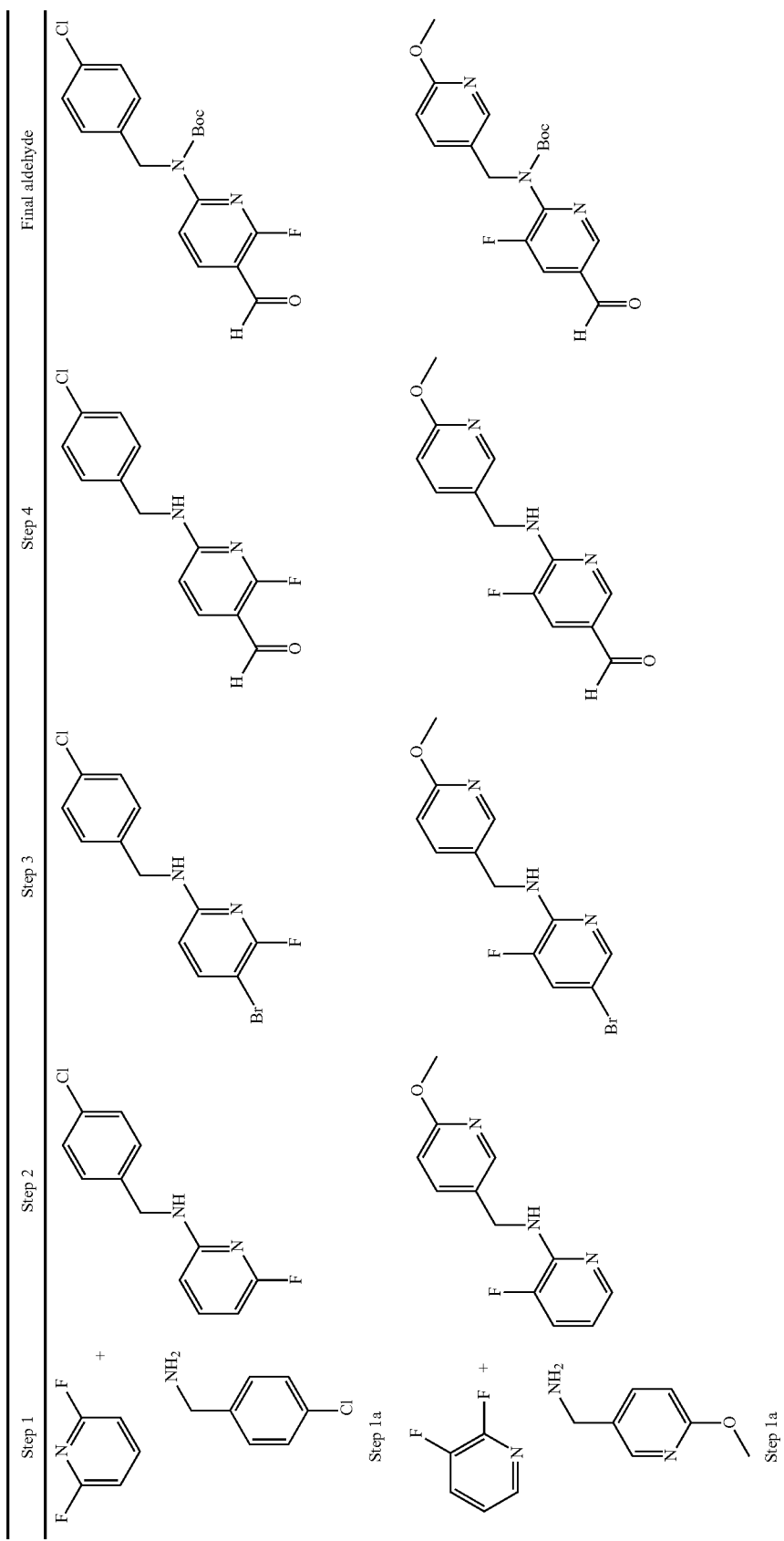

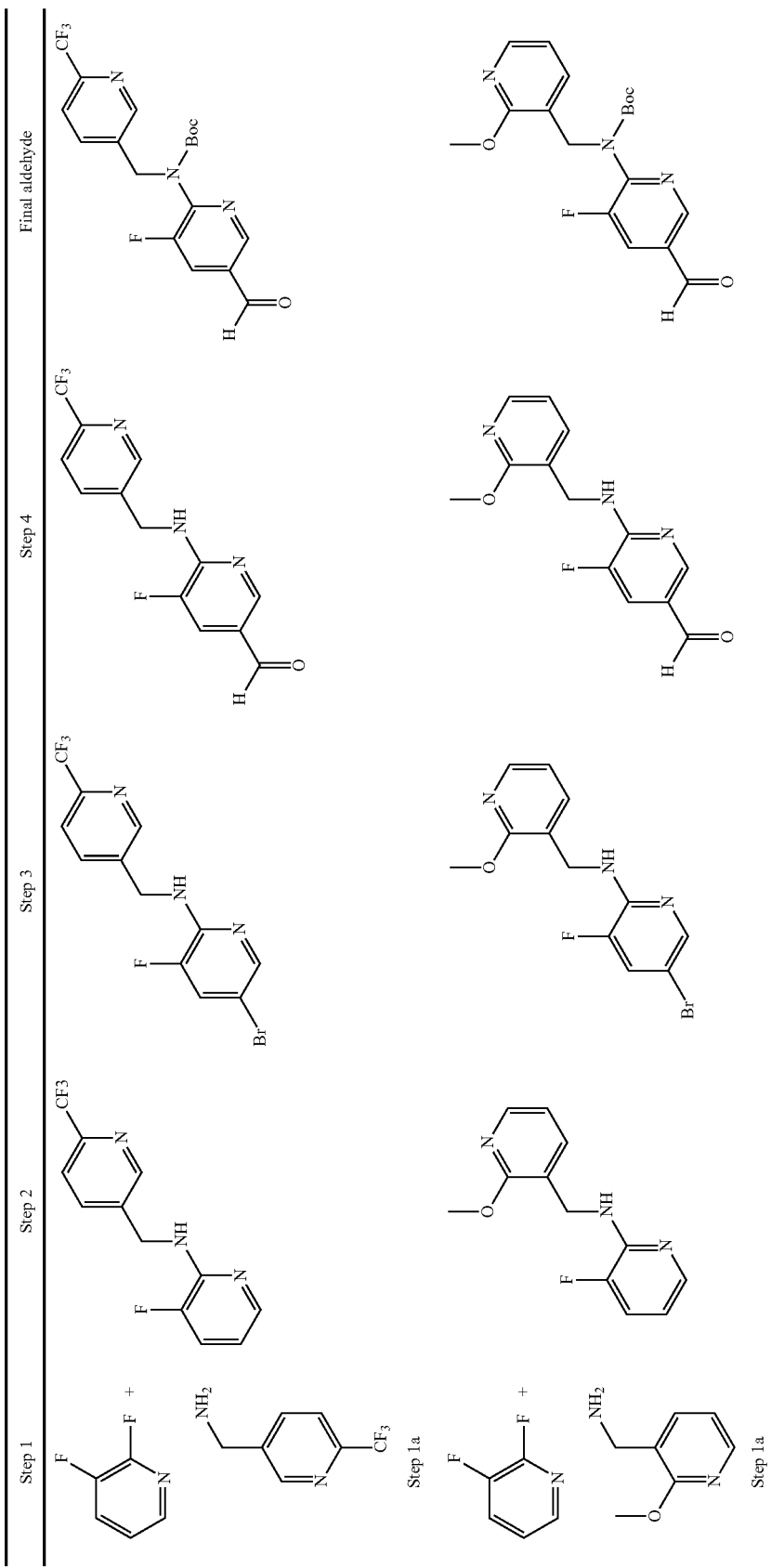

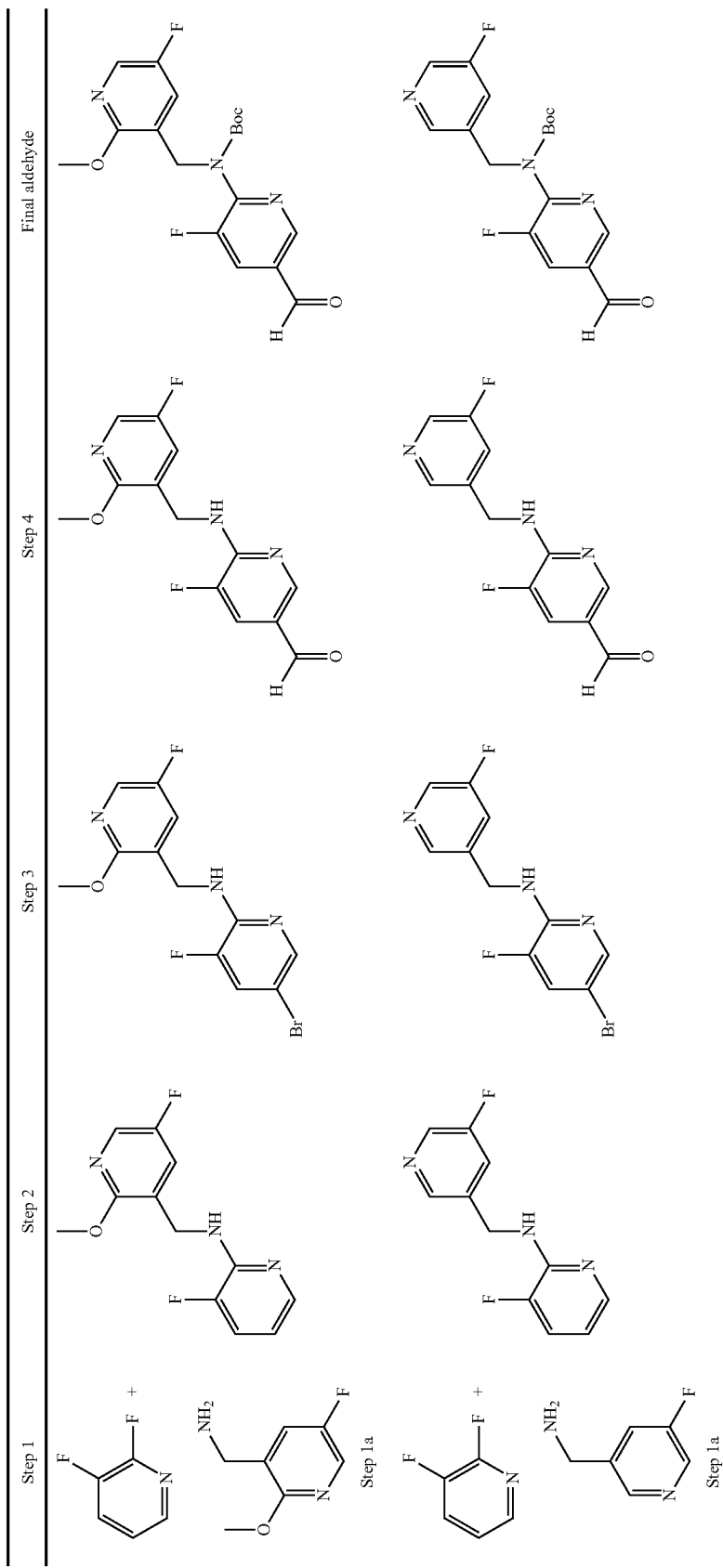

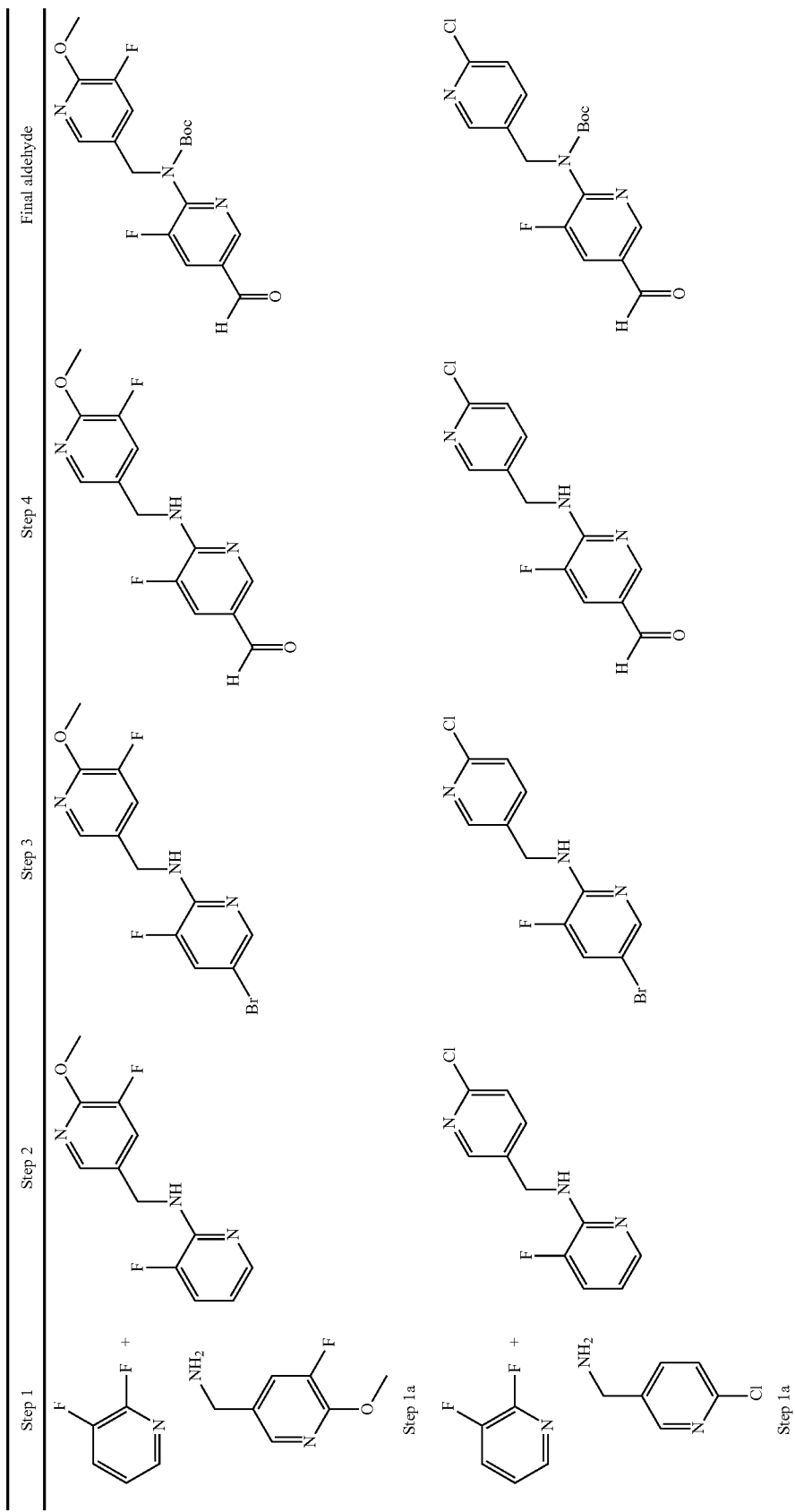

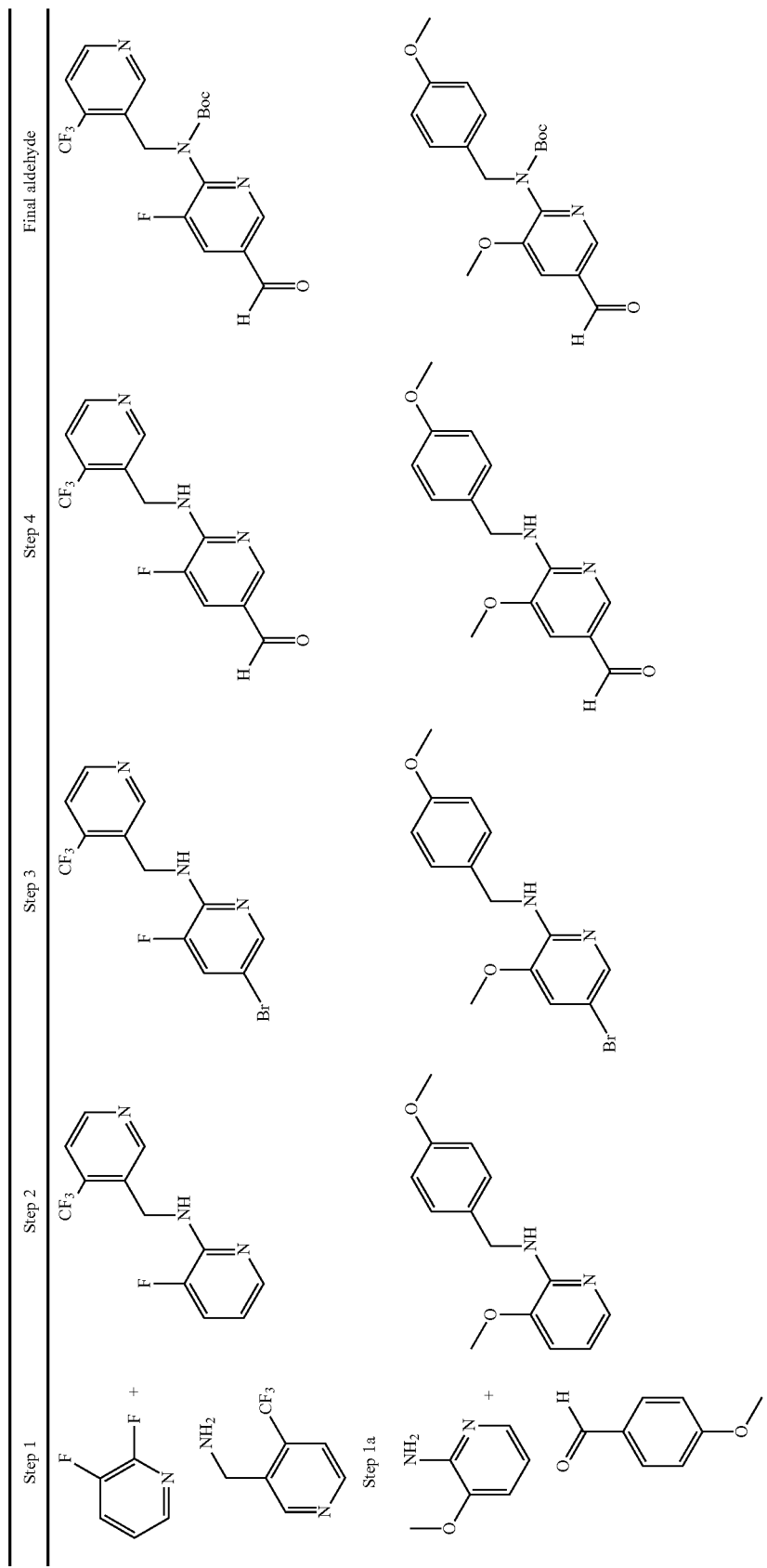

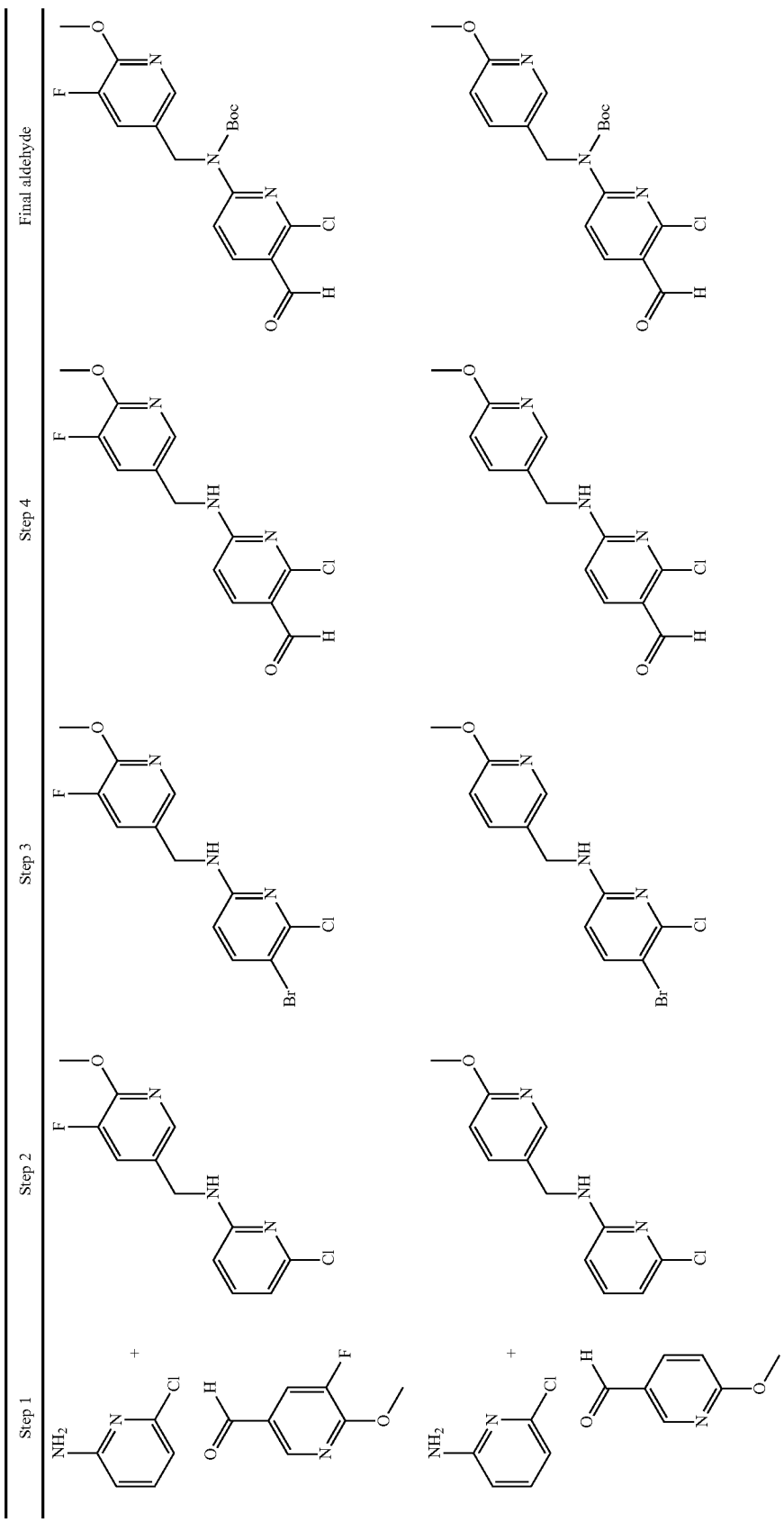

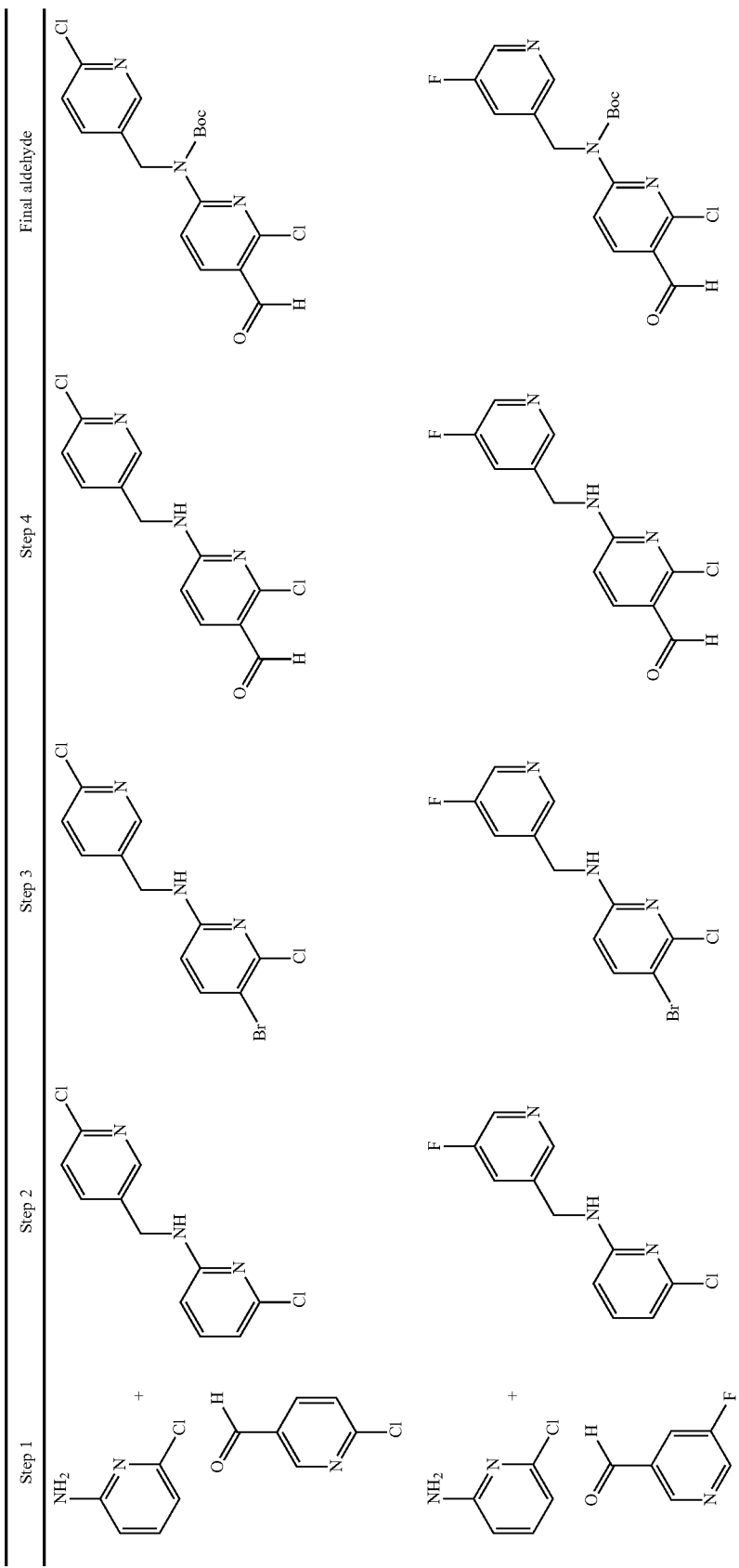

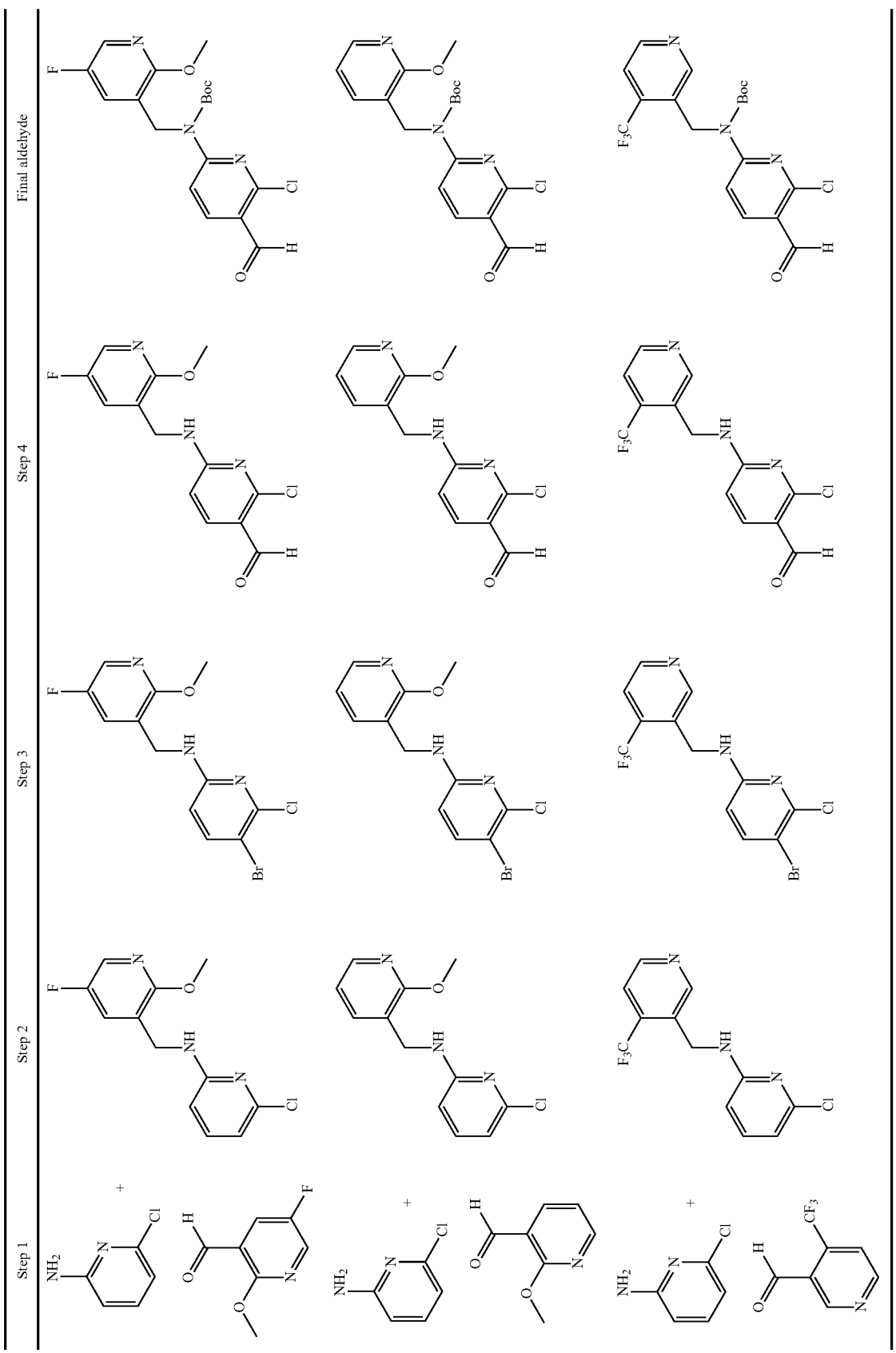

(5-Bromo-6-fluoro-pyridin-2-yl)-(6-methoxy-pyridin-3-ylmethyl)-carbamic acid tert-butyl ester 56

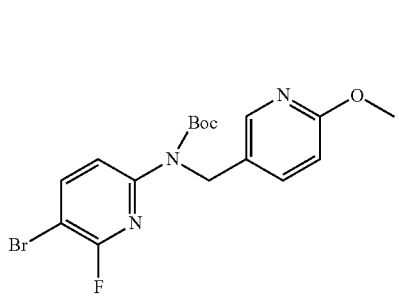

56 was prepared from the product of step 2 for the first entry of the table, which was then Boc protected similarly to the protocol of Scheme 10d step 4.

(6-Fluoro-5-formyl-pyridin-2-yl)-(5-fluoro-6-methoxy-pyridin-3-ylmethyl)-carbamic acid tert-butyl ester 61 was prepared in four steps from 6-fluoro-pyridin-2-ylamine 43 and 5-fluoro-6-methoxy-pyridine-3-carbaldehyde 57 as shown in Scheme 10e.

Scheme 10e

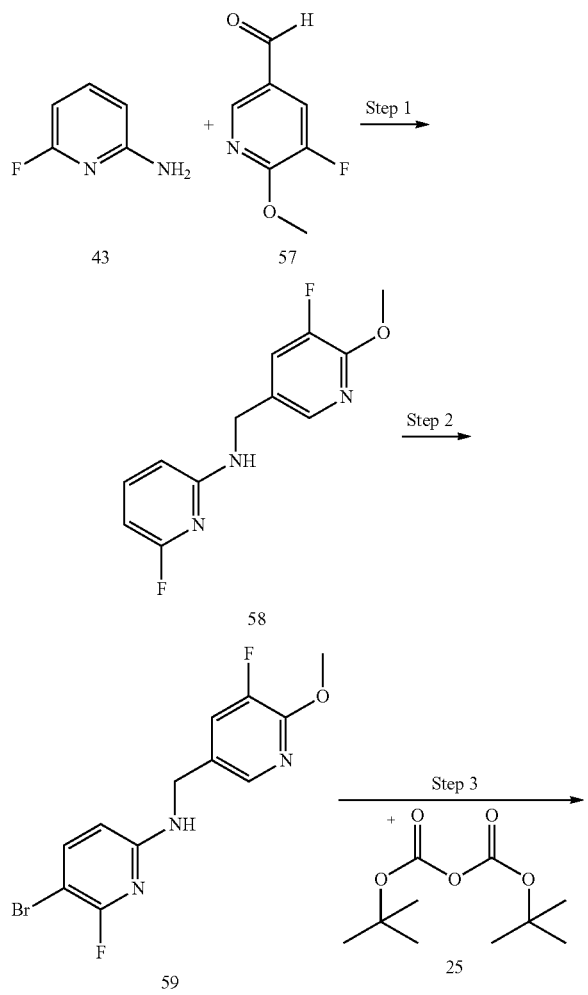

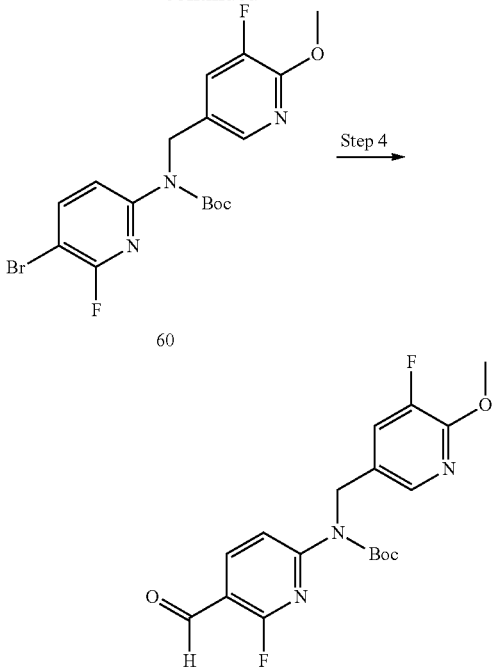

Step 1—Preparation of (5-fluoro-6-methoxy-pyridin-3-ylmethyl)-(6-fluoro-pyridin-2-yl)-amine (58)

To 6-fluoro-pyridin-2-ylamine (43, 1.50 g, 13.4 mmol) in 52.9 mL of acetonitrile, 5-fluoro-6-methoxy-pyridine-3-carbaldehyde (57, 2.00 g, 12.9 mmol), triethylsilane (10.6 mL, 66.3 mmol), and trifluoroacetic acid (5.3 mL, 69.0 mmol) were added. The reaction was stirred at 80° C. overnight, then concentrated under vacuum, combined with water and extracted with ethyl acetate. The organic layer was dried over sodium sulfate, filtered and the filtrate concentrated under vacuum. The resulting material was purified by silica gel column chromatography, eluting with 15-100% ethyl acetate in hexane. Appropriate fractions were combined and concentrated under vacuum to provide the desired compound as white solid (58, 3.21 g).

Step 2—Preparation of (5-bromo-6-fluoro-pyridin-2-yl)-(5-fluoro-6-methoxy-pyridin-3-ylmethyl)-amine (59)

To (5-fluoro-6-methoxy-pyridin-3-ylmethyl)-(6-fluoro-pyridin-2-yl)-amine (58, 3.21 g, 12.8 mmol) in 100 mL of acetonitrile, N-bromosuccinimide (2.30 g, 12.9 mmol) in 30 mL of acetonitrile was added slowly at room temperature. The reaction was stirred at room temperature for 4 hours, then poured into aqueous potassium carbonate and extracted with ethyl acetate. The organic layer was dried over sodium sulfate, filtered and the filtrate concentrated under vacuum. The resulting material was purified by silica gel column chromatography, eluting with 20% ethyl acetate in hexane. Appropriate fractions were combined and concentrated under vacuum to provide the desired compound (59, 3.60 g).

Step 3—Preparation of (5-bromo-6-fluoro-pyridin-2-yl)-(5-fluoro-6-methoxy-pyridin-3-ylmethyl)-carbamic acid tert-butyl ester (60)

To (5-bromo-6-fluoro-pyridin-2-yl)-(5-fluoro-6-methoxy-pyridin-3-ylmethyl)-amine (59, 2.70 g, 8.18 mmol) in 58.7 mL of tetrahydrofuran, di-tert-butyldicarbonate (25, 2.2 g, 9.9 mmol) and 4-dimethylaminopyridine (0.29 g, 2.4 mmol) were added. The reaction was stirred at room temperature for 90 minutes, then concentrated under vacuum. The resulting material was purified by silica gel column chromatography, eluting with 20-100% ethyl acetate in hexane. Appropriate fractions were combined and concentrated under vacuum to provide the desired compound as a colorless oil (60, 3.0 g).

Step 4—Preparation of (6-fluoro-5-formyl-pyridin-2-yl)-(5-fluoro-6-methoxy-pyridin-3-ylmethyl)-carbamic acid tert-butyl ester (61)

To (5-bromo-6-fluoro-pyridin-2-yl)-(5-fluoro-6-methoxy-pyridin-3-ylmethyl)-carbamic acid tert-butyl ester (60, 2.90 g, 6.74 mmol) in 25.0 mL of tetrahydrofuran at −35° C. under nitrogen, isopropylmagnesium chloride (3.54 mL, 2.00 M in tetrahydrofuran, 7.08 mmol) was added and the reaction was allowed to come to 0° C. over an hour. The reaction was cooled to −45° C. and N,N-dimethylformamide (1.0 mL, 13.0 mmol) was added. The reaction was allowed to warm to room temperature over 2 hours, then poured into aqueous ammonium chloride and extracted with ethyl acetate. The organic layer was dried over sodium sulfate, filtered and the filtrate concentrated under vacuum. The resulting material was purified by silica gel column chromatography, eluting with 20% ethyl acetate in hexane. Appropriate fractions were combined and concentrated under vacuum to provide the desired compound (61, 1.80 g).

Additional aldehydes are prepared similarly to the protocol of Scheme 10e, as shown in the following table, where Step 1, Step 2, Step 3 and Step 4 reactants are provided in columns 1, 2, 3, and 4, respectively, with the resulting Boc protected aldehyde provided in column 5. In some instances, the desired compound is the Boc protected bromo compound isolated after step 3 for use in subsequent reactions. Reaction conditions are similar to those described for Scheme 10e, and may vary slightly for each step, for example, any of the solvents, reagents, reaction times, temperatures, work up conditions, or other reaction parameters may be varied employing alternate solvents, reagents, reaction times, temperatures, work up conditions, and the like, as are readily available to one skilled in the art. For example, without limitation, step 2 is performed under nitrogen; step 3 includes N,N-diisopropylethylamine. Compounds in the following table were characterized by $^1$H and $^{13}$C NMR spectroscopy as well as mass spectrometry.

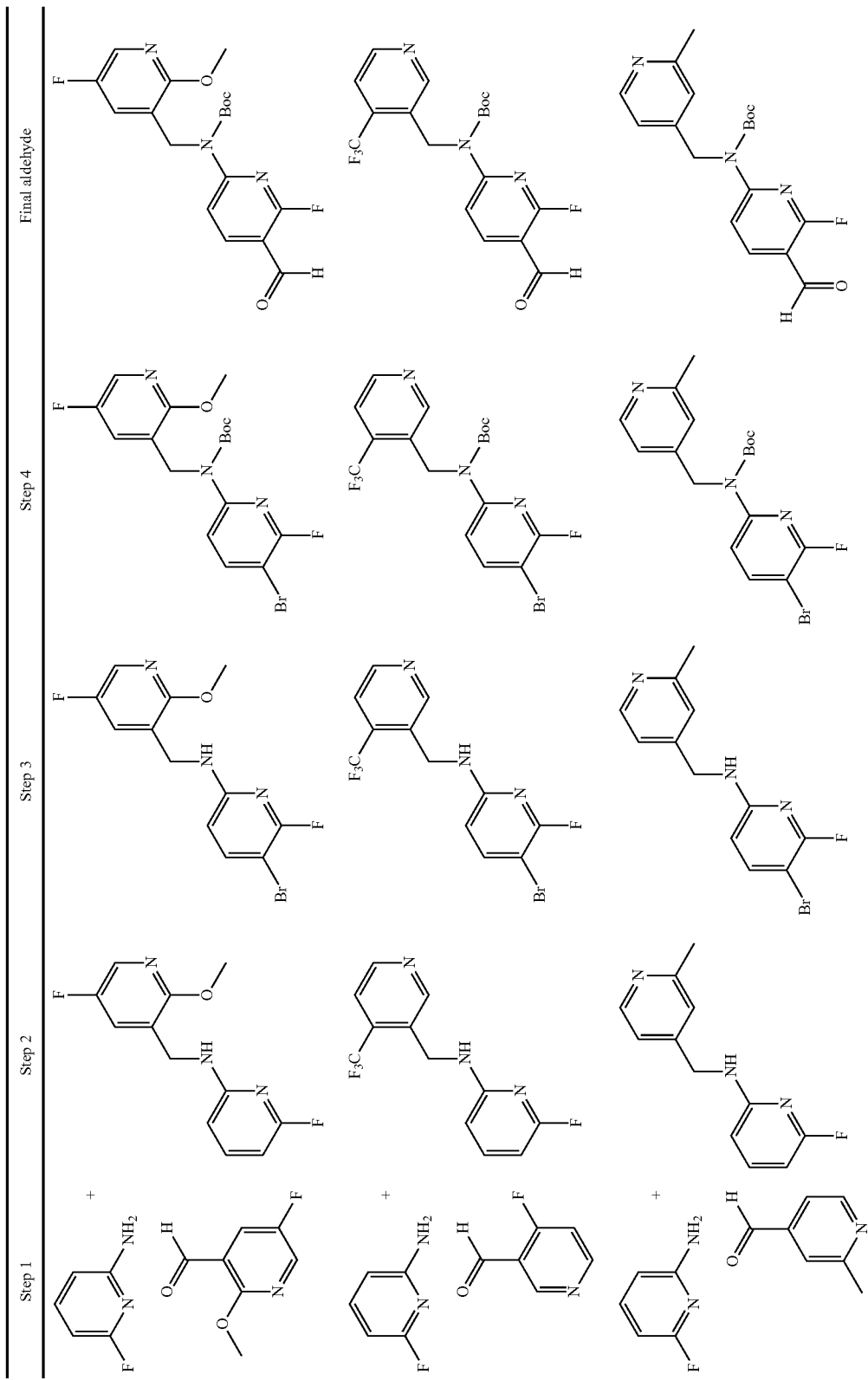

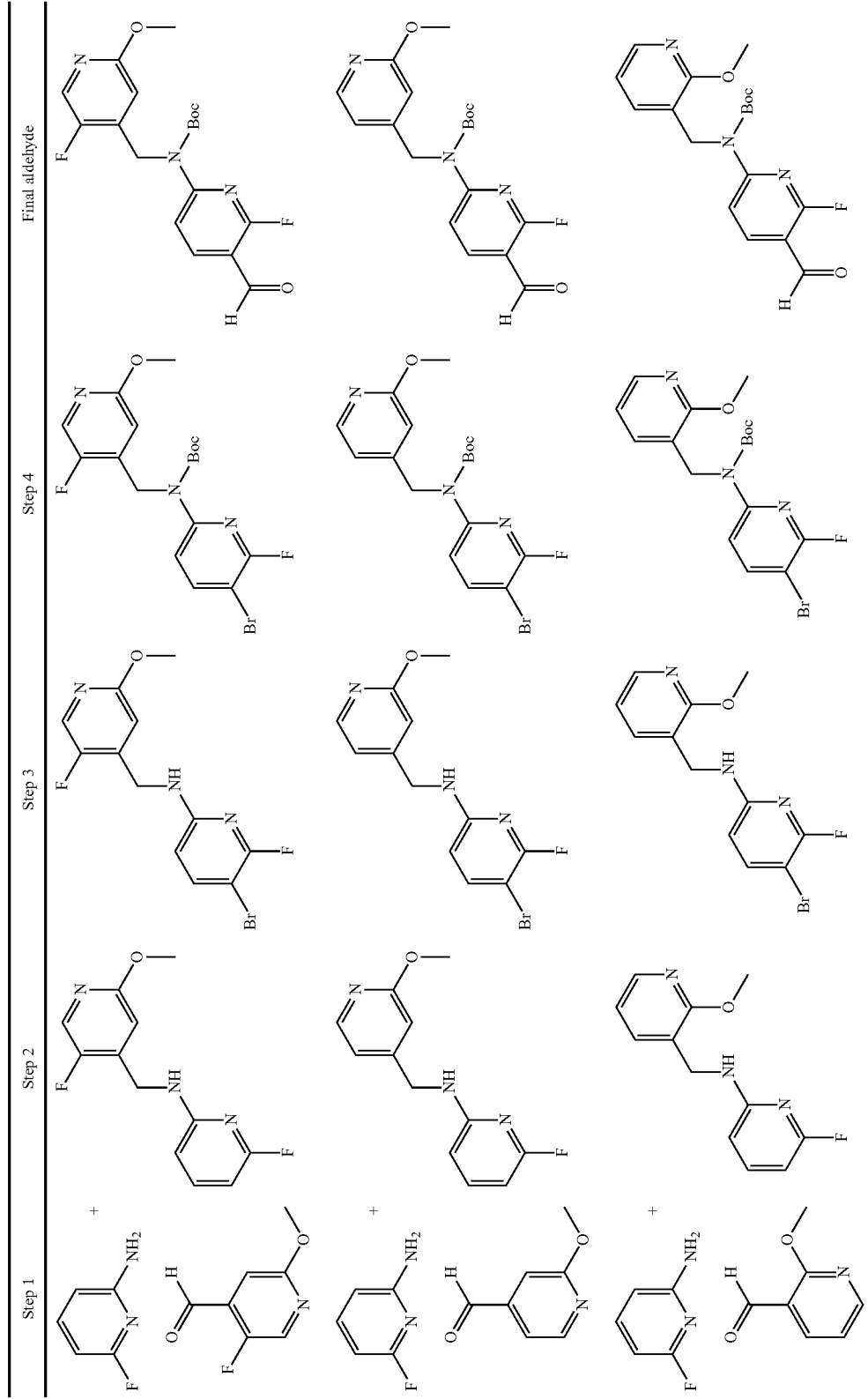

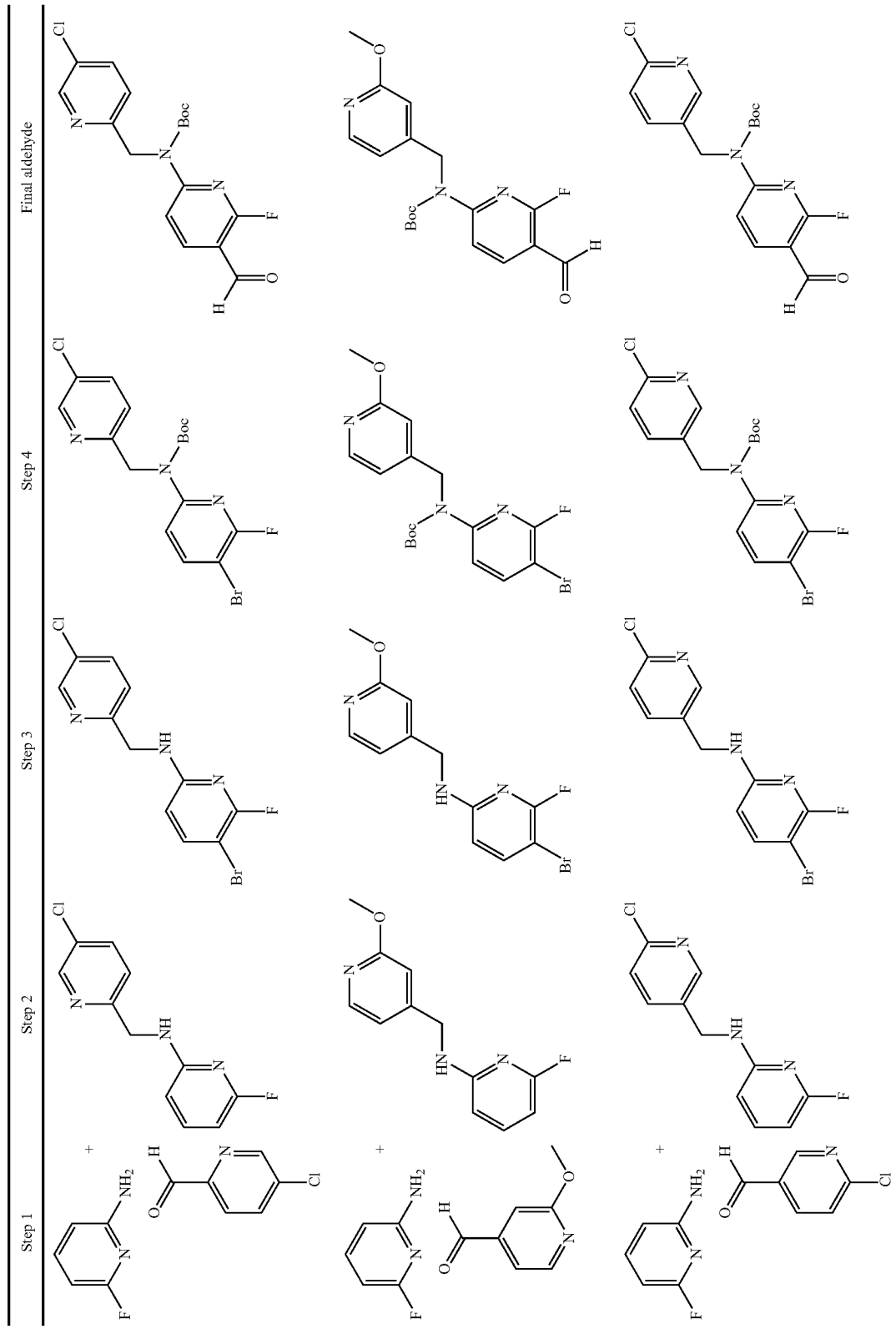

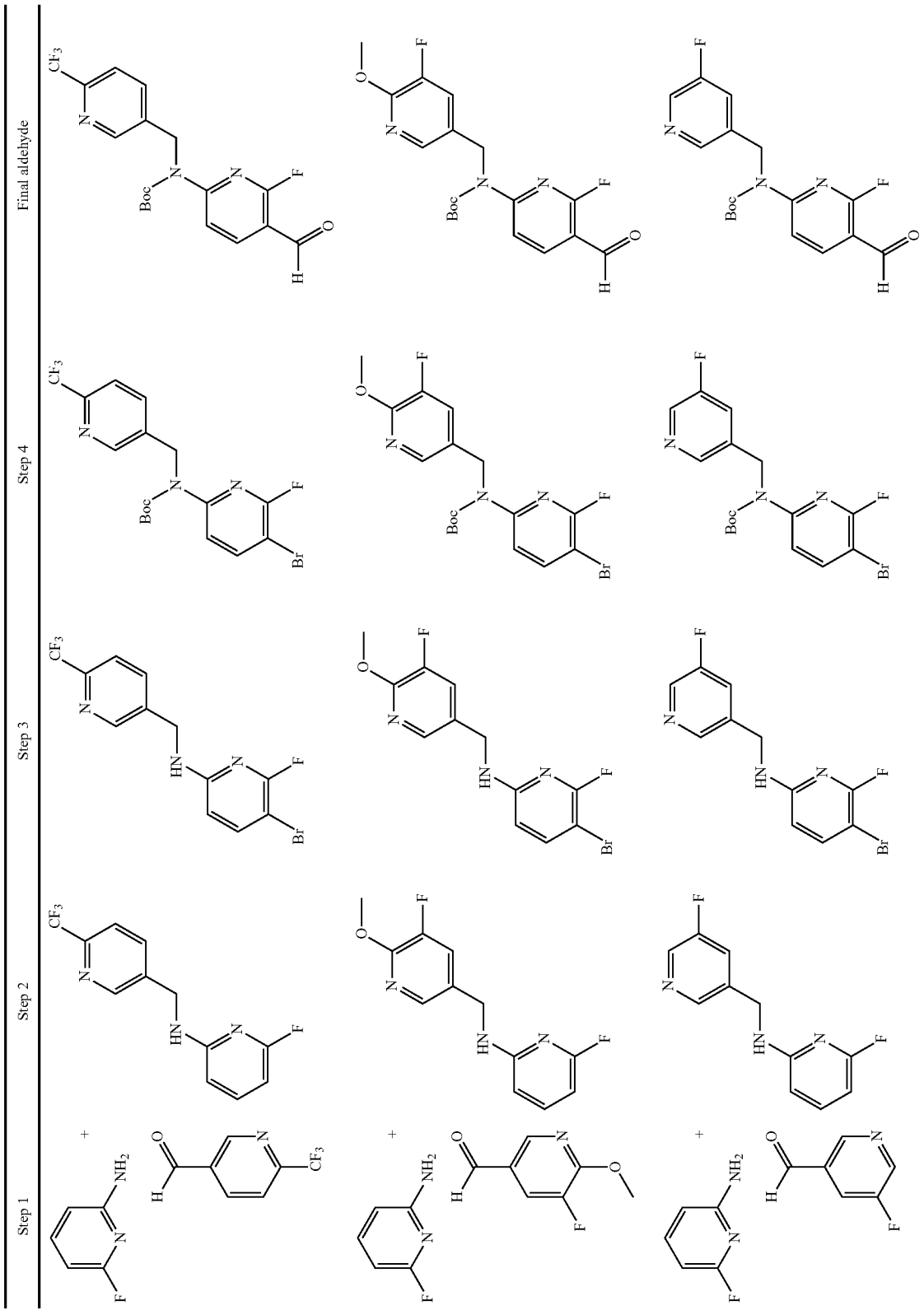

(6-Fluoro-5-formyl-pyridin-2-yl)-[(S)-1-(4-fluoro-phenyl)-ethyl]-carbamic acid tert-butyl ester 62

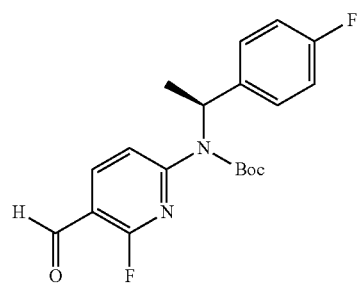

was prepared from 2,6-difluoro-pyridine 49 and (S)-1-(4-fluoro-phenyl)-ethylamine similarly to the protocol of step 1a of Scheme 10d, then steps 2-4 of Scheme 10e. Step 3 also included N,N-diisopropylethylamine, as well as a subsequent addition of di-tert-butyldicarbonate and N,N-diisopropylethylamine.

(5-Formyl-6-methyl-pyridin-2-yl)-(6-methoxy-pyridin-3-ylmethyl)-carbamic acid tert-butyl ester 66

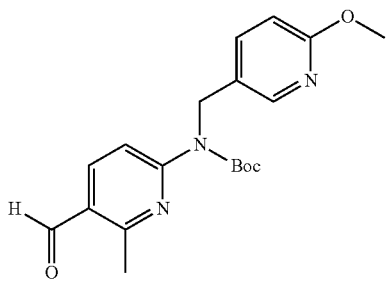 [SMILES: COc1ccc(CN(C(=O)OC(C)(C)C)c2ncc(C=O)cn2)cc1]

was prepared by reacting (5-iodo-6-methyl-pyridin-2-yl)-(6-methoxy-pyridin-3-ylmethyl)-amine 65 similarly to the protocol of Scheme 10c, steps 3 and 4, where step 3 included N,N-diisopropylethylamine. (5-Iodo-6-methyl-pyridin-2-yl)-(6-methoxy-pyridin-3-ylmethyl)-amine 65 was prepared in one step from 5-iodo-6-methyl-pyridin-2-ylamine 63 and 6-methoxy-pyridine-3-carbaldehyde 64 as shown in Scheme 10f.

Scheme 10f

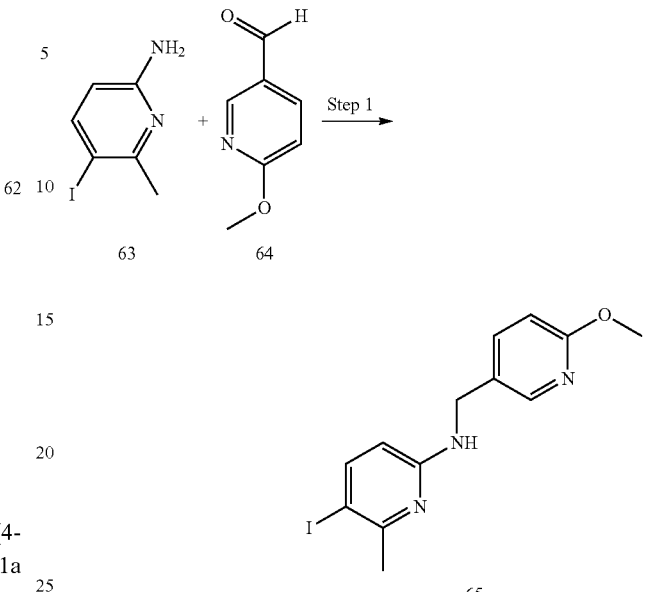

Step 1—Preparation of (5-iodo-6-methyl-pyridin-2-yl)-(6-methoxy-pyridin-3-ylmethyl)-amine (65)

5-Iodo-6-methyl-pyridin-2-ylamine (63, 1.7 g, 7.3 mmol) and 6-methoxy-pyridine-3-carbaldehyde (64, 1.1 g, 8.0 mmol) were combined in a round bottom flask with trifluoroacetic acid (2.80 mL, 36.3 mmol), triethylsilane (5.80 mL, 36.3 mmol) and 50 mL of acetonitrile. The reaction was stirred at room temperature overnight, then heated to reflux for 6 hours. The reaction was concentrated under vacuum, combined with aqueous potassium carbonate and extracted with ethyl acetate. The organic layer was dried over sodium sulfate, filtered and the filtrate concentrated under vacuum. The resulting material was purified by silica gel flash column chromatography, eluting with 10-100% ethyl acetate in hexane. Appropriate fractions were combined and concentrated under vacuum to provide the desired compound (65, 1.80 g). MS (ESI)[M+H$^+$]$^+$=356.80.

Additional aldehydes are prepared similarly to the protocol of Scheme 10f followed by Scheme 10e steps 2 and 3, as shown in the following table, where Step 1 (Scheme 10f), Step 3 and Step 4 reactants are provided in columns 1, 2, and 3, respectively, with the resulting Boc protected aldehyde provided in column 5. Reaction conditions are similar to those described for Schemes 10e and 10f, and may vary slightly for each step, for example, any of the solvents, reagents, reaction times, temperatures, work up conditions, or other reaction parameters may be varied employing alternate solvents, reagents, reaction times, temperatures, work up conditions, and the like, as are readily available to one skilled in the art.

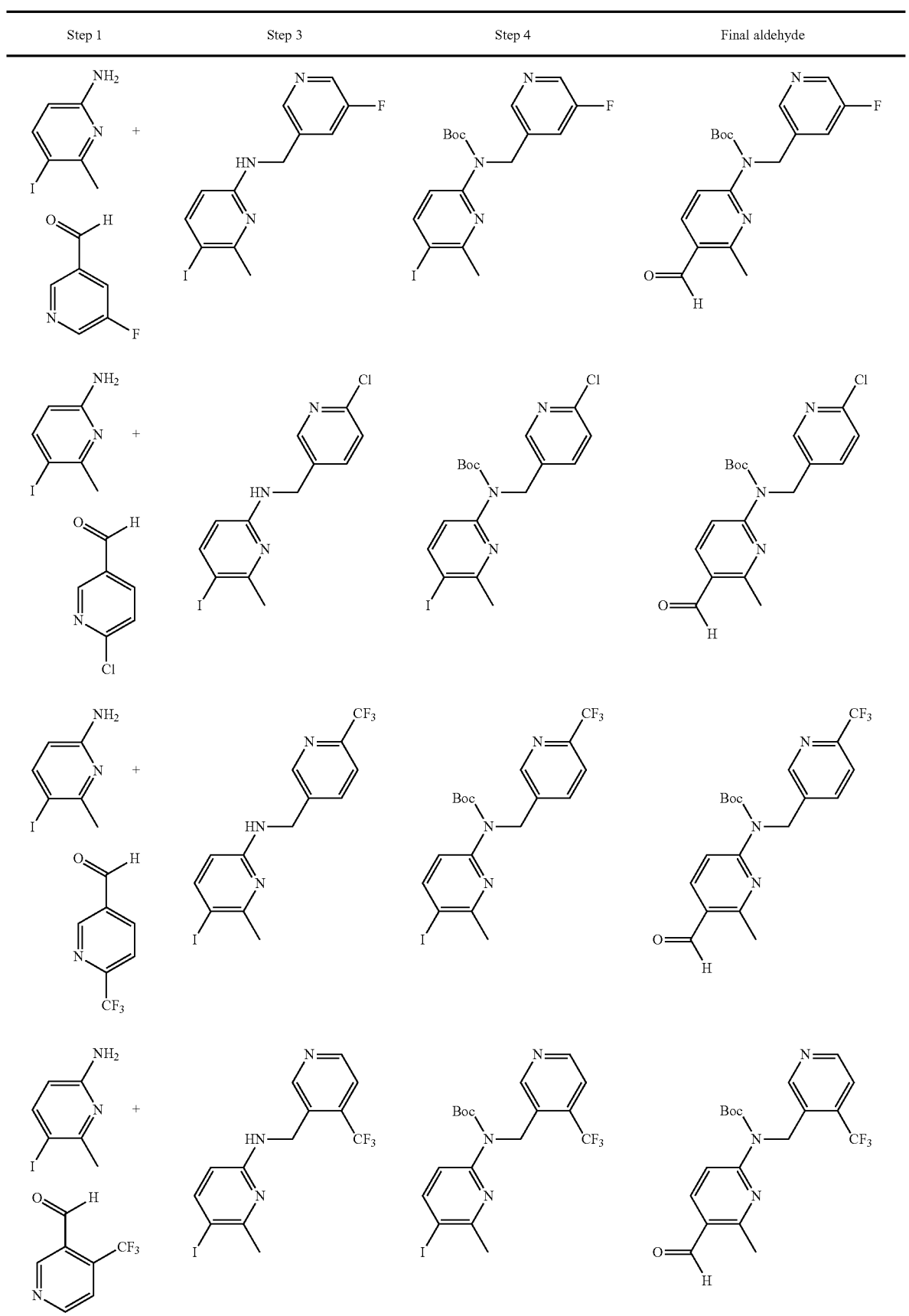

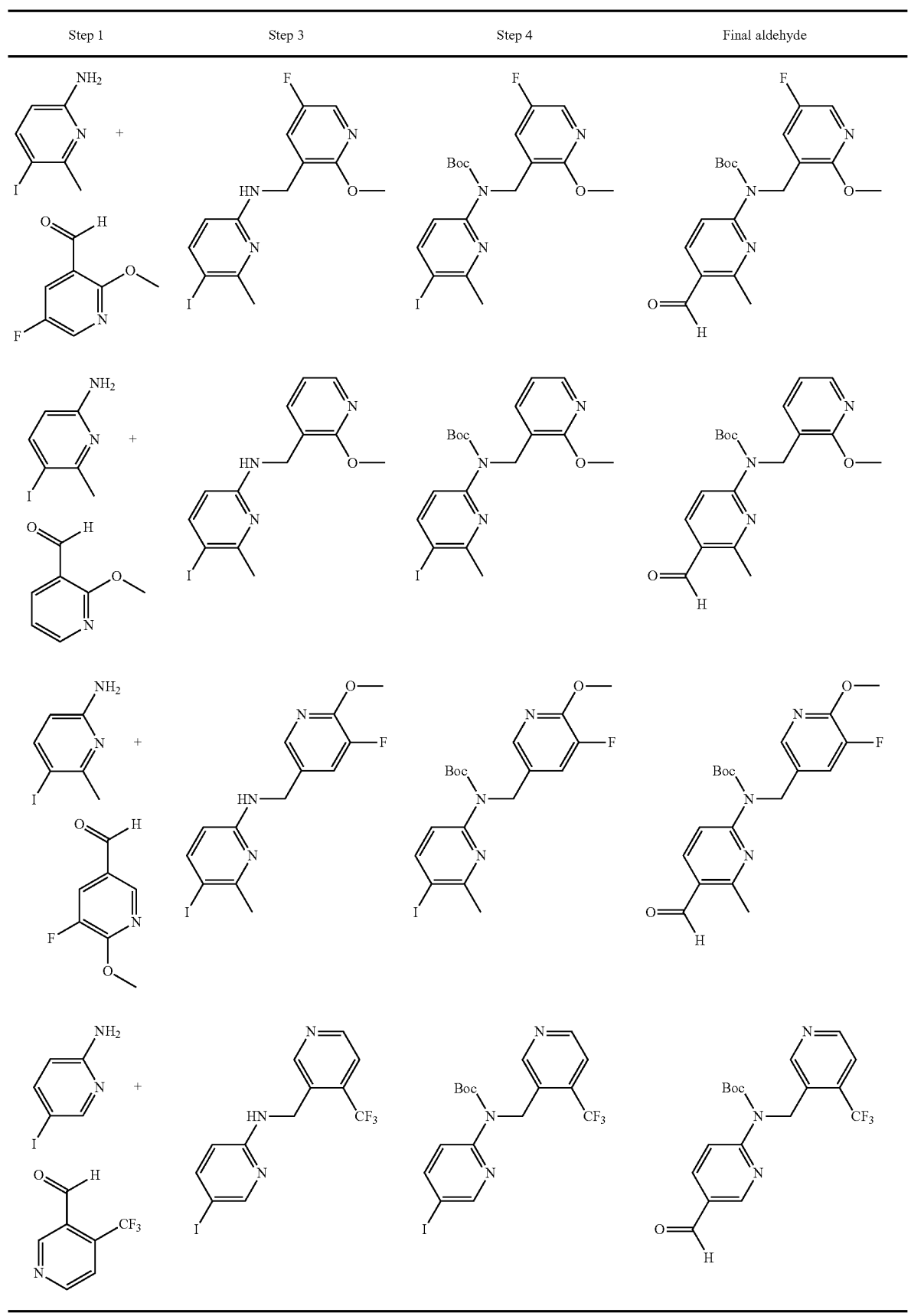

151

(5-fluoro-pyridin-3-ylmethyl)-(5-iodo-pyrimidin-2-yl)-carbamic acid tert-butyl ester 67

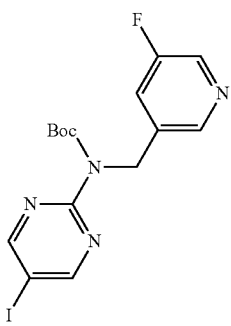

67 was prepared similarly to Scheme 10f, replacing 5-iodo-6-methyl-pyridin-2-ylamine 63 with 5-iodo-pyrimidin-2-ylamine and 6-methoxy-pyridine-3-carbaldehyde 64 with 5-fluoro-pyridine-3-carbaldehyde and Boc-protecting the nitrogen, for example following similar protocol to Scheme 10e, step 3.

(5-Formyl-pyrimidin-2-yl)-(6-methoxy-pyridin-3-ylmethyl)-carbamic acid tert-butyl ester 72 was prepared in three steps from vinamidinium salt 68 and guanidine hydrochloride 69 as shown in Scheme 10 g.

Scheme 10g

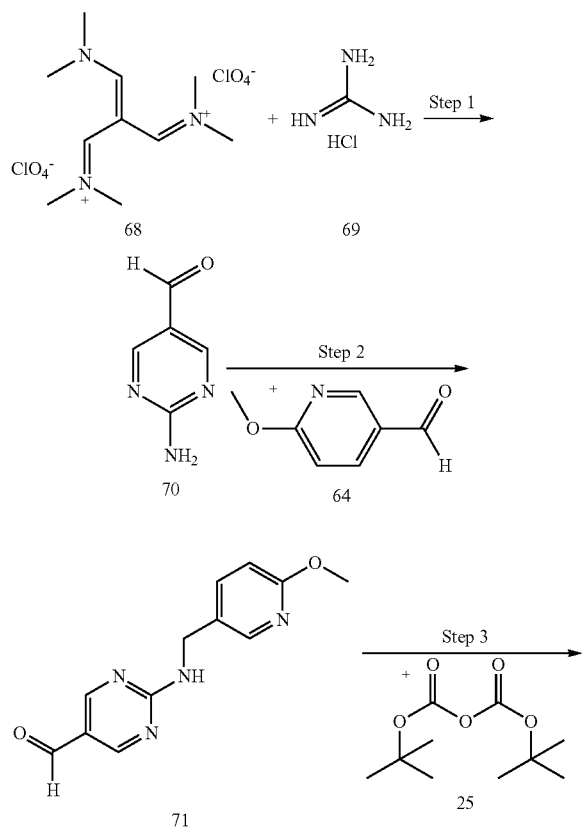

152

-continued

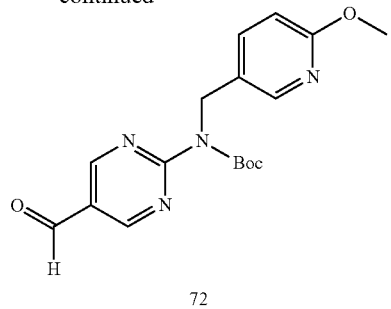

72

Step 2—Preparation of 2-amino-pyrimidine-5-carbaldehyde (70)

Vinamidinium salt (68, 158 g, 413 mmol) and guanidine hydrochloride (69, 63.3 g, 455 mmol) were dissolved in 527 mL of acetonitrile and cooled on an ice/water bath. Sodium hydroxide (66.1 mL, 50% w/w, 827 mmol) was added dropwise, keeping the temperature below 25° C. The reaction was allowed to warm to 25° C. and stirred for 4 hours, then diluted with water and filtered, stripped from ethanol/heptane, then triturated with heptane. The resulting solid was dried under vacuum to provide the desired compound (70, 37 g, 301 mmol, 72.7% yield).

Step 2—Preparation of 2-[(6-methoxy-pyridin-3-ylmethyl)-amino]-pyrimidine-5-carbaldehyde (71)

In a round bottom flask, 2-amino-pyrimidine-5-carbaldehyde (70, 0.750 g, 6.09 mmol), 6-methoxy-pyridine-3-carbaldehyde (64, 1.67 g, 12.2 mmol), trifluoroacetic acid (2.5 mL, 32.0 mmol), and triethylsilane (5.00 mL, 31.3 mmol) were combined with 10 mL of acetonitrile. The reaction was stirred at room temperature overnight, then concentrated under vacuum and combined with aqueous potassium carbonate and extracted with ethyl acetate. The organic layer was dried over sodium sulfate, filtered and the filtrate concentrated under vacuum. The resulting material was purified by silica gel flash column chromatography, eluting with 15-100% ethyl acetate in hexane. Appropriate fractions were combined and concentrated under vacuum to provide the desired compound.

Step 3—Preparation of (5-formyl-pyrimidin-2-yl)-(6-methoxy-pyridin-3-ylmethyl)-carbamic acid tert-butyl ester (72)

To 2-[(6-methoxy-pyridin-3-ylmethyl)-amino]-pyrimidine-5-carbaldehyde (71, 0.462 g, 1.89 mmol) in 15 mL of tetrahydrofuran, N,N-diisopropylethylamine (0.72 mL, 4.2 mmol), 4-dimethylaminopyridine (0.02 g, 0.2 mmol) and di-tert-butyldicarbonate (25, 0.45 g, 2.1 mmol) were added. The reaction was stirred at room temperature overnight, then poured into water and extracted with ethyl acetate. The organic layer was concentrated under vacuum and the resulting material was purified by silica gel column chromatography, eluting with 20-100% ethyl acetate in hexane. Appropriate fractions were combined and concentrated under vacuum to provide the desired compound. $^1$H NMR was consistent with the compound structure.

Additional aldehydes are prepared similarly to the protocol of Scheme 10 g, as shown in the following table, where Step 1 and Step 2 reactants are provided in columns 1 and 2, respectively, with the resulting Boc protected aldehyde provided in column 3. Reaction conditions are similar to those described for Scheme 10 g, and may vary slightly for each step, for example, any of the solvents, reagents, reaction times, temperatures, work up conditions, or other reaction parameters may be varied employing alternate solvents, reagents, reaction times, temperatures, work up conditions, and the like, as are readily available to one skilled in the art. For example, without limitation, for step 2, N,N-diisopropylethylamine is not included in the reaction. Compounds in the following table were characterized by $^1$H and $^{13}$C NMR spectroscopy as well as mass spectrometry.

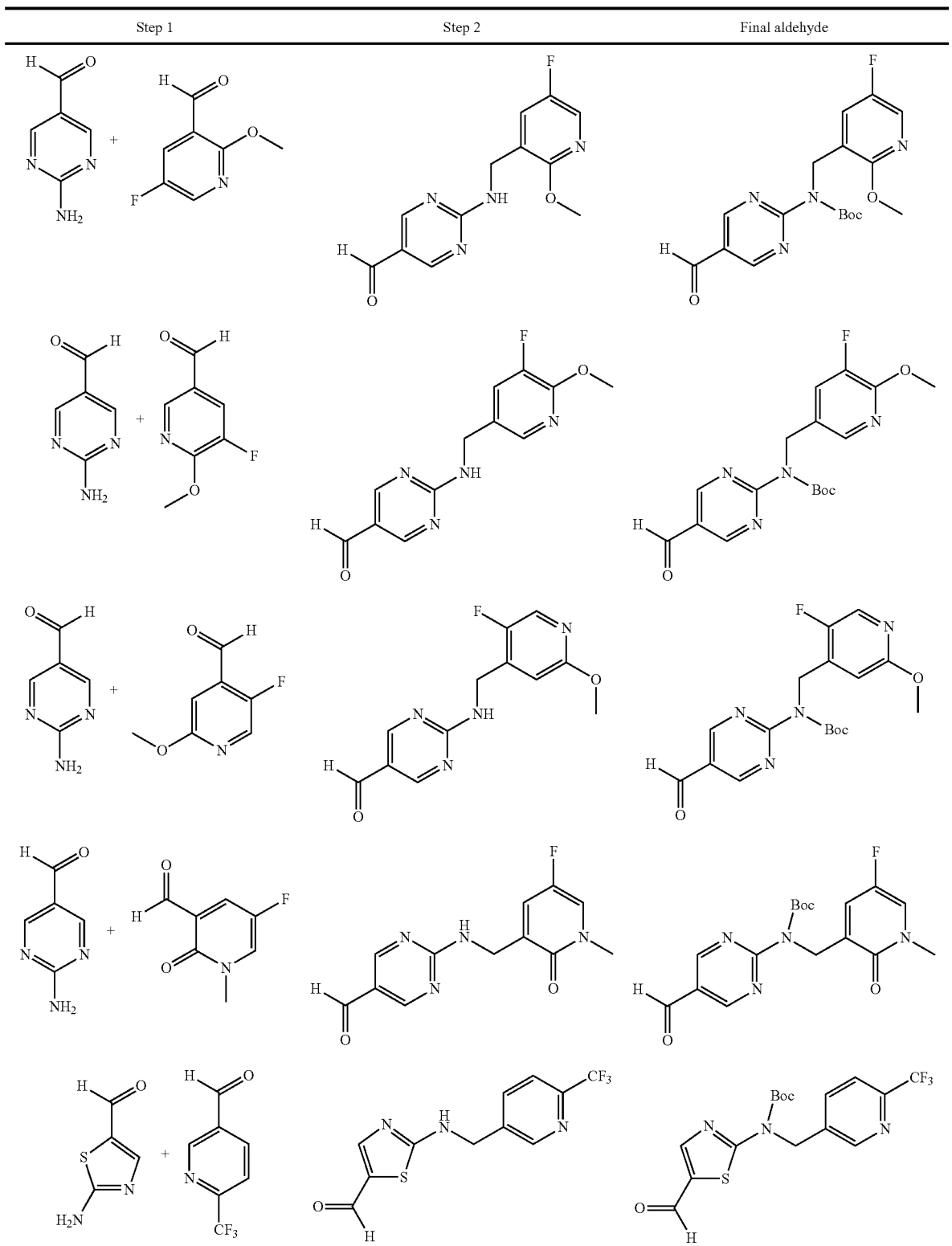

-continued
| Step 1 | Step 2 | Final aldehyde |
|---|---|---|
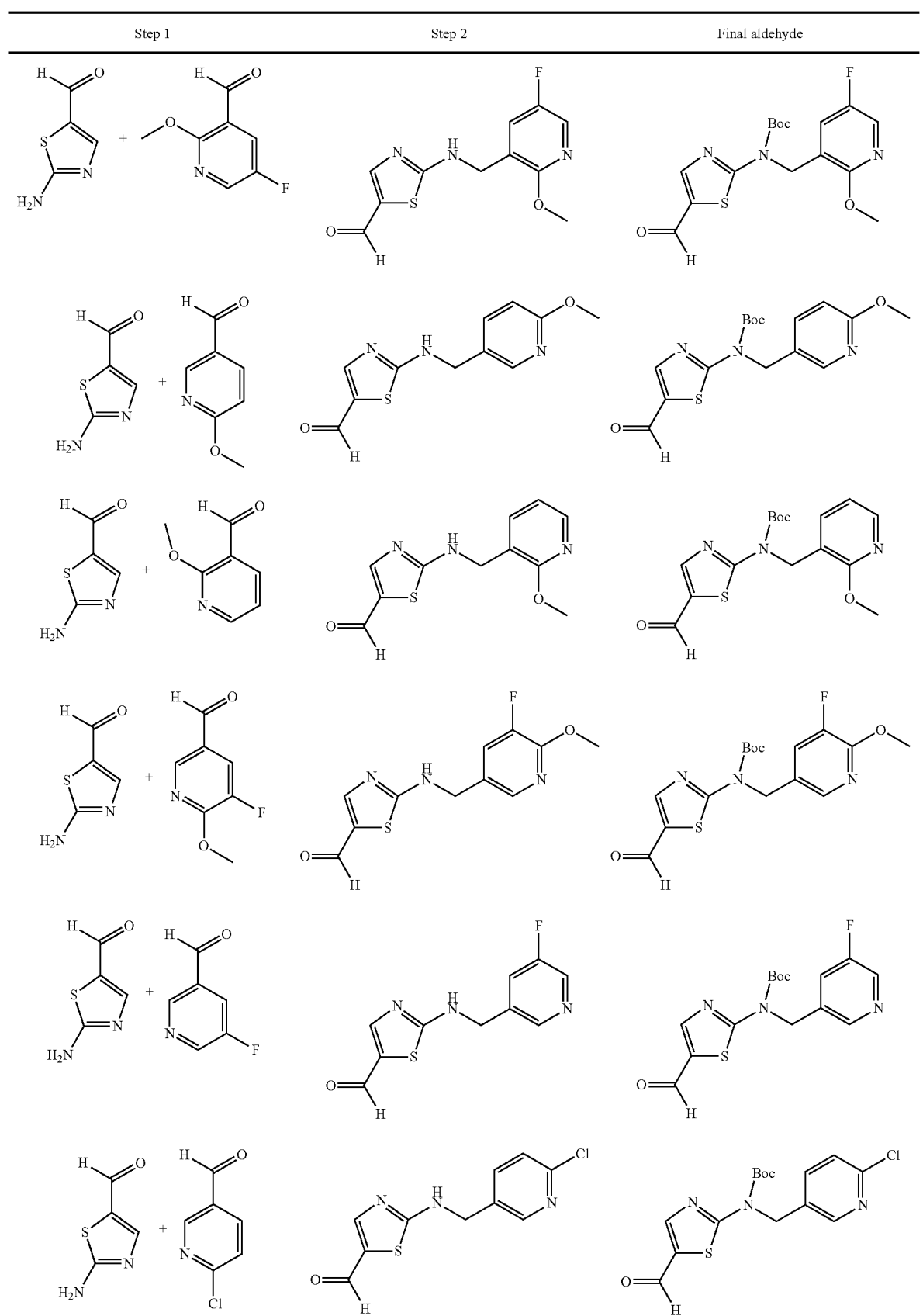

| Step 1 | Step 2 | Final aldehyde |
|---|---|---|
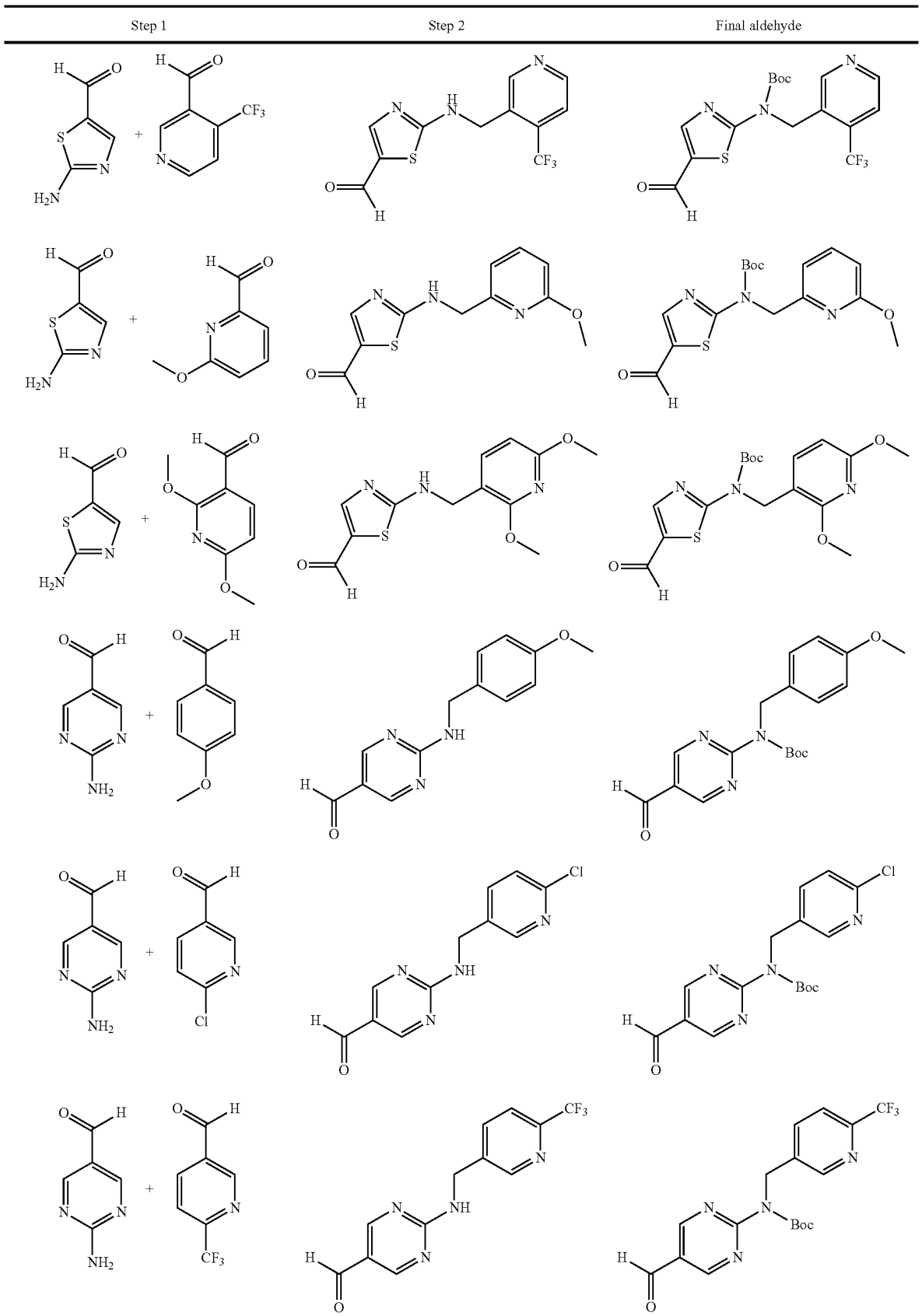

-continued
| Step 1 | Step 2 | Final aldehyde |
|---|---|---|
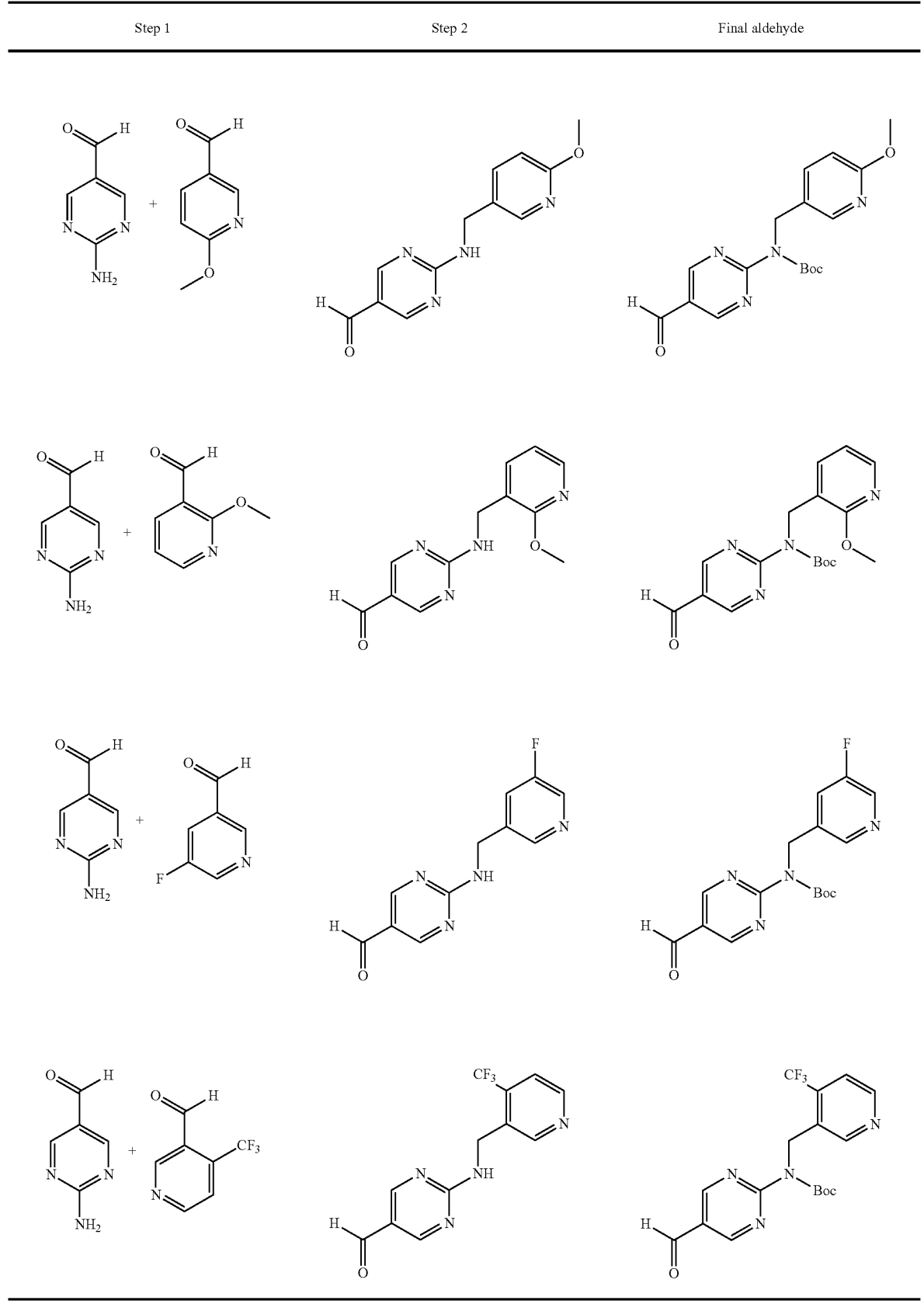

(4-Chloro-5-formyl-thiazol-2-yl)-(6-trifluoromethyl-pyridin-3-ylmethyl)-carbamic acid tert-butyl ester 76 was prepared in two steps from 2,4-dichloro-thiazole-5-carbaldehyde 73 and C-(6-trifluoromethyl-pyridin-3-yl)-methylamine 74 as shown in Scheme 10 h.

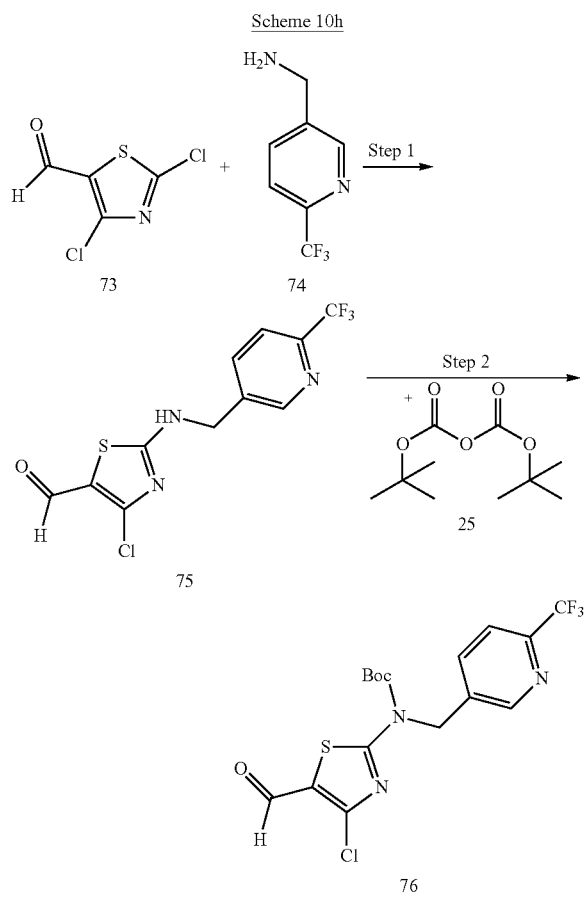

Step 1—Preparation of 4-chloro-2-[(6-trifluoromethyl-pyridin-3-ylmethyl)-amino]-thiazole-5-carbaldehyde (75)

To a solution of C-(6-trifluoromethyl-pyridin-3-yl)-methylamine (74, 1.0 g, 5.7 mmol) and N,N-diisopropylethylamine (2.0 mL, 11 mmol) in 100 mL of tetrahydrofuran, 2,4-dichloro-thiazole-5-carbaldehyde (73, 1.1 g, 6.2 mmol) in 10 mL of tetrahydrofuran was added dropwise at room temperature. The reaction mixture was stirred at room temperature overnight. The reaction mixture was poured into ice water, extracted with ethyl acetate, washed with brine, dried over sodium sulfate, filtered and the filtrate concentrated under vacuum. The resulting material was purified by silica gel column chromatography, eluting with ethyl acetate in hexane. Appropriate fractions were combined and concentrated under vacuum to provide the desired compound (75, 1.2 g, 66%). MS (ESI)=[M+H$^+$]$^+$=322.11

Step 2—Preparation of (4-chloro-5-formyl-thiazol-2-yl)-(6-trifluoromethyl-pyridin-3-ylmethyl)-carbamic acid tert-butyl ester (76)

4-Chloro-2-[(6-trifluoromethyl-pyridin-3-ylmethyl)-amino]-thiazole-5-carbaldehyde (75, 1.2 g, 3.7 mmol), di-tert-butyldicarbonate (25, 0.98 g, 4.5 mol), 4-dimethylaminopyridine (0.09 g, 0.7 mmol) and N,N-diisopropylethylamine (0.96 g, 7.5 mmol) were combined in 170 mL of dichloromethane and stirred at room temperature overnight. The reaction mixture was poured into ice water, extracted with dichloromethane, washed with brine, dried over sodium sulfate, filtered and the filtrate concentrated under vacuum. The resulting material was purified by silica gel column chromatography, eluting with ethyl acetate in hexane. Appropriate fractions were combined and concentrated under vacuum to provide the desired compound as a yellow solid (76, 1.5 g, 95%).

Additional aldehydes are prepared similarly to the protocol of Scheme 100 h, as shown in the following table, where Step 1 and Step 2 reactants are provided in columns 1 and 2, respectively, with the resulting Boc protected aldehyde provided in column 3. Reaction conditions are similar to those described for Scheme 10 h, and may vary slightly for each step, for example, any of the solvents, reagents, reaction times, temperatures, work up conditions, or other reaction parameters may be varied employing alternate solvents, reagents, reaction times, temperatures, work up conditions, and the like, as are readily available to one skilled in the art. Compounds in the following table were characterized by $^1$H and $^{13}$C NMR spectroscopy as well as mass spectrometry.

| Step 1 | Step 2 | Final aldehyde |
|---|---|---|
| | | |

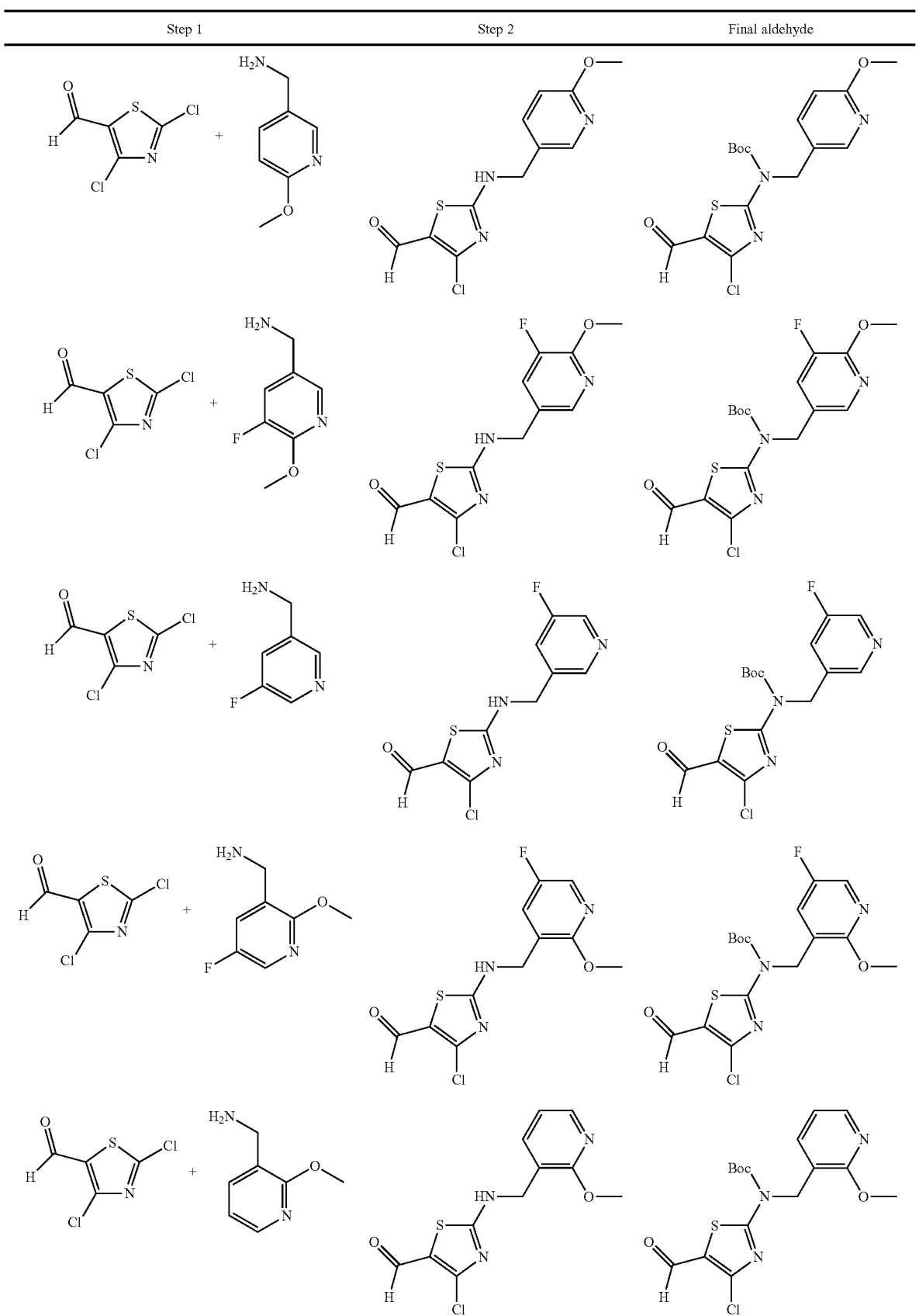

-continued
| Step 1 | Step 2 | Final aldehyde |
|---|---|---|
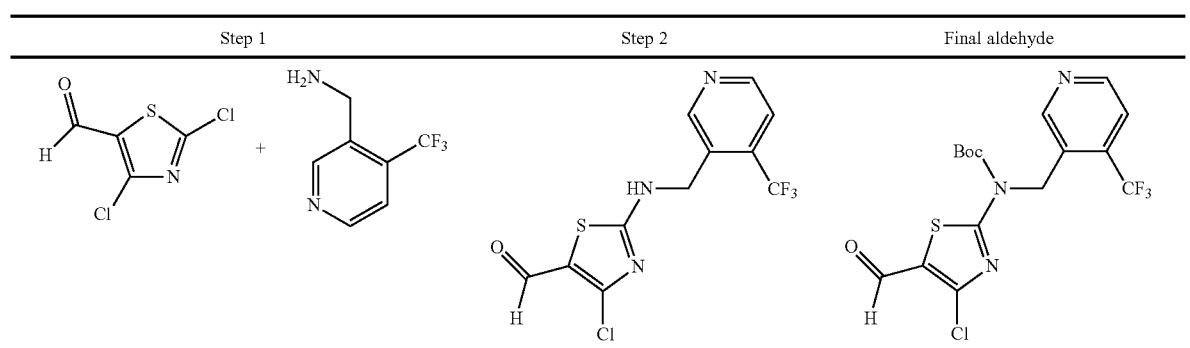
(6-fluoro-5-formyl-pyridin-2-yl)-(4-methoxy-benzyl)-carbamic acid tert-butyl ester 83 was prepared in six steps from 2,6-difluoro-pyridine 49 as shown in Scheme 10i.
Scheme 10i
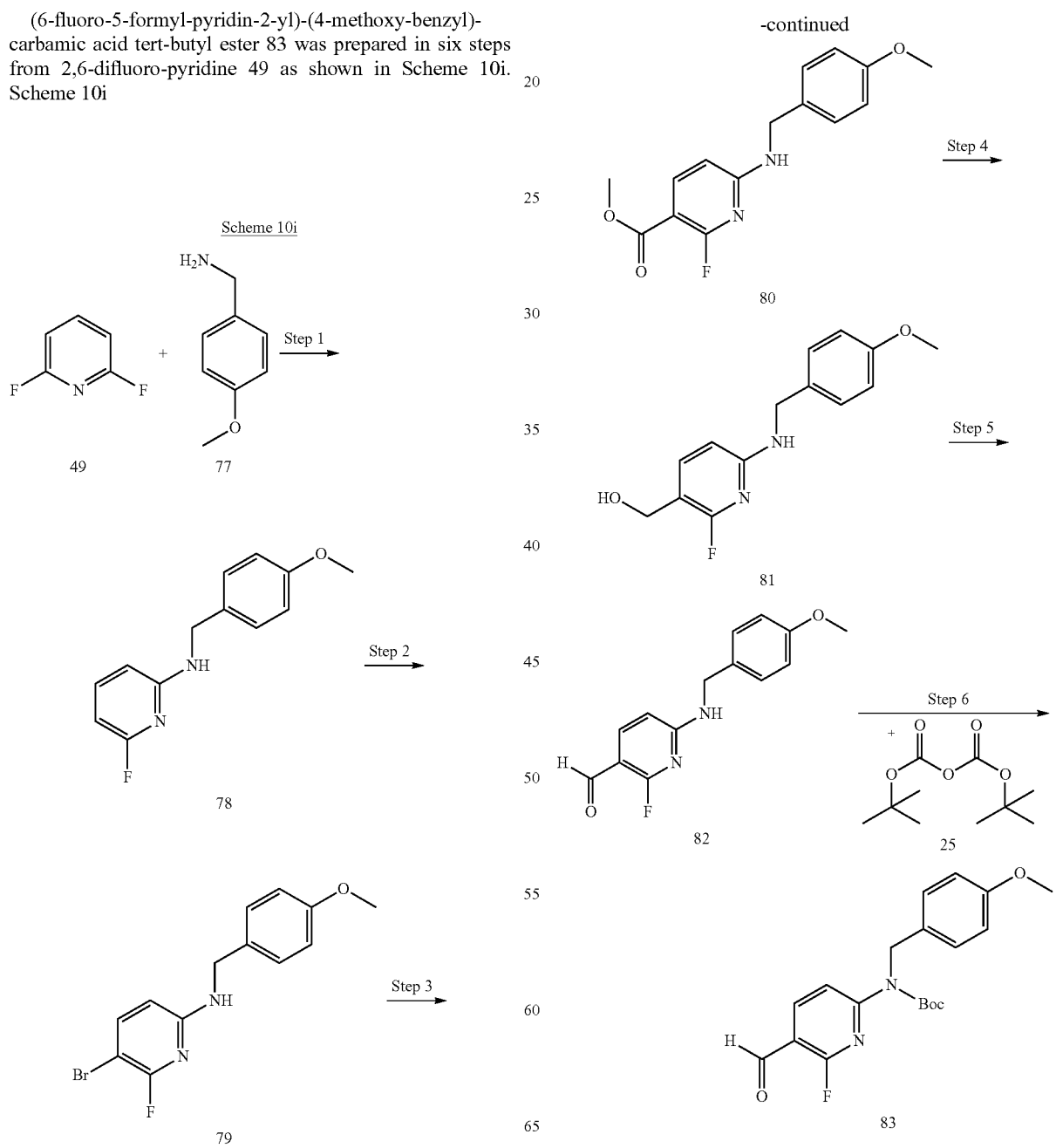

Step 1—Preparation of (6-fluoro-pyridin-2-yl)-(4-methoxy-benzyl)-amine (78)

To 2,6-difluoro-pyridine (49, 100 g, 869 mmol) in 500 mL of N-methylpyrrolidinone, 4-methoxy-benzylamine (77, 136 mL, 1.043 mol) and N,N-diisopropylethylamine (304 mL, 1.738 mol) were added. The reaction was stirred at 90° C. overnight, then poured into 8 L of water. The precipitate collected by filtration and washed with water, then taken up in ethyl acetate and washed with water. The organic layer was dried over sodium sulfate, filtered and the filtrate concentrated under vacuum. The resulting material was triturated with heptane and collected by filtration to provide the desired compound (78, 151 g, 650 mmol, 74.8% yield).

Step 2—Preparation of (5-bromo-6-fluoro-pyridin-2-yl)-(4-methoxy-benzyl)-amine (79)

To (6-fluoro-pyridin-2-yl)-(4-methoxy-benzyl)-amine (78, 151 g, 650 mmol) in 4 L of acetonitrile under nitrogen, N-bromosuccinimide (116 g, 650 mmol) was added in portions. After reacting for 2 hours, the solvent was removed under vacuum and the residue taken up in ethyl acetate, then poured into aqueous sodium thiosulfate. The organic layer was washed with warm water, dried over sodium sulfate, filtered and the filtrate concentrated under vacuum. The resulting material was crystallized from heptane to provide the desired compound (79, 172 g, 553 mmol, 85% yield).

Step 3—Preparation of 2-fluoro-6-(4-methoxy-benzylamino)-nicotinic acid methyl ester (80)

To (5-bromo-6-fluoro-pyridin-2-yl)-(4-methoxy-benzyl)-amine (79, 85 g, 273 mmol) in 1.5 L methanol in a 2 L Parr flask, triethylamine (77 mL, 546 mmol) and [1,1'-bis(diphenylphosphino)ferrocene]dichloropalladium(II) (5.80 g, 7.10 mmol) were added. The reaction was heated at 100° C. under 100 psi of carbon monoxide overnight. The reaction was cooled and filtered through celite and the filtrate was concentrated under vacuum. The resulting material was dissolved in dichloromethane and passed through a plug of silica gel, eluting with ethyl acetate. The solvent was removed under vacuum to provide the desired compound as a peach colored solid (80, 70 g, 241 mmol, 88% yield).

Step 4—Preparation of [2-fluoro-6-(4-methoxy-benzylamino)-pyridin-3-yl]-methanol (81)

To 2-fluoro-6-(4-methoxy-benzylamino)-nicotinic acid methyl ester (80, 70 g, 241 mmol) in 350 mL of tetrahydrofuran, lithium aluminum hydride (362 mL, 1 M in tetrahydrofuran, 362 mmol) was added dropwise while cooling. The reaction was stirred at room temperature for 2 hours, then quenched with dropwise addition of 14 mL of water, 14 mL of 15% aqueous sodium hydroxide, and 42 mL of water, sequentially. Methyl tert-butyl ether (500 mL) was added and the solids removed by filtration. The filtrate was concentrated under vacuum and the resulting solid was dissolved in dichloromethane, passed through a plug of silica gel and eluted with 50-100% ethyl acetate in heptane. The solvent was removed under vacuum to provide the desired compound as an off-white solid (81, 63 g, 240 mmol, 100% yield).

Step 5—Preparation of 2-fluoro-6-(4-methoxy-benzylamino)-pyridine-3-carbaldehyde (82)

To [2-fluoro-6-(4-methoxy-benzylamino)-pyridin-3-yl]-methanol (81, 63 g, 240 mmol) in 1.25 L of ethyl acetate, manganese(IV) oxide (210 g, 2.416 mol) was added. The reaction was stirred overnight at room temperature, then filtered through celite and the celite rinsed with ethyl acetate. The combined filtrates were concentrated under vacuum and the resulting solid was triturated with heptane and collected by filtration to provide the desired compound as a white solid (82, 62 g, 238 mmol, 99% yield).

Step 6—Preparation of (6-fluoro-5-formyl-pyridin-2-yl)-(4-methoxy-benzyl)-carbamic acid tert-butyl ester (83)

2-Fluoro-6-(4-methoxy-benzylamino)-pyridine-3-carbaldehyde (82, 62 g, 238 mmol), 600 mL of tert-butyl alcohol, di-tert-butyldicarbonate (25, 83 mL, 357 mmol) and dimethylaminopyridine (2.91 g, 23.82 mmol) were combined in a round bottom flask. The reaction was stirred at 30° C. overnight and then concentrated under vacuum. The resulting material was purified by silica gel column chromatography, eluting with 0-20% ethyl acetate in hexane. Appropriate fractions were combined and the solvents removed under vacuum to provide the desired compound (83, 54 g, 150 mmol, 62.9% yield).

(5-Fluoro-2-methoxy-pyridin-3-ylmethyl)-(5-formyl-pyridin-2-yl)-carbamic acid tert-butyl ester 94 was prepared in four steps from 6-amino-nicotinic acid methyl ester 90 and 5-fluoro-2-methoxy-pyridine-3-carbaldehyde 37 as shown in Scheme 10k.

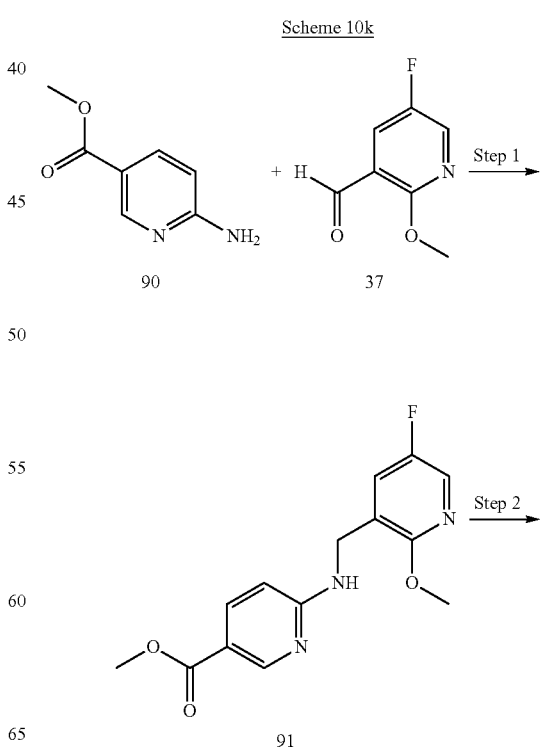

Scheme 10k

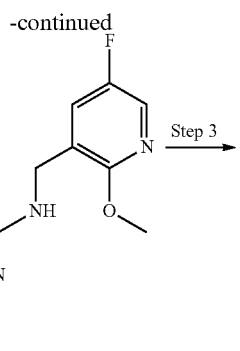

92

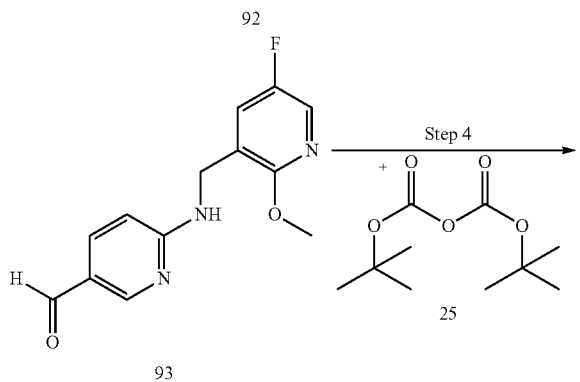

93

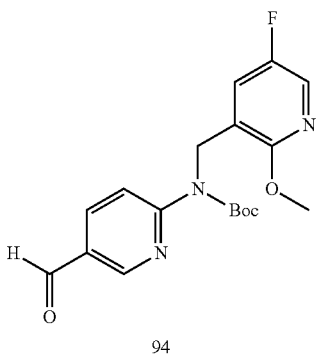

94

Step 1—Preparation of 6-[(5-fluoro-2-methoxy-pyridin-3-ylmethyl)-amino]-nicotinic acid methyl ester (91)

In a round bottom flask, 6-amino-nicotinic acid methyl ester (90, 0.678 g, 4.46 mmol) was combined with 5-fluoro-2-methoxy-pyridine-3-carbaldehyde (37, 0.532 g, 3.43 mmol), 10.6 mL of acetonitrile, trifluoroacetic acid (1.32 mL, 17.1 mmol) and triethylsilane (3.29 mL, 20.6 mol). The reaction was heated to reflux for 3 hours, then poured into water and extracted with ethyl acetate. The organic layer was washed with brine, dried over sodium sulfate, filtered and the filtrate concentrated under vacuum. The resulting material was purified by silica gel column chromatography eluting with ethyl acetate and hexane. Appropriate fractions were combined and concentrated under vacuum to provide the desired compound (91, 832 mg). MS (ESI) [M+H$^+$]$^+$=292.4.

Step 2—Preparation of {6-[(5-fluoro-2-methoxy-pyridin-3-ylmethyl)-amino]-pyridin-3-yl}-methanol (92)

To 6-[(5-fluoro-2-methoxy-pyridin-3-ylmethyl)-amino]-nicotinic acid methyl ester (91, 0.825 g, 2.83 mmol) in 11 mL of tetrahydrofuran, lithium tetrahydroaluminate (5.66 mL, 1.0 M in tetrahydrofuran, 5.66 mmol) was added at −40° C. under nitrogen. The reaction was allowed to warm to room temperature and stirred overnight. The reaction was poured into aqueous 1M sodium hydroxide, then neutralized with aqueous 1M hydrochloric acid. The solids were filtered out through celite, the celite washed with ethyl acetate and tetrahydrofuran. The isolated aqueous layer was extracted with ethyl acetate and all organic layers were combined, washed with brine, then dried over sodium sulfate, filtered and the filtrate was concentrated under vacuum. The resulting material was purified by silica gel column chromatography eluting with ethyl acetate and hexane. Appropriate fractions were combined and concentrated under vacuum to provide the desired compound (92, 357 mg). MS (ESI) [M+H$^+$]$^+$=264.4.

Step 3—Preparation of 6-[(5-fluoro-2-methoxy-pyridin-3-ylmethyl)-amino]-pyridine-3-carbaldehyde (93)

To {6-[(5-fluoro-2-methoxy-pyridin-3-ylmethyl)-amino]-pyridin-3-yl}-methanol (92, 0.353 g, 1.34 mmol) dissolved in 8 mL of tetrahydrofuran, Dess-Maritn periodinane (0.626 g, 1.47 mmol) was added and the reaction stirred at room temperature for 1 hour. The reaction was poured into aqueous saturated sodium thiosulfite and the aqueous layer was extracted with ethyl acetate. The combined organic layer was washed with brine, dried over sodium sulfate, filtered and the filtrate concentrated under vacuum. The resulting material was purified by silica gel column chromatography eluting with ethyl acetate and hexane. Appropriate fractions were combined and concentrated under vacuum to provide the desired compound. MS (ESI) [M+H$^+$]$^+$=262.3.

Step 4—Preparation of (5-fluoro-2-methoxy-pyridin-3-ylmethyl)-(5-formyl-pyridin-2-yl)-carbamic acid tert-butyl ester (94)

To 6-[(5-fluoro-2-methoxy-pyridin-3-ylmethyl)-amino]-pyridine-3-carbaldehyde (93, 0.310 g, 1.19 mmol) dissolved in 4.72 mL of tetrahydrofuran, 4-dimethylaminopyridine (14.5 mg, 0.119 mmol) was added, followed by di-tert-butyl-dicarbonate (25, 0.285 g, 1.30 mmol). The reaction was stirred at room temperature overnight, then concentrated under vacuum. The resulting material was purified by silica gel column chromatography eluting with ethyl acetate and hexane. Appropriate fractions were combined and concentrated under vacuum to provide the desired compound (94, 301 mg).

(5-Fluoro-6-methoxy-pyridin-3-ylmethyl)-(5-formyl-pyridin-2-yl)-carbamic acid tert-butyl ester 95

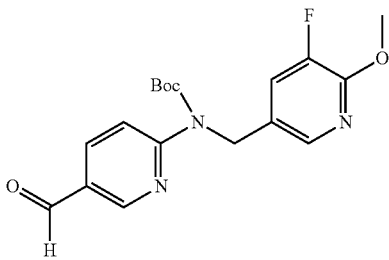

95 was prepared similarly to the protocol of Scheme 10k, replacing 5-fluoro-2-methoxy-pyridine-3-carbaldehyde 37 with 5-fluoro-6-methoxy-pyridine-3-carbaldehyde in step 1.

5-(3-Chloro-benzylamino)-2-methyl-2H-pyrazole-3-carbaldehyde 96

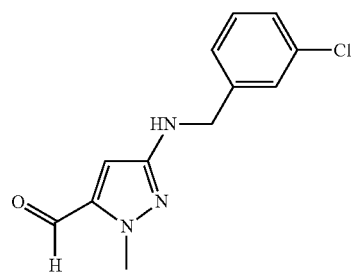

96 was prepared similarly to the protocol of Scheme 10k, steps 1-2 and Scheme 100i, step 3, where 6-amino-nicotinic acid methyl ester 90 was replaced with 5-amino-2-methyl-2H-pyrazole-3-carboxylic acid methyl ester and 5-fluoro-2-methoxy-pyridine-3-carbaldehyde 37 was replaced with 3-chloro-benzaldehyde in step 1.

5-(4-Fluoro-benzylamino)-2-(4-methoxy-benzyl)-2H-pyrazole-3-carbaldehyde 113 was prepared in nine steps from 1H-pyrazole-3,5-dicarboxylic acid 101 as shown in Scheme 10n.

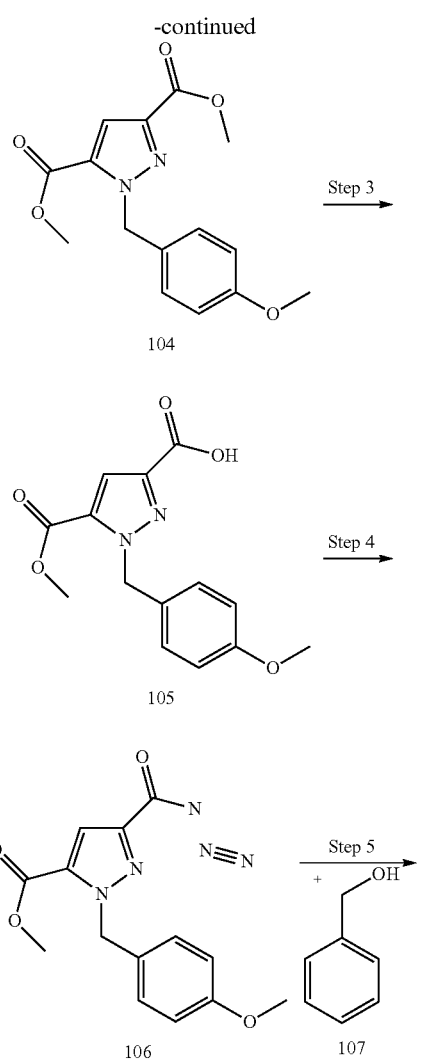

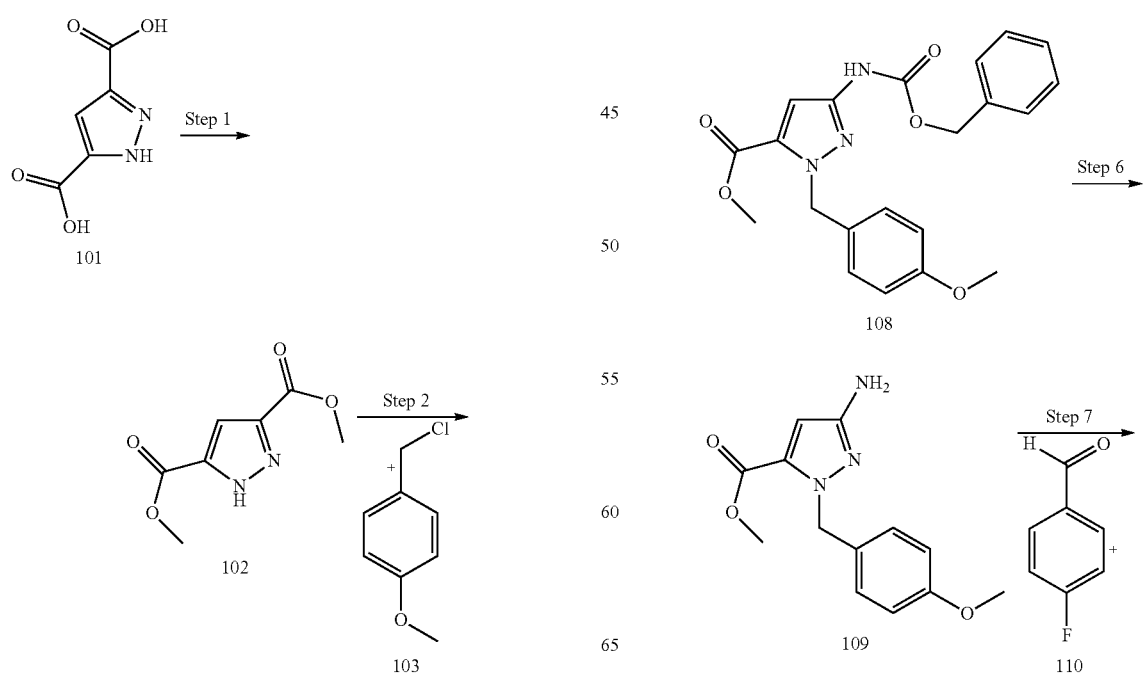

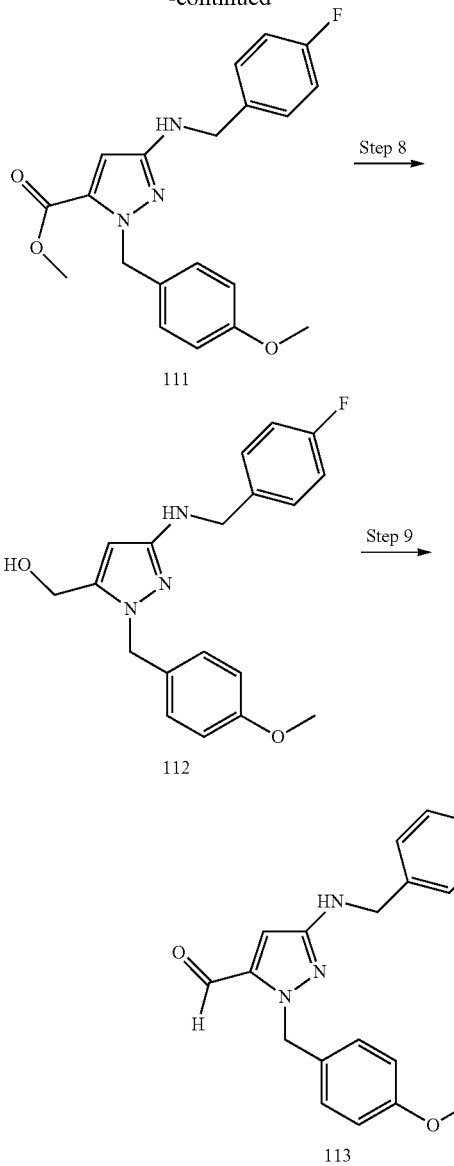

Step 1—Preparation of 1H-pyrazole-3,5-dicarboxylic acid dimethyl ester (102)

In a round bottom flask, 1H-pyrazole-3,5-dicarboxylic acid, hydrate (101, 21.1 g, 121 mmol) was combined with 350 mL of methanol and 10 mL of hydrochloric acid was added. The reaction was stirred at reflux overnight and the following day at room temperature. The reaction was concentrated under vacuum and the solid washed with ethyl acetate and hexanes to provide the desired compound. MS (ESI) [M+H$^+$]$^+$=185.

Step 2—Preparation of 1-(4-methoxy-benzyl)-1H-pyrazole-3,5-dicarboxylic acid dimethyl ester (104)

In a round bottom flask, 1H-pyrazole-3,5-dicarboxylic acid dimethyl ester (102, 15.0 g, 81.4 mmol) was combined with 1500 mL of acetone and potassium carbonate (15 g, 110 mmol). 1-Chloromethyl-4-methoxy-benzene (103, 10.0 mL, 73.8 mmol) was added and the reaction was stirred at 60° C. overnight. The mixture was separated into two flasks and continued stirring for 5 hours. The reactions were concentrated under vacuum and the solids washed with cold water and dried under vacuum to provide the desired compound (104, 20.48 g). $^1$H NMR was consistent with the compound structure.

Step 3—Preparation of 1-(4-methoxy-benzyl)-1H-pyrazole-3,5-dicarboxylic acid 5-methyl ester (105)

In a round bottom flask, 1-(4-methoxy-benzyl)-1H-pyrazole-3,5-dicarboxylic acid dimethyl ester (104, 28.5 g, 93.6 mmol) was combined with 100 mL of water and 20 mL of 1,4-dioxane. Sulfuric acid (5.5 mL, 100 mmol) and 2.0 mL of water were added and the reaction was stirred for 2 days at 60-70° C. The reaction was concentrated under vacuum until a precipitate formed. The solid was collected by filtration and washed with cold water several times to provide the desired compound. $^1$H NMR was consistent with the compound structure.

Step 4—Preparation of 5-azidocarbonyl-2-(4-methoxy-benzyl)-2H-pyrazole-3-carboxylic acid methyl ester (106)

In a round bottom flask, 1-(4-methoxy-benzyl)-1H-pyrazole-3,5-dicarboxylic acid 5-methyl ester (105, 5.48 g, 18.9 mmol) was combined with 20 mL of toluene and thionyl chloride (6 mL, 80 mmol). The reaction was heated at reflux for 40 minutes, then concentrated 2× from toluene and the resulting solid dried under vacuum. This was dissolved in 30.0 mL of acetone and sodium azide (3.8 g, 58 mmol) in 10.0 mL of water was added and stirred for 1 minute. The reaction was poured into 250 mL of ice water and stirred slowly. The resulting precipitate was collected by filtration and dried under vacuum to provide the desired compound.

Step 5—Preparation of 5-benzyloxycarbonylamino-2-(4-methoxy-benzyl)-2H-pyrazole-3-carboxylic acid methyl ester (108)

In a round bottom flask, 5-azidocarbonyl-2-(4-methoxy-benzyl)-2H-pyrazole-3-carboxylic acid methyl ester (106, 5.6 g, 18.0 mmol) was combined with 30 mL of toluene and benzyl alcohol (107, 1.91 mL, 18.5 mmol) was added and the reaction heated at reflux for 1 hour. The reaction was concentrated under vacuum and the resulting material washed with 2× methanol to provide the desired compound as a white solid. $^1$H NMR was consistent with the compound structure.

Step 6—Preparation of 5-amino-2-(4-methoxy-benzyl)-2H-pyrazole-3-carboxylic acid methyl ester (109)

In a round bottom flask, 5-benzyloxycarbonylamino-2-(4-methoxy-benzyl)-2H-pyrazole-3-carboxylic acid methyl ester (108, 2.3 g, 5.8 mmol) was combined with 30 mL of methanol and 10 mL of tetrahydrofuran under nitrogen and 10% palladium on carbon (0.23 g, 13.0 mmol) was added. The reaction was stirred under hydrogen at 1 atmosphere for 2 hours. The reaction was filtered and the filtrate concentrated under vacuum to provide the desired compound (109, 1.4 g).

Step 7—Preparation of 5-(4-fluoro-benzylamino)-2-(4-methoxy-benzyl)-2H-pyrazole-3-carboxylic acid methyl ester (111)

In a round bottom flask, 5-amino-2-(4-methoxy-benzyl)-2H-pyrazole-3-carboxylic acid methyl ester (109, 1.4 g, 5.4 mmol) was combined with 4-fluoro-benzaldehyde (110, 0.565 mL, 5.36 mmol), trifluoroacetic acid (2.06 mL, 26.8 mmol), triethylsilane (4.28 mL, 26.8 mmol) and 50 mL of acetonitrile. The reaction was stirred at room temperature for 15 minutes, then concentrated under vacuum, combined with aqueous potassium carbonate and extracted with ethyl acetate. The organic layer was dried over sodium sulfate, filtered and the filtrate concentrated under vacuum. The residue was recrystallized from a mixture of ethyl acetate and hexane to provide the desired compound (111, 1.6 g). $^1$H NMR was consistent with the compound structure.

Step 8—Preparation of [5-(4-fluoro-benzylamino)-2-(4-methoxy-benzyl)-2-(4-methoxy-benzyl)-2-pyrazol-3-yl]-methanol (112)

In a round bottom flask, 5-(4-fluoro-benzylamino)-2-(4-methoxy-benzyl)-2H-pyrazole-3-carboxylic acid methyl ester (111, 1.6 g, 4.3 mmol) was combined with 100 mL of tetrahydrofuran and cooled to −40° C. Lithium tetrahydroaluminate (4.8 mL, 1.0 M in tetrahydrofuran, 4.8 mmol) was added and the reaction allowed to warm to 10° C. The reaction was quenched with sodium sulfate decahydrate, then stirred for 2 hours, filtered through celite and the filtrate concentrated under vacuum. The resulting material was washed with ethyl acetate and hexanes and the solid dried to provide the desired compound. MS (ESI) [M+H$^+$]$^+$=342.30

Step 9—Preparation of 5-(4-fluoro-benzylamino)-2-(4-methoxy-benzyl)-2H-pyrazole-3-carbaldehyde (113)

In a round bottom flask, [5-(4-fluoro-benzylamino)-2-(4-methoxy-benzyl)-2H-pyrazol-3-yl]-methanol (112, 1.6 g, 4.2 mmol) was combined with 300 mL of dichloromethane and manganese(IV) oxide (0.61 g, 7.0 mmol) and stirred overnight under nitrogen. The reaction was filtered through celite and the filtrate concentrated under vacuum. The resulting material was purified by silica gel column chromatography, eluting with 10-100% ethyl acetate in hexane. Appropriate fractions were combined and concentrated under vacuum to provide the desired compound (113, 1.4 g). $^1$H NMR was consistent with the compound structure.

Example 11

Synthesis of (6-bromo-pyridin-3-ylmethyl)-[5-(5-chloro-1H-pyrrolo[2,3-b]pyridin-3-ylmethyl)-pyridin-2-yl]-amine P-2002

(6-Bromo-pyridin-3-ylmethyl)-[5-(5-chloro-1H-pyrrolo[2,3-b]pyridin-3-ylmethyl)-pyridin-2-yl]-amine P-2002 was prepared in five steps from 5-chloro-1H-pyrrolo[2,3-b]pyridine 1 as shown in Scheme 11.

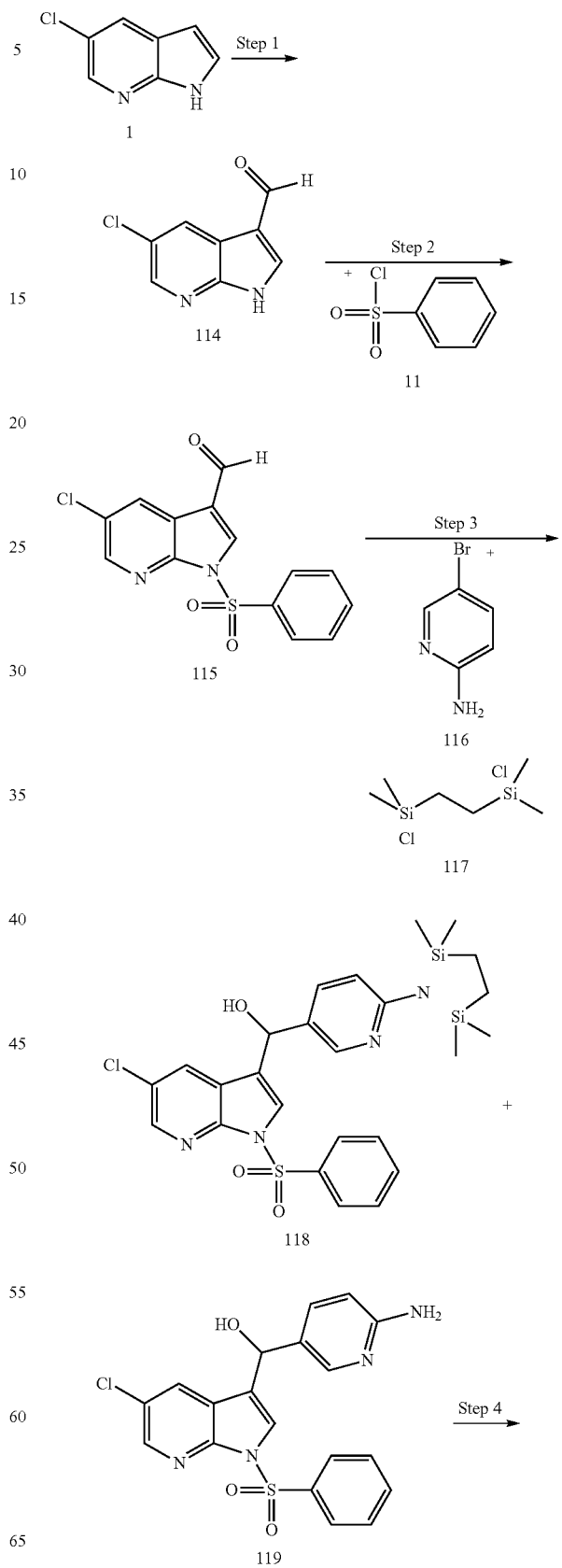

Scheme 11

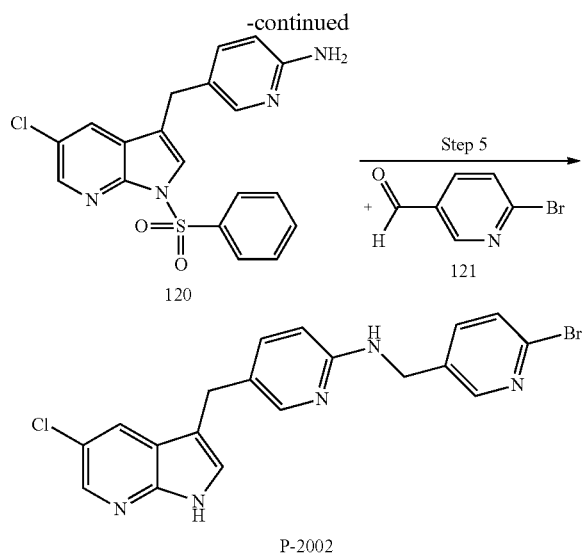

Step 1—Preparation of 5-chloro-1H-pyrrolo[2,3-b]pyridine-3-carbaldehyde (114)

In a round bottom flask, 5-chloro-1H-pyrrolo[2,3-b]pyridine (1, 10.0 g, 65.5 mmol) was combined with hexamethylenetetramine (11.9 g, 85.2 mmol), acetic acid (28.3 mL, 0.498 mol) and 56.7 mL of water. The reaction was heated at reflux overnight, then 200 mL of water was added. After 30 minutes, solid material was collected by filtration and dried to give the desired compound (114, 7.0 g).

Step 2—Preparation of 1-benzenesulfonyl-5-chloro-1H-pyrrolo[2,3-b]pyridine-3-carbaldehyde (115)

To 5-chloro-1H-pyrrolo[2,3-b]pyridine-3-carbaldehyde (114, 3.60 g, 19.9 mmol) in 100 mL of dichloromethane, potassium hydroxide (50 mL, 9M aqueous, 0.45 mol), tetrabutylammonium hydrogen sulfate (400 mg, 1.0 mmol) and benzenesulfonyl chloride (11, 2.9 mL, 23.0 mmol) were added. The reaction was stirred at room temperature for 3 hours, then poured into water and extracted with ethyl acetate. The organic layer was dried over sodium sulfate, filtered and the filtrate concentrated under vacuum. The resulting material was washed with ethyl acetate to provide the desired compound as a white solid (115, 2.3 g).

Step 3—Preparation of (1-benzenesulfonyl-5-chloro-1H-pyrrolo[2,3-b]pyridin-3-yl)-[6-(2,2,5,5-tetramethyl-[1,2,5]azadisilolidin-1-yl)-pyridin-3-yl]-methanol (118) and (6-amino-pyridin-3-yl)-(1-benzenesulfonyl-5-chloro-1H-pyrrolo[2,3-b]pyridin-3-yl)-methanol (119)

In a round bottom flask, 2-amino-5-bromopyridine (116, 3.10 g, 17.9 mmol) was combined with 80.0 mL of tetrahydrofuran under nitrogen at −78° C. and n-butyllithium (7.10 mL, 2.50 M in hexane, 17.8 mmol) was slowly added. After 30 minutes, 1,2-bis-(chloro-dimethyl-silanyl)-ethane (117, 3.90 g, 18.1 mmol) in 20 mL of tetrahydrofuran was added slowly, and the reaction was allowed to come to room temperature over an hour. The reaction was cooled to −78° C. and additional n-butyllithium (7.10 mL, 2.50 M in hexane, 17.8 mmol) was added. The reaction was stirred for 30 minutes at −78° C. and allowed to warm to room temperature over an hour. The reaction was cooled to −78° C. and additional n-butyllithium (7.50 mL, 2.50 M in hexane, 18.8 mmol) was added slowly. After 1 hour, 1-benzenesulfonyl-5-chloro-1H-pyrrolo[2,3-b]pyridine-3-carbaldehyde (115, 1.90 g, 5.92 mmol) in 30 mL of tetrahydrofuran was added and the reaction stirred at −78° C. for 2 hours, then allowed to warm to room temperature over 1 hour. The reaction was poured into water, extracted with ethyl acetate and the organic layer was dried over sodium sulfate, filtered and the filtrate concentrated under vacuum. The resulting material was purified by silica gel column chromatography eluting with 2-20% methanol in dichloromethane to provide a mixture of compounds (118, 1.7 g) and (119, 1.25 g). MS (ESI) [M+H$^+$]$^+$=554.4 for 118 and [M−H$^+$]$^+$=415.2 for 119.

Step 4—Preparation of 5-(1-benzenesulfonyl-5-chloro-1H-pyrrolo[2,3-b]pyridin-3-ylmethyl)-pyridin-2-ylamine (120)

To (1-benzenesulfonyl-5-chloro-1H-pyrrolo[2,3-b]pyridin-3-yl)-[6-(2,2,5,5-tetramethyl-[1,2,5]azadisilolidin-1-yl)-pyridin-3-yl]-methanol and (6-amino-pyridin-3-yl)-(1-benzenesulfonyl-5-chloro-1H-pyrrolo[2,3-b]pyridin-3-yl)-methanol (118, 119, 1.70/1.25 g mix, 2.41 mmol) in 25.0 mL of dichloromethane, triethylsilane (3.00 mL, 18.8 mmol) and trifluoroacetic acid (1.50 mL, 19.5 mmol) were added and the reaction stirred at room temperature overnight. The reaction was concentrated under vacuum, combined with aqueous potassium carbonate and extracted with ethyl acetate. The organic layer was dried over sodium sulfate, filtered and the filtrate concentrated under vacuum. The resulting material was purified by silica gel column chromatography eluting with 20-100% ethyl acetate in hexane to provide the desired compound (120, 0.70 g).

Step 5—Preparation of (6-bromo-pyridin-3-ylmethyl)-[5-(5-chloro-1H-pyrrolo[2,3-b]pyridin-3-ylmethyl)-pyridin-2-yl]-amine (P-2002)

To 5-(1-benzenesulfonyl-5-chloro-1H-pyrrolo[2,3-b]pyridin-3-ylmethyl)-pyridin-2-ylamine (120, 80.0 mg, 0.200 mmol) in 2.00 mL of ethanol and 0.10 mL of acetic acid, 6-bromo-pyridine-3-carbaldehyde (121, 100.0 mg, 0.538 mmol) and silica supported cyanoborohydride (0.50 g, 1.21 mmol/g) were added. The reaction was heated at 110° C. for 25 minutes in microwave. Sodium hydroxide (2.0 mL, 6.0 M aqueous) was added and the reaction heated at 100° C. for 10 minutes in microwave, then poured into aqueous ammonium chloride and extracted with ethyl acetate. The organic layer was separated, dried over sodium sulfate, filtered and the filtrate concentrated under vacuum. The resulting material was purified by silica gel column chromatography eluting with 20% ethyl acetate in hexane. Appropriate fractions were combined and the solvent removed under vacuum to provide the desired compound (P-2002, 26.6 mg). MS (ESI) [M+H$^+$]$^+$=427.7, 429.7.

(6-Chloro-pyridin-3-ylmethyl)-[5-(5-chloro-1H-pyrrolo[2,3-b]pyridin-3-ylmethyl)-(pyridin-2-yl]-amine P-2003, and [5-(5-chloro-1H-pyrrolo[2,3-b]pyridin-3-ylmethyl)-pyridin-2-yl]-(6-fluoro-pyridin-3-ylmethyl)-amine P-2004.

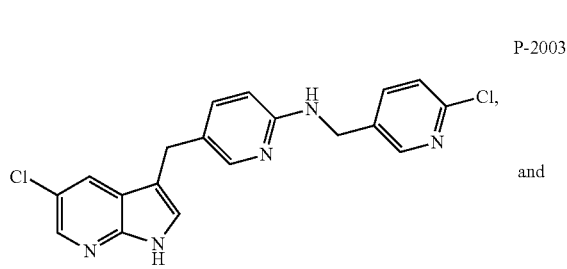

P-2003 and

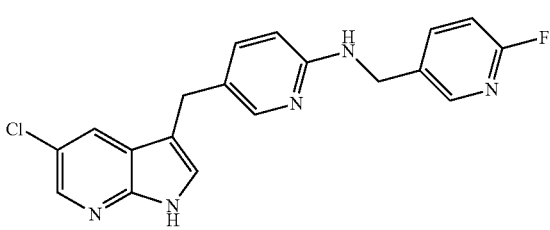

P-2004

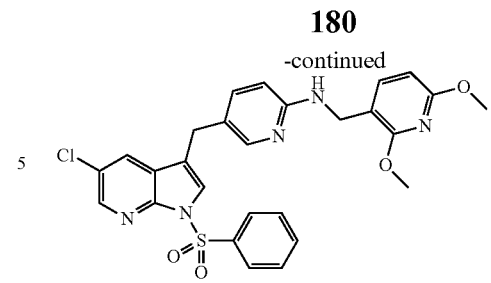

were prepared similarly to the protocol of Scheme 11, replacing 6-bromo-pyridine-3-carbaldehyde 121 with 6-chloro-pyridine-3-carbaldehyde and 6-fluoro-pyridine-3-carbaldehyde, respectively. MS (ESI) [M+H$^+$]$^+$=383.9, 385.9 (P-2003) and 367.9, 368.9 (P-2004).

Example 12

Synthesis of [5-(5-chloro-1H-pyrrolo[2,3-b]pyridin-3-ylmethyl)-pyridin-2-yl]-(2,6-dimethoxy-pyridin-3-ylmethyl)-amine P-1496

[5-(5-Chloro-1H-pyrrolo[2,3-b]pyridin-3-ylmethyl)-pyridin-2-yl]-(2,6-dimethoxy-pyridin-3-ylmethyl)-amine P-1496 was prepared in two steps from 5-(1-benzenesulfonyl-5-chloro-1H-pyrrolo[2,3-b]pyridin-3-ylmethyl)-pyridin-2-ylamine 120 and 2,6-dimethoxy-pyridine-3-carbaldehyde 121 as shown in Scheme 12.

Scheme 12

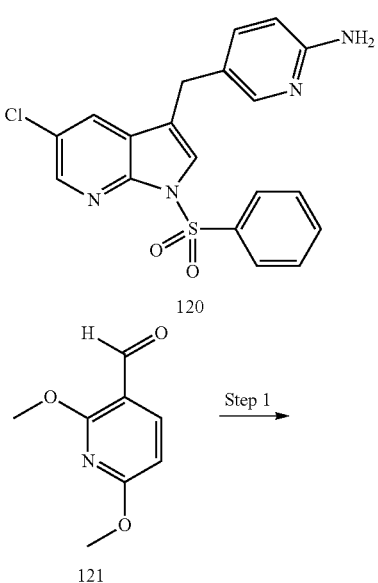

Step 1 — Preparation of [5-(1-Benzenesulfonyl-5-chloro-1H-pyrrolo[2,3-b]pyridin-3-ylmethyl)-pyridin-2-yl]-(2,6-dimethoxy-pyridin-3-ylmethyl)-amine (122)

To 5-(1-benzenesulfonyl-5-chloro-1H-pyrrolo[2,3-b]pyridin-3-ylmethyl)-pyridin-2-ylamine (120, 60.0 mg, 0.150 mmol) in 2.0 mL of ethanol and 0.1 mL of acetic acid, 2,6-dimethoxy-pyridine-3-carbaldehyde (121, 120 mg, 0.75 mmol) and silica supported cyanoborohydride (0.40 g, 0.484 mmol) were added. The reaction was heated to 100° C. for 18 minutes at 300 Watts in microwave, then poured into aqueous potassium carbonate and extracted with ethyl acetate. The organic layer was dried over sodium sulfate, filtered and the filtrate concentrated under vacuum. The resulting material was purified by silica gel column chromatography, eluting with 20% ethyl acetate in hexane. Appropriate fractions were combined and concentrated under vacuum to provide the desired compound (122, 60 mg).

Step 2 — Preparation of [5-(5-chloro-1H-pyrrolo[2,3-b]pyridin-3-ylmethyl)-pyridin-2-yl]-(2,6-dimethoxy-pyridin-3-ylmethyl)-amine (P-1496)

To [5-(1-Benzenesulfonyl-5-chloro-1H-pyrrolo[2,3-b]pyridin-3-ylmethyl)-pyridin-2-yl]-(2,6-dimethoxy-pyridin-3-ylmethyl)-amine (122, 60 mg, 0.11 mmol) in 10.0 mL of methanol, potassium hydroxide (0.20 g, 3.6 mmol) was added. The reaction was stirred at 60° C. for 4 hours, then poured into water and extracted with ethyl acetate. The organic layer was dried over sodium sulfate, filtered and the filtrate concentrated under vacuum. The resulting material was purified by silica gel column chromatography, eluting with 20-100% ethyl acetate in hexane. Appropriate fractions were combined and concentrated under vacuum to provide the desired compound (P-1496, 26.1 mg). MS (ESI) [M+H$^+$]$^+$=410.0.

Additional compounds are prepared following the protocol of Scheme 12, where conditions may vary, for example, any of the solvents, reaction times, reagents, temperatures, work up conditions, or other reaction parameters may be varied employing alternate solvents, reagents, reaction times, temperatures, work up conditions, and the like, as are readily available to one skilled in the art. For example, without limitation, tetrabutylammonium fluoride trihydrate is used in place of potassium hydroxide in step 2. Compounds are prepared optionally substituting 2,6-dimethoxy-pyridine-3-carbaldehyde 121 with a suitable aldehyde and optionally substituting 5-(1-benzenesulfonyl-5-chloro-1H-pyrrolo[2,3-b]pyridin-3-ylmethyl)-pyridin-2-ylamine 120 with a suitable 1-benzenesulfonyl protected 1H-pyrrolo[2,3-b]pyridine. The following compounds are made using this procedure. Compounds in the following table were characterized by ¹H and ¹³C NMR spectroscopy as well as mass spectrometry.

(6-Chloro-pyridin-3-ylmethyl)-[5-(1H-pyrrolo[2,3-b]pyridin-3-ylmethyl)-pyridin-2-yl]-amine (P-1498), (5-Fluoro-6-methoxy-pyridin-3-ylmethyl)-[5-(1H-pyrrolo[2,3-b]pyridin-3-ylmethyl)-pyridin-2-yl]-amine (P-1502), (5-Fluoro-2-methoxy-pyridin-3-ylmethyl)-[5-(1H-pyrrolo[2,3-b]pyridin-3-ylmethyl)-pyridin-2-yl]-amine (P-1503),

[5-(1H-Pyrrolo[2,3-b]pyridin-3-ylmethyl)-pyridin-2-yl]-(4-trifluoromethyl-pyridin-3-ylmethyl)-amine (P-1504), and

[5-(5-Chloro-1H-pyrrolo[2,3-b]pyridin-3-ylmethyl)-pyridin-2-yl]-(5-fluoro-2-methoxy-pyridin-3-ylmethyl)-amine (P-1505).

The following table indicates the 1-benzenesulfonyl protected 1H-pyrrolo[2,3-b]pyridine (column 2) and aldehyde compound (column 3) used in step 1 to afford the desired compound (column 4). The compound number is provided in column 1, and the observed mass is in column 5.

| Comp. number | 1H-pyrrolo[2,3-b]pyridine | Aldehyde structure | Compound structure | MS (ESI) [M + H⁺]⁺ |
|---|---|---|---|---|
| P-1498 | 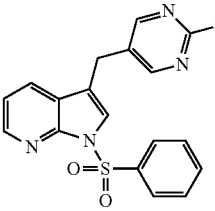 | 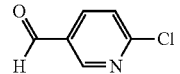 | 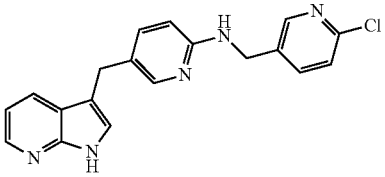 [SMILES: Clc1ccc(CNc2ccc(Cc3c[nH]c4ncccc34)cn2)cn1] | |
| P-1502 | 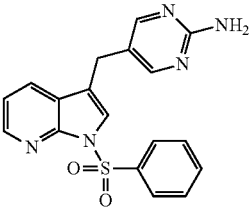 [SMILES: Nc1ncc(Cc2cn(S(=O)(=O)c3ccccc3)c3ncccc23)cn1] | 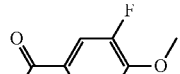 | 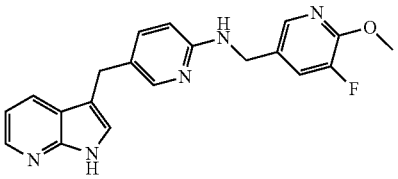 [SMILES: COc1ncc(CNc2ccc(Cc3c[nH]c4ncccc34)cn2)cc1F] | |
| P-1503 | 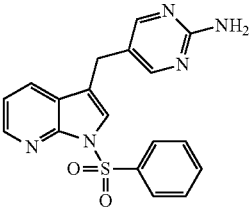 [SMILES: Nc1ncc(Cc2cn(S(=O)(=O)c3ccccc3)c3ncccc23)cn1] | 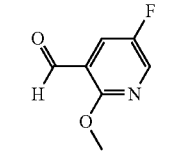 | 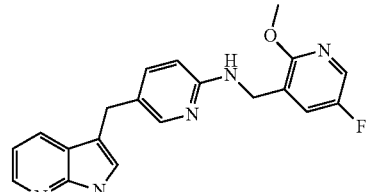 | |
| P-1504 | 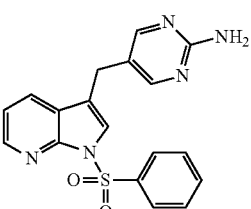 | 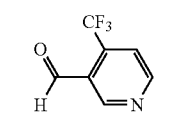 | 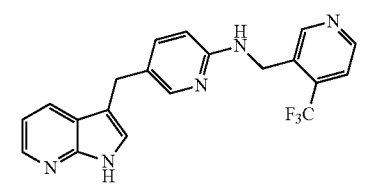 [SMILES: FC(F)(F)c1ccncc1CNc1ccc(Cc2c[nH]c3ncccc23)cn1] | |
| P-1505 | 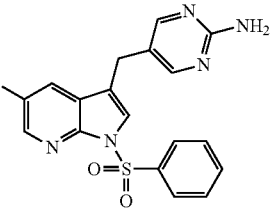 | 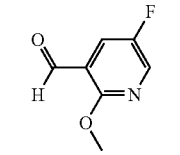 | 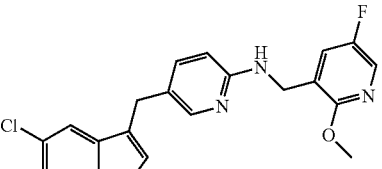 | |

Example 13

Synthesis of (5-fluoro-2-methoxy-pyridin-3-ylmethyl)-[5-(5-methoxy-1H-pyrrolo[2,3-b]pyridin-3-ylmethyl)-pyrimidin-2-yl]-amine P-1599

(5-Fluoro-2-methoxy-pyridin-3-ylmethyl)-[5-(5-methoxy-1H-pyrrolo[2,3-b]pyridin-3-ylmethyl)-pyrimidin-2-yl]-amine P-1599 is prepared in three steps from 1-benzenesulfonyl-3-iodo-5-methoxy-1H-pyrrolo[2,3-b]pyridine 16 and (5-fluoro-2-methoxy-pyridin-3-ylmethyl)-(5-formyl-pyrimidin-2-yl)-carbamic acid tert-butyl ester 123 as shown in Scheme 13.

Scheme 13

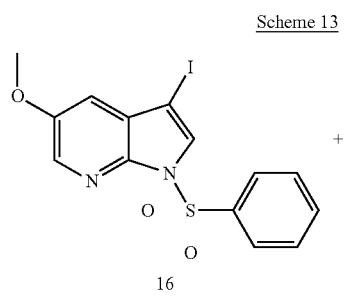

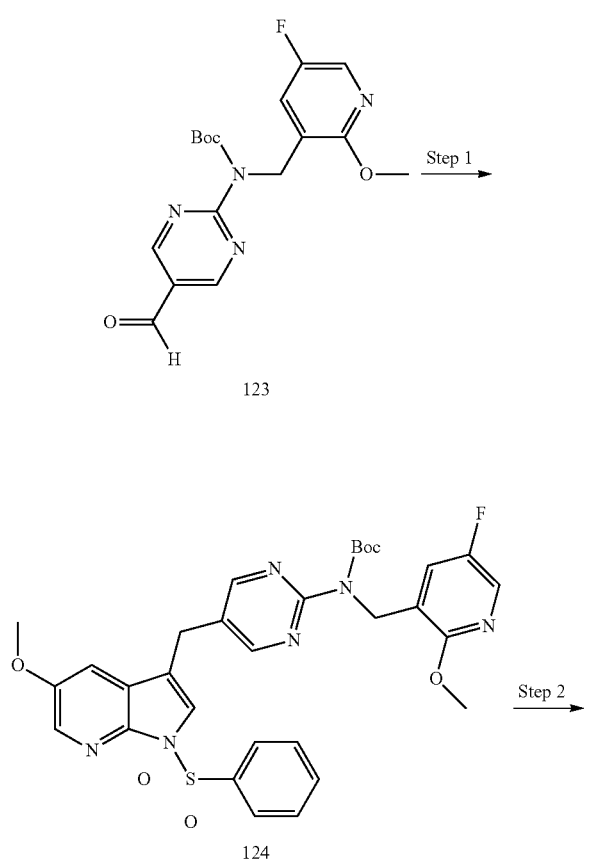

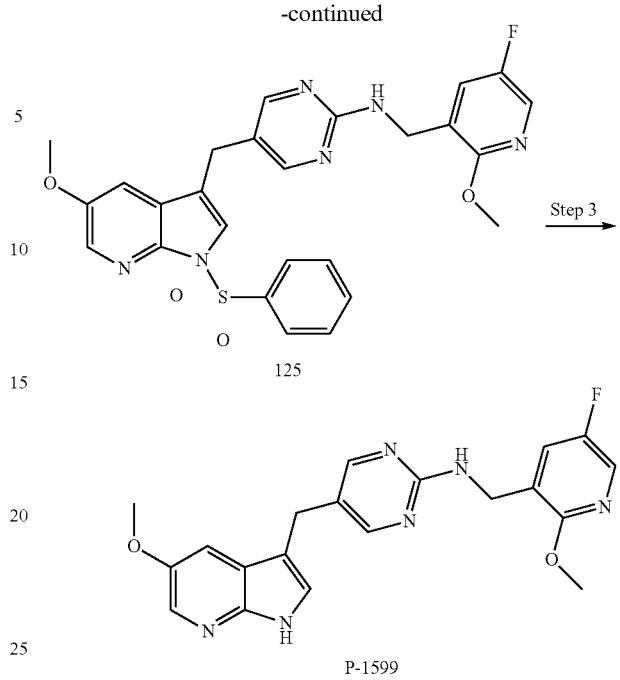

Step 1—Preparation of ({5-[(1-benzenesulfonyl-5-methoxy-1H-pyrrolo[2,3-b]pyridin-3-yl)-hydroxymethyl]-pyrimidin-2-yl}-(5-fluoro-2-methoxy-pyridin-3-ylmethyl)-carbamic acid tert-butyl ester (124)

To a solution of 1-benzenesulfonyl-3-iodo-5-methoxy-1H-pyrrolo[2,3-b]pyridine (16, 1 equivalent) in 4.0 mL of tetrahydrofuran, isopropylmagnesium chloride (2.0 M in tetrahydrofuran, 1 equivalent) is added slowly at −50° C. The reaction is allowed to warm to 5° C. over 70 minutes, then cooled to −45° C. and (5-fluoro-2-methoxy-pyridin-3-ylmethyl)-(5-formyl-pyrimidin-2-yl)-carbamic acid tert-butyl ester (123, 0.78 equivalent) in 2.0 mL of tetrahydrofuran is added. The reaction is allowed to warm to room temperature over 1 hour, then poured into aqueous ammonium chloride and extracted with ethyl ether. The organic layer is dried over sodium sulfate, filtered and the filtrate concentrated under vacuum. The resulting material is purified by silica gel column chromatography eluting with 20-100% ethyl acetate in hexane. Appropriate fractions are combined and concentrated under vacuum to provide the desired compound.

Step 2—Preparation of [5-(1-benzenesulfonyl-5-methoxy-1H-pyrrolo[2,3-b]pyridin-3-ylmethyl)-pyrimidin-2-yl]-(5-fluoro-2-methoxy-pyridin-3-ylmethyl)-amine (125)

To {5-[(1-benzenesulfonyl-5-methoxy-1H-pyrrolo[2,3-b]pyridin-3-yl)-hydroxy-methyl]-pyrimidin-2-yl}-(5-fluoro-2-methoxy-pyridin-3-ylmethyl)-carbamic acid tert-butyl ester (124, 1 equivalent) in 10.0 mL of acetonitrile, triethylsilane (15.6 equivalents) and trifluoroacetic acid (16.9 equivalents) are added. The reaction is heated at 80° C. for 2 hours, then poured into aqueous potassium carbonate and extracted with ethyl acetate. The organic layer is dried over sodium sulfate, filtered and the filtrate concentrated under vacuum to provide the desired compound, which is used in the next step without further purification.

Step 3—Preparation of (5-fluoro-2-methoxy-pyridin-3-ylmethyl)-[5-(5-methoxy-1H-pyrrolo[2,3-b]pyridin-3-ylmethyl)-pyrimidin-2-yl]-amine (P-1599)

To [5-(1-benzenesulfonyl-5-methoxy-1H-pyrrolo[2,3-b]pyridin-3-ylmethyl)-pyrimidin-2-yl]-(5-fluoro-2-methoxy-pyridin-3-ylmethyl)-amine (125, 1 equivalent) in 15.0 mL of tetrahydrofuran, tetrabutylammonium fluoride trihydrate (2 equivalent) is added. The reaction is stirred at room temperature overnight, then poured into water and extracted with ethyl acetate. The organic layer is dried over sodium sulfate, filtered and the filtrate concentrated under vacuum. The resulting material is purified by silica gel column chromatography eluting with 20-100% ethyl acetate in hexane. Appropriate fractions are combined and concentrated under vacuum to provide the desired compound as a yellow solid.

Additional compounds are prepared following the protocol of Scheme 13, where conditions may vary, for example, any of the solvents, reaction times, reagents, temperatures, work up conditions, or other reaction parameters may be varied employing alternate solvents, reagents, reaction times, temperatures, work up conditions, and the like, as are readily available to one skilled in the art. Compounds are prepared using a suitable Boc protected aldehyde in place of (5-fluoro-2-methoxy-pyridin-3-ylmethyl)-(5-formyl-pyrimidin-2-yl)-carbamic acid tert-butyl ester 123 in step 1. The following compounds are made using this procedure. Compounds in the following table were characterized by $^1$H and $^{13}$C NMR spectroscopy as well as mass spectrometry.

(5-Fluoro-6-methoxy-pyridin-3-ylmethyl)-[5-(5-methoxy-1H-pyrrolo[2,3-b]pyridin-3-ylmethyl)-pyrimidin-2-yl]-amine (P-1600),
(5-Fluoro-pyridin-3-ylmethyl)-[5-(5-methoxy-1H-pyrrolo[2,3-b]pyridin-3-ylmethyl)-pyrimidin-2-yl]-amine (P-1601),
(6-Chloro-pyridin-3-ylmethyl)-[5-(5-methoxy-1H-pyrrolo[2,3-b]pyridin-3-ylmethyl)-pyrimidin-2-yl]-amine (P-1602),
[5-(5-Methoxy-1H-pyrrolo[2,3-b]pyridin-3-ylmethyl)-pyrimidin-2-yl]-(4-trifluoromethyl-pyridin-3-ylmethyl)-amine (P-1603),
(6-Methoxy-pyridin-3-ylmethyl)-[5-(5-methoxy-1H-pyrrolo[2,3-b]pyridin-3-ylmethyl)-pyrimidin-2-yl]-amine (P-1604),
[5-(5-Methoxy-1H-pyrrolo[2,3-b]pyridin-3-ylmethyl)-pyrimidin-2-yl]-(6-trifluoromethyl-pyridin-3-ylmethyl)-amine (P-1605),
(2-Methoxy-pyridin-3-ylmethyl)-[5-(5-methoxy-1H-pyrrolo[2,3-b]pyridin-3-ylmethyl)-pyrimidin-2-yl]-amine (P-1606),
5-[(5-bromo-1H-pyrrolo[2,3-b]pyridin-3-yl)methyl]-6-fluoro-N-[(5-fluoro-6-methoxy-3-pyridyl)methyl]pyridin-2-amine (P-2203), and
3-[[2-fluoro-6-[(5-fluoro-6-methoxy-3-pyridyl)methylamino]-3-pyridyl]methyl]-1H-pyrrolo[2,3-b]pyridine-5-carbonitrile (P-2204).

The following table indicates the aldehyde compound (column 2) used in step 1 to afford the desired compound (column 3). The compound number is provided in column 1, and the observed mass is in column 4.

| Compound number | Aldehyde | Compound | MS (ESI) [M + H$^+$]$^+$ |
|---|---|---|---|
| P-1600 | | | |
| P-1601 | | | |
| P-1602 | | | |

| Compound number | Aldehyde | Compound | MS (ESI) [M + H+]+ |
|---|---|---|---|
| P-1603 | | | |
| P-1604 | | | |
| P-1605 | | | |
| P-1606 | | | |

Example 14

Synthesis of (5-fluoro-2-methoxy-pyridin-3-ylmethyl)-[3-methoxy-5-(5-methyl-1H-pyrrolo[2,3-b]pyridin-3-ylmethyl)-pyridin-2-yl]-amine P-1547

(5-Fluoro-2-methoxy-pyridin-3-ylmethyl)-[3-methoxy-5-(5-methyl-1H-pyrrolo[2,3-b]pyridin-3-ylmethyl)-pyridin-2-yl]-amine P-1547 is prepared in three steps from (5-formyl-3-methoxy-pyridin-2-yl)-(4-methoxy-benzyl)-carbamic acid tert-butyl ester 55 and 5-methyl-1H-[2,3-b]pyridine 126 as shown in Scheme 14.

Scheme 14

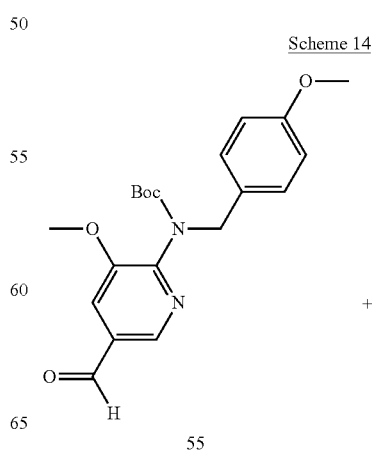

55

+

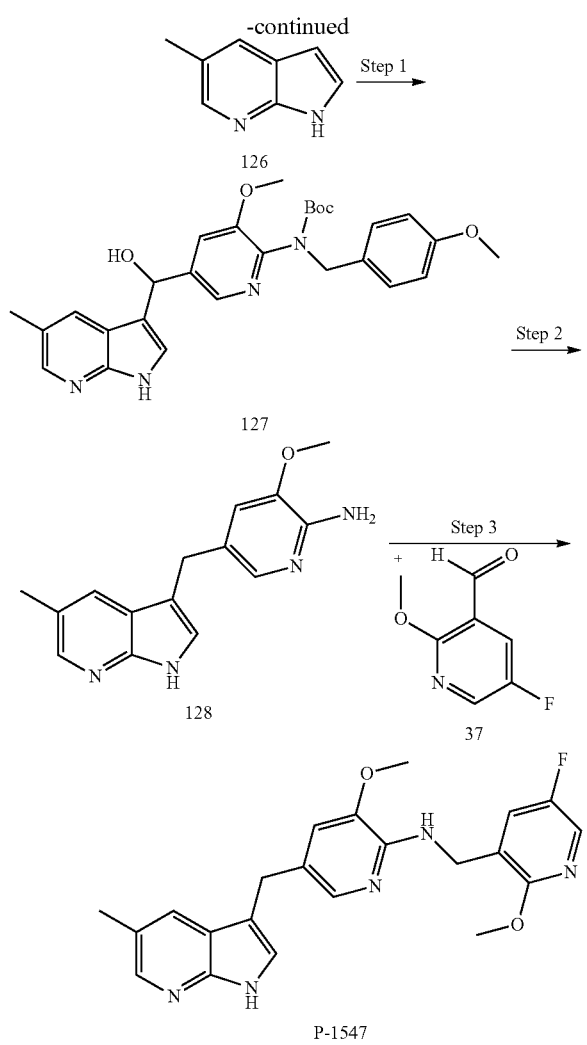

(4-methoxy-benzyl)-carbamic acid tert-butyl ester (127, 1 equivalent) is combined with 100 mL of acetonitrile, triethylsilane (18 equivalents), and trifluoroacetic acid (18 equivalents). The reaction is heated at reflux for 24 hours, then concentrated under vacuum. The resulting material is dissolved in 40 mL of trifluoroacetic acid and stirred at room temperature for 18 hours. This is concentrated under vacuum and combined with water and sodium bicarbonate, then extracted with ethyl acetate. The organic layer is washed with sodium bicarbonate, water, brine, then dried with magnesium sulfate, filtered and the filtrate is concentrated under vacuum. The resulting material is purified by silica gel column chromatography eluting with ethyl acetate and hexane. Appropriate fractions are combined and concentrated under vacuum to provide the desired compound.

Step 3—Preparation of (5-fluoro-2-methoxy-pyridin-3-ylmethyl)-[3-methoxy-5-(5-methyl-1H-pyrrolo[2,3-b]pyridin-3-ylmethyl)-pyridin-2-yl]-amine (P-1547)

To 3-methoxy-5-(5-methyl-1H-pyrrolo[2,3-b]pyridin-3-ylmethyl)-pyridin-2-ylamine (128, 1 equivalent) in 2 mL of acetonitrile, 5-fluoro-2-methoxy-pyridine-3-carbaldehyde (37, 1 equivalent), triethylsilane (5 equivalents) and trifluoroacetic acid (6.9 equivalents) are added. The reaction is heated at 80° C. for 18 hours, then concentrated under vacuum and mixed with aqueous potassium carbonate and extracted with ethyl acetate. The organic layer is washed with water, brine, then dried over magnesium sulfate, filtered and the filtrate concentrated under vacuum. The resulting material is purified by silica gel column chromatography eluting with ethyl acetate and hexane. Appropriate fractions are combined and concentrated under vacuum to provide the desired compound.

Additional compounds are prepared following the protocol of Scheme 14, where conditions may vary, for example, any of the solvents, reaction times, reagents, temperatures, work up conditions, or other reaction parameters may be varied employing alternate solvents, reagents, reaction times, temperatures, work up conditions, and the like, as are readily available to one skilled in the art. Compounds are prepared using a suitable aldehyde in place 5-fluoro-2-methoxy-pyridine-3-carbaldehyde 37 in step 3. The following compounds are made using this procedure. Compounds in the following table were characterized by $^1$H and $^{13}$C NMR spectroscopy as well as mass spectrometry.

(5-Fluoro-6-methoxy-pyridin-3-ylmethyl)-[3-methoxy-5-(5-methyl-1H-pyrrolo[2,3-b]pyridin-3-ylmethyl)-pyridin-2-yl]-amine (P-1548), (5-Fluoro-pyridin-3-ylmethyl)-[3-methoxy-5-(5-methyl-1H-pyrrolo[2,3-b]pyridin-3-ylmethyl)-pyridin-2-yl]-amine (P-1549), (6-Chloro-pyridin-3-ylmethyl)-[3-methoxy-5-(5-methyl-1H-pyrrolo[2,3-b]pyridin-3-ylmethyl)-pyridin-2-yl]-amine (P-1550),

[3-Methoxy-5-(5-methyl-1H-pyrrolo[2,3-b]pyridin-3-ylmethyl)-pyridin-2-yl]-(4-trifluoromethyl-pyridin-3-ylmethyl)-amine (P-1551),

[3-Methoxy-5-(5-methyl-1H-pyrrolo[2,3-b]pyridin-3-ylmethyl)-pyridin-2-yl]-(6-methoxy-pyridin-3-ylmethyl)-amine (P-1552), and

[3-Methoxy-5-(5-methyl-1H-pyrrolo[2,3-b]pyridin-3-ylmethyl)-pyridin-2-yl]-(2-methoxy-pyridin-3-ylmethyl)-amine (P-1553).

The following table indicates the aldehyde compound (column 2) used in step 3 to afford the desired compound (column 3). The compound number is provided in column 1, and the observed mass is in column 4.

Step 1—Preparation of {5-[hydroxy-(5-methyl-1H-pyrrolo[2,3-b]pyridin-3-yl)-methyl]-3-methoxy-pyridin-2-yl}-(4-methoxy-benzyl)-carbamic acid tert-butyl ester (127)

In a vial, 5-methyl-1H-[2,3-b]pyridine (126, 1 equivalent) is combined with (5-formyl-3-methoxy-pyridin-2-yl)-(4-methoxy-benzyl)-carbamic acid tert-butyl ester (55, 1.1 equivalents), 5 mL of methanol, and potassium hydroxide (3 equivalents). The reaction is stirred at room temperature overnight, then aqueous 1N hydrochloric acid is added and the mixture is extracted with ethyl acetate. The organic layer is washed with water, brine, then dried over magnesium sulfate, filtered and the filtrate concentrated under vacuum. The resulting material is purified by silica gel column chromatography eluting with methanol and dichloromethane. Appropriate fractions are combined and concentrated under vacuum to provide the desired compound.

Step 2—Preparation of 3-methoxy-5-(5-methyl-1H-pyrrolo[2,3-b]pyridin-3-ylmethyl)-pyridin-2-ylamine (128)

In a round bottom flask, {5-[hydroxy-(5-methyl-1H-pyrrolo[2,3-b]pyridin-3-yl)-methyl]-3-methoxy-pyridin-2-yl}-

| Compound number | Aldehyde | Compound | MS (ESI) [M + H+]+ |
|---|---|---|---|
| P-1548 | | | |
| P-1549 | | | |
| P-1550 | | | |
| P-1551 | | | |
| P-1552 | | | |
| P-1553 | | | |

Example 15

Synthesis of [5-(5-chloro-1H-pyrrolo[2,3-b]pyridin-3-ylmethyl)-pyrimidin-2-yl]-[(S)-1-(4-fluoro-phenyl)-ethyl]-amine P-2005

[5-(5-chloro-1H-pyrrolo[2,3-b]pyridin-3-ylmethyl)-pyrimidin-2-yl]-[(S)-1-(4-fluoro-phenyl)-ethyl]-amine P-2005 was prepared in 4 steps from 1-benzenesulfonyl-5-chloro-3-iodo-1H-pyrrolo[2,3-b]pyridine 12 and 2-methylsulfanyl-pyrimidine-5-carbaldehyde 129 as shown in Scheme 15.

Scheme 15

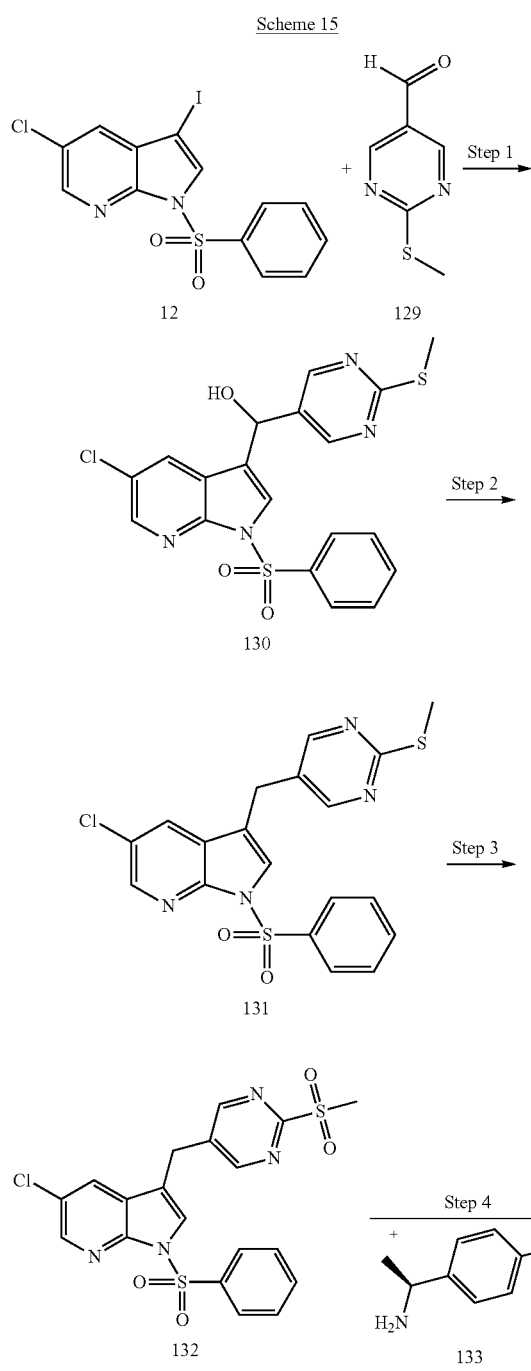

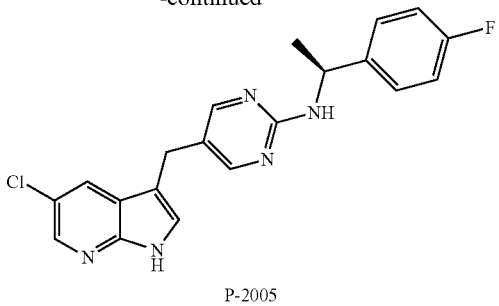

P-2005

Step 1—Preparation of (1-benzenesulfonyl-5-chloro-1H-pyrrolo[2,3-b]pyridin-3-yl)-(2-methylsulfanyl-pyrimidin-5-yl)-methanol (130)

To a solution of 1-benzenesulfonyl-5-chloro-3-iodo-1H-pyrrolo[2,3-b]pyridine (12, 8.40 g, 20.1 mmol) in 96.3 mL of tetrahydrofuran at −40° C. under nitrogen, isopropylmagnesium chloride (10.1 mL, 2.0 M in tetrahydrofuran, 20.3 mmol) was added slowly. The reaction was allowed to warm to 5° C. over 60 minutes, then cooled to −40° C., followed by addition of 2-methylsulfanyl-pyrimidine-5-carbaldehyde (129, 2.50 g, 16.2 mmol) in 15.0 mL of tetrahydrofuran. The reaction was allowed to warm to 10° C. over 2 hours, then poured into aqueous ammonium chloride and extracted with ethyl acetate. The organic layer was dried over sodium sulfate, filtered and the filtrate was concentrated under vacuum. The resulting material was purified by silica gel column chromatography eluting with 40-100% ethyl acetate in hexane. Appropriate fractions were combined and the solvents removed under vacuum to provide the desired compound as an off-white solid (130, 4.0 g). MS (ESI) $[M+H^+]^+=447.2$.

Step 2—Preparation of 1-benzenesulfonyl-5-chloro-3-(2-methylsulfanyl-pyrimidin-5-ylmethyl)-1H-pyrrolo[2,3-b]pyridine (131)

To (1-benzenesulfonyl-5-chloro-1H-pyrrolo[2,3-b]pyridin-3-yl)-(2-methylsulfanyl-pyrimidin-5-yl)-methanol (130, 4.70 g, 10.5 mmol) in 120.0 mL of acetonitrile, triethylsilane (22.0 mL, 138 mmol) and trifluoroacetic acid (11.0 mL, 143 mmol) were added. The reaction was stirred at 80° C. for 3 hours, then concentrated under vacuum and mixed with aqueous potassium carbonate and extracted with ethyl acetate. The organic layer was dried over sodium sulfate, filtered and the filtrate concentrated under vacuum. The resulting material was purified by silica gel column chromatography eluting with 20-100% ethyl acetate in hexane. Appropriate fractions were combined and solvents removed under vacuum to provide the desired compound (131, 2.90 g).

Step 3—Preparation of 1-benzenesulfonyl-5-chloro-3-(2-methanesulfonyl-pyrimidin-5-ylmethyl)-1H-pyrrolo[2,3-b]pyridine (132)

To 1-benzenesulfonyl-5-chloro-3-(2-methylsulfanyl-pyrimidin-5-ylmethyl)-1H-pyrrolo[2,3-b]pyridine (131, 4.40 g, 10.2 mmol) in 100.0 mL of dichloromethane, meta-chloroperoxybenzoic acid (max. 77%, 4.90 g, 21.9 mmol) was added at 0° C. The reaction was stirred at 0° C. for 40 minutes, then poured into water and extracted with ethyl acetate. The organic layer was dried over sodium sulfate, filtered, and the filtrate was concentrated under vacuum. The resulting material was purified by silica gel column chromatography eluting with 20% ethyl acetate in hexane. Appropriate fractions were combined and solvents removed under vacuum to provide the desired compound (132, 3.76 g). MS (ESI) [M+H$^+$]$^+$=463.0.

Step 4—Preparation of [5-(5-chloro-1H-pyrrolo[2,3-b]pyridin-3-ylmethyl)-pyrimidin-2-yl]-[(S)-1-(4-fluoro-phenyl)-ethyl]-amine (P-2005)

In a microwave vial, 1-benzenesulfonyl-5-chloro-3-(2-methanesulfonyl-pyrimidin-5-ylmethyl)-1H-pyrrolo[2,3-b]pyridine (132, 12 mg, 0.026 mmol) was mixed with 600 µL of N-methylpyrrolidinone and (S)-1-(4-fluoro-phenyl)-ethylamine (133, 25.2 mg, 0.18 mmol). The reaction was irradiated at 200° C. for 40 minutes in microwave, then potassium hydroxide (500 µL, 4.00 M in water) was added and the reaction irradiated at 90° C. for 10 minutes in microwave. The reaction was neutralized with the addition of 120 µL of acetic acid, solvents were removed under vacuum, and the resulting material was dissolved in 400 µL of dimethyl sulfoxide for purification by HPLC. The desired compound was purified on Phenomenex C18 column (50 mm×10 mm ID) with mobile phase A of 0.1% trifluoroacetic acid in water, mobile phase B of 0.1% trifluoroacetic acid in acetonitrile, 20-100% B over 16 minutes at a flow rate of 6 mL/min. Appropriate fractions were collected and solvents removed under vacuum to provide the desired compound. MS (ESI) [M+H']'=381.9.

1-Benzenesulfonyl-5-fluoro-3-(2-methanesulfonyl-pyrimidin-5-ylmethyl)-1H-pyrrolo[2,3-b]pyridine 134 and 1-benzenesulfonyl-3-(2-methanesulfonyl-pyrimidin-5-ylmethyl)-5-methyl-1H-pyrrolo[2,3-b]pyridine 135

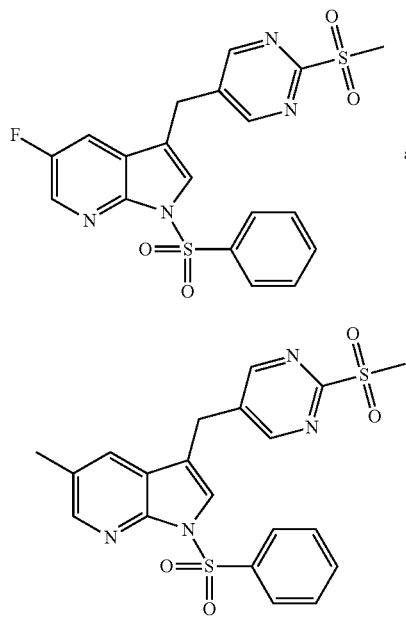

are similarly prepared following the protocol of Scheme 15, steps 1-3, replacing 1-benzenesulfonyl-5-chloro-3-iodo-1H-pyrrolo[2,3-b]pyridine 12 with 1-benzenesulfonyl-5-fluoro-3-iodo-1H-pyrrolo[2,3-b]pyridine or 1-benzenesulfonyl-3-iodo-5-methyl-1H-pyrrolo[2,3-b]pyridine respectively in step 1. These are used following the protocol of Scheme 15 step 4 to make additional compounds. In some instances for the 5-fluoro substituted compounds, removal of the benzenesulfonyl protecting group is done in an additional step by reacting with tetrabutylammonium fluoride trihydrate in tetrahydrofuran.

Additional compounds are prepared following the protocol of Scheme 15, step 4, where conditions may vary, for example, any of the solvents, reaction times, reagents, temperatures, work up conditions, or other reaction parameters may be varied employing alternate solvents, reagents, reaction times, temperatures, work up conditions, and the like, as are readily available to one skilled in the art. Compounds are prepared substituting (S)-1-(4-fluoro-phenyl)-ethylamine 133 with a suitable amine and optionally substituting 1-benzenesulfonyl-5-chloro-3-(2-methanesulfonyl-pyrimidin-5-ylmethyl)-1H-pyrrolo[2,3-b]pyridine 132 with 1-benzenesulfonyl-5-fluoro-3-(2-methanesulfonyl-pyrimidin-5-ylmethyl)-1H-pyrrolo[2,3-b]pyridine 134 or 1-benzenesulfonyl-3-(2-methanesulfonyl-pyrimidin-5-ylmethyl)-5-methyl-1H-pyrrolo[2,3-b]pyridine 135. The following compounds are made using this procedure. Compounds in the following table were characterized by $^1$H and $^{13}$C NMR spectroscopy as well as mass spectrometry.

(3-Chloro-4-methyl-benzyl)-[5-(5-chloro-1H-pyrrolo[2,3-b]pyridin-3-ylmethyl)-pyrimidin-2-yl]-amine (P-2007),
[5-(5-Chloro-1H-pyrrolo[2,3-b]pyridin-3-ylmethyl)-pyrimidin-2-yl]-(3,4-difluoro-benzyl)-amine (P-2008),
[5-(5-Chloro-1H-pyrrolo[2,3-b]pyridin-3-ylmethyl)-pyrimidin-2-yl]-(3-fluoro-5-trifluoromethyl-benzyl)-amine (P-2009),
[5-(5-Chloro-1H-pyrrolo[2,3-b]pyridin-3-ylmethyl)-pyrimidin-2-yl]-(3-trifluoromethoxy-benzyl)-amine (P-2010),
[5-(5-Chloro-1H-pyrrolo[2,3-b]pyridin-3-ylmethyl)-pyrimidin-2-yl]-(3-fluoro-4-trifluoromethyl-benzyl)-amine (P-2011),
(4-Chloro-benzyl)-[5-(5-chloro-1H-pyrrolo[2,3-b]pyridin-3-ylmethyl)-pyrimidin-2-yl]-methyl-amine (P-2012),
[5-(5-Chloro-1H-pyrrolo[2,3-b]pyridin-3-ylmethyl)-pyrimidin-2-yl]-(3-methyl-benzyl)-amine (P-2013),
[5-(5-Chloro-1H-pyrrolo[2,3-b]pyridin-3-ylmethyl)-pyrimidin-2-yl]-(3-fluoro-4-methyl-benzyl)-amine (P-2014),
[2-(3-Chloro-phenyl)-ethyl]-[5-(5-chloro-1H-pyrrolo[2,3-b]pyridin-3-ylmethyl)-pyrimidin-2-yl]-amine (P-2015),
[2-(2-Chloro-phenyl)-ethyl]-[5-(5-chloro-1H-pyrrolo[2,3-b]pyridin-3-ylmethyl)-pyrimidin-2-yl]-amine (P-2020),
[5-(5-Chloro-1H-pyrrolo[2,3-b]pyridin-3-ylmethyl)-pyrimidin-2-yl]-[2-(4-fluoro-phenyl)-ethyl]-amine (P-2021),
[5-(5-Chloro-1H-pyrrolo[2,3-b]pyridin-3-ylmethyl)-pyrimidin-2-yl]-[2-(6-methyl-pyridin-2-yl)-ethyl]-amine (P-2022),
Butyl-[5-(5-chloro-1H-pyrrolo[2,3-b]pyridin-3-ylmethyl)-pyrimidin-2-yl]-amine (P-2026),
[5-(5-Fluoro-1H-pyrrolo[2,3-b]pyridin-3-ylmethyl)-pyrimidin-2-yl]-(1-thiazol-2-yl-ethyl)-amine (P-2039),
[1-(4-Fluoro-phenyl)-propyl]-[5-(5-fluoro-1H-pyrrolo[2,3-b]pyridin-3-ylmethyl)-pyrimidin-2-yl]-amine (P-2053),
[1-(4-Fluoro-phenyl)-cyclopropyl]-[5-(5-fluoro-1H-pyrrolo[2,3-b]pyridin-3-ylmethyl)-pyrimidin-2-yl]-amine (P-2055),
[(S)-1-(4-Fluoro-phenyl)-ethyl]-[5-(5-fluoro-1H-pyrrolo[2,3-b]pyridin-3-ylmethyl)-pyrimidin-2-yl]-amine (P-2056),
(2-Methoxy-pyridin-4-ylmethyl)-[5-(5-methyl-1H-pyrrolo[2,3-b]pyridin-3-ylmethyl)-pyrimidin-2-yl]-amine (P-2069),
[5-(5-Chloro-1H-pyrrolo[2,3-b]pyridin-3-ylmethyl)-pyrimidin-2-yl]-(2-methoxy-pyridin-4-ylmethyl)-amine (P-2074),
[5-(5-Methyl-1H-pyrrolo[2,3-b]pyridin-3-ylmethyl)-pyrimidin-2-yl]-pyridin-2-ylmethyl-amine (P-2076),

[5-(5-Methyl-1H-pyrrolo[2,3-b]pyridin-3-ylmethyl)-pyrimidin-2-yl]-pyridin-3-ylmethyl-amine (P-2077),
(6-Chloro-pyridin-3-ylmethyl)-[5-(5-methyl-1H-pyrrolo[2,3-b]pyridin-3-ylmethyl)-pyrimidin-2-yl]-amine (P-2078),
(6-Methyl-pyridin-2-ylmethyl)-[5-(5-methyl-1H-pyrrolo[2,3-b]pyridin-3-ylmethyl)-pyrimidin-2-yl]-amine (P-2079),
[5-(5-Methyl-1H-pyrrolo[2,3-b]pyridin-3-ylmethyl)-pyrimidin-2-yl]-(6-trifluoromethyl-pyridin-3-ylmethyl)-amine (P-2080),
[5-(5-Methyl-1H-pyrrolo[2,3-b]pyridin-3-ylmethyl)-pyrimidin-2-yl]-(6-morpholin-4-yl-pyridin-2-ylmethyl)-amine (P-2081),
[5-(5-Methyl-1H-pyrrolo[2,3-b]pyridin-3-ylmethyl)-pyrimidin-2-yl]-(6-pyrrolidin-1-yl-pyridin-2-ylmethyl)-amine (P-2082),
(5-Ethyl-pyridin-2-ylmethyl)-[5-(5-methyl-1H-pyrrolo[2,3-b]pyridin-3-ylmethyl)-pyrimidin-2-yl]-amine (P-2083),
(3-Methyl-pyridin-4-ylmethyl)-[5-(5-methyl-1H-pyrrolo[2,3-b]pyridin-3-ylmethyl)-pyrimidin-2-yl]-amine (P-2084),
[5-(5-Methyl-1H-pyrrolo[2,3-b]pyridin-3-ylmethyl)-pyrimidin-2-yl]-(2-morpholin-4-yl-pyridin-4-ylmethyl)-amine (P-2085),
[5-(5-Methyl-1H-pyrrolo[2,3-b]pyridin-3-ylmethyl)-pyrimidin-2-yl]-pyridin-4-ylmethyl-amine (P-2138),
(2-Methoxy-pyridin-3-ylmethyl)-[5-(5-methyl-1H-pyrrolo[2,3-b]pyridin-3-ylmethyl)-pyrimidin-2-yl]-amine (P-2139),
[6-(4-Methyl-piperazin-1-yl)-pyridin-3-ylmethyl]-[5-(5-methyl-1H-pyrrolo[2,3-b]pyridin-3-ylmethyl)-pyrimidin-2-yl]-amine (P-2140),
(2-Methyl-pyridin-4-ylmethyl)-[5-(5-methyl-1H-pyrrolo[2,3-b]pyridin-3-ylmethyl)-pyrimidin-2-yl]-amine (P-2141),
(2-Ethoxy-pyridin-3-ylmethyl)-[5-(5-methyl-1H-pyrrolo[2,3-b]pyridin-3-ylmethyl)-pyrimidin-2-yl]-amine (P-2142),
(2-Cyclopentyloxy-pyridin-3-ylmethyl)-[5-(5-methyl-1H-pyrrolo[2,3-b]pyridin-3-ylmethyl)-pyrimidin-2-yl]-amine (P-2148), and
(2-Cyclopentyloxy-pyridin-4-ylmethyl)-[5-(5-methyl-1H-pyrrolo[2,3-b]pyridin-3-ylmethyl)-pyrimidin-2-yl]-amine (P-2149).

The following table indicates the 1H-pyrrolo[2,3-b]pyridine (column 2) and the amine compound (column 3) used in step 4 to afford the desired compound (column 4). The compound number is provided in column 1, and the observed mass is in column 5.

| Comp. number | 1H-pyrrolo[2,3-b]pyridine | Amine structure | Compound structure | MS (ESI) [M + H]+ |
|---|---|---|---|---|
| P-2007 | | | 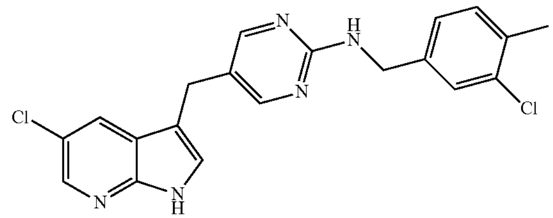 | 397.9 |
| P-2008 | | | 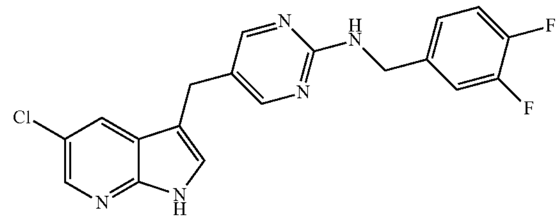 [SMILES: Fc1ccc(CNc2ncc(Cc3c[nH]c4ncc(Cl)cc34)cn2)cc1F] | 386.3 |
| P-2009 | | | 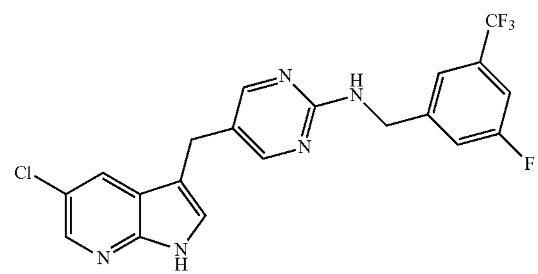 [SMILES: Fc1cc(CNc2ncc(Cc3c[nH]c4ncc(Cl)cc34)cn2)cc(C(F)(F)F)c1] | 436.3 |

| Comp. number | 1H-pyrrolo[2,3-b]pyridine | Amine structure | Compound structure | MS (ESI) [M + H⁺]⁺ |
|---|---|---|---|---|
| P-2010 | 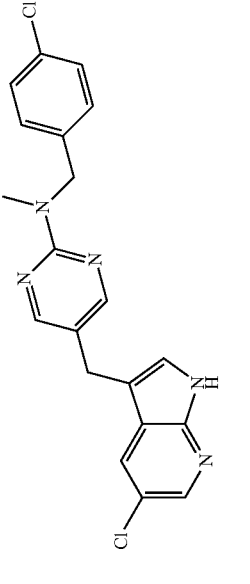 | 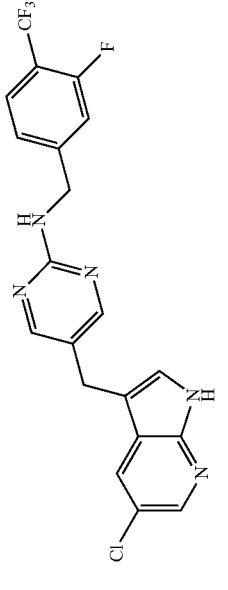 | 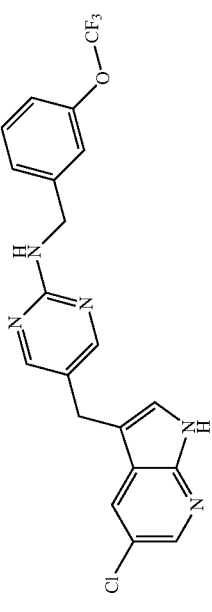 | 434.3 |
| P-2011 | 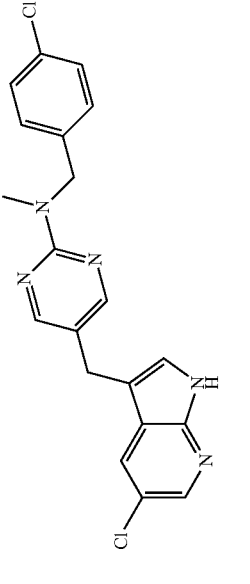 | 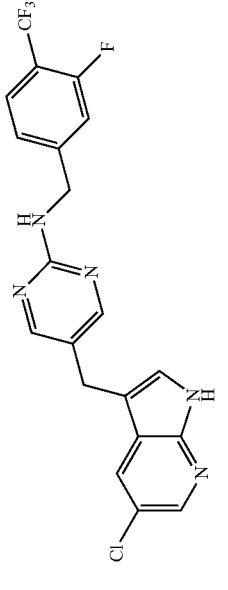 | 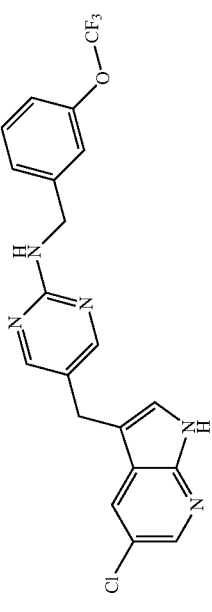 | 435.9 |
| P-2012 | 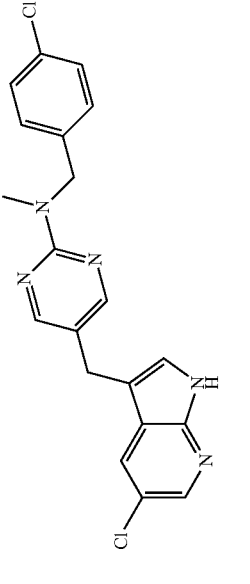 | 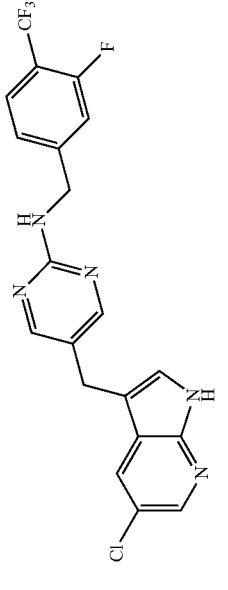 | 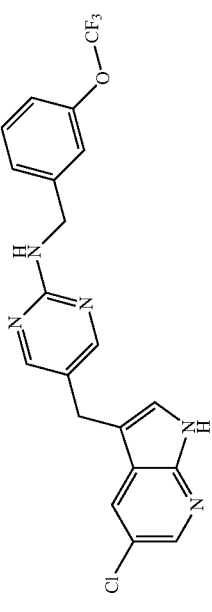 | |

| Comp. number | 1H-pyrrolo[2,3-b]pyridine | Amine structure | Compound structure | MS (ESI) [M + H+]+ |
|---|---|---|---|---|
| P-2013 | | | 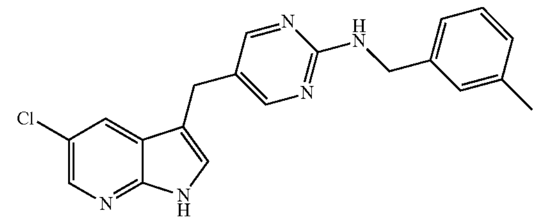 [SMILES: Cc1cccc(CNc2ncc(Cc3c[nH]c4ncc(Cl)cc34)cn2)c1] | 364.3 |
| P-2014 | | | 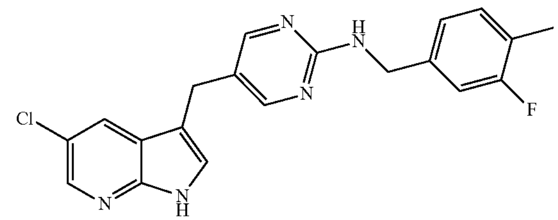 [SMILES: Cc1ccc(CNc2ncc(Cc3c[nH]c4ncc(Cl)cc34)cn2)cc1F] | 381.9 |
| P-2015 | | | 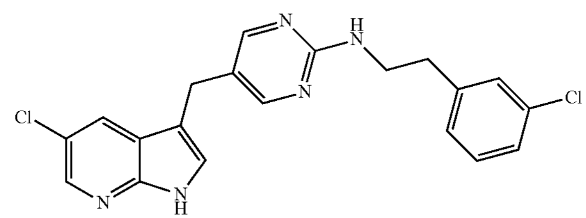 [SMILES: Clc1cccc(CCNc2ncc(Cc3c[nH]c4ncc(Cl)cc34)cn2)c1] | 397.9 |

| Comp. number | 1H-pyrrolo[2,3-b]pyridine | Amine structure | Compound structure | MS (ESI) [M + H+]+ |
|---|---|---|---|---|
| P-2020 | | | 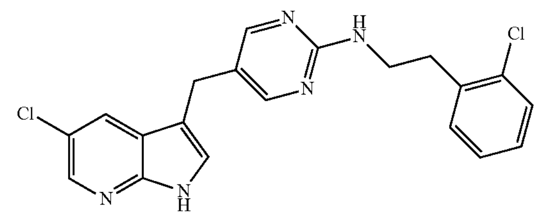 [SMILES: Clc1cnc2[nH]cc(Cc3cnc(NCCc4ccccc4Cl)nc3)c2c1] | 397.9 399.95 |
| P-2021 | | | 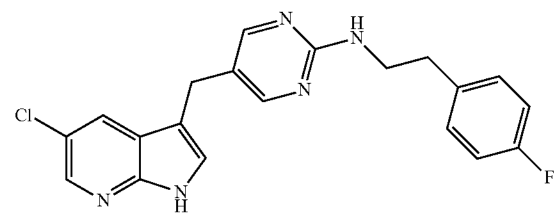 [SMILES: Fc1ccc(CCNc2ncc(Cc3c[nH]c4ncc(Cl)cc34)cn2)cc1] | 384.0 |
| P-2022 | | | 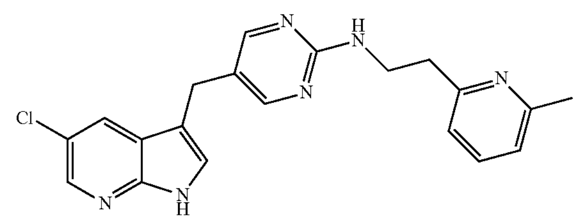 [SMILES: Cc1cccc(CCNc2ncc(Cc3c[nH]c4ncc(Cl)cc34)cn2)n1] | 379.4 |

-continued

| Comp. number | 1H-pyrrolo[2,3-b]pyridine | Amine structure | Compound structure | MS (ESD) [M + H+]+ |
|---|---|---|---|---|
| P-2026 | | | 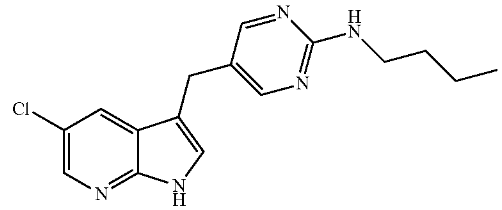 [SMILES: CCCCNc1ncc(Cc2c[nH]c3ncc(Cl)cc23)cn1] | |
| P-2039 | | | 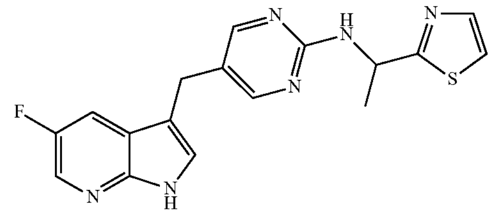 [SMILES: CC(Nc1ncc(Cc2c[nH]c3ncc(F)cc23)cn1)c1nccs1] | |
| P-2053 | | | 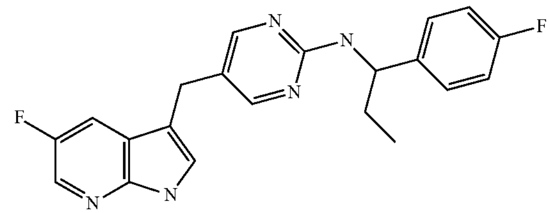 [SMILES: CCC(Nc1ncc(Cc2c[nH]c3ncc(F)cc23)cn1)c1ccc(F)cc1] | |

| Comp. number | 1H-pyrrolo[2,3-b]pyridine | Amine structure | Compound structure | MS (ESD) [M + H⁺]⁺ |
|---|---|---|---|---|
| P-2055 | | | 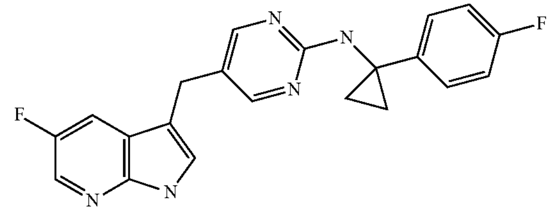 [SMILES: Fc1ccc(C2(Nc3ncc(Cc4c[nH]c5ncc(F)cc45)cn3)CC2)cc1] | |
| P-2056 | | | 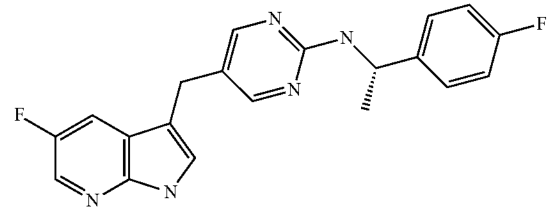 [SMILES: C[C@H](Nc1ncc(Cc2c[nH]c3ncc(F)cc23)cn1)c1ccc(F)cc1] | 366.0 |
| P-2069 | | | 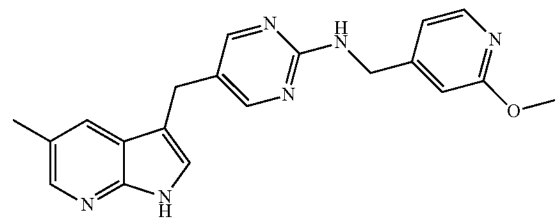 | |

| Comp. number | 1H-pyrrolo[2,3-b]pyridine | Amine structure | Compound structure | MS (ESI) [M + H⁺]⁺ |
|---|---|---|---|---|
| P-2074 | | | 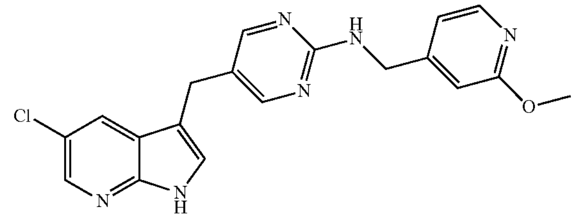 [SMILES: COc1cc(CNc2ncc(Cc3c[nH]c4ncc(Cl)cc34)cn2)ccn1] | 380.9 |
| P-2076 | | | 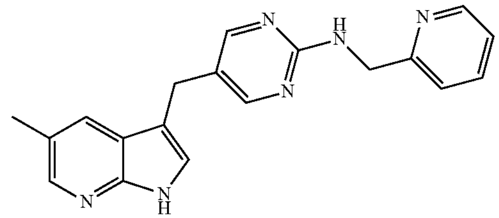 [SMILES: Cc1cnc2[nH]cc(Cc3cnc(NCc4ccccn4)nc3)c2c1] | |
| P-2077 | | | 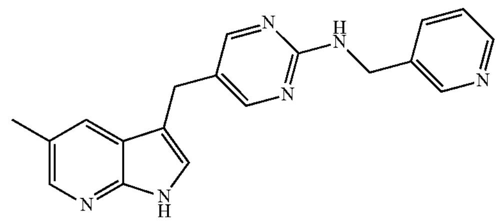 [SMILES: Cc1cnc2[nH]cc(Cc3cnc(NCc4cccnc4)nc3)c2c1] | |

| Comp. number | 1H-pyrrolo[2,3-b]pyridine | Amine structure | Compound structure | MS (ESI) [M + H+]+ |
|---|---|---|---|---|
| P-2078 | | | 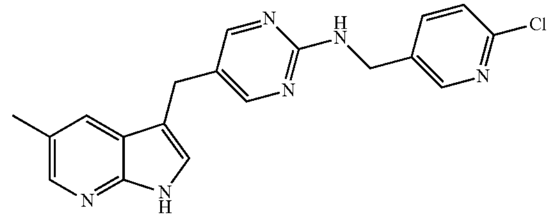 [SMILES: Cc1cnc2[nH]cc(Cc3cnc(NCc4ccc(Cl)nc4)nc3)c2c1] | 365.1 |
| P-2079 | | | 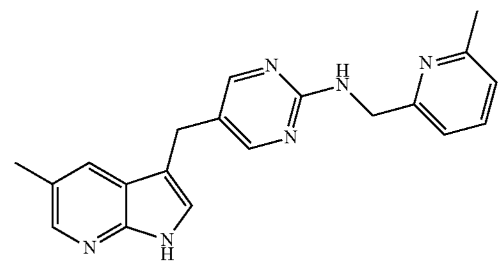 [SMILES: Cc1cnc2[nH]cc(Cc3cnc(NCc4cccc(C)n4)nc3)c2c1] | 345.1 |
| P-2080 | | | 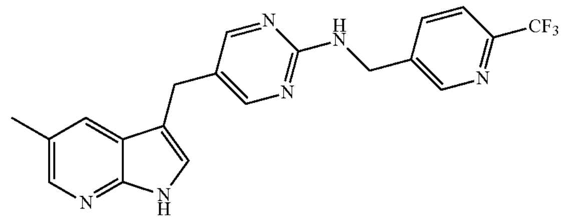 [SMILES: Cc1cnc2[nH]cc(Cc3cnc(NCc4ccc(C(F)(F)F)nc4)nc3)c2c1] | |

| Comp. number | 1H-pyrrolo[2,3-b]pyridine | Amine structure | Compound structure | MS (ESI) [M + H⁺]⁺ |
|---|---|---|---|---|
| P-2081 |  |  | 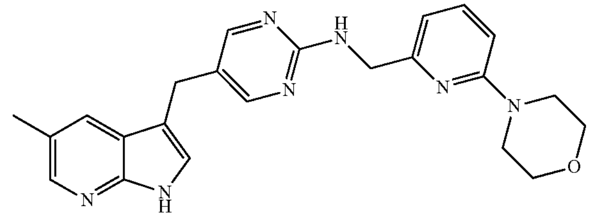 [SMILES: Cc1cnc2[nH]cc(Cc3cnc(NCc4cccc(N5CCOCC5)n4)nc3)c2c1] | 416.3 |
| P-2082 |  |  | 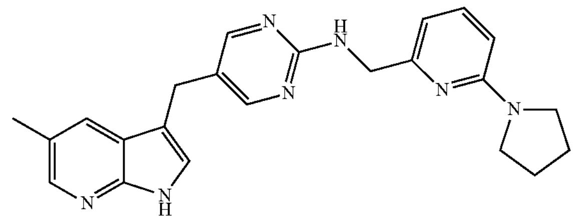 [SMILES: Cc1cnc2[nH]cc(Cc3cnc(NCc4cccc(N5CCCC5)n4)nc3)c2c1] | 400.3 |
| P-2083 |  |  | 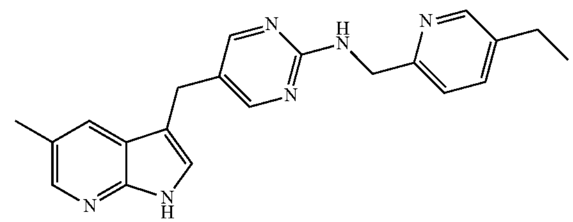 [SMILES: CCc1ccc(CNc2ncc(Cc3c[nH]c4ncc(C)cc34)cn2)nc1] | |

| Comp. number | 1H-pyrrolo[2,3-b]pyridine | Amine structure | Compound structure | MS (ESI) [M + H⁺]⁺ |
|---|---|---|---|---|
| P-2084 | | | 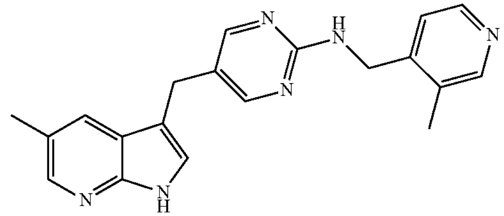 [SMILES: Cc1cnc2[nH]cc(Cc3cnc(NCc4ccncc4C)nc3)c2c1] | |
| P-2085 | | | 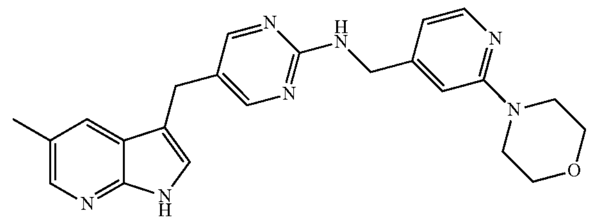 [SMILES: Cc1cnc2[nH]cc(Cc3cnc(NCc4ccnc(N5CCOCC5)c4)nc3)c2c1] | |
| P-2138 | | | 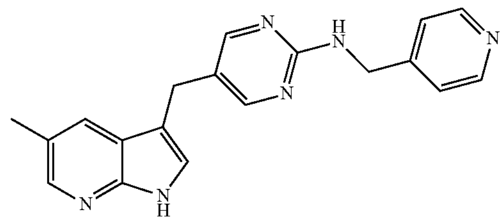 [SMILES: Cc1cnc2[nH]cc(Cc3cnc(NCc4ccncc4)nc3)c2c1] | |

-continued
| Comp. number | 1H-pyrrolo[2,3-b]pyridine | Amine structure | Compound structure | MS (ESI) [M + H+]+ |
|---|---|---|---|---|
| P-2139 | 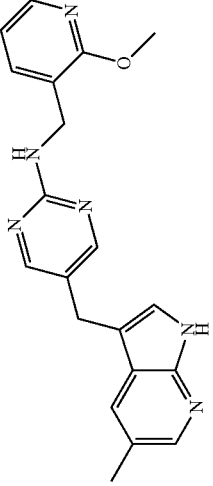 | 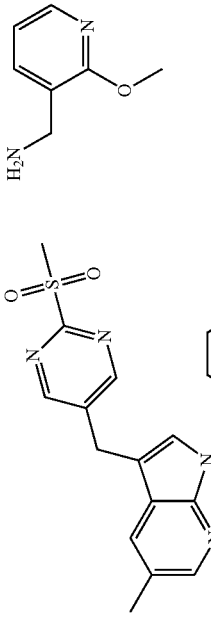 | 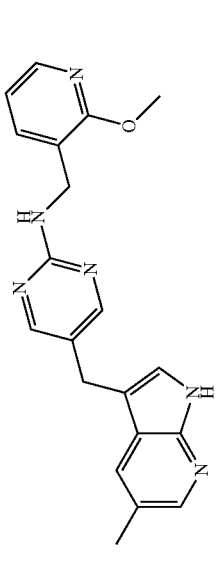 | 361.5 |
| P-2140 | 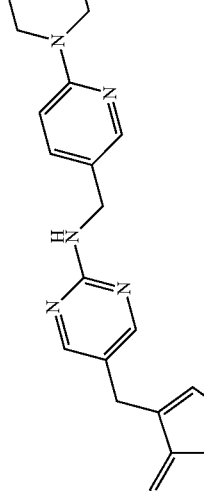 | 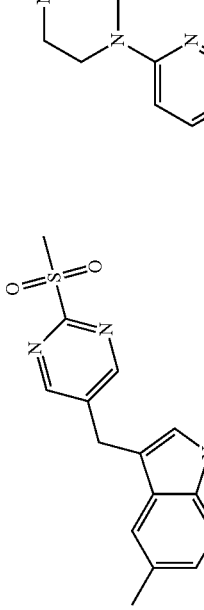 | 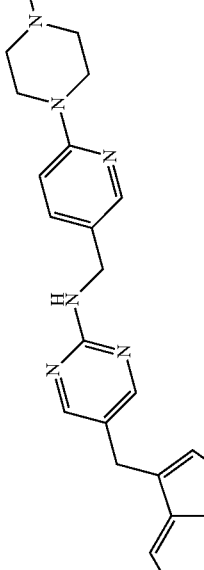 | |
| P-2141 | 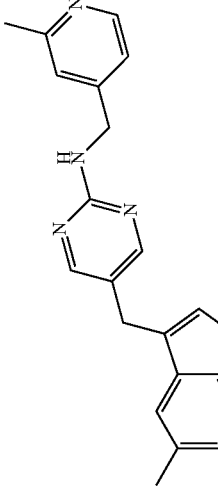 | 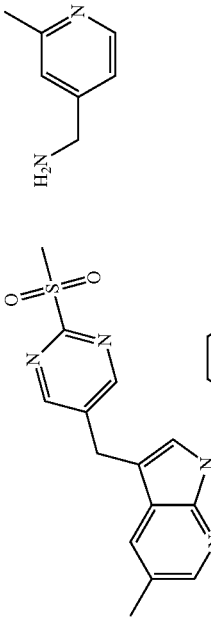 | 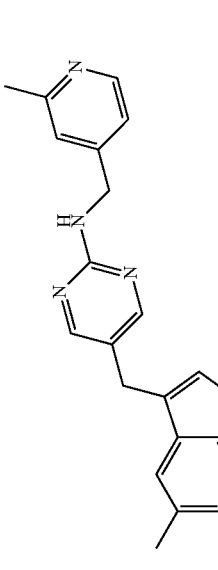 | |

-continued
| Comp. number | 1H-pyrrolo[2,3-b]pyridine | Amine structure | Compound structure | MS (ESD) [M + H+]+ |
|---|---|---|---|---|
| P-2142 | 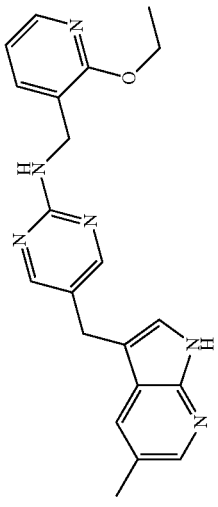 | 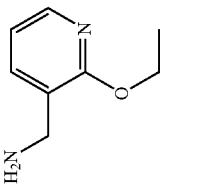 | 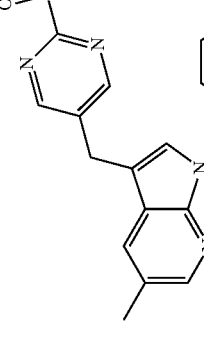 | |
| P-2148 | 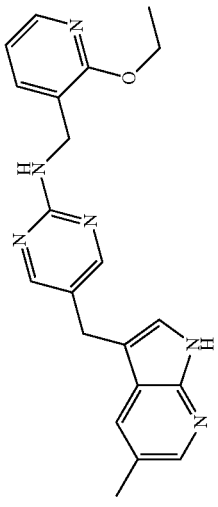 | 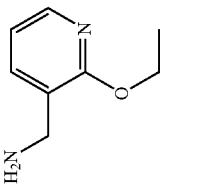 | 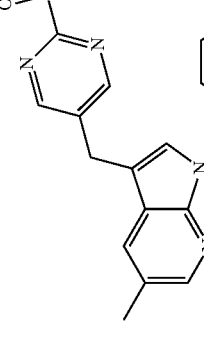 | 415.5 |
| P-2149 | 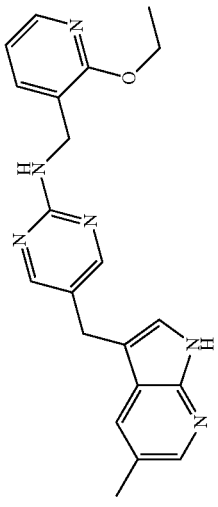 | 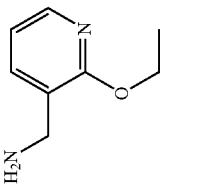 | 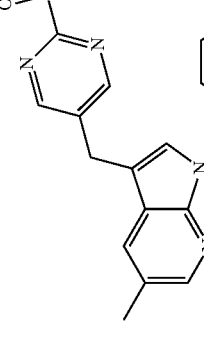 | |

Example 16

Synthesis of (5-{[6-fluoro-5-(5-methyl-1H-pyrrolo[2,3-b]pyridin-3-ylmethyl)-pyridin-2-ylamino]-methyl}-pyrimidin-2-yl)-methyl-amine P-2095

(5-{[6-Fluoro-5-(5-methyl-1H-pyrrolo[2,3-b]pyridin-3-ylmethyl)-pyridin-2-ylamino]-methyl}-pyrimidin-2-yl)-methyl-amine P-2095 was prepared in three steps from 3-iodo-5-methyl-1-triisopropylsilanyl-1H-pyrrolo[2,3-b]pyridine 9 and (6-fluoro-5-formyl-pyridin-2-yl)-(4-methoxy-benzyl)-carbamic acid tert-butyl ester 83 as shown in Scheme 16.

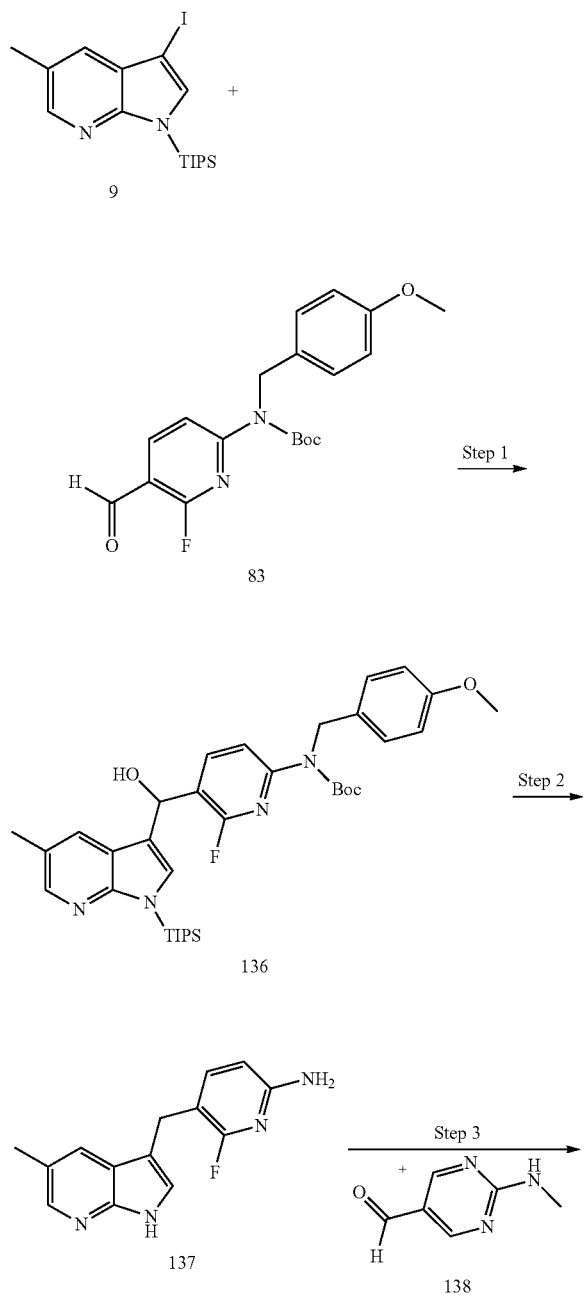

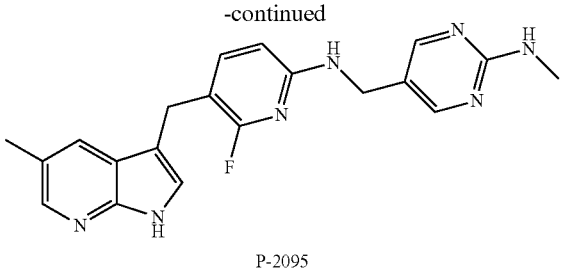

P-2095

Step 1—Preparation of {6-fluoro-5-[hydroxy-(5-methyl-1-triisopropylsilanyl-1H-pyrrolo[2,3-b]pyridin-3-yl)-methyl]-pyridin-2-yl}-(4-methoxy-benzyl)-carbamic acid tert-butyl ester (136)

To 3-iodo-5-methyl-1-triisopropylsilanyl-1H-pyrrolo[2,3-b]pyridine (9, 40 g, 97.0 mmol) in 400 mL of tetrahydrofuran under nitrogen at −20° C., isopropylmagnesium chloride (54.8 mL, 2 M in tetrahydrofuran, 110 mmol) was added and the reaction allowed to warm to 0° C. over 30 minutes. The reaction was cooled to −40° C. and (6-fluoro-5-formyl-pyridin-2-yl)-(4-methoxy-benzyl)-carbamic acid tert-butyl ester (83, 15.81 g, 43.9 mmol) in tetrahydrofuran was added. The reaction was allowed to warm to 0° C. over an hour, then quenched with brine and extracted with ethyl acetate. The organic layer was dried over sodium sulfate, filtered and the filtrate concentrated under vacuum. The resulting material was purified by silica gel column chromatography, eluting with 0-40% ethyl acetate in hexane. Appropriate fractions were combined and the solvents removed under vacuum to provide the desired compound (136, 21 g, 32.4 mmol, 73.8% yield).

Step 2—Preparation of 6-fluoro-5-(5-methyl-1H-pyrrolo[2,3-b]pyridin-3-ylmethyl)-pyridin-2-ylamine (137)

To {6-fluoro-5-[hydroxy-(5-methyl-1-triisopropylsilanyl-1H-pyrrol [2,3-b]pyridin-3-yl)-methyl]-pyridin-2-yl}-(4-methoxy-benzyl)-carbamic acid tert-butyl ester (136, 21 g, 32.4 mmol) in 500 mL of acetonitrile, triethylsilane (51.7 mL, 324 mmol) and trifluoroacetic acid (24.93 mL, 324 mmol) were added. The reaction was stirred at 50° C. for several hours, solvents removed under vacuum, and the residue taken up in 250 mL of dichloromethane and 250 mL of trifluoroacetic acid was added. The mixture was stirred at reflux for several hours, then concentrated under vacuum. The residue was taken up in ethyl acetate and poured into aqueous potassium carbonate. The organic layer was separated, concentrated under vacuum and purified by silica gel column chromatography, eluting with 0-5% methanol in dichloromethane. Appropriate fractions were combined and the solvents removed under vacuum to provide the desired compound (137, 5.2 g, 20.29 mmol, 62.7% yield).

Step 3—Preparation of (5-{[6-fluoro-5-(5-methyl-1H-pyrrolo[2,3-b]pyridin-3-ylmethyl)-pyridin-2-ylamino]-methyl}-pyrimidin-2-yl)-methyl-amine (P-2095)

In a 2 mL microwave vial, 6-fluoro-5-(5-methyl-1H-pyrrolo[2,3-b]pyridin-3-ylmethyl)-pyridin-2-ylamine (137, 9.72 mg, 0.04 mmol) and 2-methylamino-pyrimidine-5-carbaldehyde (138, 11.0 mg, 0.08 mmol) were dissolved in 600

μL of 95:5 ethanol:acetic acid, and silica supported cyanoborohydride (50 mg, 1 mmol/g, 0.05 mmol) was added. The reaction was irradiated for 10 minutes at 160° C. in a microwave. The vial was centrifuged to condense the silica and the supernatant was removed by pipette into another vial. The residual silica was rinsed with 500 μL of ethanol, centrifuged and the supernatant added to the first supernatant. The solvents were removed under vacuum and the resulting material dissolved in 400 μL of dimethyl sulfoxide for purification by HPLC. Samples were purified on Phenomenex C18 column (50 mm×10 mm ID) with mobile phase A of 0.1% trifluoroacetic acid in water, mobile phase B of 0.1% trifluoroacetic acid in acetonitrile, 20-100% B over 16 minutes at a flow rate of 6 mL/min. Appropriate fractions were collected and solvents removed under vacuum to provide the desired compound. MS (ESI) [M+H$^+$]$^+$=378.3.

5-Fluoro-3-{[6-fluoro-5-(5-methyl-1H-pyrrolo[2,3-b]pyridin-3-ylmethyl)-pyridin-2-ylamino]-methyl}-1-methyl-1H-pyridin-2-one P-2156

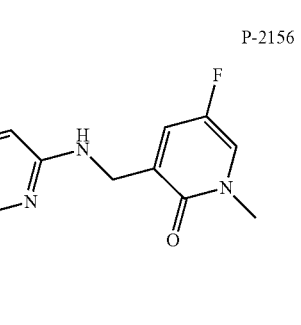

P-2156 was prepared similarly to the protocol of Scheme 16, where step 3 was replaced by the following step 3a:

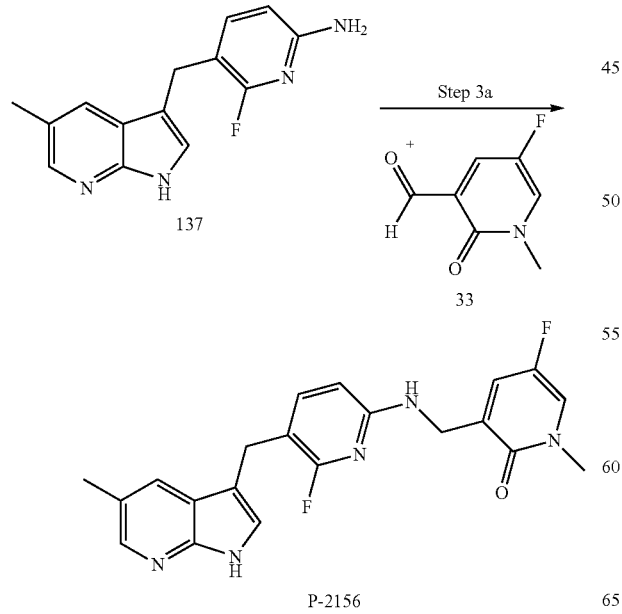

Step 3a—Preparation of 5-fluoro-3-{[6-fluoro-5-(5-methyl-1H-pyrrolo[2,3-b]pyridin-3-ylmethyl)-pyridin-2-ylamino]-methyl}-1-methyl-1H-pyridin-2-one (P-2156)

To 6-fluoro-5-(5-methyl-1H-pyrrolo[2,3-b]pyridin-3-ylmethyl)-pyridin-2-ylamine (137, 3.99 g, 15.59 mmol) and 5-fluoro-1-methyl-2-oxo-1,2-dihydro-pyridine-3-carbaldehyde (33, 2.66 g, 17.15 mmol) in 50 mL of acetonitrile, triethylsilane (9.96 mL, 62.4 mmol) and trifluoroacetic acid (4.80 mL, 62.4 mmol) were added. The reaction was stirred at 80° C. for several hours, then concentrated under vacuum and the residue was taken up in ethyl acetate and poured into aqueous potassium carbonate. The organic layer was separated, concentrated under vacuum, and the residue purified by silica gel column chromatography, eluting with 0-5% methanol in dichloromethane. Appropriate fractions were combined and concentrated under vacuum, and the residue triturated with methanol to provide the desired compound (P-2156, 3.1 g, 7.84 mmol, 50.3% yield).

N-[6-Fluoro-5-(5-methyl-1H-pyrrolo[2,3-b]pyridin-3-ylmethyl)-pyridin-2-yl]-C-phenyl-methanesulfonamide P-2181

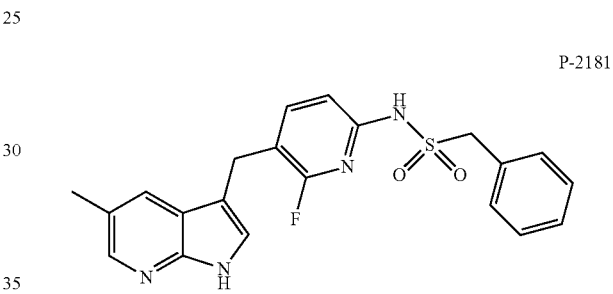

P-2181 similarly to the protocol of Scheme 16, where step 3 was replaced by the following step 3b:

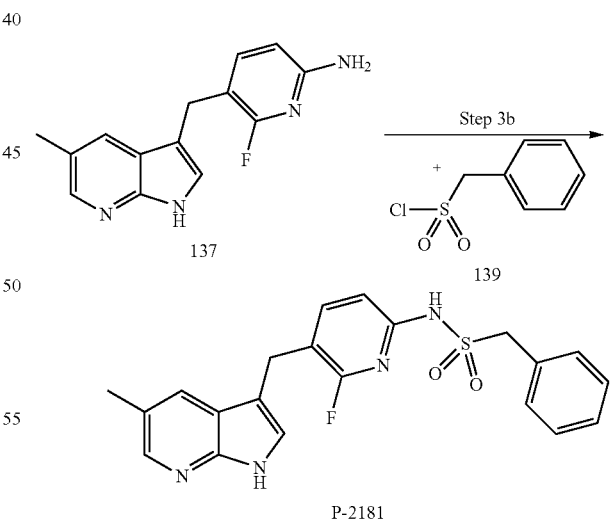

Step 3b—Preparation of N-[6-fluoro-5-(5-methyl-1H-pyrrolo[2,3-b]pyridin-3-ylmethyl)-pyridin-2-yl]-C-phenyl-methanesulfonamide (P-2181)

In a vial, 6-fluoro-5-(5-methyl-1H-pyrrolo[2,3-b]pyridin-3-ylmethyl)-pyridin-2-ylamine (137, 157 mg, 0.614 mmol)

was mixed with 4 mL of dichloromethane and pyridine (149 µL, 1.84 mmol) and cooled to 0° C. in an ice water bath. Phenyl-methanesulfonyl chloride (139, 0.234 g, 1.23 mmol) was added and the reaction stirred at 0° C. for 1 hour, then warmed to room temperature and stirred overnight. Aqueous saturated sodium bicarbonate was added and extracted with ethyl acetate. The organic layer was washed with water and brine, then dried over magnesium sulfate, filtered and the filtrate concentrated under vacuum. The resulting material was purified by silica gel column chromatography, eluting with 0-10% methanol in dichloromethane. Appropriate fractions were combined and concentrated under vacuum to provide the desired compound as a yellow solid (P-2181, 39 mg). MS (ESI) [M+H]$^+$=411.1.

Additional compounds are prepared following the protocol of Scheme 16 (step 3a may be substituted for step 3) where conditions may vary, for example, any of the solvents, reaction times, reagents, temperatures, work up conditions, or other reaction parameters may be varied employing alternate solvents, reagents, reaction times, temperatures, work up conditions, and the like, as are readily available to one skilled in the art. Compounds are prepared optionally substituting 3-iodo-5-methyl-1-triisopropylsilanyl-1H-pyrrolo[2,3-b]pyridine 9 with a suitable 1-triisopropylsilanyl-1H-pyrrolo[2,3-b]pyridine in step 1; optionally replacing (6-fluoro-5-formyl-pyridin-2-yl)-(4-methoxy-benzyl)-carbamic acid tert-butyl ester 83 with (5-formyl-pyrimidin-2-yl)-(4-methoxy-benzyl)-carbamic acid tert-butyl ester in step 1; and optionally replacing 2-methylamino-pyrimidine-5-carbaldehyde 138 with a suitable aldehyde in step 3. The following compounds are made using this procedure. Compounds in the following table were characterized by $^1$H and $^{13}$C NMR spectroscopy as well as mass spectrometry.

(5-Fluoro-pyridin-3-ylmethyl)-[5-(5-methyl-1H-pyrrolo[2,3-b]pyridin-3-ylmethyl)-pyrimidin-2-yl]-amine (P-1569),
[5-(5-Methyl-1H-pyrrolo[2,3-b]pyridin-3-ylmethyl)-pyrimidin-2-yl]-(4-trifluoromethyl-pyridin-3-ylmethyl)-amine (P-1570),
[5-(5-Chloro-1H-pyrrolo[2,3-b]pyridin-3-ylmethyl)-pyrimidin-2-yl]-(5-fluoro-6-methoxy-pyridin-3-ylmethyl)-amine (P-1611),
(6-Chloro-pyridin-3-ylmethyl)-[5-(5-chloro-1H-pyrrolo[2,3-b]pyridin-3-ylmethyl)-pyrimidin-2-yl]-amine (P-1612),
[5-(5-Chloro-1H-pyrrolo[2,3-b]pyridin-3-ylmethyl)-pyrimidin-2-yl]-(4-trifluoromethyl-pyridin-3-ylmethyl)-amine (P-1613),
[5-(5-Chloro-1H-pyrrolo[2,3-b]pyridin-3-ylmethyl)-pyrimidin-2-yl]-(2-methoxy-pyridin-3-ylmethyl)-amine (P-1614),
(5-Fluoro-6-methoxy-pyridin-3-ylmethyl)-[6-fluoro-5-(5-trifluoromethyl-1H-pyrrolo[2,3-b]pyridin-3-ylmethyl)-pyridin-2-yl]-amine (P-1646),
(5-Fluoro-pyridin-3-ylmethyl)-[6-fluoro-5-(5-trifluoromethyl-1H-pyrrolo[2,3-b]pyridin-3-ylmethyl)-pyridin-2-yl]-amine (P-1647),
(6-Chloro-pyridin-3-ylmethyl)-[6-fluoro-5-(5-trifluoromethyl-1H-pyrrolo[2,3-b]pyridin-3-ylmethyl)-pyridin-2-yl]-amine (P-1648),
(5-Fluoro-2-methoxy-pyridin-3-ylmethyl)-[6-fluoro-5-(5-trifluoromethyl-1H-pyrrolo[2,3-b]pyridin-3-ylmethyl)-pyridin-2-yl]-amine (P-1649),
[6-Fluoro-5-(5-trifluoromethyl-1H-pyrrolo[2,3-b]pyridin-3-ylmethyl)-pyridin-2-yl]-(4-trifluoromethyl-pyridin-3-yl-methyl)-amine (P-1650),
[6-Fluoro-5-(5-trifluoromethyl-1H-pyrrolo[2,3-b]pyridin-3-ylmethyl)-pyridin-2-yl]-(6-methoxy-pyridin-3-ylmethyl)-amine (P-1651),
[6-Fluoro-5-(5-trifluoromethyl-1H-pyrrolo[2,3-b]pyridin-3-ylmethyl)-pyridin-2-yl]-(6-trifluoromethyl-pyridin-3-yl-methyl)-amine (P-1652),
[6-Fluoro-5-(5-trifluoromethyl-1H-pyrrolo[2,3-b]pyridin-3-ylmethyl)-pyridin-2-yl]-(2-methoxy-pyridin-3-ylmethyl)-amine (P-1653),
(5-Fluoro-2-methoxy-pyridin-3-ylmethyl)-[6-fluoro-5-(5-methyl-1H-pyrrolo[2,3-b]pyridin-3-ylmethyl)-pyridin-2-yl]-amine (P-2049),
(5-Fluoro-2-methoxy-pyridin-3-ylmethyl)-[5-(5-methyl-1H-pyrrolo[2,3-b]pyridin-3-ylmethyl)-pyrimidin-2-yl]-amine (P-2061),
[5-(5-Chloro-1H-pyrrolo[2,3-b]pyridin-3-ylmethyl)-pyrimidin-2-yl]-(5-fluoro-2-methoxy-pyridin-3-ylmethyl)-amine (P-2064),
(2,5-Dimethoxy-benzyl)-[6-fluoro-5-(5-methyl-1H-pyrrolo[2,3-b]pyridin-3-ylmethyl)-pyridin-2-yl]-amine (P-2086),
(3,5-Dimethoxy-benzyl)-[6-fluoro-5-(5-methyl-1H-pyrrolo[2,3-b]pyridin-3-ylmethyl)-pyridin-2-yl]-amine (P-2087),
(6-Chloro-pyridin-3-ylmethyl)-[6-fluoro-5-(5-methyl-1H-pyrrolo[2,3-b]pyridin-3-ylmethyl)-pyridin-2-yl]-amine (P-2088),
(3-Bromo-pyridin-4-ylmethyl)-[6-fluoro-5-(5-methyl-1H-pyrrolo[2,3-b]pyridin-3-ylmethyl)-pyridin-2-yl]-amine (P-2089),
[6-Fluoro-5-(5-methyl-1H-pyrrolo[2,3-b]pyridin-3-ylmethyl)-pyridin-2-yl]-(2-morpholin-4-yl-pyridin-3-ylmethyl)-amine (P-2090),
[6-Fluoro-5-(5-methyl-1H-pyrrolo[2,3-b]pyridin-3-ylmethyl)-pyridin-2-yl]-(6-morpholin-4-yl-pyridin-3-ylmethyl)-amine (P-2091),
(3-Chloro-pyridin-4-ylmethyl)-[6-fluoro-5-(5-methyl-1H-pyrrolo[2,3-b]pyridin-3-ylmethyl)-pyridin-2-yl]-amine (P-2092),
[6-Fluoro-5-(5-methyl-1H-pyrrolo[2,3-b]pyridin-3-ylmethyl)-pyridin-2-yl]-(5-fluoro-pyridin-2-ylmethyl)-amine (P-2093),
[6-Fluoro-5-(5-methyl-1H-pyrrolo[2,3-b]pyridin-3-ylmethyl)-pyridin-2-yl]-(3-fluoro-pyridin-4-ylmethyl)-amine (P-2094),
[6-Fluoro-5-(5-methyl-1H-pyrrolo[2,3-b]pyridin-3-ylmethyl)-pyridin-2-yl]-[2-(2,2,2-trifluoro-ethoxy)-pyridin-3-ylmethyl]-amine (P-2096),
(2,6-Dimethoxy-pyridin-3-ylmethyl)-[6-fluoro-5-(5-methyl-1H-pyrrolo[2,3-b]pyridin-3-ylmethyl)-pyridin-2-yl]-amine (P-2097),
(5-Fluoro-2-methanesulfonyl-benzyl)-[6-fluoro-5-(5-methyl-1H-pyrrolo[2,3-b]pyridin-3-ylmethyl)-pyridin-2-yl]-amine (P-2098),
(5-Chloro-pyridin-3-ylmethyl)-[6-fluoro-5-(5-methyl-1H-pyrrolo[2,3-b]pyridin-3-ylmethyl)-pyridin-2-yl]-amine (P-2099),
(5-Bromo-pyridin-2-ylmethyl)-[6-fluoro-5-(5-methyl-1H-pyrrolo[2,3-b]pyridin-3-ylmethyl)-pyridin-2-yl]-amine (P-2100),
[6-Fluoro-5-(5-methyl-1H-pyrrolo[2,3-b]pyridin-3-ylmethyl)-pyridin-2-yl]-(3-methyl-pyridin-4-ylmethyl)-amine (P-2101),
(3-Chloro-5-fluoro-benzyl)-[6-fluoro-5-(5-methyl-1H-pyrrolo[2,3-b]pyridin-3-ylmethyl)-pyridin-2-yl]-amine (P-2102),
[6-Fluoro-5-(5-methyl-1H-pyrrolo[2,3-b]pyridin-3-ylmethyl)-pyridin-2-yl]-(2-fluoro-pyridin-3-ylmethyl)-amine (P-2103),
(3,5-Dimethyl-benzyl)-[6-fluoro-5-(5-methyl-1H-pyrrolo[2,3-b]pyridin-3-ylmethyl)-pyridin-2-yl]-amine (P-2104),

[6-Fluoro-5-(5-methyl-1H-pyrrolo[2,3-b]pyridin-3-ylmethyl)-pyridin-2-yl]-(5-methoxy-pyridin-3-ylmethyl)-amine (P-2105),

[6-Fluoro-5-(5-methyl-1H-pyrrolo[2,3-b]pyridin-3-ylmethyl)-pyridin-2-yl]-(2-methyl-pyrimidin-5-ylmethyl)-amine (P-2106),

[6-Fluoro-5-(5-methyl-1H-pyrrolo[2,3-b]pyridin-3-ylmethyl)-pyridin-2-yl]-(2-methylamino-pyridin-3-ylmethyl)-amine (P-2107), (3,5-Bis-trifluoromethyl-benzyl)-[6-fluoro-5-(5-methyl-1H-pyrrolo[2,3-b]pyridin-3-ylmethyl)-pyridin-2-yl]-amine (P-2108),

[6-Fluoro-5-(5-methyl-1H-pyrrolo[2,3-b]pyridin-3-ylmethyl)-pyridin-2-yl]-(4-methoxy-pyridin-3-ylmethyl)-amine (P-2109), (2-Ethoxy-pyridin-3-ylmethyl)-[6-fluoro-5-(5-methyl-1H-pyrrolo[2,3-b]pyridin-3-ylmethyl)-pyridin-2-yl]-amine (P-2110),

[6-Fluoro-5-(5-methyl-1H-pyrrolo[2,3-b]pyridin-3-ylmethyl)-pyridin-2-yl]-(2-isopropoxy-pyridin-3-ylmethyl)-amine (P-2111),

[6-Fluoro-5-(5-methyl-1H-pyrrolo[2,3-b]pyridin-3-ylmethyl)-pyridin-2-yl]-(4-methyl-pyridin-2-ylmethyl)-amine (P-2112), (2-Cyclopentyloxy-pyridin-3-ylmethyl)-[6-fluoro-5-(5-methyl-1H-pyrrolo[2,3-b]pyridin-3-ylmethyl)-pyridin-2-yl]-amine (P-2113), (2-Cyclohexyloxy-pyridin-3-ylmethyl)-[6-fluoro-5-(5-methyl-1H-pyrrolo[2,3-b]pyridin-3-ylmethyl)-pyridin-2-yl]-amine (P-2114),

[6-Fluoro-5-(5-methyl-1H-pyrrolo[2,3-b]pyridin-3-ylmethyl)-pyridin-2-yl]-(2-trifluoromethyl-pyridin-3-ylmethyl)-amine (P-2115), (2-Chloro-5-fluoro-pyridin-4-ylmethyl)-[6-fluoro-5-(5-methyl-1H-pyrrolo[2,3-b]pyridin-3-ylmethyl)-pyridin-2-yl]-amine (P-2116), 4-{[6-Fluoro-5-(5-methyl-1H-pyrrolo[2,3-b]pyridin-3-ylmethyl)-pyridin-2-ylamino]-methyl}-pyridine-2-carbonitrile (P-2117),

[6-Fluoro-5-(5-methyl-1H-pyrrolo[2,3-b]pyridin-3-ylmethyl)-pyridin-2-yl]-(2-fluoro-pyridin-4-ylmethyl)-amine (P-2118),

[6-Fluoro-5-(5-methyl-1H-pyrrolo[2,3-b]pyridin-3-ylmethyl)-pyridin-2-yl]-(2-trifluoromethyl-pyridin-4-ylmethyl)-amine (P-2119), (2-Chloro-pyridin-4-ylmethyl)-[6-fluoro-5-(5-methyl-1H-pyrrolo[2,3-b]pyridin-3-ylmethyl)-pyridin-2-yl]-amine (P-2120),

[6-Fluoro-5-(5-methyl-1H-pyrrolo[2,3-b]pyridin-3-ylmethyl)-pyridin-2-yl]-(2-morpholin-4-yl-pyridin-4-ylmethyl)-amine (P-2121),

[6-Fluoro-5-(5-methyl-1H-pyrrolo[2,3-b]pyridin-3-ylmethyl)-pyridin-2-yl]-(2-pyrrolidin-1-yl-pyridin-4-ylmethyl)-amine (P-2122), (5-Chloro-2-fluoro-pyridin-3-ylmethyl)-[6-fluoro-5-(5-methyl-1H-pyrrolo[2,3-b]pyridin-3-ylmethyl)-pyridin-2-yl]-amine (P-2123), (4-Chloro-2-methanesulfonyl-benzyl)-[6-fluoro-5-(5-methyl-1H-pyrrolo[2,3-b]pyridin-3-ylmethyl)-pyridin-2-yl]-amine (P-2124), (2-Dimethylamino-benzyl)-[6-fluoro-5-(5-methyl-1H-pyrrolo[2,3-b]pyridin-3-ylmethyl)-pyridin-2-yl]-amine (P-2125), (2-Ethyl-pyrimidin-5-ylmethyl)-[6-fluoro-5-(5-methyl-1H-pyrrolo[2,3-b]pyridin-3-ylmethyl)-pyridin-2-yl]-amine (P-2126),

[6-Fluoro-5-(5-methyl-1H-pyrrolo[2,3-b]pyridin-3-ylmethyl)-pyridin-2-yl]-(2-propyl-pyrimidin-5-ylmethyl)-amine (P-2127),

[6-Fluoro-5-(5-methyl-1H-pyrrolo[2,3-b]pyridin-3-ylmethyl)-pyridin-2-yl]-(2-isopropyl-pyrimidin-5-ylmethyl)-amine (P-2128),

[6-Fluoro-5-(5-methyl-1H-pyrrolo[2,3-b]pyridin-3-ylmethyl)-pyridin-2-yl]-[2-(2-methoxy-ethyl)-pyrimidin-5-ylmethyl]-amine (P-2129), (2-Butyl-pyrimidin-5-ylmethyl)-[6-fluoro-5-(5-methyl-1H-pyrrolo[2,3-b]pyridin-3-ylmethyl)-pyridin-2-yl]-amine (P-2130),

[6-Fluoro-5-(5-methyl-1H-pyrrolo[2,3-b]pyridin-3-ylmethyl)-pyridin-2-yl]-(5-methyl-pyridin-2-ylmethyl)-amine (P-2131), (3-Fluoro-5-methyl-benzyl)-[6-fluoro-5-(5-methyl-1H-pyrrolo[2,3-b]pyridin-3-ylmethyl)-pyridin-2-yl]-amine (P-2132),

[6-Fluoro-5-(5-methyl-1H-pyrrolo[2,3-b]pyridin-3-ylmethyl)-pyridin-2-yl]-(3-methoxy-5-trifluoromethyl-benzyl)-amine (P-2133), (3-Fluoro-5-methoxy-benzyl)-[6-fluoro-5-(5-methyl-1H-pyrrolo[2,3-b]pyridin-3-ylmethyl)-pyridin-2-yl]-amine (P-2134),

[6-Fluoro-5-(5-methyl-1H-pyrrolo[2,3-b]pyridin-3-ylmethyl)-pyridin-2-yl]-(3,4,5-trimethoxy-benzyl)-amine (P-2150),

[6-Fluoro-5-(5-methyl-1H-pyrrolo[2,3-b]pyridin-3-ylmethyl)-pyridin-2-yl]-(5-pyrrolidin-1-yl-pyridin-2-ylmethyl)-amine (P-2151),

[6-Fluoro-5-(5-methyl-1H-pyrrolo[2,3-b]pyridin-3-ylmethyl)-pyridin-2-yl]-(2-methoxy-6-trifluoromethyl-pyridin-3-ylmethyl)-amine (P-2166),

[6-Fluoro-5-(5-methyl-1H-pyrrolo[2,3-b]pyridin-3-ylmethyl)-pyridin-2-yl]-(2-dimethylamino-6-trifluoromethyl-pyridin-3-ylmethyl)-amine (P-2167),

[6-Fluoro-5-(5-methyl-1H-pyrrolo[2,3-b]pyridin-3-ylmethyl)-pyridin-2-yl]-(6-methoxy-4-trifluoromethyl-pyridin-3-ylmethyl)-amine (P-2186), Ethanesulfonic acid (2-{[6-fluoro-5-(5-methyl-1H-pyrrolo[2,3-b]pyridin-3-ylmethyl)-pyridin-2-ylamino]-methyl}-phenyl)-amide (P-2198), Ethanesulfonic acid (4-fluoro-3-{[6-fluoro-5-(5-methyl-1H-pyrrolo[2,3-b]pyridin-3-ylmethyl)-pyridin-2-ylamino]-methyl}-phenyl)-amide (P-2199), and Ethanesulfonic acid (3-fluoro-5-{[6-fluoro-5-(5-methyl-1H-pyrrolo[2,3-b]pyridin-3-ylmethyl)-pyridin-2-ylamino]-methyl}-phenyl)-amide (P-2202).

The following table indicates the 1H-pyrrolo[2,3-b]pyridine (column 2) and Boc-protected aldehyde (column 3) used in step 1, and the aldehyde compound (column 4) used in step 3 (or 3a if indicated in column 1) to afford the desired compound (column 5). The compound number is provided in column 1, and the observed mass is in column 6.

| Comp. number | pyrrolo[2,3-b]pyridine | Boc Aldehyde | Step 3 aldehyde | Compound | MS (ESI) [M + H+]+ |
|---|---|---|---|---|---|
| P-1569 | | | | | |
| P-1570 | | | | | |

| Comp. number | pyrrolo[2,3-b]pyridine | Boc Aldehyde | Step 3 aldehyde | Compound | MS (ESI) [M + H⁺]⁺ |
|---|---|---|---|---|---|
| P-1611 | | | | | |
| P-1612 | | | | | |

-continued

| Comp. number | pyrrolo[2,3-b]pyridine | Boc Aldehyde | Step 3 aldehyde | Compound | MS (ESI) [M + H⁺]⁺ |
|---|---|---|---|---|---|
| P-1613 | | | | | |
| P-1614 | | | | | |

| Comp. number | pyrrolo[2,3-b]pyridine | Boc Aldehyde | Step 3 aldehyde | Compound | MS (ESI) [M+H+]+ |
|---|---|---|---|---|---|
| P-1646 (3a) | | | | | 450.0 |
| P-1647 (3a) | | | | | |

| Comp. number | pyrrolo[2,3-b]pyridine | Boc Aldehyde | Step 3 aldehyde | Compound | MS (ESI) [M + H+]+ |
|---|---|---|---|---|---|
| P-1648 (3a) | | | | | |
| P-1649 (3a) | | | | | 450.1 |

| Comp. number | pyrrolo[2,3-b]pyridine | Boc Aldehyde | Step 3 aldehyde | Compound | MS (ESI) [M+H+]+ |
|---|---|---|---|---|---|
| P-1650 (3a) | 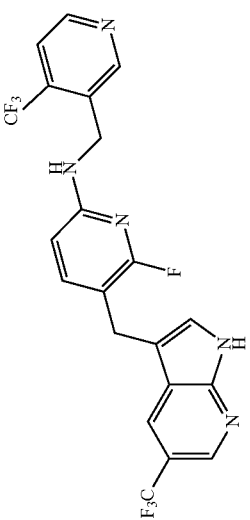 | 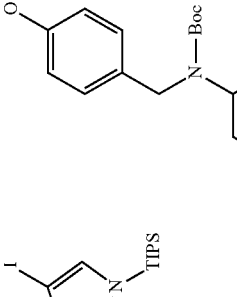 | 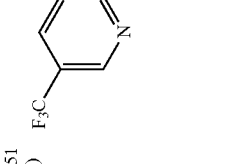 | 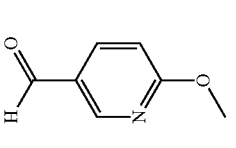 | |
| P-1651 (3a) | 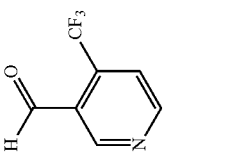 | 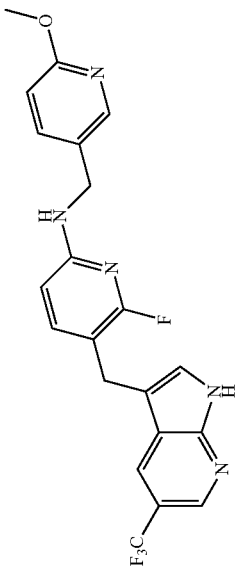 | 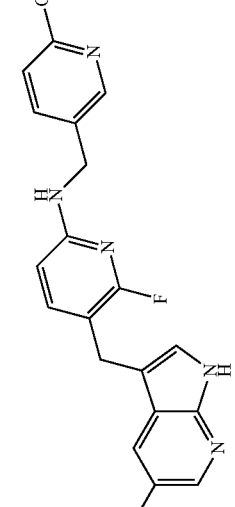 | 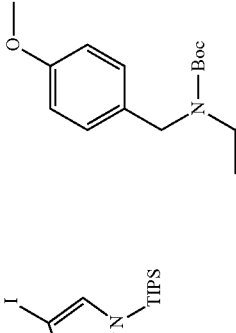 | |

-continued

| Comp. number | pyrrolo[2,3-b]pyridine | Boc Aldehyde | Step 3 aldehyde | Compound | MS (ESI) [M + H+]+ |
|---|---|---|---|---|---|
| P-1652 (3a) | | | | | |
| P-1653 (3a) | | | | | |

| Comp. number | pyrrolo[2,3-b]pyridine | Boc Aldehyde | Step 3 aldehyde | Compound | MS (ESI) [M+H+]+ |
|---|---|---|---|---|---|
| P-2049 (3a) | | | | | 369.0 |
| P-2061 | | | | | 379.0 |

| Comp. number | pyrrolo[2,3-b]pyridine | Boc Aldehyde | Step 3 aldehyde | Compound | MS (ESI) [M+H+]+ |
|---|---|---|---|---|---|
| P-2064 | | | | | 398.9 |
| P-2086 | | | | | |

| Comp. number | pyrrolo[2,3-b]pyridine | Boc Aldehyde | Step 3 aldehyde | Compound | MS (ESI) [M + H+]+ |
|---|---|---|---|---|---|
| P-2087 | | | | | |
| P-2088 | | | | | 382.3 |

| Comp. number | pyrrolo[2,3-b]pyridine | Boc Aldehyde | Step 3 aldehyde | Compound | MS (ESI) [M + H⁺]⁺ |
|---|---|---|---|---|---|
| P-2089 | | | | | |
| P-2090 | | | | | 433.1 |

| Comp. number | pyrrolo[2,3-b]pyridine | Boc Aldehyde | Step 3 aldehyde | Compound | MS (ESI) [M+H+]+ |
|---|---|---|---|---|---|
| P-2092 | | | | | 382.3 |
| P-2093 | | | | | |

| Comp. number | pyrrolo[2,3-b]pyridine | Boc Aldehyde | Step 3 aldehyde | Compound | MS (ESI) [M + H⁺]⁺ |
|---|---|---|---|---|---|
| P-2094 | | | | | 366.3 |
| P-2096 | | | | | |

| Comp. number | pyrrolo[2,3-b]pyridine | Boc Aldehyde | Step 3 aldehyde | Compound | MS (ESI) [M + H+]+ |
|---|---|---|---|---|---|
| P-2097 | | | | | 408.3 |
| P-2098 | | | | | 443.1 |

| Comp. number | pyrrolo[2,3-b]pyridine | Boc Aldehyde | Step 3 aldehyde | Compound | MS (ESI) [M + H+]+ |
|---|---|---|---|---|---|
| P-2099 | | | | | 382.3 |
| P-2100 | | | | | |

-continued
| Comp. number | pyrrolo[2,3-b]pyridine | Boc Aldehyde | Step 3 aldehyde | Compound | MS (ESI) [M + H⁺]⁺ |
|---|---|---|---|---|---|
| P-2101 | 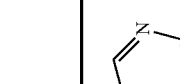 |  | 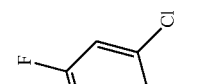 |  | |
| P-2102 | 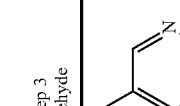 |  | 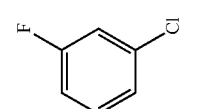 |  | |

| Comp. number | pyrrolo[2,3-b]pyridine | Boc Aldehyde | Step 3 aldehyde | Compound | MS (ESI) [M + H⁺]⁺ |
|---|---|---|---|---|---|
| P-2103 | | | | | 366.3 |
| P-2104 | | | | | |

| Comp. number | pyrrolo[2,3-b]pyridine | Boc Aldehyde | Step 3 aldehyde | Compound | MS (ESI) [M + H⁺]⁺ |
|---|---|---|---|---|---|
| P-2105 | | | | | 378.3 |
| P-2106 | | | | | |

-continued

| Comp. number | pyrrolo[2,3-b]pyridine | Boc Aldehyde | Step 3 aldehyde | Compound | MS (ESI) [M + H+]+ |
|---|---|---|---|---|---|
| P-2107 | | | | | |
| P-2108 | | | | | |

-continued
| Comp. number | pyrrolo[2,3-b]pyridine | Boc Aldehyde | Step 3 aldehyde | Compound | MS (ESI) [M + H+]+ |
|---|---|---|---|---|---|
| P-2109 | 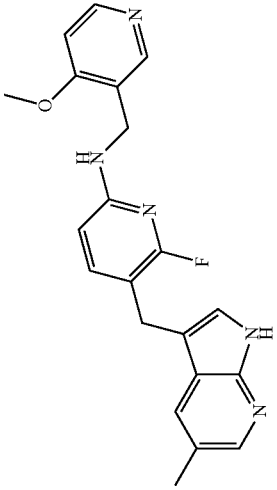 | 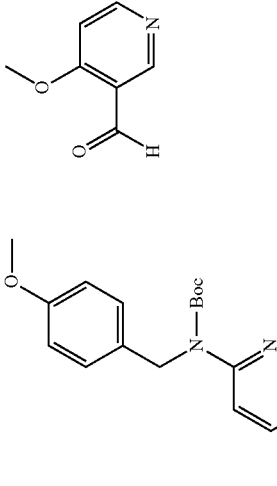 | 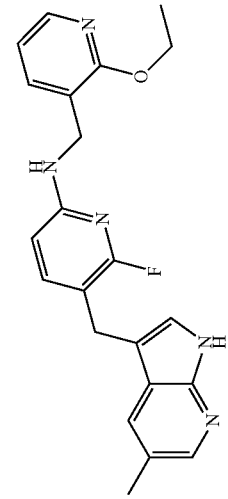 | 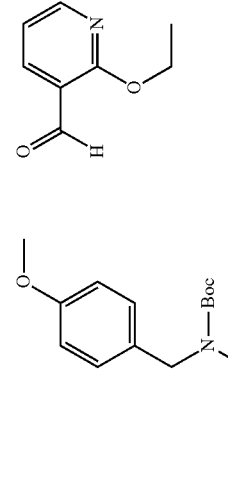 | 378.3 |
| P-2110 | 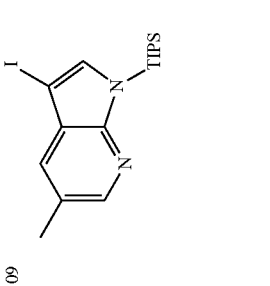 | 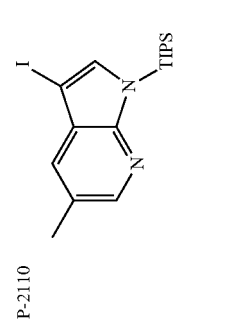 | 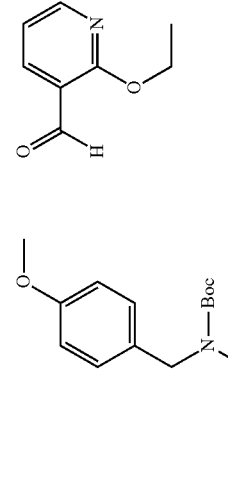 | 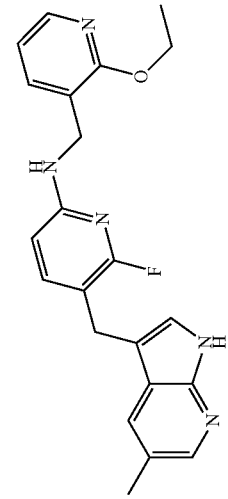 | |

| Comp. number | pyrrolo[2,3-b]pyridine | Boc Aldehyde | Step 3 aldehyde | Compound | MS (ESI) [M + H+]+ |
|---|---|---|---|---|---|
| P-2111 | | | | | |
| P-2112 | | | | | |

| Comp. number | pyrrolo[2,3-b]pyridine | Boc Aldehyde | Step 3 aldehyde | Compound | MS (ESI) [M + H⁺]⁺ |
|---|---|---|---|---|---|
| P-2113 | | | | | |
| P-2114 | | | | | |

| Comp. number | pyrrolo[2,3-b]pyridine | Boc Aldehyde | Step 3 aldehyde | Compound | MS (ESI) [M + H+]+ |
|---|---|---|---|---|---|
| P-2115 | | | | | 416.3 |
| P-2116 | | | | | |

-continued

| Comp. number | pyrrolo[2,3-b]pyridine | Boc Aldehyde | Step 3 aldehyde | Compound | MS (ESI) [M + H⁺]⁺ |
|---|---|---|---|---|---|
| P-2117 | | | | | |
| P-2118 | | | | | 366.3 |

-continued
| Comp. number | pyrrolo[2,3-b]pyridine | Boc Aldehyde | Step 3 aldehyde | Compound | MS (ESI) [M + H+]+ |
|---|---|---|---|---|---|
| P-2119 | 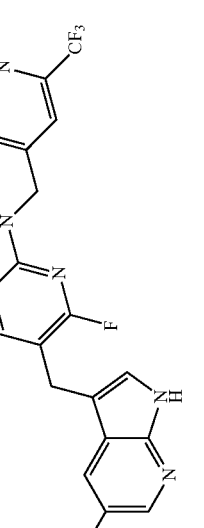 | 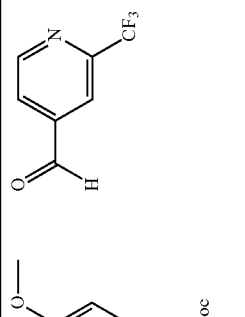 | 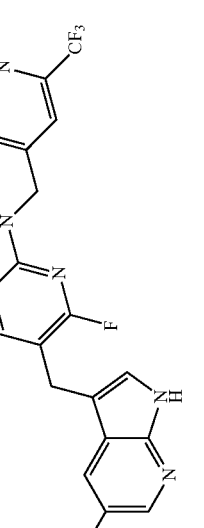 | 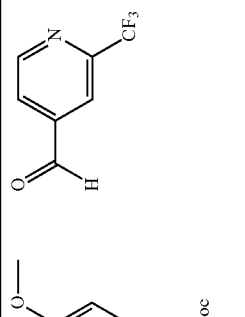 | 416.3 |
| P-2120 | 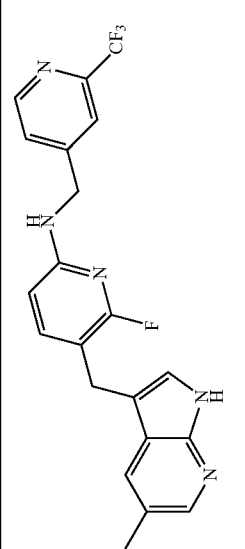 | 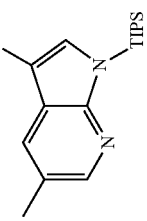 | 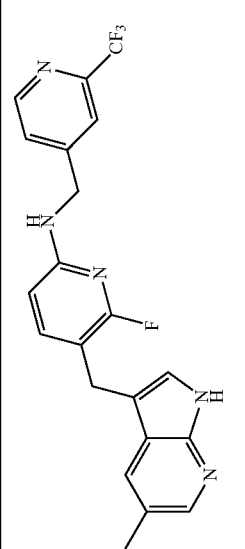 | 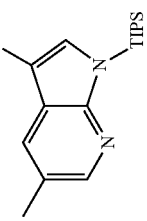 | 382.3 |

-continued

| Comp. number | pyrrolo[2,3-b]pyridine | Boc Aldehyde | Step 3 aldehyde | Compound | MS (ESI) [M + H+]+ |
|---|---|---|---|---|---|
| P-2121 | | | | | |
| P-2122 | | | | | |

| Comp. number | pyrrolo[2,3-b]pyridine | Boc Aldehyde | Step 3 aldehyde | Compound | MS (ESI) [M + H⁺]⁺ |
|---|---|---|---|---|---|
| P-2123 | | | | | |
| P-2124 | | | | | |

| Comp. number | pyrrolo[2,3-b]pyridine | Boc Aldehyde | Step 3 aldehyde | Compound | MS (ESI) [M + H⁺]⁺ |
|---|---|---|---|---|---|
| P-2125 | | | | | |
| P-2126 | | | | | |

| Comp. number | pyrrolo[2,3-b]pyridine | Boc Aldehyde | Step 3 aldehyde | Compound | MS (ESI) [M + H⁺]⁺ |
|---|---|---|---|---|---|
| P-2127 | | | | | |
| P-2128 | | | | | |

| Comp. number | pyrrolo[2,3-b]pyridine | Boc Aldehyde | Step 3 aldehyde | Compound | MS (ESI) [M + H⁺]⁺ |
|---|---|---|---|---|---|
| P-2129 | | | | | |
| P-2130 | | | | | |

-continued

| Comp. number | pyrrolo[2,3-b]pyridine | Boc Aldehyde | Step 3 aldehyde | Compound | MS (ESI) [M + H+]+ |
|---|---|---|---|---|---|
| P-2131 | | | | | 362.3 |
| P-2132 | | | | | |

| Comp. number | pyrrolo[2,3-b]pyridine | Boc Aldehyde | Step 3 aldehyde | Compound | MS (ESI) [M + H+]+ |
|---|---|---|---|---|---|
| P-2133 | | | | | |
| P-2134 | | | | | 395.1 |

-continued

| Comp. number | pyrrolo[2,3-b]pyridine | Boc Aldehyde | Step 3 aldehyde | Compound | MS (ESI) [M + H+]+ |
|---|---|---|---|---|---|
| P-2150 | | | | | |
| P-2151 | | | | | |

| Comp. number | pyrrolo[2,3-b]pyridine | Boc Aldehyde | Step 3 aldehyde | Compound | MS (ESI) [M + H+]+ |
|---|---|---|---|---|---|
| P-2166 (step 3a) | | | | | 446.2 |
| P-2167 (step 3a) | | | | | 459.1 |

-continued

| Comp. number | pyrrolo[2,3-b]pyridine | Boc Aldehyde | Step 3 aldehyde | Compound | MS (ESI) [M + H+]+ |
|---|---|---|---|---|---|
| P-2186 (step 3a) | | | | | 446.4 |
| P-2198 (step 3a) | | | | | 454.0 |

| Comp. number | pyrrolo[2,3-b]pyridine | Boc Aldehyde | Step 3 aldehyde | Compound | MS (ESI) [M + H⁺]⁺ |
|---|---|---|---|---|---|
| P-2199 (step 3a) | | | | | 472.0 |
| P-2202 (step 3a) | | | | | 472.1 |

Example 17

Synthesis of [5-(5-chloro-1H-pyrrolo[2,3-b]pyridin-3-ylmethyl)-6-fluoro-pyridin-2-yl]-(5-fluoro-pyridin-3-ylmethyl)-amine P-2001

[5-(5-Chloro-1H-pyrrolo[2,3-b]pyridin-3-ylmethyl)-6-fluoro-pyridin-2-yl]-(5-fluoro-pyridin-3-ylmethyl)-amine P-2001 was prepared in five steps from 5-chloro-1H-pyrrolo[2,3-b]pyridine 1 as shown in Scheme 17.

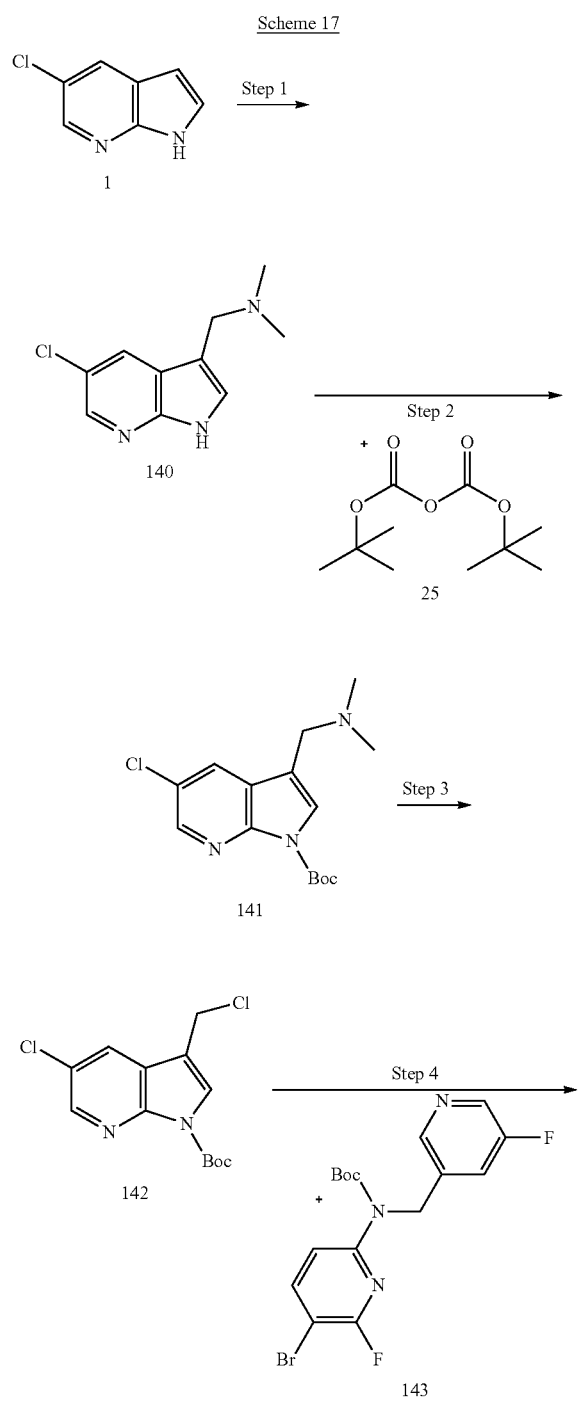

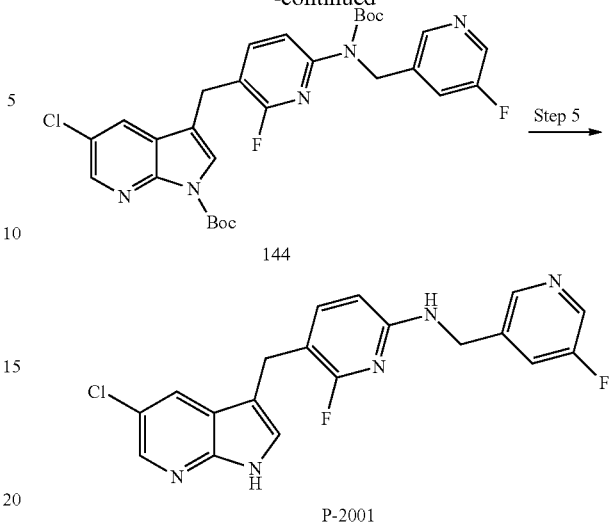

Step 1—Preparation of (5-chloro-1H-pyrrolo[2,3-b]pyridin-3-ylmethyl)-dimethyl-amine (140)

To 5-chloro-1H-pyrrolo[2,3-b]pyridine (1, 8.00 g, 0.0524 mol) in 250 mL of isopropyl alcohol, dimethylamine hydrochloride (4.79 g, 0.0587 mol) and formaldehyde (1.77 g, 0.0589 mol) were added. The reaction was stirred at room temperature overnight, followed by refluxing for 4 hours. The reaction was concentrated, poured into water, and extracted with ethyl acetate. The organic layer was dried over anhydrous sodium sulfate and filtered. The filtrate was concentrated to give crude compound (140, 10.0 g, 91%), that was used directly in the next step.

Step 2: Preparation of 5-chloro-3-dimethylaminomethyl-pyrrolo[2,3-b]pyridine-1-carboxylic acid tert-butyl ester (141)

To (5-chloro-1H-pyrrolo[2,3-b]pyridin-3-ylmethyl)-dimethyl-amine (140, 5.00 g, 23.8 mmol,) in 60.0 mL of N,N-dimethylformamide, sodium hydride (1.05 g, 60% in mineral oil, 26.2 mmol) was added. After 10 minutes, di-tert-butyldicarbonate (25, 6.24 g, 28.6 mmol) was added and the reaction was stirred at room temperature overnight, then poured into water and extracted with ethyl acetate. The organic layer was dried over sodium sulfate, filtered and the filtrate was concentrated under vacuum. The resulting material was purified by silica gel column chromatography eluting with 5% methanol in dichloromethane. Appropriate fractions were combined and concentrated under vacuum to provide the desired compound as a white solid (141, 5.20 g).

Step 3: Preparation of 5-chloro-3-chloromethyl-pyrrolo[2,3-b]pyridine-1-carboxylic acid tert-butyl ester (142)

To 5-chloro-3-dimethylaminomethyl-pyrrolo[2,3-b]pyridine-1-carboxylic acid tert-butyl ester (141, 4.20 g, 13.6 mmol) in 100 mL of toluene, ethyl chloroformate (1.48 mL, 15.5 mmol) was added under nitrogen. The reaction was stirred at room temperature for 2 hours, then concentrated under vacuum and combined with water and extracted with ethyl acetate. The organic layer was dried over sodium sulfate, filtered and the filtrate was concentrated under vacuum.

The resulting material was purified by silica gel column chromatography eluting with 25% ethyl acetate in hexane to provide the desired compound (142, 1.60 g).

Step 4—Preparation of 3-{6-[tert-butoxycarbonyl-(5-fluoro-pyridin-3-ylmethyl)-amino]-2-fluoro-pyridin-3-ylmethyl}-5-chloro-pyrrolo[2,3-b]pyridine-1-carboxylic acid tert-butyl ester (144)

To (5-bromo-6-fluoro-pyridin-2-yl)-(5-fluoro-pyridin-3-ylmethyl)-carbamic acid tert-butyl ester (143, 0.600 g, 1.50 mmol) in 10.0 mL of tetrahydrofuran at −25° C. under nitrogen, isopropylmagnesium chloride (0.730 mL, 2.0 M in tetrahydrofuran, 1.46 mmol) was added and the reaction allowed to come to 5° C. over 1 hour. The reaction was then cooled to −35° C., and CuCN·2LiCl (2.0 mL, 0.75 M in tetrahydrofuran, 1.5 mmol) was added. After 5 minutes, 5-chloro-3-chloromethyl-pyrrolo[2,3-b]pyridine-1-carboxylic acid tert-butyl ester (142, 0.300 g, 0.996 mmol) in 4.0 mL of tetrahydrofuran was added and the reaction allowed to come to room temperature over 1 hour. The reaction was poured into dilute ammonia solution and extracted with ethyl acetate. The organic layer was separated, dried over sodium sulfate, filtered and the filtrate concentrated under vacuum. The resulting material was purified by silica gel column chromatography eluting with 20-100% ethyl acetate in hexane. Appropriate fractions were combined and the solvent removed under vacuum to provide the desired compound (144, 130 mg). MS (ESI) [M+H]$^+$=586.2.

Step 5—Preparation of [5-(5-chloro-1H-pyrrolo[2,3-b]pyridin-3-ylmethyl)-6-fluoro-pyridin-2-yl]-(5-fluoro-pyridin-3-ylmethyl)-amine (P-2001)

To 3-{6-[tert-butoxycarbonyl-(5-fluoro-pyridin-3-ylmethyl)-amino]-2-fluoro-pyridin-3-ylmethyl}-5-chloro-pyrrolo[2,3-b]pyridine-1-carboxylic acid tert-butyl ester (144, 0.280 g, 0.478 mmol) in 10.0 mL of dichloromethane, trifluoroacetic acid (1.00 mL, 13.0 mmol) was added and the reaction stirred at room temperature overnight. This was pooled with a separate reaction run similarly and concentrated under vacuum. The resulting material was combined with aqueous potassium carbonate and ethyl acetate and mixed. The aqueous layer was separated and the organic layer was dried over sodium sulfate, filtered and the filtrate concentrated under vacuum. The resulting material was purified by silica gel column chromatography eluting with 20% ethyl acetate in hexane. Appropriate fractions were combined and the solvent removed under vacuum to provide the desired compound (P-2001, 99 mg). MS (ESI) [M+H$^+$]$^+$=386.0.

Preparation of 3-[[2-fluoro-6-[(5-fluoro-6-methoxy-3-pyridyl)methylamino]-3-pyridyl]methyl]-1H-pyrrolo[2,3-b]pyridine-5-carbonitrile (P-2204)

To 5-[(5-bromo-1H-pyrrolo[2,3-b]pyridin-3-yl)methyl]-6-fluoro-N-[(5-fluoro-6-methoxy-3-pyridyl)methyl]pyridin-2-amine (125 mg, 0.27 mmol) was added 2 mL of N,N-dimethylacetamide. The mixture suspension was degassed by bubbling with argon. To this suspension was added Zinc (5 mg, 0.08 mmol), 1,1'-Bis(diphenylphosphino)ferrocene (6 mg, 0.01 mmol), Zinc Cyanide (0.01 ml, 0.19 mmol), and Tris(dibenzylideneacetone)dipalladium (0) (7 mg, 0.01 mmol) at room temperature under argon. The mixture was heated to 120° C. for 2 hrs and cooled to room temperature. The reaction mixture was extracted with ethyl acetate and water (+saturated sodium chloride). The organic layer was washed with water and brine, dried by MgSO$_4$. The volatiles were removed under vacuum. The residue was suspended in acetonitrile and sonicated for 45 mins. The precipitate was collected by filtration and washed with acetonitrile. A tan solid was obtained (98 mg, 88.8% yield). LC-MS showed one major peak with 98.6% purity. The structure of the product is confirmed by H$^1$-NMR (DMSO-d6). MS (ESI) [M+H]$^+$ =406.9.

Additional compounds are prepared following the protocol of Scheme 17, where conditions may vary, for example, any of the solvents, reaction times, reagents, temperatures, work up conditions, or other reaction parameters may be varied employing alternate solvents, reagents, reaction times, temperatures, work up conditions, and the like, as are readily available to one skilled in the art. Compounds are prepared optionally replacing 5-chloro-1H-pyrrolo[2,3-b]pyridine 1 with a suitable 5-substituted-1H-pyrrolo[2,3-b]pyridine in step 1 and optionally replacing (5-bromo-6-fluoro-pyridin-2-yl)-(5-fluoro-pyridin-3-ylmethyl)-carbamic acid tert-butyl ester 143 with a suitable N-protected bromo (or other suitable halo) compound in step 4. The following compounds are made using this procedure. Compounds in the following table were characterized by $^1$H and $^{13}$C NMR spectroscopy as well as mass spectrometry.

3-{2-Fluoro-6-[(5-fluoro-6-methoxy-pyridin-3-ylmethyl)-amino]-pyridin-3-ylmethyl}-1H-pyrrolo[2,3-b]pyridine-5-carbonitrile (P-1654), 3-{6-[(6-Chloro-pyridin-3-ylmethyl)-amino]-2-fluoro-pyridin-3-ylmethyl}-1H-pyrrolo[2,3-b]pyridine-5-carbonitrile (P-1655), 3-{2-Fluoro-6-[(5-fluoro-2-methoxy-pyridin-3-ylmethyl)-amino]-pyridin-3-ylmethyl}-1H-pyrrolo[2,3-b]pyridine-5-carbonitrile (P-1656), 3-{2-Fluoro-6-[(4-trifluoromethyl-pyridin-3-ylmethyl)-amino]-pyridin-3-ylmethyl}-1H-pyrrolo[2,3-b]pyridine-5-carbonitrile (P-1657), 3-{2-Fluoro-6-[(6-methoxy-pyridin-3-ylmethyl)-amino]-pyridin-3-ylmethyl}-1H-pyrrolo[2,3-b]pyridine-5-carbonitrile (P-1658), 3-{2-Fluoro-6-[(6-trifluoromethyl-pyridin-3-ylmethyl)-amino]-pyridin-3-ylmethyl}-1H-pyrrolo[2,3-b]pyridine-5-carbonitrile (P-1659), 3-{2-Fluoro-6-[(2-methoxy-pyridin-3-ylmethyl)-amino]-pyridin-3-ylmethyl}-1H-pyrrolo[2,3-b]pyridine-5-carbonitrile (P-1660),

[6-Fluoro-5-(5-methyl-1H-pyrrolo[2,3-b]pyridin-3-ylmethyl)-pyridin-2-yl]-(5-fluoro-pyridin-3-ylmethyl)-amine (P-2027),

[6-Fluoro-5-(5-methoxy-1H-pyrrolo[2,3-b]pyridin-3-ylmethyl)-pyridin-2-yl]-(5-fluoro-pyridin-3-ylmethyl)-amine (P-2028),

[6-Fluoro-5-(5-methyl-1H-pyrrolo[2,3-b]pyridin-3-ylmethyl)-pyridin-2-yl]-(6-methoxy-pyridin-3-ylmethyl)-amine (P-2029),

[6-Fluoro-5-(5-methoxy-1H-pyrrolo[2,3-b]pyridin-3-ylmethyl)-pyridin-2-yl]-(6-methoxy-pyridin-3-ylmethyl)-amine (P-2030),

[6-Fluoro-5-(5-methyl-1H-pyrrolo[2,3-b]pyridin-3-ylmethyl)-pyridin-2-yl]-(6-trifluoromethyl-pyridin-3-ylmethyl)-amine (P-2031), (4-Chloro-benzyl)-[6-fluoro-5-(5-methoxy-1H-pyrrolo[2,3-b]pyridin-3-ylmethyl)-pyridin-2-yl]-amine (P-2032), (5-Fluoro-6-methoxy-pyridin-3-ylmethyl)-[6-fluoro-5-(1H-pyrrolo[2,3-b]pyridin-3-ylmethyl)-pyridin-2-yl]-amine (P-2041),

[5-(5-Chloro-1H-pyrrolo[2,3-b]pyridin-3-ylmethyl)-pyrimidin-2-yl]-(5-fluoro-pyridin-3-ylmethyl)-amine (P-2176), 5-[(5-bromo-1H-pyrrolo[2,3-b]pyridin-3-yl)methyl]-6-fluoro-N-[(5-fluoro-6-methoxy-3-pyridyl)methyl]pyridin-2-amine (P-2203), 3-[[2-fluoro-6-[(5-fluoro-6-methoxy-3-pyridyl)methylamino]-3-pyridyl]methyl]-1H-pyrrolo[2,3-b]pyridine-5-carbonitrile (P-2204), 6-chloro-N-[(5-fluoro-2-methoxy-3-pyridyl)methyl]-5-[(5-methyl-1H-pyrrolo[2,3-b]pyridin-3-yl)methyl]pyridin-2-amine (P-2205), and 6-fluoro-N-[(5-fluoro-6-methoxy-3-pyridyl)methyl]-5-[[5-(trifluoromethyl)-1H-pyrrolo[2,3-b]pyridin-3-yl]methyl]pyridin-2-amine (P-2206).

The following table indicates the 1H-pyrrolo[2,3-b]pyridine compound (column 2) used in step 1 and halogen substituted compound (column 3) used in step 4 to afford the desired compound (column 4). The compound number is provided in column 1, and the observed mass is in column 5.

| Comp. number | 1H-pyrrolo[2,3-b]pyridine | Halogen compound |
| --- | --- | --- |
| P-1654 | | |
| P-1655 | | |
| P-1656 | | |
| P-1657 | | |
| P-1658 | | |

-continued
P-1659 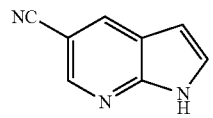 [SMILES: N#Cc1cnc2[nH]ccc2c1] 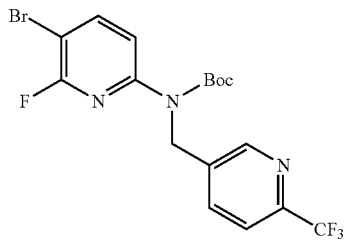
P-1660 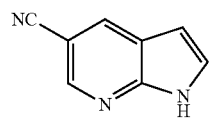 [SMILES: N#Cc1cnc2[nH]ccc2c1] 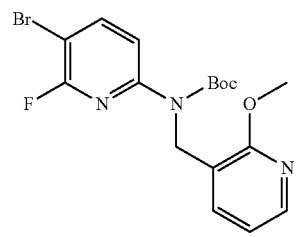 [SMILES: COc1ncccc1CN(C(=O)OC(C)(C)C)c1ccc(Br)c(F)n1]
P-2027 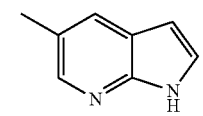 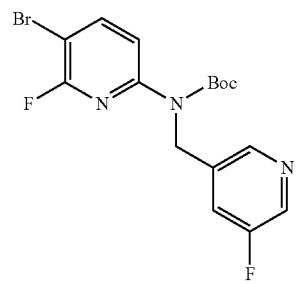 [SMILES: CC(C)(C)OC(=O)N(Cc1cncc(F)c1)c1ccc(Br)c(F)n1]
P-2028 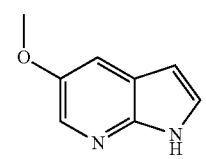 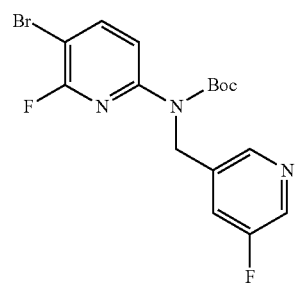 [SMILES: CC(C)(C)OC(=O)N(Cc1cncc(F)c1)c1ccc(Br)c(F)n1]
P-2029 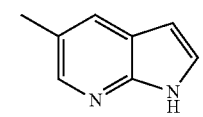 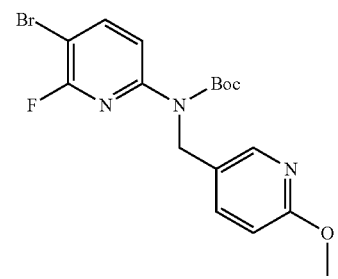 [SMILES: COc1ccc(CN(C(=O)OC(C)(C)C)c2ccc(Br)c(F)n2)cn1]
P-2030 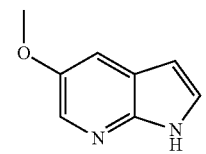 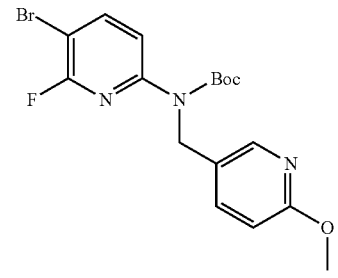 [SMILES: COc1ccc(CN(C(=O)OC(C)(C)C)c2ccc(Br)c(F)n2)cn1]

-continued
| | | |
|---|---|---|
| P-2031 | 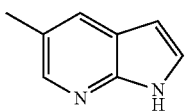 | 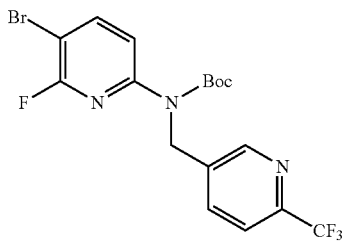 |
| P-2032 | 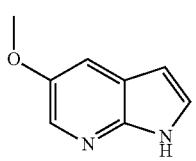 | 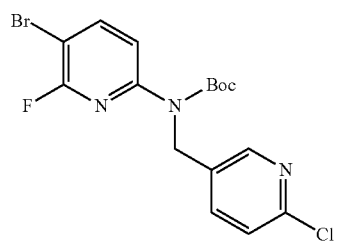 [SMILES: CC(C)(C)OC(=O)N(Cc1ccc(Cl)nc1)c1ccc(Br)c(F)n1] |
| P-2041 | 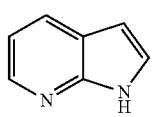 | 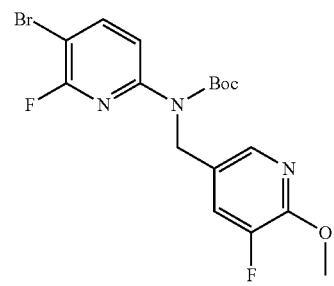 [SMILES: COc1ncc(CN(C(=O)OC(C)(C)C)c2ccc(Br)c(F)n2)cc1F] |
| P-2176 | 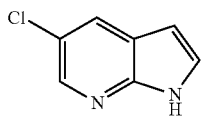 | 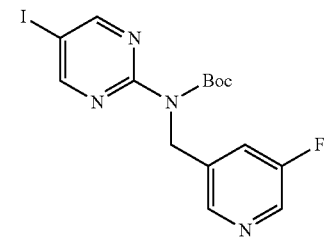 [SMILES: CC(C)(C)OC(=O)N(Cc1cncc(F)c1)c1ncc(I)cn1] |
| Comp. number | Compound structure | MS (ESI) [M + H⁺]⁺ |
|---|---|---|
| P-1654 | 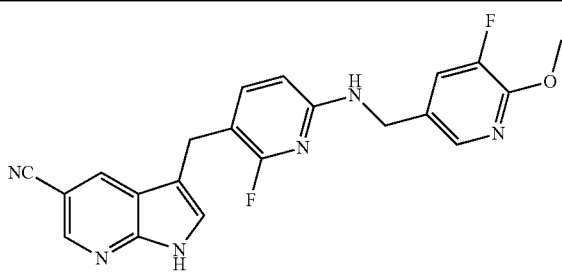 | |
| P-1655 | 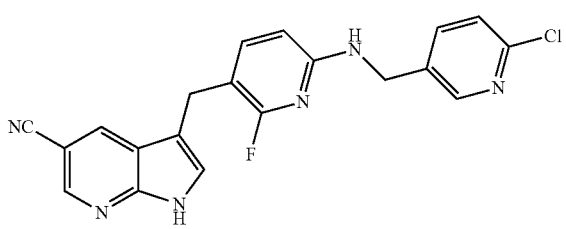 [SMILES: N#Cc1cnc2[nH]cc(Cc3ccc(NCc4ccc(Cl)nc4)nc3F)c2c1] | |

| | | |
|---|---|---|
| P-1656 | 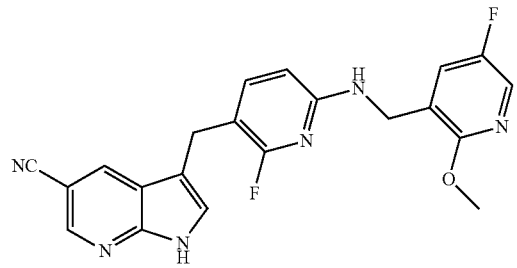 [SMILES: COc1ncc(F)cc1CNc1ccc(Cc2c[nH]c3ncc(C#N)cc23)c(F)n1] | 407.2 |
| P-1657 | 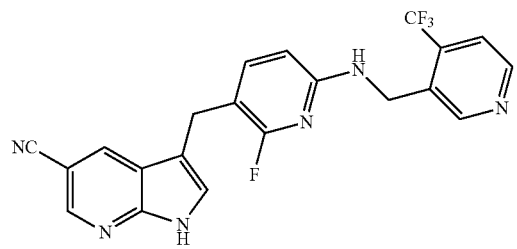 [SMILES: N#Cc1cnc2[nH]cc(Cc3ccc(NCc4cnccc4C(F)(F)F)nc3F)c2c1] | |
| P-1658 | 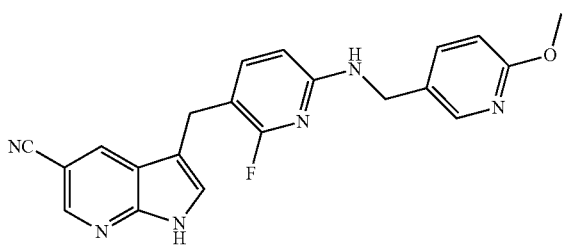 [SMILES: COc1ccc(CNc2ccc(Cc3c[nH]c4ncc(C#N)cc34)c(F)n2)cn1] | |
| P-1659 | 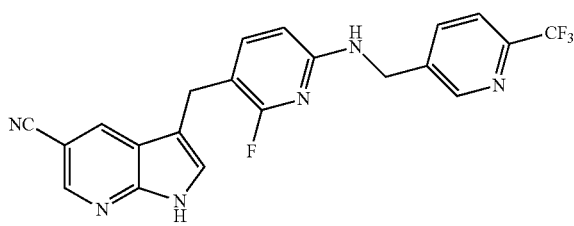 [SMILES: N#Cc1cnc2[nH]cc(Cc3ccc(NCc4ccc(C(F)(F)F)nc4)nc3F)c2c1] | |
| P-1660 | 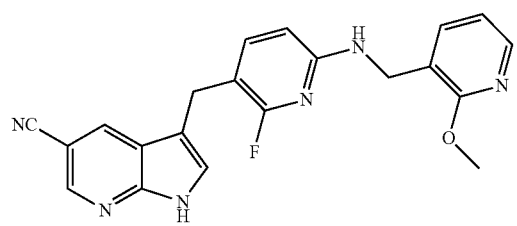 [SMILES: COc1ncccc1CNc1ccc(Cc2c[nH]c3ncc(C#N)cc23)c(F)n1] | |
| P-2027 | 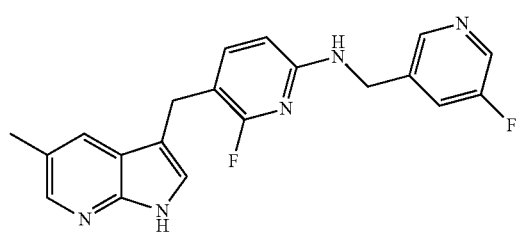 [SMILES: Cc1cnc2[nH]cc(Cc3ccc(NCc4cncc(F)c4)nc3F)c2c1] | 366.0 |

-continued
| P-2028 | 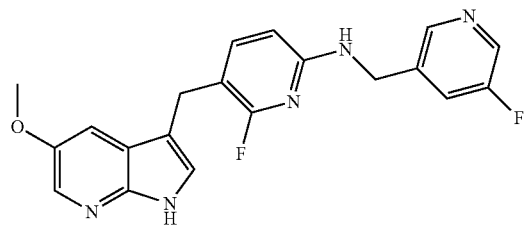 [SMILES: COc1cnc2[nH]cc(Cc3ccc(NCc4cncc(F)c4)nc3F)c2c1] | 381.9 |
| P-2029 | 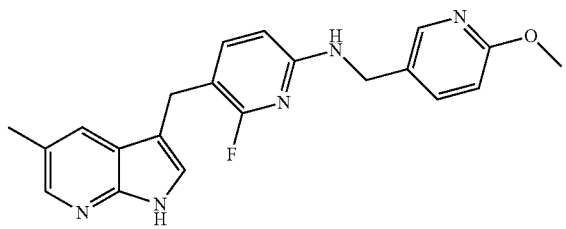 | 378.0 |
| P-2030 | 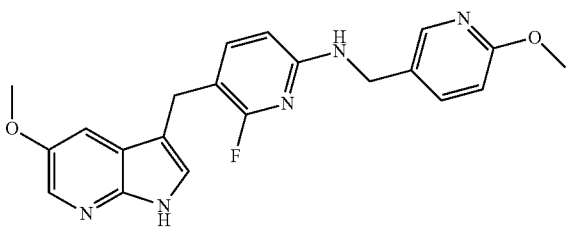 [SMILES: COc1cnc2[nH]cc(Cc3ccc(NCc4ccc(OC)nc4)nc3F)c2c1] | 394.2 |
| P-2031 | 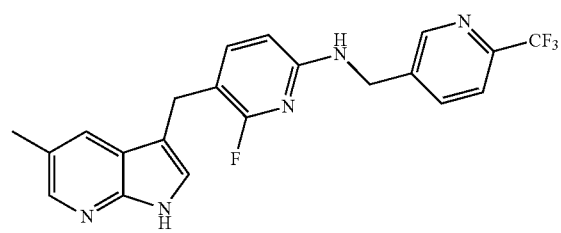 [SMILES: Cc1cnc2[nH]cc(Cc3ccc(NCc4ccc(C(F)(F)F)nc4)nc3F)c2c1] | 381.9 |
| P-2032 | 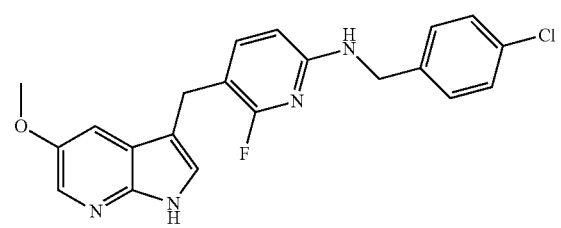 [SMILES: COc1cnc2[nH]cc(Cc3ccc(NCc4ccc(Cl)cc4)nc3F)c2c1] | 396.9 |
P-2041
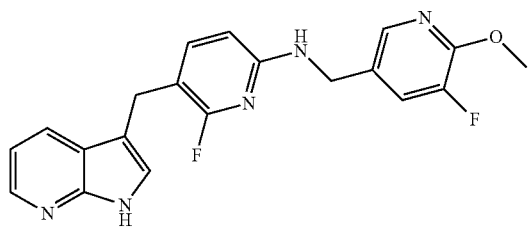 [SMILES: COc1ncc(CNc2ccc(Cc3c[nH]c4ncccc34)c(F)n2)cc1F]

P-2176

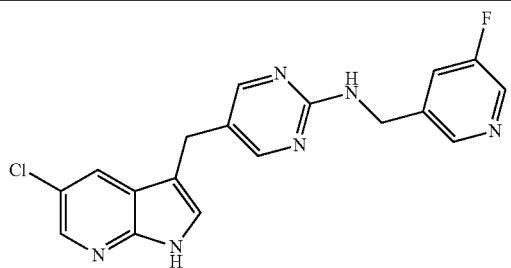

369.1

Example 18

Synthesis of (3-chloro-benzyl)-[5-(5-fluoro-1H-pyrrolo[2,3-b]pyridin-3-ylmethyl)-1-methyl-1H-pyrazol-3-yl]-amine P-2006

(3-Chloro-benzyl)-[5-(5-fluoro-1H-pyrrolo[2,3-b]pyridin-3-ylmethyl)-1-methyl-1H-pyrazol-3-yl]-amine P-2006 was prepared in two steps from 5-(3-chloro-benzylamino)-2-methyl-2H-pyrazole-3-carbaldehyde 145 and 5-fluoro-3-iodo-1-triisopropylsilanyl-1H-pyrrolo[2,3-b]pyridine 146 as shown in Scheme 18.

Scheme 18

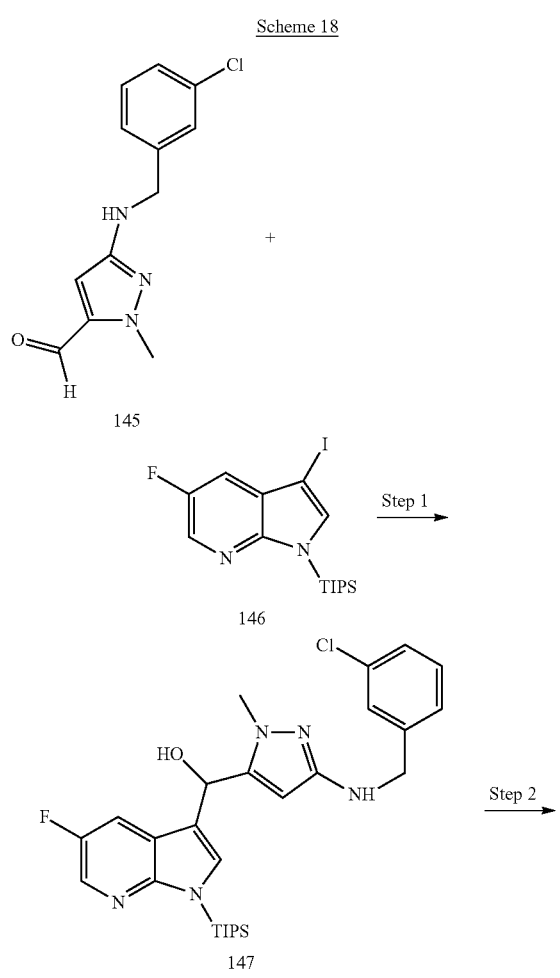

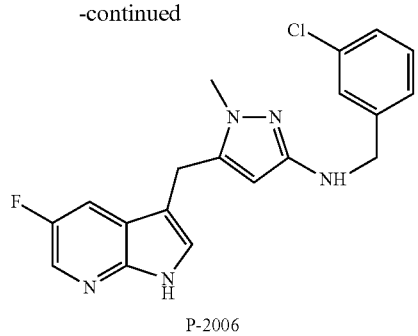

P-2006

Step 1—Preparation of [5-(3-chloro-benzylamino)-2-methyl-2H-pyrazol-3-yl]-(5-fluoro-1-triisopropylsilanyl-1H-pyrrolo[2,3-b]pyridin-3-yl)-methanol (147)

5-Fluoro-3-iodo-1-triisopropylsilanyl-1H-pyrrolo[2,3-b]pyridine (146, 0.33 g, 0.79 mmol) and 1.5 mL of tetrahydrofuran were combined in a round bottom flask and cooled to −20° C. Isopropylmagnesium chloride (400 µL, 2.0 M in tetrahydrofuran, 0.8 mmol) was added dropwise and the reaction stirred and brought to −5° C. The reaction was cooled to −20° C. and 5-(3-chloro-benzylamino)-2-methyl-2H-pyrazole-3-carbaldehyde (145, 0.090 g, 0.36 mmol) in tetrahydrofuran was added and the reaction stirred and brought to 0° C. The reaction was concentrated under vacuum, diluted with ethyl acetate and washed with saturated aqueous sodium bicarbonate, then brine. The organic layer was separated and dried over sodium sulfate, filtered and the filtrate purified by silica gel flash column chromatography eluting with a gradient of 5-80% ethyl acetate in hexane. Appropriate fractions were combined and concentrated under vacuum to provide the desired compound. MS (ESI) [M+H$^+$]$^+$=542.7, 543.95.

Step 2—Preparation of (3-chloro-benzyl)-[5-(5-fluoro-1H-pyrrolo[2,3-b]pyridin-3-ylmethyl)-1-methyl-1H-pyrazol-3-yl]-amine (P-2006)

To [5-(3-chloro-benzylamino)-2-methyl-2H-pyrazol-3-yl]-(5-fluoro-1-triisopropylsilanyl-1H-pyrrolo[2,3-b]pyridin-3-yl)-methanol (147, 0.070 g, 0.13 mmol) in 4 mL of dichloromethane, triethylsilane (0.210 mL, 1.31 mmol) and trifluoroacetic acid (0.100 mL, 1.30 mmol) were added and the reaction stirred overnight at room temperature. The reaction was concentrated under vacuum, then ethyl acetate was added, then washed with 1M aqueous potassium carbonate, then brine. The organic layer was dried over sodium sulfate, filtered and the filtrate purified by silica gel flash column chromatography eluting with a gradient of 2-20% methanol in dichloromethane. Appropriate fractions were combined and concentrated under vacuum and the resulting solid washed with ethyl acetate in hexane to provide the desired compound.

The following compounds are prepared following the protocol of Scheme 18, where conditions may vary, for example, any of the solvents, reaction times, reagents, temperatures, work up conditions, or other reaction parameters may be varied employing alternate solvents, reagents, reaction times, temperatures, work up conditions, and the like, as are readily available to one skilled in the art. The following compounds were characterized by $^1$H and $^{13}$C NMR spectroscopy as well as mass spectrometry.

6-chloro-N-[(5-fluoro-2-methoxy-3-pyridyl)methyl]-5-[(5-methyl-1H-pyrrolo[2,3-b]pyridin-3-yl)methyl]pyridin-2-amine (P-2205), and 6-fluoro-N-[(5-fluoro-6-methoxy-3-pyridyl)methyl]-5-[[5-(trifluoromethyl)-1H-pyrrolo[2,3-b]pyridin-3-yl]methyl]pyridin-2-amine (P-2206).

Example 19

Synthesis of [5-(5-chloro-1H-pyrrolo[2,3-b]pyridin-3-ylmethyl)-1H-pyrazol-3-yl]-(4-fluoro-benzyl)-amine P-2016

[5-(5-Chloro-1H-pyrrolo[2,3-b]pyridin-3-ylmethyl)-1H-pyrazol-3-yl]-(4-fluoro-benzyl)-amine P-2016 was prepared in three steps from 5-(4-fluoro-benzylamino)-2-(4-methoxy-benzyl)-2H-pyrazole-3-carbaldehyde 113 and 5-chloro-3-iodo-1-triisopropylsilanyl-1H-pyrrolo[2,3-b]pyridine 4 as shown in Scheme 19.

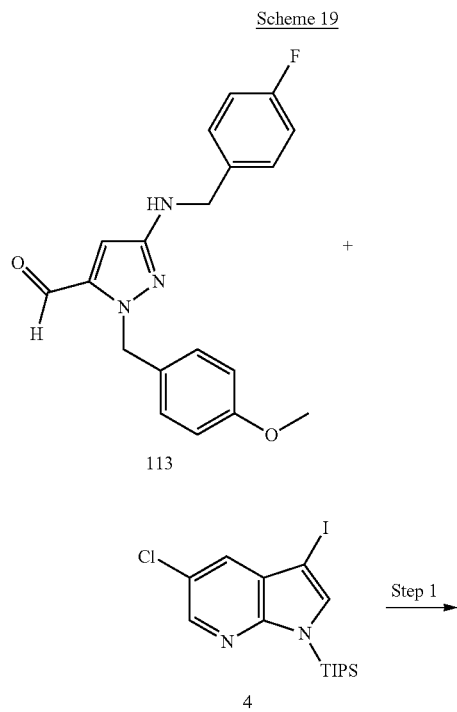

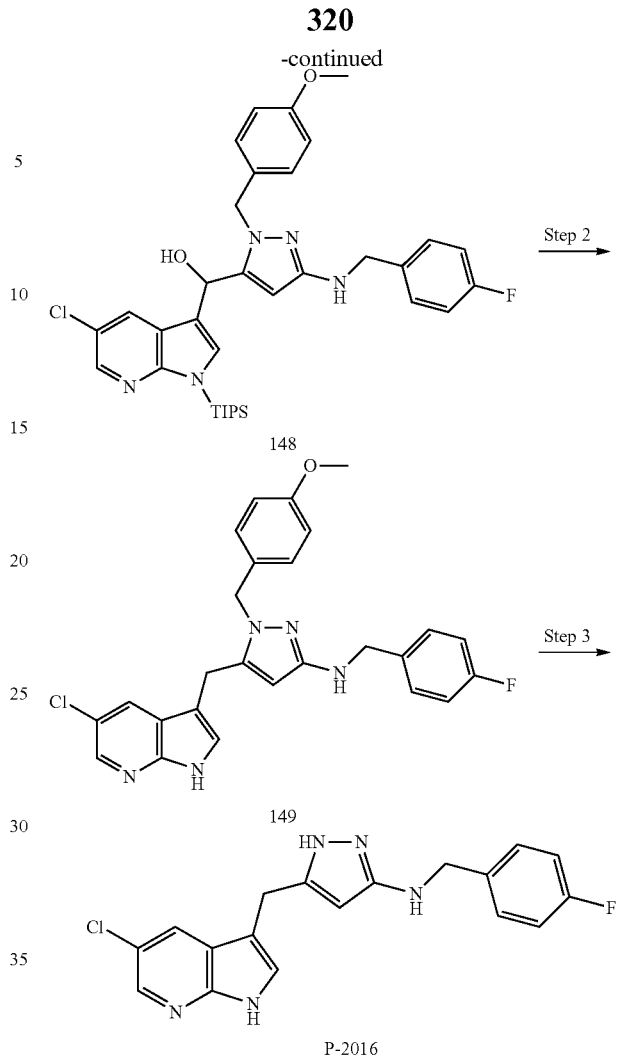

Step 1—Preparation of (5-chloro-1-triisopropylsilanyl-1H-pyrrolo[2,3-b]pyridin-3-yl)-[5-(4-fluoro-benzylamino)-2-(4-methoxy-benzyl)-2H-pyrazol-3-yl]-methanol (148)

In a round bottom flask, 5-chloro-3-iodo-1-triisopropylsilanyl-1H-pyrrolo[2,3-b]pyridine (4, 1.7 g, 3.9 mmol) was combined with 1.3 mL of tetrahydrofuran and cooled to −20° C. Isopropylmagnesium chloride (2.0 mL, 2 M in tetrahydrofuran, 4.0 mmol) was added dropwise and the reaction stirred at −5° C. The reaction was cooled to −20° C. and 5-(4-fluoro-benzylamino)-2-(4-methoxy-benzyl)-2H-pyrazole-3-carbaldehyde (113, 0.622 g, 1.83 mmol) in 2 mL of tetrahydrofuran was added and the reaction stirred at 0° C. The reaction was concentrated under vacuum, diluted with ethyl acetate and washed with sodium bicarbonate and brine. The organic layer was dried with sodium sulfate and purified by silica gel column chromatography, eluting with 5-80% ethyl acetate in hexanes. Appropriate fractions were combined and concentrated under vacuum to provide the desired compound. MS (ESI) [M+H$^+$]$^+$=648.38 and 649.74.

Step 2—Preparation of [5-(5-chloro-1H-pyrrolo[2,3-b]pyridin-3-ylmethyl)-1-(4-methoxy-benzyl)-1H-pyrazol-3-yl]-(4-fluoro-benzyl)-amine (149)

In a quartz vial, (5-chloro-1-triisopropylsilanyl-1H-pyrrolo[2,3-b]pyridin-3-yl)-[5-(4-fluoro-benzylamino)-2-(4- methoxy-benzyl)-2H-pyrazol-3-yl]-methanol (148, 0.328 g, 0.506 mmol) was combined with 20 mL of dichloromethane, triethylsilane (0.4 mL, 2.0 mmol) was added, followed by trifluoroacetic acid (0.2 mL, 2.0 mmol). The reaction was stirred overnight at room temperature, then concentrated under vacuum and ethyl acetate was added. This was washed with 1 M aqueous potassium carbonate and brine, dried with sodium sulfate, and purified by silica gel column chromatography, eluting with 2-20% methanol in dichloromethane. Appropriate fractions were combined and concentrated under vacuum, and the solid further washed with ethyl acetate and hexane to provide the desired compound. $^1$H NMR was consistent with compound structure.

Step 3—Preparation of [5-(5-chloro-1H-pyrrolo[2,3-b]pyridin-3-ylmethyl)-1H-pyrazol-3-yl]-(4-fluoro-benzyl)-amine (P-2016)

Into a round bottom flask, [5-(5-chloro-1H-pyrrolo[2,3-b]pyridin-3-ylmethyl)-1-(4-methoxy-benzyl)-1H-pyrazol-3-yl]-(4-fluoro-benzyl)-amine (149, 0.060 g, 0.13 mmol) was dissolved in 5 mL of trifluoroacetic acid (60 mmol) and the reaction was heated at 70° C. overnight. The reaction was cooled to room temperature, then concentrated under vacuum and ethyl acetate was added. This was washed with 1 M aqueous potassium carbonate and brine, dried with sodium sulfate and purified by silica gel column chromatography, eluting with 2-20% methanol in dichloromethane. Appropriate fractions were combined and concentrated under vacuum, and the solid further washed with ethyl acetate and hexane to provide the desired compound. $^1$H NMR was consistent with compound structure. MS (ESI) [M+H$^+$]$^+$=356.85.

Example 20

Synthesis of 5-fluoro-N-[6-fluoro-5-(5-methyl-1H-pyrrolo[2,3-b]pyridin-3-ylmethyl)-pyridin-2-yl]-2-methoxy-nicotinamide P-2168

5-Fluoro-N-[6-fluoro-5-(5-methyl-1H-pyrrolo[2,3-b]pyridin-3-ylmethyl)-pyridin-2-yl]-2-methoxy-nicotinamide P-2168 was prepared in three steps from 5-fluoro-2-methoxy-pyridine-3-carbaldehyde 37 as shown in Scheme 20.

Scheme 20

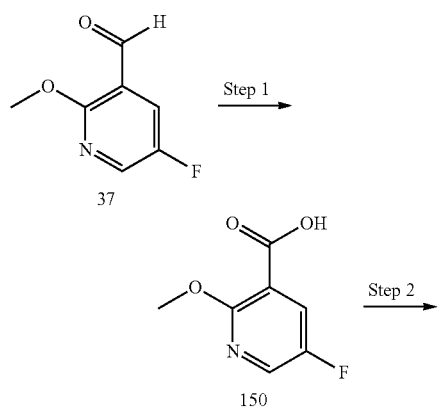

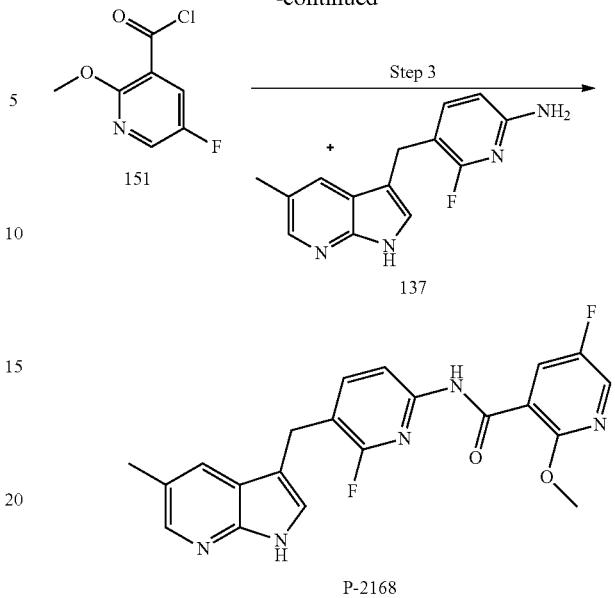

Step 2—Preparation of 5-fluoro-2-methoxy-nicotinic acid (150)

In a round bottom flask, 5-fluoro-2-methoxy-pyridine-3-carbaldehyde (37, 0.500 g, 3.22 mmol) was combined with sodium chlorite (0.6734 g, 5.957 mmol), 30 mL of 1,4-dioxane, 10 mL of water, and sulfamic acid (2.39 g, 24.6 mmol). The reaction mixture was stirred at room temperature for 5 minutes, then poured into 100 mL of water and extracted with 100 mL of ethyl acetate. The organic layer was washed with water, brine, then dried over magnesium sulfate, filtered and the filtrate concentrated under vacuum to provide the desired compound (150, 512 mg), used in the next step without further purification.

Step 2—Preparation of 5-fluoro-2-methoxy-nicotinoyl chloride (151)

In a round bottom flask, 5-fluoro-2-methoxy-nicotinic acid (150, 250 mg, 1.46 mmol) was combined with thionyl chloride (3.00 mL, 41.1 mmol) and the suspension was stirred at room temperature for 3 hours. The reaction was concentrated to dryness under vacuum to provide the desired compound, used in the next step without further purification.

Step 3—Preparation of 5-fluoro-N-[6-fluoro-5-(5-methyl-1H-pyrrolo[2,3-b]pyridin-3-ylmethyl)-pyridin-2-yl]-2-methoxy-nicotinamide (P-2168)

In a reaction flask, 6-fluoro-5-(5-methyl-1H-pyrrolo[2,3-b]pyridin-3-ylmethyl)-pyridin-2-ylamine (137, 100 mg, 0.3902 mmol) was combined with 5-fluoro-2-methoxy-nicotinoyl chloride (151, 81.37 mg, 0.4292 mmol), 3.00 mL of tetrahydrofuran, and pyridine (0.06312 mL, 0.7804 mmol). The reaction was stirred at room temperature overnight, then poured into aqueous 1N hydrochloric acid and extracted with ethyl acetate. The organic layer was dried over sodium sulfate, filtered and the filtrate concentrated under vacuum. The resulting material was purified by silica gel column chromatography, eluting with 1-5% methanol in dichloromethane.

Appropriate fractions were combined and concentrated under vacuum to provide the desired compound (P-2168, 100 mg). MS (ESI) [M+H⁺]⁺=409.9.

Example 21

Synthesis of [5-(5-bromo-1H-pyrrolo[2,3-b]pyridin-3-ylmethyl)-pyridin-2-yl]-(6-methoxy-pyridin-3-ylmethyl)-amine P-2017

[5-(5-Bromo-1H-pyrrolo[2,3-b]pyridin-3-ylmethyl)-pyridin-2-yl]-(6-methoxy-pyridin-3-ylmethyl)-amine P-2017 was prepared in two steps from 5-bromo-1H-pyrrolo[2,3-b]pyridine 152 and (5-formyl-pyridin-2-yl)-(6-methoxy-pyridin-3-ylmethyl)-carbamic acid tert-butyl ester 153 as shown in Scheme 21.

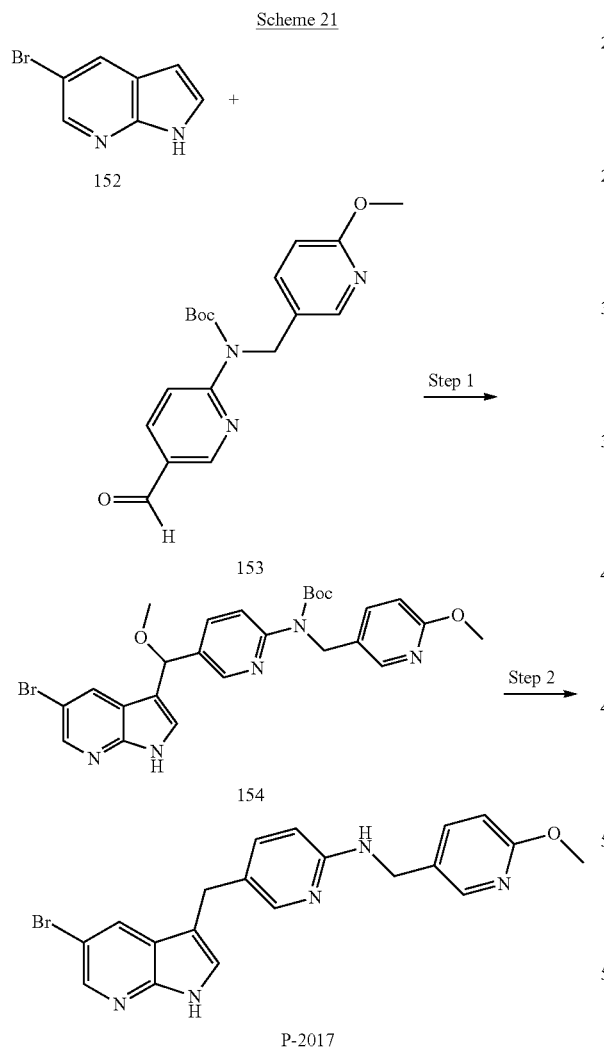

Step 1—Preparation {5-[(5-bromo-1H-pyrrolo[2,3-b]pyridin-3-yl)-methoxy-methyl]-pyridin-2-yl}-(6-methoxy-pyridin-3-ylmethyl)-carbamic acid tert-butyl ester (154)

To 5-bromo-1H-pyrrolo[2,3-b]pyridine (152, 0.622 g, 3.16 mmol) in 50.0 mL of methanol under nitrogen, (5-formyl-pyridin-2-yl)-(6-methoxy-pyridin-3-ylmethyl)-carbamic acid tert-butyl ester (153, 1.05 g, 3.06 mmol) and potassium hydroxide (1.50 g, 26.7 mmol) were added and the reaction stirred at room temperature overnight. The reaction was poured into water, extracted with ethyl acetate, the organic layer dried over sodium sulfate, filtered and the filtrate concentrated under vacuum. The resulting material was purified by silica gel column chromatography eluting with a gradient of 20-100% ethyl acetate in hexane. Appropriate fractions were combined and concentrated under vacuum to provide the desired compound (154, 0.35 g). {5-[(5-Bromo-1H-pyrrolo[2,3-b]pyridin-3-yl)-hydroxy-methyl]-pyridin-2-yl}-(6-methoxy-pyridin-3-ylmethyl)-carbamic acid tert-butyl ester was also formed in this procedure and could be isolated and reacted similarly to the following step to form the desired product.

Step 2—Preparation of [5-(5-bromo-1H-pyrrolo[2,3-b]pyridin-3-ylmethyl)-pyridin-2-yl]-(6-methoxy-pyridin-3-ylmethyl)-amine (P-2017)

To {5-[(5-bromo-1H-pyrrolo[2,3-b]pyridin-3-yl)-methoxy-methyl]-pyridin-2-yl}-(6-methoxy-pyridin-3-ylmethyl)-carbamic acid tert-butyl ester (154, 0.35 g, 0.63 mmol) in 20.0 mL of acetonitrile, triethylsilane (1.0 mL, 6.3 mmol) and trifluoroacetic acid (0.50 mL, 6.5 mmol) were added and the reaction stirred at 80° C. for 4 hours. The reaction was concentrated under vacuum and combined with aqueous potassium carbonate and extracted with ethyl acetate. The organic layer was filtered and the filtrate concentrated under vacuum. The resulting material was purified by silica gel column chromatography eluting with 20-100% ethyl acetate in hexane. Appropriate fractions were combined and concentrated under vacuum to provide the desired compound (P-2017, 165.1 mg). MS (ESI) [M+H⁺]⁺=423.8, 425.8

[6-Fluoro-5-(5-fluoro-1H-pyrrolo[2,3-b]pyridin-3-ylmethyl)-pyridin-2-yl]-(6-methoxy-pyridin-3-ylmethyl)-amine P-1622 is prepared similarly to Scheme 21, reacting in a single step 1a as follows.

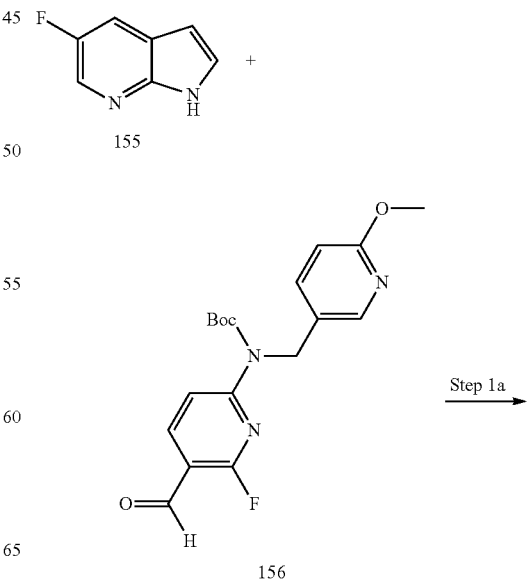

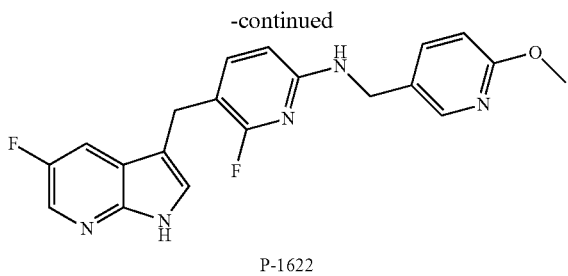

P-1622

Step 1a—Preparation of [6-fluoro-5-(5-fluoro-1H-pyrrolo[2,3-b]pyridin-3-ylmethyl)-pyridin-2-yl]-(6-methoxy-pyridin-3-ylmethyl)-amine (P-1622)

In a round bottom flask, 5-fluoro-1H-pyrrolo[2,3-b]pyridine (155, 0.115 g, 0.845 mmol) was combined with (6-fluoro-5-formyl-pyridin-2-yl)-(6-methoxy-pyridin-3-ylmethyl)-carbamic acid tert-butyl ester (156, 0.397 g, 1.10 mmol), 2.60 mL of acetonitrile, trifluoroacetic acid (0.325 mL, 4.22 mmol) and triethylsilane (0.810 mL, 5.07 mmol) and the reaction was heated to reflux for 3 hours. The reaction was poured into water and extracted with ethyl acetate. The organic layer was washed with brine, dried over sodium sulfate, filtered and the filtrate concentrated under vacuum. The resulting material was purified by silica gel column chromatography eluting with ethyl acetate in hexane. Appropriate fractions were combined and concentrated under vacuum to provide the desired compound (P-1622, 28 mg). MS (ESI) $[M+H^+]^+=382.1$.

Additional compounds are prepared following the protocol of Scheme 21 (or single step 1a), where conditions may vary, for example, any of the solvents, reaction times, reagents, temperatures, work up conditions, or other reaction parameters may be varied employing alternate solvents, reagents, reaction times, temperatures, work up conditions, and the like, as are readily available to one skilled in the art. Compounds are prepared optionally using a suitable 1H-pyrrolo[2,3-b]pyridine in place of 5-bromo-1H-pyrrolo[2,3-b]pyridine 152 and optionally using a suitable aldehyde in place of (5-formyl-pyridin-2-yl)-(6-methoxy-pyridin-3-ylmethyl)-carbamic acid tert-butyl ester 153 in step 1. Further, either or both of the methoxy or hydroxy intermediate formed in step 1 are reacted in the second step. The following compounds are made using this procedure. Compounds in the following table were characterized by $^1$H and $^{13}$C NMR spectroscopy as well as mass spectrometry.

[6-Chloro-5-(1H-pyrrolo[2,3-b]pyridin-3-ylmethyl)-pyridin-2-yl]-(5-fluoro-6-methoxy-pyridin-3-ylmethyl)-amine (P-1506),
[6-Chloro-5-(1H-pyrrolo[2,3-b]pyridin-3-ylmethyl)-pyridin-2-yl]-(5-fluoro-pyridin-3-ylmethyl)-amine (P-1507),
(6-Chloro-pyridin-3-ylmethyl)-[6-chloro-5-(1H-pyrrolo[2,3-b]pyridin-3-ylmethyl)-pyridin-2-yl]-amine (P-1508),
[6-Chloro-5-(1H-pyrrolo[2,3-b]pyridin-3-ylmethyl)-pyridin-2-yl]-(5-fluoro-2-methoxy-pyridin-3-ylmethyl)-amine (P-1509),
[6-Chloro-5-(1H-pyrrolo[2,3-b]pyridin-3-ylmethyl)-pyridin-2-yl]-(4-trifluoromethyl-pyridin-3-ylmethyl)-amine (P-1510),
[6-Chloro-5-(1H-pyrrolo[2,3-b]pyridin-3-ylmethyl)-pyridin-2-yl]-(6-methoxy-pyridin-3-ylmethyl)-amine (P-1511),
[6-Chloro-5-(1H-pyrrolo[2,3-b]pyridin-3-ylmethyl)-pyridin-2-yl]-(2-methoxy-pyridin-3-ylmethyl)-amine (P-1512),
(5-Fluoro-2-methoxy-pyridin-3-ylmethyl)-[5-(5-methyl-1H-pyrrolo[2,3-b]pyridin-3-ylmethyl)-pyridin-2-yl]-amine (P-1528),
(5-Fluoro-6-methoxy-pyridin-3-ylmethyl)-[5-(5-methyl-1H-pyrrolo[2,3-b]pyridin-3-ylmethyl)-pyridin-2-yl]-amine (P-1529),
(5-Fluoro-pyridin-3-ylmethyl)-[5-(5-methyl-1H-pyrrolo[2,3-b]pyridin-3-ylmethyl)-pyridin-2-yl]-amine (P-1530),
(6-Chloro-pyridin-3-ylmethyl)-[5-(5-methyl-1H-pyrrolo[2,3-b]pyridin-3-ylmethyl)-pyridin-2-yl]-amine (P-1531),
[5-(5-Methoxy-1H-pyrrolo[2,3-b]pyridin-3-ylmethyl)-pyridin-2-yl]-(6-trifluoromethyl-pyridin-3-ylmethyl)-amine (P-1583),
(5-Fluoro-6-methoxy-pyridin-3-ylmethyl)-[5-(5-methoxy-1H-pyrrolo[2,3-b]pyridin-3-ylmethyl)-pyridin-2-yl]-amine (P-1584),
(5-Fluoro-pyridin-3-ylmethyl)-[5-(5-methoxy-1H-pyrrolo[2,3-b]pyridin-3-ylmethyl)-pyridin-2-yl]-amine (P-1585),
(6-Chloro-pyridin-3-ylmethyl)-[5-(5-methoxy-1H-pyrrolo[2,3-b]pyridin-3-ylmethyl)-pyridin-2-yl]-amine (P-1586),
(5-Fluoro-2-methoxy-pyridin-3-ylmethyl)-[5-(5-methoxy-1H-pyrrolo[2,3-b]pyridin-3-ylmethyl)-pyridin-2-yl]-amine (P-1587),
[5-(5-Methoxy-1H-pyrrolo[2,3-b]pyridin-3-ylmethyl)-pyridin-2-yl]-(4-trifluoromethyl-pyridin-3-ylmethyl)-amine (P-1588),
(2-Methoxy-pyridin-3-ylmethyl)-[5-(5-methoxy-1H-pyrrolo[2,3-b]pyridin-3-ylmethyl)-pyridin-2-yl]-amine (P-1589),
[6-Chloro-5-(5-methoxy-1H-pyrrolo[2,3-b]pyridin-3-ylmethyl)-pyridin-2-yl]-(5-fluoro-6-methoxy-pyridin-3-ylmethyl)-amine (P-1590),
[6-Chloro-5-(5-methoxy-1H-pyrrolo[2,3-b]pyridin-3-ylmethyl)-pyridin-2-yl]-(5-fluoro-pyridin-3-ylmethyl)-amine (P-1591),
[6-Chloro-5-(5-methoxy-1H-pyrrolo[2,3-b]pyridin-3-ylmethyl)-pyridin-2-yl]-(6-chloro-pyridin-3-ylmethyl)-amine (P-1592),
[6-Chloro-5-(5-methoxy-1H-pyrrolo[2,3-b]pyridin-3-ylmethyl)-pyridin-2-yl]-(5-fluoro-2-methoxy-pyridin-3-ylmethyl)-amine (P-1593),
[6-Chloro-5-(5-methoxy-1H-pyrrolo[2,3-b]pyridin-3-ylmethyl)-pyridin-2-yl]-(4-trifluoromethyl-pyridin-3-ylmethyl)-amine (P-1594),
[6-Chloro-5-(5-methoxy-1H-pyrrolo[2,3-b]pyridin-3-ylmethyl)-pyridin-2-yl]-(6-methoxy-pyridin-3-ylmethyl)-amine (P-1595),
[6-Chloro-5-(5-methoxy-1H-pyrrolo[2,3-b]pyridin-3-ylmethyl)-pyridin-2-yl]-(2-methoxy-pyridin-3-ylmethyl)-amine (P-1596),
[6-Fluoro-5-(5-fluoro-1H-pyrrolo[2,3-b]pyridin-3-ylmethyl)-pyridin-2-yl]-(5-fluoro-6-methoxy-pyridin-3-ylmethyl)-amine (P-1623),
[6-Fluoro-5-(5-fluoro-1H-pyrrolo[2,3-b]pyridin-3-ylmethyl)-pyridin-2-yl]-(5-fluoro-pyridin-3-ylmethyl)-amine (P-1624),
(6-Chloro-pyridin-3-ylmethyl)-[6-fluoro-5-(5-fluoro-1H-pyrrolo[2,3-b]pyridin-3-ylmethyl)-pyridin-2-yl]-amine (P-1625),
[6-Fluoro-5-(5-fluoro-1H-pyrrolo[2,3-b]pyridin-3-ylmethyl)-pyridin-2-yl]-(5-fluoro-2-methoxy-pyridin-3-ylmethyl)-amine (P-1626),
[6-Fluoro-5-(5-fluoro-1H-pyrrolo[2,3-b]pyridin-3-ylmethyl)-pyridin-2-yl]-(4-trifluoromethyl-pyridin-3-ylmethyl)-amine (P-1627),
[6-Fluoro-5-(5-fluoro-1H-pyrrolo[2,3-b]pyridin-3-ylmethyl)-pyridin-2-yl]-(6-trifluoromethyl-pyridin-3-ylmethyl)-amine (P-1628),

[6-Fluoro-5-(5-fluoro-1H-pyrrolo[2,3-b]pyridin-3-ylmethyl)-pyridin-2-yl]-(2-methoxy-pyridin-3-ylmethyl)-amine (P-1629),
(5-Fluoro-6-methoxy-pyridin-3-ylmethyl)-[5-(5-trifluoromethyl-1H-pyrrolo[2,3-b]pyridin-3-ylmethyl)-pyridin-2-yl]-amine (P-1638),
(5-Fluoro-pyridin-3-ylmethyl)-[5-(5-trifluoromethyl-1H-pyrrolo[2,3-b]pyridin-3-ylmethyl)-pyridin-2-yl]-amine (P-1639),
(6-Chloro-pyridin-3-ylmethyl)-[5-(5-trifluoromethyl-1H-pyrrolo[2,3-b]pyridin-3-ylmethyl)-pyridin-2-yl]-amine (P-1640),
(5-Fluoro-2-methoxy-pyridin-3-ylmethyl)-[5-(5-trifluoromethyl-1H-pyrrolo[2,3-b]pyridin-3-ylmethyl)-pyridin-2-yl]-amine (P-1641),
(4-Trifluoromethyl-pyridin-3-ylmethyl)-[5-(5-trifluoromethyl-1H-pyrrolo[2,3-b]pyridin-3-ylmethyl)-pyridin-2-yl]-amine (P-1642),
(6-Methoxy-pyridin-3-ylmethyl)-[5-(5-trifluoromethyl-1H-pyrrolo[2,3-b]pyridin-3-ylmethyl)-pyridin-2-yl]-amine (P-1643),
(6-Trifluoromethyl-pyridin-3-ylmethyl)-[5-(5-trifluoromethyl-1H-pyrrolo[2,3-b]pyridin-3-ylmethyl)-pyridin-2-yl]-amine (P-1644),
(2-Methoxy-pyridin-3-ylmethyl)-[5-(5-trifluoromethyl-1H-pyrrolo[2,3-b]pyridin-3-ylmethyl)-pyridin-2-yl]-amine (P-1645),
[5-(5-Cyclopropyl-1H-pyrrolo[2,3-b]pyridin-3-ylmethyl)-pyridin-2-yl]-(5-fluoro-6-methoxy-pyridin-3-ylmethyl)-amine (P-1661),
[5-(5-Cyclopropyl-1H-pyrrolo[2,3-b]pyridin-3-ylmethyl)-pyridin-2-yl]-(5-fluoro-pyridin-3-ylmethyl)-amine (P-1662),
(6-Chloro-pyridin-3-ylmethyl)-[5-(5-cyclopropyl-1H-pyrrolo[2,3-b]pyridin-3-ylmethyl)-pyridin-2-yl]-amine (P-1663),
[5-(5-Cyclopropyl-1H-pyrrolo[2,3-b]pyridin-3-ylmethyl)-pyridin-2-yl]-(5-fluoro-2-methoxy-pyridin-3-ylmethyl)-amine (P-1664),
[5-(5-Cyclopropyl-1H-pyrrolo[2,3-b]pyridin-3-ylmethyl)-pyridin-2-yl]-(4-trifluoromethyl-pyridin-3-ylmethyl)-amine (P-1665),
[5-(5-Cyclopropyl-1H-pyrrolo[2,3-b]pyridin-3-ylmethyl)-pyridin-2-yl]-(6-methoxy-pyridin-3-ylmethyl)-amine (P-1666),
[5-(5-Cyclopropyl-1H-pyrrolo[2,3-b]pyridin-3-ylmethyl)-pyridin-2-yl]-(6-trifluoromethyl-pyridin-3-ylmethyl)-amine (P-1667),
[5-(5-Cyclopropyl-1H-pyrrolo[2,3-b]pyridin-3-ylmethyl)-pyridin-2-yl]-(2-methoxy-pyridin-3-ylmethyl)-amine (P-1668),
3-{6-[(5-Fluoro-pyridin-3-ylmethyl)-amino]-pyridin-3-ylmethyl}-1H-pyrrolo[2,3-b]pyridine-4-carbonitrile (P-1719),
3-{6-[(6-Chloro-pyridin-3-ylmethyl)-amino]-pyridin-3-ylmethyl}-1H-pyrrolo[2,3-b]pyridine-4-carbonitrile (P-1720),
3-{6-[(5-Fluoro-2-methoxy-pyridin-3-ylmethyl)-amino]-pyridin-3-ylmethyl}-1H-pyrrolo[2,3-b]pyridine-4-carbonitrile (P-1721),
3-{6-[(4-Trifluoromethyl-pyridin-3-ylmethyl)-amino]-pyridin-3-ylmethyl}-1H-pyrrolo[2,3-b]pyridine-4-carbonitrile (P-1722),
3-{6-[(6-Methoxy-pyridin-3-ylmethyl)-amino]-pyridin-3-ylmethyl}-1H-pyrrolo[2,3-b]pyridine-4-carbonitrile (P-1723),
3-{6-[(6-Trifluoromethyl-pyridin-3-ylmethyl)-amino]-pyridin-3-ylmethyl}-1H-pyrrolo[2,3-b]pyridine-4-carbonitrile (P-1724),
3-{6-[(2-Methoxy-pyridin-3-ylmethyl)-amino]-pyridin-3-ylmethyl}-1H-pyrrolo[2,3-b]pyridine-4-carbonitrile (P-1725),
3-{6-[(5-Fluoro-6-methoxy-pyridin-3-ylmethyl)-amino]-pyridin-3-ylmethyl}-1H-pyrrolo[2,3-b]pyridine-4-carbonitrile (P-1726),
[5-(4-Methoxy-1H-pyrrolo[2,3-b]pyridin-3-ylmethyl)-pyridin-2-yl]-(6-trifluoromethyl-pyridin-3-ylmethyl)-amine (P-2018),
[5-(5-Methyl-1H-pyrrolo[2,3-b]pyridin-3-ylmethyl)-pyridin-2-yl]-(6-trifluoromethyl-pyridin-3-ylmethyl)-amine (P-2019),
[5-(5-Fluoro-1H-pyrrolo[2,3-b]pyridin-3-ylmethyl)-pyridin-2-yl]-(6-trifluoromethyl-pyridin-3-ylmethyl)-amine (P-2023),
(2-Fluoro-benzyl)-[5-(4-methoxy-1H-pyrrolo[2,3-b]pyridin-3-ylmethyl)-pyridin-2-yl]-amine (P-2033), and
[5-(4-Chloro-1H-pyrrolo[2,3-b]pyridin-3-ylmethyl)-pyridin-2-yl]-(5-fluoro-2-methoxy-pyridin-3-ylmethyl)-amine (P-2170).

The following table indicates the 1H-pyrrolo[2,3-b]pyridine compound (column 2) and aldehyde compound (column 3) used in step 1 to afford the desired compound (column 4). The compound number is provided in column 1, and the observed mass is in column 5.

| Comp. Number | 1H-pyrrolo[2,3-b]pyridine | Aldehyde |
|---|---|---|
| P-1506 | | |

P-1507
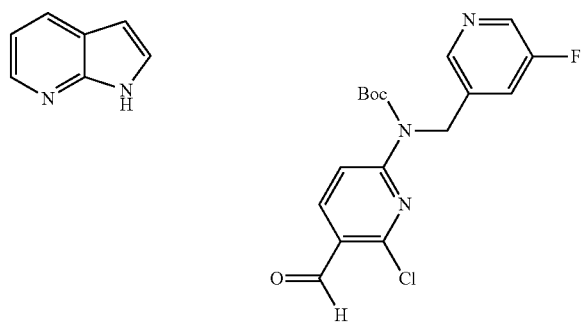
P-1508
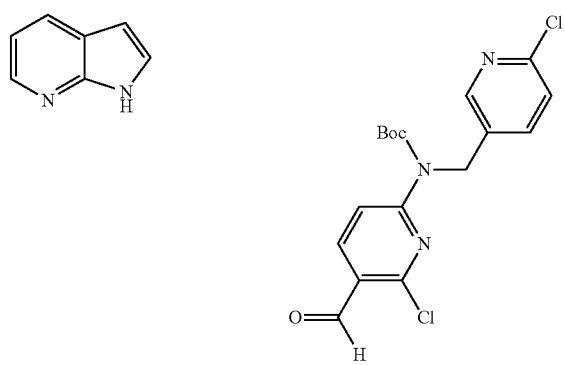
P-1509
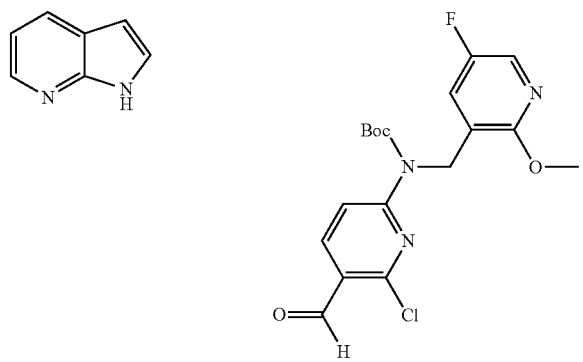
P-1510
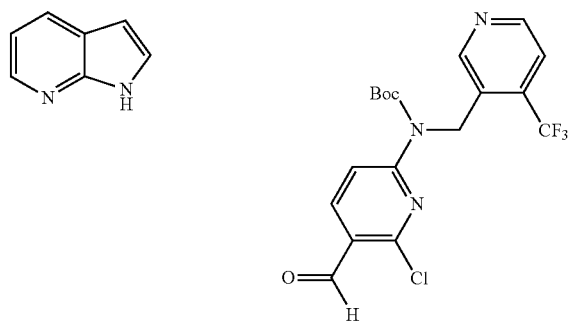

| | | |
|---|---|---|
| P-1511 | 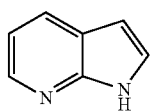 | 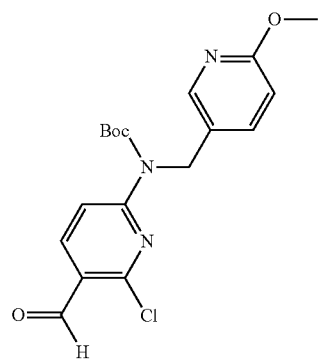 [SMILES: COc1ccc(CN(C(=O)OC(C)(C)C)c2ccc(C=O)c(Cl)n2)cn1] |
| P-1512 | 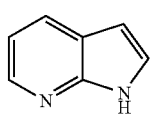 | 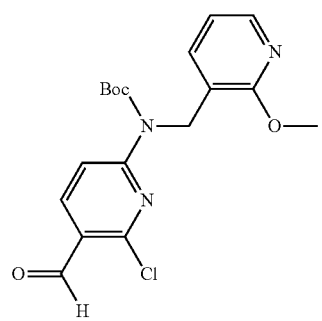 [SMILES: COc1ncccc1CN(C(=O)OC(C)(C)C)c1ccc(C=O)c(Cl)n1] |
| P-1528 | 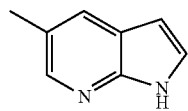 | 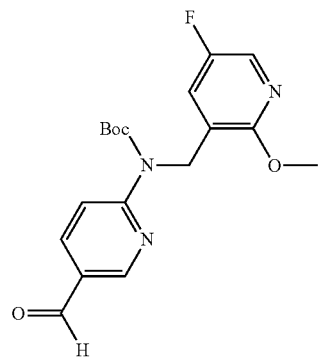 |
| P-1529 | 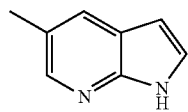 | 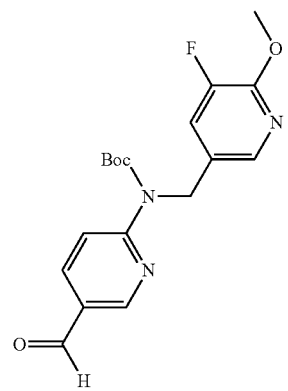 [SMILES: COc1ncc(CN(C(=O)OC(C)(C)C)c2ccc(C=O)cn2)cc1F] |

| | | |
|---|---|---|
| P-1530 | 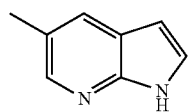 | 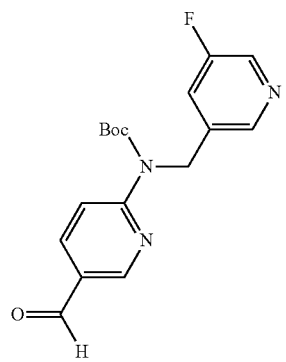 [SMILES: CC(C)(C)OC(=O)N(Cc1cncc(F)c1)c1ccc(C=O)cn1] |
| P-1531 | 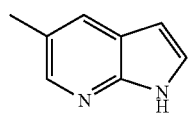 | 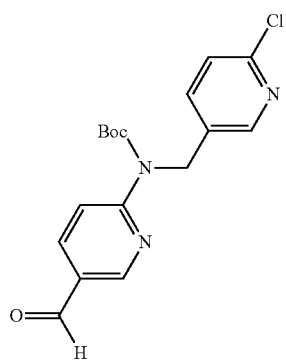 [SMILES: CC(C)(C)OC(=O)N(Cc1ccc(Cl)nc1)c1ccc(C=O)cn1] |
| P-1540 | 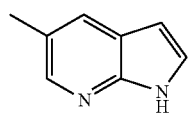 | 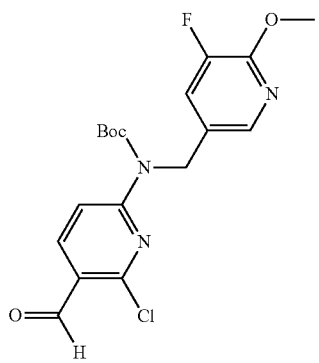 [SMILES: COc1ncc(CN(C(=O)OC(C)(C)C)c2ccc(C=O)c(Cl)n2)cc1F] |
| P-1541 | 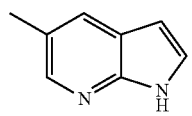 | 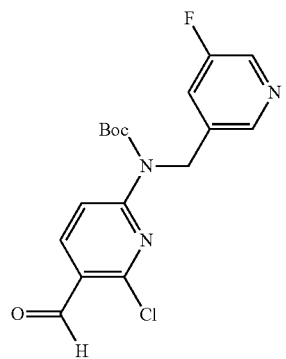 [SMILES: CC(C)(C)OC(=O)N(Cc1cncc(F)c1)c1ccc(C=O)c(Cl)n1] |

-continued
P-1542 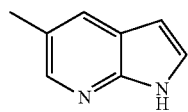 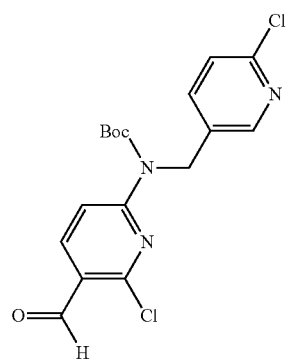 [SMILES: CC(C)(C)OC(=O)N(Cc1ccc(Cl)nc1)c1ccc(C=O)c(Cl)n1]
P-1543 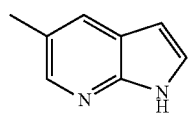 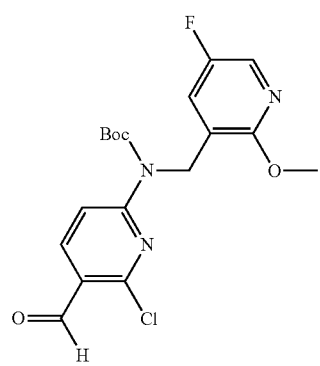 [SMILES: COc1ncc(F)cc1CN(C(=O)OC(C)(C)C)c1ccc(C=O)c(Cl)n1]
P-1544 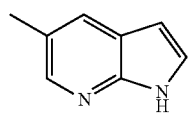 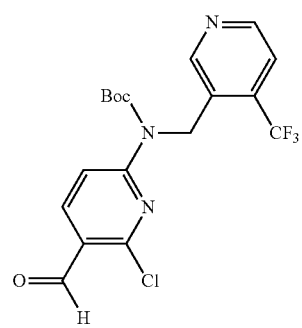 [SMILES: CC(C)(C)OC(=O)N(Cc1cnccc1C(F)(F)F)c1ccc(C=O)c(Cl)n1]
P-1545 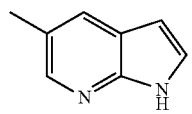 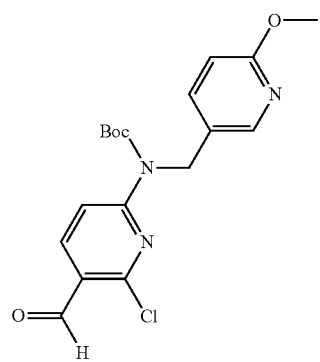 [SMILES: COc1ccc(CN(C(=O)OC(C)(C)C)c2ccc(C=O)c(Cl)n2)cn1]

| | | |
|---|---|---|
| P-1546 | 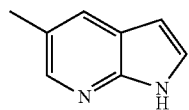 | 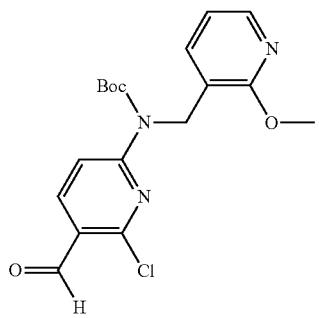 [SMILES: COc1ncccc1CN(C(=O)OC(C)(C)C)c1ccc(C=O)c(Cl)n1] |
| P-1583 | 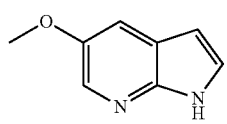 | 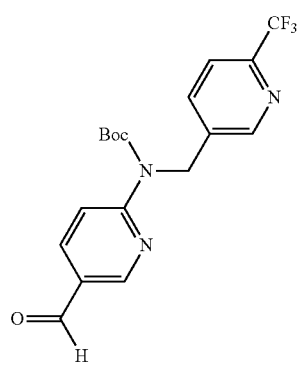 |
| P-1584 | 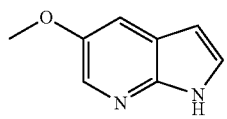 | 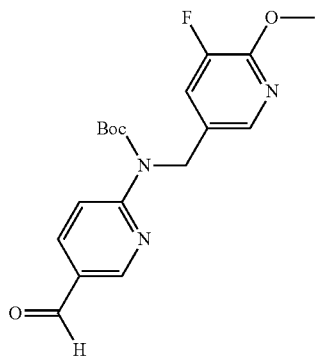 [SMILES: COc1ncc(CN(C(=O)OC(C)(C)C)c2ccc(C=O)cn2)cc1F] |
| P-1585 | 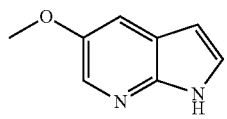 | 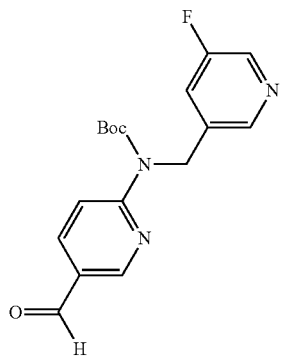 [SMILES: CC(C)(C)OC(=O)N(Cc1cncc(F)c1)c1ccc(C=O)cn1] |

| | | |
|---|---|---|
| P-1586 | 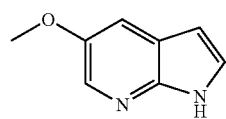 | 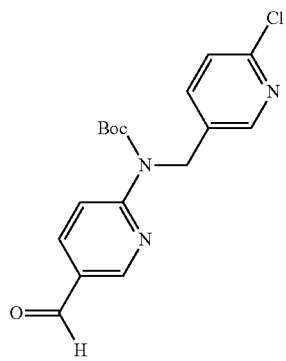 [SMILES: CC(C)(C)OC(=O)N(Cc1ccc(Cl)nc1)c1ccc(C=O)cn1] |
| P-1587 | 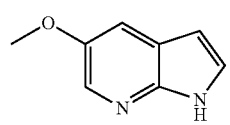 | 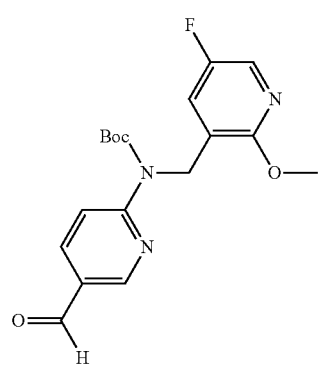 [SMILES: COc1ncc(F)cc1CN(C(=O)OC(C)(C)C)c1ccc(C=O)cn1] |
| P-1588 | 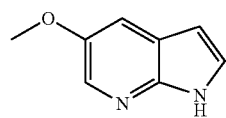 | 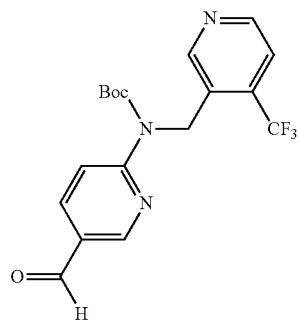 |
| P-1589 | 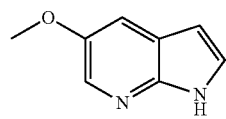 | 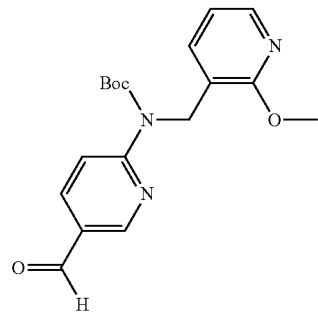 [SMILES: COc1ncccc1CN(C(=O)OC(C)(C)C)c1ccc(C=O)cn1] |

| | | |
|---|---|---|
| P-1590 | 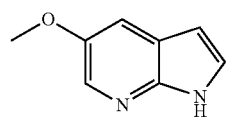 | 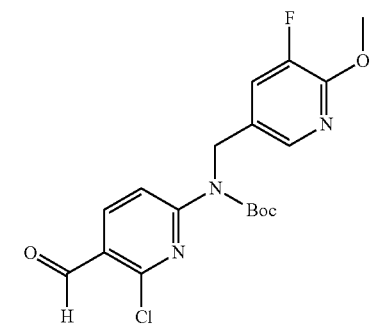 [SMILES: COc1ncc(CN(C(=O)OC(C)(C)C)c2ccc(C=O)c(Cl)n2)cc1F] |
| P-1591 | 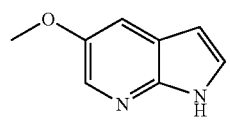 | 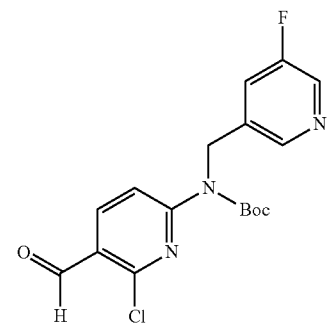 [SMILES: CC(C)(C)OC(=O)N(Cc1cncc(F)c1)c1ccc(C=O)c(Cl)n1] |
| P-1592 | 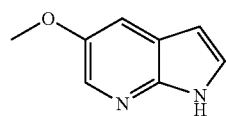 | 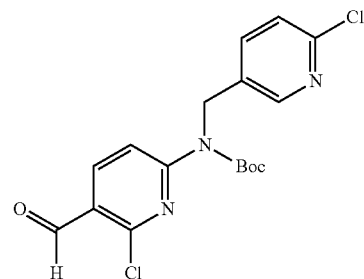 [SMILES: CC(C)(C)OC(=O)N(Cc1ccc(Cl)nc1)c1ccc(C=O)c(Cl)n1] |
| P-1593 | 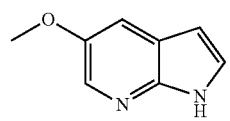 | 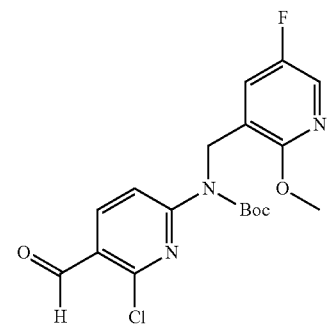 [SMILES: COc1ncc(F)cc1CN(C(=O)OC(C)(C)C)c1ccc(C=O)c(Cl)n1] |
| P-1594 | 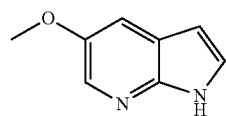 | 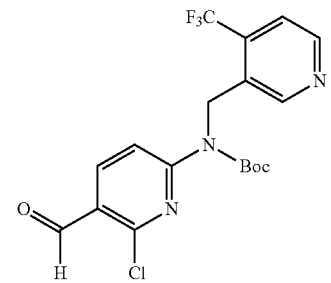 [SMILES: CC(C)(C)OC(=O)N(Cc1cnccc1C(F)(F)F)c1ccc(C=O)c(Cl)n1] |

P-1595 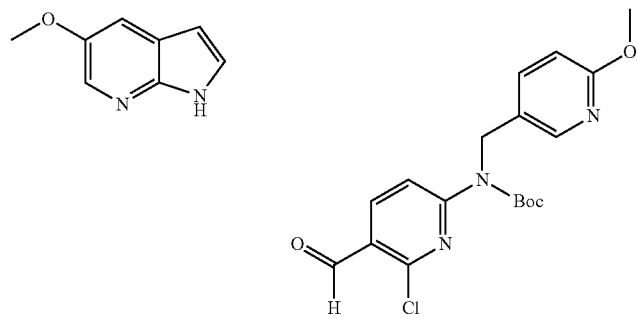
P-1596 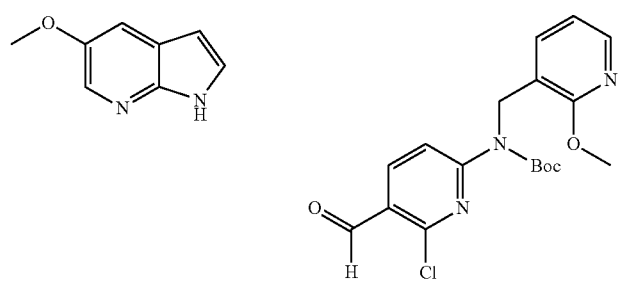
P-1623 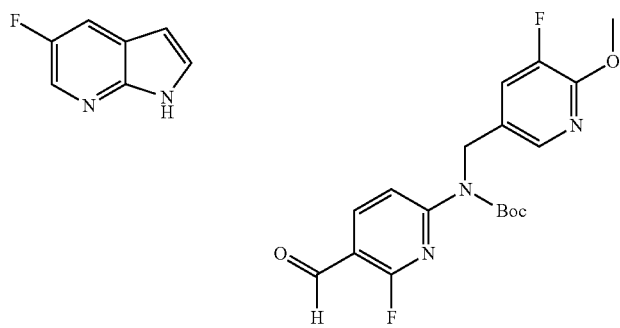
P-1624 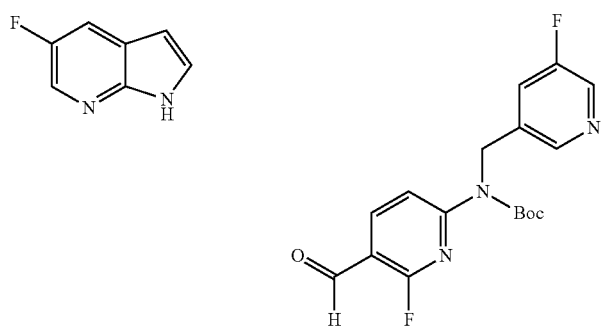
P-1625 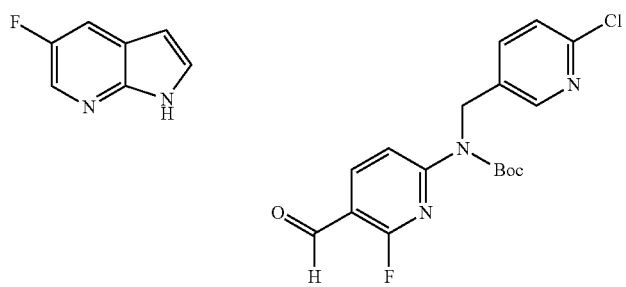

| | | |
|---|---|---|
| P-1626 | 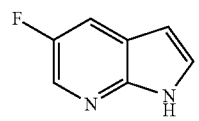 | 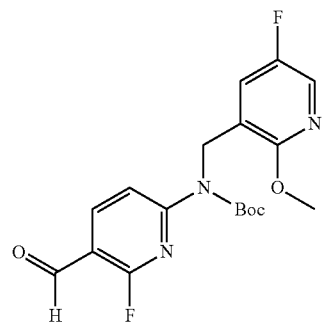 |
| P-1627 | 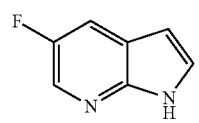 | 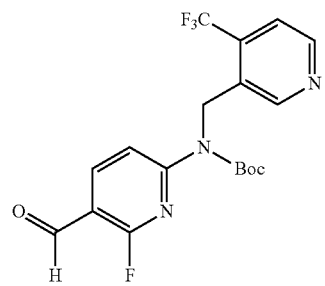 [SMILES: CC(C)(C)OC(=O)N(Cc1cnccc1C(F)(F)F)c1ccc(C=O)c(F)n1] |
| P-1628 | 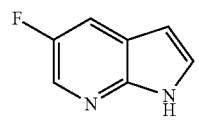 | 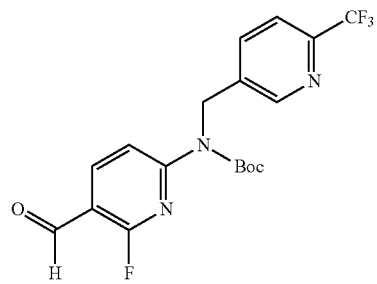 [SMILES: CC(C)(C)OC(=O)N(Cc1ccc(C(F)(F)F)nc1)c1ccc(C=O)c(F)n1] |
| P-1629 | 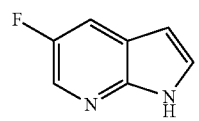 | 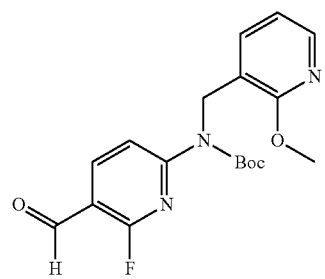 [SMILES: COc1ncccc1CN(C(=O)OC(C)(C)C)c1ccc(C=O)c(F)n1] |
| P-1638 | 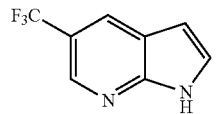 [SMILES: FC(F)(F)c1cnc2[nH]ccc2c1] | 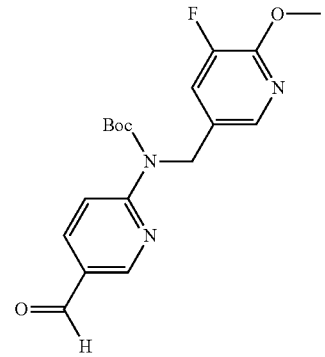 [SMILES: COc1ncc(CN(C(=O)OC(C)(C)C)c2ccc(C=O)cn2)cc1F] |

| | | |
|---|---|---|
| P-1639 | 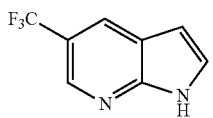 | 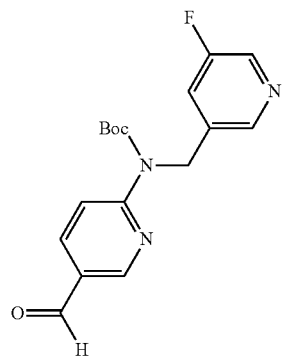 [SMILES: CC(C)(C)OC(=O)N(Cc1cncc(F)c1)c1ccc(C=O)cn1] |
| P-1640 | 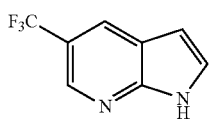 [SMILES: FC(F)(F)c1cnc2[nH]ccc2c1] | 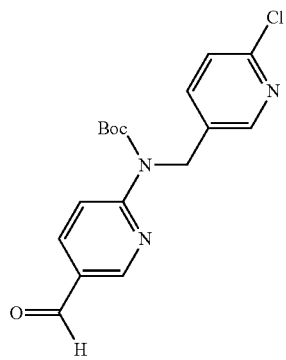 [SMILES: CC(C)(C)OC(=O)N(Cc1ccc(Cl)nc1)c1ccc(C=O)cn1] |
| P-1641 | 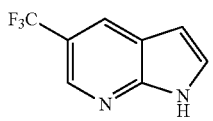 | 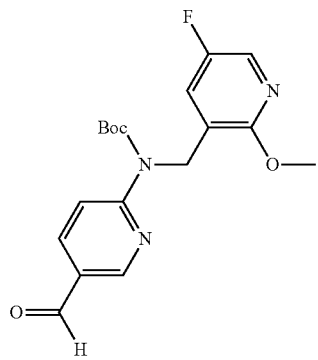 [SMILES: COc1ncc(F)cc1CN(C(=O)OC(C)(C)C)c1ccc(C=O)cn1] |
| P-1642 | 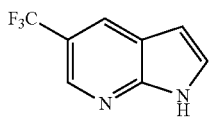 | 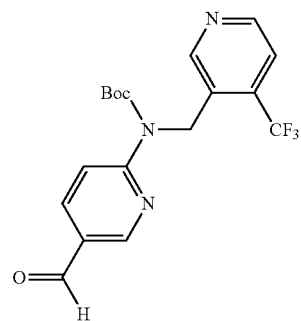 [SMILES: CC(C)(C)OC(=O)N(Cc1cnccc1C(F)(F)F)c1ccc(C=O)cn1] |

-continued
P-1643 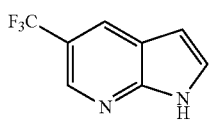 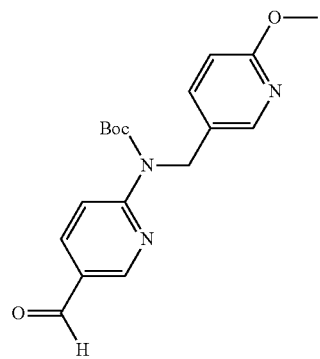 [SMILES: COc1ccc(CN(C(=O)OC(C)(C)C)c2ccc(C=O)cn2)cn1]
P-1644 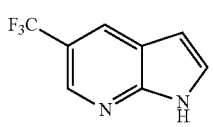 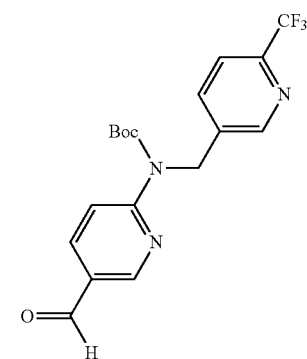 [SMILES: CC(C)(C)OC(=O)N(Cc1ccc(C(F)(F)F)nc1)c1ccc(C=O)cn1]
P-1645 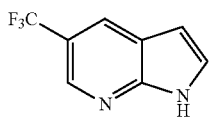 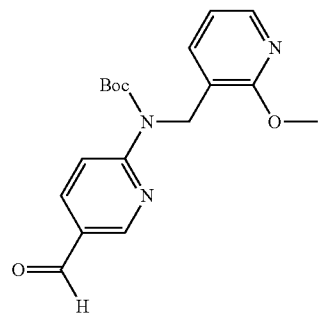 [SMILES: COc1ncccc1CN(C(=O)OC(C)(C)C)c1ccc(C=O)cn1]
P-1661 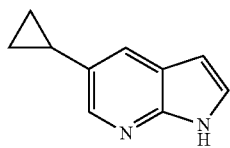 [SMILES: c1cc2cc(C3CC3)cnc2[nH]1] 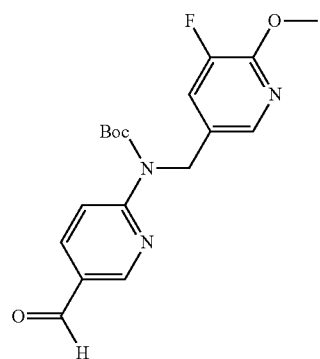 [SMILES: COc1ncc(CN(C(=O)OC(C)(C)C)c2ccc(C=O)cn2)cc1F]

| | | |
|---|---|---|
| P-1662 | 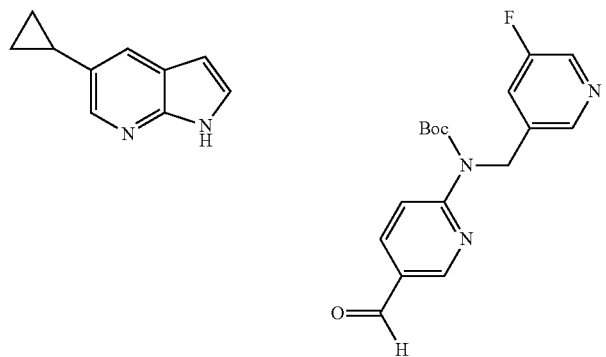 | |
| P-1663 | 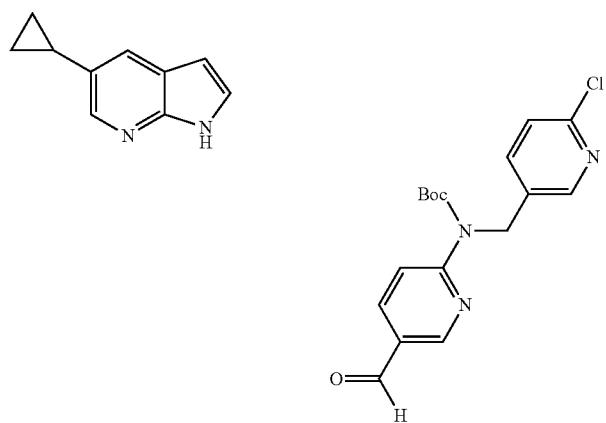 | |
| P-1664 | 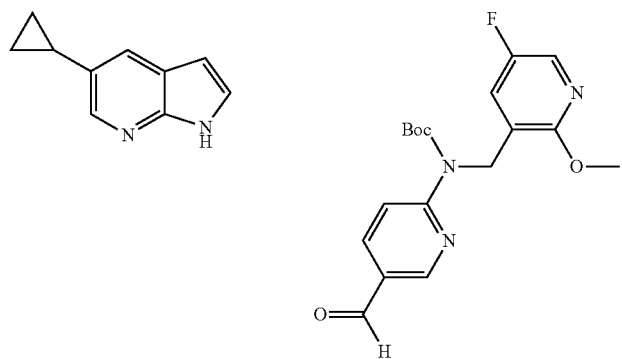 | |
| P-1665 | 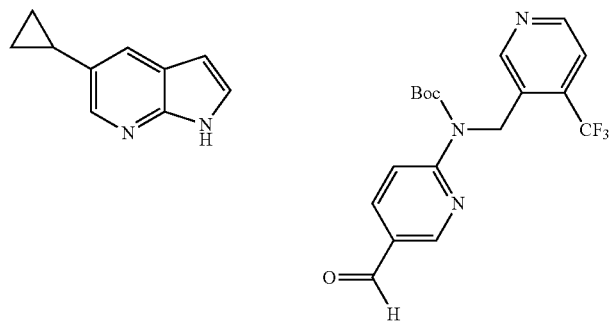 | |

-continued
P-1666 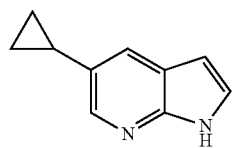 [SMILES: c1cc2cc(C3CC3)cnc2[nH]1] 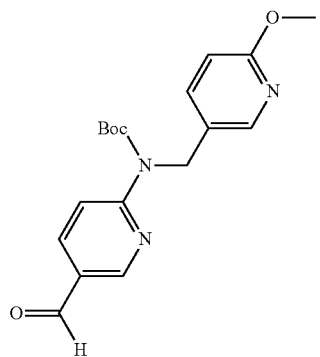 [SMILES: COc1ccc(CN(C(=O)OC(C)(C)C)c2ccc(C=O)cn2)cn1]
P-1667 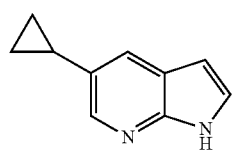 [SMILES: c1cc2cc(C3CC3)cnc2[nH]1] 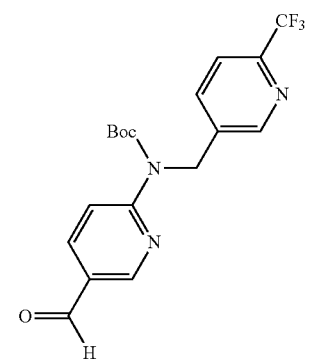 [SMILES: CC(C)(C)OC(=O)N(Cc1ccc(C(F)(F)F)nc1)c1ccc(C=O)cn1]
P-1668 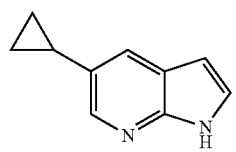 [SMILES: c1cc2cc(C3CC3)cnc2[nH]1] 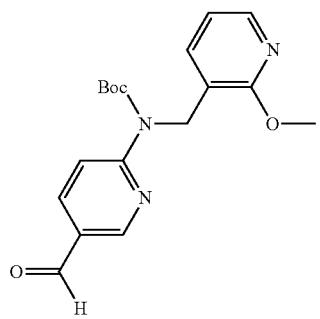 [SMILES: COc1ncccc1CN(C(=O)OC(C)(C)C)c1ccc(C=O)cn1]
P-1719  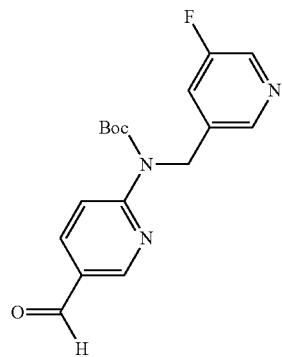 [SMILES: CC(C)(C)OC(=O)N(Cc1cncc(F)c1)c1ccc(C=O)cn1]

P-1720 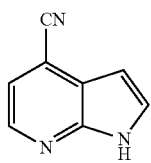 [SMILES: N#Cc1ccnc2[nH]ccc12] 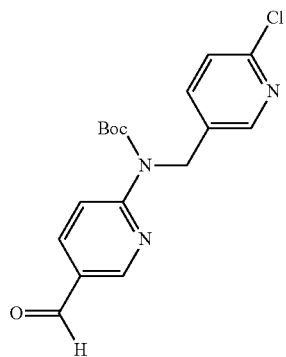 [SMILES: CC(C)(C)OC(=O)N(Cc1ccc(Cl)nc1)c1ccc(C=O)cn1]
P-1721 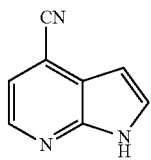 [SMILES: N#Cc1ccnc2[nH]ccc12] 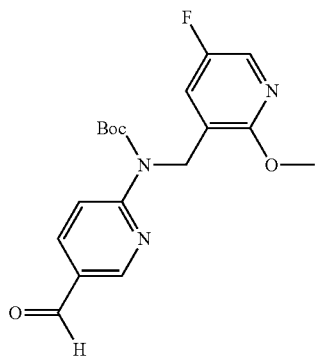 [SMILES: COc1ncc(F)cc1CN(C(=O)OC(C)(C)C)c1ccc(C=O)cn1]
P-1722 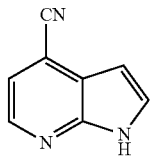 [SMILES: N#Cc1ccnc2[nH]ccc12] 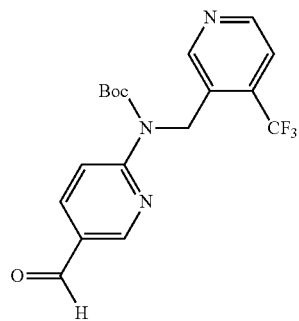 [SMILES: CC(C)(C)OC(=O)N(Cc1cnccc1C(F)(F)F)c1ccc(C=O)cn1]
P-1723 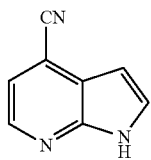 [SMILES: N#Cc1ccnc2[nH]ccc12] 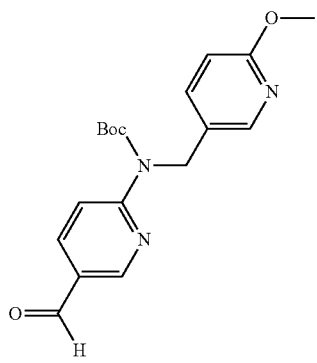 [SMILES: COc1ccc(CN(C(=O)OC(C)(C)C)c2ccc(C=O)cn2)cn1]

| | | |
|---|---|---|
| P-1724 |  | 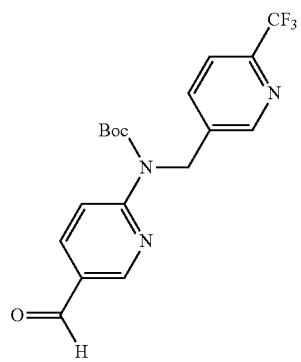 [SMILES: CC(C)(C)OC(=O)N(Cc1ccc(C(F)(F)F)nc1)c1ccc(C=O)cn1] |
| P-1725 |  | 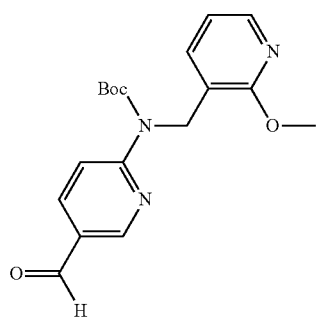 |
| P-1726 |  | 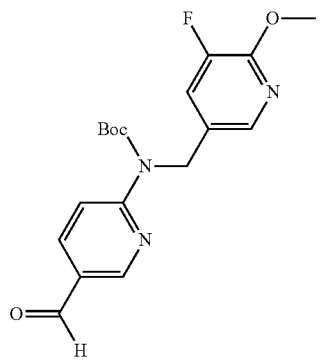 [SMILES: COc1ncc(CN(C(=O)OC(C)(C)C)c2ccc(C=O)cn2)cc1F] |
| P-2018 | 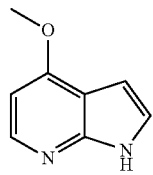 | 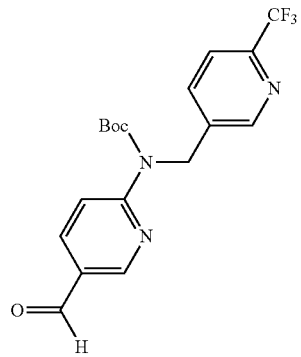 [SMILES: CC(C)(C)OC(=O)N(Cc1ccc(C(F)(F)F)nc1)c1ccc(C=O)cn1] |

-continued
P-2019 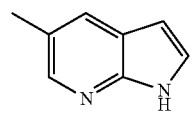 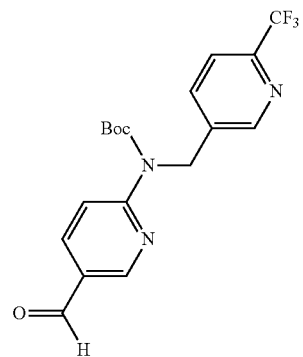 [SMILES: CC(C)(C)OC(=O)N(Cc1ccc(C(F)(F)F)nc1)c1ccc(C=O)cn1]
P-2023 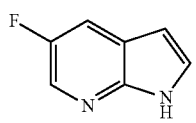 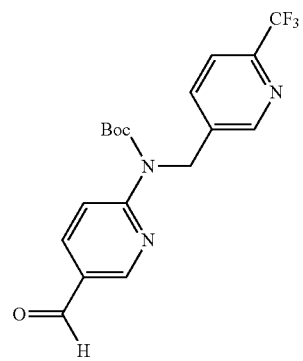 [SMILES: CC(C)(C)OC(=O)N(Cc1ccc(C(F)(F)F)nc1)c1ccc(C=O)cn1]
P-2033 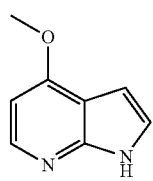 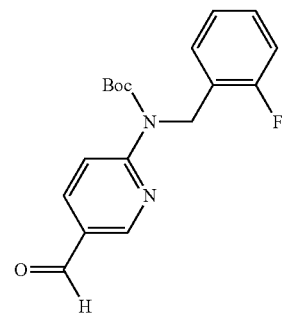 [SMILES: CC(C)(C)OC(=O)N(Cc1ccccc1F)c1ccc(C=O)cn1]
P-2170 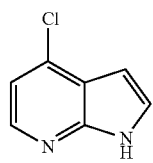 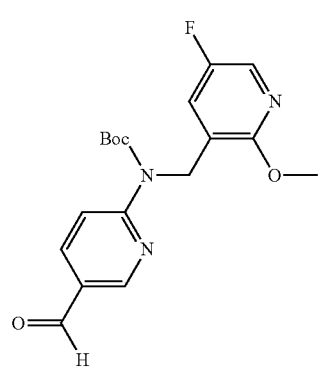 [SMILES: COc1ncc(F)cc1CN(C(=O)OC(C)(C)C)c1ccc(C=O)cn1]

-continued
| Comp. number | Compound structure | MS (ESI) [M + H+]+ |
|---|---|---|
| P-1506 | 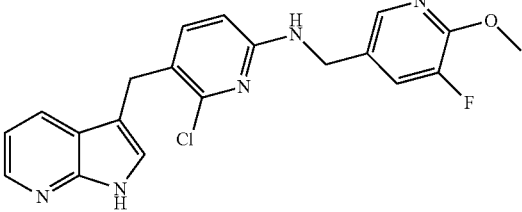 | |
| P-1507 | 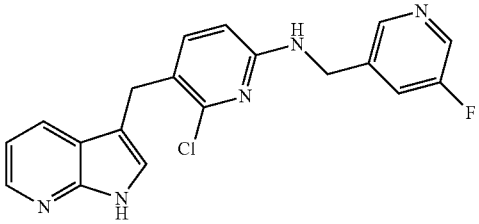 [SMILES: Fc1cncc(CNc2ccc(Cc3c[nH]c4ncccc34)c(Cl)n2)c1] | |
| P-1508 | 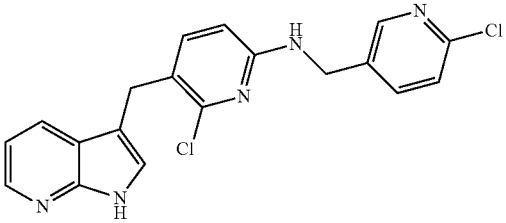 [SMILES: Clc1ccc(CNc2ccc(Cc3c[nH]c4ncccc34)c(Cl)n2)cn1] | |
| P-1509 | 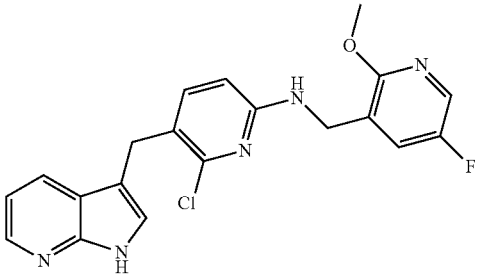 [SMILES: COc1ncc(F)cc1CNc1ccc(Cc2c[nH]c3ncccc23)c(Cl)n1] | |
| P-1510 | 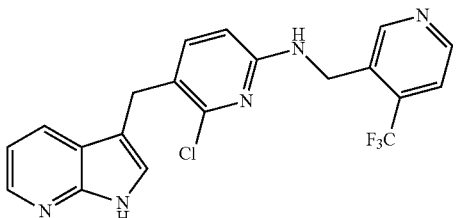 | |
| P-1511 | 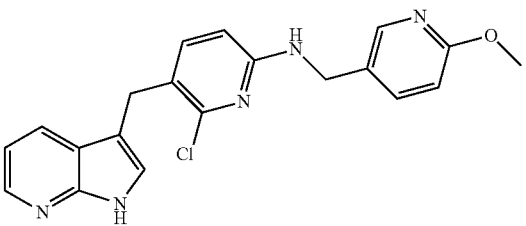 [SMILES: COc1ccc(CNc2ccc(Cc3c[nH]c4ncccc34)c(Cl)n2)cn1] | |

-continued
P-1512
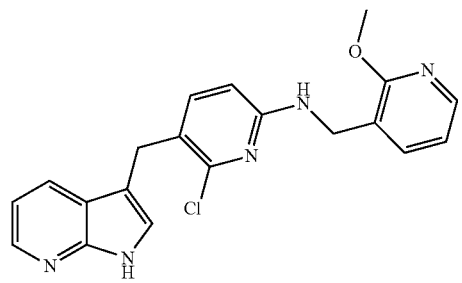 [SMILES: COc1ncccc1CNc1ccc(Cc2c[nH]c3ncccc23)c(Cl)n1]
P-1528
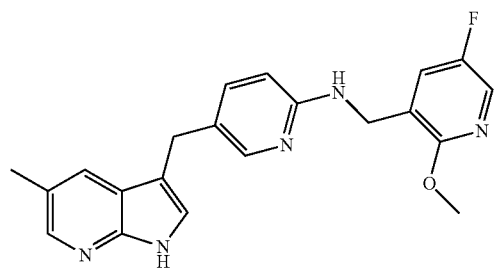 [SMILES: COc1ncc(F)cc1CNc1ccc(Cc2c[nH]c3ncc(C)cc23)cn1]
P-1529
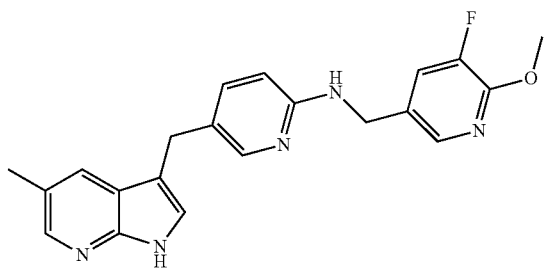
P-1530
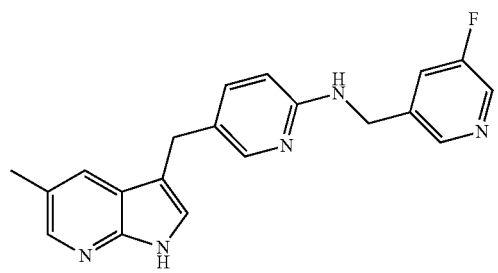 [SMILES: Cc1cnc2[nH]cc(Cc3ccc(NCc4cncc(F)c4)nc3)c2c1]
P-1531
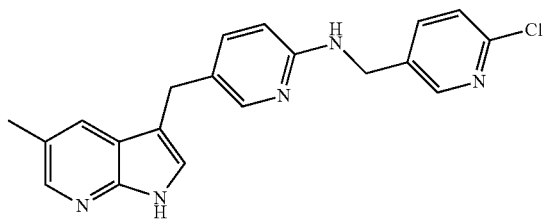 [SMILES: Cc1cnc2[nH]cc(Cc3ccc(NCc4ccc(Cl)nc4)nc3)c2c1]
P-1540
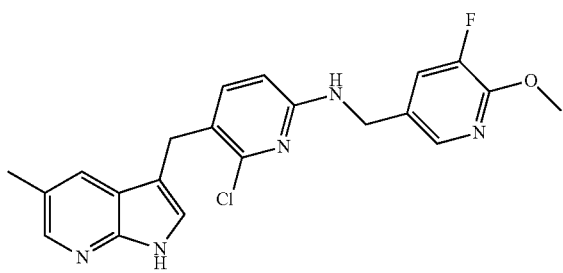

-continued
P-1541
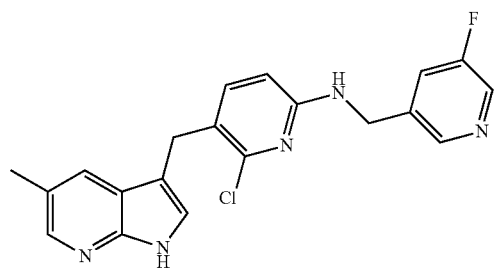 [SMILES: Cc1cnc2[nH]cc(Cc3ccc(NCc4cncc(F)c4)nc3Cl)c2c1]
P-1542
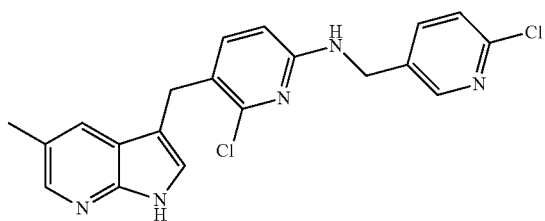
P-1543
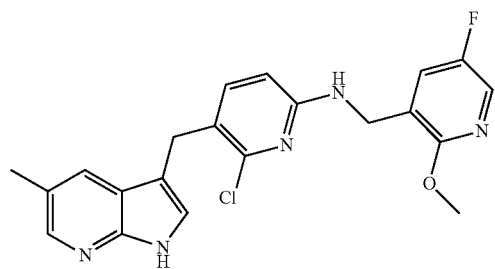 [SMILES: COc1ncc(F)cc1CNc1ccc(Cc2c[nH]c3ncc(C)cc23)c(Cl)n1]
P-1544
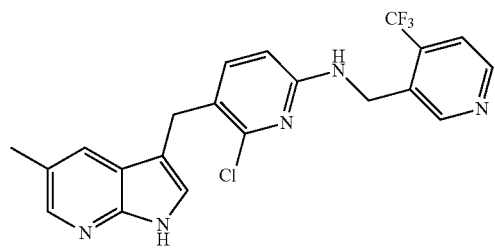 [SMILES: Cc1cnc2[nH]cc(Cc3ccc(NCc4cnccc4C(F)(F)F)nc3Cl)c2c1]
P-1545
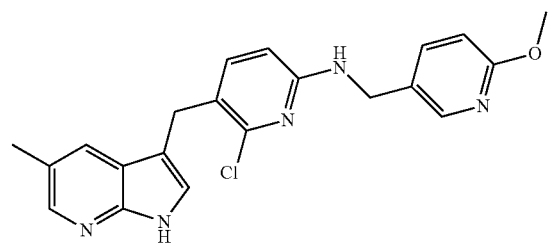
P-1546
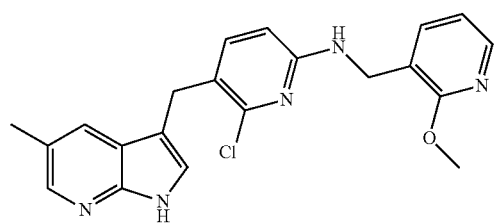 [SMILES: COc1ncccc1CNc1ccc(Cc2c[nH]c3ncc(C)cc23)c(Cl)n1]

P-1583 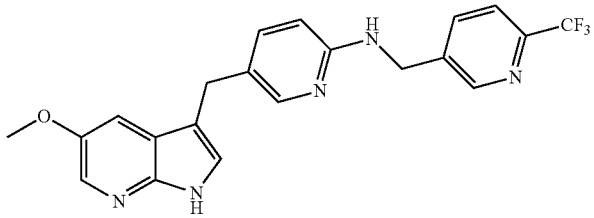 [SMILES: COc1cnc2[nH]cc(Cc3ccc(NCc4ccc(C(F)(F)F)nc4)nc3)c2c1]
P-1584 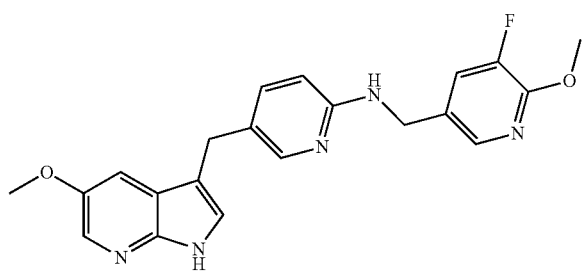
P-1585 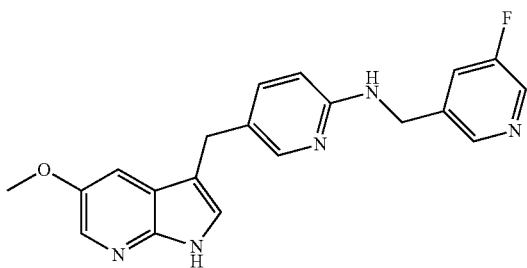 [SMILES: COc1cnc2[nH]cc(Cc3ccc(NCc4cncc(F)c4)nc3)c2c1]
P-1586 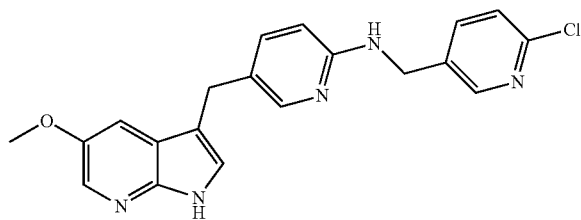 [SMILES: COc1cnc2[nH]cc(Cc3ccc(NCc4ccc(Cl)nc4)nc3)c2c1]
P-1587 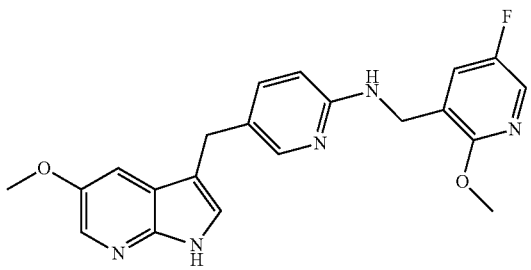 [SMILES: COc1cnc2[nH]cc(Cc3ccc(NCc4cc(F)cnc4OC)nc3)c2c1]
P-1588 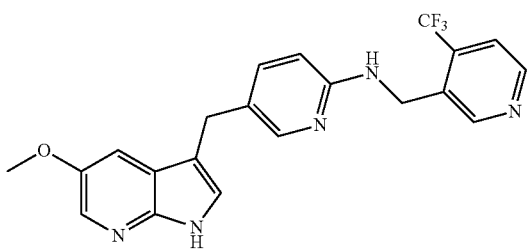 [SMILES: COc1cnc2[nH]cc(Cc3ccc(NCc4cnccc4C(F)(F)F)nc3)c2c1]

P-1589 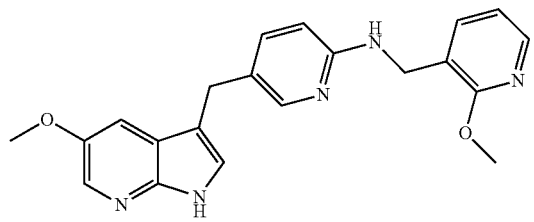 [SMILES: COc1cnc2[nH]cc(Cc3ccc(NCc4cccnc4OC)nc3)c2c1]
P-1590 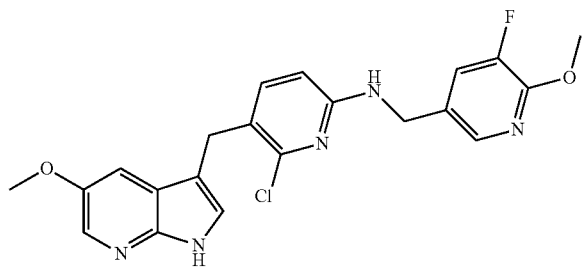
P-1591 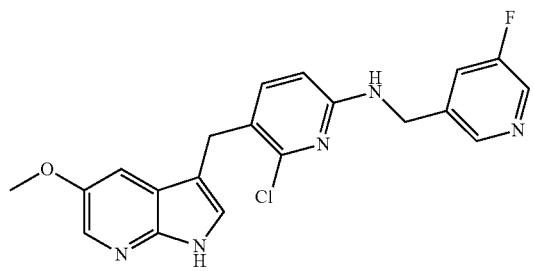 [SMILES: COc1cnc2[nH]cc(Cc3ccc(NCc4cncc(F)c4)nc3Cl)c2c1]
P-1592 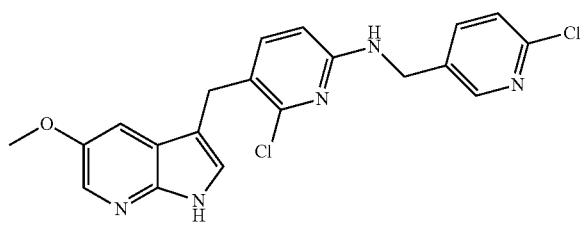 [SMILES: COc1cnc2[nH]cc(Cc3ccc(NCc4ccc(Cl)nc4)nc3Cl)c2c1]
P-1593 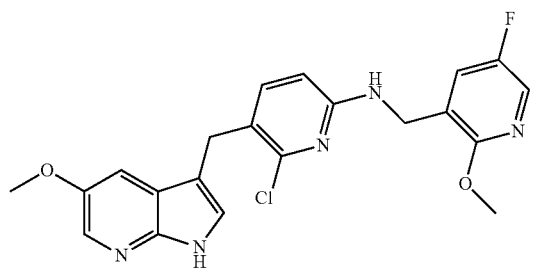 [SMILES: COc1cnc2[nH]cc(Cc3ccc(NCc4cc(F)cnc4OC)nc3Cl)c2c1]
P-1594 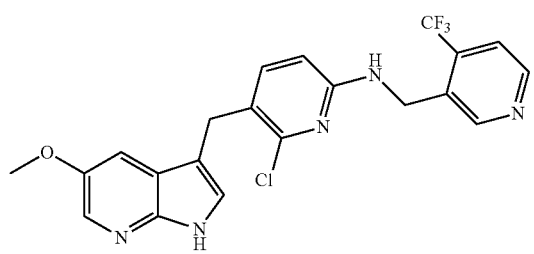 [SMILES: COc1cnc2[nH]cc(Cc3ccc(NCc4cnccc4C(F)(F)F)nc3Cl)c2c1]

P-1595 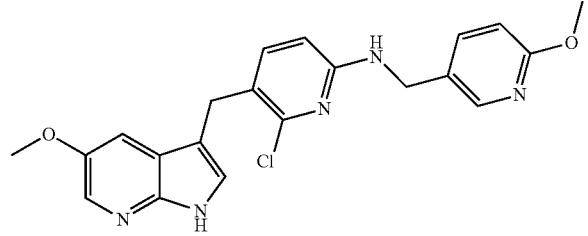
P-1596 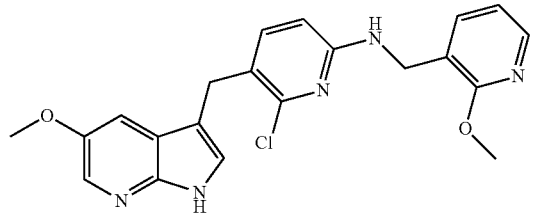 [SMILES: COc1cnc2[nH]cc(Cc3ccc(NCc4cccnc4OC)nc3Cl)c2c1]
P-1623 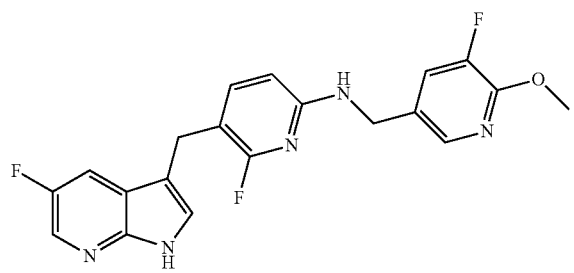 [SMILES: COc1ncc(CNc2ccc(Cc3c[nH]c4ncc(F)cc34)c(F)n2)cc1F]
P-1624 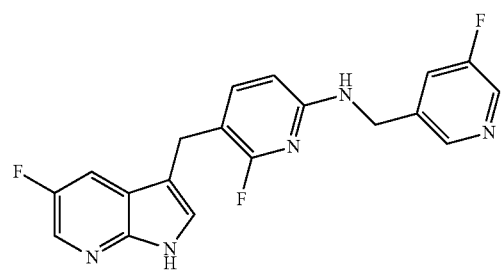 [SMILES: Fc1cncc(CNc2ccc(Cc3c[nH]c4ncc(F)cc34)c(F)n2)c1]
P-1625 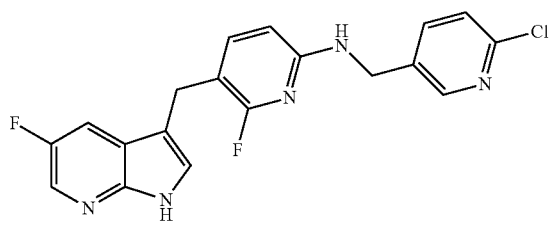 [SMILES: Fc1cnc2[nH]cc(Cc3ccc(NCc4ccc(Cl)nc4)nc3F)c2c1]
P-1626 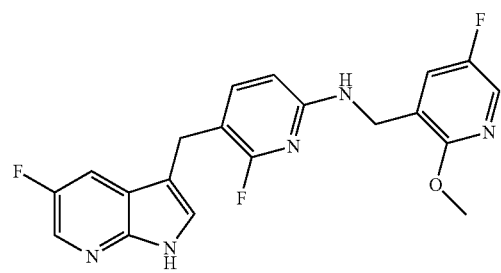 [SMILES: COc1ncc(F)cc1CNc1ccc(Cc2c[nH]c3ncc(F)cc23)c(F)n1]

P-1627
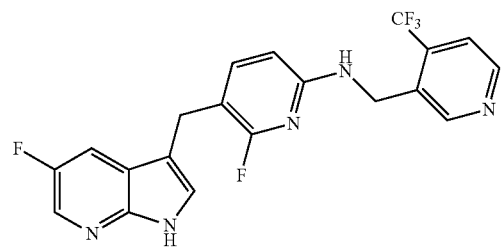 [SMILES: Fc1cnc2[nH]cc(Cc3ccc(NCc4cnccc4C(F)(F)F)nc3F)c2c1]
P-1628
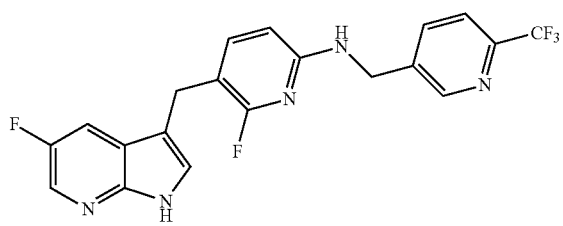 [SMILES: Fc1cnc2[nH]cc(Cc3ccc(NCc4ccc(C(F)(F)F)nc4)nc3F)c2c1]
P-1629
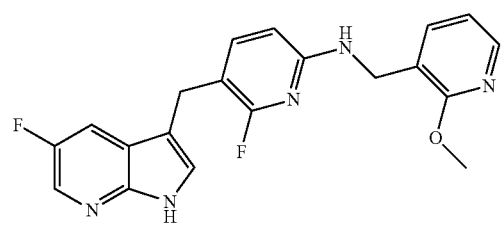 [SMILES: COc1ncccc1CNc1ccc(Cc2c[nH]c3ncc(F)cc23)c(F)n1]
P-1638
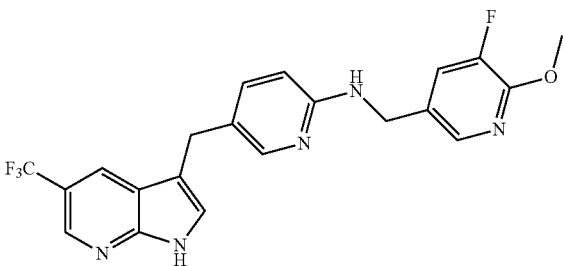 [SMILES: COc1ncc(CNc2ccc(Cc3c[nH]c4ncc(C(F)(F)F)cc34)cn2)cc1F]
P-1639
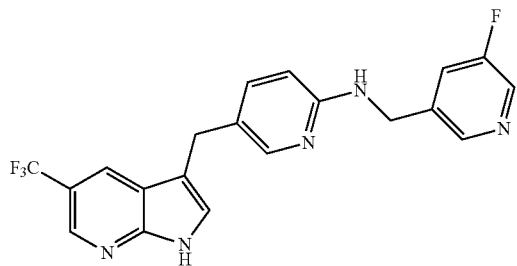 [SMILES: Fc1cncc(CNc2ccc(Cc3c[nH]c4ncc(C(F)(F)F)cc34)cn2)c1]
P-1640
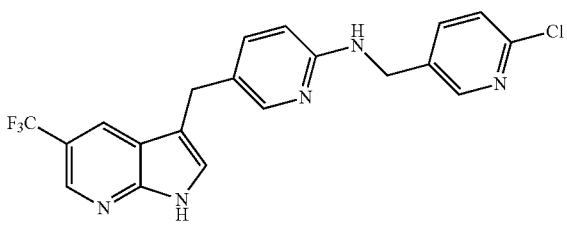 [SMILES: FC(F)(F)c1cnc2[nH]cc(Cc3ccc(NCc4ccc(Cl)nc4)nc3)c2c1]

P-1641 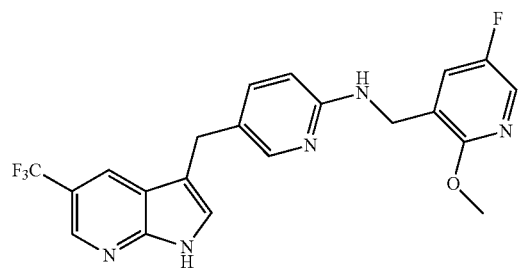 [SMILES: COc1ncc(F)cc1CNc1ccc(Cc2c[nH]c3ncc(C(F)(F)F)cc23)cn1]
P-1642 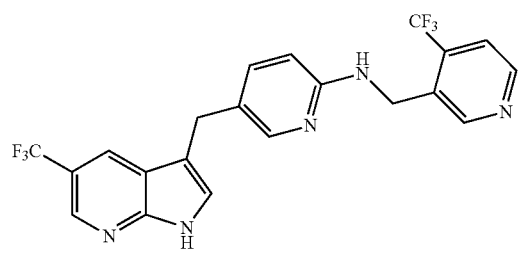 [SMILES: FC(F)(F)c1cnc2[nH]cc(Cc3ccc(NCc4cnccc4C(F)(F)F)nc3)c2c1]
P-1643 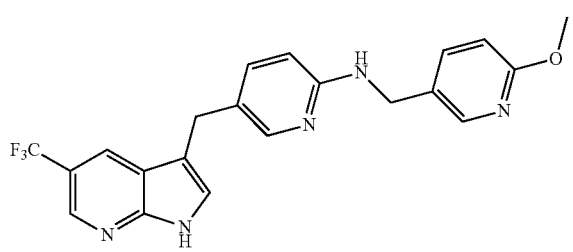 [SMILES: COc1ccc(CNc2ccc(Cc3c[nH]c4ncc(C(F)(F)F)cc34)cn2)cn1]
P-1644 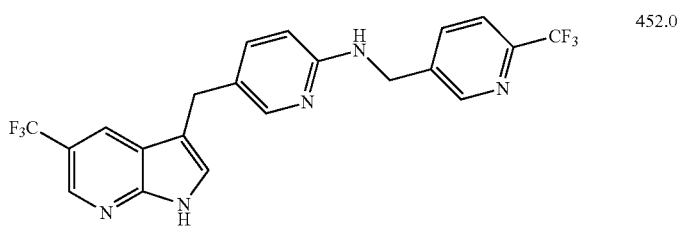 452.0
P-1645 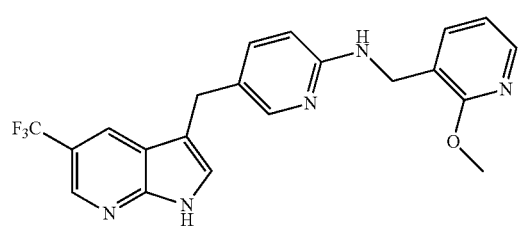 [SMILES: COc1ncccc1CNc1ccc(Cc2c[nH]c3ncc(C(F)(F)F)cc23)cn1]
P-1661 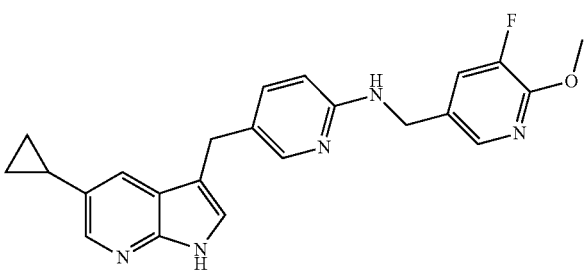 [SMILES: COc1ncc(CNc2ccc(Cc3c[nH]c4ncc(C5CC5)cc34)cn2)cc1F]

P-1662 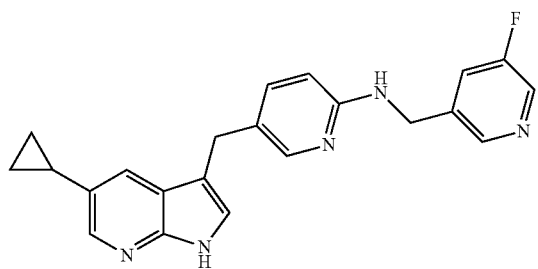 [SMILES: Fc1cncc(CNc2ccc(Cc3c[nH]c4ncc(C5CC5)cc34)cn2)c1]
P-1663 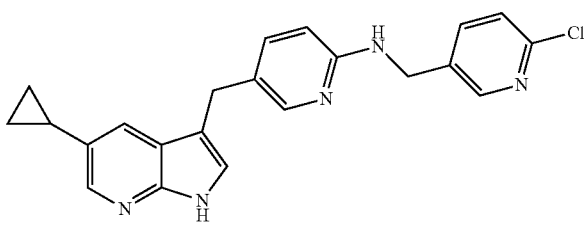 [SMILES: Clc1ccc(CNc2ccc(Cc3c[nH]c4ncc(C5CC5)cc34)cn2)cn1]
P-1664 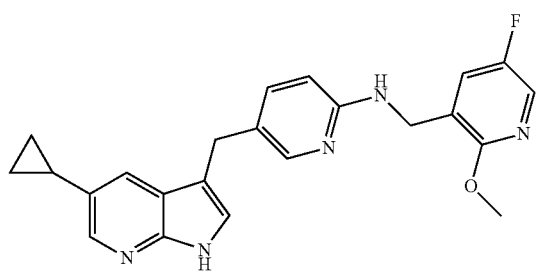 [SMILES: COc1ncc(F)cc1CNc1ccc(Cc2c[nH]c3ncc(C4CC4)cc23)cn1]
P-1665 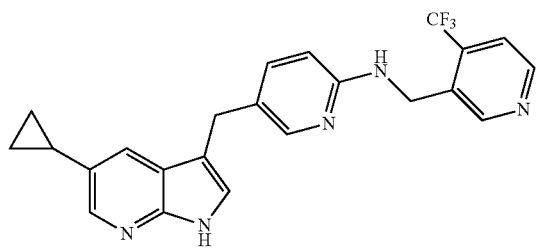 [SMILES: FC(F)(F)c1ccncc1CNc1ccc(Cc2c[nH]c3ncc(C4CC4)cc23)cn1]
P-1666 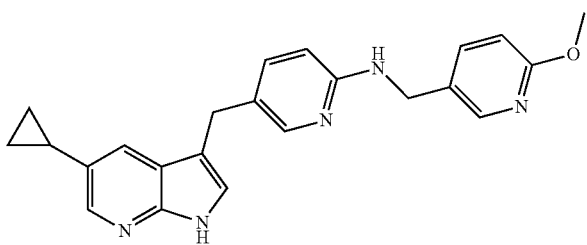 [SMILES: COc1ccc(CNc2ccc(Cc3c[nH]c4ncc(C5CC5)cc34)cn2)cn1]
P-1667 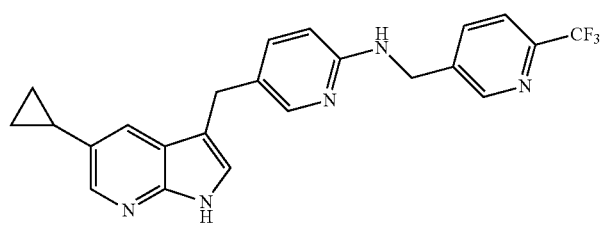 [SMILES: FC(F)(F)c1ccc(CNc2ccc(Cc3c[nH]c4ncc(C5CC5)cc34)cn2)cn1]

P-1668 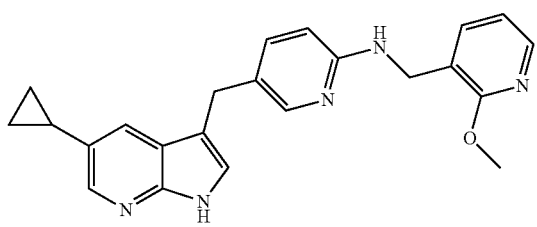 [SMILES: COc1ncccc1CNc1ccc(Cc2c[nH]c3ncc(C4CC4)cc23)cn1]
P-1719 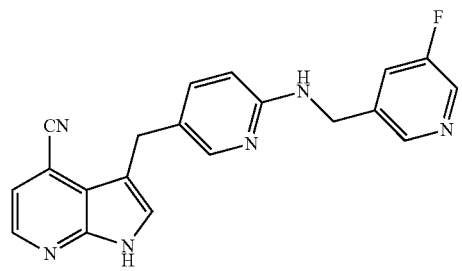 [SMILES: N#Cc1ccnc2[nH]cc(Cc3ccc(NCc4cncc(F)c4)nc3)c12]
P-1720 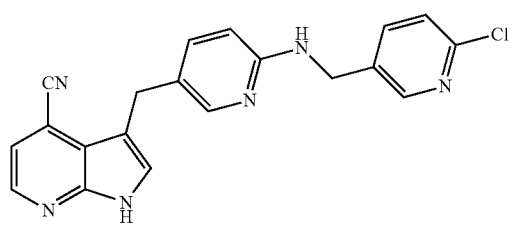 [SMILES: N#Cc1ccnc2[nH]cc(Cc3ccc(NCc4ccc(Cl)nc4)nc3)c12]
P-1721 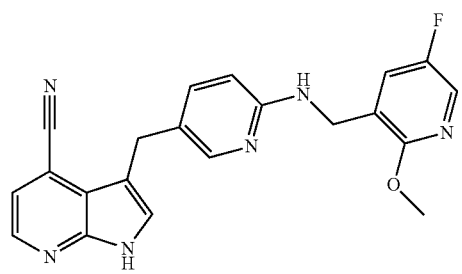 [SMILES: COc1ncc(F)cc1CNc1ccc(Cc2c[nH]c3nccc(C#N)c23)cn1]
P-1722 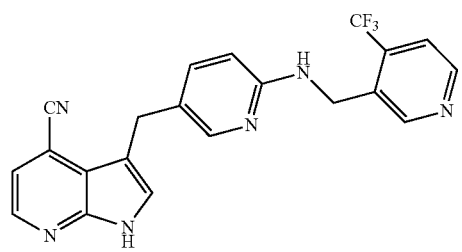 [SMILES: N#Cc1ccnc2[nH]cc(Cc3ccc(NCc4cnccc4C(F)(F)F)nc3)c12]
P-1723 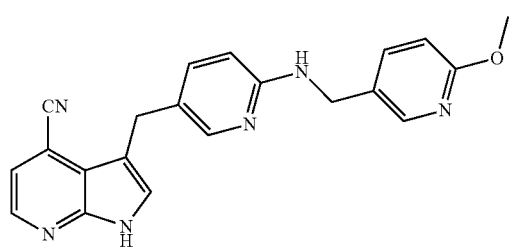 [SMILES: COc1ccc(CNc2ccc(Cc3c[nH]c4nccc(C#N)c34)cn2)cn1]

P-1724 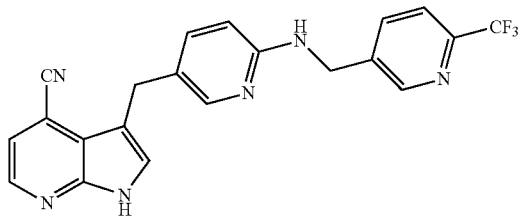 [SMILES: N#Cc1ccnc2[nH]cc(Cc3ccc(NCc4ccc(C(F)(F)F)nc4)nc3)c12]
P-1725 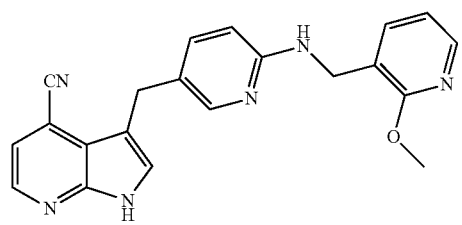 [SMILES: COc1ncccc1CNc1ccc(Cc2c[nH]c3nccc(C#N)c23)cn1]
P-1726 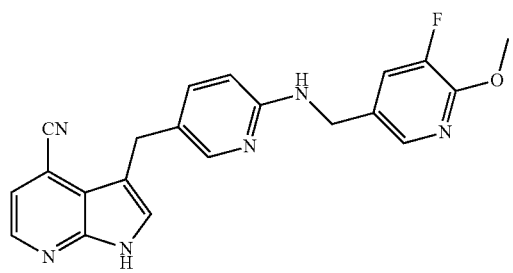 [SMILES: COc1ncc(CNc2ccc(Cc3c[nH]c4nccc(C#N)c34)cn2)cc1F]
P-2018 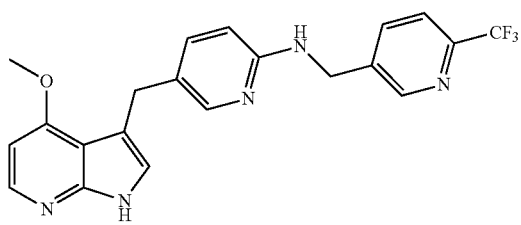 [SMILES: COc1ccnc2[nH]cc(Cc3ccc(NCc4ccc(C(F)(F)F)nc4)nc3)c12]
P-2019 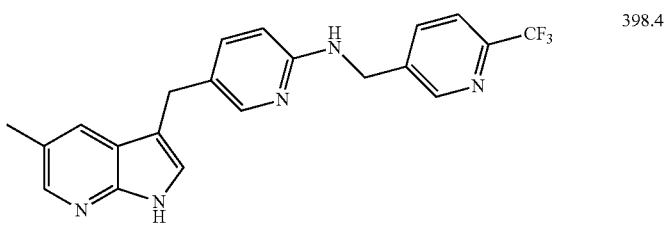 398.4
P-2023 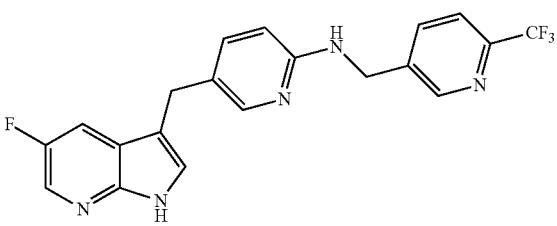 [SMILES: Fc1cnc2[nH]cc(Cc3ccc(NCc4ccc(C(F)(F)F)nc4)nc3)c2c1]
P-2033 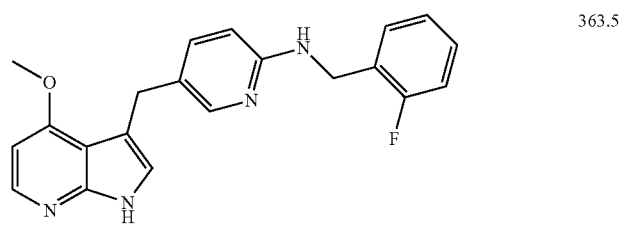 363.5

P-2170

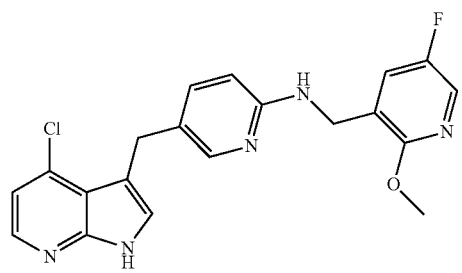 [SMILES: COc1ncc(F)cc1CNc1ccc(Cc2c[nH]c3nccc(Cl)c23)cn1]

[5-(4-Chloro-1H-pyrrolo[2,3-b]pyridin-3-ylmethyl)-pyridin-2-yl]-(5-fluoro-2-methoxy-pyridin-3-ylmethyl)-amine P-2170 is further reacted to provide (5-fluoro-2-methoxy-pyridin-3-ylmethyl)-[5-(4-phenyl-1H-pyrrolo[2,3-b]pyridin-3-ylmethyl)-pyridin-2-yl]-amine P-2171 following the protocol of the following step 3.

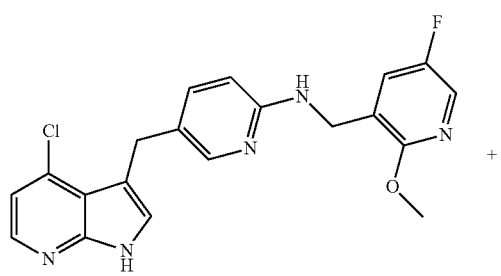

P-2170

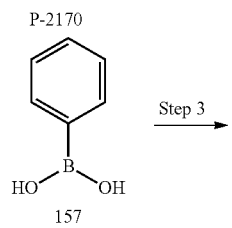

157

Step 3 →

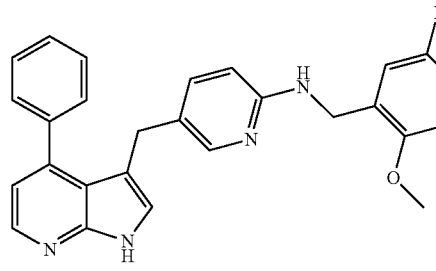

P-2171

Step 3—Preparation of 5-Fluoro-2-methoxy-pyridin-3-ylmethyl)-[5-(4-phenyl-1H-pyrrolo[2,3-b]pyridin-3-ylmethyl)-pyridin-2-yl]-amine (P-2171)

[5-(4-Chloro-1H-pyrrolo[2,3-b]pyridin-3-ylmethyl)-pyridin-2-yl]-(5-fluoro-2-methoxy-pyridin-3-ylmethyl)-amine (P-2170, 1 equivalent), phenyl boronic acid (157, 1.5 equivalents) and tetrakis(triphenylphosphine)palladium(0) (catalyst) are combined with 0.33 mL of aqueous potassium carbonate (1.00 M, 3 equivalents) and 0.34 mL of acetonitrile. The resulting mixture is heated in a microwave at 120° C. for 10 minutes, followed by 130° C. for 55 minutes. The mixture is diluted with ethyl acetate and water and the aqueous layer is separated and extracted with ethyl acetate. The organic layers are combined and washed with brine, dried over sodium sulfate, filtered and the filtrate concentrated under vacuum. The resulting material is purified by silica gel column chromatography eluting with methanol and dichloromethane. Appropriate fractions are combined and concentrated under vacuum to provide the desired compound.

Example 22

Synthesis of [5-(4-ethynyl-1H-pyrrolo[2,3-b]pyridin-3-ylmethyl)-pyridin-2-yl]-(6-trifluoromethyl-pyridin-3-ylmethyl)-amine P-1717

[5-(4-Ethynyl-1H-pyrrolo[2,3-b]pyridin-3-ylmethyl)-pyridin-2-yl]-(6-trifluoromethyl-pyridin-3-ylmethyl)-amine P-1717 was prepared in three steps from 4-ethynyl-1-triisopropylsilanyl-1H-pyrrolo[2,3-b]pyridine 161 and (5-formyl-pyridin-2-yl)-di-carbamic acid tert-butyl ester 162 as shown in Scheme 22.

Scheme 22

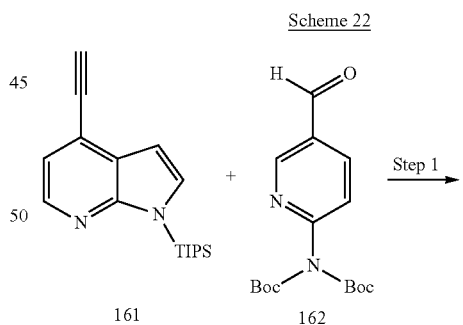

161        162

Step 1 →

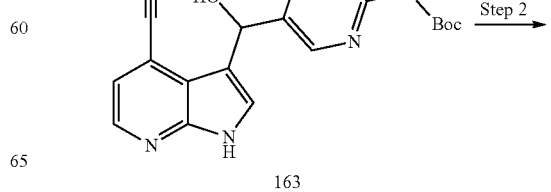

163

Step 2 →

385

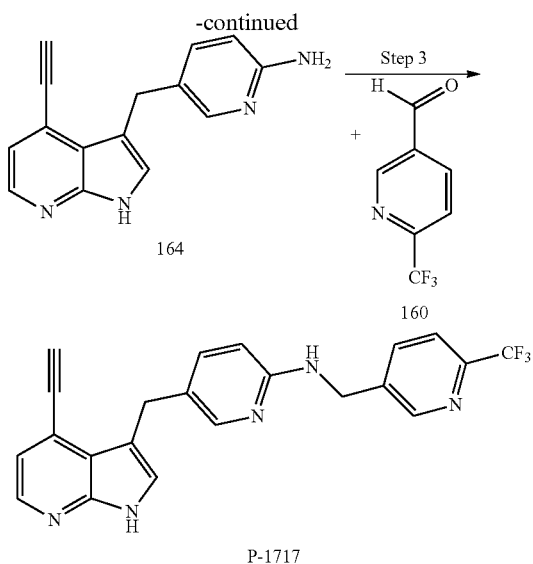

Step 1—Preparation of {5-[(4-ethynyl-1H-pyrrolo[2,3-b]pyridin-3-yl)-hydroxy-methyl]-pyridin-2-yl}-di-carbamic acid tert-butyl ester (163)

In a round bottom flask, 4-ethynyl-1-triisopropylsilanyl-1H-pyrrolo[2,3-b]pyridine (161, 0.321 g, 1.08 mmol) was combined with (5-formyl-pyridin-2-yl)-di-carbamic acid tert-butyl ester (162, 0.416 g, 1.29 mmol), 2.1 mL of methanol, and potassium hydroxide (0.302 g, 5.38 mmol) and stirred at room temperature for 24 hours. The reaction was neutralized with aqueous 0.1 N hydrochloric acid, then extracted 3× with ethyl acetate. The combined organic layer was washed with brine, then dried over sodium sulfate, filtered and the filtrate concentrated under vacuum. The resulting material was purified by silica gel column chromatography eluting with methanol and dichloromethane. Appropriate fractions were combined and concentrated under vacuum to provide the desired compound (163, 229 mg). MS (ESI) [M−H+]−=337.2.

Step 2—Preparation of 5-(4-ethynyl-1H-pyrrolo[2,3-b]pyridin-3-ylmethyl)-pyridin-2-ylamine (164)

In a round bottom flask, {5-[(4-ethynyl-1H-pyrrolo[2,3-b]pyridin-3-yl)-hydroxy-methyl]-pyridin-2-yl}-di-carbamic acid tert-butyl ester (163, 0.225 g, 0.484 mmol) was combined with trifluoroacetic acid (0.70 mL, 9.1 mmol), triethylsilane (1.8 mL, 11.0 mmol) and 5.2 mL of acetonitrile and the reaction was heated to reflux for 6 hours. The reaction was poured into water and extracted with ethyl acetate. The organic layer was washed with brine, then dried over sodium sulfate, filtered and the filtrate concentrated under vacuum. The resulting material was purified by silica gel column chromatography eluting with methanol and dichloromethane. Appropriate fractions were combined and concentrated under vacuum to provide the desired compound (164, 57 mg). MS (ESI) [M+H+]+=248.9.

386

Step 3—Preparation of [5-(4-Ethynyl-1H-pyrrolo[2,3-b]pyridin-3-ylmethyl)-pyridin-2-yl]-(6-trifluoromethyl-pyridin-3-ylmethyl)-amine (P-1717)

In a round bottom flask, 5-(4-ethynyl-1H-pyrrolo[2,3-b]pyridin-3-ylmethyl)-pyridin-2-ylamine (164, 0.055 g, 0.22 mmol) was combined with 6-trifluoromethyl-pyridine-3-carbaldehyde (160, 50.4 mg, 0.288 mmol), 0.682 mL of acetonitrile, trifluoroacetic acid (0.0853 mL, 1.11 mmol), and triethylsilane (0.212 mL, 1.33 mmol) and the reaction heated to reflux for 3 hours. The reaction was poured into water and extracted with ethyl acetate. The organic layer was washed with brine, then dried over sodium sulfate, filtered and the filtrate concentrated under vacuum. The resulting material was purified by silica gel column chromatography eluting with methanol and dichloromethane. Appropriate fractions were combined and concentrated under vacuum to provide the desired compound (P-1717, 9.3 mg). MS (ESI) [M+H+]+=408.5.

Additional compounds are prepared following the protocol of Scheme 22, where conditions may vary, for example, any of the solvents, reaction times, reagents, temperatures, work up conditions, or other reaction parameters may be varied employing alternate solvents, reagents, reaction times, temperatures, work up conditions, and the like, as are readily available to one skilled in the art. Compounds are prepared optionally replacing 6-trifluoromethyl-pyridine-3-carbaldehyde 160 with a suitable aldehyde in step 3. The following compounds are made using this procedure. Compounds in the following table were characterized by $^1$H and $^{13}$C NMR spectroscopy as well as mass spectrometry.

[5-(4-Ethynyl-1H-pyrrolo[2,3-b]pyridin-3-ylmethyl)-pyridin-2-yl]-(5-fluoro-6-methoxy-pyridin-3-ylmethyl)-amine (P-1711),

[5-(4-Ethynyl-1H-pyrrolo[2,3-b]pyridin-3-ylmethyl)-pyridin-2-yl]-(5-fluoro-pyridin-3-ylmethyl)-amine (P-1712), (6-Chloro-pyridin-3-ylmethyl)-[5-(4-ethynyl-1H-pyrrolo[2,3-b]pyridin-3-ylmethyl)-pyridin-2-yl]-amine (P-1713),

[5-(4-Ethynyl-1H-pyrrolo[2,3-b]pyridin-3-ylmethyl)-pyridin-2-yl]-(5-fluoro-2-methoxy-pyridin-3-ylmethyl)-amine (P-1714),

[5-(4-Ethynyl-1H-pyrrolo[2,3-b]pyridin-3-ylmethyl)-pyridin-2-yl]-(4-trifluoromethyl-pyridin-3-ylmethyl)-amine (P-1715),

[5-(4-Ethynyl-1H-pyrrolo[2,3-b]pyridin-3-ylmethyl)-pyridin-2-yl]-(6-methoxy-pyridin-3-ylmethyl)-amine (P-1716), and

[5-(4-Ethynyl-1H-pyrrolo[2,3-b]pyridin-3-ylmethyl)-pyridin-2-yl]-(2-methoxy-pyridin-3-ylmethyl)-amine (P-1718).

The following table indicates the aldehyde compound (column 2) used in step 3 to afford the desired compound (column 3). The compound number is provided in column 1, and the observed mass is in column 4.

| Compound number | Aldehyde | Compound | MS (ESI) [M + H+]+ |
| --- | --- | --- | --- |
| P-1711 | | | |
| P-1712 | | | |
| P-1713 | | | |
| P-1714 | | | |
| P-1715 | | | |
| P-1716 | | | |

| Compound number | Aldehyde | Compound | MS (ESI) [M + H⁺]⁺ |
|---|---|---|---|
| P-1718 | 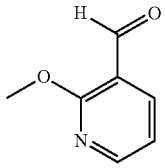 | 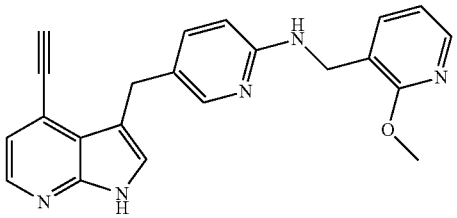 | |

Example 23

Synthesis of (5-fluoro-2-methoxy-pyridin-3-ylmethyl)-{6-fluoro-5-[5-(1-piperidin-4-yl-1H-pyrazol-4-yl)-1H-pyrrolo[2,3-b]pyridin-3-ylmethyl]-pyridin-2-yl}-amine P-1703

(5-Fluoro-2-methoxy-pyridin-3-ylmethyl)-{6-fluoro-5-[5-(1-piperidin-4-yl-1H-pyrazol-4-yl)-1H-pyrrolo[2,3-b]pyridin-3-ylmethyl]-pyridin-2-yl}-amine P-1703 was prepared in five steps from 1-benzenesulfonyl-5-bromo-3-iodo-1H-pyrrolo[2,3-b]pyridine 165 and (6-fluoro-5-formyl-pyridin-2-yl)-(4-methoxy-benzyl)-carbamic acid tert-butyl ester 83 as shown in Scheme 23. Scheme 23

Scheme 23

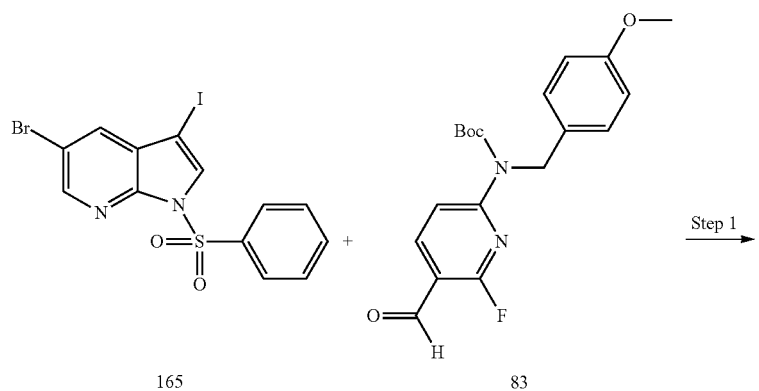

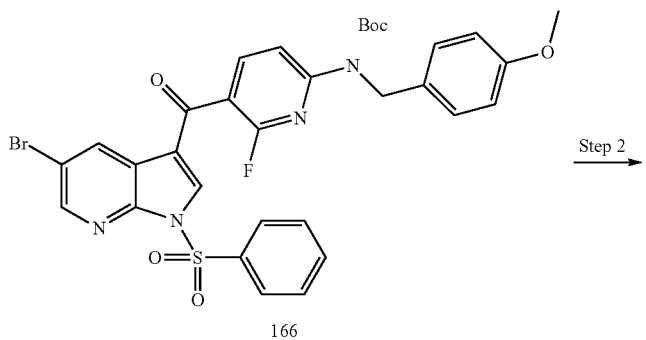

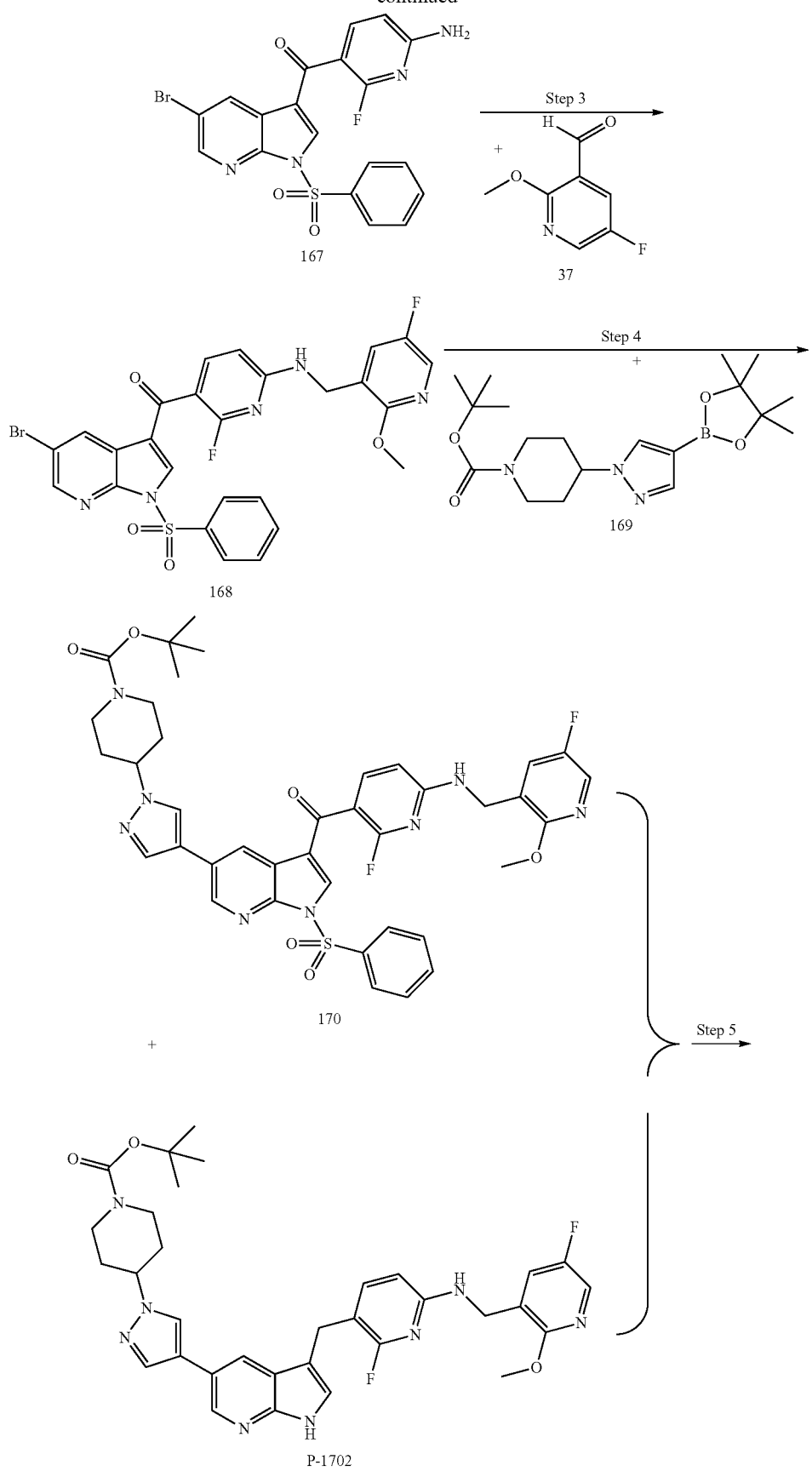

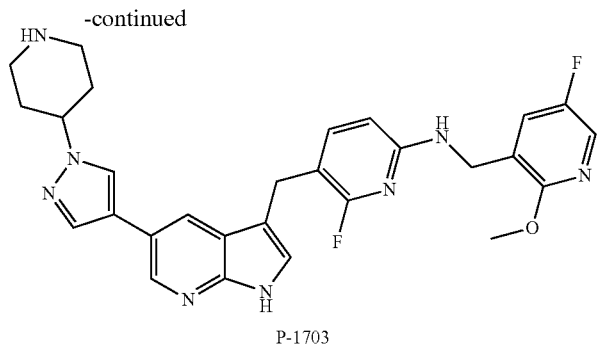

P-1703

Step 1—Preparation of {5-[(1-benzenesulfonyl-5-bromo-1H-pyrrolo[2,3-b]pyridin-3-yl)-hydroxy-methyl]-6-fluoro-pyridin-2-yl}-(4-methoxy-benzyl)-carbamic acid tert-butyl ester (166)

To a solution of 1-benzenesulfonyl-5-bromo-3-iodo-1H-pyrrolo[2,3-b]pyridine (165, 1.00 g, 2.16 mmol) in 7 mL of tetrahydrofuran at −50° C. under nitrogen, isopropylmagnesium chloride (1.18 mL, 2.35 mmol) was added slowly. The reaction was warmed to 5° C. over 70 minutes, then cooled to −45° C. and (6-fluoro-5-formyl-pyridin-2-yl)-(4-methoxy-benzyl)-carbamic acid tert-butyl ester (83, 0.678 g, 1.88 mmol) in 3.0 mL of tetrahydrofuran was added. The reaction was allowed to warm to room temperature over 2-3 hours. The reaction was mixed with aqueous 1 N citric acid and extracted with ethyl acetate. The organic layer was washed with water and brine, then dried over magnesium sulfate, filtered and the filtrate concentrated under vacuum. The resulting material was purified by silica gel column chromatography eluting with ethyl acetate and hexane. Appropriate fractions were combined and concentrated under vacuum to provide the desired compound as a white solid (166, 1.155 g). MS (ESI) $[M+H]^+$=696.4 and 698.3.

Step 2—Preparation of 5-(1-benzenesulfonyl-5-bromo-1H-pyrrolo[2,3-b]pyridin-3-ylmethyl)-6-fluoro-pyridin-2-ylamine (167)

In a round bottom flask, {5-[(1-benzenesulfonyl-5-bromo-1H-pyrrolo[2,3-b]pyridin-3-yl)-hydroxy-methyl]-6-fluoro-pyridin-2-yl}-(4-methoxy-benzyl)-carbamic acid tert-butyl ester (166, 1.15 g, 1.65 mmol) was combined with 50 mL of 1,2-dichloroethane, trifluoroacetic acid (0.635 mL, 8.24 mmol), and triethylsilane (1.32 mL, 8.24 mmol). The reaction was heated at reflux for 20 hours, then concentrated under vacuum. The residue was dissolved in 10 mL of trifluoroacetic acid and stirred at room temperature for 18 hours, then concentrated under vacuum and combined with aqueous sodium bicarbonate and extracted with ethyl acetate. The organic layer was washed with sodium bicarbonate, water and brine, then dried over magnesium sulfate, filtered and the filtrate concentrated under vacuum. The resulting material was purified by silica gel column chromatography eluting with ethyl acetate and hexane. Appropriate fractions were combined and concentrated under vacuum to provide the desired compound (167, 403 mg). MS (ESI) $[M−H^+]^−$=460.8 and 462.8.

Step 3—Preparation of [5-(1-benzenesulfonyl-5-bromo-1H-pyrrolo[2,3-b]pyridin-3-ylmethyl)-6-fluoro-pyridin-2-yl]-(5-fluoro-2-methoxy-pyridin-3-ylmethyl)-amine (168)

To 5-(1-benzenesulfonyl-5-bromo-1H-pyrrolo[2,3-b]pyridin-3-ylmethyl)-6-fluoro-pyridin-2-ylamine (167, 0.342 g, 0.741 mmol) in 10 mL of acetonitrile, 5-fluoro-2-methoxy-pyridine-3-carbaldehyde (37, 0.118 g, 0.763 mmol), triethylsilane (0.529 mL, 3.71 mmol) and trifluoroacetic acid (0.286 mL, 3.71 mmol) were added. The reaction was heated at 80° C. for 4 hours, then concentrated under vacuum and combined with aqueous potassium carbonate and extracted with ethyl acetate. The organic layer was washed with water and brine, then dried over magnesium sulfate, filtered and the filtrate concentrated under vacuum. The resulting material was purified by silica gel column chromatography eluting with ethyl acetate and hexane. Appropriate fractions were combined and concentrated under vacuum to provide the desired compound as an off-white solid (168, 367 mg). MS (ESI) $[M−H+]^−$=599.6 and 601.6.

Step 4—Preparation of 4-[4-(1-benzenesulfonyl-3-{2-fluoro-6-[(5-fluoro-2-methoxy-pyridin-3-ylmethyl)-amino]-pyridin-3-ylmethyl}-1H-pyrrolo[2,3-b]pyridin-5-yl)-pyrazol-1-yl]-piperidine-1-carboxylic acid tert-butyl ester (170) and 4-[4-(3-{2-fluoro-6-[(5-fluoro-2-methoxy-pyridin-3-ylmethyl)-amino]-pyridin-3-ylmethyl}-1H-pyrrolo[2,3-b]pyridin-5-yl)-pyrazol-1-yl]-piperidine-1-carboxylic acid tert-butyl ester (P-1702)

In a microwave vial, [5-(1-benzenesulfonyl-5-bromo-1H-pyrrolo[2,3-b]pyridin-3-ylmethyl)-6-fluoro-pyridin-2-yl]-(5-fluoro-2-methoxy-pyridin-3-ylmethyl)-amine (168, 218 mg, 0.363 mmol) and 4-[4-(4,4,5,5-tetramethyl-[1,3,2]dioxaborolan-2-yl)-pyrazol-1-yl]-piperidine-1-carboxylic acid tert-butyl ester (169, 205 mg, 0.545 mmol) were combined and 2.22 mL of acetonitrile and potassium carbonate (1.11 mL, 1.0 M in water, 1.11 mmol) were added. Then [1,1'-bis(diphenylphosphino)ferrocene]dichloropalladium(11) (27 mg, 0.037 mmol) was added to the reaction mixture and heated at 160° C. in a microwave for 5 minutes. Water was added and the mixture was extracted with ethyl acetate. The organic layer was washed with water and brine, then dried over magnesium sulfate, filtered and the filtrate concentrated under vacuum. The resulting material was purified by silica gel column chromatography eluting with ethyl acetate and hexane. Appropriate fractions were combined and concentrated under vacuum to provide the desired compounds (170, 137 mg) and (P-1702, 66 mg). 170 MS (ESI) [M+H]=770.7. P-1702 MS (ESI) $[M+H^+]^+$=631.1.

Step 5—Preparation of (5-fluoro-2-methoxy-pyridin-3-ylmethyl)-{6-fluoro-5-[5-(1-piperidin-4-yl-1H-pyrazol-4-yl)-1H-pyrrolo[2,3-b]pyridin-3-ylmethyl]-pyridin-2-yl}-amine (P-1703)

In a vial, 4-[4-(1-benzenesulfonyl-3-{2-fluoro-6-[(5-fluoro-2-methoxy-pyridin-3-ylmethyl)-amino]-pyridin-3- ylmethyl}-1H-pyrrolo[2,3-b]pyridin-5-yl)-pyrazol-1-yl]-piperidine-1-carboxylic acid tert-butyl ester (170, 0.137 g, 0.178 mmol) was dissolved in a solution of potassium hydroxide (0.392 g, 6.99 mmol) in 7.0 mL of methanol and the reaction was heated at 50° C. for 3 hours. Aqueous 1 M citric acid was added, then the reaction was extracted with ethyl acetate. The organic layer was washed with water and brine, then dried over magnesium sulfate, filtered and the filtrate concentrated under vacuum. 4-[4-(3-{2-fluoro-6-[(5-fluoro-2-methoxy-pyridin-3-ylmethyl)-amino]-pyridin-3-ylmethyl}-1H-pyrrolo[2,3-b]pyridin-5-yl)-pyrazol-1-yl]-piperidine-1-carboxylic acid tert-butyl ester (P-1702, 56 mg, 0.0888 mmol) was combined with this and 10 mL of dichloromethane and trifluoroacetic acid (0.50 mL, 6.5 mmol) were added, then stirred at room temperature for 2 hours. Aqueous saturated sodium bicarbonate was added to pH=8, then concentrated under vacuum and ethyl acetate and water were added. The organic layer was isolated and washed with aqueous saturated sodium bicarbonate, then dried with magnesium sulfate, filtered and the filtrate concentrated under vacuum to provide the desired compound as a yellow solid (P-1703, 74 mg). MS (ESI) [M+H$^+$]$^+$=631.1.

Additional compounds are prepared following the protocol of Scheme 23, where conditions may vary, for example, any of the solvents, reaction times, reagents, temperatures, work up conditions, or other reaction parameters may be varied employing alternate solvents, reagents, reaction times, temperatures, work up conditions, and the like, as are readily available to one skilled in the art. Compounds are prepared optionally replacing 5-fluoro-2-methoxy-pyridine-3-carbaldehyde 37, with a suitable aldehyde in step 3. The following compounds are made using this procedure. Compounds in the following table were characterized by $^1$H and $^{13}$C NMR spectroscopy as well as mass spectrometry.

(5-Fluoro-6-methoxy-pyridin-3-ylmethyl)-{6-fluoro-5-[5-(1-piperidin-4-yl-1H-pyrazol-4-yl)-1H-pyrrolo[2,3-b]pyridin-3-ylmethyl]-pyridin-2-yl}-amine (P-1704), {6-Fluoro-5-[5-(1-piperidin-4-yl-1H-pyrazol-4-yl)-1H-pyrrolo[2,3-b]pyridin-3-ylmethyl]-pyridin-2-yl}-(5-fluoro-pyridin-3-ylmethyl)-amine (P-1705), (6-Chloro-pyridin-3-ylmethyl)-{6-fluoro-5-[5-(1-piperidin-4-yl-1H-pyrazol-4-yl)-1H-pyrrolo[2,3-b]pyridin-3-ylmethyl]-pyridin-2-yl}-amine (P-1706), {6-Fluoro-5-[5-(1-piperidin-4-yl-1H-pyrazol-4-yl)-1H-pyrrolo[2,3-b]pyridin-3-ylmethyl]-pyridin-2-yl}-(4-trifluoromethyl-pyridin-3-ylmethyl)-amine (P-1707), {6-Fluoro-5-[5-(1-piperidin-4-yl-1H-pyrazol-4-yl)-1H-pyrrolo[2,3-b]pyridin-3-ylmethyl]-pyridin-2-yl}-(6-methoxy-pyridin-3-ylmethyl)-amine (P-1708), {6-Fluoro-5-[5-(1-piperidin-4-yl-1H-pyrazol-4-yl)-1H-pyrrolo[2,3-b]pyridin-3-ylmethyl]-pyridin-2-yl}-(6-trifluoromethyl-pyridin-3-ylmethyl)-amine (P-1709), and {6-Fluoro-5-[5-(1-piperidin-4-yl-1H-pyrazol-4-yl)-1H-pyrrolo[2,3-b]pyridin-3-ylmethyl]-pyridin-2-yl}-(2-methoxy-pyridin-3-ylmethyl)-amine (P-1710).

The following table indicates the aldehyde compound (column 2) used in step 3 to afford the desired compound (column 3). The compound number is provided in column 1, and the observed mass is in column 4.

| Compound number | Aldehyde | Compound | MS (ESI) [M + H$^+$]$^+$ |
|---|---|---|---|
| P-1704 | | | |
| P-1705 | | | |
| P-1706 | | | |

-continued

| Compound number | Aldehyde | Compound | MS (ESI) [M + H+]+ |
|---|---|---|---|
| P-1707 | | | |
| P-1708 | | | |
| P-1709 | | | |
| P-1710 | | | |

Example 24

Synthesis of N-(3-{2-fluoro-6-[(5-fluoro-2-methoxy-pyridin-3-ylmethyl)-amino]-pyridin-3-ylmethyl}-1H-pyrrolo[2,3-b]pyridin-5-yl)-acetamide P-1669

N-(3-{2-Fluoro-6-[(5-fluoro-2-methoxy-pyridin-3-ylmethyl)-amino]-pyridin-3-ylmethyl}-1H-pyrrolo[2,3-b]pyridin-5-yl)-acetamide P-1669 is prepared in four steps from 5-bromo-3-iodo-pyrrolo[2,3-b]pyridine-1-carboxylic acid tert-butyl ester 171 and (6-fluoro-5-formyl-pyridin-2-yl)-(4-methoxy-benzyl)-carbamic acid tert-butyl ester 83 as shown in Scheme 24.

Scheme 24

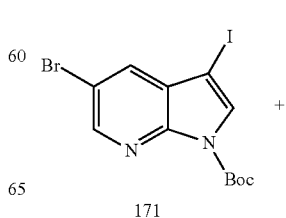

171

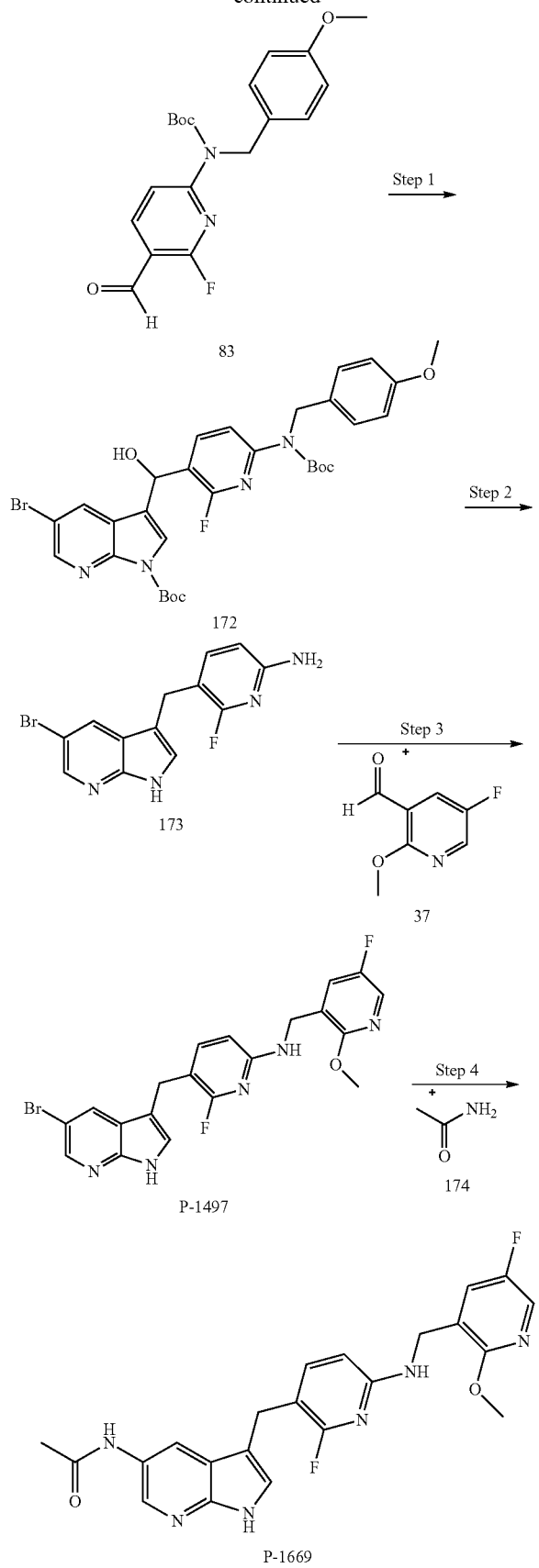

Step 1—Preparation of 5-bromo-3-({6-[tert-butoxy-carbonyl-(4-methoxy-benzyl)-amino]-2-fluoro-pyridin-3-yl}-hydroxy-methyl)-pyrrolo[2,3-b]pyrrolopyridine-1-carboxylic acid tert-butyl ester (172)

To 5-bromo-3-iodo-pyrrolo[2,3-b]pyridine-1-carboxylic acid tert-butyl ester (171, 1 equivalent) in 500 mL of tetrahydrofuran under nitrogen at −20° C., iso-propylmagnesium chloride (1.2 equivalent) is added. The reaction is allowed to warm to 0° C. over 30 minutes, then cooled to −40° C., followed by adding (6-fluoro-5-formyl-pyridin-2-yl)-(4-methoxy-benzyl)-carbamic acid tert-butyl ester (83, 0.8 equivalent). The reaction is allowed to warm to 0° C. over an hour, then quenched with brine and extracted with ethyl acetate. The organic layer is concentrated under vacuum to provide the desired compound, used in the next step without further purification.

Step 2—Preparation of 5-(5-bromo-1H-pyrrolo[2,3-b]pyridin-3-ylmethyl)-6-fluoro-pyridin-2-ylamine (173)

To 5-bromo-3-({6-[tert-butoxycarbonyl-(4-methoxy-benzyl)-amino]-2-fluoro-pyridin-3-yl}-hydroxy-methyl)-pyrrolo[2,3-b]pyridine-1-carboxylic acid tert-butyl ester (172, 1 equivalent) in 451 mL of acetonitrile, triethylsilane (10 equivalents) and trifluoroacetic acid (10 equivalents) are added. The reaction is stirred at 80° C. for several hours, then concentrated under vacuum. The resulting material is taken up in 250 mL of dichloromethane and 250 mL of trifluoroacetic acid is added, then stirred at reflux for several hours. The reaction is concentrated under vacuum and the resulting material is taken up in ethyl acetate and extraction with the addition of aqueous saturated potassium carbonate. The organic layer is concentrated under vacuum and the resulting material is purified by silica gel column chromatography, eluting with 0-5% methanol in dichloromethane. Appropriate fractions are combined and concentrated under vacuum to provide the desired compound.

Step 3—Preparation of [5-(5-bromo-1H-pyrrolo[2,3-b]pyridin-3-ylmethyl)-6-fluoro-pyridin-2-yl]-(5-fluoro-2-methoxy-pyridin-3-ylmethyl)-amine (P-1497)

To 5-(5-bromo-1H-pyrrolo[2,3-b]pyridin-3-ylmethyl)-6-fluoro-pyridin-2-ylamine (173, 1 equivalent) and 5-fluoro-2-methoxy-pyridine-3-carbaldehyde (37, 1 equivalent), triethylsilane (4 equivalents) and trifluoroacetic acid (4 equivalents) are added. The reaction is stirred at 80° C. for several hours, then concentrated under vacuum. The resulting material is taken up in ethyl acetate and extracted with addition of aqueous potassium carbonate. The organic layer is concentrated under vacuum, then triturated with dichloromethane to provide the desired compound.

Step 4—Preparation of N-(3-{2-fluoro-6-[(5-fluoro-2-methoxy-pyridin-3-ylmethyl)-amino]-pyridin-3-ylmethyl}-1H-pyrrolo[2,3-b]pyridin-5-yl)-acetamide (P-1669)

[5-(5-Bromo-1H-pyrrolo[2,3-b]pyridin-3-ylmethyl)-6-fluoro-pyridin-2-yl]-(5-fluoro-2-methoxy-pyridin-3-ylmethyl)-amine (P-1497, 1 equivalent) is dissolved in 25 mL of dioxane in a sealable vial. Cesium carbonate (2.1 equivalents), copper(I) iodide (1.5 equivalents), acetamide (174, 22 equivalents) and N,N'-dimethylethylenediamine (17 equivalents) are added. The vial is sealed and heated at 100° C. overnight. The reaction is added to ethyl acetate and brine and extracted. The organic layer is concentrated under vacuum and the resulting material dissolved in dichloromethane and purified by silica gel column chromatography, eluting with 0-10% methanol in dichloromethane. Appropriate fractions are concentrated, and the material dissolved in tetrahydrofuran for further purification on a C18 reverse phase column, eluting with 0-100% methanol (with 10% tetrahydrofuran)/water. Appropriated fractions are combined and concentrated under vacuum. The resulting material is triturated with methyl tert-butyl ether and filtered, washing with methyl tert-butyl ether, then heptane. The solid is dried under vacuum to provide the desired compound.

Additional compounds are prepared following the protocol of Scheme 24, where conditions may vary, for example, any of the solvents, reaction times, reagents, temperatures, work up conditions, or other reaction parameters may be varied employing alternate solvents, reagents, reaction times, temperatures, work up conditions, and the like, as are readily available to one skilled in the art. Compounds are prepared optionally replacing 5-fluoro-2-methoxy-pyridine-3-carbaldehyde 37, with a suitable aldehyde in step 3 and optionally replacing acetamide 174 with methanesulfonamide in step 4. The following compounds are made using this procedure. Compounds in the following table were characterized by $^1$H and $^{13}$C NMR spectroscopy as well as mass spectrometry.

N-(3-{2-Fluoro-6-[(5-fluoro-6-methoxy-pyridin-3-ylmethyl)-amino]-pyridin-3-ylmethyl}-1H-pyrrolo[2,3-b]pyridin-5-yl)-acetamide (P-1670), N-(3-{2-Fluoro-6-[(5-fluoro-pyridin-3-ylmethyl)-amino]-pyridin-3-ylmethyl}-1H-pyrrolo[2,3-b]pyridin-5-yl)-acetamide (P-1671), N-(3-{6-[(6-Chloro-pyridin-3-ylmethyl)-amino]-2-fluoro-pyridin-3-ylmethyl}-1H-pyrrolo[2,3-b]pyridin-5-yl)-acetamide (P-1672), N-(3-{2-Fluoro-6-[(4-trifluoromethyl-pyridin-3-ylmethyl)-amino]-pyridin-3-ylmethyl}-1H-pyrrolo[2,3-b]pyridin-5-yl)-acetamide (P-1673), N-(3-{2-Fluoro-6-[(6-methoxy-pyridin-3-ylmethyl)-amino]-pyridin-3-ylmethyl}-1H-pyrrolo[2,3-b]pyridin-5-yl)-acetamide (P-1674), N-(3-{2-Fluoro-6-[(6-trifluoromethyl-pyridin-3-ylmethyl)-amino]-pyridin-3-ylmethyl}-1H-pyrrolo[2,3-b]pyridin-5-yl)-acetamide (P-1675), N-(3-{2-Fluoro-6-[(2-methoxy-pyridin-3-ylmethyl)-amino]-pyridin-3-ylmethyl}-1H-pyrrolo[2,3-b]pyridin-5-yl)-acetamide (P-1676), N-(3-{2-Fluoro-6-[(5-fluoro-6-methoxy-pyridin-3-ylmethyl)-amino]-pyridin-3-ylmethyl}-1H-pyrrolo[2,3-b]pyridin-5-yl)-methanesulfonamide (P-1677), N-(3-{2-Fluoro-6-[(5-fluoro-pyridin-3-ylmethyl)-amino]-pyridin-3-ylmethyl}-1H-pyrrolo[2,3-b]pyridin-5-yl)-methanesulfonamide (P-1678), N-(3-{6-[(6-Chloro-pyridin-3-ylmethyl)-amino]-2-fluoro-pyridin-3-ylmethyl}-1H-pyrrolo[2,3-b]pyridin-5-yl)-methanesulfonamide (P-1679), N-(3-{2-Fluoro-6-[(5-fluoro-2-methoxy-pyridin-3-ylmethyl)-amino]-pyridin-3-ylmethyl}-1H-pyrrolo[2,3-b]pyridin-5-yl)-methanesulfonamide (P-1680), N-(3-{2-Fluoro-6-[(4-trifluoromethyl-pyridin-3-ylmethyl)-amino]-pyridin-3-ylmethyl}-1H-pyrrolo[2,3-b]pyridin-5-yl)-methanesulfonamide (P-1681), N-(3-{2-Fluoro-6-[(6-methoxy-pyridin-3-ylmethyl)-amino]-pyridin-3-ylmethyl}-1H-pyrrolo[2,3-b]pyridin-5-yl)-methanesulfonamide (P-1682), N-(3-{2-Fluoro-6-[(6-trifluoromethyl-pyridin-3-ylmethyl-pyridin-3-ylmethyl)-amino]-pyridin-3-ylmethyl}-1H-pyrrolo[2,3-b]pyridin-5-yl)-methanesulfonamide (P-1683), and N-(3-{2-Fluoro-6-[(2-methoxy-pyridin-3-ylmethyl)-amino]-pyridin-3-ylmethyl}-1H-pyrrolo[2,3-b]pyridin-5-yl)-methanesulfonamide (P-1684).

The following table indicates the aldehyde compound (column 2) used in step 3 and acetamide or methanesulfonamide (column 3) used in step 4 to afford the desired compound (column 4). The compound number is provided in column 1, and the observed mass is in column 5.

| Compound number | Aldehyde | Step 4 | Compound | MS (ESI) [M + H$^+$]$^+$ |
|---|---|---|---|---|
| P-1670 | | | | |

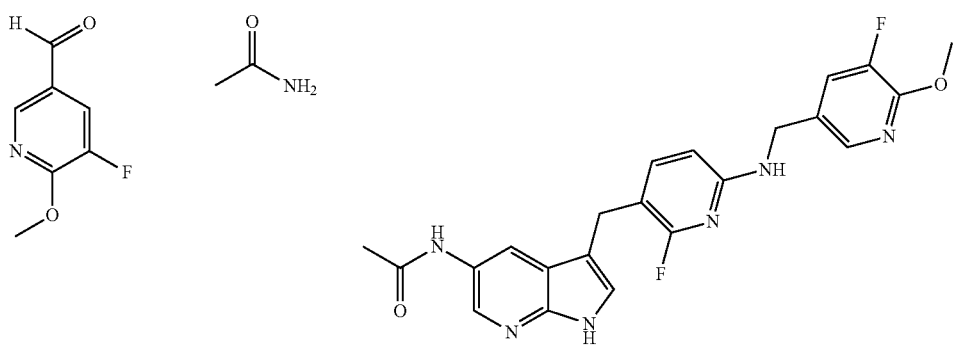

-continued

| Compound number | Aldehyde | Step 4 | Compound | MS (ESI) [M + H+]+ |
|---|---|---|---|---|
| P-1671 | | | | |
| P-1672 | | | | |
| P-1673 | | | | |
| P-1674 | | | | |

-continued

| Compound number | Aldehyde | Step 4 | Compound | MS (ESI) [M + H⁺]⁺ |
| --- | --- | --- | --- | --- |
| P-1675 | | | | |
| P-1676 | | | | |
| P-1677 | | | | |
| P-1678 | | | | |
| P-1679 | | | | |

-continued
| Compound number | Aldehyde | Step 4 | Compound | MS (ESI) [M + H+]+ |
|---|---|---|---|---|
| P-1680 | 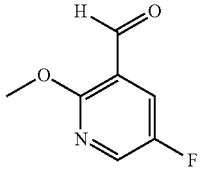 | 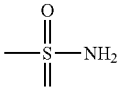 | 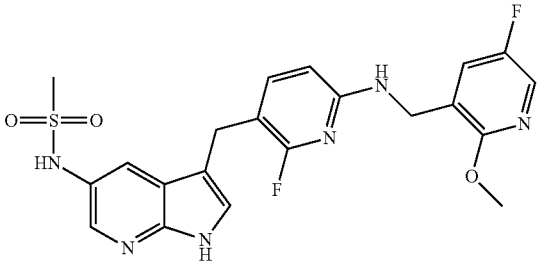 [SMILES: COc1ncc(F)cc1CNc1ccc(Cc2c[nH]c3ncc(NS(C)(=O)=O)cc23)c(F)n1] | |
| P-1681 | 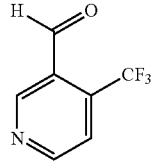 | 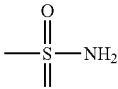 | 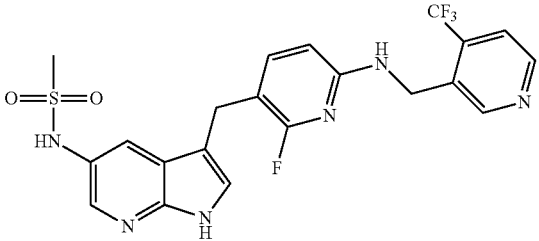 [SMILES: CS(=O)(=O)Nc1cnc2[nH]cc(Cc3ccc(NCc4cnccc4C(F)(F)F)nc3F)c2c1] | |
| P-1682 | 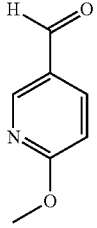 | 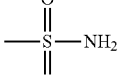 | 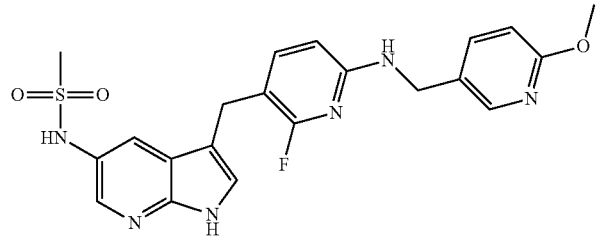 [SMILES: COc1ccc(CNc2ccc(Cc3c[nH]c4ncc(NS(C)(=O)=O)cc34)c(F)n2)cn1] | |
| P-1683 | 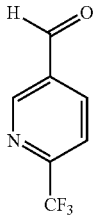 | 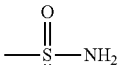 | 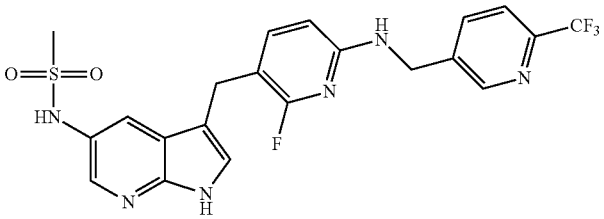 [SMILES: CS(=O)(=O)Nc1cnc2[nH]cc(Cc3ccc(NCc4ccc(C(F)(F)F)nc4)nc3F)c2c1] | |
| P-1684 | 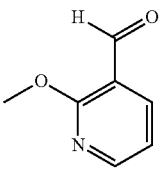 | 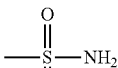 | 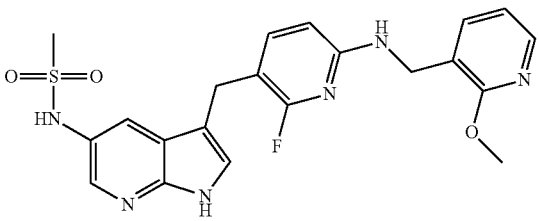 [SMILES: COc1ncccc1CNc1ccc(Cc2c[nH]c3ncc(NS(C)(=O)=O)cc23)c(F)n1] | |

[6-Fluoro-5-(5-methanesulfonyl-1H-pyrrolo[2,3-b]pyridin-3-ylmethyl)-pyridin-2-yl]-(5-fluoro-2-methoxy-pyridin-3-ylmethyl)-amine P-1688 is prepared from [5-(5-bromo-1H-pyrrolo[2,3-b]pyridin-3-ylmethyl)-6-fluoro-pyridin-2-yl]-(5-fluoro-2-methoxy-pyridin-3-ylmethyl)-amine P-1497 by the following step 4a.

[5-(5-bromo-1H-pyrrolo[2,3-b]pyridin-3-ylmethyl)-6-fluoro-pyridin-2-yl]-(5-fluoro-2-methoxy-pyridin-3-ylmethyl)-amine P-1497 by the following steps 4b and 5.

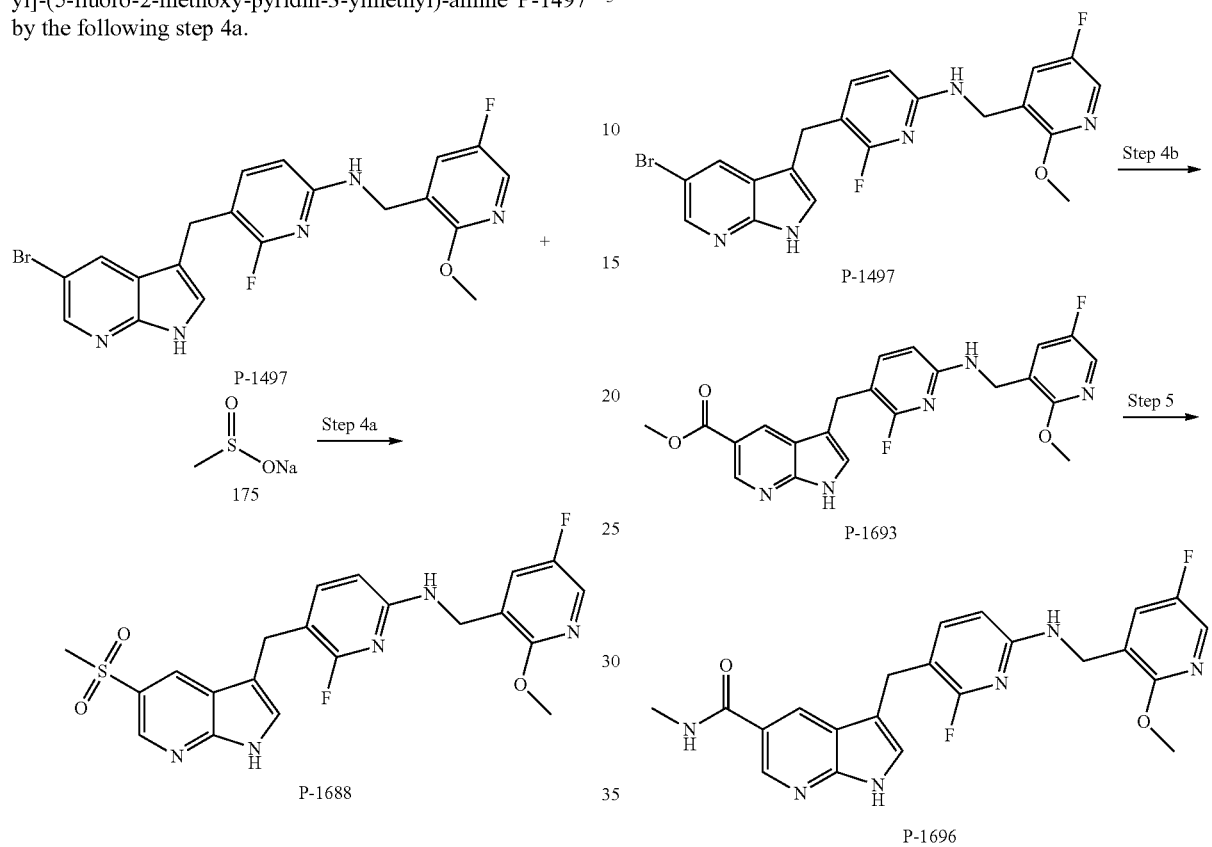

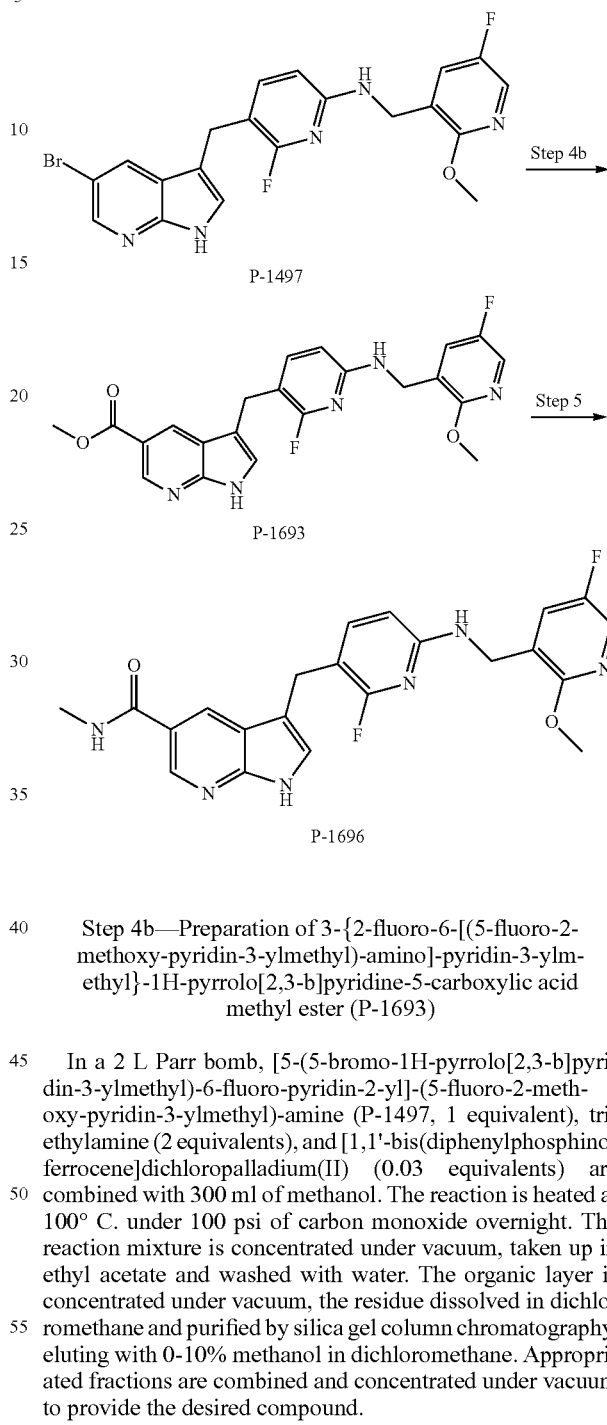

Step 4a—Preparation of [6-fluoro-5-(5-methanesulfonyl-1H-pyrrolo[2,3-b]pyridin-3-ylmethyl)-pyridin-2-yl]-(5-fluoro-2-methoxy-pyridin-3-ylmethyl)-amine (P-1688)

[5-(5-Bromo-1H-pyrrolo[2,3-b]pyridin-3-ylmethyl)-6-fluoro-pyridin-2-yl]-(5-fluoro-2-methoxy-pyridin-3-ylmethyl)-amine (P-1497, 1 equivalent) is dissolved in 5 mL of dimethyl sulfoxide in a sealable vial. Copper(I) iodide (0.2 equivalent), L-proline (0.2 equivalent), sodium methanesulfinate (175, 1.2 equivalents), and sodium hydroxide (0.2 equivalent) are added. The vial is sealed and heated at 100° C. overnight, then additional copper(I) iodide (0.2 equivalent), L-proline (0.2 equivalent), sodium methanesulfinate (1.2 equivalent), and sodium hydroxide (0.2 equivalent) are added, and the reaction is sealed and heated at 120° C. overnight. The reaction is added to ethyl acetate and brine and extracted. The organic layer is concentrated under vacuum and the resulting material dissolved in tetrahydrofuran for purification on a C18 reverse phase column, eluting with 0-100% methanol (with 10% tetrahydrofuran)/water. Appropriate fractions are combined and concentrated under vacuum. The resulting material is triturated with methyl tert-butyl ether and filtered, washing with methyl tert-butyl ether, then heptane. The solid is dried under vacuum to provide the desired compound.

3-{2-Fluoro-6-[(5-fluoro-2-methoxy-pyridin-3-ylmethyl)-amino]-pyridin-3-ylmethyl}-1H-pyrrolo[2,3-b]pyridine-5-carboxylic acid methylamide P-1696 is prepared from Step 4b—Preparation of 3-{2-fluoro-6-[(5-fluoro-2-methoxy-pyridin-3-ylmethyl)-amino]-pyridin-3-ylmethyl}-1H-pyrrolo[2,3-b]pyridine-5-carboxylic acid methyl ester (P-1693)

In a 2 L Parr bomb, [5-(5-bromo-1H-pyrrolo[2,3-b]pyridin-3-ylmethyl)-6-fluoro-pyridin-2-yl]-(5-fluoro-2-methoxy-pyridin-3-ylmethyl)-amine (P-1497, 1 equivalent), triethylamine (2 equivalents), and [1,1'-bis(diphenylphosphino)ferrocene]dichloropalladium(II) (0.03 equivalents) are combined with 300 ml of methanol. The reaction is heated at 100° C. under 100 psi of carbon monoxide overnight. The reaction mixture is concentrated under vacuum, taken up in ethyl acetate and washed with water. The organic layer is concentrated under vacuum, the residue dissolved in dichloromethane and purified by silica gel column chromatography, eluting with 0-10% methanol in dichloromethane. Appropriated fractions are combined and concentrated under vacuum to provide the desired compound.

Step 5—Preparation of 3-{2-fluoro-6-[(5-fluoro-2-methoxy-pyridin-3-ylmethyl)-amino]-pyridin-3-ylmethyl}-1H-pyrrolo[2,3-b]pyridine-5-carboxylic acid methylamide (P-1696)

3-{2-Fluoro-6-[(5-fluoro-2-methoxy-pyridin-3-ylmethyl)-amino]-pyridin-3-ylmethyl}-1H-pyrrolo[2,3-b]pyridine-5-carboxylic acid methyl ester (P-1693, 1 equivalent) is slurried with methylamine (2N in methanol, 15 equivalents) in a sealable vial, sealed and heated at 50° C. overnight. Additional methylamine (2N in methanol, 15 equivalents) is added and heated at 50° C. overnight. The reaction is concentrated under vacuum, the residue dissolved in tetrahydrofuran for purification on a C18 reverse phase column, eluting with 0-100% methanol (with 10% tetrahydrofuran)/water. Appropriated fractions are combined and concentrated under vacuum. The resulting material is triturated with ethyl acetate/heptane and filtered, washing with heptane. The solid is dried under vacuum to provide the desired compound.

Additional compounds are prepared following the protocol of Scheme 24, using steps 4a or steps 4b and step 5, where conditions may vary, for example, any of the solvents, reaction times, reagents, temperatures, work up conditions, or other reaction parameters may be varied employing alternate solvents, reagents, reaction times, temperatures, work up conditions, and the like, as are readily available to one skilled in the art. Compounds are prepared optionally replacing 5-fluoro-2-methoxy-pyridine-3-carbaldehyde 37, with a suitable aldehyde in step 3. The following compounds are made using this procedure. Compounds in the following table were characterized by $^1$H and $^{13}$C NMR spectroscopy as well as mass spectrometry.

[6-Fluoro-5-(5-methanesulfonyl-1H-pyrrolo[2,3-b]pyridin-3-ylmethyl)-pyridin-2-yl]-(5-fluoro-6-methoxy-pyridin-3-ylmethyl)-amine (P-1685),

[6-Fluoro-5-(5-methanesulfonyl-1H-pyrrolo[2,3-b]pyridin-3-ylmethyl)-pyridin-2-yl]-(5-fluoro-pyridin-3-ylmethyl)-amine (P-1686), (6-Chloro-pyridin-3-ylmethyl)-[6-fluoro-5-(5-methanesulfonyl-1H-pyrrolo[2,3-b]pyridin-3-ylmethyl)-pyridin-2-yl]-amine (P-1687),

[6-Fluoro-5-(5-methanesulfonyl-1H-pyrrolo[2,3-b]pyridin-3-ylmethyl)-pyridin-2-yl]-(4-trifluoromethyl-pyridin-3-ylmethyl)-amine (P-1689),

[6-Fluoro-5-(5-methanesulfonyl-1H-pyrrolo[2,3-b]pyridin-3-ylmethyl)-pyridin-2-yl]-(6-methoxy-pyridin-3-ylmethyl)-amine (P-1690),

[6-Fluoro-5-(5-methanesulfonyl-1H-pyrrolo[2,3-b]pyridin-3-ylmethyl)-pyridin-2-yl]-(6-trifluoromethyl-pyridin-3-ylmethyl)-amine (P-1691),

[6-Fluoro-5-(5-methanesulfonyl-1H-pyrrolo[2,3-b]pyridin-3-ylmethyl)-pyridin-2-yl]-(2-methoxy-pyridin-3-ylmethyl)-amine (P-1692), 3-{2-Fluoro-6-[(5-fluoro-6-methoxy-pyridin-3-ylmethyl)-amino]-pyridin-3-ylmethyl}-1H-pyrrolo[2,3-b]pyridine-5-carboxylic acid methylamide (P-1694), 3-{2-Fluoro-6-[(5-fluoro-pyridin-3-ylmethyl)-amino]-pyridin-3-ylmethyl}-1H-pyrrolo[2,3-b]pyridine-5-carboxylic acid methylamide (P-1695), 3-{6-[(6-Chloro-pyridin-3-ylmethyl)-amino]-2-fluoro-pyridin-3-ylmethyl}-1H-pyrrolo[2,3-b]pyridine-5-carboxylic acid methylamide (P-1697), 3-{2-Fluoro-6-[(4-trifluoromethyl-pyridin-3-ylmethyl)-amino]-pyridin-3-ylmethyl}-1H-pyrrolo[2,3-b]pyridine-5-carboxylic acid methylamide (P-1698), 3-{2-Fluoro-6-[(6-methoxy-pyridin-3-ylmethyl)-amino]-pyridin-3-ylmethyl}-1H-pyrrolo[2,3-b]pyridine-5-carboxylic acid methylamide (P-1699), 3-{2-Fluoro-6-[(6-trifluoromethyl-pyridin-3-ylmethyl)-amino]-pyridin-3-ylmethyl}-1H-pyrrolo[2,3-b]pyridine-5-carboxylic acid methylamide (P-1700), and 3-{2-Fluoro-6-[(2-methoxy-pyridin-3-ylmethyl)-amino]-pyridin-3-ylmethyl}-1H-pyrrolo[2,3-b]pyridine-5-carboxylic acid methylamide (P-1701).

The following table indicates the aldehyde compound (column 2) used in step 3 and whether step 4a or step 4b/5 is used (column 3) used in step 4 to afford the desired compound (column 4). The compound number is provided in column 1, and the observed mass is in column 5.

| Compound number | Aldehyde | Steps used | Compound | MS (ESI) [M + H$^+$]$^+$ |
|---|---|---|---|---|
| P-1685 | | 4a | | |
| P-1686 | | 4a | | |

-continued

| Compound number | Aldehyde | Steps used | Compound | MS (ESI) [M + H⁺]⁺ |
|---|---|---|---|---|
| P-1687 | 6-chloropyridine-3-carbaldehyde | 4a | | |
| P-1689 | 4-(trifluoromethyl)pyridine-3-carbaldehyde | 4a | | |
| P-1690 | 6-methoxypyridine-3-carbaldehyde | 4a | | |
| P-1691 | 6-(trifluoromethyl)pyridine-3-carbaldehyde | 4a | | |
| P-1692 | 2-methoxypyridine-3-carbaldehyde | 4a | | |
| P-1694 | 5-fluoro-6-methoxypyridine-3-carbaldehyde | 4b/5 | | |

| Compound number | Aldehyde | Steps used | Compound | MS (ESI) [M + H+]+ |
|---|---|---|---|---|
| P-1695 | 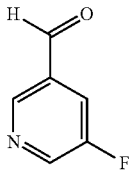 | 4b/5 | 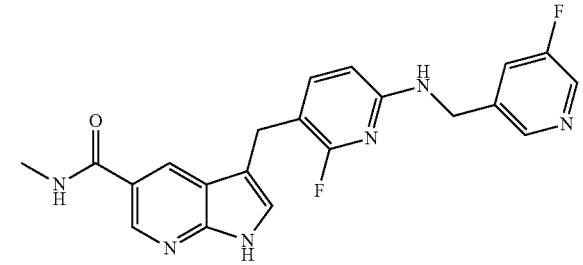 [SMILES: CNC(=O)c1cnc2[nH]cc(Cc3ccc(NCc4cncc(F)c4)nc3F)c2c1] | |
| P-1697 | 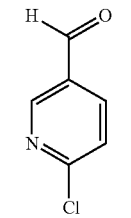 | 4b/5 | 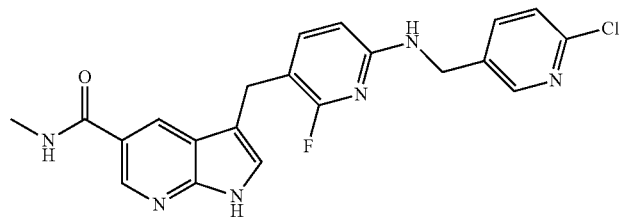 [SMILES: CNC(=O)c1cnc2[nH]cc(Cc3ccc(NCc4ccc(Cl)nc4)nc3F)c2c1] | |
| P-1698 |  | 4b/5 | 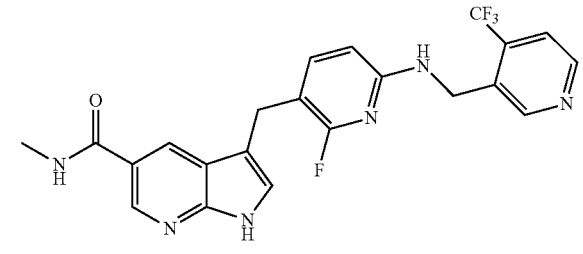 [SMILES: CNC(=O)c1cnc2[nH]cc(Cc3ccc(NCc4cnccc4C(F)(F)F)nc3F)c2c1] | |
| P-1699 | 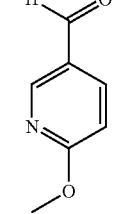 | 4b/5 | 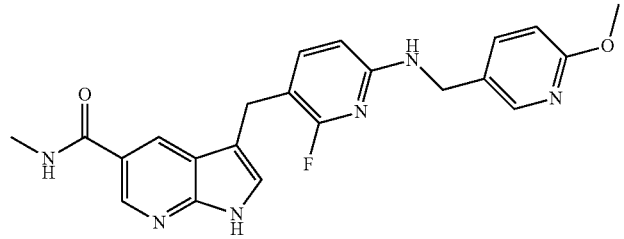 | |
| P-1700 | 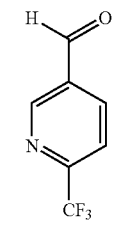 | 4b/5 | 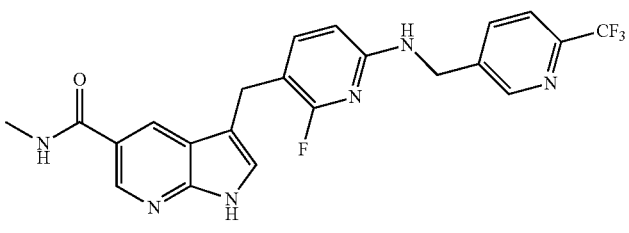 [SMILES: CNC(=O)c1cnc2[nH]cc(Cc3ccc(NCc4ccc(C(F)(F)F)nc4)nc3F)c2c1] | |
| P-1701 | 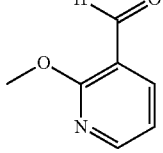 | 4b/5 | 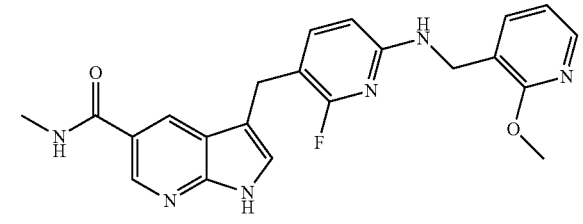 [SMILES: CNC(=O)c1cnc2[nH]cc(Cc3ccc(NCc4cccnc4OC)nc3F)c2c1] | |

Example 25

Synthesis of (2-chloro-benzyl)-[6-fluoro-5-(5-methoxy-1H-pyrrolo[2,3-b]pyridin-3-ylmethyl)-pyridin-2-yl]-amine P-2034

(2-Chloro-benzyl)-[6-fluoro-5-(5-methoxy-1H-pyrrolo[2,3-b]pyridin-3-ylmethyl)-pyridin-2-yl]-amine P-2034 was prepared in two steps from (2-chloro-benzyl)-(6-fluoro-5-formyl-pyridin-2-yl)-carbamic acid tert-butyl ester 48 and 3-iodo-5-methoxy-1-triisopropylsilanyl-1H-pyrrolo[2,3-b]pyridine 5 as shown in Scheme 25.

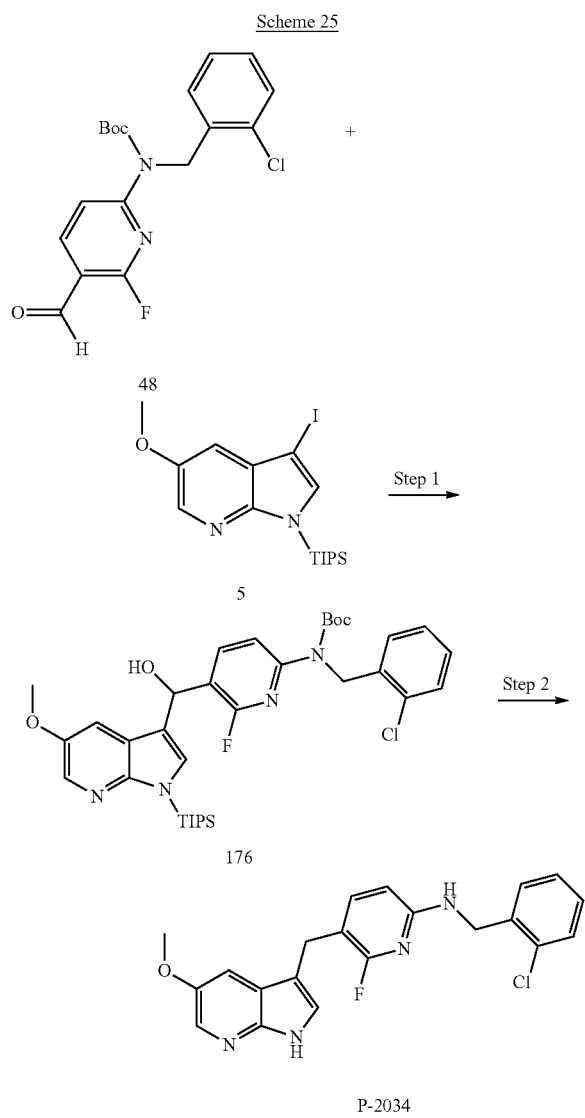

Scheme 25

Step 1—Preparation of (2-chloro-benzyl)-6-fluoro-5-[hydroxy-(5-methoxy-1-triisopropylsilanyl-1H-pyrrolo[2,3-b]pyridin-3-yl)-methyl]-pyridin-2-yl)-carbamic acid tert-butyl ester (176)

To 3-iodo-5-methoxy-1-triisopropylsilanyl-1H-pyrrolo[2,3-b]pyridine (5, 0.49 g, 1.14 mmol) in 6.8 mL of tetrahydrofuran at −50° C. under nitrogen, isopropylmagnesium chloride (0.569 mL, 2.0 M in tetrahydrofuran, 1.14 mmol) was added slowly. The reaction was allowed to warm to 5° C. over 70 minutes, then cooled to −60° C. and (2-chloro-benzyl)-(6-fluoro-5-formyl-pyridin-2-yl)-carbamic acid tert-butyl ester (48, 0.23 g, 0.63 mmol) in 30.0 mL of tetrahydrofuran was added. The reaction was allowed to warm to room temperature over 1 hour, then poured into aqueous ammonium chloride and extracted with ethyl acetate. The organic layer was dried over sodium sulfate, filtered and the filtrate concentrated under vacuum. The resulting material was purified by silica gel column chromatography eluting with 20-100% ethyl acetate in hexane. Appropriate fractions were combined and the solvents removed under vacuum to provide the desired compound as a white solid (176, 0.400 g). MS (ESI) $[M+H^+]^+=669.4$.

Step 2—Preparation of (2-chloro-benzyl)-[6-fluoro-5-(5-methoxy-1H-pyrrolo[2,3-b]pyridin-3-ylmethyl)-pyridin-2-yl]-amine (P-2034)

To (2-chloro-benzyl)-{6-fluoro-5-[hydroxy-(5-methoxy-1-triisopropylsilanyl-1H-pyrrolo[2,3-b]pyridin-3-yl)-methyl]-pyridin-2-yl}-carbamic acid tert-butyl ester (176, 400 mg, 0.598 mmol) in 20.0 mL of dichloromethane, triethylsilane (2.00 mL, 12.5 mmol) and trifluoroacetic acid (1.00 mL, 13.0 mmol) were added. The reaction was stirred at room temperature for 4 hours, then poured into aqueous potassium carbonate and extracted with ethyl acetate. The organic layer was dried over sodium sulfate, filtered and the filtrate concentrated under vacuum. The resulting material was purified by silica gel column chromatography eluting with 20-100% ethyl acetate in hexane. Appropriate fractions were combined and the solvents removed under vacuum to provide the desired compound as a white solid (P-2034, 60.7 mg). MS (ESI) $[M+H^+]^+=397.1$.

Additional compounds are prepared following the protocol of Scheme 25, where conditions may vary, for example, any of the solvents, reaction times, reagents, temperatures, work up conditions, or other reaction parameters may be varied employing alternate solvents, reagents, reaction times, temperatures, work up conditions, and the like, as are readily available to one skilled in the art. Compounds are prepared using a suitable 3-iodo-1-triisopropylsilanyl-1H-pyrrolo[2,3-b]pyridine in place of 3-iodo-5-methoxy-1-triisopropylsilanyl-1H-pyrrolo[2,3-b]pyridine 5 and suitable aldehyde in place (2-chloro-benzyl)-(6-fluoro-5-formyl-pyridin-2-yl)-carbamic acid tert-butyl ester 48 in step 1. The following compounds are made using this procedure. Compounds in the following table were characterized by $^1$H and $^{13}$C NMR spectroscopy as well as mass spectrometry.

(6-Chloro-pyridin-3-ylmethyl)-[6-fluoro-5-(1H-pyrrolo[2,3-b]pyridin-3-ylmethyl)-pyridin-2-yl]-amine (P-1499), (5-Fluoro-2-methoxy-pyridin-3-ylmethyl)-[6-fluoro-5-(1H-pyrrolo[2,3-b]pyridin-3-ylmethyl)-pyridin-2-yl]-amine (P-1500),

[6-Fluoro-5-(1H-pyrrolo[2,3-b]pyridin-3-ylmethyl)-pyridin-2-yl]-(4-trifluoromethyl-pyridin-3-ylmethyl)-amine (P-1501), (5-Fluoro-6-methoxy-pyridin-3-ylmethyl)-[5-(1H-pyrrolo[2,3-b]pyridin-3-ylmethyl)-pyrimidin-2-yl]-amine (P-1513), (5-Fluoro-pyridin-3-ylmethyl)-[5-(1H-pyrrolo[2,3-b]pyridin-3-ylmethyl)-pyrimidin-2-yl]-amine (P-1514), (6-Chloro-pyridin-3-ylmethyl)-[5-(1H-pyrrolo[2,3-b]pyridin-3-ylmethyl)-pyrimidin-2-yl]-amine (P-1515),

[5-(1H-Pyrrolo[2,3-b]pyridin-3-ylmethyl)-pyrimidin-2-yl]-(4-trifluoromethyl-pyridin-3-ylmethyl)-amine (P-1516), (6-Methoxy-pyridin-3-ylmethyl)-[5-(1H-pyrrolo[2,3-b]pyridin-3-ylmethyl)-pyrimidin-2-yl]-amine (P-1517),
[5-(1H-Pyrrolo[2,3-b]pyridin-3-ylmethyl)-pyrimidin-2-yl]-(6-trifluoromethyl-pyridin-3-ylmethyl)-amine (P-1518),
(2-Methoxy-pyridin-3-ylmethyl)-[5-(1H-pyrrolo[2,3-b]pyridin-3-ylmethyl)-pyrimidin-2-yl]-amine (P-1519),
(5-Fluoro-2-methoxy-pyridin-3-ylmethyl)-[5-(1H-pyrrolo[2,3-b]pyridin-3-ylmethyl)-pyrimidin-2-yl]-amine (P-1520),
[4-Chloro-5-(1H-pyrrolo[2,3-b]pyridin-3-ylmethyl)-thiazol-2-yl]-(5-fluoro-6-methoxy-pyridin-3-ylmethyl)-amine (P-1521),
[4-Chloro-5-(1H-pyrrolo[2,3-b]pyridin-3-ylmethyl)-thiazol-2-yl]-(5-fluoro-pyridin-3-ylmethyl)-amine (P-1522),
(6-Chloro-pyridin-3-ylmethyl)-[4-chloro-5-(1H-pyrrolo[2,3-b]pyridin-3-ylmethyl)-thiazol-2-yl]-amine (P-1523),
[4-Chloro-5-(1H-pyrrolo[2,3-b]pyridin-3-ylmethyl)-thiazol-2-yl]-(5-fluoro-2-methoxy-pyridin-3-ylmethyl)-amine (P-1524),
[4-Chloro-5-(1H-pyrrolo[2,3-b]pyridin-3-ylmethyl)-thiazol-2-yl]-(4-trifluoromethyl-pyridin-3-ylmethyl)-amine (P-1525),
[4-Chloro-5-(1H-pyrrolo[2,3-b]pyridin-3-ylmethyl)-thiazol-2-yl]-(6-methoxy-pyridin-3-ylmethyl)-amine (P-1526),
[4-Chloro-5-(1H-pyrrolo[2,3-b]pyridin-3-ylmethyl)-thiazol-2-yl]-(2-methoxy-pyridin-3-ylmethyl)-amine (P-1527),
(6-Methoxy-pyridin-3-ylmethyl)-[6-methyl-5-(5-methyl-1H-pyrrolo[2,3-b]pyridin-3-ylmethyl)-pyridin-2-yl]-amine (P-1532),
(5-Fluoro-6-methoxy-pyridin-3-ylmethyl)-[6-methyl-5-(5-methyl-1H-pyrrolo[2,3-b]pyridin-3-ylmethyl)-pyridin-2-yl]-amine (P-1533),
(5-Fluoro-pyridin-3-ylmethyl)-[6-methyl-5-(5-methyl-1H-pyrrolo[2,3-b]pyridin-3-ylmethyl)-pyridin-2-yl]-amine (P-1534),
(6-Chloro-pyridin-3-ylmethyl)-[6-methyl-5-(5-methyl-1H-pyrrolo[2,3-b]pyridin-3-ylmethyl)-pyridin-2-yl]-amine (P-1535),
(5-Fluoro-2-methoxy-pyridin-3-ylmethyl)-[6-methyl-5-(5-methyl-1H-pyrrolo[2,3-b]pyridin-3-ylmethyl)-pyridin-2-yl]-amine (P-1536),
[6-Methyl-5-(5-methyl-1H-pyrrolo[2,3-b]pyridin-3-ylmethyl)-pyridin-2-yl]-(4-trifluoromethyl-pyridin-3-ylmethyl)-amine (P-1537),
[6-Methyl-5-(5-methyl-1H-pyrrolo[2,3-b]pyridin-3-ylmethyl)-pyridin-2-yl]-(6-trifluoromethyl-pyridin-3-ylmethyl)-amine (P-1538),
(2-Methoxy-pyridin-3-ylmethyl)-[6-methyl-5-(5-methyl-1H-pyrrolo[2,3-b]pyridin-3-ylmethyl)-pyridin-2-yl]-amine (P-1539),
(6-Methoxy-pyridin-3-ylmethyl)-[3-methyl-5-(5-methyl-1H-pyrrolo[2,3-b]pyridin-3-ylmethyl)-pyridin-2-yl]-amine (P-1554),
(5-Fluoro-6-methoxy-pyridin-3-ylmethyl)-[3-methyl-5-(5-methyl-1H-pyrrolo[2,3-b]pyridin-3-ylmethyl)-pyridin-2-yl]-amine (P-1555),
(5-Fluoro-pyridin-3-ylmethyl)-[3-methyl-5-(5-methyl-1H-pyrrolo[2,3-b]pyridin-3-ylmethyl)-pyridin-2-yl]-amine (P-1556),
(6-Chloro-pyridin-3-ylmethyl)-[3-methyl-5-(5-methyl-1H-pyrrolo[2,3-b]pyridin-3-ylmethyl)-pyridin-2-yl]-amine (P-1557),
(5-Fluoro-2-methoxy-pyridin-3-ylmethyl)-[3-methyl-5-(5-methyl-1H-pyrrolo[2,3-b]pyridin-3-ylmethyl)-pyridin-2-yl]-amine (P-1558),
[3-Methyl-5-(5-methyl-1H-pyrrolo[2,3-b]pyridin-3-ylmethyl)-pyridin-2-yl]-(4-trifluoromethyl-pyridin-3-ylmethyl)-amine (P-1559),
[3-Methyl-5-(5-methyl-1H-pyrrolo[2,3-b]pyridin-3-ylmethyl)-pyridin-2-yl]-(6-trifluoromethyl-pyridin-3-ylmethyl)-amine (P-1560),
(2-Methoxy-pyridin-3-ylmethyl)-[3-methyl-5-(5-methyl-1H-pyrrolo[2,3-b]pyridin-3-ylmethyl)-pyridin-2-yl]-amine (P-1561),
[3-Fluoro-5-(5-methyl-1H-pyrrolo[2,3-b]pyridin-3-ylmethyl)-pyridin-2-yl]-(6-methoxy-pyridin-3-ylmethyl)-amine (P-1562),
(5-Fluoro-6-methoxy-pyridin-3-ylmethyl)-[3-fluoro-5-(5-methyl-1H-pyrrolo[2,3-b]pyridin-3-ylmethyl)-pyridin-2-yl]-amine (P-1563),
[3-Fluoro-5-(5-methyl-1H-pyrrolo[2,3-b]pyridin-3-ylmethyl)-pyridin-2-yl]-(5-fluoro-pyridin-3-ylmethyl)-amine (P-1564),
(6-Chloro-pyridin-3-ylmethyl)-[3-fluoro-5-(5-methyl-1H-pyrrolo[2,3-b]pyridin-3-ylmethyl)-pyridin-2-yl]-amine (P-1565),
(5-Fluoro-2-methoxy-pyridin-3-ylmethyl)-[3-fluoro-5-(5-methyl-1H-pyrrolo[2,3-b]pyridin-3-ylmethyl)-pyridin-2-yl]-amine (P-1566),
[3-Fluoro-5-(5-methyl-1H-pyrrolo[2,3-b]pyridin-3-ylmethyl)-pyridin-2-yl]-(4-trifluoromethyl-pyridin-3-ylmethyl)-amine (P-1567),
[3-Fluoro-5-(5-methyl-1H-pyrrolo[2,3-b]pyridin-3-ylmethyl)-pyridin-2-yl]-(2-methoxy-pyridin-3-ylmethyl)-amine (P-1568),
(5-Fluoro-6-methoxy-pyridin-3-ylmethyl)-[5-(5-methyl-1H-pyrrolo[2,3-b]pyridin-3-ylmethyl)-thiazol-2-yl]-amine (P-1579),
(5-Fluoro-pyridin-3-ylmethyl)-[5-(5-methyl-1H-pyrrolo[2,3-b]pyridin-3-ylmethyl)-thiazol-2-yl]-amine (P-1580),
(6-Chloro-pyridin-3-ylmethyl)-[5-(5-methyl-1H-pyrrolo[2,3-b]pyridin-3-ylmethyl)-thiazol-2-yl]-amine (P-1581),
[5-(5-Methyl-1H-pyrrolo[2,3-b]pyridin-3-ylmethyl)-thiazol-2-yl]-(4-trifluoromethyl-pyridin-3-ylmethyl)-amine (P-1582),
(6-Chloro-pyridin-3-ylmethyl)-[6-fluoro-5-(5-methoxy-1H-pyrrolo[2,3-b]pyridin-3-ylmethyl)-pyridin-2-yl]-amine (P-1597),
[6-Fluoro-5-(5-methoxy-1H-pyrrolo[2,3-b]pyridin-3-ylmethyl)-pyridin-2-yl]-(4-trifluoromethyl-pyridin-3-ylmethyl)-amine (P-1598),
(6-Chloro-pyridin-3-ylmethyl)-[5-(5-chloro-1H-pyrrolo[2,3-b]pyridin-3-ylmethyl)-6-fluoro-pyridin-2-yl]-amine (P-1607),
[5-(5-Chloro-1H-pyrrolo[2,3-b]pyridin-3-ylmethyl)-6-fluoro-pyridin-2-yl]-(4-trifluoromethyl-pyridin-3-ylmethyl)-amine (P-1608),
[5-(5-Chloro-1H-pyrrolo[2,3-b]pyridin-3-ylmethyl)-6-fluoro-pyridin-2-yl]-(2-methoxy-pyridin-3-ylmethyl)-amine (P-1609),
(5-Fluoro-6-methoxy-pyridin-3-ylmethyl)-[5-(5-fluoro-1H-pyrrolo[2,3-b]pyridin-3-ylmethyl)-pyrimidin-2-yl]-amine (P-1630),
(5-Fluoro-pyridin-3-ylmethyl)-[5-(5-fluoro-1H-pyrrolo[2,3-b]pyridin-3-ylmethyl)-pyrimidin-2-yl]-amine (P-1631),
(6-Chloro-pyridin-3-ylmethyl)-[5-(5-fluoro-1H-pyrrolo[2,3-b]pyridin-3-ylmethyl)-pyrimidin-2-yl]-amine (P-1632),
(5-Fluoro-2-methoxy-pyridin-3-ylmethyl)-[5-(5-fluoro-1H-pyrrolo[2,3-b]pyridin-3-ylmethyl)-pyrimidin-2-yl]-amine (P-1633),

[5-(5-Fluoro-1H-pyrrolo[2,3-b]pyridin-3-ylmethyl)-pyrimidin-2-yl]-(4-trifluoromethyl-pyridin-3-ylmethyl)-amine (P-1634),

[5-(5-Fluoro-1H-pyrrolo[2,3-b]pyridin-3-ylmethyl)-pyrimidin-2-yl]-(6-methoxy-pyridin-3-ylmethyl)-amine (P-1635),

[5-(5-Fluoro-1H-pyrrolo[2,3-b]pyridin-3-ylmethyl)-pyrimidin-2-yl]-(6-trifluoromethyl-pyridin-3-ylmethyl)-amine (P-1636),

[5-(5-Fluoro-1H-pyrrolo[2,3-b]pyridin-3-ylmethyl)-pyrimidin-2-yl]-(2-methoxy-pyridin-3-ylmethyl)-amine (P-1637),

[6-Fluoro-5-(4-methyl-7H-pyrrolo[2,3-d]pyrimidin-5-ylmethyl)-pyridin-2-yl]-(5-fluoro-pyridin-3-ylmethyl)-amine (P-1727), (6-Chloro-pyridin-3-ylmethyl)-[6-fluoro-5-(4-methyl-7H-pyrrolo[2,3-d]pyrimidin-5-ylmethyl)-pyridin-2-yl]-amine (P-1728), (5-Fluoro-2-methoxy-pyridin-3-ylmethyl)-[6-fluoro-5-(4-methyl-7H-pyrrolo[2,3-d]pyrimidin-5-ylmethyl)-pyridin-2-yl]-amine (P-1729),

[6-Fluoro-5-(4-methyl-7H-pyrrolo[2,3-d]pyrimidin-5-ylmethyl)-pyridin-2-yl]-(4-trifluoromethyl-pyridin-3-ylmethyl)-amine (P-1730),

[6-Fluoro-5-(4-methyl-7H-pyrrolo[2,3-d]pyrimidin-5-ylmethyl)-pyridin-2-yl]-(6-methoxy-pyridin-3-ylmethyl)-amine (P-1731),

[6-Fluoro-5-(4-methyl-7H-pyrrolo[2,3-d]pyrimidin-5-ylmethyl)-pyridin-2-yl]-(6-trifluoromethyl-pyridin-3-ylmethyl)-amine (P-1732), (5-Fluoro-6-methoxy-pyridin-3-ylmethyl)-[6-fluoro-5-(4-methyl-7H-pyrrolo[2,3-d]pyrimidin-5-ylmethyl)-pyridin-2-yl]-amine (P-1733),

[6-Fluoro-5-(4-methyl-7H-pyrrolo[2,3-d]pyrimidin-5-ylmethyl)-pyridin-2-yl]-(2-methoxy-pyridin-3-ylmethyl)-amine (P-1734), (2-Chloro-benzyl)-[6-fluoro-5-(4-methoxy-1H-pyrrolo[2,3-b]pyridin-3-ylmethyl)-pyridin-2-yl]-amine (P-2035), (2-Chloro-benzyl)-[5-(4-methoxy-1H-pyrrolo[2,3-b]pyridin-3-ylmethyl)-pyridin-2-yl]-amine (P-2036), (4-Chloro-benzyl)-[6-fluoro-5-(4-methoxy-1H-pyrrolo[2,3-b]pyridin-3-ylmethyl)-pyridin-2-yl]-amine (P-2037),

[5-(5-Chloro-1H-pyrrolo[2,3-b]pyridin-3-ylmethyl)-pyrimidin-2-yl]-(6-methoxy-pyridin-3-ylmethyl)-amine (P-2038), (5-Fluoro-6-methoxy-pyridin-3-ylmethyl)-[6-fluoro-5-(5-methoxy-1H-pyrrolo[2,3-b]pyridin-3-ylmethyl)-pyridin-2-yl]-amine (P-2040), (5-Fluoro-2-methoxy-pyridin-3-ylmethyl)-[6-fluoro-5-(5-methoxy-1H-pyrrolo[2,3-b]pyridin-3-ylmethyl)-pyridin-2-yl]-amine (P-2042),

[6-Fluoro-5-(5-methoxy-1H-pyrrolo[2,3-b]pyridin-3-ylmethyl)-pyridin-2-yl]-(2-methoxy-pyridin-3-ylmethyl)-amine (P-2043), (5-Chloro-pyridin-2-ylmethyl)-[6-fluoro-5-(1H-pyrrolo[2,3-b]pyridin-3-ylmethyl)-pyridin-2-yl]-amine (P-2044),

[6-Fluoro-5-(1H-pyrrolo[2,3-b]pyridin-3-ylmethyl)-pyridin-2-yl]-(2-methoxy-pyridin-3-ylmethyl)-amine (P-2045), (5-Chloro-pyridin-2-ylmethyl)-[6-fluoro-5-(5-methyl-1H-pyrrolo[2,3-b]pyridin-3-ylmethyl)-pyridin-2-yl]-amine (P-2047), (5-Fluoro-6-methoxy-pyridin-3-ylmethyl)-[6-fluoro-5-(5-methyl-1H-pyrrolo[2,3-b]pyridin-3-ylmethyl)-pyridin-2-yl]-amine (P-2048), (5-Fluoro-2-methoxy-pyridin-3-ylmethyl)-[6-fluoro-5-(5-methyl-1H-pyrrolo[2,3-b]pyridin-3-ylmethyl)-pyridin-2-yl]-amine (P-2049), (4-Chloro-benzyl)-[6-fluoro-5-(5-methyl-1H-pyrrolo[2,3-b]pyridin-3-ylmethyl)-pyridin-2-yl]-amine (P-2050), (2-Chloro-benzyl)-[6-fluoro-5-(5-methyl-1H-pyrrolo[2,3-b]pyridin-3-ylmethyl)-pyridin-2-yl]-amine (P-2051),

[6-Fluoro-5-(5-methyl-1H-pyrrolo[2,3-b]pyridin-3-ylmethyl)-pyridin-2-yl]-(2-methoxy-pyridin-3-ylmethyl)-amine (P-2052), (6-Methoxy-pyridin-3-ylmethyl)-[5-(5-methyl-1H-pyrrolo[2,3-b]pyridin-3-ylmethyl)-pyrimidin-2-yl]-amine (P-2057),

[6-Fluoro-5-(5-methyl-1H-pyrrolo[2,3-b]pyridin-3-ylmethyl)-pyridin-2-yl]-[(S)-1-(4-fluoro-phenyl)-ethyl]-amine (P-2058), (5-Fluoro-2-methoxy-pyridin-3-ylmethyl)-[5-(5-methyl-1H-pyrrolo[2,3-b]pyridin-3-ylmethyl)-pyrimidin-2-yl]-amine (P-2061),

[6-Fluoro-5-(5-methyl-1H-pyrrolo[2,3-b]pyridin-3-ylmethyl)-pyridin-2-yl]-(4-trifluoromethyl-pyridin-3-ylmethyl)-amine (P-2062),

[5-(5-Chloro-1H-pyrrolo[2,3-b]pyridin-3-ylmethyl)-pyridin-2-yl]-(4-trifluoromethyl-pyridin-3-ylmethyl)-amine (P-2063),

[5-(5-Chloro-1H-pyrrolo[2,3-b]pyridin-3-ylmethyl)-pyrimidin-2-yl]-(5-fluoro-2-methoxy-pyridin-3-ylmethyl)-amine (P-2064),

[6-Fluoro-5-(5-methyl-1H-pyrrolo[2,3-b]pyridin-3-ylmethyl)-pyridin-2-yl]-(2-methoxy-pyridin-4-ylmethyl)-amine (P-2065),

[6-Fluoro-5-(5-methyl-1H-pyrrolo[2,3-b]pyridin-3-ylmethyl)-pyridin-2-yl]-(2-methyl-pyridin-4-ylmethyl)-amine (P-2067),

[5-(5-Methyl-1H-pyrrolo[2,3-b]pyridin-3-ylmethyl)-pyridin-2-yl]-(4-trifluoromethyl-pyridin-3-ylmethyl)-amine (P-2070), (5-Fluoro-2-methoxy-pyridin-4-ylmethyl)-[6-fluoro-5-(5-methyl-1H-pyrrolo[2,3-b]pyridin-3-ylmethyl)-pyridin-2-yl]-amine (P-2071), (5-Fluoro-2-methoxy-pyridin-4-ylmethyl)-[5-(5-methyl-1H-pyrrolo[2,3-b]pyridin-3-ylmethyl)-pyrimidin-2-yl]-amine (P-2072), (5-Fluoro-6-methoxy-pyridin-3-ylmethyl)-[5-(5-methyl-1H-pyrrolo[2,3-b]pyridin-3-ylmethyl)-pyrimidin-2-yl]-amine (P-2073),

[5-(5-Chloro-1H-pyrrolo[2,3-b]pyridin-3-ylmethyl)-6-fluoro-pyridin-2-yl]-(2-methyl-pyridin-4-ylmethyl)-amine (P-2075), (5-Fluoro-2-methoxy-pyridin-4-ylmethyl)-[5-(1H-pyrrolo[2,3-b]pyridin-3-ylmethyl)-pyrimidin-2-yl]-amine (P-2135), (5-Fluoro-2-methoxy-pyridin-4-ylmethyl)-[5-(5-methoxy-1H-pyrrolo[2,3-b]pyridin-3-ylmethyl)-pyrimidin-2-yl]-amine (P-2136),

[3-Methoxy-5-(5-methyl-1H-pyrrolo[2,3-b]pyridin-3-ylmethyl)-pyridin-2-yl]-(6-trifluoromethyl-pyridin-3-ylmethyl)-amine (P-2143),

[5-(5-Chloro-1H-pyrrolo[2,3-b]pyridin-3-ylmethyl)-thiazol-2-yl]-(6-trifluoromethyl-pyridin-3-ylmethyl)-amine (P-2144),

[5-(5-Methyl-1H-pyrrolo[2,3-b]pyridin-3-ylmethyl)-thiazol-2-yl]-(6-trifluoromethyl-pyridin-3-ylmethyl)-amine (P-2145),

[3-Fluoro-5-(5-methyl-1H-pyrrolo[2,3-b]pyridin-3-ylmethyl)-pyridin-2-yl]-(6-trifluoromethyl-pyridin-3-ylmethyl)-amine (P-2146),

[3-Fluoro-5-(5-methoxy-1H-pyrrolo[2,3-b]pyridin-3-ylmethyl)-pyridin-2-yl]-(6-trifluoromethyl-pyridin-3-ylmethyl)-amine (P-2147),
[5-(5-Chloro-1H-pyrrolo[2,3-b]pyridin-3-ylmethyl)-thiazol-2-yl]-(5-fluoro-2-methoxy-pyridin-3-ylmethyl)-amine (P-2152),
(5-Fluoro-2-methoxy-pyridin-3-ylmethyl)-[5-(5-methyl-1H-pyrrolo[2,3-b]pyridin-3-yl)-thiazol-2-yl]-amine (P-2153),
[5-(5-Chloro-1H-pyrrolo[2,3-b]pyridin-3-ylmethyl)-thiazol-2-yl]-(6-methoxy-pyridin-3-ylmethyl)-amine (P-2154),
(6-Methoxy-pyridin-3-ylmethyl)-[5-(5-methyl-1H-pyrrolo[2,3-b]pyridin-3-ylmethyl)-thiazol-2-yl]-amine (P-2155),
3-{[5-(5-Chloro-1H-pyrrolo[2,3-b]pyridin-3-ylmethyl)-pyrimidin-2-ylamino]-methyl}-5-fluoro-1-methyl-1H-pyridin-2-one (P-2157),
[5-(5-Chloro-1H-pyrrolo[2,3-b]pyridin-3-ylmethyl)-thiazol-2-yl]-(2-methoxy-pyridin-3-ylmethyl)-amine (P-2158),
(2-Methoxy-pyridin-3-ylmethyl)-[5-(5-methyl-1H-pyrrolo[2,3-b]pyridin-3-ylmethyl)-thiazol-2-yl]-amine (P-2159),
(6-Methoxy-pyridin-2-ylmethyl)-[5-(5-methyl-1H-pyrrolo[2,3-b]pyridin-3-ylmethyl)-thiazol-2-yl]-amine (P-2162),
[5-(5-Chloro-1H-pyrrolo[2,3-b]pyridin-3-ylmethyl)-thiazol-2-yl]-(6-methoxy-pyridin-2-ylmethyl)-amine (P-2163),
[5-(5-Chloro-1H-pyrrolo[2,3-b]pyridin-3-ylmethyl)-thiazol-2-yl]-(2,6-dimethoxy-pyridin-3-ylmethyl)-amine (P-2164),
[5-(5-Chloro-1H-pyrrolo[2,3-b]pyridin-3-ylmethyl)-6-fluoro-pyridin-2-yl]-(5-fluoro-6-methoxy-pyridin-3-ylmethyl)-amine (P-2165), and
[5-(5-Chloro-1H-pyrrolo[2,3-b]pyridin-3-ylmethyl)-3-fluoro-pyridin-2-yl]-(6-trifluoromethyl-pyridin-3-ylmethyl)-amine (P-2172).

The following table indicates the 1H-pyrrolo[2,3-b]pyridine compound (column 2) and aldehyde compound (column 3) used in step 1 to afford the desired compound (column 4). The compound number is provided in column 1, and the observed mass is in column 5.

| Comp. number | 1H-pyrrolo[2,3-b]pyridine | Aldehyde | Compound structure | MS (ESI) [M + H$^+$]$^+$ |
|---|---|---|---|---|
| P-1499 | | | 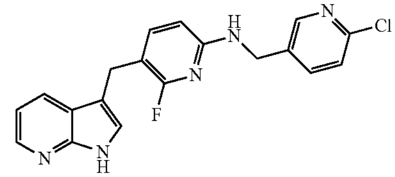 [SMILES: Fc1nc(NCc2ccc(Cl)nc2)ccc1Cc1c[nH]c2ncccc12] | |
| P-1500 | | | 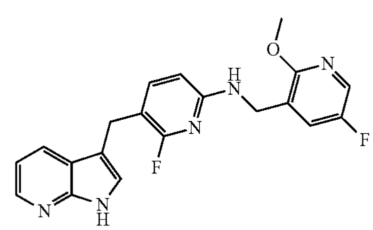 [SMILES: COc1ncc(F)cc1CNc1ccc(Cc2c[nH]c3ncccc23)c(F)n1] | |
| P-1501 | | | 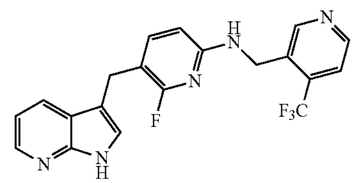 [SMILES: Fc1nc(NCc2cnccc2C(F)(F)F)ccc1Cc1c[nH]c2ncccc12] | |

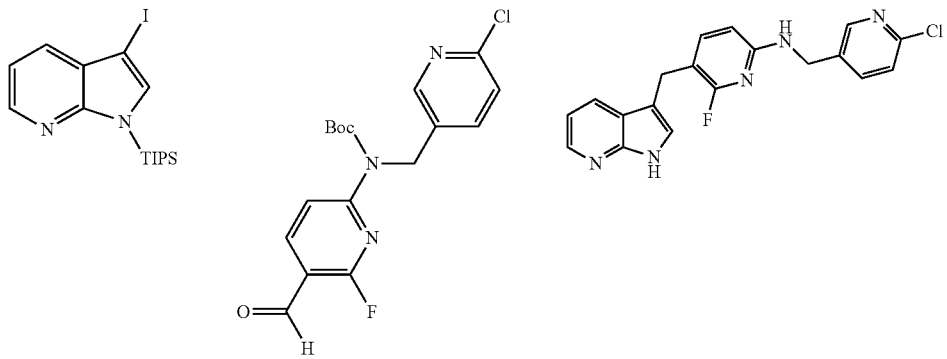

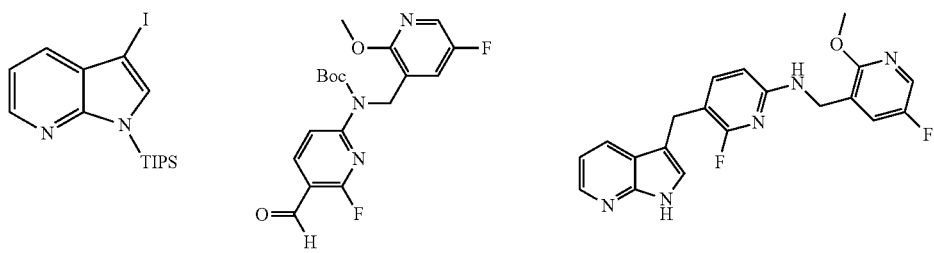

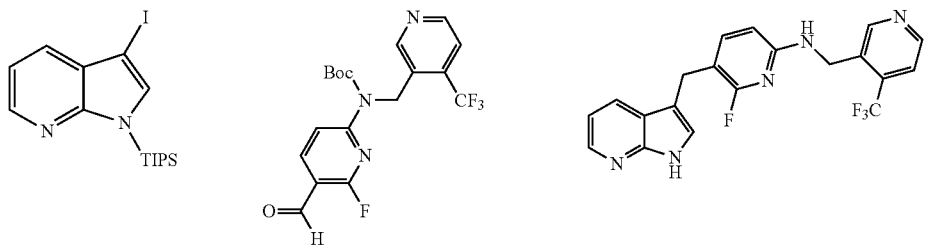

| Comp. number | 1H-pyrrolo[2,3-b]pyridine | Aldehyde | Compound structure | MS (ESI) [M + H⁺]⁺ |
|---|---|---|---|---|
| P-1513 | 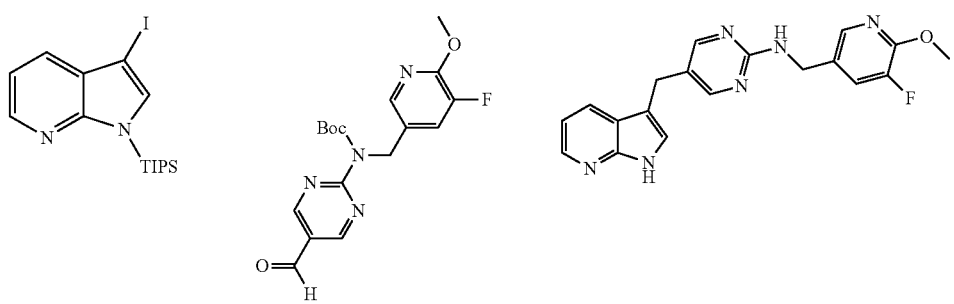 | | 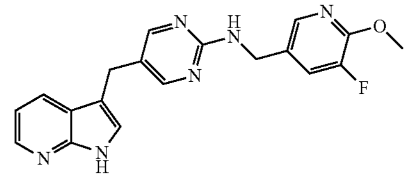 [SMILES: COc1ncc(CNc2ncc(Cc3c[nH]c4ncccc34)cn2)cc1F] | |
| P-1514 | 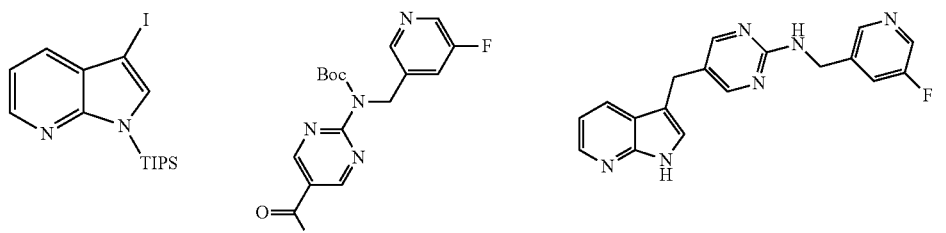 | | 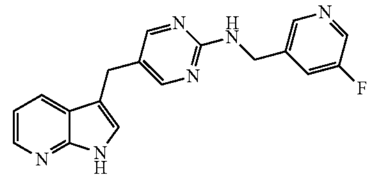 [SMILES: Fc1cncc(CNc2ncc(Cc3c[nH]c4ncccc34)cn2)c1] | |
| P-1515 | 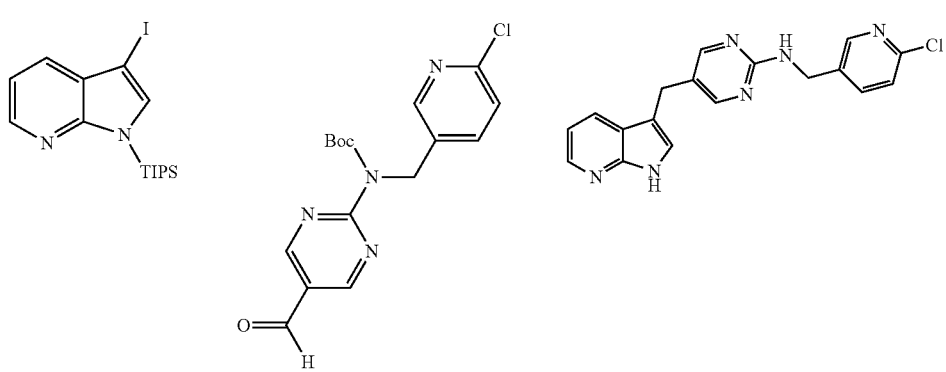 | | 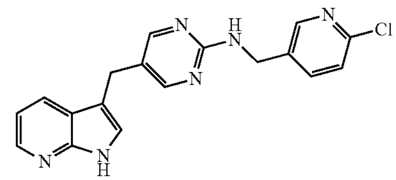 [SMILES: Clc1ccc(CNc2ncc(Cc3c[nH]c4ncccc34)cn2)cn1] | |
| P-1516 | 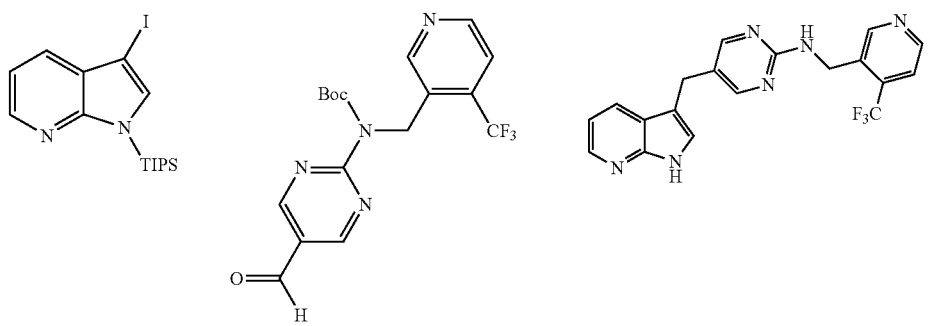 | | 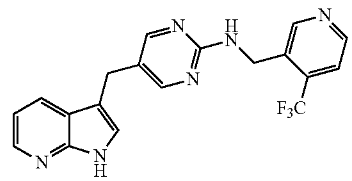 [SMILES: FC(F)(F)c1ccncc1CNc1ncc(Cc2c[nH]c3ncccc23)cn1] | |

| Comp. number | 1H-pyrrolo[2,3-b]pyridine | Aldehyde | Compound structure | MS (ESI) [M + H⁺]⁺ |
|---|---|---|---|---|
| P-1517 | | | 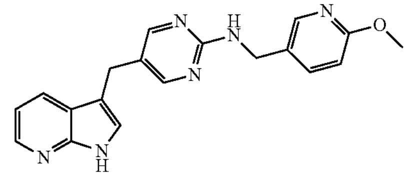 [SMILES: COc1ccc(CNc2ncc(Cc3c[nH]c4ncccc34)cn2)cn1] | |
| P-1518 | | | 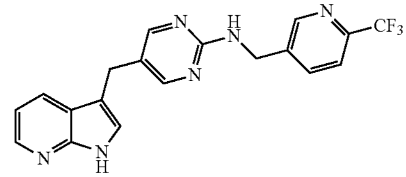 [SMILES: FC(F)(F)c1ccc(CNc2ncc(Cc3c[nH]c4ncccc34)cn2)cn1] | |
| P-1519 | | | 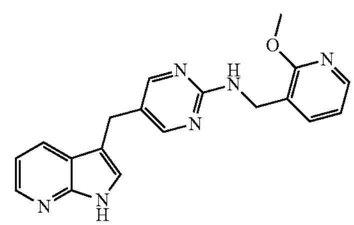 [SMILES: COc1ncccc1CNc1ncc(Cc2c[nH]c3ncccc23)cn1] | |
| P-1520 | | | 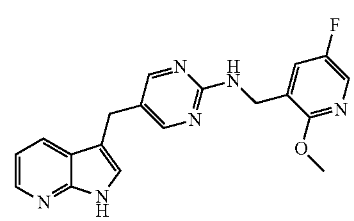 [SMILES: COc1ncc(F)cc1CNc1ncc(Cc2c[nH]c3ncccc23)cn1] | |

-continued

| Comp. number | 1H-pyrrolo[2,3-b]pyridine | Aldehyde | Compound structure | MS (ESI) [M + H+]+ |
|---|---|---|---|---|
| P-1521 | | | 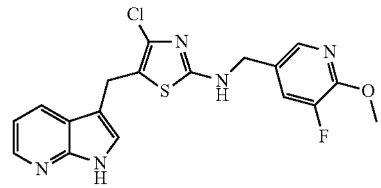 [SMILES: COc1ncc(CNc2nc(Cl)c(Cc3c[nH]c4ncccc34)s2)cc1F] | |
| P-1522 | | | 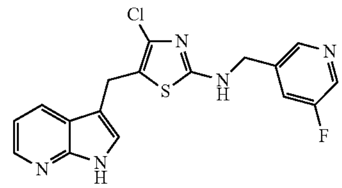 [SMILES: Fc1cncc(CNc2nc(Cl)c(Cc3c[nH]c4ncccc34)s2)c1] | |
| P-1523 | | | 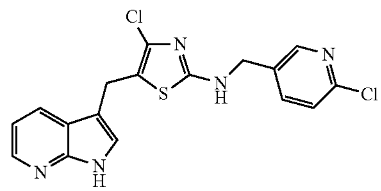 [SMILES: Clc1ccc(CNc2nc(Cl)c(Cc3c[nH]c4ncccc34)s2)cn1] | |
| P-1524 | | | 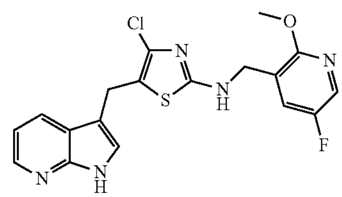 [SMILES: COc1ncc(F)cc1CNc1nc(Cl)c(Cc2c[nH]c3ncccc23)s1] | |
| P-1525 | | | 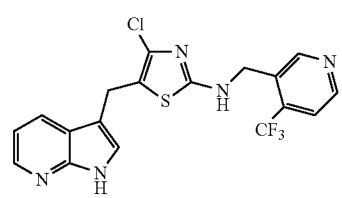 [SMILES: FC(F)(F)c1ccncc1CNc1nc(Cl)c(Cc2c[nH]c3ncccc23)s1] | |
| P-1526 | | | 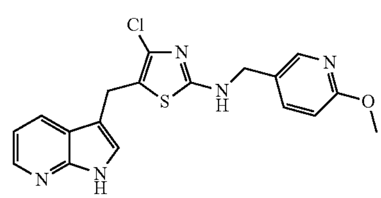 [SMILES: COc1ccc(CNc2nc(Cl)c(Cc3c[nH]c4ncccc34)s2)cn1] | |

-continued

| Comp. number | 1H-pyrrolo[2,3-b]pyridine | Aldehyde | Compound structure | MS (ESI) [M + H+]+ |
|---|---|---|---|---|
| P-1527 | | | 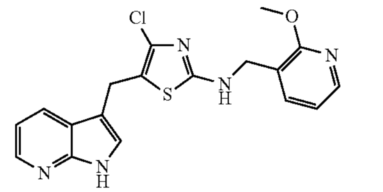 [SMILES: COc1ncccc1CNc1nc(Cl)c(Cc2c[nH]c3ncccc23)s1] | |
| P-1532 | | | 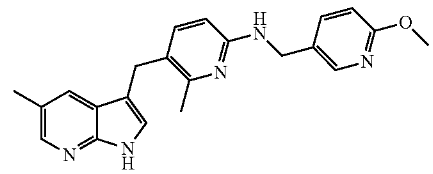 | |
| P-1533 | | | 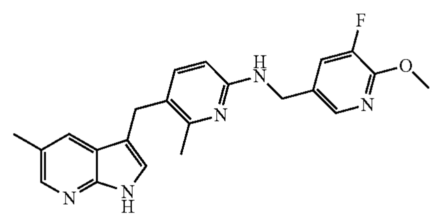 | |
| P-1534 | | | 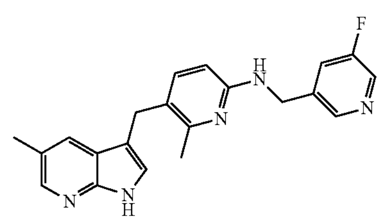 [SMILES: Cc1cnc2[nH]cc(Cc3ccc(NCc4cncc(F)c4)nc3C)c2c1] | |
| P-1535 | | | 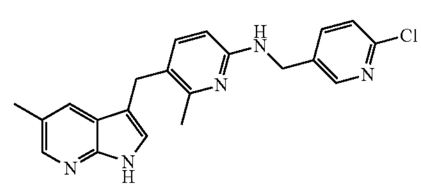 [SMILES: Cc1cnc2[nH]cc(Cc3ccc(NCc4ccc(Cl)nc4)nc3C)c2c1] | |

| Comp. number | 1H-pyrrolo[2,3-b]pyridine | Aldehyde | Compound structure | MS (ESI) [M + H⁺]⁺ |
|---|---|---|---|---|
| P-1536 | 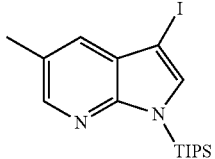 | 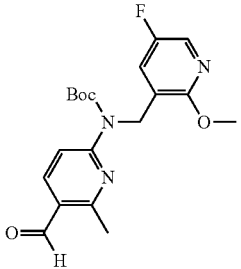 [SMILES: COc1ncc(F)cc1CN(C(=O)OC(C)(C)C)c1ccc(C=O)c(C)n1] | 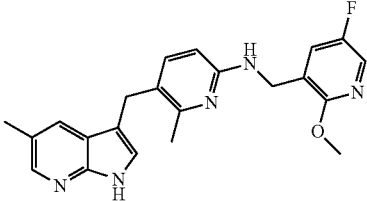 [SMILES: COc1ncc(F)cc1CNc1ccc(Cc2c[nH]c3ncc(C)cc23)c(C)n1] | |
| P-1537 | 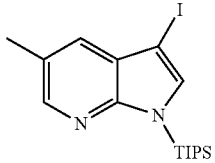 | 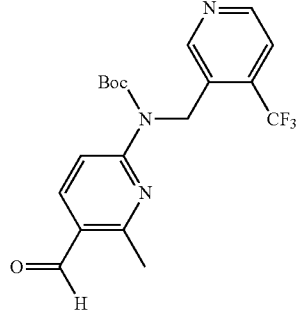 [SMILES: Cc1nc(N(Cc2cnccc2C(F)(F)F)C(=O)OC(C)(C)C)ccc1C=O] | 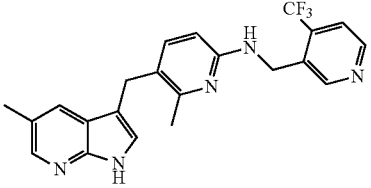 [SMILES: Cc1cnc2[nH]cc(Cc3ccc(NCc4cnccc4C(F)(F)F)nc3C)c2c1] | |
| P-1538 | 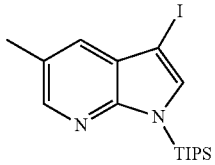 | 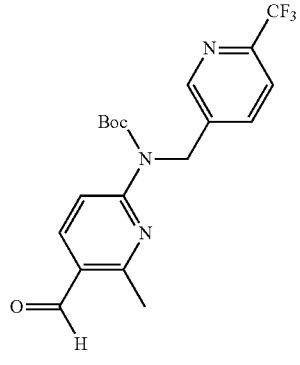 [SMILES: Cc1nc(N(Cc2ccc(C(F)(F)F)nc2)C(=O)OC(C)(C)C)ccc1C=O] | 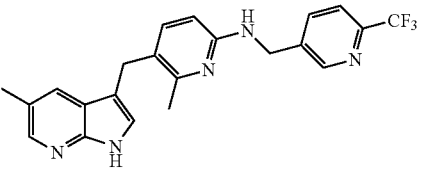 [SMILES: Cc1cnc2[nH]cc(Cc3ccc(NCc4ccc(C(F)(F)F)nc4)nc3C)c2c1] | |
| P-1539 | 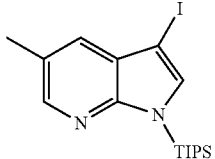 | 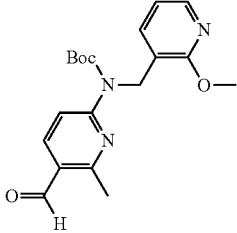 [SMILES: COc1ncccc1CN(C(=O)OC(C)(C)C)c1ccc(C=O)c(C)n1] | 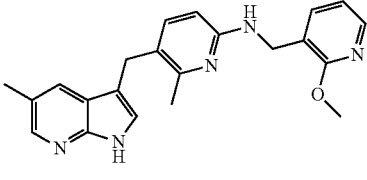 [SMILES: COc1ncccc1CNc1ccc(Cc2c[nH]c3ncc(C)cc23)c(C)n1] | |

-continued

| Comp. number | 1H-pyrrolo[2,3-b]pyridine | Aldehyde | Compound structure | MS (ESI) [M + H⁺]⁺ |
|---|---|---|---|---|
| P-1554 | | | 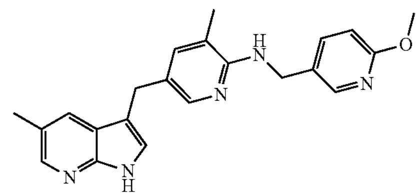 | 374.4 |
| P-1555 | | | 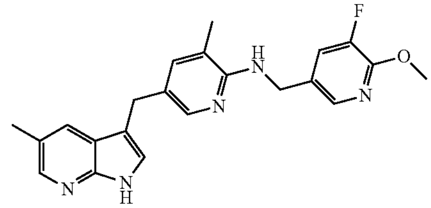 | |
| P-1556 | | | 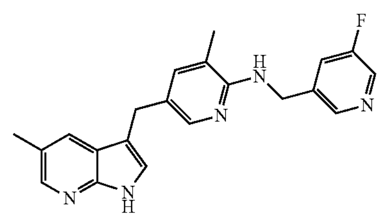 [SMILES: Cc1cnc2[nH]cc(Cc3cnc(NCc4cncc(F)c4)c(C)c3)c2c1] | |
| P-1557 | | | 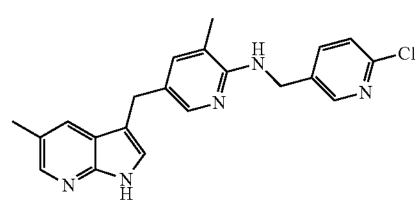 [SMILES: Cc1cnc2[nH]cc(Cc3cnc(NCc4ccc(Cl)nc4)c(C)c3)c2c1] | |

| Comp. number | 1H-pyrrolo[2,3-b]pyridine | Aldehyde | Compound structure | MS (ESI) [M + H+]+ |
|---|---|---|---|---|
| P-1558 | | | 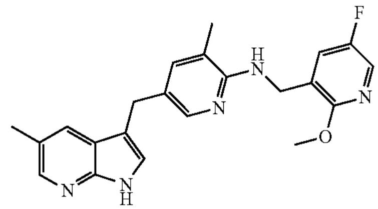 [SMILES: COc1ncc(F)cc1CNc1ncc(Cc2c[nH]c3ncc(C)cc23)cc1C] | |
| P-1559 | | | 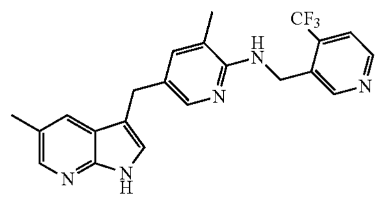 [SMILES: Cc1cnc2[nH]cc(Cc3cnc(NCc4cnccc4C(F)(F)F)c(C)c3)c2c1] | |
| P-1560 | | | 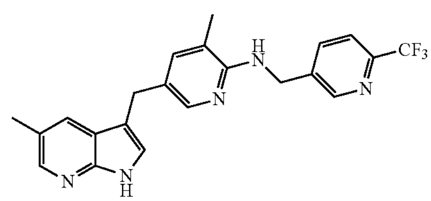 [SMILES: Cc1cnc2[nH]cc(Cc3cnc(NCc4ccc(C(F)(F)F)nc4)c(C)c3)c2c1] | |
| P-1561 | | | 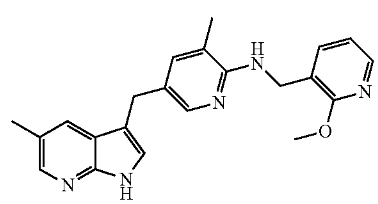 [SMILES: COc1ncccc1CNc1ncc(Cc2c[nH]c3ncc(C)cc23)cc1C] | |

-continued

| Comp. number | 1H-pyrrolo[2,3-b]pyridine | Aldehyde | Compound structure | MS (ESI) [M + H⁺]⁺ |
|---|---|---|---|---|
| P-1562 | | | 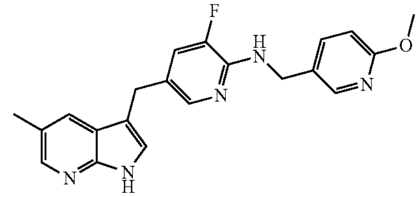 | 378.0 |
| P-1563 | | | 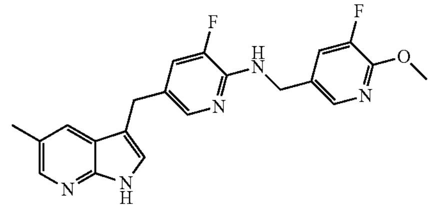 | |
| P-1564 | | | 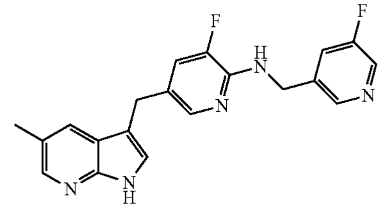 | |
| P-1565 | | | 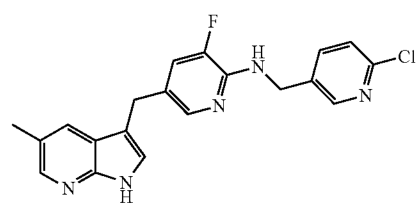 [SMILES: Cc1cnc2[nH]cc(Cc3cnc(NCc4ccc(Cl)nc4)c(F)c3)c2c1] | |

| Comp. number | 1H-pyrrolo[2,3-b]pyridine | Aldehyde | Compound structure | MS (ESI) [M + H+]+ |
|---|---|---|---|---|
| P-1566 | | | 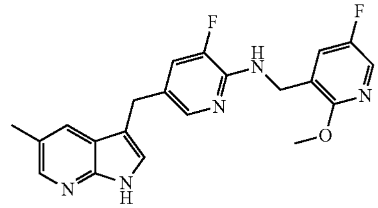 [SMILES: COc1ncc(F)cc1CNc1ncc(Cc2c[nH]c3ncc(C)cc23)cc1F] | |
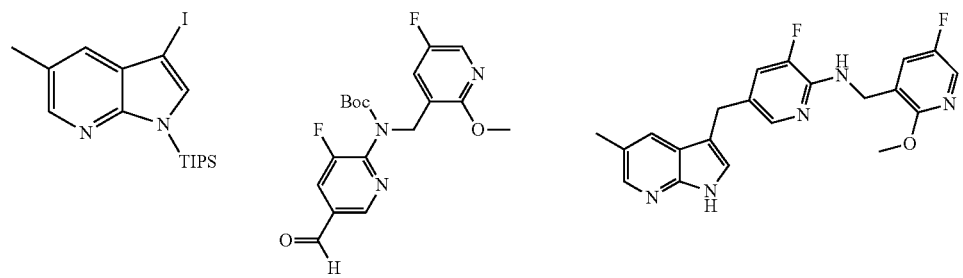
| P-1567 | | | | |
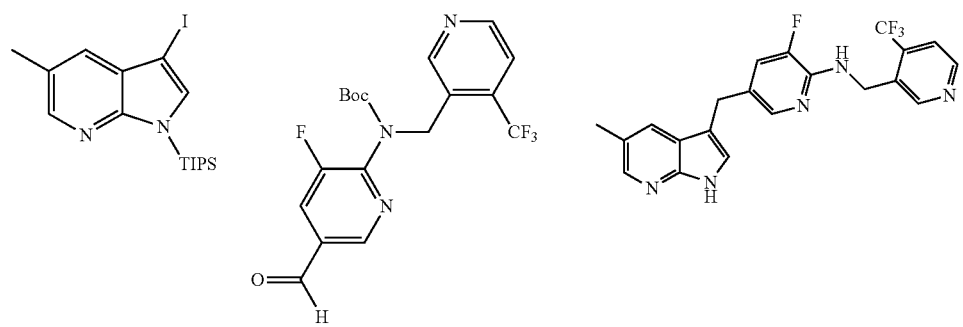
| P-1568 | | | | |
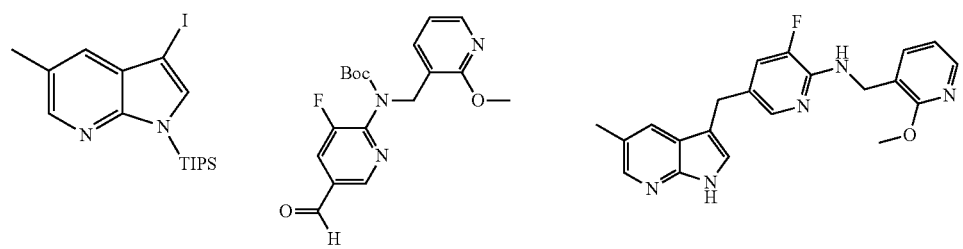
| P-1579 | | | | |
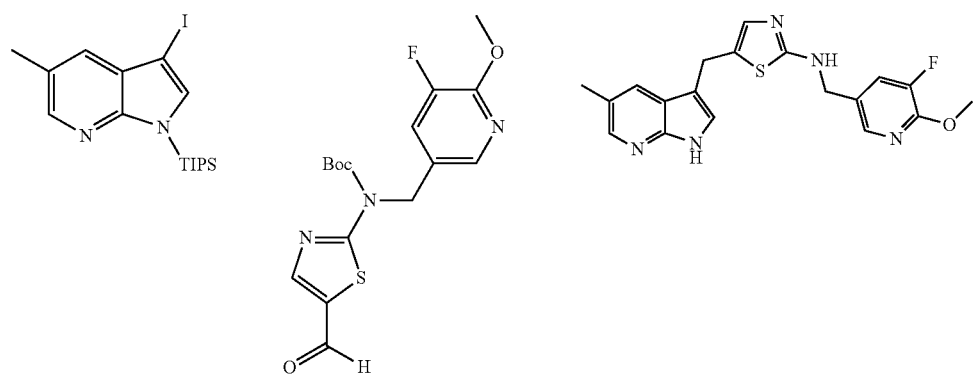

-continued

| Comp. number | 1H-pyrrolo[2,3-b]pyridine | Aldehyde | Compound structure | MS (ESI) [M + H$^+$]$^+$ |
|---|---|---|---|---|
| P-1580 | | | 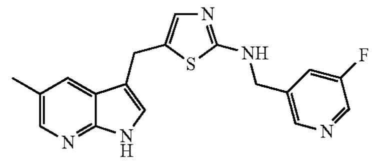 [SMILES: Cc1cnc2[nH]cc(Cc3cnc(NCc4cncc(F)c4)s3)c2c1] | |
| P-1581 | | | 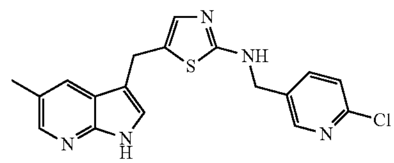 [SMILES: Cc1cnc2[nH]cc(Cc3cnc(NCc4ccc(Cl)nc4)s3)c2c1] | |
| P-1582 | | | 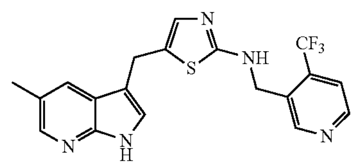 [SMILES: Cc1cnc2[nH]cc(Cc3cnc(NCc4cnccc4C(F)(F)F)s3)c2c1] | |
| P-1597 | | | 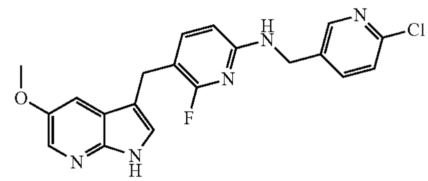 [SMILES: COc1cnc2[nH]cc(Cc3ccc(NCc4ccc(Cl)nc4)nc3F)c2c1] | |

| Comp. number | 1H-pyrrolo[2,3-b]pyridine | Aldehyde | Compound structure | MS (ESI) [M + H+]+ |
|---|---|---|---|---|
| P-1598 | | | 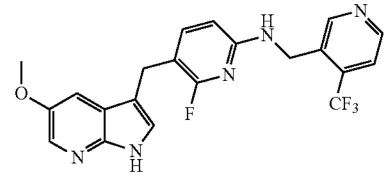 [SMILES: COc1cnc2[nH]cc(Cc3ccc(NCc4cnccc4C(F)(F)F)nc3F)c2c1] | |
| P-1607 | | | 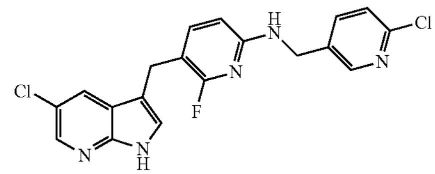 [SMILES: Fc1nc(NCc2ccc(Cl)nc2)ccc1Cc1c[nH]c2ncc(Cl)cc12] | |
| P-1608 | | | 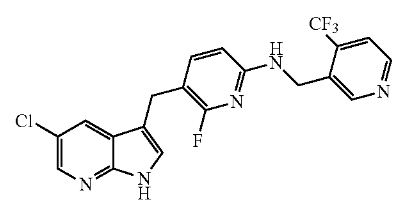 [SMILES: Fc1nc(NCc2cnccc2C(F)(F)F)ccc1Cc1c[nH]c2ncc(Cl)cc12] | |
| P-1609 | | | 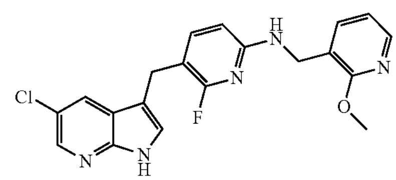 [SMILES: COc1ncccc1CNc1ccc(Cc2c[nH]c3ncc(Cl)cc23)c(F)n1] | |

-continued

| Comp. number | 1H-pyrrolo[2,3-b]pyridine | Aldehyde | Compound structure | MS (ESI) [M + H⁺]⁺ |
| --- | --- | --- | --- | --- |
| P-1630 | | | 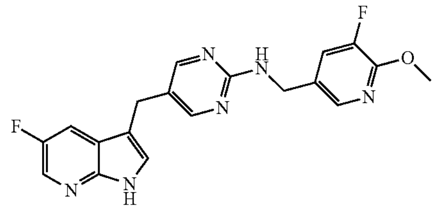 [SMILES: COc1ncc(CNc2ncc(Cc3c[nH]c4ncc(F)cc34)cn2)cc1F] | |
| P-1631 | | | 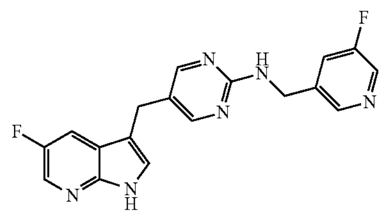 [SMILES: Fc1cncc(CNc2ncc(Cc3c[nH]c4ncc(F)cc34)cn2)c1] | |
| P-1632 | | | 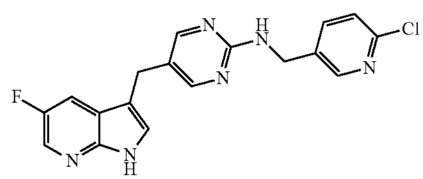 [SMILES: Fc1cnc2[nH]cc(Cc3cnc(NCc4ccc(Cl)nc4)nc3)c2c1] | |
| P-1633 | | | 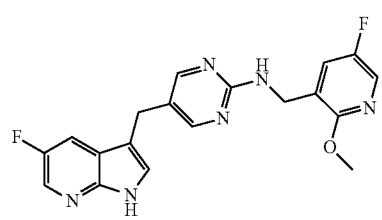 [SMILES: COc1ncc(F)cc1CNc1ncc(Cc2c[nH]c3ncc(F)cc23)cn1] | |
| P-1634 | | | 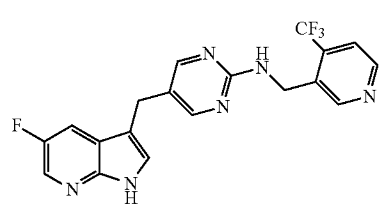 [SMILES: Fc1cnc2[nH]cc(Cc3cnc(NCc4cnccc4C(F)(F)F)nc3)c2c1] | |

| Comp. number | 1H-pyrrolo[2,3-b]pyridine | Aldehyde | Compound structure | MS (ESI) [M + H+]+ |
|---|---|---|---|---|
| P-1635 | | | 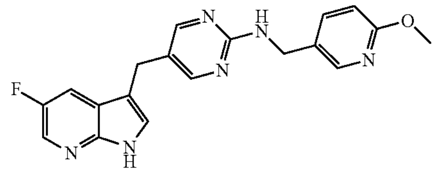 [SMILES: COc1ccc(CNc2ncc(Cc3c[nH]c4ncc(F)cc34)cn2)cn1] | |
| P-1636 | | | 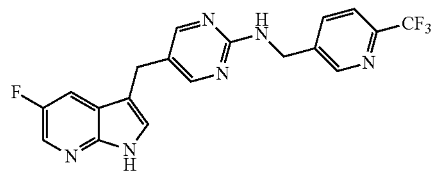 | |
| P-1637 | | | 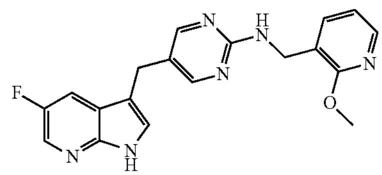 [SMILES: COc1ncccc1CNc1ncc(Cc2c[nH]c3ncc(F)cc23)cn1] | |
| P-1727 | | | 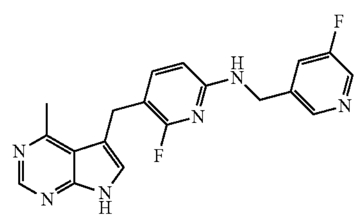 [SMILES: Cc1ncnc2[nH]cc(Cc3ccc(NCc4cncc(F)c4)nc3F)c12] | |
| P-1728 | | | 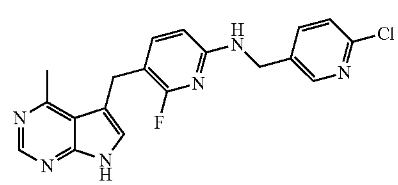 [SMILES: Cc1ncnc2[nH]cc(Cc3ccc(NCc4ccc(Cl)nc4)nc3F)c12] | |

-continued

| Comp. number | 1H-pyrrolo[2,3-b]pyridine | Aldehyde | Compound structure | MS (ESI) [M + H+]+ |
|---|---|---|---|---|
| P-1729 | | | 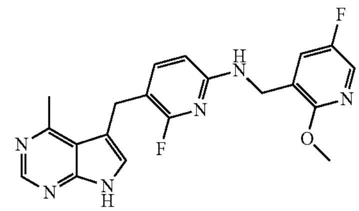 [SMILES: COc1ncc(F)cc1CNc1ccc(Cc2c[nH]c3ncnc(C)c23)c(F)n1] | |
| P-1730 | | | 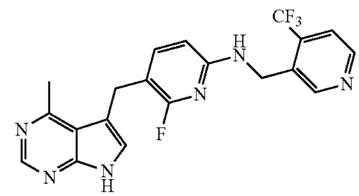 [SMILES: Cc1ncnc2[nH]cc(Cc3ccc(NCc4cnccc4C(F)(F)F)nc3F)c12] | |
| P-1731 | | | 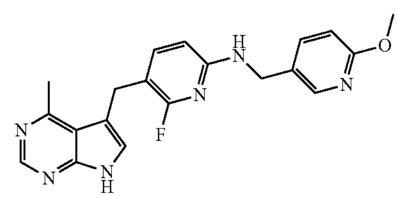 [SMILES: COc1ccc(CNc2ccc(Cc3c[nH]c4ncnc(C)c34)c(F)n2)cn1] | |
| P-1732 | | | 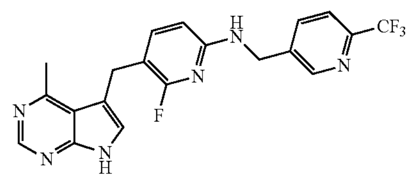 [SMILES: Cc1ncnc2[nH]cc(Cc3ccc(NCc4ccc(C(F)(F)F)nc4)nc3F)c12] | |
| P-1733 | | | 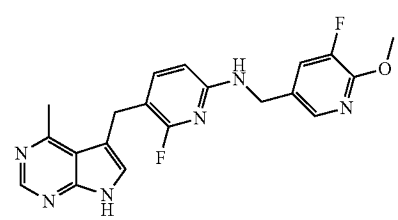 [SMILES: COc1ncc(CNc2ccc(Cc3c[nH]c4ncnc(C)c34)c(F)n2)cc1F] | |
| P-1734 | | | 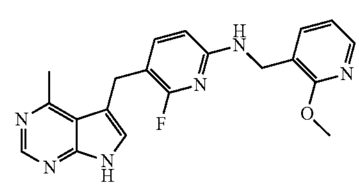 [SMILES: COc1ncccc1CNc1ccc(Cc2c[nH]c3ncnc(C)c23)c(F)n1] | |

-continued
| Comp. number | 1H-pyrrolo[2,3-b]pyridine | Aldehyde | Compound structure | MS (ESI) [M + H+]+ |
|---|---|---|---|---|
| P-2035 | 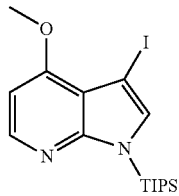 | 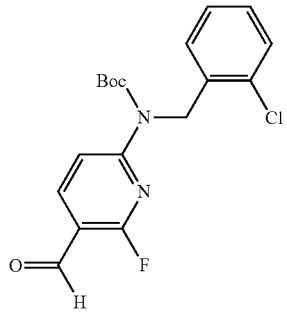 [SMILES: CC(C)(C)OC(=O)N(Cc1ccccc1Cl)c1ccc(C=O)c(F)n1] | 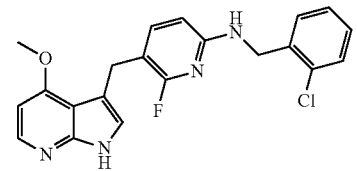 [SMILES: COc1ccnc2[nH]cc(Cc3ccc(NCc4ccccc4Cl)nc3F)c12] | 397.0 |
| P-2036 | 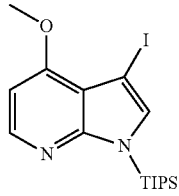 | 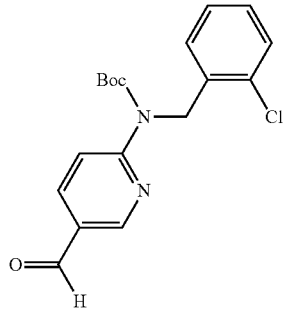 [SMILES: CC(C)(C)OC(=O)N(Cc1ccccc1Cl)c1ccc(C=O)cn1] | 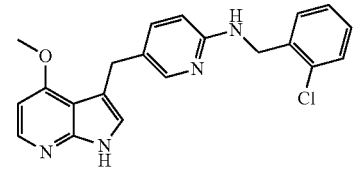 [SMILES: COc1ccnc2[nH]cc(Cc3ccc(NCc4ccccc4Cl)nc3)c12] | 379.1 |
| P-2037 | 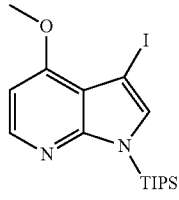 | 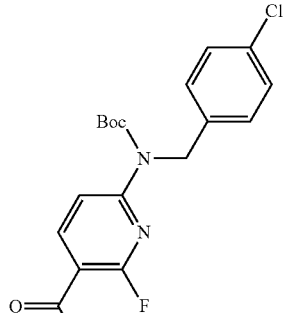 | 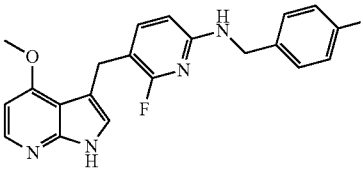 | 397.1 |
| P-2038 | 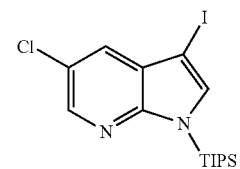 | 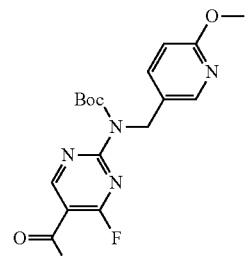 | 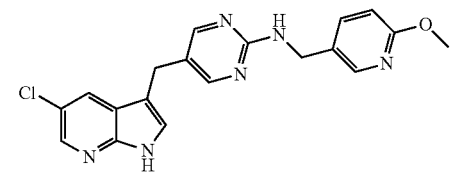 [SMILES: COc1ccc(CNc2ncc(Cc3c[nH]c4ncc(Cl)cc34)cn2)cn1] | 380.8 |

| Comp. number | 1H-pyrrolo[2,3-b]pyridine | Aldehyde | Compound structure | MS (ESI) [M + H+]+ |
|---|---|---|---|---|
| P-2040 | | | 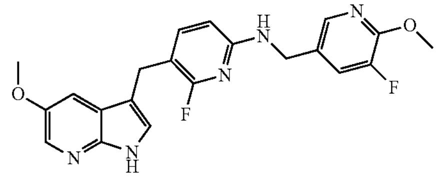 [SMILES: COc1cnc2[nH]cc(Cc3ccc(NCc4cnc(OC)c(F)c4)nc3F)c2c1] | |
| P-2042 | | | 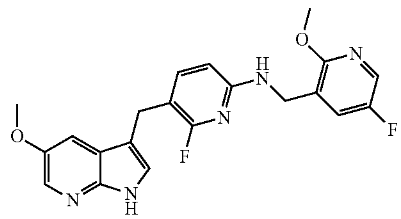 [SMILES: COc1cnc2[nH]cc(Cc3ccc(NCc4cc(F)cnc4OC)nc3F)c2c1] | |
| P-2043 | | | 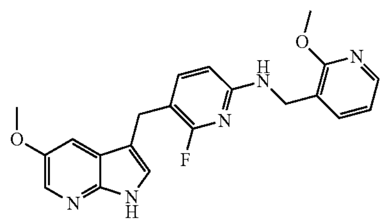 [SMILES: COc1cnc2[nH]cc(Cc3ccc(NCc4cccnc4OC)nc3F)c2c1] | 393.4 |
| P-2044 | | | 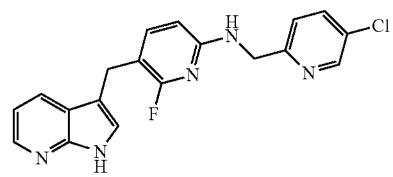 [SMILES: Fc1nc(NCc2ccc(Cl)cn2)ccc1Cc1c[nH]c2ncccc12] | 368.0 |
| P-2045 | | | 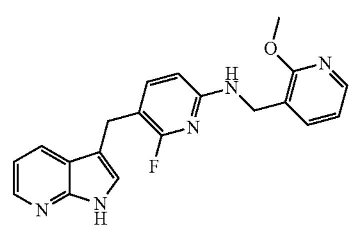 [SMILES: COc1ncccc1CNc1ccc(Cc2c[nH]c3ncccc23)c(F)n1] | 364.0 |

| Comp. number | 1H-pyrrolo[2,3-b]pyridine | Aldehyde | Compound structure | MS (ESI) [M + H+]+ |
|---|---|---|---|---|
| P-2047 | | | 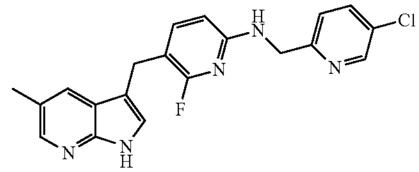 [SMILES: Cc1cnc2[nH]cc(Cc3ccc(NCc4ccc(Cl)cn4)nc3F)c2c1] | |
| P-2048 | | | 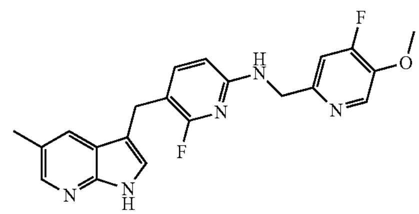 | 396.0 |
| P-2049 | | | 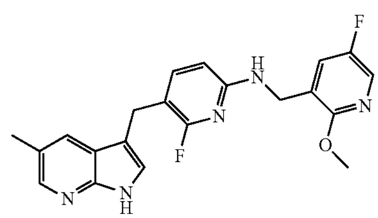 [SMILES: COc1ncc(F)cc1CNc1ccc(Cc2c[nH]c3ncc(C)cc23)c(F)n1] | 396.0 |
| P-2050 | | | 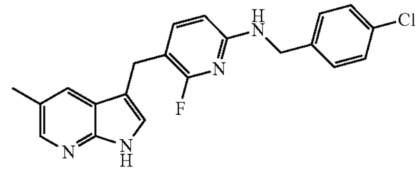 [SMILES: Cc1cnc2[nH]cc(Cc3ccc(NCc4ccc(Cl)cc4)nc3F)c2c1] | |

US 9,096,593 B2

-continued

| Comp. number | 1H-pyrrolo[2,3-b]pyridine | Aldehyde | Compound structure | MS (ESI) [M + H⁺]⁺ |
|---|---|---|---|---|
| P-2051 | | | 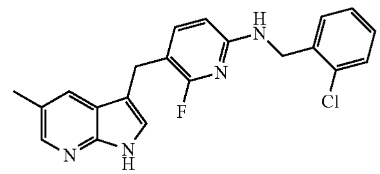 [SMILES: Cc1cnc2[nH]cc(Cc3ccc(NCc4ccccc4Cl)nc3F)c2c1] | |
| P-2052 | | | 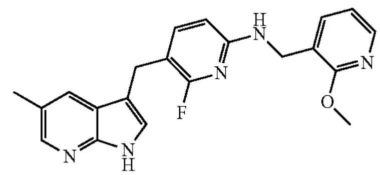 [SMILES: COc1ncccc1CNc1ccc(Cc2c[nH]c3ncc(C)cc23)c(F)n1] | 378.0 |
| P-2057 | | | 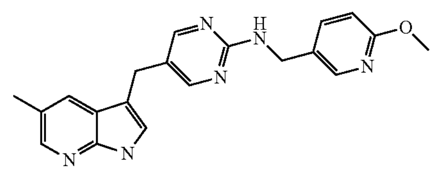 | 360.95 |
| P-2058 | | | 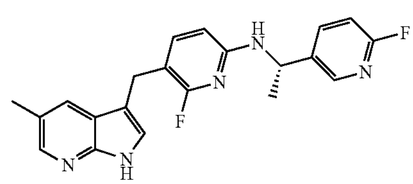 [SMILES: Cc1cnc2[nH]cc(Cc3ccc(N[C@@H](C)c4ccc(F)nc4)nc3F)c2c1] | |

-continued

| Comp. number | 1H-pyrrolo[2,3-b]pyridine | Aldehyde | Compound structure | MS (ESI) [M + H⁺]⁺ |
|---|---|---|---|---|
| P-2061 | | | 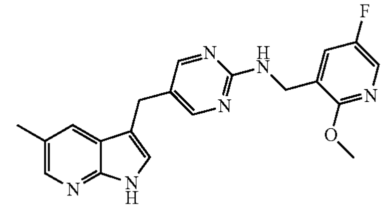 [SMILES: COc1ncc(F)cc1CNc1ncc(Cc2c[nH]c3ncc(C)cc23)cn1] | 379.0 |
| P-2062 | | | 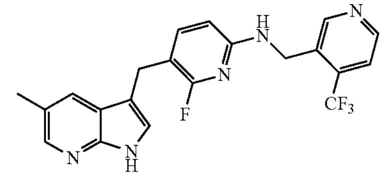 [SMILES: Cc1cnc2[nH]cc(Cc3ccc(NCc4cnccc4C(F)(F)F)nc3F)c2c1] | 416.0 |
| P-2063 | | | 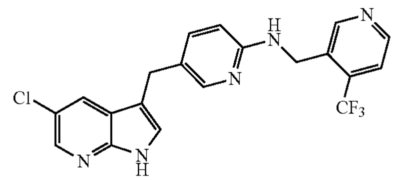 [SMILES: FC(F)(F)c1ccncc1CNc1ccc(Cc2c[nH]c3ncc(Cl)cc23)cn1] | 418.1 |
| P-2064 | | | 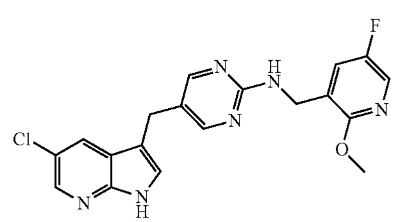 [SMILES: COc1ncc(F)cc1CNc1ncc(Cc2c[nH]c3ncc(Cl)cc23)cn1] | 398.9 |
| P-2065 | | | 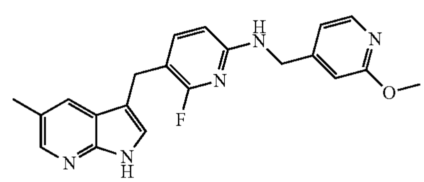 | |

-continued

| Comp. number | 1H-pyrrolo[2,3-b]pyridine | Aldehyde | Compound structure | MS (ESI) [M + H+]+ |
|---|---|---|---|---|
| P-2067 | | | 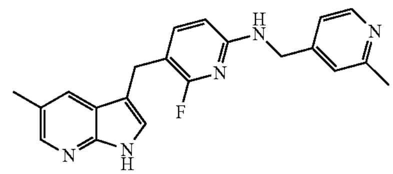 | 361.85 |
| P-2070 | | | 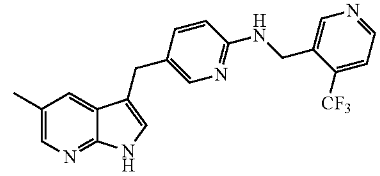 [SMILES: Cc1cnc2[nH]cc(Cc3ccc(NCc4cnccc4C(F)(F)F)nc3)c2c1] | 398.2 |
| P-2071 | | | 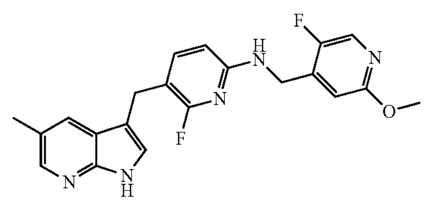 | 396.2 |
| P-2072 | | | 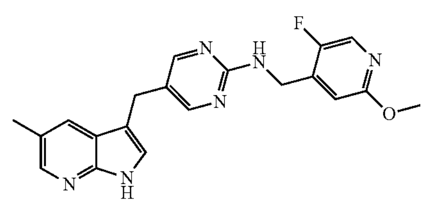 | 379.0 |
| P-2073 | | | 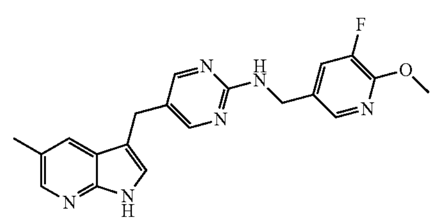 | 379.0 |

-continued

| Comp. number | 1H-pyrrolo[2,3-b]pyridine | Aldehyde | Compound structure | MS (ESI) [M + H$^+$]$^+$ |
|---|---|---|---|---|
| P-2075 | | | 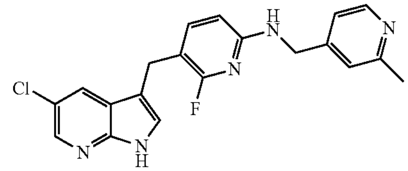 [SMILES: Cc1cc(CNc2ccc(Cc3c[nH]c4ncc(Cl)cc34)c(F)n2)ccn1] | 381.9 |
| P-2135 | | | 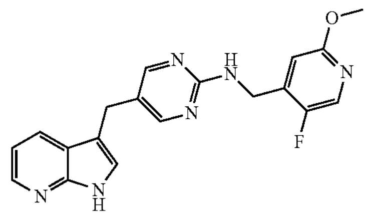 [SMILES: COc1cc(CNc2ncc(Cc3c[nH]c4ncccc34)cn2)c(F)cn1] | 365.3 |
| P-2136 | | | 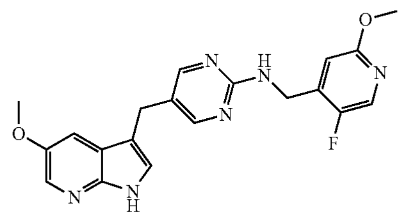 [SMILES: COc1cnc2[nH]cc(Cc3cnc(NCc4cc(OC)ncc4F)nc3)c2c1] | 395.3 |
| P-2143 | | | 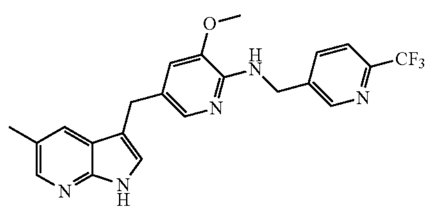 [SMILES: COc1cc(Cc2c[nH]c3ncc(C)cc23)cnc1NCc1ccc(C(F)(F)F)nc1] | |
| P-2144 | | | 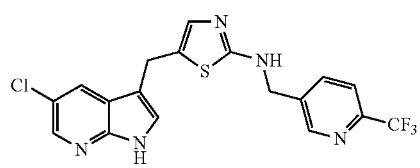 [SMILES: FC(F)(F)c1ccc(CNc2ncc(Cc3c[nH]c4ncc(Cl)cc34)s2)cn1] | |

| Comp. number | 1H-pyrrolo[2,3-b]pyridine | Aldehyde | Compound structure | MS (ESI) [M + H⁺]⁺ |
|---|---|---|---|---|
| P-2145 | | | 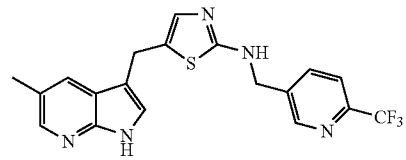 [SMILES: Cc1cnc2[nH]cc(Cc3cnc(NCc4ccc(C(F)(F)F)nc4)s3)c2c1] | |
| P-2146 | | | 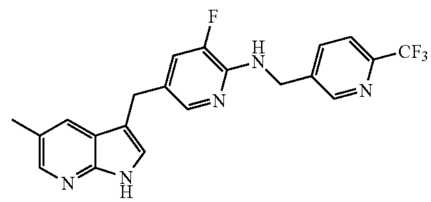 [SMILES: Cc1cnc2[nH]cc(Cc3cnc(NCc4ccc(C(F)(F)F)nc4)c(F)c3)c2c1] | 416.0 |
| P-2147 | | | 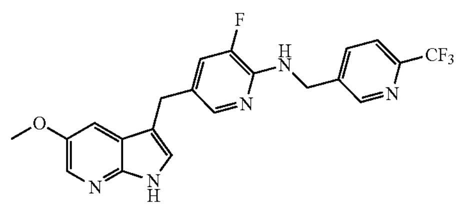 [SMILES: COc1cnc2[nH]cc(Cc3cnc(NCc4ccc(C(F)(F)F)nc4)c(F)c3)c2c1] | 431.9 |
| P-2152 | | | 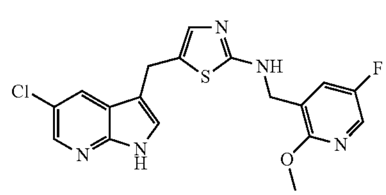 [SMILES: COc1ncc(F)cc1CNc1ncc(Cc2c[nH]c3ncc(Cl)cc23)s1] | |

-continued

| Comp. number | 1H-pyrrolo[2,3-b]pyridine | Aldehyde | Compound structure | MS (ESI) [M + H⁺]⁺ |
|---|---|---|---|---|
| P-2153 | | | 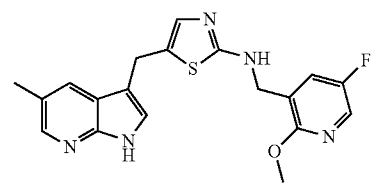 [SMILES: COc1ncc(F)cc1CNc1ncc(Cc2c[nH]c3ncc(C)cc23)s1] | |
| P-2154 | | | 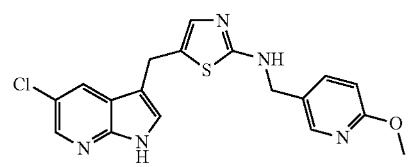 [SMILES: COc1ccc(CNc2ncc(Cc3c[nH]c4ncc(Cl)cc34)s2)cn1] | 385.9 |
| P-2155 | | | 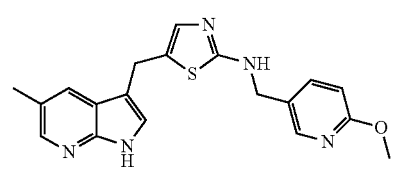 | 365.9 |
| P-2157 | | | 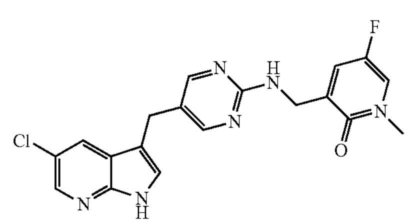 | |

-continued

| Comp. number | 1H-pyrrolo[2,3-b]pyridine | Aldehyde | Compound structure | MS (ESI) [M + H+]+ |
|---|---|---|---|---|
| P-2158 | | | 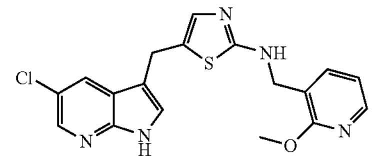 [SMILES: COc1ncccc1CNc1ncc(Cc2c[nH]c3ncc(Cl)cc23)s1] | 385.9 |
| P-2159 | | | 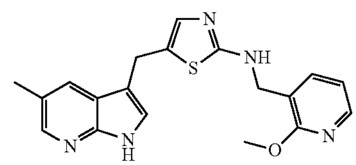 [SMILES: COc1ncccc1CNc1ncc(Cc2c[nH]c3ncc(C)cc23)s1] | 365.9 |
| P-2162 | | | 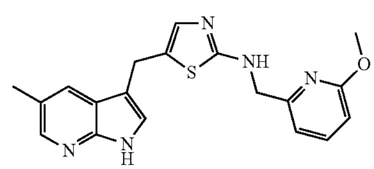 [SMILES: COc1cccc(CNc2ncc(Cc3c[nH]c4ncc(C)cc34)s2)n1] | |
| P-2163 | | | 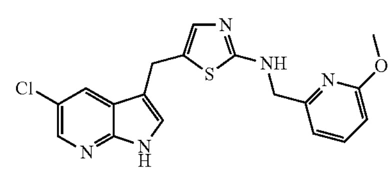 [SMILES: COc1cccc(CNc2ncc(Cc3c[nH]c4ncc(Cl)cc34)s2)n1] | 385.9 |
| P-2164 | | | 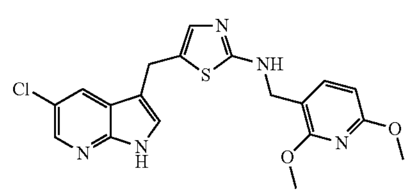 [SMILES: COc1ccc(CNc2ncc(Cc3c[nH]c4ncc(Cl)cc34)s2)c(OC)n1] | 415.9 |

| Comp. number | 1H-pyrrolo[2,3-b]pyridine | Aldehyde | Compound structure | MS (ESI) [M + H⁺]⁺ |
|---|---|---|---|---|
| P-2165 | 5-Cl, 3-I, 1-TIPS 7-azaindole | Boc-N(CH₂-(5-F,6-OMe-pyridin-3-yl))-(6-F-pyridine-3-carbaldehyde) | structure | 416.0 |
| P-2172 | 5-Cl, 3-I, 1-TIPS 7-azaindole | Boc-N(CH₂-(6-CF₃-pyridin-3-yl))-(5-F-pyridine-3-carbaldehyde) | structure | 435.8 |

Example 26

Compound Forms and Formulations

The compounds disclosed herein can be prepared in additional forms, such as polymorphs, salt forms and complexes. Such solid forms can further improve the biopharmaceutical properties, and can be further formulated to enhance biopharmaceutical properties. For example, compounds of the invention form acid addition salts such as hydrochloride or tosylate salts or form a complex with polyprotic acids, such as citric acid, preferably wherein the complex is substantially amorphous. Such an amorphous complex can also be processed with addition of a polymer, such as HPMCAS, that further stabilizes the amorphous form. The process can also include spray drying of the material. Compound is dissolved in 400-500 mL of acetone and added with stirring and heat to 1 equivalent of citric acid dissolved in ethanol. The solution is spray dried to provide the dried complex. Additional material is formulated with addition of the compound/citrate complex to polymer in the same ratio of acetone/ethanol, for example using either HPMCAS or a mixture of Eudragit® L100-55 and Poloxamer 407. In one sample, components are combined in the weight ratios of 40-50% compound, 15-25% citric acid, 25-35% Eudragit® L100-55 and 1-10% Poloxamer 407. In one sample, components are combined in the weight ratios of 40-50% compound, 15-25% citric acid, and 30-40% HPMCAS. The amorphous nature of the resulting complex or formulation of the complex can be determined by X-Ray Powder Diffraction (XRPD), infra-red spectrometry, and differential scanning calorimetry. For example using a ShimadzuXRD-6000X-ray powder diffractometer using Cu Kα radiation. The tube voltage and amperage are set to 40 kV and 40 mA, respectively. The divergence and scattering slits are set at 1° and the receiving slit was set at 0.15 mm. Diffracted radiation is detected by a NaI scintillation detector. A θ-2θ continuous scan at 3°/min (0.4 sec/0.02° step) from 2.5° to 40° 2θ is used. A silicon standard is analyzed to check the instrument alignment. Data are collected and analyzed using XRD-6100/7000 v.5.0. Sample is prepared for analysis by placing it in an aluminum holder with silicon insert. The DSC is used to demonstrate that the complexes lack a characteristic transition and have completely melted before any free base crystalline transition, further supporting that these complexes are amorphous.

Example 27

Compound Properties

While the inhibitory activity of the compounds on any of Fms, Flt-3 and Kit kinase is important to their activity in treating of disease, the compounds described herein show favorable properties that provide advantages as a pharmaceutical as well. In some instances, Fms selectivity relative to Kit and other kinases provides preferred activity for treating certain diseases, such as rheumatoid arthritis, Alzheimer's disease, Parkinson's disease, osteoarthritis, glomerulonephritis, interstitial nephritis, Lupus nephritis, tubular necrosis, diabetic nephropathy, or renal hypertrophy. In some instances, Fms selectivity of compounds in combination with the compounds inability to cross the blood brain barrier provides preferred activity for treating certain diseases, such as osteoarthritis, glomerulonephritis, interstitial nephritis, Lupus nephritis, tubular necrosis, diabetic nephropathy, or renal hypertrophy. In some instances, Fms selectivity of compounds in combination with the compounds ability to effectively cross the blood brain barrier provides preferred activity for treating certain diseases, such as rheumatoid arthritis, Alzheimer's disease, or Parkinson's disease. In some instances, dual Fms/Kit activity provides preferred activity for treating certain diseases, such as metastatic breast cancer, prostate cancer, multiple myeloma, melanoma, acute myeloid leukemia, brain metastases, neurofibromatosis, gastrointestinal stromal tumors, rheumatoid arthritis, or multiple sclerosis. In some instances, dual Fms/Flt-3 activity provides preferred activity for treating certain diseases, such as acute myeloid leukemia. In addition to demonstrating kinase inhibitory activity against Fms, Kit, Flt-3 or at least both Fms and Kit or at least both Fms and Flt-3 in both biochemical and cell based assays, compounds have improved solubility, improved pharmacokinetic properties, and low Cyp inhibition. The compounds are assessed in the following assays or similar assays available to one skilled in the art.

Assays for biochemical and cell based activity are known in the art, for example, U.S. Patent Application Publication Number 2009/0076046, the disclosure of which is hereby incorporated by reference as it relates to such assays. In one assay the biochemical activity $IC_{50}$ values are determined with respect to inhibition of c-Kit kinase activity, where inhibition of phosphorylation of a peptide substrate is measured as a function of compound concentration. Compounds to be tested are dissolved in DMSO to a concentration of 20 mM. These are diluted 30 µL into 120 µL of DMSO (4 mM) and 1 µL is added to an assay plate. These are then serially diluted 1:2 (50 µL to 100 µL DMSO) for a total of 8 points. Plates are prepared such that each kinase reaction is 20 µL in 1× kinase buffer (25 mM HEPES, pH 7.5, 2 mM $MgCl_2$, 2 mM $MnCl_2$, 0.01% Tween-20, 1 mM DTT, 0.01% BSA), 5% DMSO and 100 µM ATP. Substrate is 30 nM biotin-(E4Y)10 (Millipore). C-kit kinase (obtained from Millipore (#14-559) or is prepared as described in U.S. Patent Application Publication Number 2009/0076046, the disclosure of which is hereby incorporated by reference as it relates to this assay) is at 0.75 ng per sample. After incubation of the kinase reaction for 1 hour at room temperature, 5 µL of donor beads (Streptavidin coated beads (Perkin Elmer Life Science) final concentration 10 µg/mL) in stop buffer (25 mM Hepes pH 7.5, 100 mM EDTA, 0.01% BSA) is added, the sample is mixed and incubated for 20 minutes at room temperature before adding 5 µL of acceptor beads (PY20 coated beads (Perkin Elmer Life Science) final concentration 10 µg/mL) in stop buffer. The samples are incubated for 60 minutes at room temperature and the signal per well is read on Envision reader. Phosphorylated substrate results in binding of the PY20 antibody and association of the donor and acceptor beads such that signal correlates with kinase activity. The signal vs. compound concentration is used to determine the $IC_{50}$.

In one assay the biochemical activity $IC_{50}$ values are determined with respect to inhibition of Fms kinase activity, where inhibition of phosphorylation of a peptide substrate is measured as a function of compound concentration. Compounds to be tested, dissolved in DMSO (1 µL), are added to a white 384-well plate (Costar #3705). Working stocks of Fms kinase (Invitrogen #PV3249), biotin-$(E4Y)_{10}$ substrate (Upstate Biotech, Cat#12-440), and ATP (Sigma, Cat#A-3377) are prepared in 25 mM Hepes pH 7.5, 0.5 mM $MgCl_2$, 2 mM $MnCl_2$, 2 mM DTT, 0.01% BSA, and 0.01% Tween-20. All components are added to the 384-well plate for a final concentration of 1 ng/well Fms, 30 nM biotin-$(E4Y)_{10}$ (Upstate Biotechnology) and 100 µM ATP in a volume of 20 µL. Each sample is at 5% DMSO. The plate is then incubated for 20 minutes at 30° C. Just before use, working stocks of donor and acceptor beads from the AlphaScreen PY20 Detection Kit (PerkinElmer, Cat#676601M) are prepared in 25 mM Hepes pH 7.5, pH 7.4, 100 mM EDTA, 0.01% BSA. To stop the reaction, the plate is uncovered in the dark and 5 µL of Donor Beads solution (Streptavidin beads) is added to each well. The plate is incubated at room temperature for 20 minutes. Five microliters of Acceptor Beads solution (PY20 coated beads) are then added to each well. The final concentration of each bead is 10 µg/mL. The plates are incubated at room temperature for 60 minutes. Fluorescence signal is recorded on the Envision reader. Phosphorylated substrate results in binding of the PY20 antibody and association of the donor and acceptor beads such that signal correlates with kinase activity. The signal vs. compound concentration is used to determine the $IC_{50}$.

In one assay the biochemical activity $IC_{50}$ values are determined with respect to inhibition of Flt-3 kinase activity, where inhibition of phosphorylation of a peptide substrate is measured as a function of compound concentration. Compounds to be tested, dissolved in DMSO (1 µL), are added to a white 384-well plate (Costar #3705). Working stocks of Flt-3 kinase (Invitrogen), biotin-$(E4Y)_{10}$ substrate (Upstate Biotech, Cat#12-440), and ATP (Sigma, Cat#A-3377) are prepared in 25 mM Hepes pH 7.5, 5 mM $MgCl_2$, 5 mM $MnCl_2$, 1 mM DTT, and 0.01% Tween-20. All components are added to the 384-well plate for a final concentration of 1 ng/well Flt-3, 30 nM biotin-$(E4Y)_{10}$ and 100 µM ATP in a volume of 20 µL. Each sample is at 5% DMSO. The plate is then incubated for 1 hour at room temperature. Just before use, working stocks of donor and acceptor beads from the AlphaScreen PY20 Detection Kit (PerkinElmer, Cat#676601M) are prepared in 25 mM Hepes pH 7.5, pH 7.4, 100 mM EDTA. 0.3% BSA. To stop the reaction, the plate is uncovered in the dark and 5 µL of Donor Beads solution (Streptavidin beads) is added to each well. The plate is incubated at room temperature for 20 minutes. Five microliters of Acceptor Beads solution (PY20 coated beads) are then added to each well. The final concentration of each bead is 10 µg/mL. The plates are incubated at room temperature for 60 minutes. Fluorescence signal is recorded on the Envision reader. Phosphorylated substrate results in binding of the PY20 antibody and association of the donor and acceptor beads such that signal correlates with kinase activity. The signal vs. compound concentration is used to determine the $IC_{50}$.

Compounds are assessed in a variety of cell based assays. For example BCR-FMS/BaF3, BCR-KIT/BaF3, M-NFS-60, M-07e, and BAC1.2F5 cell proliferation assays are used to assess inhibitory activity of Fms or Kit and MV-4-11 cell proliferation assay is used to assess inhibitory activity in Flt-3. Reagent and assay conditions are as follows:

BCR-FMS/BaF3 and BCR-KIT/BaF3 cells:
  Maintained in RPMI containing 10% FBS, 1% PenStrep, 1% NEAA, and 1% L-Glutamine, supplemented with 1 mg/mL G418 and 5% WEHI-CM (or recombinant murine IL-3).
  Confluent cells are split 1:50 to 1:100 every 3-4 days.
M-NFS-60 cells (ATCC #CRL-1838):
  Maintained in RPMI containing 10% FBS, 1% Hepes, 1% NaPyruvate, and 0.45% Glucose, supplemented with 62 ng/mL murine M-CSF.
  Confluent cells are split 1:20 every 3-4 days.
M-07e cells (DSMZ #ACC 104):
  Maintained in IMDM containing 10% FBS, supplemented with either 200 ng/mL human SCF or 75 ng/L SCF (R&D Systems 255-SC).
  Confluent cells are split 1:5 to 1:10 every 3-4 days.

BAC1.2F5 cells:
Maintained in Alpha-MEM containing 10% Newborn Calf Serum (Invitrogen #26010-074) supplemented with 36 ng/mL murine M-CSF.
Confluent cells are split 1:4 every 3-4 days.
MV-4-11 cells:
Maintained in Iscove's Modified Dulbecco's Medium containing 10% FBS.
Confluent cells are split 1:4 every 3-4 days.

On day 1, cells are counted, then centrifuged in a conical tube for 5 minutes at 1000 rpm. The supernatant is removed and cells are re-suspended as follows:

BCR-FMS/BaF3 and BCR-KIT/BaF3: resuspend in growth media+1 mg/mL G418 (without WEHI/IL-3) to $2 \times 10^5$ cells/mL.
M-NFS-60: resuspend in growth media +62 ng/mL murine M-CSF to $5 \times 10^5$ cells/mL.
M-07e: resuspend in growth media +200 ng/mL human SCF to $5 \times 10^5$ cells/mL.
BAC1.2F5: resuspend in growth media +36 ng/mL murine M-CSF to $1.4 \times 10^5$ cells/mL.
MV-4-11: resuspend in growth media +10% FBS to $5 \times 10^5$ cells/mL.

The cells are plated (50 μL) in each well of a 96-well dish (Corning 3610) and incubated at 37° C. in 5% $CO_2$ overnight, cells plated to a final concentration of cells as follows:

BCR-FMS/BaF3 and BCR-KIT/BaF3: 10,000 cells per well.
M-NFS-60: 25,000 cells per well.
M-07e: 25,000 cells per well.
BAC1.2F5: 7,000 cells per well.
MV-4-11: 25,000 cells per well.

On day 2, compound at a maximum concentration of 5 mM is serially diluted 1:3 for a total of 8 point titration with DMSO as a control. A 1 μL aliquot of each dilution point is added to 249 μL growth media and 50 μL is added to a well containing cells, providing 10 μM compound for the maximum concentration point. The cells are incubated for 3 days at 37° C. in 5% $CO_2$.

On day 5, ATPlite 1 step Luminescence Assay System (Perkin Elmer #6016739) is brought to room temperature along with the cell cultures. ATPlite is added to each well as follows:

BCR-FMS/BaF3 and BCR-KIT/BaF3: 25 μL per well.
M-NFS-60: 25 μL per well.
M-07c: 40 μL per well.
BAC1.2F5: 50 μL per well.
MV-4-11: 40 μL per well.

The cells are incubated at room temperature for 10 minutes, then luminescence is read on Safire reader. The measured luminescence correlates directly with cell number, such that the reading as a function of compound concentration is used to determine the $IC_{50}$ value.

Further, an osteoclast differentiation assay is used to assess the efficacy of Fms inhibitors for treating bone disease such as osteoarthritis. On day 0, Osteoclast Medium BulletKit (Lonza catalog #PT-8001, containing Media, FBS, L-Glutamine, PenStrep, RANKL, and M-CSF) media is thawed and the FBS, L-glutamine and PenStrep from the kit is added to 100 mL of Osteoclast Precursor Basal medium to provide the Osteoclast Precursor Growth Medium (OPGM). This is warmed to 37° C. Osteoclast precursor cells (Lonza catalog #2T-110) frozen in cryovial are warmed to 37° C. and transferred to a 50 mL conical tube. The cryovial is rinsed with OPGM and added dropwise to the conical tube of cells with swirling, then the volume is adjusted to 20-30 mL with addition of OPGM. The cells are centrifuged at 200×g for 15 minutes at room temperature and all but approximately 3 mL of supernatant is removed to a new conical tube. The cells are suspended in the remaining supernatant and the volume is adjusted to 10-15 mL with OPGM added dropwise with swirling. The cells are centrifuged at 200×g for 15 minutes at room temperature and all but approximately 1 mL of supernatant is removed. The cells are resuspended in the remaining supernatant, counted, and the volume adjusted with an appropriate amount of OPGM to provide approximately $1 \times 10^5$ cells/mL. A 0.1 mL aliquot of cells is added to each well of a 96-well plate. Compound to be tested is prepared in DMSO for plating at a high concentration of 2.5 mM, with 8 point 1:3 serial dilutions. A 1 μL aliquot of each compound dilution is added to a 96 well v-bottom polypropylene plate and 0.124 mL of OPGM is added to the compound. Then 50 μL of the compound in OPGM is added to the osteoclast precursor cells in 96-well plate (providing highest test concentration of 5 μM). RANKL (2 μg) from the BulletKit is reconstituted in 1 mL of OPGM, then vortexed and centrifuged briefly. A 792 μL aliquot of RANKL is added to 6 mL of OPGM and 50 μL is added to low control wells. Then 76.6 μL M-CSF (10 μg/mL) from the BulletKit is added to the remaining 5.8 mL of OPGM/RANKL solution (4×RANKL/M-CSF/OPGM). A 50 μL aliquot of this is added to the remaining wells, and the remainder is stored at 4° C. for later use. The plate is incubated at 37° C. for 6 days, then the remaining OPGM/RANKL/M-CSF solution is warmed to 37° C. The remaining approximately 198 μL is combined with 6 mL of OPGM. The media is aspirated from the ostcoclast wells and 100 μL of RANKL/OPGM is added to the low controls. The remaining RANKL/OPGM is combined with the approximately 18.5 μL of remaining M-CSF. The remaining 4×RANKL/M-CSF/OPGM from day 0 is diluted to 1× and combined with the freshly prepared solution. A 0.1 mL aliquot of this is added to each osteoclast well and incubated for 37° C. for 1 day. The Acid Phosphatase kit (Cayman Chemical catalog #10008051) is warmed to room temperature. The assay buffer is diluted 5 mL with 45 mL of water. For each plate, two substrate tablets are dissolved in 4.5 mL of the assay buffer, mixing by vortex to break up the tablet. Stop solution is diluted 12 mL with 36 mL of water. In a tissue culture hood, 20 μL of each osteoclast well supernatant is transferred to a 96 well plate. A 30 μL aliquot of the substrate solution is added to each well and incubated at 37° C. for 20 minutes, then added 100 μL stop solution to each well. The absorbance of each well is read at 405 nM on Safire plate reader. The absorbance reading is plotted vs. concentration to provide the $IC_{50}$ for each compound.

The following table indicates the Fms and Kit biochemical inhibitory activity and selectivity (Kit $IC_{50}$/FmsIC$_{50}$) and the BCR-FMS/BaF3 and BCR-KIT/BaF3 cell based inhibitory activity selectivity (Kit $IC_{50}$/FmsIC$_{50}$) for exemplary compounds according to the invention as indicated

| Compound number | Biochemical activity ($IC_{50}$ μM) | | | BCR/BaF3 ($IC_{50}$ μM) | | |
|---|---|---|---|---|---|---|
| | Fms | Kit | selectivity | Fms | Kit | selectivity |
| P-1496 | <0.1 | | | <0.1 | >0.1 | >20 |
| P-1554 | <0.1 | <0.1 | <20 | <0.1 | >0.1 | <20 |
| P-1562 | <0.1 | <0.1 | <20 | <0.1 | >0.1 | <20 |
| P-1622 | <0.1 | >0.1 | >20 | <0.1 | >0.1 | >20 |
| P-1669 | | | | <0.1 | >0.1 | >20 |
| P-1679 | <0.1 | >0.1 | >20 | <0.1 | >0.1 | >20 |
| P-2001 | <0.1 | >0.1 | >20 | <0.1 | >0.1 | >20 |
| P-2003 | <0.1 | <0.1 | <20 | <0.1 | <0.1 | <20 |
| P-2004 | <0.1 | <0.1 | <20 | <0.1 | <0.1 | <20 |
| P-2008 | <0.1 | <0.1 | <20 | <0.1 | >0.1 | <20 |
| P-2013 | <0.1 | <0.1 | <20 | <0.1 | >0.1 | <20 |

-continued

| Compound | Biochemical activity (IC$_{50}$ µM) | | | BCR/BaF3 (IC$_{50}$ µM) | | |
|---|---|---|---|---|---|---|
| number | Fms | Kit | selectivity | Fms | Kit | selectivity |
| P-2019 | <0.1 | <0.1 | <20 | <0.1 | <0.1 | <20 |
| P-2028 | <0.1 | >0.1 | >20 | <0.1 | >0.1 | >20 |
| P-2029 | <0.1 | >0.1 | >20 | <0.1 | >0.1 | >20 |
| P-2030 | <0.1 | >0.1 | >20 | <0.1 | >0.1 | >20 |
| P-2031 | <0.1 | >0.1 | <20 | <0.1 | >0.1 | >20 |
| P-2032 | <0.1 | <0.1 | <20 | <0.1 | <0.1 | <20 |
| P-2037 | <0.1 | >0.1 | <20 | <0.1 | >0.1 | <20 |
| P-2038 | <0.1 | >0.1 | >20 | <0.1 | >0.1 | >20 |
| P-2043 | <0.1 | >0.1 | >20 | <0.1 | >0.1 | >20 |
| P-2045 | <0.1 | >0.1 | >20 | <0.1 | >0.1 | >20 |
| P-2048 | <0.1 | >0.1 | >20 | <0.1 | >0.1 | >20 |
| P-2049 | <0.1 | >0.1 | >20 | <0.1 | >0.1 | >20 |
| P-2052 | <0.1 | >0.1 | >20 | <0.1 | >0.1 | >20 |
| P-2057 | <0.1 | >0.1 | >20 | <0.1 | >0.1 | >20 |
| P-2061 | <0.1 | >0.1 | >20 | <0.1 | >0.1 | >20 |
| P-2062 | <0.1 | >0.1 | >20 | <0.1 | >0.1 | >20 |
| P-2063 | <0.1 | <0.1 | <20 | <0.1 | >0.1 | >20 |
| P-2064 | <0.1 | >0.1 | >20 | <0.1 | >0.1 | >20 |
| P-2067 | <0.1 | >0.1 | >20 | | | |
| P-2070 | <0.1 | <0.1 | <20 | <0.1 | >0.1 | >20 |
| P-2071 | <0.1 | >0.1 | >20 | >0.1 | >0.1 | >20 |
| P-2073 | <0.1 | >0.1 | >20 | <0.1 | >0.1 | >20 |
| P-2075 | <0.1 | >0.1 | >20 | | | |
| P-2078 | <0.1 | <0.1 | <20 | <0.1 | >0.1 | >20 |
| P-2079 | <0.1 | <0.1 | <20 | <0.1 | >0.1 | <20 |
| P-2081 | <0.1 | <0.1 | <20 | >0.1 | >0.1 | <20 |
| P-2082 | <0.1 | <0.1 | <20 | <0.1 | <0.1 | <20 |
| P-2088 | <0.1 | >0.1 | >20 | <0.1 | >0.1 | <20 |
| P-2097 | <0.1 | >0.1 | >20 | <0.1 | >0.1 | >20 |
| P-2103 | <0.1 | >0.1 | >20 | <0.1 | >0.1 | <20 |
| P-2118 | <0.1 | >0.1 | >20 | <0.1 | >0.1 | >20 |
| P-2131 | <0.1 | >0.1 | >20 | <0.1 | >0.1 | <20 |
| P-2139 | <0.1 | >0.1 | >20 | >0.1 | >0.1 | <20 |
| P-2146 | <0.1 | <0.1 | <20 | <0.1 | <0.1 | <20 |
| P-2147 | <0.1 | <0.1 | <20 | <0.1 | <0.1 | <20 |
| P-2148 | <0.1 | <0.1 | <20 | <0.1 | <0.1 | <20 |
| P-2154 | <0.1 | <0.1 | <20 | <0.1 | <0.1 | <20 |
| P-2157 | >0.1 | >0.1 | <20 | <0.1 | <0.1 | <20 |
| P-2163 | <0.1 | >0.1 | >20 | <0.1 | >0.1 | <20 |
| P-2165 | <0.1 | >0.1 | >20 | <0.1 | >0.1 | <20 |
| P-2172 | <0.1 | >0.1 | >20 | <0.1 | <0.1 | <20 |
| P-2176 | <0.1 | >0.1 | >20 | <0.1 | >0.1 | <20 |
| P-2193 | <0.1 | >0.1 | >20 | <0.1 | >0.1 | >20 |
| P-2198 | <0.1 | >0.1 | <20 | <0.1 | >0.1 | <20 |
| P-2202 | <0.1 | >0.1 | <20 | <0.1 | >0.1 | <20 |

The following table indicates the Fms and Flt-3 biochemical inhibitory activity and the BCR-FMS/BaF3 and MV-4-11 cell based inhibitory activity for exemplary compounds according to the invention that are approximately equipotent inhibitors of Fms/Flt-3 as indicated:

| Compound | Biochemical (IC$_{50}$ µM) | | Cell based (IC$_{50}$ µM) | |
|---|---|---|---|---|
| number | Fms | Flt-3 | BCR/BaF3 (Fms) | MV-4-11 (Flt-3) |
| P-1644 | <0.1 | <0.1 | <0.1 | |
| P-1646 | <0.1 | <0.1 | <0.1 | |
| P-2003 | <0.1 | <0.1 | <0.1 | >0.1 |
| P-2004 | <0.1 | <0.1 | <0.1 | |
| P-2009 | <0.1 | <0.1 | <0.1 | |
| P-2019 | <0.1 | <0.1 | <0.1 | |
| P-2029 | <0.1 | <0.1 | <0.1 | <0.1 |
| P-2030 | <0.1 | <0.1 | <0.1 | <0.1 |
| P-2031 | <0.1 | <0.1 | <0.1 | <0.1 |
| P-2032 | <0.1 | <0.1 | <0.1 | <0.1 |
| P-2034 | <0.1 | <0.1 | <0.1 | >0.1 |
| P-2037 | <0.1 | <0.1 | <0.1 | >0.1 |
| P-2038 | <0.1 | <0.1 | <0.1 | <0.1 |
| P-2044 | <0.1 | >0.1 | <0.1 | <0.1 |
| P-2048 | <0.1 | <0.1 | <0.1 | >0.1 |
| P-2057 | <0.1 | <0.1 | <0.1 | <0.1 |
| P-2165 | <0.1 | <0.1 | <0.1 | >0.1 |

Compounds P-1554, P-2001, P-2003, P-2004, P-2019, P-2028, P-2029, P-2030, P-2031, P-2032, P-2037, P-2038, P-2045, P-2048, P-2049, P-2052, P-2057, P-2061, P-2063, P-2064, P-2070, P-2146, P-2147, P-2157, P-2165, P-2176, and P-2193 demonstrated an IC$_{50}$ below 0.1 µM in the osteoclast differentiation assay.

As an indication of relative solubility, the turbidity of compounds in aqueous solutions is assessed. To assess possible compound properties in different physiological compartments, such as stomach, intestine, and blood, a series of aqueous buffers with varying pH is used. Thus each compound is diluted into four different physiologically relevant buffers and solution turbidity is measured by spectrophotometry. The concentration of compound that demonstrates turbidity by forming enough insoluble suspension to raise the average optical density above 0.01 at three wavelengths (490, 535, and 650 nm) is used to define the limit of the compound solubility in that buffer.

Compounds are dissolved at a concentration of 25 mM in dimethyl sulfoxide, then serially diluted 1:1 into a 96 well plate, diluting 10 times in pure dimethyl sulfoxide, with the final well of each row a dimethyl sulfoxide blank. In an assay plate, 99 µL of appropriate buffer is added to each well, and 1 µL of each sample dilution is added to the buffer, achieving a range of final total concentrations in aqueous solutions having different pH. The buffers used are Simulated Gastric Fluid (SGF-pH 1.5) 0.5M NaCl, pH 1.5; Simulated Intestinal fluid (SIF-pH 4.5 and pH 6.8) 0.05M NaH$_2$PO$_4$, pH 4.5 and 6.8; and Hepes Buffer (HEPES-pH 7.4) 10 mM HEPES, 150 mM NaCl, pH 7.4. Control compounds pyrene, estriol and propranolol HCl are also assessed. Plates are spun and then mixed for 1 minute, and the absorbance is read using a Tecan Safire II to read wavelengths in the visible range (490, 535, and 650 nm) at four locations per well, reflecting the degree of turbidity present. The average optical density for each wavelength in each well is graphed vs. compound concentration, and the concentration at which the curve crosses a threshold O.D. of 0.01 for each wavelength is reported as the endpoint turbidity assay result. The average of the three wavelengths is used to compare turbidity of compounds. Compounds are considered to have low solubility if the threshold concentration is <31.3 µM, moderate solubility if the threshold concentration is 31.3 µM to 250 µM, and high solubility if the threshold concentration is >250 µM.

The following table indicates the relative solubility (L=low, M=moderate, H=high) based on turbidity threshold concentration at each pH for exemplary compounds according to the invention as indicated:

| Compound | turbidity threshold (L, M, H) | | | |
|---|---|---|---|---|
| number | 1.4 | 4.5 | 6.8 | 7.4 |
| P-1554 | H | H | M | M |
| P-1562 | H | H | M | M |
| P-1622 | H | M | M | M |
| P-1669 | M | M | M | M |

-continued

| Compound number | turbidity threshold (L, M, H) | | | |
|---|---|---|---|---|
| | 1.4 | 4.5 | 6.8 | 7.4 |
| P-1679 | M | L | L | L |
| P-2001 | M | L | L | L |
| P-2003 | H | M | L | L |
| P-2004 | H | M | M | M |
| P-2019 | H | M | M | L |
| P-2028 | H | M | M | M |
| P-2029 | H | M | M | M |
| P-2030 | H | M | M | L |
| P-2031 | M | L | L | L |
| P-2032 | M | L | L | L |
| P-2037 | M | L | L | L |
| P-2038 | H | L | L | L |
| P-2043 | H | M | M | M |
| P-2045 | H | M | M | M |
| P-2048 | M | L | L | L |
| P-2049 | M | L | L | L |
| P-2052 | H | L | L | L |
| P-2057 | H | L | L | M |
| P-2061 | H | M | M | L |
| P-2062 | H | L | L | L |
| P-2064 | H | M | L | L |
| P-2067 | H | H | H | H |
| P-2071 | M | L | L | L |
| P-2073 | H | M | M | M |
| P-2075 | H | M | L | M |
| P-2146 | H | M | M | L |
| P-2165 | L | L | L | L |
| P-2172 | H | L | L | L |
| P-2193 | | L | | |
| P-2198 | M | L | L | L |

CYP (Cytochrome P450) enzymes are the major drug metabolizing enzymes present in the liver. The inhibition of CYP enzyme activity ($IC_{50}$) for each of CYP1A2, CYP2C19, CYP2C9, CYP2D6, CYP3A4(BFC) and CYP3A4(BQ) is determined for compounds, where inhibition of metabolism of a known substrate leads to a decrease in the fluorescence of the metabolized product. The fluorescence of the product is monitored as a function of compound concentration.

Compounds are dissolved in DMSO to a concentration of 100 mM. These are diluted 1 μL into 82 μL of acetonitrile. An 11 μL aliquot of this solution is then added to 204 μL of cofactor mix (1.3% NADPH Regeneration system Solution A, 1.04% NADPH Regeneration system Solution B from BD Biosciences, 5% acetonitrile and 0.05% DMSO). These are then serially diluted 1:1 (160 μL to 160 μL co-factor mix) for a total of 10 points. A 10 μL aliquot of this final mixture is dispensed into 384 well assay plates and incubated for 10 minutes at 37° C. Enzyme and substrate mix (10 μL; 0.5 μmol CYP1A2/5 μM CEC; 1.0 μmol CYP2C9/75 μM MFC; 0.5 μmol CYP2C19/25 μM CEC; 1.5 μmol CYP2D6/1.5 μM AMMC; 1.0 μmol CYP3A4/50 μM BFC; or 1.0 μmol CYP3A4/40 μM BQ) is added to these assay plates. Assay plates are incubated at 37° C. (CYP1A2-15 min; CYP2C9-45 min; CYP2C19, 2D6 and 3A4-30 min) and read in a Tecan Safire 2 plate reader (CYP1A2, 2C19 and 3A4 409 ex/460 em; CYP2C9 and 2D6 409 ex/530 em). The signal versus compound concentration is used to determine the $IC_{50}$. The enzymes and substrates for this assay are obtained from BD Biosciences. While other factors are involved in determining CYP effects in vivo, compounds preferably have $IC_{50}$ values of >5 μM, more preferably $IC_{50}$ values of >10 μM.

The following table indicates the Cyp inhibition for exemplary compounds according to the invention as indicated:

| Compound number | Cyp $IC_{50}$ (μM) | | | | | |
|---|---|---|---|---|---|---|
| | 1A2 | 2C19 | 2C9 | 2D6 | 3A4(BFC) | 3A4(BQ) |
| P-1562 | >10 | >10 | <5 | >10 | 5-10 | 5-10 |
| P-1622 | >10 | <5 | 5-10 | >10 | 5-10 | 5-10 |
| P-1669 | >10 | >10 | <5 | >10 | 5-10 | |
| P-1679 | >10 | <5 | <5 | >10 | >10 | |
| P-2001 | >10 | <5 | 5-10 | >10 | 5-10 | 5-10 |
| P-2003 | >10 | 5-10 | <5 | >10 | 5-10 | >10 |
| P-2004 | >10 | 5-10 | <5 | 5-10 | <5 | 5-10 |
| P-2019 | >10 | 5-10 | <5 | <5 | <5 | >10 |
| P-2028 | >10 | >10 | <5 | >10 | <5 | <5 |
| P-2029 | >10 | <5 | <5 | >10 | 5-10 | 5-10 |
| P-2030 | >10 | <5 | <5 | >10 | 5-10 | >10 |
| P-2031 | >10 | <5 | <5 | >10 | 5-10 | 5-10 |
| P-2032 | 5-10 | <5 | <5 | >10 | >10 | >10 |
| P-2037 | >10 | <5 | <5 | >10 | 5-10 | >10 |
| P-2038 | >10 | >10 | 5-10 | >10 | >10 | >10 |
| P-2043 | >10 | >10 | 5-10 | >10 | >10 | 5-10 |
| P-2045 | >10 | 5-10 | >10 | >10 | 5-10 | >10 |
| P-2048 | >10 | >10 | >10 | >10 | >10 | >10 |
| P-2049 | >10 | 5-10 | 5-10 | >10 | 5-10 | >10 |
| P-2052 | >10 | >10 | 5-10 | >10 | 5-10 | 5-10 |
| P-2057 | >10 | 5-10 | 5-10 | >10 | >10 | >10 |
| P-2061 | >10 | >10 | 5-10 | >10 | >10 | 5-10 |
| P-2062 | >10 | <5 | <5 | >10 | 5-10 | 5-10 |
| P-2063 | >10 | 5-10 | >10 | >10 | 5-10 | 5-10 |
| P-2064 | >10 | >10 | 5-10 | >10 | >10 | >10 |
| P-2067 | >10 | <5 | <5 | >10 | <5 | >10 |
| P-2071 | >10 | >10 | 5-10 | >10 | 5-10 | 5-10 |
| P-2073 | >10 | >10 | <5 | >10 | 5-10 | >10 |
| P-2075 | 5-10 | <5 | <5 | >10 | <5 | 5-10 |
| P-2078 | >10 | >10 | <5 | >10 | <5 | >10 |
| P-2079 | >10 | 5-10 | 5-10 | >10 | <5 | 5-10 |
| P-2081 | >10 | <5 | <5 | >10 | <5 | 5-10 |
| P-2082 | >10 | <5 | <5 | >10 | <5 | <5 |
| P-2088 | >10 | <5 | <5 | >10 | 5-10 | 5-10 |
| P-2097 | >10 | <5 | <5 | >10 | 5-10 | 5-10 |
| P-2103 | >10 | <5 | <5 | >10 | 5-10 | 5-10 |
| P-2118 | >10 | <5 | 5-10 | >10 | 5-10 | >10 |
| P-2131 | >10 | 5-10 | <5 | >10 | <5 | >10 |
| P-2139 | >10 | >10 | 5-10 | >10 | 5-10 | >10 |
| P-2146 | >10 | <5 | 5-10 | >10 | >10 | >10 |
| P-2147 | >10 | <5 | >10 | >10 | 5-10 | 5-10 |
| P-2157 | >10 | >10 | >10 | >10 | 5-10 | >10 |
| P-2165 | >10 | >10 | >10 | >10 | >10 | >10 |
| P-2172 | >10 | <5 | 5-10 | >10 | >10 | |
| P-2193 | >10 | >10 | >10 | >10 | >10 | >10 |
| P-2198 | >10 | <5 | 5-10 | >10 | <5 | |

Pharmacokinetic properties of compounds (including any solid forms or formulations thereof) are assessed in male Sprague Dawley rats or male Beagle dogs. Rats are dosed daily with compound either by IV injections via surgically implanted jugular catheters or by oral gavage (PO). Each compound is prepared as a 20 mg/mL stock solution in dimethyl sulfoxide, which is further diluted to provide the dosing stock at the desired concentration for the IV or PO formulations. For IV dosing, the dosing stock is diluted into a 1:1:8 mixture of Solutol®:ethanol:water. For PO dosing, the dosing stock is diluted into 1% methylcellulose. In a cassette format (or each compound, solid form thereof or formulation thereof is done individually), compounds are diluted to 0.5 mg/mL each for IV dosing and 0.4 mg/mL each for PO dosing and dosed at 1 mg/kg (2 mL/kg) or 2 mg/kg (5 mL/kg), respectively. For IV dosed animals, tail vein blood samples are collected with lithium heparin anticoagulant at 5, 15, 30, and 60 minutes and 4, 8, and 24 hours post dosing each day. For PO dosed animals, tail vein blood samples are collected with lithium heparin anticoagulant at 30 minutes, 1, 2, 4, 8 and 24 hours post dosing each day. Dogs are dosed daily by oral capsules in a suitable formulation at 50 mg/mL. Cephalic vein blood samples are collected with lithium heparin anticoagulant at 30 minutes, 1, 2, 4, 8 and 24 hours post dosing each day. All samples are processed to plasma and frozen for later analysis of each compound by LC/MS/MS. Plasma levels as a function of time are plotted to assess the AUC (ng*hr/mL). Compounds according to the present invention preferably show improved pharmacokinetic properties relative to previously described compounds, i.e. they have substantially higher values for one or more of AUC, Cmax and half-life relative to previously described compounds.

Analysis of penetration of compound into the brain can be assessed similarly. Each compound is prepared as a 100 mg/mL stock solution in dimethyl sulfoxide, as well as control compounds atenolol at 100 mg/mL and antipyrine at 50 mg/mL. In a cassette format, up to three test compounds, along with atenolol and antipyrine, are combined, 180 µL each, and added to 17.1 mL of 1% methylcellulose. The compounds are in a suspension that is administered in a single dose (10 mL per kg body weight) to 2 groups of CD rats (8-9 weeks, n=3 per group) by oral gavage, an additional group of rats dosed with vehicle only. One group of compound treated rats is sacrificed at 2 hours post dosing, the other group at 6 hours. Plasma is collected in Li-heparin and the brains are collected, cut into right and left hemispheres, weighed and flash frozen. Brain homogenate (30%) and plasma samples are assessed by equilibrium dialysis using a 96 well equilibrium dialysis apparatus with a 5K MW cut off membrane (The Nest Group, Inc.) as per the vendor's protocol with the samples on one side of the dialysis membrane and an equal volume of 1×PBS on the other side. The apparatus is incubated overnight at 37° C. on a plate rotator (The Nest Group, Inc.). The compound concentrations on both sides are analyzed by LC/MS/MS to calculate the mass balance recovery. The concentration in the PBS side is calculated using a standard curve generated for each compound. The PBS concentration is the free compound concentration, while the side with the biological sample provides the concentration in plasma or brain.

Additional features of the complex can be used to demonstrate improved properties, such as comparison of the intrinsic dissolution rate of a similarly prepared substantially amorphous citrate complex or formulation thereof as compared to that of a crystalline form of the compound or similar formulation thereof in simulated gastric fluid (SGF) without enzyme and in simulated intestinal fluid (SIF). A pellet of test sample is dissolved in the appropriate fluid, and the UV absorbance as a function of time is measured at 254 nm (SGF) or 310 nm (SIF) and plotted.

Example 28

In Vivo Model System Testing

For in vivo testing, a suitable animal model system can be selected for use. For example, for multiple scerosis, the rodent experimental allergic encephalomyelitis (EAE) system is commonly used. This system is described, for example, in Steinman, 1996, Cell 85:299-302 and Secor et al., 2000, J. Exp. Med. 5:813-821, which are incorporated herein by reference in their entireties. For rheumatoid arthritis (RA), the type II collagen-induced arthritis (CIA) small animal model of rheumatoid arthritis (RA) can be used for testing. This model is described, for example, in Wooley, et al. Current Rheumatology Reviews, 2008, 4: 277-287, which is incorporated herein by reference in its entirety.

Similarly, other model systems can be used to evaluate compounds described herein. Numerous compounds described herein, including compounds of Formulas I, I', II, II', IIa, III, and III' (e.g., P-1496, P-1622, P-1669, P-1679, P-2001, P-2028, P-2029, P-2030, P-2038, P-2043, P-2045, P-2048, P-2049, P-2052, P-2057, P-2061, P-2062, P-2063, P-2064, P-2067, P-2070, P-2071, P-2073, P-2075, P-2078, P-2088, P-2097, P-2103, P-2118, P-2139, P-2157, P-2165, P-2176, P-2193, P-1554, P-1562, P-2003, P-2004, P-2008, P-2013, P-2019, P-2031, P-2032, P-2037, P-2079, P-2081, P-2082, P-2131, P-2146, P-2147, P-2148, P-2154, P-2163, P-2172, P-2198, P-2202, P-1644, P-1646, P-1667, P-2003, P-2004, P-2009, P-2019, P-2029, P-2030, P-2031, P-2032, P-2034, P-2037, P-2038, P-2040, P-2041, P-2044, P-2047, P-2048, P-2050, P-2057 and P-2065; the compounds disclosed in paragraphs [0038], [0079], [0094], [0102], [0103], and [0104]; and the compounds described in the Examples), or compositions thereof, hydrates or solvates thereof, are tested in mice for the treatment of various diseases and conditions as described herein.

Collagen Induced Rheumatoid Arthritis (RA) Mouse Model. Methods: Intradermal injections with collagen-CFA, followed by a collagen boost by intraperitoneal (ip) injection on day 21 induces rheumatoid arthritis in a variety of mouse strains, especially the DBA/1 genotype used in this study (Brand et al., 2004; Wooley et al., 1981). Disease is quantified and recorded by clinical scores using a scale of 0-4 per paw. The score records the degree and extent of swelling and redness in each digit and joint and culminates in the absence of use of individual front or rear paws. Scores are accumulated per animal resulting in a maximum score of 16, which indicates that animals avoid the use of all paws. Groups were balanced for disease score at day 21 after the initial immunization when the average clinical score was 2.5 for all animals. Treatment was for 21 days with daily oral dosing with the following dosing groups: vehicle, and 10 mg/kg, 20 mg/kg and 50 mg/kg the compounds of the invention.

Results

Oral administration of the compounds of the invention inhibited the clinical disease development in the murine CIA model in a dose dependent fashion with significant responses at all doses tested (10, 20 and 50 mg/kg qd). Histopathological analysis of the joints showed inhibition of inflammation, bone resorption, cartilage damage and pannus formation by compounds of the invention treatment. The mechanism of action of compounds of the invention was confirmed by the decreased scores for macrophage and osteoclast-cells in the joints.

Daily oral administration of Fms kinase inhibitors described herein showed at all dose levels tested (10, 20 and 50 mg/kg) a rapid benefit as compared to the vehicle control, as evidenced by decreased clinical scores, reflecting less swelling and redness of limbs. This clinical benefit was confirmed by decreased histopathological scores for inflammation, cartilage damage, pannus formation and bone destruction. Scores for both macrophage and osteoclast-cells were decreased in the joint tissues confirming that the mode of action of the compounds described herein is by inhibiting the Fms receptor tyrosine kinase, which is crucial for the proliferation and differentiation of these cell lineages. Plasma concentrations of the dose groups drawn at the 2 hr time point after dosing showed a clear dose proportional response.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the invention using one of the terms, the invention also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:

1. A compound having Formula II':

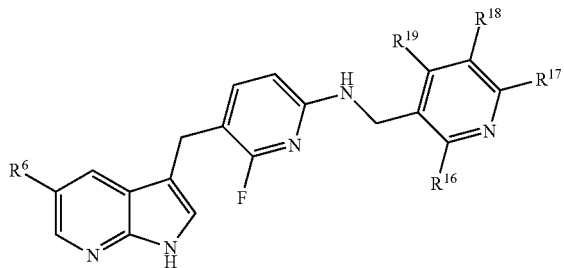

Formula II' or a salt, a tautomer or a stereoisomer thereof, wherein:

$R^6$ is selected from the group consisting of methyl, —C(O)—N(H)—$R^{14}$, and —N(H)—C(O)—$R^{15}$;

$R^{14}$ is lower alkyl;

$R^{15}$ is lower alkyl; and (i) $R^{16}$ is H and $R^{17}$ is —F, —Cl, —Br, lower alkyl, fluoro substituted lower alkyl, methoxy substituted lower alkyl, —CN or —O—$R^{20}$; or (ii) $R^{17}$ is H and $R^{16}$ is —F, —Cl, —Br, lower alkyl, fluoro substituted lower alkyl, methoxy substituted lower alkyl, —CN or —O—$R^{20}$;

$R^{18}$ is —F or —Cl;

$R^{19}$ is H; and $R^{20}$ is lower alkyl, fluoro substituted lower alkyl, methoxy substituted lower alkyl, or cycloalkyl.

2. The compound of claim 1, wherein $R^6$ is —C(O)—N(H)—$R^{14}$.

3. The compound of claim 1, wherein $R^6$ is —N(H)—C(O)—$R^{15}$.

4. The compound of claim 1, having the following formula:

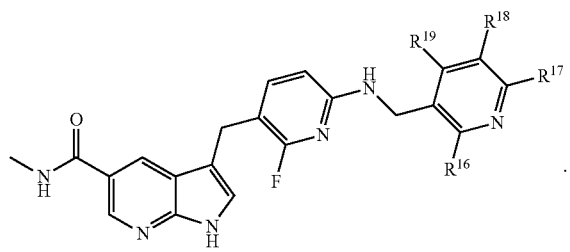

5. The compound of claim 1, having Formula II:

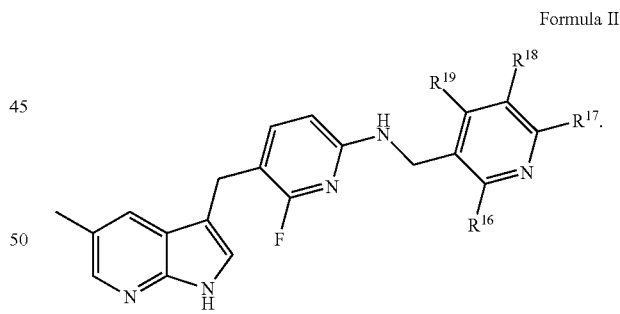

Formula II

6. The compound of claim 5, wherein $R^{16}$ is H and $R^{17}$ is selected from —F, —Cl, —Br, lower alkyl, fluoro substituted lower alkyl, —OR$^{20}$, or methoxy substituted lower alkyl; or $R^{17}$ is H and $R^{16}$ is selected from —F, —Cl, —Br, lower alkyl, fluoro substituted lower alkyl, —OR$^{20}$, or methoxy substituted lower alkyl.

7. The compound of claim 5, wherein $R^{16}$ is H and $R^{17}$ is selected from the group consisting of —F, —Cl, —Br, lower alkyl, fluoro substituted lower alkyl, and methoxy substituted lower alkyl; or $R^{17}$ is H and $R^{16}$ is selected from the group consisting of —F, —Cl, —Br, lower alkyl, fluoro substituted lower alkyl, and methoxy substituted lower alkyl.

8. The compound of claim 1, wherein the compound is selected from the group consisting of:

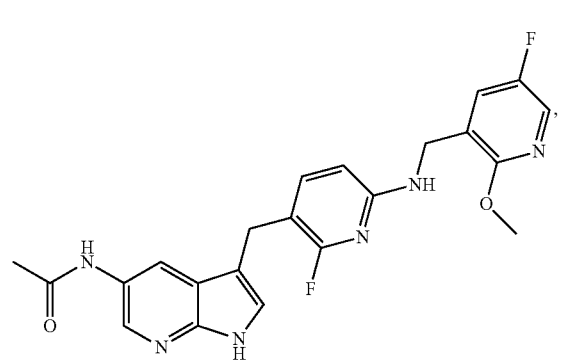 [SMILES: COc1ncc(F)cc1CNc1ccc(Cc2c[nH]c3ncc(NC(C)=O)cc23)c(F)n1]

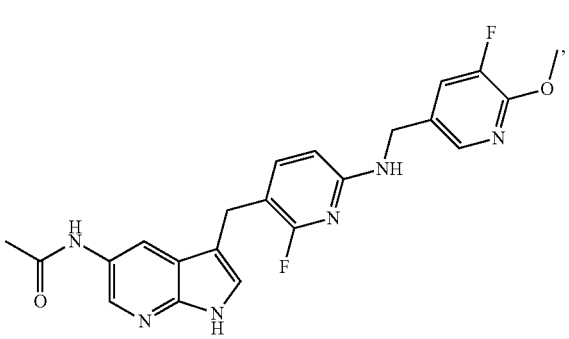 [SMILES: COc1ncc(CNc2ccc(Cc3c[nH]c4ncc(NC(C)=O)cc34)c(F)n2)cc1F]

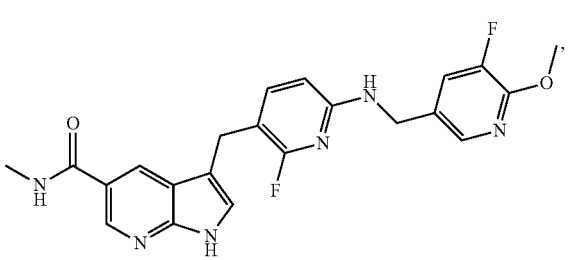

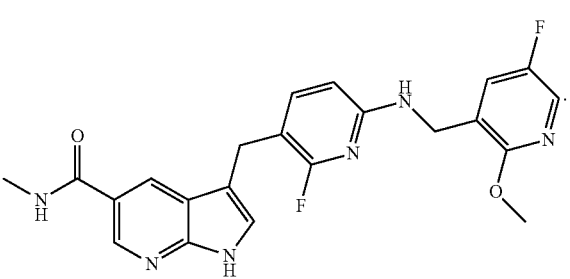 [SMILES: CNC(=O)c1cnc2[nH]cc(Cc3ccc(NCc4cc(F)cnc4OC)nc3F)c2c1]

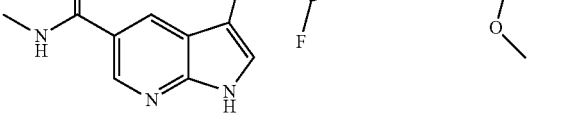

9. The compound of claim 5, wherein the compound is

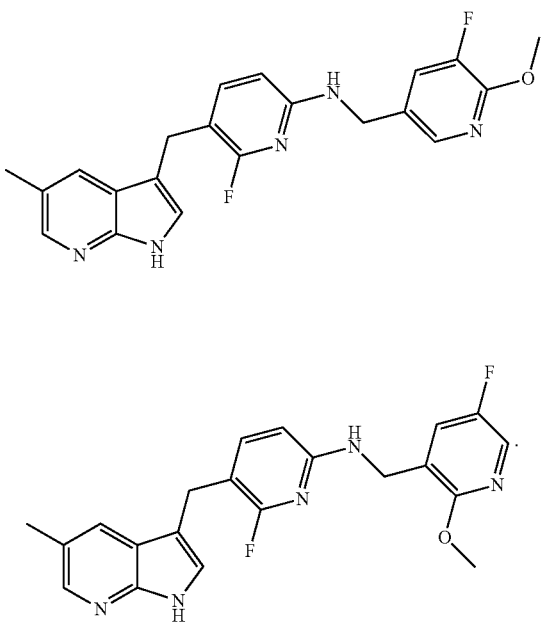

10. A composition comprising a compound of claim 1 and a pharmaceutically acceptable excipient or carrier.

11. A kit comprising a compound of claim 1.

12. A composition comprising a compound of claim 8 and a pharmaceutically acceptable excipient or carrier.

13. A composition comprising a compound of claim 9 and a pharmaceutically acceptable excipient or carrier.

14. A method for treating a subject suffering from or at risk of a disease or condition, said method comprising administering to the subject in need thereof an effective amount of a compound of claim 1, wherein the disease or condition is rheumatoid arthritis and osteoarthritis.

15. A method for treating a subject suffering from or at risk a disease or condition, said method comprising administering to the subject in need thereof an effective amount of a compound of claim 8, wherein the disease or condition is rheumatoid arthritis or osteoarthritis.

16. A method for treating a subject suffering from or at risk a disease or condition, said method comprising administering to the subject in need thereof an effective amount of a compound of claim 9, wherein the disease or condition is osteoarthritis or rheumatoid arthritis.

17. A method for preparing a compound of Formula II' according to claim 1, said method comprising:

contacting a compound of Formula VI:

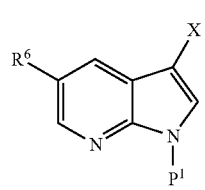

Formula VI with a compound of Formula VII:

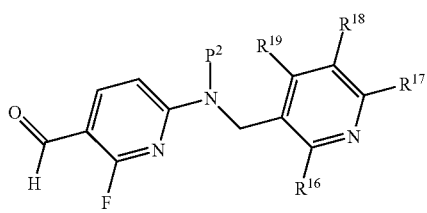

Formula VII under conditions sufficient to form the compound of Formula II', wherein:
P¹ and P² are each independently an amino protecting group; and
X is H or halogen.

18. A compound of formula:

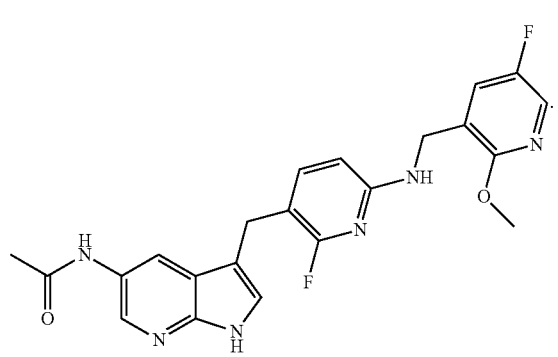 [SMILES: COc1ncc(F)cc1CNc1ccc(Cc2c[nH]c3ncc(NC(C)=O)cc23)c(F)n1]

or a salt, a tautomer, or a stereoisomer thereof.

19. A compound of formula:

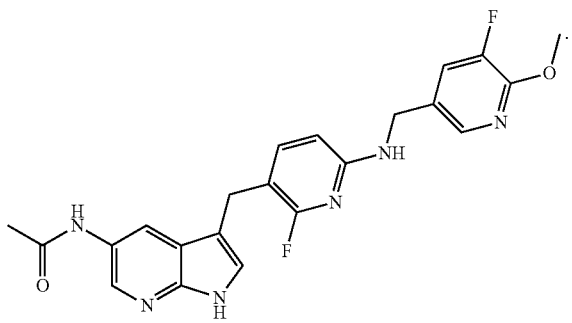 [SMILES: COc1ncc(CNc2ccc(Cc3c[nH]c4ncc(NC(C)=O)cc34)c(F)n2)cc1F]

or a salt, a tautomer, or a stereoisomer thereof.

20. A compound of formula

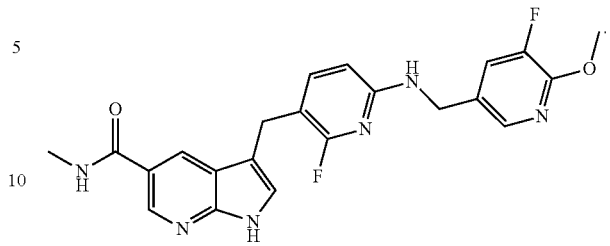

or a salt, a tautomer, or a stereoisomer thereof.

21. A compound of formula:

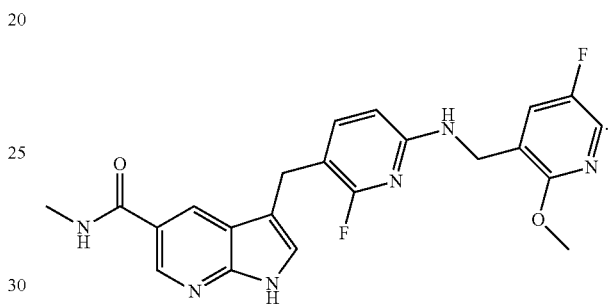

or a salt, a tautomer, or a stereoisomer thereof.

22. A compound of formula:

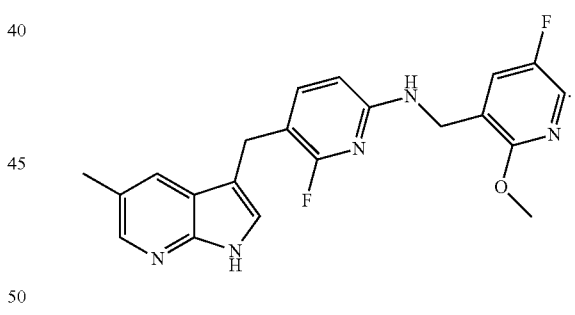

or a salt, a tautomer, or a stereoisomer thereof.

* * * * *